US008088770B2

(12) United States Patent
Desai et al.

(10) Patent No.: US 8,088,770 B2
(45) Date of Patent: Jan. 3, 2012

(54) MODULATORS OF PHARMACOKINETIC PROPERTIES OF THERAPEUTICS

(75) Inventors: Manoj C. Desai, Pleasant Hill, CA (US); Hon C. Hui, San Mateo, CA (US); Hongtao Liu, Cupertino, CA (US); Jianyu Sun, San Mateo, CA (US); Lianhong Xu, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 12/217,496

(22) Filed: Jul. 3, 2008

(65) Prior Publication Data
US 2009/0181902 A1 Jul. 16, 2009

Related U.S. Application Data

(60) Provisional application No. 60/958,716, filed on Jul. 6, 2007.

(51) Int. Cl.
A61K 31/5355 (2006.01)
A61K 31/4985 (2006.01)
A61K 31/437 (2006.01)
A61K 31/4402 (2006.01)
A61K 31/426 (2006.01)
C07D 417/04 (2006.01)
C07D 487/04 (2006.01)
C07D 277/24 (2006.01)

(52) U.S. Cl. ............ 514/236.8; 514/249; 514/303; 514/342; 514/365; 544/133; 544/236; 546/118; 546/269.7; 548/181; 548/204

(58) Field of Classification Search .............. None
See application file for complete search history.

(56) References Cited

U.S. PATENT DOCUMENTS

| 5,142,056 A | 8/1992 | Kempe et al. |
| 5,354,866 A | 10/1994 | Kempf et al. |
| 5,362,912 A | 11/1994 | Sowin et al. |
| 5,539,122 A | 7/1996 | Kempf et al. |
| 5,541,206 A | 7/1996 | Kempf et al. |
| 5,552,558 A | 9/1996 | Kempf et al. |
| 5,565,418 A | 10/1996 | Kempf et al. |
| 5,580,984 A | 12/1996 | Kempf et al. |
| 5,583,232 A | 12/1996 | Kempf et al. |
| 5,583,233 A | 12/1996 | Kempf et al. |
| 5,591,860 A | 1/1997 | Kempf et al. |
| 5,597,927 A | 1/1997 | Kempf et al. |
| 5,597,928 A | 1/1997 | Kempf et al. |
| 5,608,072 A | 3/1997 | Kempf et al. |
| 5,616,720 A | 4/1997 | Kempf et al. |
| 5,625,072 A | 4/1997 | Kempf et al. |
| 5,635,523 A | 6/1997 | Kempf et al. |
| 5,659,044 A | 8/1997 | Kempf et al. |
| 5,659,045 A | 8/1997 | Kempf et al. |
| 5,674,882 A | 10/1997 | Kempf et al. |
| 5,679,797 A | 10/1997 | Kempf et al. |
| 5,696,270 A | 12/1997 | Kempf et al. |
| 5,763,464 A | 6/1998 | Randad et al. |
| 5,892,052 A | 4/1999 | Kempf et al. |
| 6,448,245 B1 | 9/2002 | DePetrillo et al. |
| 2002/0115665 A1 | 8/2002 | DePetrillo et al. |
| 2003/0191319 A1 | 10/2003 | Vazquez et al. |
| 2004/0127689 A1 | 7/2004 | Sigler et al. |
| 2006/0199851 A1 | 9/2006 | Kempf et al. |
| 2008/0108617 A1 | 5/2008 | Desai et al. |

FOREIGN PATENT DOCUMENTS

| EP | 0428849 | 5/1991 |
| EP | 486948 A2 | 5/1992 |
| EP | 0674513 | 10/1995 |
| EP | 1090914 | 4/2001 |
| EP | 1183026 | 3/2002 |
| EP | 1302468 | 4/2003 |
| FR | 2773994 | 7/1999 |
| WO | WO-94/14436 | 7/1994 |
| WO | WO-97/01349 | 1/1997 |
| WO | WO-01/25240 | 4/2001 |
| WO | WO-2005/111006 A1 | 11/2005 |
| WO | WO-2008/010921 | 1/2008 |

OTHER PUBLICATIONS

"Analogue." Merriam-Webster Online Dictionary. 2010. Merriam-Webster Online. Accessed May 3, 2010. <http://merriam-webster.com/dictionary/analogue>.*
"Derivative." Merriam-Webster Online Dictionary. 2010. Merriam-Webster Online. Accessed Apr. 20, 2010. <http://merriam-webster.com/dictionary/derivative>.*
Morissette et al. "High-throughput crystallization: polymorphs, salts, co-crystals and solvates of pharmaceutical solids." Advanced Drug Delivery Reviews 2004, 56, 275-300.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta, Sudha R. "Crystalline Solids." Advanced Drug Delivery Reviews 48(2001): 3-26.*
Gurjar et al. (1997) "Synthesis of Novel C2-symmetric and Pseudo C2-symmetric Based Diols, Epoxides and Dideoxy Derivatives of HIV Protease Inhibitors," *Tetrahedron* 53(13):4769-4778.

(Continued)

Primary Examiner — Rebecca Anderson
Assistant Examiner — Alicia L Otton
(74) Attorney, Agent, or Firm — Allan Kutzenco

(57) ABSTRACT

The present application provides for a compound of Formula IV:

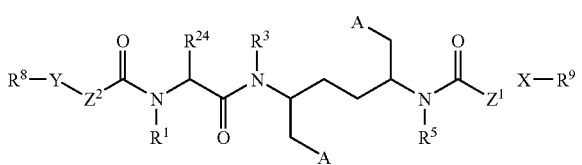

Formula IV or a pharmaceutically acceptable salt, solvate, and/or ester thereof, compositions containing such compounds, therapeutic methods that include the administration of such compounds, and therapeutic methods and include the administration of such compounds with at least one additional therapeutic agent.

21 Claims, No Drawings

OTHER PUBLICATIONS

Kempf et al. (1998) "Discovery of Ritonavir, a Patent Inhibitor of HIV Protease with High Oral Bioavailability and Clinical Efficacy," *J. Med. Chem*, 41:602-617.

Molla et al. (1996) "Ordered Accumulation of Mutations in HIV Protease Confers Resistance to Ritonavir," *Nature Medicine* 2:(7):760-766.

Bai, J. et al. (2004) "Use of Classification Regression Tree in Predicting Oral Absorption in Humans," *J. Chem Inf. Comput. Sci* 44:2061-2069.

Frecer, V. et al. (2005) "Structure Based Design of Inhibitors of Aspartic Protease of HIV-1," *Letters in Drug Design& Discovery* 2:638-646.

Kempf,D. et al. (1997) "Lack of Stereospecificity in the Binding of the P2 Amino Acid of Ritonavir to HIV Protease," *Bioorganic& Medicinal Chemistry Letters* 7(6):699-704.

Mekapati, S.B. et al. (2001) "Quantitative Structure-Activity Relationship of some HIV-1 Protease Inhibitors: A Fujita-Ban Type Analysis," *J. Enzyme Inhibition* 16:185-197.

Nair, A. et al. (1998) "A Computational Study of the Resistance of HIV-1 Aspartic Protease to the Inhibitors ABT-538 and VX-478 and Design of New Analogues," *Biochemical and Biophysical Research Communications* 242:545-551.

* cited by examiner

MODULATORS OF PHARMACOKINETIC PROPERTIES OF THERAPEUTICS

CROSS-REFERENCE TO RELATED APPLICATIONS

This application claims priority to U.S. Provisional Application Ser. No. 60/958,716, entitled "Modulators of Pharmacokinetic Properties of Therapeutics," filed Jul. 6, 2007. The content of this provisional application is herein incorporated by reference in its entirety for all purposes.

FIELD OF THE INVENTION

This application relates generally to compounds and pharmaceutical compositions which modify, e.g., improve, the pharmacokinetics of a co-administered drug, and methods of modifying, e.g., improving, the pharmacokinetics of a drug by co-administration of the compounds with the drug.

BACKGROUND OF THE INVENTION

Oxidative metabolism by cytochrome P450 enzymes is one of the primary mechanisms of drug metabolism. It can be difficult to maintain therapeutically effective blood plasma levels of drugs which are rapidly metabolized by cytochrome P450 enzymes. Accordingly, the blood plasma levels of drugs which are susceptible to cytochrome P450 enzyme degradation can be maintained or enhanced by co-administration of cytochrome P450 inhibitors, thereby improving the pharmacokinetics of the drug.

While certain drugs are known to inhibit cytochrome P450 enzymes, more and/or improved inhibitors for cytochrome P450 monooxygenase are desirable. Particularly, it would be desirable to have cytochrome P450 monooxygenase inhibitors which do not have appreciable biological activity other than cytochrome P450 inhibition. Such inhibitors can be useful for minimizing undesirable biological activity, e.g., side effects. In addition, it would be desirable to have P450 monooxygenase inhibitors that lack significant or have a reduced level of protease inhibitor activity. Such inhibitors could be useful for enhancing the effectiveness of antiretroviral drugs, while minimizing the possibility of eliciting viral resistance, especially against protease inhibitors.

SUMMARY OF THE INVENTION

One aspect of the present application is directed to compounds and pharmaceutical compositions which modify, e.g., improve, the pharmacokinetics of a co-administered drug, e.g., by inhibiting cytochrome P450 monooxygenase.

In one embodiment, the present application provides for compounds having a structure according to Formula IV:

Formula IV

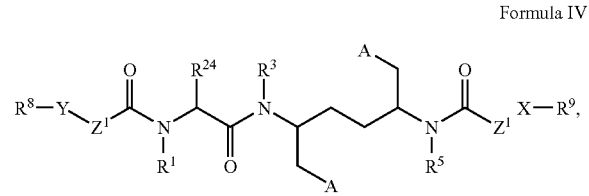

or a pharmaceutically acceptable salt, solvate, and/or ester thereof, wherein:
each A is independently aryl or heterocyclyl;
$Z^1$ and $Z^2$ are each independently —O— or —N($R^7$)—;
X and Y are each independently aryl, arylalkyl, heterocyclyl, or heterocyclylalkyl;
$R^1$, $R^3$, and $R^5$ are each independently selected from the group consisting of H, alkyl, substituted alkyl, arylalkyl, and substituted arylalkyl;
each $R^7$ is independently selected from the group consisting of H, alkyl, substituted alkyl, heteroalkyl, substituted heteroalkyl, carbocyclyl, substituted carbocyclyl, heterocyclyl, and substituted heterocyclyl;
$R^8$ and $R^9$ are each one or more substituents independently selected from the group consisting of H, alkyl, halogen, aryl, heterocyclyl, and CN; and
$R^{24}$ is selected from the group consisting of -alkylene-$NR^5$—C(O)—$R^{25}$, -alkylene-C(O)—$NR^5$—$R^{26}$, -alkylene-N($R^{27}$)$_2$, —$CH_2$-heterocyclyl, and substituted —$CH_2$-heterocyclyl;
$R^{25}$ is alkyl, heterocyclylalkyl, or substituted heterocyclylalkyl;
$R^{26}$ is a substituted or unsubstituted heterocyclyl; or
$R^5$ and $R^{26}$ together with the nitrogen atom to which they are both shown attached, form a substituted or unsubstituted bicyclic heterocyclyl;
each $R^{27}$ is independently a substituted alkyl which may be the same or different; or
each $R^{27}$, together with the nitrogen atom to which they are both shown attached, form a substituted or unsubstituted bicyclic heterocyclyl;
with the following provisos:
(i) when X and Y are both thiazolylmethyl, $Z^1$ is —N($R^7$)—, $Z^2$ is —O—, each A is phenyl, and $R^{24}$ is —$CH_2CH_2$—$NR^5$—C(O)-alkyl, then each $R^8$ and $R^9$ are H; and
(ii) when X and Y are both thiazolylmethyl, $Z^1$ is —N($R^7$)—, $Z^2$ is —O—, each A is phenyl, and $R^{24}$ is —$CH_2$—C(O)—$NR^5$-pyridyl or —$CH_2$—C(O)—$NR^5$-pyrrolidinyl,
then $R^5$ is alkyl, substituted alkyl, arylalkyl, or substituted arylalkyl; and
(iii) when X and Y are both thiazolylmethyl, $Z^1$ is —N($R^7$)—, $Z^2$ is —O—, each A is phenyl, and $R^{24}$ is substituted or unsubstituted —$CH_2$-heterocyclyl,
then said substituted or unsubstituted —$CH_2$-heterocyclyl is not pyridylmethyl, pyrazolylmethyl, imidazolidine-2,4-dione-5-yl-methyl, imidazolylmethyl, or morpholinylmethyl.

In another embodiment, the present application provides for a pharmaceutical composition comprising a compound of Formula IV and a pharmaceutically acceptable carrier or excipient.

In another embodiment, the present application provides for a pharmaceutical composition comprising a compound of Formula IV and at least one additional therapeutic agent, and a pharmaceutically acceptable carrier or excipient.

In another embodiment, the present application provides for a method for improving the pharmacokinetics of a drug, comprising administering to a patient treated with said drug, a therapeutically effective amount of a compound of Formula IV or a pharmaceutically acceptable salt, solvate, and/or ester thereof.

In another embodiment, the present application provides for a method for inhibiting cytochrome P450 monooxygenase in a patient comprising administering to a patient in need thereof an amount of a compound of Formula IV or a pharmaceutically acceptable salt, solvate, and/or ester thereof, effective to inhibit cytochrome P450 monooxygenase.

In another embodiment, the present application provides for a method for treating a viral infection, e.g., HIV, comprising administering to a patient in need thereof a therapeutically effective amount of a compound of Formula IV or a pharmaceutically acceptable salt, solvate, and/or ester thereof, in combination with a therapeutically effective amount of one or more additional therapeutic agents which are metabolized by cytochrome P450 monooxygenase, and are suitable for treating a viral infection, e.g., HIV.

In another embodiment, the present application provides for a combination pharmaceutical agent comprising:

a) a first pharmaceutical composition comprising a compound of Formula IV or a pharmaceutically acceptable salt, solvate, and/or ester thereof; and b) a second pharmaceutical composition comprising at least one additional active agent which is metabolized by cytochrome P450 monooxygenase.

DETAILED DESCRIPTION

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

Definitions

Unless stated otherwise, the following terms and phrases as used herein are intended to have the following meanings:

When trade names are used herein, applicants intend to independently include the tradename product and the active pharmaceutical ingredient(s) of the tradename product.

As used herein, "a compound of the invention" or "a compound of Formula IV" means a compound of Formula IV or a pharmaceutically acceptable salt, solvate, ester or stereoisomer thereof, or a physiologically functional derivative thereof. Similarly, with respect to isolatable intermediates, the phrase "a compound of formula (number)" means a compound of that formula and pharmaceutically acceptable salts, solvates and physiologically functional derivatives thereof.

"Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (1-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

The term "acyl" refers to a carbonyl group (—C(O)—). For example, arylacyl refers to groups such as phenyl-C(O)—, alkylacyl refers to acetyl, aminoacyl refers to $H_2N$—C(O)— (wherein the N atom can be substituted with aryl, alkyl, heterocyclyl, etc). When the acyl group forms, for example, a ketone, a carboxy group, a carbonate group, a urea group, a thio ester, etc, the non-carbonyl moiety of the such a group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. In one embodiment, aryl groups in the esters comprise a phenyl group. The term "lower acyl" refers to an acyl group in which the non-carbonyl moiety is a lower alkyl.

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or -OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2CH$=$CH_2$), cyclopentenyl (—$C_5H_7$), and 5-hexenyl (—$CH_2CH_2CH_2CH_2CH$=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne,), or 2 to 6 carbon atoms (i.e., $C_2$-$C_6$ alkynyl). Examples of suitable alkynyl groups include, but are not limited to, acetylenic (—C≡CH), propargyl (—$CH_2C$≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡CH—).

"Amino" means an —NFL or a —NR$_2$ group in which the "R" groups are independently H, alkyl, carbocyclyl (substituted or unsubstituted, including saturated or partially unsaturated cycloalkyl and aryl groups), heterocyclyl (substituted or unsubstituted, including saturated or unsaturated heterocycloalkyl and heteroaryl groups), arylalkyl (substituted or unsubstituted) or arylalkyl (substituted or unsubstituted) groups. Non-limiting examples of amino groups include —NH$_2$, —NH(alkyl), —NH(carbocyclyl), —NH(heterocyclyl), —N(alkyl)$_2$, —N(carbocyclyl)$_2$, —N(heterocyclyl)$_2$, —N(alkyl)(carbocyclyl), —N(alkyl)(heterocyclyl), —N(carbocyclyl)(heterocyclyl), etc., wherein alkyl, carbocyclyl, and heterocyclyl can be substituted or unsubstituted and as defined and described herein. "Substituted" or "protected" amino means an aminoalkyl as described and defined herein in which a H of the amino group is replaced with e.g., acyl groups, for example conventional amine protecting groups such as 9-Fluorenylmethyl carbamate ("Fmoc"), t-Butyl carbamate ("Boc"), Benzyl carbamate ("Cbz"), acetyl, trifluoroacetyl, phthalimidyl, triphenylmethyl, p-Toluenesulfonyl ("Tosyl"), methylsulfonyl ("mesyl"), etc.

"Aminoalkyl" means an acyclic alkyl radical in which one of the hydrogen atoms bonded to a carbon atom, typically a terminal or sp$^3$ carbon atom, is replaced with an amino radical as defined and described herein. Non-limiting examples of aminoalkyl include —CH$_2$—NH$_2$, —CH$_2$CH$_2$—NH$_2$, —CH$_2$CH$_2$CH$_2$—NH$_2$, —CH$_2$CH$_2$CH$_2$CH$_2$—NH$_2$, —CH$_2$CH(CH$_3$)—NH$_2$, —CH$_2$CH$_2$CH(CH$_3$)—NH$_2$, —CH$_2$—NH(CH$_3$), —CH$_2$CH$_2$—NH(CH$_3$), —CH$_2$CH$_2$CH$_2$—NH(CH$_3$), —CH$_2$CH$_2$CH$_2$CH$_2$—NH(CH$_3$), —CH$_2$CH(CH$_3$)—NH(CH$_3$), —CH$_2$CH$_2$CH(CH$_3$)—NH(CH$_3$), —CH$_2$—NH(CH$_3$)$_2$, —CH$_2$CH$_2$—N(CH$_3$)$_2$, —CH$_2$CH$_2$CH$_2$—N(CH$_3$)$_2$, —CH$_2$CH$_2$CH$_2$CH$_2$—N(CH$_3$)$_2$, —CH$_2$CH(CH$_3$)—N(CH$_3$)$_2$, —CH$_2$CH$_2$CH(CH$_3$)—N(CH$_3$)$_2$, —CH$_2$—NH(CH$_2$CH$_3$), —CH$_2$CH$_2$—NH(CH$_2$CH$_3$), —CH$_2$CH$_2$CH$_2$—NH(CH$_2$CH$_3$), —CH$_2$CH$_2$CH$_2$CH$_2$—NH(CH$_2$CH$_3$), —CH$_2$CH(CH$_3$)—NH(CH$_2$CH$_3$), —CH$_2$CH$_2$CH(CH$_3$)—NH(CH$_2$CH$_3$), —CH$_2$—N(CH$_2$CH$_3$)$_2$, —CH$_2$CH$_2$—N(CH$_2$CH$_3$)$_2$, —CH$_2$CH$_2$CH$_2$—N(CH$_2$CH$_3$)$_2$, —CH$_2$CH$_2$CH$_2$CH$_2$—N(CH$_2$CH$_3$)$_2$, —CH$_2$CH(CH$_3$)—N(CH$_2$CH$_3$)$_2$, —CH$_2$CH$_2$CH(CH$_3$)—N(CH$_2$CH$_3$)$_2$, etc. "Substituted" or "protected" aminoalkyl means an aminoalkyl as described and defined herein in which the H of the amino group is replaced with e.g., acyl groups, for example conventional amine protecting groups such as 9-fluorenylmethyl carbamate ("Fmoc"), t-Butyl carbamate ("Boc"), Benzyl carbamate ("Cbz"), acetyl, trifluoroacetyl, phthalimidyl, triphenylmethyl, p-Toluenesulfonyl ("Tosyl"), methylsulfonyl ("mesyl"), etc.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or Sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or Sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 6 to 20 carbon atoms, e.g., the alkenyl moiety is 1 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 6 to 20 carbon atoms, e.g., the alkynyl moiety is 1 to 6 carbon atoms and the aryl moiety is 6 to 14 carbon atoms.

The term "substituted" in reference to alkyl, alkylene, aryl, arylalkyl, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R, —O$^-$, =O, —OR, —SR, —S$^-$, —NR$_2$, —N$^+$R$_3$, =NR, —CX$_3$, —CN, —OCN, —SCN, —N=C=O, —NCS, —NO, —NO$_2$, =N$_2$, —N3, —NHC(=O)R, —NHS(=O)$_2$R, —C(=O)R, —C(=O)NRR—S(=O)$_2$O—, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —P(=O)(O$^-$)$_2$, —P(=O)(OH)$_2$, —P(O)(OR)(O$^-$), —C(=O)R, —C(=O)OR, —C(=O)X, —C(S)R, —C(O)OR, —C(O)O—, —C(S)OR, —C(O)SR, —C(S)SR, —C(O)NRR, —C(S)NRR, —C(=NR)NRR, where each X is independently a halogen: F, Cl, Br, or I; and each R is independently H, alkyl, aryl, arylalkyl, a heterocycle, or a protecting group or prodrug moiety. Alkylene, alkenylene, and alkynylene groups may also be similarly substituted. When the number of carbon atoms is designated for a substituted group, the number of carbon atoms refers to the group, not the substituent (unless otherwise indicated). For example, a C$_{1-4}$ substituted alkyl refers to a C$_{1-4}$ alkyl, which can be substituted with groups having more the, e.g., 4 carbon atoms.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula IV should be selected in order to provide a compound which is sufficiently stable to provide a pharmaceutically useful compound which can be formulated into an acceptably stable pharmaceutical composition. Compounds of Formula IV which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

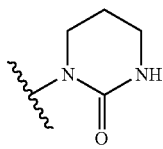

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

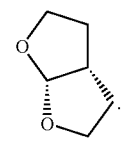

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

Non-limiting examples of substituted or unsubstituted bicyclic heterocyclyl ring systems include the following:

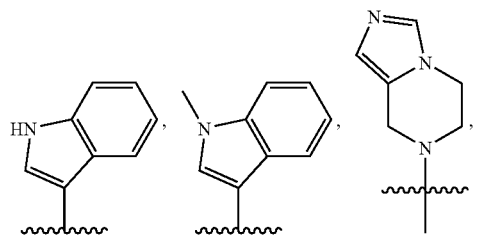

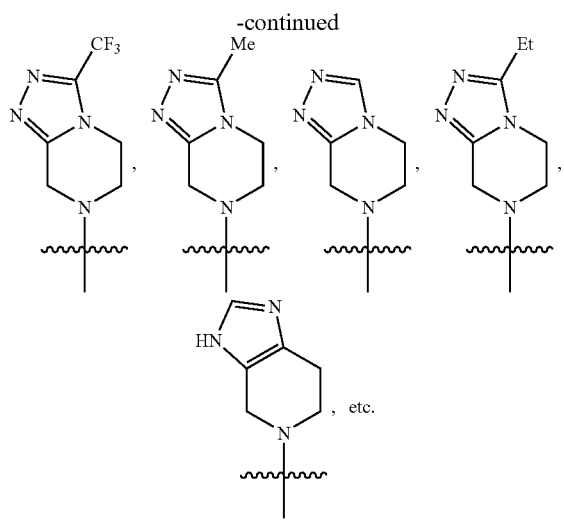

"Heterocyclylalkyl" refers to an acyclic alkyl radical in which one of the hydrogen atoms bonded to a carbon atom, typically a terminal or sp$^3$ carbon atom, is replaced with a heterocyclyl radical (i.e., a heterocyclyl-alkylene-moiety). Typical heterocyclyl alkyl groups include, but are not limited to heterocyclyl-CH$_2$—, heterocyclyl-CH(CH$_3$)—, heterocyclyl-CH$_2$CH$_2$—, 2-(heterocyclyl)ethane-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclylalkyl group comprises 2 to 20 carbon atoms, e.g., the alkyl portion of the heterocyclylalkyl group is 1 to 6 carbon atoms and the heterocyclyl moiety is 1 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or Sp$^3$ carbon atom, but also a sp$^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclylalkenyl group comprises 3 to 20 carbon atoms, e.g., the alkenyl portion of the heterocyclyl alkenyl group is 2 to 6 carbon atoms and the heterocyclyl moiety is 1 to 14 carbon atoms.

"Heterocyclylalkynyl" refers to an acyclic alkynyl radical in which one of the hydrogen atoms bonded to a carbon atom, typically a terminal or Sp$^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclylalkenyl group comprises 3 to 20 carbon atoms, e.g., the alkynyl portion of the heterocyclylalkenyl group is 2 to 6 carbon atoms and the heterocyclyl moiety is 1 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH (CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, etc.

The term "optionally substituted" in reference to a particular moiety of the compound of Formula IV (e.g., an optionally substituted aryl group) refers to a moiety having 0, 1, 2, or more substituents.

"Ac" means acetyl (—C(O)CH$_3$).
"Ac$_2$O" means acetic anhydride.
"CDI" means cyclohexyl carbodiimide.
"DCM" means dichloromethane (CH$_2$Cl$_2$).
"DIBAL" means diisobutylaluminum hydride.
"DIPEA" means diisopropylethylamine.
"DMAP" means dimethylaminopyridine.
"EDC" means 1-(3-Dimethylaminopropyl)-3-ethylcarbodiimide.
"Et" means ethyl.
"EtOAc" means ethylacetate.
"HOBt" means N-hydroxybenzotriazole.
"Me" means methyl (—CH$_3$).
"MeOH" means methanol.
"MeCN" means acetonitrile.
"Pr" means propyl.
"i-Pr" means isopropyl (—CH(CH$_3$)$_2$).
"i-PrOH" means isopropanol.
"rt" means room temperature.
"TFA" means trifluoroacetic acid.
"THF" means tetrahydrofuran.
"TMSI" means iodotrimethylsilane.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enanfromeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether-nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

Compounds of Formula I

In one embodiment, the present application provides compounds according to Formula I, as described herein.

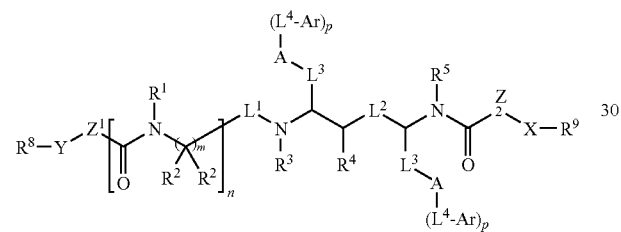

In another embodiment of the compounds of Formula I, n is 1.

In another embodiment of the compounds of Formula I, n is 0.

In another embodiment of the compounds of Formula I, n is 1 and $L^2$ is —CH($R^6$)—, wherein $R^6$ is selected from the group consisting of H, alkyl, substituted alkyl, and heteroalkyl.

In another embodiment of the compounds of Formula I, n is 1 and $L^2$ is —$CH_2$—.

In another embodiment of the compounds of Formula I, n is 1 and $L^2$ is —C(O)—.

In another embodiment of the compounds of Formula I, n is 1 and Y is heterocyclylalkyl.

In another embodiment of the compounds of Formula I, n is 1 and Y—$R^8$ is —$CH_2$-(substituted heteroaryl).

In another embodiment of the compounds of Formula I, n is 1 and Y—$R^8$ is

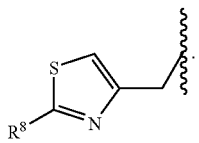

In another embodiment of the compounds of Formula I, n is 1 and Y—$R^8$ is

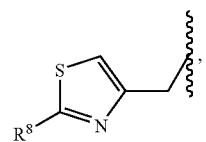

wherein $R^8$ is alkyl for example 2-propyl.

In another embodiment of the compounds of Formula I, n is 1 and X is heterocyclylalkyl.

In another embodiment of the compounds of Formula I, n is 1 and X is —$CH_2$-heteroaryl.

In another embodiment of the compounds of Formula I, n is 1 and X—$R^9$ is

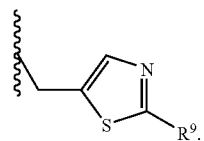

In another embodiment of the compounds of Formula I, n is 1 and X—$R^9$ is

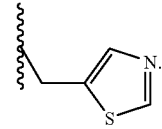

In another embodiment of the compounds of Formula I, n is 1 and $Z^1$ is —N($R^7$)—.

In another embodiment of the compounds of Formula I, n is 1 and $Z^1$ is —N(alkyl)- or —N(carbocyclyl)-.

In another embodiment of the compounds of Formula I, n is 1 and $Z^1$ is —N($CH_3$)— or —N(cyclopropyl)-.

In another embodiment of the compounds of Formula I, n is 1 and $Z^1$ is —NH—.

In another embodiment of the compounds of Formula I, n is 1 and each A is independently aryl or substituted aryl.

In another embodiment of the compounds of Formula I, n is 1 and each A is phenyl.

In another embodiment of the compounds of Formula I, n is 1 and each A is phenyl and each p is 0.

In another embodiment of the compounds of Formula I, n is 1 and $R^2$ is H, alkyl, substituted alkyl, or heteroalkyl.

In another embodiment of the compounds of Formula I, n is 1 and $R^2$ is 2-propyl, methyl, —$CH_2$—O-benzyl, —CH($CH_3$)(O-t-Bu), or —CH($CH_3$)(OH).

In another embodiment of the compounds of Formula I, $L^1$ is —C(O)—;

each A is independently aryl, substituted aryl, alkyl, or substituted alkyl;
$R^1$ is H or alkyl;
each $R^2$ is independently H, alkyl, substituted alkyl, or heteroalkyl;
$R^3$, $R^4$, $R^5$, and $R^6$ are each H;
each $R^7$ is independently H, alkyl, or carbocyclyl;
$R^8$ is H or alkyl;
$R^9$ is H;
X and Y are both heterocyclylalkyl;
$Z^2$ is —O—; and
p is 0.

In another embodiment of the compounds of Formula I, each A is phenyl;
R¹ is H or —CH₃;
each R² is H, methyl, ethyl, 2-propyl, —CH₂—O-benzyl, —CH(CH₃)—OH, or —CH(CH₃)(O-t-Bu);
each R⁷ is H, methyl or cyclopropyl;
R⁸ is H or 2-propyl;
X is

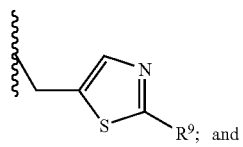

Y is

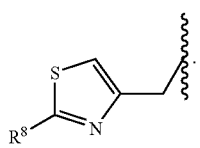

In another embodiment, the compounds of Formula I have the following general Formula IA:

In another embodiment of the compounds of Formula IA, L² is —C(R⁶)₂—, wherein one R⁶ is H and the other R⁶ is alkyl, wherein said alkyl includes any alkyl disclosed herein.

In another embodiment of the compounds of Formula IA, m is 1 and R² is H.

In another embodiment of the compounds of Formula IA, m is 1 and R² is alkyl, wherein said alkyl includes any alkyl disclosed herein.

In another embodiment of the compounds of Formula IA, m is 1 and R² is i-propyl.

In another embodiment of the compounds of Formula IA, m is 1 and R² is i-butyl.

In another embodiment of the compounds of Formula IA, m is 1 and R² is ethyl.

In another embodiment of the compounds of Formula IA, m is 1 and R² is methyl.

In another embodiment of the compounds of Formula IA, m is 2 and each R² is independently selected from H and alkyl.

In another embodiment of the compounds of Formula IA, m is 2 and each R² is H.

In another embodiment, the compounds of Formula I have the following general Formula IB:

Formula IA

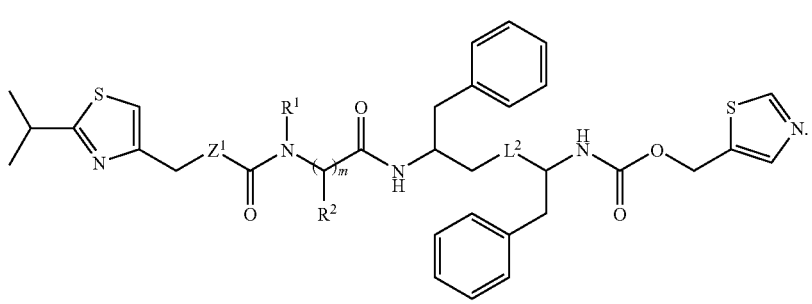

In another embodiment of the compounds of Formula IA, Z¹ is —N(R⁷)—. In a particular embodiment, R⁷ is H. In another particular embodiment, R⁷ is alkyl, for example any of the alkyl groups disclosed herein. In another particular embodiment, R⁷ is heteroalkyl, for example any of the heteroalkyl groups disclosed herein. In another particular embodiment, R⁷ is substituted or unsubstituted carbocyclyl, wherein for example, said carbocyclyl is any of the carbocyclyl groups disclosed herein. In another particular embodiment, R⁷ is substituted or unsubstituted heterocyclyl, wherein for example, said heterocyclyl is any of the heterocyclyl groups disclosed herein.

In another embodiment of the compounds of Formula IA, Z¹ is —O—.

In another embodiment of the compounds of Formula IA, L² is —C(R⁶)₂—, wherein each R⁶ is H.

In another embodiment of the compounds of Formula IA, L² is —C(R⁶)₂—, wherein each R⁶ is independently H or alkyl, and said alkyl includes any alkyl disclosed herein.

Formula IB

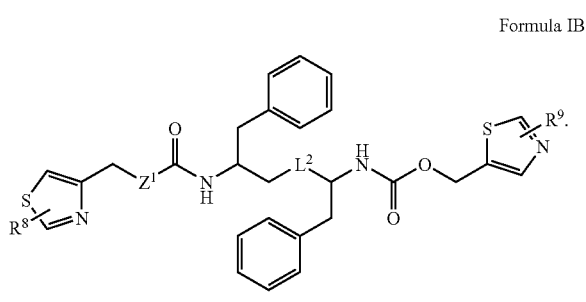

In another embodiment of the compounds of Formula IB, Z¹ is —N(R⁷)—. In a particular embodiment, R⁷ is H. In another particular embodiment, R⁷ is alkyl, for example any of the alkyl groups disclosed herein. In another particular embodiment, R⁷ is heteroalkyl, for example any of the heteroalkyl groups disclosed herein. In another particular embodiment, R⁷ is substituted or unsubstituted carbocyclyl, wherein for example, said carbocyclyl is any of the carbocyclyl groups disclosed herein. In another particular embodiment, $R^7$ is substituted or unsubstituted heterocyclyl, wherein for example, said heterocyclyl is any of the heterocyclyl groups disclosed herein.

In another embodiment of the compounds of Formula IB, $Z^1$ is —O—.

In another embodiment of the compounds of Formula IB, $L^2$ is —C($R^6$)$_2$—, wherein each $R^6$ is H.

In another embodiment of the compounds of Formula IB, $L^2$ is —C($R^6$)$_2$—, wherein each $R^6$ is independently H or alkyl, and said alkyl includes any alkyl disclosed herein.

In another embodiment of the compounds of Formula IB, $L^2$ is —C($R^6$)$_2$—, wherein one $R^6$ is H and the other $R^6$ is alkyl, wherein said alkyl includes any alkyl disclosed herein.

In another embodiment of the compounds of Formula IB, $R^8$ and $R^9$ are both H.

In another embodiment of the compounds of Formula IB, $R^8$ and $R^9$ are independently selected from H and alkyl, wherein said alkyl includes any alkyl disclosed herein.

In another embodiment, the compounds of Formula I have one of the following structures:

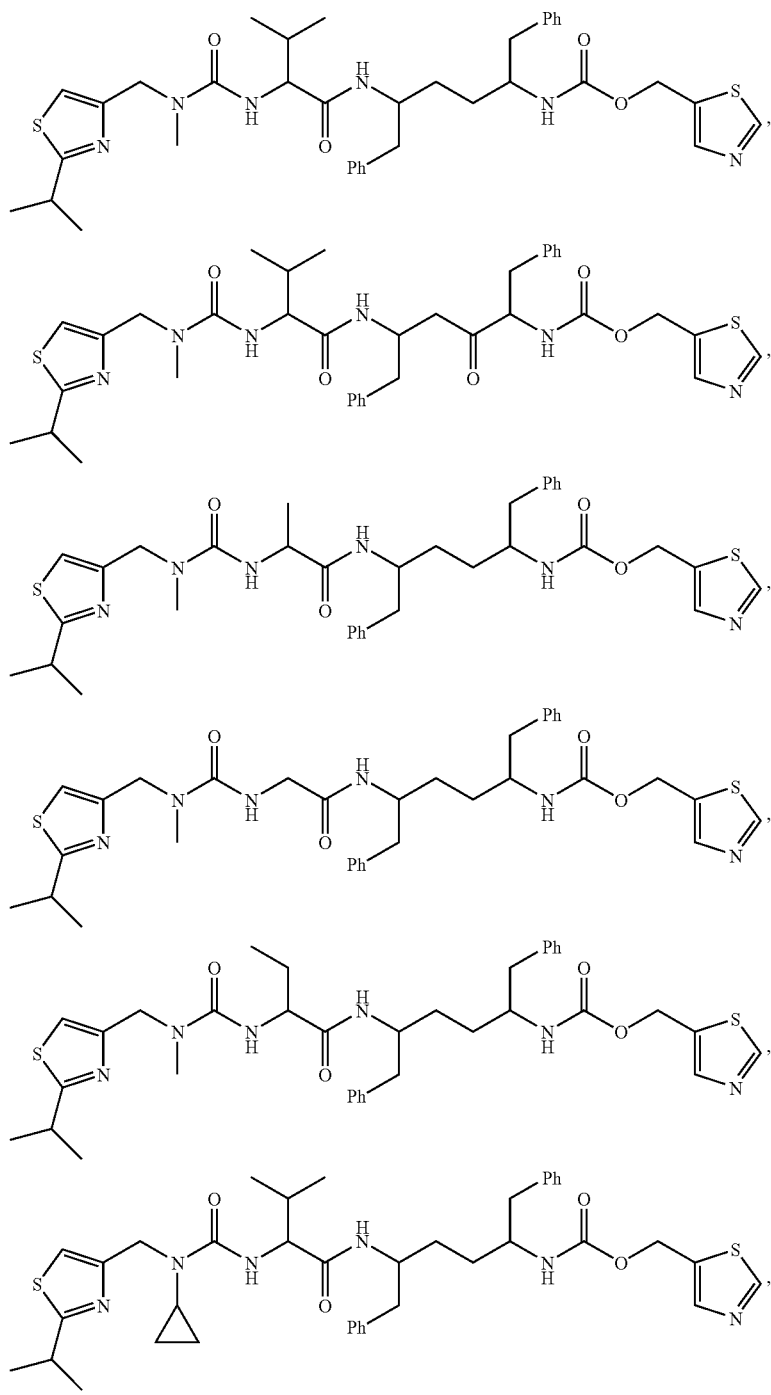

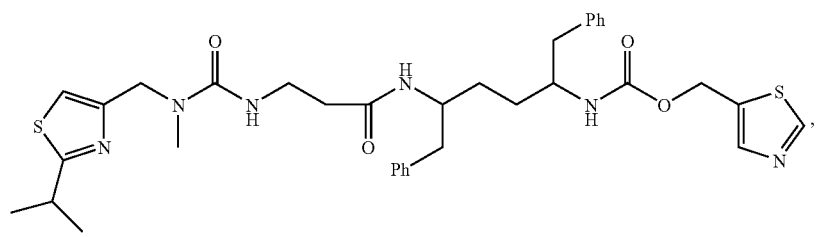
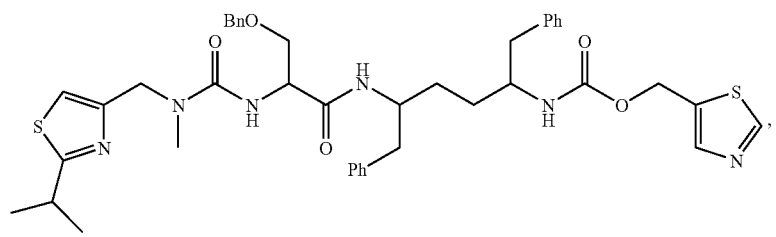
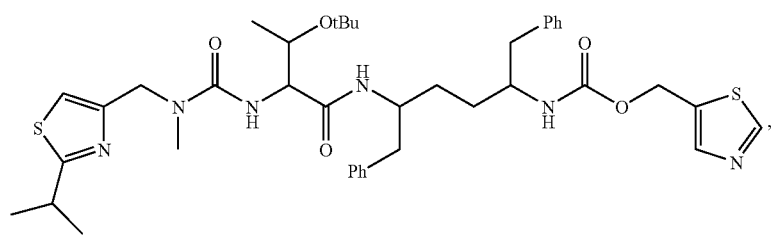
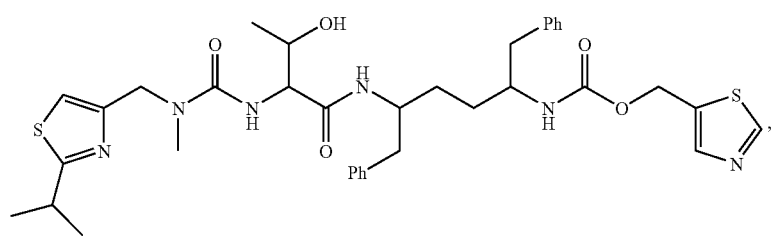
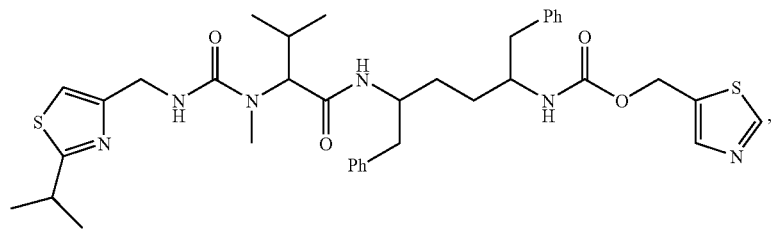
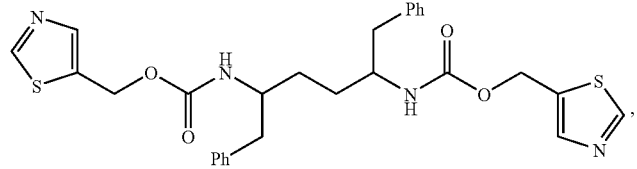
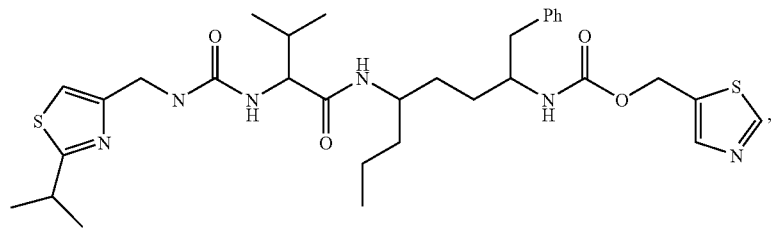

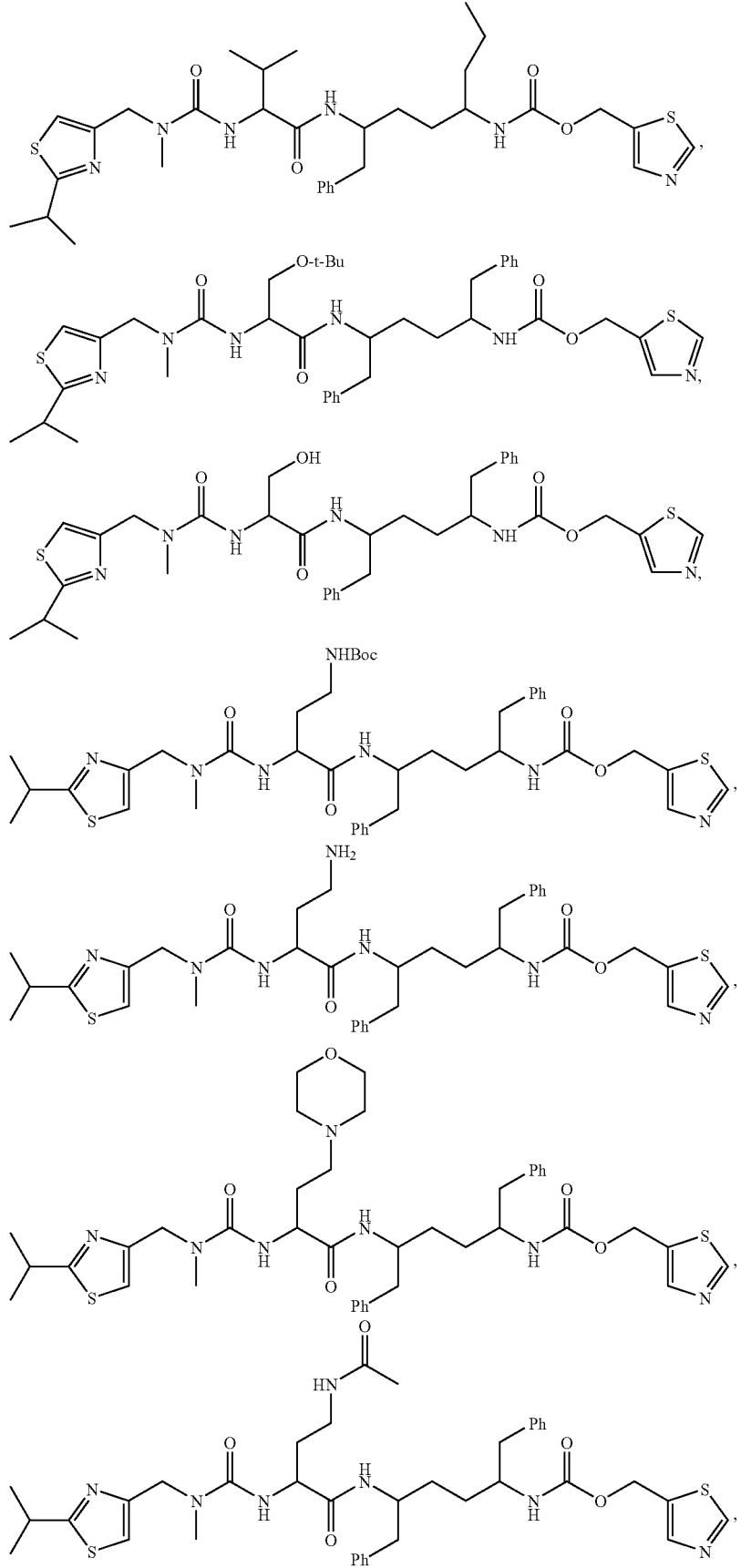

-continued
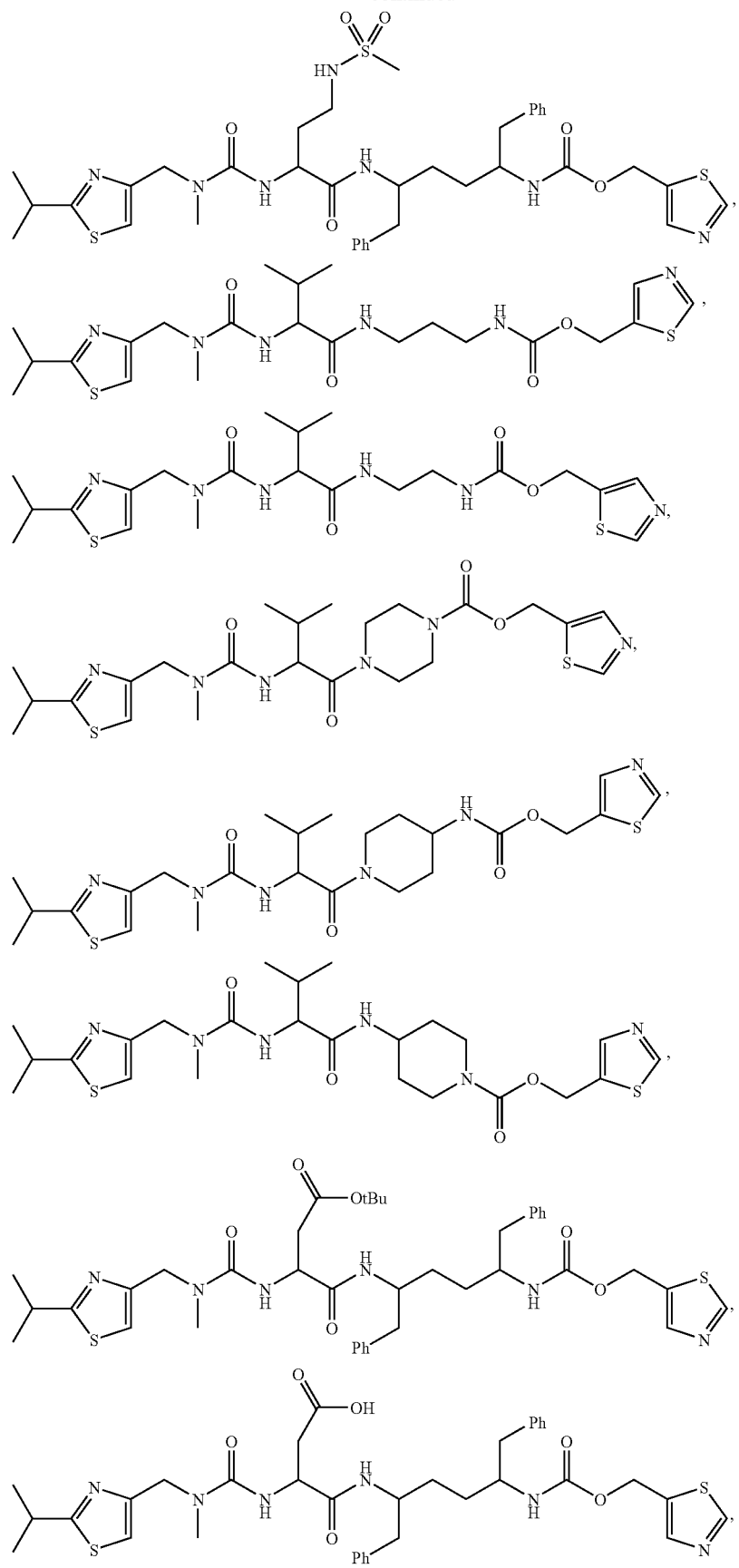

-continued
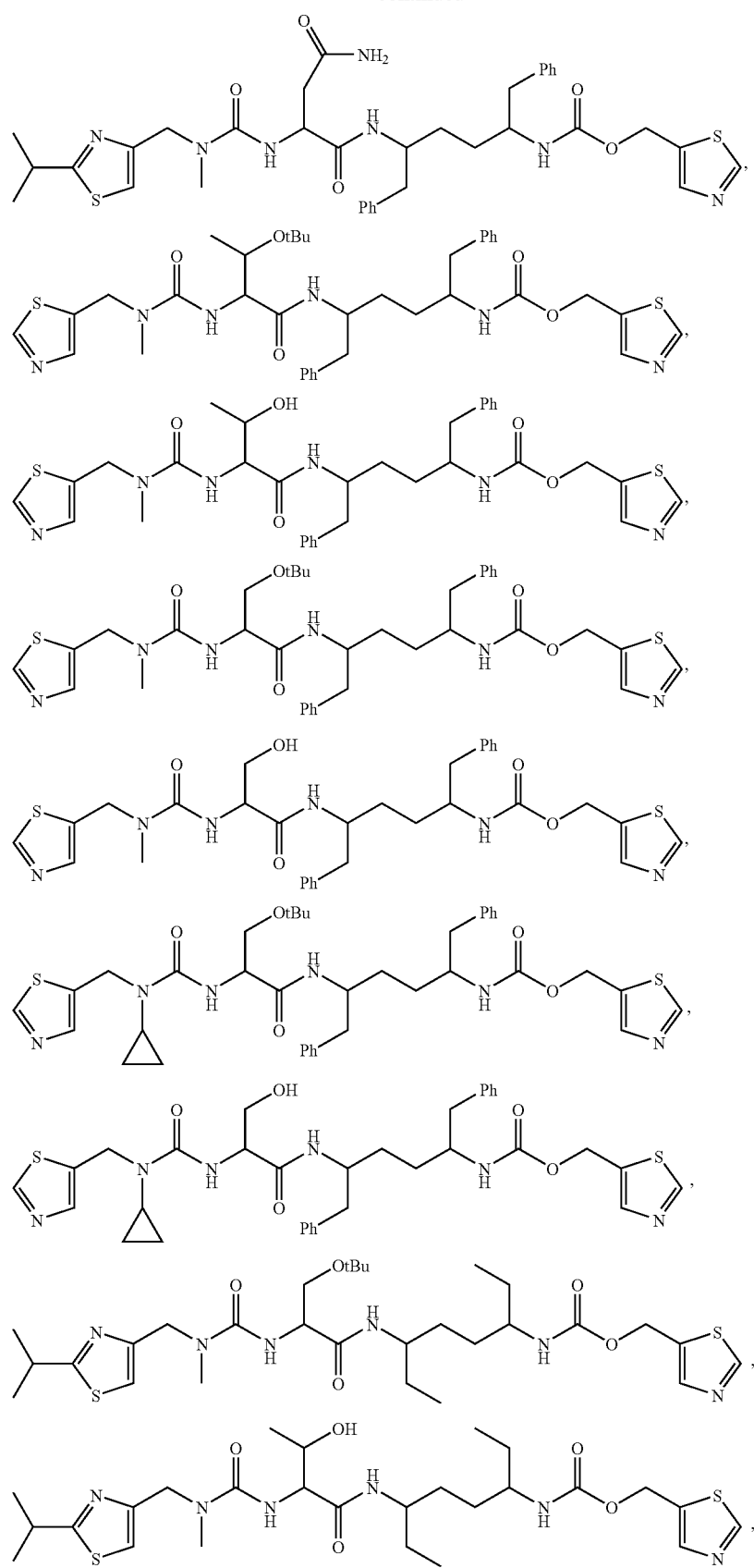

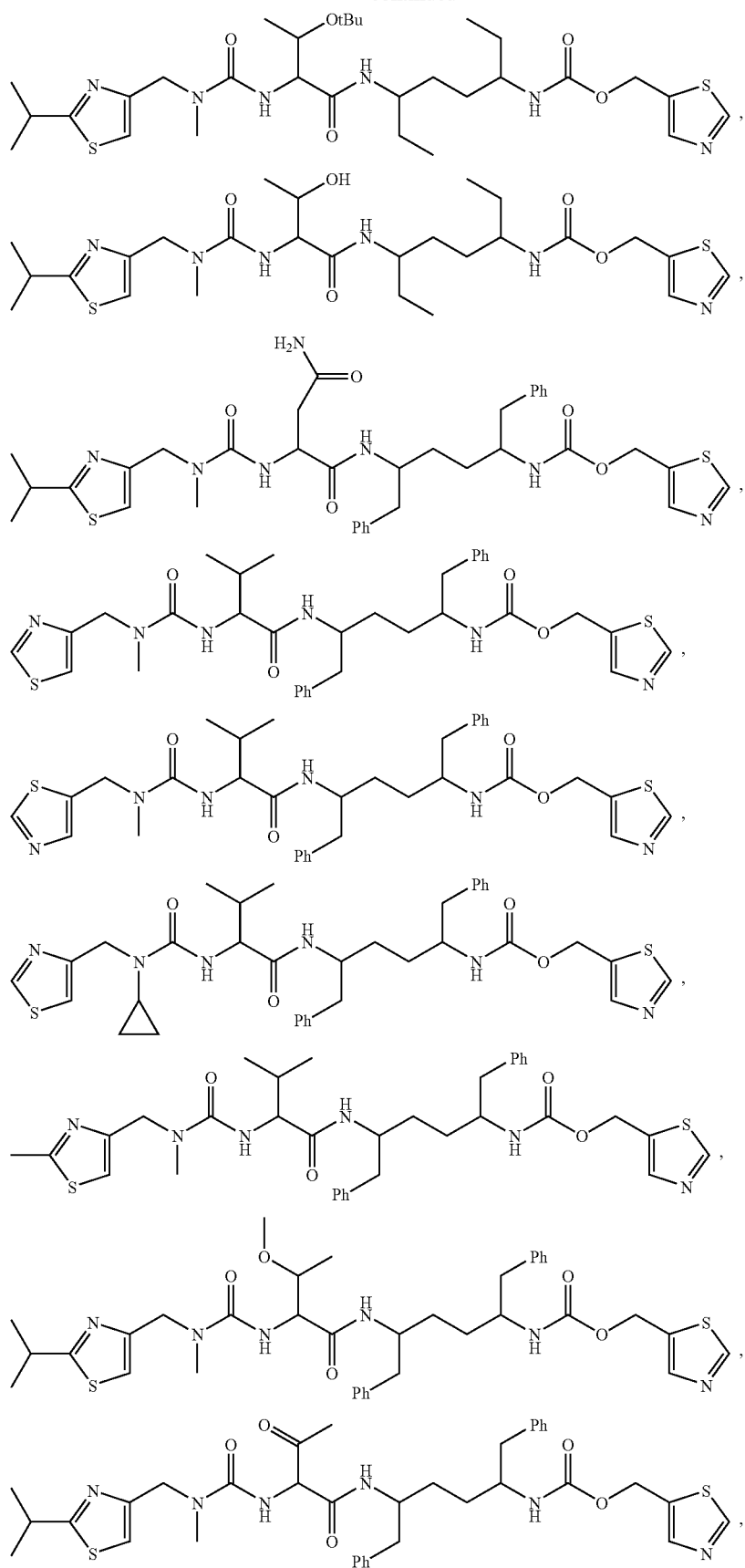

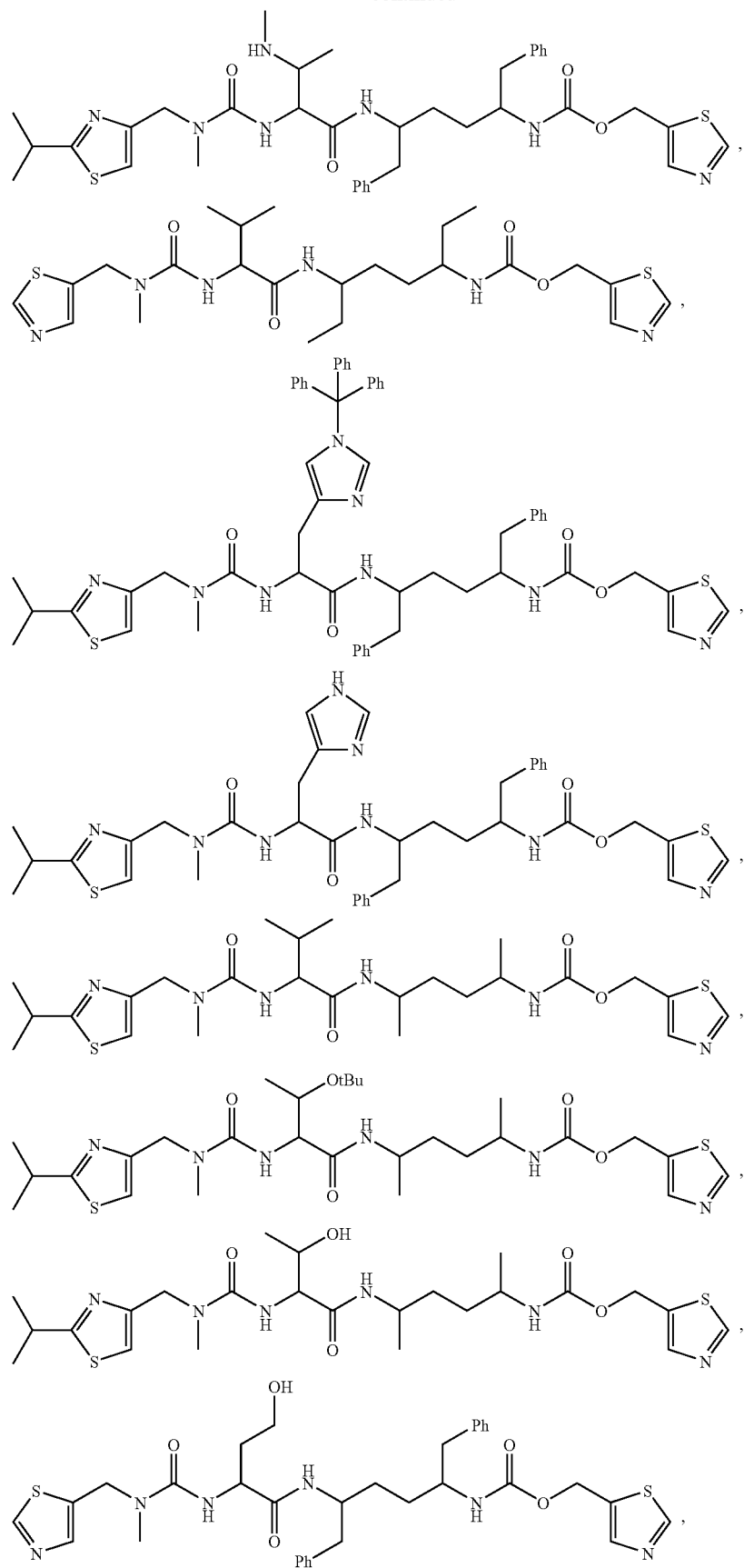

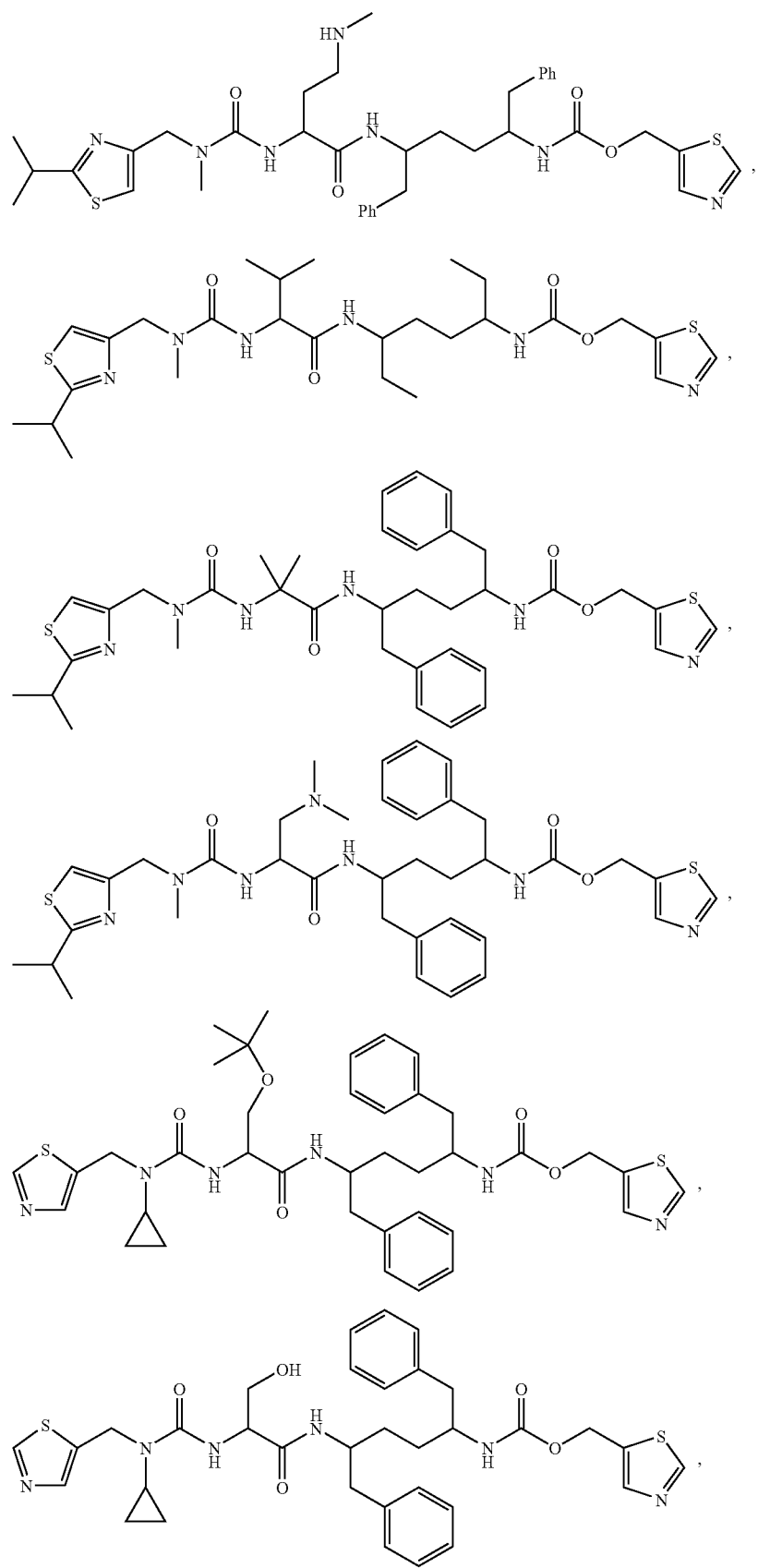

-continued
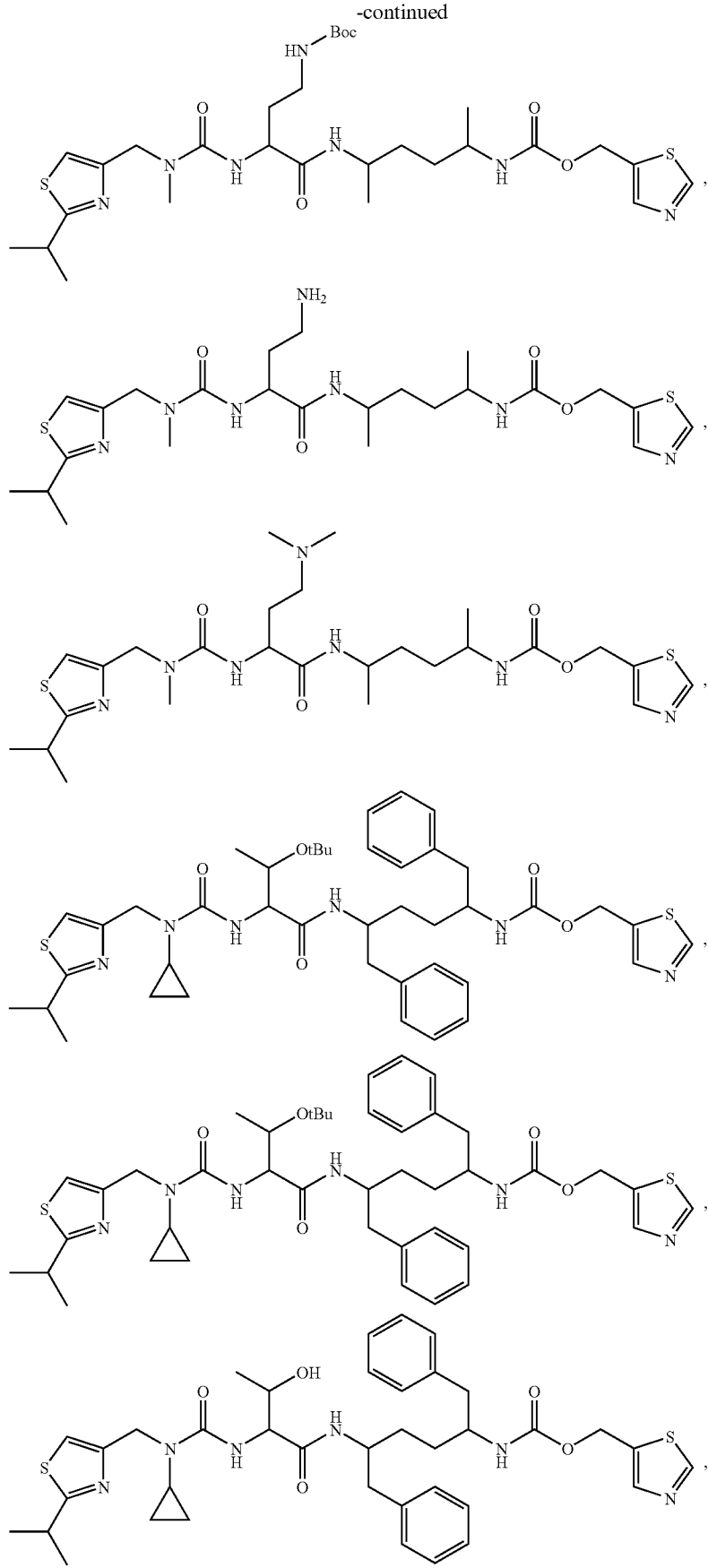

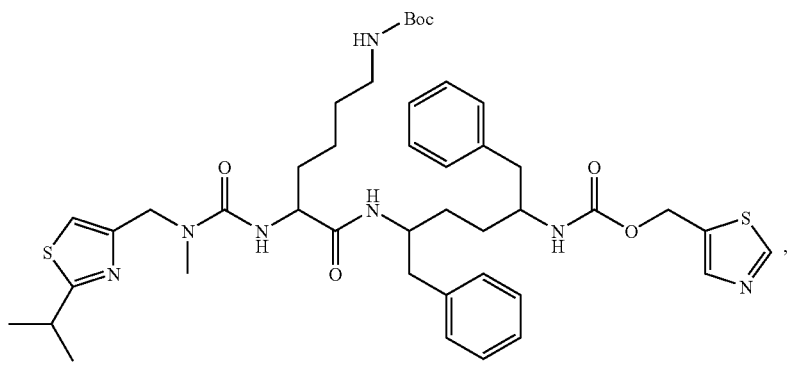
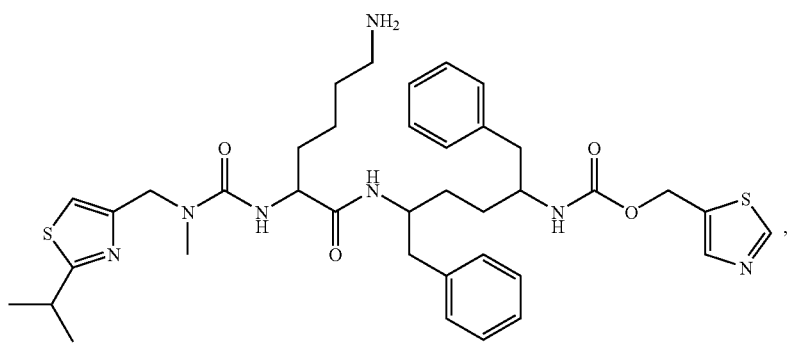
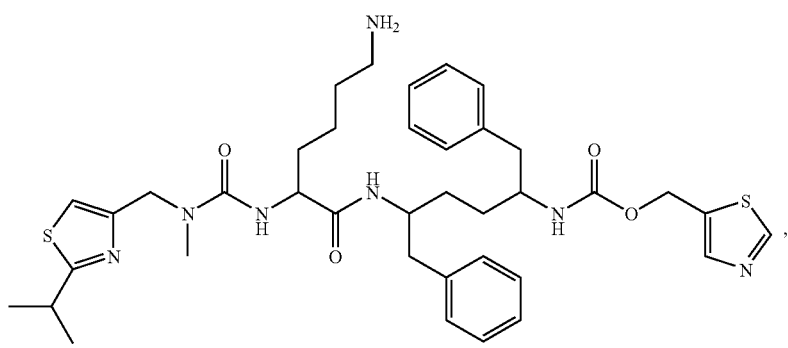
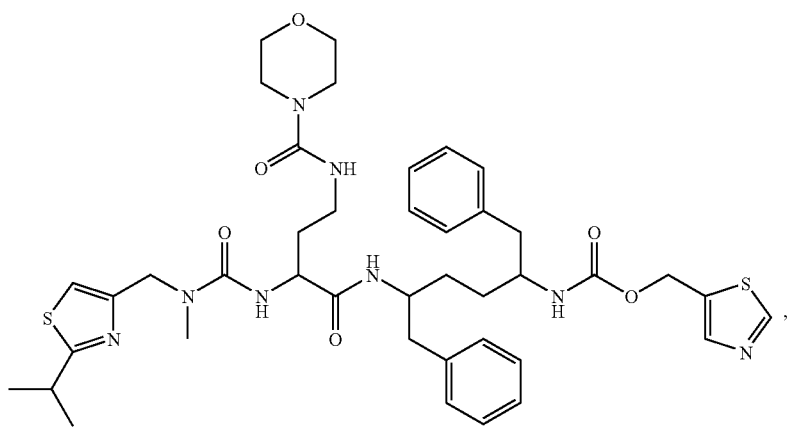

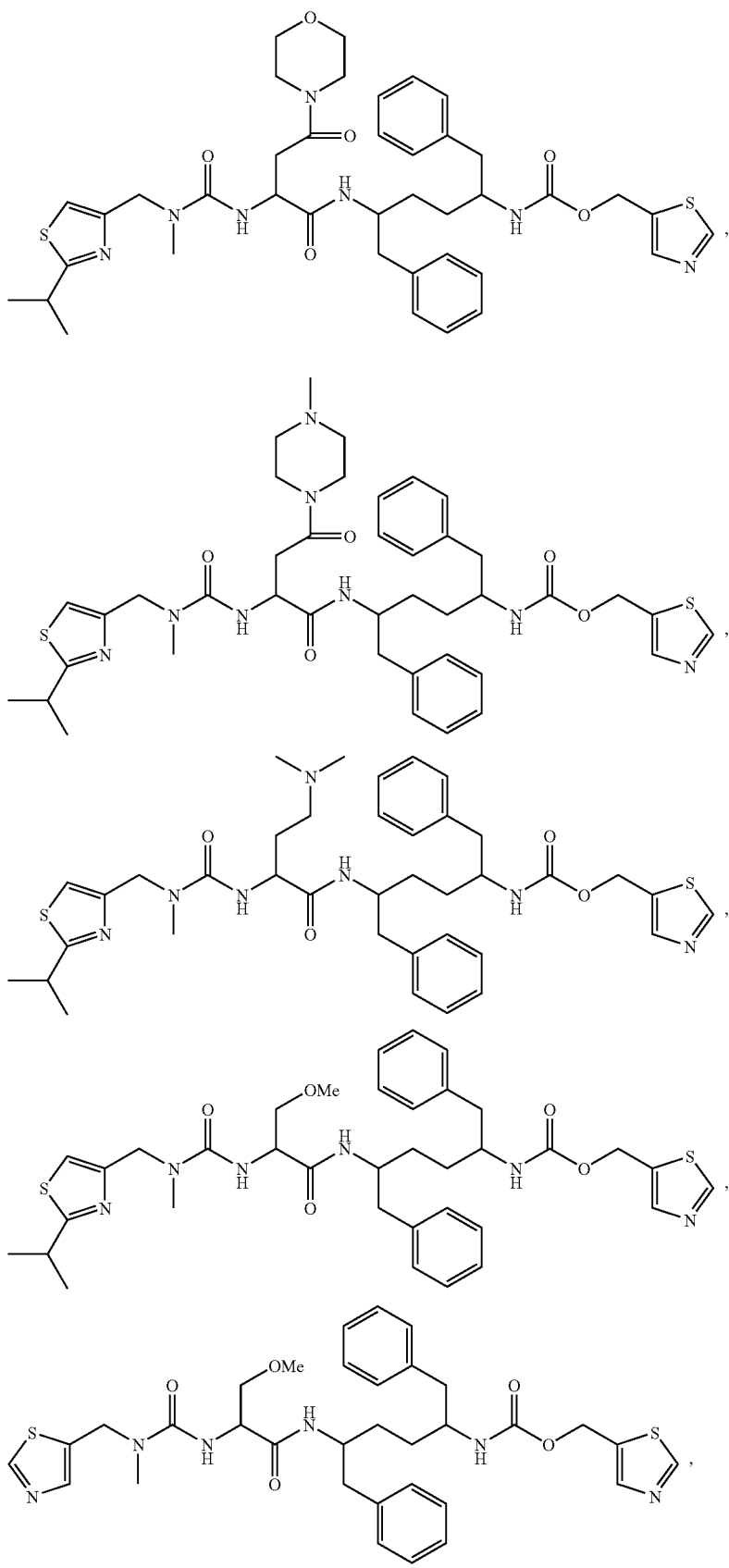

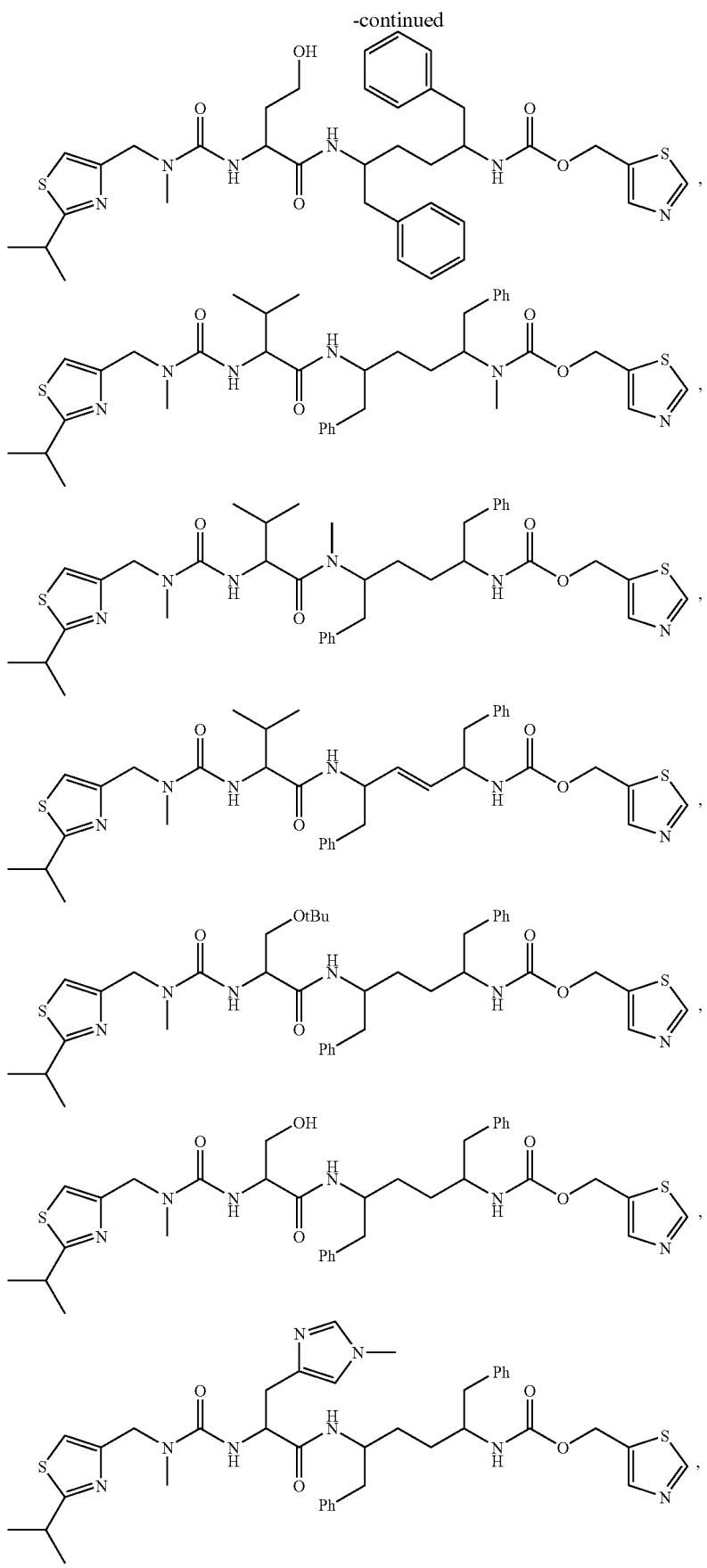

-continued
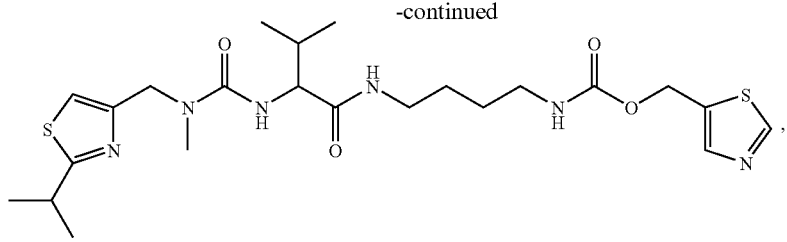
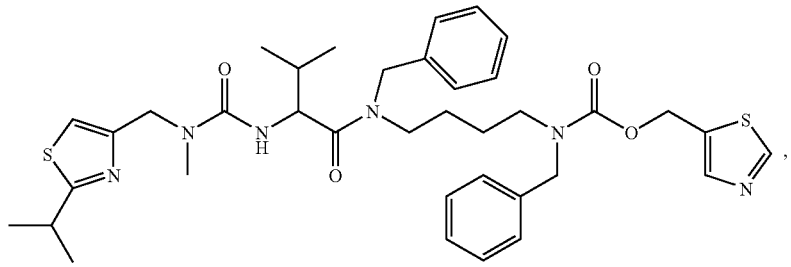
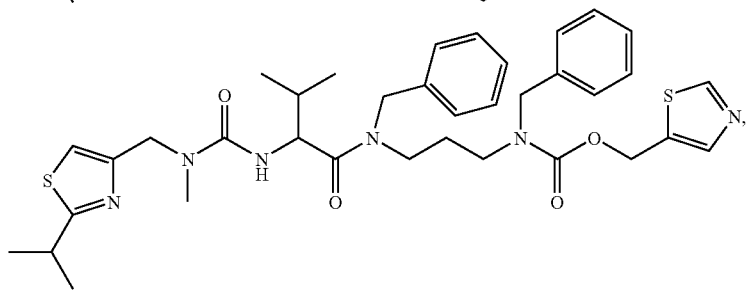
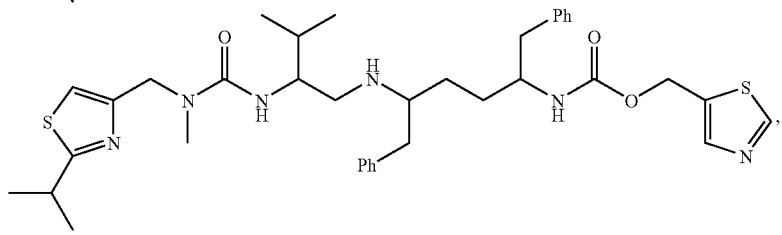
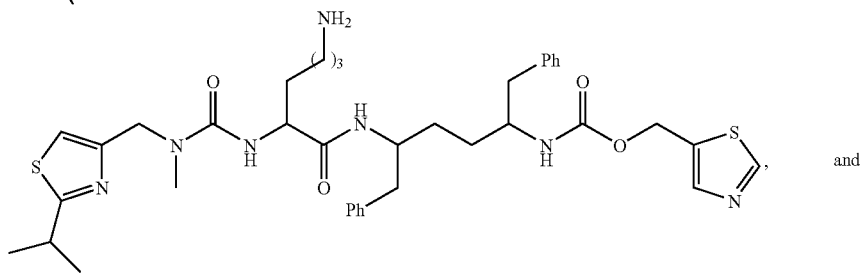 and
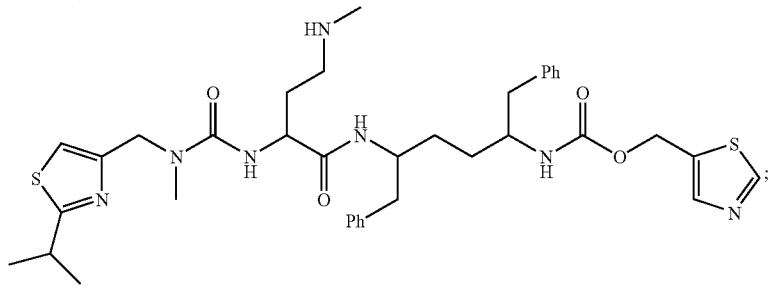
including stereoisomers or mixtures of stereoisomers thereof. One skilled in the art will recognize that stereoisomers or mixtures of stereoisomers of the compounds of the present application include enantiomers, diastereomers, and other stereoisomers. For example, for:

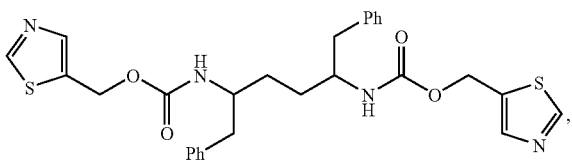

contemplated stereoisomers include at least:

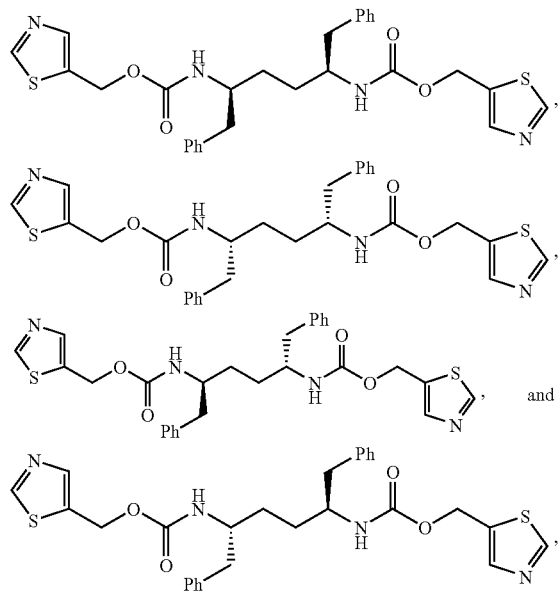

as well as mixtures of two or more of these stereoisomers.

In still another embodiment of the compounds of Formula I, $L^1$ is —$C(R^6)_2$—, —$C(O)$—, —$S(O_2)$—, —$N(R^7)$—C(O)—, or —O—$C(O)$—. When $L^1$ is —$C(R^6)_2$—, each $R^6$ is independently selected from the group consisting of H, alkyl, substituted alkyl, and heteroalkyl, wherein alkyl, substituted alkyl, and heteroalkyl are as defined and exemplified herein. Non-limiting examples of —$C(R^6)_2$— include —$CH_2$—, —CH(alkyl)-, —CH(substituted alkyl)-, —CH(heteroalkyl)-, —C(alkyl)$_2$-, —C(substituted alkyl)$_2$-, —C(heteroalkyl)$_2$-, —C(alkyl)(substituted alkyl)-, —C(heteroalkyl)(substituted alkyl)-, and —C(alkyl)(heteroalkyl)-, wherein alkyl, substituted alkyl, and heteroalkyl are as defined and exemplified herein. When $L^1$ is —$N(R^7)$—C(O)—, $R^7$ is H, alkyl, substituted alkyl, heteroalkyl, carbocyclyl, substituted carbocyclyl, heterocyclyl, or substituted heterocyclyl, wherein alkyl, substituted alkyl, heteroalkyl, carbocyclyl, substituted carbocyclyl, heterocyclyl, or substituted heterocyclyl are as defined and exemplified herein.

In still another embodiment of the compounds of Formula I, $L^2$ is —$C(R^6)_2$— or —$C(O)$—. When $L^2$ is —$C(R^6)_2$—, each $R^6$ is independently selected from H, alkyl, substituted alkyl or heteroalkyl, where each alkyl, substituted alkyl, or heteroalkyl can include any of the alkyl, substituted alkyl, or heteroalkyl groups defined or disclosed herein. Non-limiting examples of —$C(R^6)_2$— include —$CH_2$—, —$CH(CH_3)$—, —$CH(-CH_2CH_3)$—, —$CH(-CH_2CH_2CH_3)$—, —$CH(-CH(CH_3)_2)$—, —$CH(-CH_2CH_2CH_3)$—, —$CH(-CH_2CH(CH_3)_2)$—, —$CH(-CH(CH_3)CH_2CH_3)$—, —$CH(-C(CH_3)_3)$—, —$C(CH_3)_2$—, —CH(OCH$_3$)—, —CH(CH$_2$OH)—, —CH(CH$_2$CH$_2$OH)—, etc.

In still another embodiment of the compounds of Formula I, each $L^3$ is independently a covalent bond, an alkylene or substituted alkylene. When any $L^3$ is an alkylene, non-limiting examples of alkylene includes any of the alkylenes defined or disclosed herein. When any $L^3$ is a substituted alkylene, non-limiting examples of substituted alkylene includes any of the substituted alkylenes defined or disclosed herein. For example, substituted alkylenes include alkylenes substituted with one or more —OH group, alkylenes substituted with one or more ether group, e.g., a —O-Bn group, alkylenes substituted with one or more halogen, or alkylenes substituted with combinations of two or more substituents (e.g., —OH and halogen, halogen and ether, etc.).

In still another embodiment of the compounds of Formula I, each $L^3$ is the same, i.e., each $L^3$ is the same alkylene or substituted alkylene group.

In still another embodiment of the compounds of Formula I, each $L^3$ is different, i.e., one $L^3$ is an alkylene and the other $L^3$ is a substituted alkylene, one $L^3$ is an alkylene and the other $L^3$ is a different alkylene, or one $L^3$ is a substituted alkylene, and the other $L^3$ is a different substituted alkylene.

In still another embodiment of the compounds of Formula I, each $L^4$ is independently selected from the group consisting of a covalent bond, alkylene, substituted alkylene, —O—, —$CH_2$—O—, and —NH—. When $L^4$ is alkylene, said alkylene includes any alkylene defined or exemplified herein. When $L^4$ is substituted alkylene, said substituent includes any alkylene defined or exemplified herein, substituted by one or more substituents as defined herein.

In still another embodiment of the compounds of Formula I, both $L^4$ groups are the same, i.e. both $L^4$ groups are a covalent bond, both are —O—, both are —$CH_2$—O—, (wherein the $CH_2$ group is attached to either the "A" moiety or the "Ar" moiety of Formula I), both are a substituted or unsubstituted alkylene, or both are —NH—.

In still another embodiment of the compounds of Formula I, each $L^4$ is different. For example, one $L^4$ is a covalent bond and the other $L^4$ is —O—, one $L^4$ is a covalent bond and the other $L^4$ is —$CH_2$—O— (wherein the $CH_2$ group is attached to either the "A" moiety or the "Ar" moiety of Formula I), one $L^4$ is a covalent bond and the other $L^4$ is —NH—, one $L^4$ is a —O— and the other $L^4$ is —$CH_2$—O— (wherein the $CH_2$ group is attached to either the "A" moiety or the "Ar" moiety of Formula I), one $L^4$ is —O— and the other $L^4$ is —NH—, one $L^4$ is —$CH_2$—O— (wherein the $CH_2$ group is attached to either the "A" moiety or the "Ar" moiety of Formula I) and the other $L^4$ is —NH—, one $L^4$ is a covalent bond and the other $L^4$ is a substituted or unsubstituted alkylene, one $L^4$ is a substituted alkylene and the other $L^4$ is a unsubstituted alkylene, one $L^4$ is a substituted or unsubstituted alkene and the other $L^4$ is —O—, one $L^4$ is a substituted or unsubstituted alkylene and the other $L^4$ is —$CH_2$—O— (wherein the $CH_2$ group is attached to either the "A" moiety or the "Ar" moiety of Formula I), or one $L^4$ is substituted or unsubstituted alkylene and the other $L^4$ is —NH—.

In still another embodiment of the compounds of Formula I, each A is independently H, alkyl, substituted alkyl, aryl, substituted aryl, heterocyclyl, or substituted heterocyclyl, with the proviso that when A is H, p is 0. When any A is alkyl, said alkyl includes any alkyl defined or exemplified herein. When any A is substituted alkyl, said alkyl includes any alkyl defined or exemplified herein substituted with one or more of any substituent defined or exemplified herein. When any A is aryl, said aryl includes any aryl defined or exemplified herein. When any A is substituted aryl, said aryl includes any aryl defined or exemplified herein substituted with one or more of any substituent defined or exemplified herein. When any A is heterocyclyl, said heterocyclyl includes any heterocyclyl defined or exemplified herein. When any A is substituted heterocyclyl, said heterocyclyl is any heterocyclyl defined or exemplified herein substituted with one or more of any substituent defined or exemplified herein.

In still another embodiment of the compounds of Formula I, each A is H and each p is 0.

In still another embodiment of the compounds of Formula I, each A is substituted or unsubstituted alkyl, wherein alkyl is any alkyl defined or exemplified herein, and, when present, the substituents on said alkyl include one or more of any substituents defined or exemplified herein.

In still another embodiment of the compounds of Formula I, each A is substituted or unsubstituted aryl, wherein aryl is any aryl defined or exemplified herein, and, when present, the substituents on said aryl include one or more of any substituents defined or exemplified herein. In a particular embodiment, A is phenyl.

In still another embodiment of the compounds of Formula I, each A is substituted or unsubstituted heterocyclyl, wherein heterocyclyl is any heterocyclyl defined or exemplified herein, and, when present, the substituents on said heterocyclyl include one or more of any substituents defined or exemplified herein.

In still another embodiment of the compounds of Formula I, one A is H and the other A is substituted or unsubstituted alkyl, wherein alkyl is any alkyl defined or exemplified herein, and, when present, the substituent on said alkyl includes one or more of any substituent defined or exemplified herein.

In still another embodiment of the compounds of Formula I, one A is H and the other A is substituted or unsubstituted aryl, wherein aryl is any aryl defined or exemplified herein, and the substituents on said aryl are any substituents defined and exemplified herein. In a particular embodiment, one A is phenyl.

In still another embodiment of the compounds of Formula I, one A is H and the other A is substituted or unsubstituted heterocyclyl, wherein heterocyclyl is any heterocyclyl defined or exemplified herein, and, when present, the substituents on said heterocyclyl include one or more of any substituent defined or exemplified herein.

In still another embodiment of the compounds of Formula I, one A is substituted or unsubstituted alkyl, and the other A is substituted or unsubstituted aryl, wherein alkyl and aryl are any alkyl or aryl defined or exemplified herein, and, when present, the substituents on said alkyl or aryl include one or more of any substituents defined or exemplified herein.

In still another embodiment of the compounds of Formula I, one A is substituted or unsubstituted alkyl, and the other A is substituted or unsubstituted heterocyclyl, wherein alkyl and heterocyclyl are any alkyl or heterocyclyl defined or exemplified herein, and, when present, the substituents on said alkyl or heterocyclyl include one or more of any substituents defined or exemplified herein.

In still another embodiment of the compounds of Formula I, one A is substituted or unsubstituted aryl, and the other A is substituted or unsubstituted heterocyclyl, wherein aryl and heterocyclyl are any aryl or heterocyclyl defined or exemplified herein, and, when present, the substituents on said aryl or heterocyclyl include one or more of any substituents defined or exemplified herein.

In still another embodiment of the compounds of Formula I, $Z^1$ is —O— or —N($R^7$)—. When $Z^1$ is —N($R^7$)—, $R^7$ is H, alkyl, substituted alkyl, heteroalkyl, carbocyclyl, substituted carbocyclyl, heterocyclyl, or substituted heterocyclyl, wherein alkyl, substituted alkyl, heteroalkyl, carbocyclyl, substituted carbocyclyl, heterocyclyl, or substituted heterocyclyl are any alkyl, substituted alkyl, heteroalkyl, carbocyclyl, substituted carbocyclyl, heterocyclyl, or substituted heterocyclyl defined or exemplified herein.

In still another embodiment of the compounds of Formula I, $Z^2$ is —O— or —N($R^7$)—. When $Z^2$ is —N($R^7$)—, $R^7$ is H, alkyl, substituted alkyl, heteroalkyl, carbocyclyl, substituted carbocyclyl, heterocyclyl, or substituted heterocyclyl, wherein alkyl, substituted alkyl, heteroalkyl, carbocyclyl, substituted carbocyclyl, heterocyclyl, or substituted heterocyclyl are any alkyl, substituted alkyl, heteroalkyl, carbocyclyl, substituted carbocyclyl, heterocyclyl, or substituted heterocyclyl defined or exemplified herein.

In still another embodiment of the compounds of Formula I, $Z^1$ and $Z^2$ are the same, e.g., $Z^1$ and $Z^2$ are both —O—, or $Z^1$ and $Z^2$ are both —N($R^7$)—, where $R^7$ is H, alkyl, substituted alkyl, heteroalkyl, carbocyclyl, substituted carbocyclyl, heterocyclyl, or substituted heterocyclyl, wherein alkyl, substituted alkyl, heteroalkyl, carbocyclyl, substituted carbocyclyl, heterocyclyl, or substituted heterocyclyl are any alkyl, substituted alkyl, heteroalkyl, carbocyclyl, substituted carbocyclyl, heterocyclyl, or substituted heterocyclyl defined or exemplified herein.

In still another embodiment of the compounds of Formula I, $Z^1$ and $Z^2$ are different, e.g. $Z^1$ is —O— and $Z^2$ is —N($R^7$)—, $Z^1$ is —N($R^7$)— and $Z^2$ is —O—, or $Z^1$ and $Z^2$ are both —N($R^7$)— but in $Z^1$ the $R^7$ is different from the $R^7$ in $Z^2$. When either $Z^1$ of $Z^2$ is —N($R^7$)—, $R^7$ is H, alkyl, substituted alkyl, heteroalkyl, carbocyclyl, substituted carbocyclyl, heterocyclyl, or substituted heterocyclyl, wherein alkyl, substituted alkyl, heteroalkyl, carbocyclyl, substituted carbocyclyl, heterocyclyl, or substituted heterocyclyl are any alkyl, substituted alkyl, heteroalkyl, carbocyclyl, substituted carbocyclyl, heterocyclyl, or substituted heterocyclyl defined or exemplified herein.

In still another embodiment of the compounds of Formula I, Y is heterocyclyl or heterocyclylalkyl, wherein heterocyclyl and heterocyclylalkyl are any heterocyclyl or heterocyclylalkyl defined or exemplified herein. In a particular embodiment, Y is heterocyclylalkyl, e.g. thiazolylmethyl (—$CH_2$-thiazolyl).

In still another embodiment of the compounds of Formula I, X is heterocyclyl or heterocyclylalkyl, wherein heterocyclyl and heterocyclylalkyl are any heterocyclyl or heterocyclylalkyl defined or exemplified herein. In a particular embodiment, X is heterocyclylalkyl, e.g. thiazolylmethyl.

In still another embodiment of the compounds of Formula I, X and Y are different, e.g., X and Y are different heterocyclyls, X and Y are different heterocyclylalkyls, X is heterocyclyl and Y is heterocyclylalkyl, or X is heterocyclylalkyl and Y is heterocyclyl, wherein heterocyclyl and heterocyclylalkyl are any heterocyclyl or heterocyclylalkyl defined or exemplified herein.

In still another embodiment of the compounds of Formula I, X and Y are the same. In a particular embodiment both X and Y are heterocyclylalkyls, e.g. thiazolylmethyl.

In still another embodiment of the compounds of Formula I, each Ar is aryl, substituted aryl, heteroaryl, or substituted heteroaryl, wherein the aryl or heteroaryl are any aryl or heteroaryl defined or exemplified herein, and, when present, the substituents on the aryl or heteroaryl include one or more of any substituents defined or exemplified herein.

In still another embodiment of the compounds of Formula I, each Ar is the same, e.g., each Ar is an aryl such as phenyl.

In still another embodiment of the compounds of Formula I, each Ar is different, e.g. one Ar is a substituted or unsubstituted aryl and the other Ar is a substituted or unsubstituted heteroaryl, each Ar is a different substituted or unsubstituted aryl, or each Ar is a different substituted or unsubstituted heteroaryl, wherein aryl and heteroaryl are any aryl or heteroaryl defined or exemplified herein, and, when present, the substituents on the aryl or heteroaryl include one or more of any substituents defined or exemplified herein.

In still another embodiment of the compounds of Formula I, $R^1$, $R^3$, and $R^5$ are each independently H, alkyl, or substituted alkyl, wherein alkyl and substituted alkyl include any of the alkyl or substituted alkyls defined or disclosed herein.

In still another embodiment of the compounds of Formula I, $R^1$, $R^3$, and $R^5$ are each the same. In a particular embodiment $R^1$, $R^3$, and $R^5$ are each H. in another particular embodiment $R^1$, $R^3$, and $R^5$ are each alkyl, e.g. one of the alkyl groups defined or disclosed herein.

In still another embodiment of the compounds of Formula I, $R^1$, $R^3$, and $R^5$ are each different.

In still another embodiment of the compounds of Formula I, one of $R^1$, $R^3$, and $R^5$ is different from the other two groups.

In still another embodiment of the compounds of Formula I, n and m are both 1, and each $R^2$ is independently H, alkyl, substituted alkyl, arylheteroalkyl, arylalkyl, or heterocyclylalkyl, wherein alkyl, substituted alkyl, arylheteroalkyl, aryl alkyl, or heterocyclylalkyl is any alkyl, substituted alkyl, arylheteroalkyl, aryl alkyl, or heterocyclylalkyl defined or disclosed herein.

In still another embodiment of the compounds of Formula I, n and m are both 1, and $R^2$ is H.

In still another embodiment of the compounds of Formula I, n is 1, m is 2, and $R^2$ is H.

In still another embodiment of the compounds of Formula I, n and m are both 1, and at least one $R^2$ is alkyl. In a particular embodiment at least one $R^2$ is methyl. In another particular embodiment at least one $R^2$ is ethyl. In another particular embodiment at least one $R^2$ is i-propyl. In another particular embodiment at least one $R^2$ is t-butyl. In another particular embodiment, one $R^2$ is H, and the other $R^2$ is methyl. In another particular embodiment, one $R^2$ is H, and the other $R^2$ is ethyl. In another particular embodiment, one $R^2$ is H, and the other $R^2$ is i-propyl. In another particular embodiment, one $R^2$ is H, and the other $R^2$ is t-butyl.

In still another embodiment of the compounds of Formula I, n and m are both 1, and $R^2$ is substituted alkyl. In a particular embodiment at least one $R^2$ is —CH(CH$_3$)OH or —CH(CH$_3$)O(t-Bu)

In still another embodiment of the compounds of Formula I, n and m are both 1, and at least one $R^2$ is arylheteroalkyl. In particular embodiment n and m are both 1, and at least one $R^2$ is selected from the group consisting of H, methyl, ethyl, benzyl-O—CH$_2$—, i-propyl, —CH(CH$_3$)OBn, —CH$_2$CH(CH$_3$)—O-tBu, —CH(CH$_3$)OH, —CH$_2$OH, —CH$_2$OtBu, —CH$_2$CH$_2$NH$_2$, —CH$_2$CH$_2$NH—P (where P is a protecting group such as Boc, Ac, methanesulfonyl, etc.), —CH$_2$CH$_2$-morpholine, —CH$_2$C(O)OH, —CH$_2$C(O)OtBu, and —CH$_2$C(O)—NH$_2$.

In still another embodiment of the compounds of Formula I, n and m are both 1, and at least one $R^2$ is arylheteroalkyl. In particular embodiment n and m are both 1, one $R^2$ is H and one $R^2$ is selected from the group consisting of H, methyl, ethyl, benzyl-O—CH$_2$—, i-propyl, —CH(CH$_3$)OBn, —CH$_2$CH(CH$_3$)—O-tBu, —CH(CH$_3$)OH, —CH$_2$OH, —CH$_2$OtBu, —CH$_2$CH$_2$NH$_2$, —CH$_2$CH$_2$NH—P (where P is a protecting group such as Boc; Ac, methanesulfonyl, etc.), —CH$_2$CH$_2$-morpholine, —CH$_2$C(O)OH, —CH$_2$C(O)OtBu, and —CH$_2$C(O)—NH$_2$.

In still another embodiment of the compounds of Formula I, $R^4$ is H, alkyl, substituted alkyl, and heteroalkyl, wherein alkyl, substituted alkyl, and heteroalkyl are any alkyl, substituted alkyl, or heteroalkyl defined or disclosed herein. A particular embodiment, $R^4$ is H.

In still another embodiment of the compounds of Formula I, $R^6$ is H, alkyl, substituted alkyl, and heteroalkyl, wherein alkyl, substituted alkyl, and heteroalkyl are any alkyl, substituted alkyl, or heteroalkyl defined or disclosed herein. A particular embodiment, $R^6$ is H.

In still another embodiment of the compounds of Formula I, $R^8$ and $R^9$ are each one or more substituents independently selected from the group consisting of H, alkyl, substituted alkyl, halogen, aryl, substituted aryl, heterocyclyl, substituted heterocyclyl, and —CN, wherein when $R^8$ or $R^9$ are alkyl, substituted alkyl, halogen, aryl, substituted aryl, heterocyclyl, or substituted heterocyclyl, said alkyl, substituted alkyl, halogen, aryl, substituted aryl, heterocyclyl, or substituted heterocyclyl are any such groups defined or disclosed herein.

In still another embodiment of the compounds of Formula I, $R^8$ and $R^9$ are the same. In a particular embodiment $R^8$ and $R^9$ are both H.

In still another embodiment of the compounds of Formula I, $R^8$ and $R^9$ are different. In a particular embodiment $R^8$ is alkyl and $R^9$ is H. in another particular embodiment, $R^8$ is i-propyl and $R^9$ is H.

In yet another embodiment of the compounds of Formula I, at least one of the -$L^3$-A-($L^4$-Ar)$_p$ moieties is an -alkylene-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, at least one of the -$L^3$-A-($L^4$-Ar)$_p$ moieties is an -alkylene-aryl-alkylene-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, at least one of the -$L^3$-A-($L^4$-Ar)$_p$ moieties is an -alkylene-aryl-alkylene-heteroaryl group, wherein said alkylene, aryl, and heteroaryl moieties are any alkylene, aryl, and heteroaryl moieties defined or exemplified herein, optionally substituted on the alkylene and/or aryl, and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-alkylene-heteroaryl group, wherein said alkylene and heteroaryl moieties are any alkylene and heteroaryl moieties defined or exemplified herein, optionally substituted on the alkylene and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-alkylene-aryl group, wherein said alkylene, aryl, and heteroaryl moieties are any alkylene, aryl, and heteroaryl moieties defined or exemplified herein, optionally substituted on the alkylene and/or aryl, and/or heteroaryl with one or more of any substituents defined or exemplified herein.

In yet another embodiment of the compounds of Formula I, at least one of the -$L^3$-A-($L^4$-Ar)$_p$ moieties is an -alkylene-aryl-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, at least one of the -$L^3$-A-($L^4$-Ar)$_p$ moieties is an -alkylene-aryl-O-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, at least one of the -$L^3$-A-($L^4$-Ar)$_p$ moieties is an -alkylene-aryl-$CH_2$—O-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, at least one of the -$L^3$-A-($L^4$-Ar)$_p$ moieties is an -alkylene-aryl-$OCH_2$-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, at least one of the -$L^3$-A-($L^4$-Ar)$_p$ moieties is an -alkylene-aryl-NH-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, at least one of the -$L^3$-A-($L^4$-Ar)$_p$ moieties is an -alkylene-aryl-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-aryl-O-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-aryl-$CH_2$—O-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-aryl-$OCH_2$-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-aryl-NH-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-aryl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-O-aryl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-$CH_2$—O-aryl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-$OCH_2$-aryl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-NH-aryl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-O-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-$CH_2$—O-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-$OCH_2$-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-NH-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-aryl-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-aryl-O-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-aryl-$CH_2$—O-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-aryl-O$CH_2$-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-aryl-NH-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-aryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-O-aryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-$CH_2$—O-aryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-O$CH_2$-aryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-NH-aryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heterocyclyl-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heterocyclyl-O-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heterocyclyl-$CH_2$—O-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-O$CH_2$-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-NH-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an alkyl group.

In yet another embodiment of the compounds of Formula I, both of the -$L^3$-A-($L^4$-Ar)$_p$ moieties are alkyl groups, wherein the alkyl groups are the same or different.

In yet another embodiment of the compounds of Formula I, both -$L^3$-A-($L^4$-Ar)$_p$ moieties are —$CH_2$-phenyl and X and Y are both —$CH_2$-heterocyclyl.

In yet another embodiment of the compounds of Formula I, both -$L^3$-A-($L^4$-Ar)$_p$ moieties are —$CH_2$-phenyl and Y is —$CH_2$-heterocyclyl.

In yet another embodiment of the compounds of Formula I, both -$L^3$-A-($L^4$-Ar)$_p$ moieties are —$CH_2$-phenyl and X is —$CH_2$-heterocyclyl.

In yet another embodiment of the compounds of Formula I, both -$L^3$-A-($L^4$-Ar)$_p$ moieties are —$CH_2$-phenyl and Y is —$CH_2$-thiazolyl.

In yet another embodiment of the compounds of Formula I, both -$L^3$-A-($L^4$-Ar)$_p$ moieties are —$CH_2$-phenyl and X is —$CH_2$-thiazolyl.

In yet another embodiment of the compounds of Formula I, both -$L^3$-A-($L^4$-Ar)$_p$ moieties are —$CH_2$-phenyl and X and Y are both —$CH_2$-thiazolyl.

In yet another embodiment of the compounds of Formula I, both -L$^3$-A-(L$^4$-Ar)$_p$ moieties are —CH$_2$-phenyl, X and Y are both —CH$_2$-thiazolyl, and n and m are both 1.

In yet another embodiment of the compounds of Formula I, both -L$^3$-A-(L$^4$-Ar)$_p$ moieties are —CH$_2$-phenyl, X and Y are both —CH$_2$-thiazolyl, n and m are both 1, and at least one R$^2$ is a C$_1$-C$_6$ alkyl.

In yet another embodiment of the compounds of Formula I, both -L$^3$-A-(L$^4$-Ar)$_p$ moieties are —CH$_2$-phenyl, X and Y are both —CH$_2$-thiazolyl, n and m are both 1, and at least one R$^2$ is a C$_1$-C$_6$ hydroxyalkyl.

In yet another embodiment of the compounds of Formula I, both -L$^3$-A-(L$^4$-Ar)$_p$ moieties are CH$_2$-phenyl, X and Y are both —CH$_2$-thiazolyl, n and m are both 1, and at least one R$^2$ is a C$_2$-C$_{10}$ alkoxyalkyl.

In yet another embodiment of the compounds of Formula I, both -L$^3$-A-(L$^4$-Ar)$_p$ moieties are —CH$_2$-phenyl, X and Y are both —CH$_2$-thiazolyl, n and m are both 1, and at least one R$^2$ is a C$_7$-C$_{14}$ arylalkyloxyalkyl.

In yet another embodiment of the compounds of Formula I, both -L$^3$-A-(L$^4$-Ar)$_p$ moieties are —CH$_2$-phenyl, X and Y are both —CH$_2$-thiazolyl, n and m are both 1, and at least one R$^2$ is a C$_1$-C$_6$ aminoalkyl.

In yet another embodiment of the compounds of Formula I, both -L$^3$-A-(L$^4$-Ar)$_p$ moieties are —CH$_2$-phenyl, X and Y are both —CH$_2$-thiazolyl, n and m are both 1, and at least one R$^2$ is a C$_1$-C$_6$ aminoalkyl substituted on the nitrogen with an amine protecting group selected from acyl, alkylsulfonyl, arylsulfonyl, heterocyclylacyl, and benzyl.

In yet another embodiment of the compounds of Formula I, both -L$^3$-A-(L$^4$-Ar)$_p$ moieties are —CH$_2$-phenyl, X and Y are both —CH$_2$-thiazolyl, n and m are both 1, and at least one R$^2$ is a substituted or unsubstituted heterocyclylalkyl.

In yet another embodiment of the compounds of Formula I, both -L$^3$-A-(L$^4$-Ar)$_p$ moieties are —CH$_2$-phenyl, X and Y are both —CH$_2$-thiazolyl, n and m are both 1, and L$^2$ is —CH$_2$—.

In yet another embodiment of the compounds of Formula I, at least one -L$^3$-A-(L$^4$-Ar)$_p$ moiety is —CH$_2$-phenyl-CH$_2$-phenyl.

In yet another embodiment of the compounds of Formula I, at least one -L$^3$-A-(L$^4$-Ar)$_p$ moiety is —CH$_2$— heteroaryl-CH$_2$-phenyl.

In yet another embodiment of the compounds of Formula I, at least one -L$^3$-A-(L$^4$-Ar)$_p$ moiety is —CH$_2$-phenyl-CH$_2$-heteroaryl.

In yet another embodiment of the compounds of Formula I, at least one -L$^3$-A-(L$^4$-Ar)$_p$ moiety is —CH$_2$— heteroaryl-CH$_2$-heteroaryl.

In yet another embodiment of the compounds of Formula I, X and Y are both heterocyclylalkyl.

In yet another embodiment of the compounds of Formula I, X and Y are both heteroarylalkyl.

In another embodiment of the compounds of Formula I, L$^1$ is —C(O)—, R$^4$ is H, and both -L$^3$-A-(L$^4$-Ar)$_p$ groups are substituted or unsubstituted benzyl.

In another embodiment of the compounds of Formula I, L$^1$ is —C(O)—, R$^4$ is H, both -L$^3$-A-(L$^4$-Ar)$_p$ groups are substituted or unsubstituted benzyl, and L$^2$ is —CH$_2$—.

In another embodiment of the compounds of Formula I, L$^1$ is —C(O)—, R$^4$ is H, both -L$^3$-A-(L$^4$-Ar)$_p$ groups are substituted or unsubstituted benzyl, L$^2$ is —CH$_2$—, and m and n are both 1.

In another embodiment of the compounds of Formula I, L$^1$ is —C(O)—, R$^4$ is H, both -L$^3$-A-(L$^4$-Ar)$_p$ groups are substituted or unsubstituted benzyl, L$^2$ is —CH$_2$—, m and n are both 1, and R$^1$ is H.

In another embodiment of the compounds of Formula I, L$^1$ is —C(O)—, R$^4$ is H, both -L$^3$-A-(L$^4$-Ar)$_p$ groups are substituted or unsubstituted benzyl, L$^2$ is —CH$_2$—, m and n are both 1, R$^1$ is H, and Z$^1$ is —N(alkyl)-.

In another embodiment of the compounds of Formula I, L$^1$ is —C(O)—, R$^4$ is H, both -L$^3$-A-(L$^4$-Ar)$_p$ groups are substituted or unsubstituted benzyl, L$^2$ is —CH$_2$—, m and n are both 1, R$^1$ is H, and Z$^1$ is —N(CH$_3$)—.

In another embodiment of the compounds of Formula I, L$^1$ is —C(O)—, R$^4$ is H, both -L$^3$-A-(L$^4$-Ar)$_p$ groups are substituted or unsubstituted benzyl, L$^2$ is —CH$_2$—, m and n are both 1, R$^1$ is H, Z$^1$ is —N(alkyl)-, and Z$^2$ is —O—.

In another embodiment of the compounds of Formula I, L$^1$ is —C(O)—, R$^4$ is H, both -L$^3$-A-(L$^4$-Ar)$_p$ groups are substituted or unsubstituted benzyl, L$^2$ is —CH$_2$—, m and n are both 1, R$^1$ is H, Z$^1$ is —N(CH$_3$)—, and Z$^2$ is —O—.

In another embodiment of the compounds of Formula I, L$^1$ is —C(O)—, R$^4$ is H, both -L$^3$-A-(L$^4$-Ar)$_p$ groups are substituted or unsubstituted benzyl, L$^2$ is —CH$_2$—, m and n are both 1, R$^1$ is H, Z$^1$ is —N(alkyl)-, Z$^2$ is —O—, and Y is substituted or unsubstituted —CH$_2$-4-thiazole.

In another embodiment of the compounds of Formula I, L$^1$ is —C(O)—, R$^4$ is H, both -L$^3$-A-(L$^4$-Ar)$_p$ groups are substituted or unsubstituted benzyl, L$^2$ is —CH$_2$—, m and n are both 1, R$^1$ is H, Z$^1$ is —N(alkyl)-, Z$^2$ is —O—, and R$^8$—Y is —CH$_2$-(2-alkyl-4-thiazole).

In another embodiment of the compounds of Formula I, L$^1$ is —C(O)—, R$^4$ is H, both -L$^3$-A-(L$^4$-Ar)$_p$ groups are substituted or unsubstituted benzyl, L$^2$ is —CH$_2$—, m and n are both 1, R$^1$ is H, Z$^1$ is —N(H)—, Z$^2$ is —O—, and R$^8$—Y is —CH$_2$-(2-iPr-4-thiazole).

In another embodiment of the compounds of Formula I, L$^1$ is —C(O)—, R$^4$ is H, both -L$^3$-A-(L$^4$-Ar)$_p$ groups are substituted or unsubstituted benzyl, L$^2$ is —CH$_2$—, m and n are both 1, R$^1$ is H, Z$^1$ is —N(alkyl)-, Z$^2$ is —O—, Y is substituted or unsubstituted —CH$_2$-4-thiazole, and X is substituted or unsubstituted —CH$_2$-5-thiazole.

In another embodiment of the compounds of Formula I, L$^1$ is —C(O)—, R$^4$ is H, both -L$^3$-A-(L$^4$-Ar)$_p$ groups are substituted or unsubstituted benzyl, L$^2$ is —CH$_2$—, m and n are both 1, R$^1$ is H, Z$^1$ is —N(alkyl)-, Z$^2$ is —O—, Y is substituted or unsubstituted —CH$_2$-4-thiazole, and X is unsubstituted —CH$_2$-5-thiazole.

In another embodiment of the compounds of Formula I, L$^1$ is —C(O)—, R$^4$ is H, both -L$^3$-A-(L$^4$-Ar)$_p$ groups are substituted or unsubstituted benzyl, L$^2$ is —CH$_2$—, m and n are both 1, R$^1$ is H, Z$^1$ is —N(H)—, Z$^2$ is —, R$^8$—Y is —CH$_2$-(2-iPr-4-thiazole), and X is unsubstituted —CH$_2$-5-thiazole.

In another embodiment of the compounds of Formula I, each R$^2$ is independently H or hydroxyalkyl.

In another embodiment of the compounds of Formula I, each R$^2$ is independently H or heterocyclylalkyl.

In another embodiment of the compounds of Formula I, each R$^2$ is independently H or —CH$_2$-heterocyclyl, wherein said heterocyclyl is a 5- or 6-membered ring having at least one ring nitrogen atom.

In another embodiment of the compounds of Formula I, each R$^2$ is independently H or —CH$_2$-heterocyclyl, wherein said heterocyclyl is a 6-membered ring having at least one ring nitrogen atom.

In another embodiment of the compounds of Formula I, each R$^2$ is independently H or —CH$_2$-heterocyclyl, wherein said heterocyclyl is a 6-membered ring having at least one ring nitrogen atom, where the —CH$_2$-moiety thereof is bonded to the ring nitrogen atom.

In another embodiment of the compounds of Formula I, each R$^2$ is independently H or —CH$_2$-heterocyclyl, wherein said heterocyclyl is selected from the group consisting of piperidyl, piperazyl, and morpholinyl.

In another embodiment of the compounds of Formula I, each $R^2$ is independently H or —$CH_2$-heterocyclyl, wherein said heterocyclyl is selected from the group consisting of piperidyl, piperazyl, and morpholinyl, and the —$CH_2$— moiety thereof is bonded to a ring nitrogen atom of the heterocyclyl.

In another embodiment of the compounds of Formula I, each $R^2$ is independently H or aminoalkyl.

In another embodiment of the compounds of Formula I, each $R^2$ is independently H or aminoalkyl substituted with an amine protecting group selected from the group consisting of acetyl, alkylsulfonyl, Boc, Cbz, and Fmoc.

In another embodiment of the compounds of Formula I, each $R^2$ is independently H or ethylacetamide (—$CH_2CH_2NHC(O)CH_3$).

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, $Z^1$ is —N(H)—, $Z^2$ is —O—, $R^8$—Y is —$CH_2$-(2-iPr-4-thiazole), X is unsubstituted —$CH_2$-5-thiazole, and $R^2$ is independently H or hydroxyalkyl.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, $Z^1$ is —N(H)—, $Z^2$ is —, $R^8$—Y is —$CH_2$-(2-iPr-4-thiazole), X is unsubstituted —$CH_2$-5-thiazole, and one $R^2$ is H and the other $R^2$ is hydroxyalkyl.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, $Z^1$ is —N(H)—, $Z^2$ is —O—, $R^8$—Y is —$CH_2$-(2-iPr-4-thiazole), X is unsubstituted —$CH_2$-5-thiazole, and one $R^2$ is H and the other $R^2$ is hydroxymethyl.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, $Z^1$ is —N(H)—, $Z^2$ is —, $R^8$—Y is —$CH_2$-(2-iPr-4-thiazole), X is unsubstituted —$CH_2$-5-thiazole, and each $R^2$ is independently H or —$C_{1-2}$-heterocyclyl, wherein said heterocyclyl is a 5- or 6-membered ring having at least one ring nitrogen atom.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, $Z^1$ is —N(H)—, $Z^2$ is —O—, $R^8$—Y is —$CH_2$-(2-iPr-4-thiazole), X is unsubstituted —$CH_2$-5-thiazole; and each $R^2$ is independently H or —$CH_2$-heterocyclyl, wherein said heterocyclyl is selected from the group consisting of piperidyl, piperazyl, and morpholinyl, and the —$CH_2$— moiety thereof is bonded to a ring nitrogen atom of the heterocyclyl In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, $Z^1$ is —N(H)—, $Z^2$ is —O—, $R^8$—Y is —$CH_2$-(2-iPr-4-thiazole), X is unsubstituted —$CH_2$-5-thiazole, and one $R^2$ is H and the other $R^2$ is —$CH_2$-heterocyclyl, wherein said heterocyclyl is selected from the group consisting of piperidyl, piperazyl, and morpholinyl, and the —$CH_2$— moiety thereof is bonded to a ring nitrogen atom of the heterocyclyl In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, $Z^1$ is —N(H)—, $Z^2$ is —O—, $R^8$—Y is —$CH_2$-(2-iPr-4-thiazole), X is unsubstituted —$CH_2$-5-thiazole, and each $R^2$ is independently H or aminoalkyl substituted with an amine protecting group selected from the group consisting of acetyl, alkylsulfonyl, Boc, Cbz, and Fmoc.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, $Z^1$ is —N(H)—, $Z^2$ is —O—, $R^8$—Y is —$CH_2$-(2-iPr-4-thiazole), X is unsubstituted —$CH_2$-5-thiazole, and one $R^2$ is H and the other $R^2$ is aminoalkyl substituted with an amine protecting group selected from the group consisting of acetyl, alkylsulfonyl, Boc, Cbz, and Fmoc.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, $Z^1$ is —N(H)—, $Z^2$ is —O—, $R^8$—Y is —$CH_2$-(2-iPr-4-thiazole), X is unsubstituted —$CH_2$-5-thiazole, and one $R^2$ is H and the other $R^2$ is ethylacetamide (—$CH_2CH_2NHC(O)CH_3$).

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, $Z^1$ is —N(alkyl)-, $Z^2$ is —O—, and Y is substituted or unsubstituted —$CH_2$-thiazole.

In still another embodiment, the compounds of Formula I, or pharmaceutically acceptable salts, solvates, esters, or stereoisomers thereof, have the structure shown in Formula IIA:

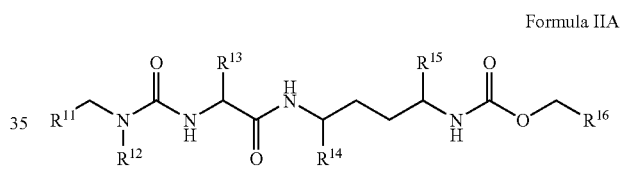

Formula IIA wherein $R^{11}$ and $R^{16}$ are each independently heterocyclyl or substituted heterocyclyl; and $R^{12}$, $R^{13}$, $R^{14}$, and $R^{15}$ are each independently H, —$C_{1-4}$ alkyl or —$C_{1-4}$ substituted alkyl.

In still another embodiment of the compounds of Formula IIA, $R^{13}$ is H, —$C_{1-4}$ alkyl, —$(CH_2)_{0-1}CR^{17}R^{18}OR^{19}$, —$(CH_2)_{0-3}CR^{17}R^{18}NR^{20}R^{21}$, —$(CH_2)_{0-3}CR^{17}R^{18}NR^{17}C(O)$—$NR^{20}R^{21}$, —$(CH_2)_{1-3}C(O)R^{22}$, —$(CH_2)_{1-3}S(O)_2R^{22}$ or —$(CH_2)_{1-3}$—$R^{23}$; $R^{14}$ and $R^{15}$ are each independently H, —$C_{1-4}$ alkyl or arylalkyl; $R^{17}$ and $R^{18}$ are each independently H or —$C_{1-3}$ alkyl; $R^{19}$ is H, —$C_{1-4}$ alkyl or arylalkyl; $R^{20}$ and $R^{21}$ are each independently H, —$C_{1-3}$ alkyl, —C(O)$R^{17}$ or —S(O)$_2R^{17}$; or $R^{20}$ and $R^{21}$, taken together with the nitrogen atom to which they are attached, form an unsubstituted or substituted 5-6 membered heterocyclyl ring containing 1-2 heteroatoms selected from the group consisting of N and O; $R^{22}$ is H, —$C_{1-3}$ alkyl, —$OR^{19}$ or —$NR^{20}R^{21}$; and $R^{23}$ is an unsubstituted or substituted 5-6 membered heterocyclyl ring containing 1-2 heteroatoms selected from the group consisting of N and O.

In still another embodiment of the compounds of Formula IIA, $R^{13}$ is —$(CH_2)_{0-3}CR^{17}R^{18}NR^{20}R^{21}$, —$(CH_2)_{0-3}CR^{17}R^{18}NR^{17}C(O)$—$NR^{20}R^{21}$, or —$(CH_2)_{1-3}$—$R^{23}$ wherein $R^{20}$ and $R^{21}$ form a 5-6 membered heterocyclyl ring containing 1-2 heteroatoms selected from the group consisting of N and O or $R^{23}$ is an unsubstituted or substituted 5-6 membered heterocyclyl ring containing 1-2 heteroatoms selected from the group consisting of N and O, and the 5-6 membered heterocyclyl ring is optionally substituted with a $C_{1-2}$ alkyl.

In still another embodiment of the compounds of Formula IIA, $R^{13}$ is —$(CH_2)_{0-1}CR^{17}R^{18}OR^{19}$. In a particular embodiment, $R^{13}$ is a $C_{1-2}$ hydroxyalkyl or a $C_{1-6}$ alkoxyalkyl group.

In still another embodiment of the compounds of Formula IIA, $R^{13}$ is —$(CH_2)_{0-3}CR^{17}R^{18}NR^{20}R^{21}$. In a particular embodiment, $R^{13}$ is a $C_{1-4}$alkylene-$NH_2$ group, $C_{1-4}$alkylene-NHP (wherein P is a protecting group such as Boc, Fmoc, Cbz, Ac, trifluoroacetyl, toluenesulfonyl group, benzyl, etc.), or $C_{1-4}$alkylene-N(alkyl)$_2$ group.

In still another embodiment of the compounds of Formula IIA, $R^{13}$ is —$(CH_2)_{0-3}CR^{17}R^{18}NR^{17}C(O)$—$NR^{20}R^{21}$. In a particular embodiment, $R^{13}$ is a $C_{1-4}$alkylene-C(O)NH$_2$ group or $C_{1-4}$alkylene-C(O)N(alkyl)$_2$ group.

In still another embodiment of the compounds of Formula IIA, $R^{11}$, $R^{12}$, $R^{13}$, $R^{14}$, $R^{15}$, and $R^{16}$ are each independently selected from the groups shown in the Table, below:

| $R^{11}$ | $R^{12}$ | $R^{13}$ | $R^{14}$ | $R^{15}$ | $R^{16}$ |
|---|---|---|---|---|---|
| 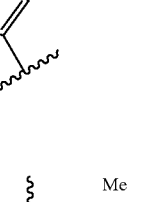 | H | 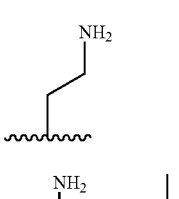 |  | 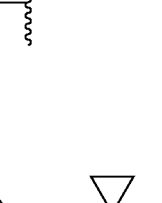 | 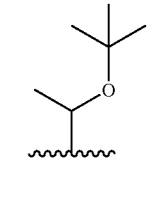 |
| | | 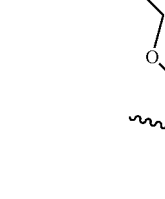 | 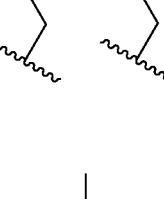 | | |
| 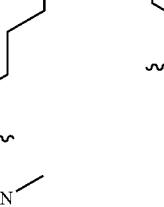 | Me |  | 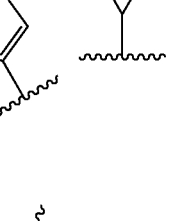 | 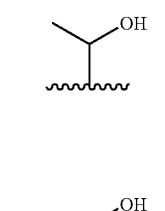 | 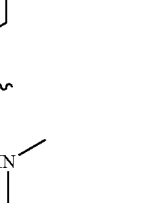 |
| | | 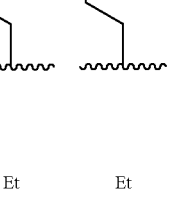 | | | |
| 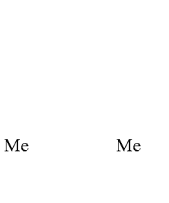 |  | H |  | 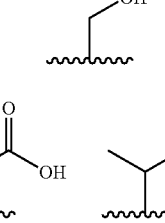 | Et | Et |
| 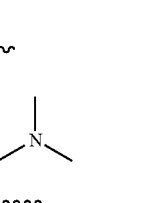 | | Et | 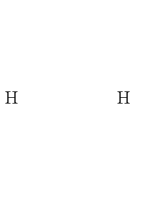 |  | Me | Me |
| | | 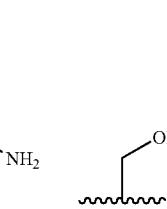 | 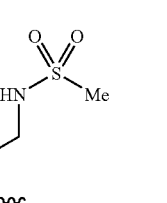 |  | H | H |
| | |  | 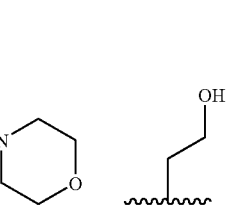 | 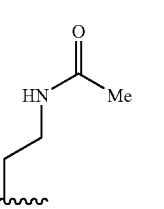 | | |
| | |  |  |  | | |
| | |  |  |  | | |

| R[11] | R[12] | R[13] | R[14] | R[15] | R[16] |
|---|---|---|---|---|---|

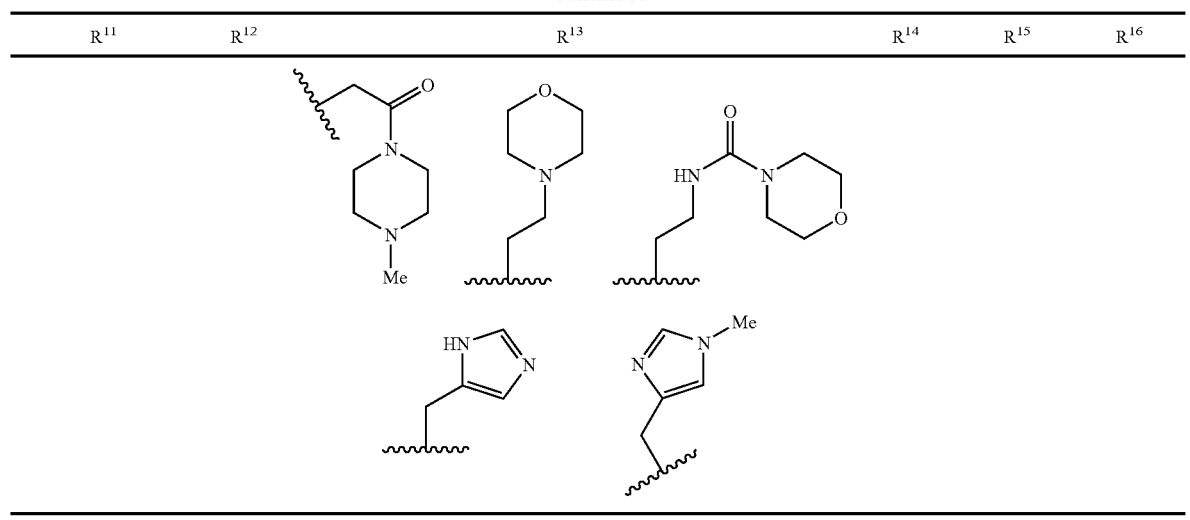

In still another embodiment of the compounds of Formula IIA, R[11] is substituted or unsubstituted heterocyclyl, R[12] is alkyl, R[13] is substituted or unsubstituted heterocyclylalkyl, R[14] and R[15] are each independently substituted or unsubstituted arylalkyl, and R[16] is substituted or unsubstituted heterocyclyl.

In still another embodiment of the compounds of Formula IIA, R[11] is substituted heterocyclyl, R[12] is alkyl, R[13] is unsubstituted heterocyclylalkyl, R[14] and R[15] are both unsubstituted arylalkyl, and R[16] is unsubstituted heterocyclyl.

In still another embodiment of the compounds of Formula IIA, R[11] is substituted or unsubstituted heterocyclyl, R[12] is alkyl, R[13] is hydroxyalkyl, R[14] and R[15] are each independently substituted or unsubstituted arylalkyl, and R[16] is substituted or unsubstituted heterocyclyl.

In still another embodiment of the compounds of Formula IIA, R[11] is substituted heterocyclyl, R[12] is alkyl, R[13] is hydroxyalkyl, R[14] and R[15] are both unsubstituted arylalkyl, and R[16] is unsubstituted heterocyclyl.

In still another embodiment of the compounds of Formula IIA, R[11] is substituted or unsubstituted heterocyclyl, R[12] is alkyl, R[13] is protected or unprotected aminoalkyl, R[14] and R[15] are each independently substituted or unsubstituted arylalkyl, and R[16] is substituted or unsubstituted heterocyclyl.

In still another embodiment of the compounds of Formula IIA, R[11] is substituted heterocyclyl, R[12] is alkyl, R[13] is protected aminoalkyl, R[14] and R[15] are both unsubstituted arylalkyl, and R[16] is unsubstituted heterocyclyl.

In still another embodiment of the compounds of Formula IIA, R[11] is substituted heterocyclyl, R[12] is alkyl, R[13] is acylated aminoalkyl, R[14] and R[15] are both unsubstituted arylalkyl, and R[16] is unsubstituted heterocyclyl.

In another embodiment, the compounds of Formula I, or pharmaceutically acceptable salts, solvates, stereoisomers and/or esters thereof, have the following structure IIB:

$R^{10a}$ and $R^{10b}$ are each independently H or —$C_{1-4}$ alkyl; $R^{12}$ is H or —$CH_3$; $R^{13}$ is H, —$C_{1-4}$ alkyl, —$(CH_2)_{0-1}$ $CR^{17}R^{18}OR^{19}$, —$(CH_2)_{0-3}CR^{17}R^{18}NR^{20}R^{21}$, —$(CH_2)_{0-3}$ $CR^{17}R^{18}NR^{17}C(O)NR^{20}R^{21}$, —$(CH_2)_{1-3}C(O)R^{22}$, —$(CH_2)_{1-3}S(O)_2R^{22}$ or —$(CH_2)_{1-3}$—$R^{23}$; $R^{14}$ and $R^{15}$ are each independently H, —$C_{1-4}$ alkyl or arylalkyl; $R^{17}$ and $R^{18}$ are each independently H or —$C_{1-3}$ alkyl; $R^{19}$ is H, —$C_{1-4}$ alkyl or arylalkyl; $R^{20}$ and $R^{21}$ are each independently H, —$C_{1-3}$ alkyl, —$C(O)R^{17}$ or —$S(O)_2R^{17}$; or $R^{20}$ and $R^{21}$, taken together with the nitrogen atom to which they are attached, form an unsubstituted or substituted 5-6 membered heterocyclyl ring containing 1-2 heteroatoms selected from the group consisting of N and O; $R^{22}$ is H, —$C_{1-3}$alkyl, —$OR^{19}$ or —$NR^{20}R^{21}$; and $R^{23}$ is an unsubstituted or substituted 5-6 membered heterocyclyl ring containing 1-2 heteroatoms selected from the group consisting of N and O.

In still another embodiment of the compounds of Formula IIB, $R^{13}$ is —$(CH_2)_{0-3}CR^{17}R^{18}NR^{20}R^{21}$, —$(CH_2)_{0-3}$ $CR^{17}R^{18}NR^{17}C(O)$—$NR^{20}R^{21}$, or —$(CH_2)_{1-3}$—$R^{23}$ wherein $R^{20}$ and $R^{21}$ form a 5-6 membered heterocyclyl ring containing 1-2 heteroatoms selected from the group consisting of N and O or $R^{23}$ is an unsubstituted or substituted 5-6 membered heterocyclyl ring containing 1-2 heteroatoms selected from the group consisting of N and O, and the 5-6 membered heterocyclyl ring is optionally substituted with a $C_{1-2}$ alkyl.

In another embodiment, the compounds of Formula I, or pharmaceutically acceptable salts, solvates, stereoisomers and/or esters thereof, have the following structure IIC:

Formula IIB

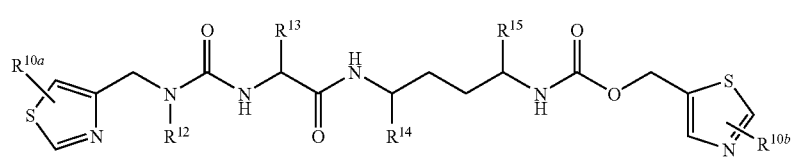

Formula IIC

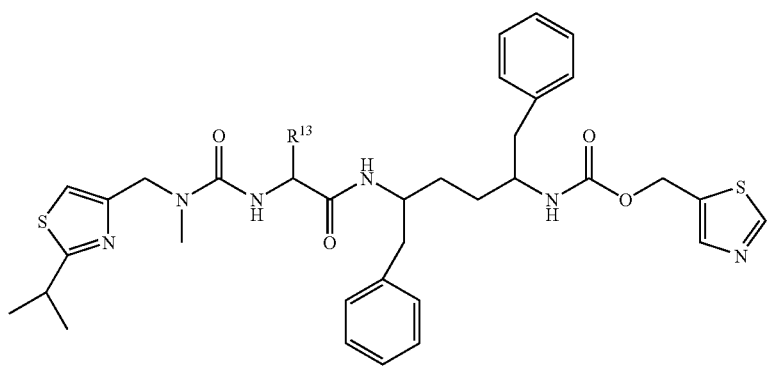

wherein
$R^{13}$ is H, —$C_{1-4}$ alkyl, —$(CH_2)_{0-1}CR^{17}R^{18}OR^{19}$, —$(CH_2)_{0-3}CR^{17}R^{18}NR^{20}R^{21}$, —$(CH_2)_{0-3}CR^{17}R^{18}NR^{17}C(O)NR^{20}R^{21}$, —$(CH_2)_{1-3}C(O)R^{22}$ or —$(CH_2)_{1-3}$—$R^{23}$; $R^{17}$ and $R^{18}$ are each independently H or $C_{1-3}$ alkyl; $R^{19}$ is H, —$C_{1-4}$ alkyl or arylalkyl; $R^{20}$ and $R^{21}$ are each independently H, —$C_{1-3}$ alkyl, —$C(O)R^{17}$ or —$S(O)_2R^{17}$; or $R^{20}$ and $R^{21}$, taken together with the nitrogen atom to which they are attached, form a 5-6 membered heterocyclyl ring containing 1-2 heteroatoms selected from the group consisting of N and O; $R^{22}$ is H, —$C_{1-3}$alkyl, —$OR^{19}$ or —$NR^{20}R^{21}$; and $R^{23}$ is a 5-6 membered heterocyclyl ring containing 1-2 heteroatoms selected from the group consisting of N and O.

In still another embodiment of the compounds of Formula IIC, $R^{13}$ is —$(CH_2)_{0-3}CR^{17}R^{18}NR^{20}R^{21}$, —$(CH_2)_{0-3}CR^{17}R^{18}NR^{17}C(O)$—$NR^{20}R^{21}$, or —$(CH_2)_{1-3}$—$R^{23}$ wherein $R^{20}$ and $R^{21}$ form a 5-6 membered heterocyclyl ring containing 1-2 heteroatoms selected from the group consisting of N and O or $R^{23}$ is an unsubstituted or substituted 5-6 membered heterocyclyl ring containing 1-2 heteroatoms selected from the group consisting of N and O, and the 5-6 membered heterocyclyl ring is optionally substituted with a $C_{1-2}$ alkyl.

In still another embodiment of the compounds of Formula IIC, $R^{13}$ is —$(CH_2)_{0-3}CR^{17}R^{18}NR^{20}R^{21}$. In a particular embodiment, $R^{13}$ is a $C_{1-4}$alkylene-$NH_2$ group, $C_{1-4}$alkylene-NHP (wherein P is a protecting group such as Boc, Fmoc, Cbz, Ac, trifluoroacetyl, toluenesulfonyl group, benzyl, etc.), or $C_{1-4}$alkylene-N(alkyl)$_2$ group.

In still another embodiment of the compounds of Formula IIC, $R^{13}$ is —$(CH_2)_{0-3}CR^{17}R^{18}NR^{17}C(O)$—$NR^{20}R^{21}$. In a particular embodiment, $R^{13}$ is a $C_{1-4}$alkylene-$C(O)NH_2$ group or $C_{1-4}$alkylene-C(O)N(alkyl)$_2$ group.

In still another embodiment of the compounds of Formula IIC, $R^{13}$ is —$CH_2OH$, —$CH_2CH_2NHC(O)CH_3$ or

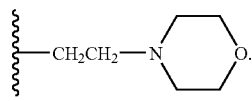

In another embodiment, the compounds of the present invention, or pharmaceutically acceptable salts, solvates, stereoisomers and/or esters thereof, have the following structure IID:

Formula IID

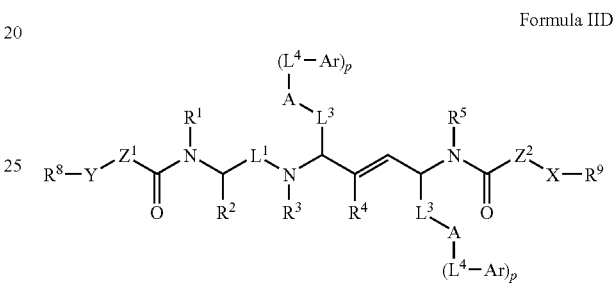

wherein,
$L^1$ is selected from the group consisting of $C(R^6)_2$—, —C(O)—, —$S(O_2)$—, —$N(R^7)$—C(O)—, and —O—C(O)—;

each $L^3$ is independently a covalent bond, an alkylene, or substituted alkylene;

each $L^4$ is independently selected from the group consisting of a covalent bond, alkylene, substituted alkylene, —O—, —$CH_2$—O—, and —NH—;

each A is independently selected from the group consisting of H, alkyl, substituted alkyl, aryl, substituted aryl, heterocyclyl, and substituted heterocyclyl,
with the proviso that when A is H, p is 0;

$Z^1$ and $Z^2$ are each independently —O— or —$N(R^7)$—;

Y and X are independently selected from the group consisting of heterocyclyl and heterocyclylalkyl;

each Ar is independently selected from the group consisting of aryl, substituted aryl, heteroaryl, and substituted heteroaryl;

$R^1$, $R^3$, and $R^5$ are each independently selected from the group consisting of H, alkyl, substituted alkyl, arylalkyl, and substituted arylalkyl;

$R^2$ is independently selected from the group consisting of H, alkyl, substituted alkyl, alkoxyalkyl, hydroxyalkyl, arylheteroalkyl, substituted arylheteroalkyl, arylalkyl, substituted arylalkyl, heterocyclylalkyl, substituted heterocyclylalkyl, aminoalkyl, substituted aminoalkyl, -alkylene-C(O)—OH, -alkylene-C(O)—Oalkyl, -alkylene-C(O)amino, -alkylene-C(O)-alkyl;

$R^4$ and $R^6$ are independently selected from the group consisting of H, alkyl, substituted alkyl, and heteroalkyl;

each $R^7$ is independently selected from the group consisting of H, alkyl, substituted alkyl, heteroalkyl, carbocyclyl, substituted carbocyclyl, heterocyclyl, and substituted heterocyclyl;

R⁸ and R⁹ are each one or more substituents independently selected from the group consisting of H, alkyl, substituted alkyl, halogen, aryl, substituted aryl, heterocyclyl, substituted heterocyclyl, and —CN; and each p is independently 0 or 1.

In another embodiment of the compounds of Formula IID, L¹ is —C(R⁶)₂—.

In another embodiment of the compounds of Formula IID, L¹ is —CH₂—.

In another embodiment of the compounds of Formula IID, each L³ is alkylene.

In another embodiment of the compounds of Formula IID, each L³ is —CH₂—.

In another embodiment of the compounds of Formula IID, each A is aryl or substituted aryl.

In another embodiment of the compounds of Formula IID, each A is phenyl or substituted phenyl.

In another embodiment of the compounds of Formula IID, X is heterocyclylalkyl.

In another embodiment of the compounds of Formula IID, X is thiazolylmethyl.

In another embodiment of the compounds of Formula IID, Y is heterocyclylalkyl.

In another embodiment of the compounds of Formula IID, Y is thiazolylmethyl.

In another embodiment of the compounds of Formula IID, Z¹ is —N(R⁷)—.

In another embodiment of the compounds of Formula IID, Z¹ is —NH—.

In another embodiment of the compounds of Formula IID, Z¹ is —N(alkyl)-.

In another embodiment of the compounds of Formula IID, Z¹ is —N(CH₃)—.

In another embodiment of the compounds of Formula IID, Z² is —O—.

In another embodiment of the compounds of Formula IID, L¹ is —C(R⁶)₂— and X and Y are heterocyclylalkyl.

In another embodiment of the compounds of Formula IID, L¹ is —CH₂— and X and Y are heterocyclylalkyl.

In another embodiment of the compounds of Formula IID, L¹ is —CH₂— and X and Y are thiazolylmethyl.

In another embodiment of the compounds of Formula IID, L¹ is —C(R⁶)₂— and Z¹ is —N(R⁷)—.

In another embodiment of the compounds of Formula IID, L¹ is —CH₂— and Z¹ is —N(R⁷)—.

In another embodiment of the compounds of Formula IID, L¹ is —CH₂— and Z¹ is —NH—.

In another embodiment of the compounds of Formula IID, L¹ is —CH₂— and Z¹ is —N(alkyl)-.

In another embodiment of the compounds of Formula IID, L¹ is —CH₂— and Z¹ is —N(CH₃)—.

In another embodiment of the compounds of Formula IID, L¹ is —C(R⁶)₂— and Z² is —O—.

In another embodiment of the compounds of Formula IID, each L³ is alkylene and each A is aryl or substituted aryl.

In another embodiment of the compounds of Formula IID, each L³ is —CH₂— and each A is aryl or substituted aryl.

In another embodiment of the compounds of Formula IID, each L³-A is benzyl or substituted benzyl.

In another embodiment of the compounds of Formula IID, X and Y are heterocyclylalkyl and Z¹ is —N(R⁷)—.

In another embodiment of the compounds of Formula IID, X and Y are thiazolylmethyl and Z¹ is —N(R⁷)—.

In another embodiment of the compounds of Formula IID, X and Y are thiazolylmethyl and Z¹ is —N(alkyl)-.

In another embodiment of the compounds of Formula IID, X and Y are thiazolylmethyl and Z¹ is —N(CH₃)—.

In another embodiment of the compounds of Formula IID, X and Y are thiazolylmethyl and Z¹ is —NH—.

In another embodiment of the compounds of Formula IID, X and Y are heterocyclylalkyl and Z² is —.

In another embodiment of the compounds of Formula IID, X and Y are thiazolylmethyl and Z² is —.

In another embodiment of the compounds of Formula IID, Z¹ is —N(R⁷)— and Z² is —O—.

In another embodiment of the compounds of Formula IID, Z¹ is —N(alkyl)- and Z² is —.

In another embodiment of the compounds of Formula IID, Z¹ is —N(CH₃)— and Z² is —.

In another embodiment of the compounds of Formula IID, Z¹ is —NH— and Z² is —O—.

In another embodiment of the compounds of Formula IID, L¹ is —C(R⁶)₂—, X and Y are heterocyclylalkyl, and Z¹ is —N(R⁷)—.

In another embodiment of the compounds of Formula IID, L¹ is —CH₂—, X and Y are heterocyclylalkyl, and Z¹ is —N(R⁷)—.

In another embodiment of the compounds of Formula IID, L¹ is —CH₂—, X and Y are thiazolylmethyl, and Z¹ is —N(R⁷)—.

In another embodiment of the compounds of Formula IID, L¹ is —CH₂—, X and Y are thiazolylmethyl, and Z¹ is —N(alkyl)-.

In another embodiment of the compounds of Formula IID, L¹ is —CH₂—, X and Y are thiazolylmethyl, and Z¹ is —N(CH₃)—.

In another embodiment of the compounds of Formula IID, L¹ is —CH₂—, X and Y are thiazolylmethyl, and Z¹ is —NH—.

In another embodiment of the compounds of Formula IID, L¹ is —C(R⁶)₂—; X and Y are heterocyclylalkyl; and Z² is —O—.

In another embodiment of the compounds of Formula IID, L¹ is —CH₂—; X and Y are heterocyclylalkyl; and Z² is —.

In another embodiment of the compounds of Formula IID, L¹ is —CH₂—; X and Y are thiazolylmethyl; and Z² is —.

In another embodiment of the compounds of Formula IID, L¹ is —C(R⁶)₂—; each L³ is alkylene; each A is aryl or substituted aryl; X and Y are heterocyclylalkyl; Z¹ is —N(R⁷)—; and Z² is —O—.

In another embodiment of the compounds of Formula IID, L¹ is —CH₂—; each L³-A is benzyl or substituted benzyl; X and Y are thiazolylmethyl; Z¹ is —N(CH₃)—; and Z² is —O—.

In another embodiment of the compounds of Formula IID, L¹ is —CH₂—; each L³-A is benzyl or substituted benzyl; Z¹ is —N(CH₃)—; Z² is —O—; X is

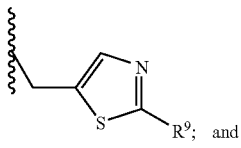

R⁹; and

Y is

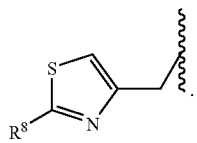

In still yet another embodiment, the compounds of Formula I are named below in tabular format (Table 6) as compounds of general Formula II:

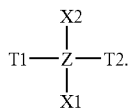

Formula II

Compounds of general formula II are depicted as a "core" structure (Z) substituted with four moieties T1, T2, X1 and X2. The core structures Z are depicted in Table 1. The points of attachment of T1, T2, X1 and X2 are indicated on each of the core structures depicted in Table 1. Tables 2-5, respectively, show the structures of the T1, T2, X1 and X2 moieties. The point of attachment of the core structure Z is indicated in each of the structures of T1, T2, X1 and X2. Each core structure Z in Table 1, and each substituent T1, T2, X1 and X2 and Tables 2-5 is represented by a "code" comprising a letter and a number. Each structure of a compound of Formula II can be designated in tabular form by combining the "code" representing each structural moiety using the following syntax: Z.T1.T2.X1.X2. Thus, for example, $Z^1$.T1A.T2B.X1A.X2A represents the following structure:

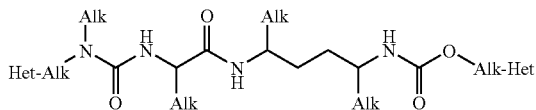

In the structures depicted in Tables 1-5, the term "Alk" means a substituted or unsubstituted alkyl, cycloalkyl, or alkylene group, wherein the terms "alkyl", "cycloalkyl", and "alkylene" are as defined herein. "Alk" means an alkyl or cycloalkyl group when depicted as monovalent, and an alkylene group when depicted as divalent. "Het" is a substituted or unsubstituted heterocyclyl or heterocyclylene group, wherein the term "heterocyclyl" is as defined herein, and the term "heterocyclylene" means a heterocyclyl group as defined herein, in which a hydrogen atom has been replaced by an open valence (in analogy to alkylene), thereby defining a divalent heterocyclyl. "Het" is a heterocyclyl when depicted as monovalent, and heterocyclylene when depicted as divalent. "Ar" is a substitute or unsubstituted aryl or arylene group, wherein the term "aryl" is as defined herein, and the term "arylene" means an aryl group as defined herein, in which a hydrogen atom has been replaced by an open valence (in analogy to alkylene), thereby defining a divalent aryl. "Ar" is aryl when depicted as monovalent, and arylene when depicted as divalent. When substituted, "Alk", "Het", and "Ar" can be substituted with any of the substituents defined or exemplified herein. For example, substituents of "Alk" can include ether, halogen, —OH, amide, amine, etc., substituents of "Het" can include alkyl, aryl, carbonyl, —OH, halogen, and substituents of "Ar" can include alkyl, aryl, —OH, halogen, etc., with the proviso that the resulting structure is chemically reasonable, and would provide compounds which are sufficiently stable for formulation in a pharmaceutically acceptable composition. When a structure or substructure shown in the tables below contains more than one "Alk", "Het" or "Ar" group, these groups are independently selected and can be the same or different. So, for example, each of the "Alk" groups of substructure T1A are independently selected and may be the same or different.

TABLE 1

| Core Structures | |
|---|---|
| Code | Core Structure |
| Z1 | |
| Z2 | |
| Z3 | |
| Z4 | |
| Z5 | |
| Z6 | |

TABLE 2

| T1 Structures | |
|---|---|
| Code | T1 Structure |
| T1A | |

TABLE 2-continued

T1 Structures

| Code | T1 Structure |
|---|---|
| T1B | 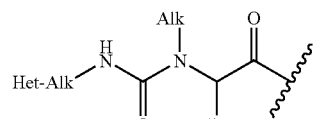 |
| T1C | 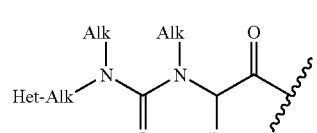 |
| T1D | 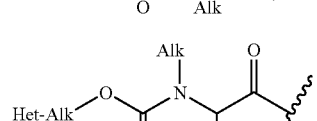 |

TABLE 3

T2 Structures

| Code | T2 Structure |
|---|---|
| T2A | —O-Alk-Het |
| T2B | —NH-Alk-Het |
| T2C | —N(Alk)-Alk-Het |
| T2D | —N(Alk)-Het |

TABLE 4

X1 Structures

| Code | X1 Structure |
|---|---|
| X1A | -Alk |
| X1B | -Alk-Ar |
| X1C | -Alk-Het |
| X1D | -Alk-Ar—O-Alk-Ar |
| X1E | -Alk-Ar—O-Alk-Het |

TABLE 5

X2 Structures

| Code | X2 Structure |
|---|---|
| X2A | -Alk |
| X2B | -Alk-Ar |
| X2C | -Alk-Het |
| X2D | -Alk-Ar—O-Alk-Ar |
| X2E | -Alk-Ar—O-Alk-Het |

TABLE 6

List of Compound Structures of Formula II

Z1.T1A.T2A.X1A.X2A, Z2.T1A.T2A.X1A.X2A,
Z3.T1A.T2A.X1A.X2A, Z4.T1A.T2A.X1A.X2A,
Z5.T1A.T2A.X1A.X2A, Z6.T1A.T2A.X1A.X2A,
Z1.T1B.T2A.X1A.X2A, Z2.T1B.T2A.X1A.X2A,
Z3.T1B.T2A.X1A.X2A, Z4.T1B.T2A.X1A.X2A,
Z5.T1B.T2A.X1A.X2A, Z6.T1B.T2A.X1A.X2A,
Z1.T1C.T2A.X1A.X2A, Z2.T1C.T2A.X1A.X2A,

TABLE 6-continued

List of Compound Structures of Formula II

Z3.T1C.T2A.X1A.X2A, Z4.T1C.T2A.X1A.X2A,
Z5.T1C.T2A.X1A.X2A, Z6.T1C.T2A.X1A.X2A,
Z1.T1D.T2A.X1A.X2A, Z2.T1D.T2A.X1A.X2A,
Z3.T1D.T2A.X1A.X2A, Z4.T1D.T2A.X1A.X2A,
Z5.T1D.T2A.X1A.X2A, Z6.T1D.T2A.X1A.X2A,
Z1.T1A.T2B.X1A.X2A, Z2.T1A.T2B.X1A.X2A,
Z3.T1A.T2B.X1A.X2A, Z4.T1A.T2B.X1A.X2A,
Z5.T1A.T2B.X1A.X2A, Z6.T1A.T2B.X1A.X2A,
Z1.T1B.T2B.X1A.X2A, Z2.T1B.T2B.X1A.X2A,
Z3.T1B.T2B.X1A.X2A, Z4.T1B.T2B.X1A.X2A,
Z5.T1B.T2B.X1A.X2A, Z6.T1B.T2B.X1A.X2A,
Z1.T1C.T2B.X1A.X2A, Z2.T1C.T2B.X1A.X2A,
Z3.T1C.T2B.X1A.X2A, Z4.T1C.T2B.X1A.X2A,
Z5.T1C.T2B.X1A.X2A, Z6.T1C.T2B.X1A.X2A,
Z1.T1D.T2B.X1A.X2A, Z2.T1D.T2B.X1A.X2A,
Z3.T1D.T2B.X1A.X2A, Z4.T1D.T2B.X1A.X2A,
Z5.T1D.T2B.X1A.X2A, Z6.T1D.T2B.X1A.X2A,
Z1.T1A.T2C.X1A.X2A, Z2.T1A.T2C.X1A.X2A,
Z3.T1A.T2C.X1A.X2A, Z4.T1A.T2C.X1A.X2A,
Z5.T1A.T2C.X1A.X2A, Z6.T1A.T2C.X1A.X2A,
Z1.T1B.T2C.X1A.X2A, Z2.T1B.T2C.X1A.X2A,
Z3.T1B.T2C.X1A.X2A, Z4.T1B.T2C.X1A.X2A,
Z5.T1B.T2C.X1A.X2A, Z6.T1B.T2C.X1A.X2A,
Z1.T1C.T2C.X1A.X2A, Z2.T1C.T2C.X1A.X2A,
Z3.T1C.T2C.X1A.X2A, Z4.T1C.T2C.X1A.X2A,
Z5.T1C.T2C.X1A.X2A, Z6.T1C.T2C.X1A.X2A,
Z1.T1D.T2C.X1A.X2A, Z2.T1D.T2C.X1A.X2A,
Z3.T1D.T2C.X1A.X2A, Z4.T1D.T2C.X1A.X2A,
Z5.T1D.T2C.X1A.X2A, Z6.T1D.T2C.X1A.X2A,
Z1.T1A.T2D.X1A.X2A, Z2.T1A.T2D.X1A.X2A,
Z3.T1A.T2D.X1A.X2A, Z4.T1A.T2D.X1A.X2A,
Z5.T1A.T2D.X1A.X2A, Z6.T1A.T2D.X1A.X2A,
Z1.T1B.T2D.X1A.X2A, Z2.T1B.T2D.X1A.X2A,
Z3.T1B.T2D.X1A.X2A, Z4.T1B.T2D.X1A.X2A,
Z5.T1B.T2D.X1A.X2A, Z6.T1B.T2D.X1A.X2A,
Z1.T1C.T2D.X1A.X2A, Z2.T1C.T2D.X1A.X2A,
Z3.T1C.T2D.X1A.X2A, Z4.T1C.T2D.X1A.X2A,
Z5.T1C.T2D.X1A.X2A, Z6.T1C.T2D.X1A.X2A,
Z1.T1D.T2D.X1A.X2A, Z2.T1D.T2D.X1A.X2A,
Z3.T1D.T2D.X1A.X2A, Z4.T1D.T2D.X1A.X2A,
Z5.T1D.T2D.X1A.X2A, Z6.T1D.T2D.X1A.X2A,
Z1.T1A.T2A.X1B.X2A, Z2.T1A.T2A.X1B.X2A,
Z3.T1A.T2A.X1B.X2A, Z4.T1A.T2A.X1B.X2A,
Z5.T1A.T2A.X1B.X2A, Z6.T1A.T2A.X1B.X2A,
Z1.T1B.T2A.X1B.X2A, Z2.T1B.T2A.X1B.X2A,
Z3.T1B.T2A.X1B.X2A, Z4.T1B.T2A.X1B.X2A,
Z5.T1B.T2A.X1B.X2A, Z6.T1B.T2A.X1B.X2A,
Z1.T1C.T2A.X1B.X2A, Z2.T1C.T2A.X1B.X2A,
Z3.T1C.T2A.X1B.X2A, Z4.T1C.T2A.X1B.X2A,
Z5.T1C.T2A.X1B.X2A, Z6.T1C.T2A.X1B.X2A,
Z1.T1D.T2A.X1B.X2A, Z2.T1D.T2A.X1B.X2A,
Z3.T1D.T2A.X1B.X2A, Z4.T1D.T2A.X1B.X2A,
Z5.T1D.T2A.X1B.X2A, Z6.T1D.T2A.X1B.X2A,
Z1.T1A.T2B.X1B.X2A, Z2.T1A.T2B.X1B.X2A,
Z3.T1A.T2B.X1B.X2A, Z4.T1A.T2B.X1B.X2A,
Z5.T1A.T2B.X1B.X2A, Z6.T1A.T2B.X1B.X2A,
Z1.T1B.T2B.X1B.X2A, Z2.T1B.T2B.X1B.X2A,
Z3.T1B.T2B.X1B.X2A, Z4.T1B.T2B.X1B.X2A,
Z5.T1B.T2B.X1B.X2A, Z6.T1B.T2B.X1B.X2A,
Z1.T1C.T2B.X1B.X2A, Z2.T1C.T2B.X1B.X2A,
Z3.T1C.T2B.X1B.X2A, Z4.T1C.T2B.X1B.X2A,
Z5.T1C.T2B.X1B.X2A, Z6.T1C.T2B.X1B.X2A,
Z1.T1D.T2B.X1B.X2A, Z2.T1D.T2B.X1B.X2A,
Z3.T1D.T2B.X1B.X2A, Z4.T1D.T2B.X1B.X2A,
Z5.T1D.T2B.X1B.X2A, Z6.T1D.T2B.X1B.X2A,
Z1.T1A.T2C.X1B.X2A, Z2.T1A.T2C.X1B.X2A,
Z3.T1A.T2C.X1B.X2A, Z4.T1A.T2C.X1B.X2A,
Z5.T1A.T2C.X1B.X2A, Z6.T1A.T2C.X1B.X2A,
Z1.T1B.T2C.X1B.X2A, Z2.T1B.T2C.X1B.X2A,
Z3.T1B.T2C.X1B.X2A, Z4.T1B.T2C.X1B.X2A,
Z5.T1B.T2C.X1B.X2A, Z6.T1B.T2C.X1B.X2A,
Z1.T1C.T2C.X1B.X2A, Z2.T1C.T2C.X1B.X2A,
Z3.T1C.T2C.X1B.X2A, Z4.T1C.T2C.X1B.X2A,
Z5.T1C.T2C.X1B.X2A, Z6.T1C.T2C.X1B.X2A,
Z1.T1D.T2C.X1B.X2A, Z2.T1D.T2C.X1B.X2A,
Z3.T1D.T2C.X1B.X2A, Z4.T1D.T2C.X1B.X2A,
Z5.T1D.T2C.X1B.X2A, Z6.T1D.T2C.X1B.X2A,
Z1.T1A.T2D.X1B.X2A, Z2.T1A.T2D.X1B.X2A,

TABLE 6-continued

List of Compound Structures of Formula II

Z3.T1A.T2D.X1B.X2A, Z4.T1A.T2D.X1B.X2A,
Z5.T1A.T2D.X1B.X2A, Z6.T1A.T2D.X1B.X2A,
Z1.T1B.T2D.X1B.X2A, Z2.T1B.T2D.X1B.X2A,
Z3.T1B.T2D.X1B.X2A, Z4.T1B.T2D.X1B.X2A,
Z5.T1B.T2D.X1B.X2A, Z6.T1B.T2D.X1B.X2A,
Z1.T1C.T2D.X1B.X2A, Z2.T1C.T2D.X1B.X2A,
Z3.T1C.T2D.X1B.X2A, Z4.T1C.T2D.X1B.X2A,
Z5.T1C.T2D.X1B.X2A, Z6.T1C.T2D.X1B.X2A,
Z1.T1D.T2D.X1B.X2A, Z2.T1D.T2D.X1B.X2A,
Z3.T1D.T2D.X1B.X2A, Z4.T1D.T2D.X1B.X2A,
Z5.T1D.T2D.X1B.X2A, Z6.T1D.T2D.X1B.X2A,
Z1.T1A.T2A.X1C.X2A, Z2.T1A.T2A.X1C.X2A,
Z3.T1A.T2A.X1C.X2A, Z4.T1A.T2A.X1C.X2A,
Z5.T1A.T2A.X1C.X2A, Z6.T1A.T2A.X1C.X2A,
Z1.T1B.T2A.X1C.X2A, Z2.T1B.T2A.X1C.X2A,
Z3.T1B.T2A.X1C.X2A, Z4.T1B.T2A.X1C.X2A,
Z5.T1B.T2A.X1C.X2A, Z6.T1B.T2A.X1C.X2A,
Z1.T1C.T2A.X1C.X2A, Z2.T1C.T2A.X1C.X2A,
Z3.T1C.T2A.X1C.X2A, Z4.T1C.T2A.X1C.X2A,
Z5.T1C.T2A.X1C.X2A, Z6.T1C.T2A.X1C.X2A,
Z1.T1D.T2A.X1C.X2A, Z2.T1D.T2A.X1C.X2A,
Z3.T1D.T2A.X1C.X2A, Z4.T1D.T2A.X1C.X2A,
Z5.T1D.T2A.X1C.X2A, Z6.T1D.T2A.X1C.X2A,
Z1.T1A.T2B.X1C.X2A, Z2.T1A.T2B.X1C.X2A,
Z3.T1A.T2B.X1C.X2A, Z4.T1A.T2B.X1C.X2A,
Z5.T1A.T2B.X1C.X2A, Z6.T1A.T2B.X1C.X2A,
Z1.T1B.T2B.X1C.X2A, Z2.T1B.T2B.X1C.X2A,
Z3.T1B.T2B.X1C.X2A, Z4.T1B.T2B.X1C.X2A,
Z5.T1B.T2B.X1C.X2A, Z6.T1B.T2B.X1C.X2A,
Z1.T1C.T2B.X1C.X2A, Z2.T1C.T2B.X1C.X2A,
Z3.T1C.T2B.X1C.X2A, Z4.T1C.T2B.X1C.X2A,
Z5.T1C.T2B.X1C.X2A, Z6.T1C.T2B.X1C.X2A,
Z1.T1D.T2B.X1C.X2A, Z2.T1D.T2B.X1C.X2A,
Z3.T1D.T2B.X1C.X2A, Z4.T1D.T2B.X1C.X2A,
Z5.T1D.T2B.X1C.X2A, Z6.T1D.T2B.X1C.X2A,
Z1.T1A.T2C.X1C.X2A, Z2.T1A.T2C.X1C.X2A,
Z3.T1A.T2C.X1C.X2A, Z4.T1A.T2C.X1C.X2A,
Z5.T1A.T2C.X1C.X2A, Z6.T1A.T2C.X1C.X2A,
Z1.T1B.T2C.X1C.X2A, Z2.T1B.T2C.X1C.X2A,
Z3.T1B.T2C.X1C.X2A, Z4.T1B.T2C.X1C.X2A,
Z5.T1B.T2C.X1C.X2A, Z6.T1B.T2C.X1C.X2A,
Z1.T1C.T2C.X1C.X2A, Z2.T1C.T2C.X1C.X2A,
Z3.T1C.T2C.X1C.X2A, Z4.T1C.T2C.X1C.X2A,
Z5.T1C.T2C.X1C.X2A, Z6.T1C.T2C.X1C.X2A,
Z1.T1D.T2C.X1C.X2A, Z2.T1D.T2C.X1C.X2A,
Z3.T1D.T2C.X1C.X2A, Z4.T1D.T2C.X1C.X2A,
Z5.T1D.T2C.X1C.X2A, Z6.T1D.T2C.X1C.X2A,
Z1.T1A.T2D.X1C.X2A, Z2.T1A.T2D.X1C.X2A,
Z3.T1A.T2D.X1C.X2A, Z4.T1A.T2D.X1C.X2A,
Z5.T1A.T2D.X1C.X2A, Z6.T1A.T2D.X1C.X2A,
Z1.T1B.T2D.X1C.X2A, Z2.T1B.T2D.X1C.X2A,
Z3.T1B.T2D.X1C.X2A, Z4.T1B.T2D.X1C.X2A,
Z5.T1B.T2D.X1C.X2A, Z6.T1B.T2D.X1C.X2A,
Z1.T1C.T2D.X1C.X2A, Z2.T1C.T2D.X1C.X2A,
Z3.T1C.T2D.X1C.X2A, Z4.T1C.T2D.X1C.X2A,
Z5.T1C.T2D.X1C.X2A, Z6.T1C.T2D.X1C.X2A,
Z1.T1D.T2D.X1C.X2A, Z2.T1D.T2D.X1C.X2A,
Z3.T1D.T2D.X1C.X2A, Z4.T1D.T2D.X1C.X2A,
Z5.T1D.T2D.X1C.X2A, Z6.T1D.T2D.X1C.X2A,
Z1.T1A.T2A.X1D.X2A, Z2.T1A.T2A.X1D.X2A,
Z3.T1A.T2A.X1D.X2A, Z4.T1A.T2A.X1D.X2A,
Z5.T1A.T2A.X1D.X2A, Z6.T1A.T2A.X1D.X2A,
Z1.T1B.T2A.X1D.X2A, Z2.T1B.T2A.X1D.X2A,
Z3.T1B.T2A.X1D.X2A, Z4.T1B.T2A.X1D.X2A,
Z5.T1B.T2A.X1D.X2A, Z6.T1B.T2A.X1D.X2A,
Z1.T1C.T2A.X1D.X2A, Z2.T1C.T2A.X1D.X2A,
Z3.T1C.T2A.X1D.X2A, Z4.T1C.T2A.X1D.X2A,
Z5.T1C.T2A.X1D.X2A, Z6.T1C.T2A.X1D.X2A,
Z1.T1D.T2A.X1D.X2A, Z2.T1D.T2A.X1D.X2A,
Z3.T1D.T2A.X1D.X2A, Z4.T1D.T2A.X1D.X2A,
Z5.T1D.T2A.X1D.X2A, Z6.T1D.T2A.X1D.X2A,
Z1.T1A.T2B.X1D.X2A, Z2.T1A.T2B.X1D.X2A,
Z3.T1A.T2B.X1D.X2A, Z4.T1A.T2B.X1D.X2A,
Z5.T1A.T2B.X1D.X2A, Z6.T1A.T2B.X1D.X2A,
Z1.T1B.T2B.X1D.X2A, Z2.T1B.T2B.X1D.X2A,
Z3.T1B.T2B.X1D.X2A, Z4.T1B.T2B.X1D.X2A,
Z5.T1B.T2B.X1D.X2A, Z6.T1B.T2B.X1D.X2A,
Z1.T1C.T2B.X1D.X2A, Z2.T1C.T2B.X1D.X2A,
Z3.T1C.T2B.X1D.X2A, Z4.T1C.T2B.X1D.X2A,
Z5.T1C.T2B.X1D.X2A, Z6.T1C.T2B.X1D.X2A,
Z1.T1D.T2B.X1D.X2A, Z2.T1D.T2B.X1D.X2A,
Z3.T1D.T2B.X1D.X2A, Z4.T1D.T2B.X1D.X2A,
Z5.T1D.T2B.X1D.X2A, Z6.T1D.T2B.X1D.X2A,
Z1.T1A.T2C.X1D.X2A, Z2.T1A.T2C.X1D.X2A,
Z3.T1A.T2C.X1D.X2A, Z4.T1A.T2C.X1D.X2A,
Z5.T1A.T2C.X1D.X2A, Z6.T1A.T2C.X1D.X2A,
Z1.T1B.T2C.X1D.X2A, Z2.T1B.T2C.X1D.X2A,
Z3.T1B.T2C.X1D.X2A, Z4.T1B.T2C.X1D.X2A,
Z5.T1B.T2C.X1D.X2A, Z6.T1B.T2C.X1D.X2A,
Z1.T1C.T2C.X1D.X2A, Z2.T1C.T2C.X1D.X2A,
Z3.T1C.T2C.X1D.X2A, Z4.T1C.T2C.X1D.X2A,
Z5.T1C.T2C.X1D.X2A, Z6.T1C.T2C.X1D.X2A,
Z1.T1D.T2C.X1D.X2A, Z2.T1D.T2C.X1D.X2A,
Z3.T1D.T2C.X1D.X2A, Z4.T1D.T2C.X1D.X2A,
Z5.T1D.T2C.X1D.X2A, Z6.T1D.T2C.X1D.X2A,
Z1.T1A.T2D.X1D.X2A, Z2.T1A.T2D.X1D.X2A,
Z3.T1A.T2D.X1D.X2A, Z4.T1A.T2D.X1D.X2A,
Z5.T1A.T2D.X1D.X2A, Z6.T1A.T2D.X1D.X2A,
Z1.T1B.T2D.X1D.X2A, Z2.T1B.T2D.X1D.X2A,
Z3.T1B.T2D.X1D.X2A, Z4.T1B.T2D.X1D.X2A,
Z5.T1B.T2D.X1D.X2A, Z6.T1B.T2D.X1D.X2A,
Z1.T1C.T2D.X1D.X2A, Z2.T1C.T2D.X1D.X2A,
Z3.T1C.T2D.X1D.X2A, Z4.T1C.T2D.X1D.X2A,
Z5.T1C.T2D.X1D.X2A, Z6.T1C.T2D.X1D.X2A,
Z1.T1D.T2D.X1D.X2A, Z2.T1D.T2D.X1D.X2A,
Z3.T1D.T2D.X1D.X2A, Z4.T1D.T2D.X1D.X2A,
Z5.T1D.T2D.X1D.X2A, Z6.T1D.T2D.X1D.X2A,
Z1.T1A.T2A.X1E.X2A, Z2.T1A.T2A.X1E.X2A,
Z3.T1A.T2A.X1E.X2A, Z4.T1A.T2A.X1E.X2A,
Z5.T1A.T2A.X1E.X2A, Z6.T1A.T2A.X1E.X2A,
Z1.T1B.T2A.X1E.X2A, Z2.T1B.T2A.X1E.X2A,
Z3.T1B.T2A.X1E.X2A, Z4.T1B.T2A.X1E.X2A,
Z5.T1B.T2A.X1E.X2A, Z6.T1B.T2A.X1E.X2A,
Z1.T1C.T2A.X1E.X2A, Z2.T1C.T2A.X1E.X2A,
Z3.T1C.T2A.X1E.X2A, Z4.T1C.T2A.X1E.X2A,
Z5.T1C.T2A.X1E.X2A, Z6.T1C.T2A.X1E.X2A,
Z1.T1D.T2A.X1E.X2A, Z2.T1D.T2A.X1E.X2A,
Z3.T1D.T2A.X1E.X2A, Z4.T1D.T2A.X1E.X2A,
Z5.T1D.T2A.X1E.X2A, Z6.T1D.T2A.X1E.X2A,
Z1.T1A.T2B.X1E.X2A, Z2.T1A.T2B.X1E.X2A,
Z3.T1A.T2B.X1E.X2A, Z4.T1A.T2B.X1E.X2A,
Z5.T1A.T2B.X1E.X2A, Z6.T1A.T2B.X1E.X2A,
Z1.T1B.T2B.X1E.X2A, Z2.T1B.T2B.X1E.X2A,
Z3.T1B.T2B.X1E.X2A, Z4.T1B.T2B.X1E.X2A,
Z5.T1B.T2B.X1E.X2A, Z6.T1B.T2B.X1E.X2A,
Z1.T1C.T2B.X1E.X2A, Z2.T1C.T2B.X1E.X2A,
Z3.T1C.T2B.X1E.X2A, Z4.T1C.T2B.X1E.X2A,
Z5.T1C.T2B.X1E.X2A, Z6.T1C.T2B.X1E.X2A,
Z1.T1D.T2B.X1E.X2A, Z2.T1D.T2B.X1E.X2A,
Z3.T1D.T2B.X1E.X2A, Z4.T1D.T2B.X1E.X2A,
Z5.T1D.T2B.X1E.X2A, Z6.T1D.T2B.X1E.X2A,
Z1.T1A.T2C.X1E.X2A, Z2.T1A.T2C.X1E.X2A,
Z3.T1A.T2C.X1E.X2A, Z4.T1A.T2C.X1E.X2A,
Z5.T1A.T2C.X1E.X2A, Z6.T1A.T2C.X1E.X2A,
Z1.T1B.T2C.X1E.X2A, Z2.T1B.T2C.X1E.X2A,
Z3.T1B.T2C.X1E.X2A, Z4.T1B.T2C.X1E.X2A,
Z5.T1B.T2C.X1E.X2A, Z6.T1B.T2C.X1E.X2A,
Z1.T1C.T2C.X1E.X2A, Z2.T1C.T2C.X1E.X2A,
Z3.T1C.T2C.X1E.X2A, Z4.T1C.T2C.X1E.X2A,
Z5.T1C.T2C.X1E.X2A, Z6.T1C.T2C.X1E.X2A,
Z1.T1D.T2C.X1E.X2A, Z2.T1D.T2C.X1E.X2A,
Z3.T1D.T2C.X1E.X2A, Z4.T1D.T2C.X1E.X2A,
Z5.T1D.T2C.X1E.X2A, Z6.T1D.T2C.X1E.X2A,
Z1.T1A.T2D.X1E.X2A, Z2.T1A.T2D.X1E.X2A,
Z3.T1A.T2D.X1E.X2A, Z4.T1A.T2D.X1E.X2A,
Z5.T1A.T2D.X1E.X2A, Z6.T1A.T2D.X1E.X2A,
Z1.T1B.T2D.X1E.X2A, Z2.T1B.T2D.X1E.X2A,
Z3.T1B.T2D.X1E.X2A, Z4.T1B.T2D.X1E.X2A,
Z5.T1B.T2D.X1E.X2A, Z6.T1B.T2D.X1E.X2A,
Z1.T1C.T2D.X1E.X2A, Z2.T1C.T2D.X1E.X2A,
Z3.T1C.T2D.X1E.X2A, Z4.T1C.T2D.X1E.X2A,
Z5.T1C.T2D.X1E.X2A, Z6.T1C.T2D.X1E.X2A,
Z1.T1D.T2D.X1E.X2A, Z2.T1D.T2D.X1E.X2A,
Z3.T1D.T2D.X1E.X2A, Z4.T1D.T2D.X1E.X2A,
Z5.T1D.T2D.X1E.X2A, Z6.T1D.T2D.X1E.X2A,
Z1.T1A.T2A.X1A.X2B, Z2.T1A.T2A.X1A.X2B,

TABLE 6-continued

List of Compound Structures of Formula II

Z3.T1A.T2A.X1A.X2B, Z4.T1A.T2A.X1A.X2B,
Z5.T1A.T2A.X1A.X2B, Z6.T1A.T2A.X1A.X2B,
Z1.T1B.T2A.X1A.X2B, Z2.T1B.T2A.X1A.X2B,
Z3.T1B.T2A.X1A.X2B, Z4.T1B.T2A.X1A.X2B,
Z5.T1B.T2A.X1A.X2B, Z6.T1B.T2A.X1A.X2B,
Z1.T1C.T2A.X1A.X2B, Z2.T1C.T2A.X1A.X2B,
Z3.T1C.T2A.X1A.X2B, Z4.T1C.T2A.X1A.X2B,
Z5.T1C.T2A.X1A.X2B, Z6.T1C.T2A.X1A.X2B,
Z1.T1D.T2A.X1A.X2B, Z2.T1D.T2A.X1A.X2B,
Z3.T1D.T2A.X1A.X2B, Z4.T1D.T2A.X1A.X2B,
Z5.T1D.T2A.X1A.X2B, Z6.T1D.T2A.X1A.X2B,
Z1.T1A.T2B.X1A.X2B, Z2.T1A.T2B.X1A.X2B,
Z3.T1A.T2B.X1A.X2B, Z4.T1A.T2B.X1A.X2B,
Z5.T1A.T2B.X1A.X2B, Z6.T1A.T2B.X1A.X2B,
Z1.T1B.T2B.X1A.X2B, Z2.T1B.T2B.X1A.X2B,
Z3.T1B.T2B.X1A.X2B, Z4.T1B.T2B.X1A.X2B,
Z5.T1B.T2B.X1A.X2B, Z6.T1B.T2B.X1A.X2B,
Z1.T1C.T2B.X1A.X2B, Z2.T1C.T2B.X1A.X2B,
Z3.T1C.T2B.X1A.X2B, Z4.T1C.T2B.X1A.X2B,
Z5.T1C.T2B.X1A.X2B, Z6.T1C.T2B.X1A.X2B,
Z1.T1D.T2B.X1A.X2B, Z2.T1D.T2B.X1A.X2B,
Z3.T1D.T2B.X1A.X2B, Z4.T1D.T2B.X1A.X2B,
Z5.T1D.T2B.X1A.X2B, Z6.T1D.T2B.X1A.X2B,
Z1.T1A.T2C.X1A.X2B, Z2.T1A.T2C.X1A.X2B,
Z3.T1A.T2C.X1A.X2B, Z4.T1A.T2C.X1A.X2B,
Z5.T1A.T2C.X1A.X2B, Z6.T1A.T2C.X1A.X2B,
Z1.T1B.T2C.X1A.X2B, Z2.T1B.T2C.X1A.X2B,
Z3.T1B.T2C.X1A.X2B, Z4.T1B.T2C.X1A.X2B,
Z5.T1B.T2C.X1A.X2B, Z6.T1B.T2C.X1A.X2B,
Z1.T1C.T2C.X1A.X2B, Z2.T1C.T2C.X1A.X2B,
Z3.T1C.T2C.X1A.X2B, Z4.T1C.T2C.X1A.X2B,
Z5.T1C.T2C.X1A.X2B, Z6.T1C.T2C.X1A.X2B,
Z1.T1D.T2C.X1A.X2B, Z2.T1D.T2C.X1A.X2B,
Z3.T1D.T2C.X1A.X2B, Z4.T1D.T2C.X1A.X2B,
Z5.T1D.T2C.X1A.X2B, Z6.T1D.T2C.X1A.X2B,
Z1.T1A.T2D.X1A.X2B, Z2.T1A.T2D.X1A.X2B,
Z3.T1A.T2D.X1A.X2B, Z4.T1A.T2D.X1A.X2B,
Z5.T1A.T2D.X1A.X2B, Z6.T1A.T2D.X1A.X2B,
Z1.T1B.T2D.X1A.X2B, Z2.T1B.T2D.X1A.X2B,
Z3.T1B.T2D.X1A.X2B, Z4.T1B.T2D.X1A.X2B,
Z5.T1B.T2D.X1A.X2B, Z6.T1B.T2D.X1A.X2B,
Z1.T1C.T2D.X1A.X2B, Z2.T1C.T2D.X1A.X2B,
Z3.T1C.T2D.X1A.X2B, Z4.T1C.T2D.X1A.X2B,
Z5.T1C.T2D.X1A.X2B, Z6.T1C.T2D.X1A.X2B,
Z1.T1D.T2D.X1A.X2B, Z2.T1D.T2D.X1A.X2B,
Z3.T1D.T2D.X1A.X2B, Z4.T1D.T2D.X1A.X2B,
Z5.T1D.T2D.X1A.X2B, Z6.T1D.T2D.X1A.X2B,
Z1.T1A.T2A.X1B.X2B, Z2.T1A.T2A.X1B.X2B,
Z3.T1A.T2A.X1B.X2B, Z4.T1A.T2A.X1B.X2B,
Z5.T1A.T2A.X1B.X2B, Z6.T1A.T2A.X1B.X2B,
Z1.T1B.T2A.X1B.X2B, Z2.T1B.T2A.X1B.X2B,
Z3.T1B.T2A.X1B.X2B, Z4.T1B.T2A.X1B.X2B,
Z5.T1B.T2A.X1B.X2B, Z6.T1B.T2A.X1B.X2B,
Z1.T1C.T2A.X1B.X2B, Z2.T1C.T2A.X1B.X2B,
Z3.T1C.T2A.X1B.X2B, Z4.T1C.T2A.X1B.X2B,
Z5.T1C.T2A.X1B.X2B, Z6.T1C.T2A.X1B.X2B,
Z1.T1D.T2A.X1B.X2B, Z2.T1D.T2A.X1B.X2B,
Z3.T1D.T2A.X1B.X2B, Z4.T1D.T2A.X1B.X2B,
Z5.T1D.T2A.X1B.X2B, Z6.T1D.T2A.X1B.X2B,
Z1.T1A.T2B.X1B.X2B, Z2.T1A.T2B.X1B.X2B,
Z3.T1A.T2B.X1B.X2B, Z4.T1A.T2B.X1B.X2B,
Z5.T1A.T2B.X1B.X2B, Z6.T1A.T2B.X1B.X2B,
Z1.T1B.T2B.X1B.X2B, Z2.T1B.T2B.X1B.X2B,
Z3.T1B.T2B.X1B.X2B, Z4.T1B.T2B.X1B.X2B,
Z5.T1B.T2B.X1B.X2B, Z6.T1B.T2B.X1B.X2B,
Z1.T1C.T2B.X1B.X2B, Z2.T1C.T2B.X1B.X2B,
Z3.T1C.T2B.X1B.X2B, Z4.T1C.T2B.X1B.X2B,
Z5.T1C.T2B.X1B.X2B, Z6.T1C.T2B.X1B.X2B,
Z1.T1D.T2B.X1B.X2B, Z2.T1D.T2B.X1B.X2B,
Z3.T1D.T2B.X1B.X2B, Z4.T1D.T2B.X1B.X2B,
Z5.T1D.T2B.X1B.X2B, Z6.T1D.T2B.X1B.X2B,
Z1.T1A.T2C.X1B.X2B, Z2.T1A.T2C.X1B.X2B,
Z3.T1A.T2C.X1B.X2B, Z4.T1A.T2C.X1B.X2B,
Z5.T1A.T2C.X1B.X2B, Z6.T1A.T2C.X1B.X2B,
Z1.T1B.T2C.X1B.X2B, Z2.T1B.T2C.X1B.X2B,
Z3.T1B.T2C.X1B.X2B, Z4.T1B.T2C.X1B.X2B,
Z5.T1B.T2C.X1B.X2B, Z6.T1B.T2C.X1B.X2B,
Z1.T1C.T2C.X1B.X2B, Z2.T1C.T2C.X1B.X2B,
Z3.T1C.T2C.X1B.X2B, Z4.T1C.T2C.X1B.X2B,
Z5.T1C.T2C.X1B.X2B, Z6.T1C.T2C.X1B.X2B,
Z1.T1D.T2C.X1B.X2B, Z2.T1D.T2C.X1B.X2B,
Z3.T1D.T2C.X1B.X2B, Z4.T1D.T2C.X1B.X2B,
Z5.T1D.T2C.X1B.X2B, Z6.T1D.T2C.X1B.X2B,
Z1.T1A.T2D.X1B.X2B, Z2.T1A.T2D.X1B.X2B,
Z3.T1A.T2D.X1B.X2B, Z4.T1A.T2D.X1B.X2B,
Z5.T1A.T2D.X1B.X2B, Z6.T1A.T2D.X1B.X2B,
Z1.T1B.T2D.X1B.X2B, Z2.T1B.T2D.X1B.X2B,
Z3.T1B.T2D.X1B.X2B, Z4.T1B.T2D.X1B.X2B,
Z5.T1B.T2D.X1B.X2B, Z6.T1B.T2D.X1B.X2B,
Z1.T1C.T2D.X1B.X2B, Z2.T1C.T2D.X1B.X2B,
Z3.T1C.T2D.X1B.X2B, Z4.T1C.T2D.X1B.X2B,
Z5.T1C.T2D.X1B.X2B, Z6.T1C.T2D.X1B.X2B,
Z1.T1D.T2D.X1B.X2B, Z2.T1D.T2D.X1B.X2B,
Z3.T1D.T2D.X1B.X2B, Z4.T1D.T2D.X1B.X2B,
Z5.T1D.T2D.X1B.X2B, Z6.T1D.T2D.X1B.X2B,
Z1.T1A.T2A.X1C.X2B, Z2.T1A.T2A.X1C.X2B,
Z3.T1A.T2A.X1C.X2B, Z4.T1A.T2A.X1C.X2B,
Z5.T1A.T2A.X1C.X2B, Z6.T1A.T2A.X1C.X2B,
Z1.T1B.T2A.X1C.X2B, Z2.T1B.T2A.X1C.X2B,
Z3.T1B.T2A.X1C.X2B, Z4.T1B.T2A.X1C.X2B,
Z5.T1B.T2A.X1C.X2B, Z6.T1B.T2A.X1C.X2B,
Z1.T1C.T2A.X1C.X2B, Z2.T1C.T2A.X1C.X2B,
Z3.T1C.T2A.X1C.X2B, Z4.T1C.T2A.X1C.X2B,
Z5.T1C.T2A.X1C.X2B, Z6.T1C.T2A.X1C.X2B,
Z1.T1D.T2A.X1C.X2B, Z2.T1D.T2A.X1C.X2B,
Z3.T1D.T2A.X1C.X2B, Z4.T1D.T2A.X1C.X2B,
Z5.T1D.T2A.X1C.X2B, Z6.T1D.T2A.X1C.X2B,
Z1.T1A.T2B.X1C.X2B, Z2.T1A.T2B.X1C.X2B,
Z3.T1A.T2B.X1C.X2B, Z4.T1A.T2B.X1C.X2B,
Z5.T1A.T2B.X1C.X2B, Z6.T1A.T2B.X1C.X2B,
Z1.T1B.T2B.X1C.X2B, Z2.T1B.T2B.X1C.X2B,
Z3.T1B.T2B.X1C.X2B, Z4.T1B.T2B.X1C.X2B,
Z5.T1B.T2B.X1C.X2B, Z6.T1B.T2B.X1C.X2B,
Z1.T1C.T2B.X1C.X2B, Z2.T1C.T2B.X1C.X2B,
Z3.T1C.T2B.X1C.X2B, Z4.T1C.T2B.X1C.X2B,
Z5.T1C.T2B.X1C.X2B, Z6.T1C.T2B.X1C.X2B,
Z1.T1D.T2B.X1C.X2B, Z2.T1D.T2B.X1C.X2B,
Z3.T1D.T2B.X1C.X2B, Z4.T1D.T2B.X1C.X2B,
Z5.T1D.T2B.X1C.X2B, Z6.T1D.T2B.X1C.X2B,
Z1.T1A.T2C.X1C.X2B, Z2.T1A.T2C.X1C.X2B,
Z3.T1A.T2C.X1C.X2B, Z4.T1A.T2C.X1C.X2B,
Z5.T1A.T2C.X1C.X2B, Z6.T1A.T2C.X1C.X2B,
Z1.T1B.T2C.X1C.X2B, Z2.T1B.T2C.X1C.X2B,
Z3.T1B.T2C.X1C.X2B, Z4.T1B.T2C.X1C.X2B,
Z5.T1B.T2C.X1C.X2B, Z6.T1B.T2C.X1C.X2B,
Z1.T1C.T2C.X1C.X2B, Z2.T1C.T2C.X1C.X2B,
Z3.T1C.T2C.X1C.X2B, Z4.T1C.T2C.X1C.X2B,
Z5.T1C.T2C.X1C.X2B, Z6.T1C.T2C.X1C.X2B,
Z1.T1D.T2C.X1C.X2B, Z2.T1D.T2C.X1C.X2B,
Z3.T1D.T2C.X1C.X2B, Z4.T1D.T2C.X1C.X2B,
Z5.T1D.T2C.X1C.X2B, Z6.T1D.T2C.X1C.X2B,
Z1.T1A.T2D.X1C.X2B, Z2.T1A.T2D.X1C.X2B,
Z3.T1A.T2D.X1C.X2B, Z4.T1A.T2D.X1C.X2B,
Z5.T1A.T2D.X1C.X2B, Z6.T1A.T2D.X1C.X2B,
Z1.T1B.T2D.X1C.X2B, Z2.T1B.T2D.X1C.X2B,
Z3.T1B.T2D.X1C.X2B, Z4.T1B.T2D.X1C.X2B,
Z5.T1B.T2D.X1C.X2B, Z6.T1B.T2D.X1C.X2B,
Z1.T1C.T2D.X1C.X2B, Z2.T1C.T2D.X1C.X2B,
Z3.T1C.T2D.X1C.X2B, Z4.T1C.T2D.X1C.X2B,
Z5.T1C.T2D.X1C.X2B, Z6.T1C.T2D.X1C.X2B,
Z1.T1D.T2D.X1C.X2B, Z2.T1D.T2D.X1C.X2B,
Z3.T1D.T2D.X1C.X2B, Z4.T1D.T2D.X1C.X2B,
Z5.T1D.T2D.X1C.X2B, Z6.T1D.T2D.X1C.X2B,
Z1.T1A.T2A.X1D.X2B, Z2.T1A.T2A.X1D.X2B,
Z3.T1A.T2A.X1D.X2B, Z4.T1A.T2A.X1D.X2B,
Z5.T1A.T2A.X1D.X2B, Z6.T1A.T2A.X1D.X2B,
Z1.T1B.T2A.X1D.X2B, Z2.T1B.T2A.X1D.X2B,
Z3.T1B.T2A.X1D.X2B, Z4.T1B.T2A.X1D.X2B,
Z5.T1B.T2A.X1D.X2B, Z6.T1B.T2A.X1D.X2B,
Z1.T1C.T2A.X1D.X2B, Z2.T1C.T2A.X1D.X2B,
Z3.T1C.T2A.X1D.X2B, Z4.T1C.T2A.X1D.X2B,
Z5.T1C.T2A.X1D.X2B, Z6.T1C.T2A.X1D.X2B,
Z1.T1D.T2A.X1D.X2B, Z2.T1D.T2A.X1D.X2B,
Z3.T1D.T2A.X1D.X2B, Z4.T1D.T2A.X1D.X2B,
Z5.T1D.T2A.X1D.X2B, Z6.T1D.T2A.X1D.X2B,
Z1.T1A.T2B.X1D.X2B, Z2.T1A.T2B.X1D.X2B,

TABLE 6-continued

List of Compound Structures of Formula II

Z3.T1A.T2B.X1D.X2B, Z4.T1A.T2B.X1D.X2B,
Z5.T1A.T2B.X1D.X2B, Z6.T1A.T2B.X1D.X2B,
Z1.T1B.T2B.X1D.X2B, Z2.T1B.T2B.X1D.X2B,
Z3.T1B.T2B.X1D.X2B, Z4.T1B.T2B.X1D.X2B,
Z5.T1B.T2B.X1D.X2B, Z6.T1B.T2B.X1D.X2B,
Z1.T1C.T2B.X1D.X2B, Z2.T1C.T2B.X1D.X2B,
Z3.T1C.T2B.X1D.X2B, Z4.T1C.T2B.X1D.X2B,
Z5.T1C.T2B.X1D.X2B, Z6.T1C.T2B.X1D.X2B,
Z1.T1D.T2B.X1D.X2B, Z2.T1D.T2B.X1D.X2B,
Z3.T1D.T2B.X1D.X2B, Z4.T1D.T2B.X1D.X2B,
Z5.T1D.T2B.X1D.X2B, Z6.T1D.T2B.X1D.X2B,
Z1.T1A.T2C.X1D.X2B, Z2.T1A.T2C.X1D.X2B,
Z3.T1A.T2C.X1D.X2B, Z4.T1A.T2C.X1D.X2B,
Z5.T1A.T2C.X1D.X2B, Z6.T1A.T2C.X1D.X2B,
Z1.T1B.T2C.X1D.X2B, Z2.T1B.T2C.X1D.X2B,
Z3.T1B.T2C.X1D.X2B, Z4.T1B.T2C.X1D.X2B,
Z5.T1B.T2C.X1D.X2B, Z6.T1B.T2C.X1D.X2B,
Z1.T1C.T2C.X1D.X2B, Z2.T1C.T2C.X1D.X2B,
Z3.T1C.T2C.X1D.X2B, Z4.T1C.T2C.X1D.X2B,
Z5.T1C.T2C.X1D.X2B, Z6.T1C.T2C.X1D.X2B,
Z1.T1D.T2C.X1D.X2B, Z2.T1D.T2C.X1D.X2B,
Z3.T1D.T2C.X1D.X2B, Z4.T1D.T2C.X1D.X2B,
Z5.T1D.T2C.X1D.X2B, Z6.T1D.T2C.X1D.X2B,
Z1.T1A.T2D.X1D.X2B, Z2.T1A.T2D.X1D.X2B,
Z3.T1A.T2D.X1D.X2B, Z4.T1A.T2D.X1D.X2B,
Z5.T1A.T2D.X1D.X2B, Z6.T1A.T2D.X1D.X2B,
Z1.T1B.T2D.X1D.X2B, Z2.T1B.T2D.X1D.X2B,
Z3.T1B.T2D.X1D.X2B, Z4.T1B.T2D.X1D.X2B,
Z5.T1B.T2D.X1D.X2B, Z6.T1B.T2D.X1D.X2B,
Z1.T1C.T2D.X1D.X2B, Z2.T1C.T2D.X1D.X2B,
Z3.T1C.T2D.X1D.X2B, Z4.T1C.T2D.X1D.X2B,
Z5.T1C.T2D.X1D.X2B, Z6.T1C.T2D.X1D.X2B,
Z1.T1D.T2D.X1D.X2B, Z2.T1D.T2D.X1D.X2B,
Z3.T1D.T2D.X1D.X2B, Z4.T1D.T2D.X1D.X2B,
Z5.T1D.T2D.X1D.X2B, Z6.T1D.T2D.X1D.X2B,
Z1.T1A.T2A.X1E.X2B, Z2.T1A.T2A.X1E.X2B,
Z3.T1A.T2A.X1E.X2B, Z4.T1A.T2A.X1E.X2B,
Z5.T1A.T2A.X1E.X2B, Z6.T1A.T2A.X1E.X2B,
Z1.T1B.T2A.X1E.X2B, Z2.T1B.T2A.X1E.X2B,
Z3.T1B.T2A.X1E.X2B, Z4.T1B.T2A.X1E.X2B,
Z5.T1B.T2A.X1E.X2B, Z6.T1B.T2A.X1E.X2B,
Z1.T1C.T2A.X1E.X2B, Z2.T1C.T2A.X1E.X2B,
Z3.T1C.T2A.X1E.X2B, Z4.T1C.T2A.X1E.X2B,
Z5.T1C.T2A.X1E.X2B, Z6.T1C.T2A.X1E.X2B,
Z1.T1D.T2A.X1E.X2B, Z2.T1D.T2A.X1E.X2B,
Z3.T1D.T2A.X1E.X2B, Z4.T1D.T2A.X1E.X2B,
Z5.T1D.T2A.X1E.X2B, Z6.T1D.T2A.X1E.X2B,
Z1.T1A.T2B.X1E.X2B, Z2.T1A.T2B.X1E.X2B,
Z3.T1A.T2B.X1E.X2B, Z4.T1A.T2B.X1E.X2B,
Z5.T1A.T2B.X1E.X2B, Z6.T1A.T2B.X1E.X2B,
Z1.T1B.T2B.X1E.X2B, Z2.T1B.T2B.X1E.X2B,
Z3.T1B.T2B.X1E.X2B, Z4.T1B.T2B.X1E.X2B,
Z5.T1B.T2B.X1E.X2B, Z6.T1B.T2B.X1E.X2B,
Z1.T1C.T2B.X1E.X2B, Z2.T1C.T2B.X1E.X2B,
Z3.T1C.T2B.X1E.X2B, Z4.T1C.T2B.X1E.X2B,
Z5.T1C.T2B.X1E.X2B, Z6.T1C.T2B.X1E.X2B,
Z1.T1D.T2B.X1E.X2B, Z2.T1D.T2B.X1E.X2B,
Z3.T1D.T2B.X1E.X2B, Z4.T1D.T2B.X1E.X2B,
Z5.T1D.T2B.X1E.X2B, Z6.T1D.T2B.X1E.X2B,
Z1.T1A.T2C.X1E.X2B, Z2.T1A.T2C.X1E.X2B,
Z3.T1A.T2C.X1E.X2B, Z4.T1A.T2C.X1E.X2B,
Z5.T1A.T2C.X1E.X2B, Z6.T1A.T2C.X1E.X2B,
Z1.T1B.T2C.X1E.X2B, Z2.T1B.T2C.X1E.X2B,
Z3.T1B.T2C.X1E.X2B, Z4.T1B.T2C.X1E.X2B,
Z5.T1B.T2C.X1E.X2B, Z6.T1B.T2C.X1E.X2B,
Z1.T1C.T2C.X1E.X2B, Z2.T1C.T2C.X1E.X2B,
Z3.T1C.T2C.X1E.X2B, Z4.T1C.T2C.X1E.X2B,
Z5.T1C.T2C.X1E.X2B, Z6.T1C.T2C.X1E.X2B,
Z1.T1D.T2C.X1E.X2B, Z2.T1D.T2C.X1E.X2B,
Z3.T1D.T2C.X1E.X2B, Z4.T1D.T2C.X1E.X2B,
Z5.T1D.T2C.X1E.X2B, Z6.T1D.T2C.X1E.X2B,
Z1.T1A.T2D.X1E.X2B, Z2.T1A.T2D.X1E.X2B,
Z3.T1A.T2D.X1E.X2B, Z4.T1A.T2D.X1E.X2B,
Z5.T1A.T2D.X1E.X2B, Z6.T1A.T2D.X1E.X2B,
Z1.T1B.T2D.X1E.X2B, Z2.T1B.T2D.X1E.X2B,
Z3.T1B.T2D.X1E.X2B, Z4.T1B.T2D.X1E.X2B,
Z5.T1B.T2D.X1E.X2B, Z6.T1B.T2D.X1E.X2B,
Z1.T1C.T2D.X1E.X2B, Z2.T1C.T2D.X1E.X2B,
Z3.T1C.T2D.X1E.X2B, Z4.T1C.T2D.X1E.X2B,
Z5.T1C.T2D.X1E.X2B, Z6.T1C.T2D.X1E.X2B,
Z1.T1D.T2D.X1E.X2B, Z2.T1D.T2D.X1E.X2B,
Z3.T1D.T2D.X1E.X2B, Z4.T1D.T2D.X1E.X2B,
Z5.T1D.T2D.X1E.X2B, Z6.T1D.T2D.X1E.X2B,
Z1.T1A.T2A.X1A.X2C, Z2.T1A.T2A.X1A.X2C,
Z3.T1A.T2A.X1A.X2C, Z4.T1A.T2A.X1A.X2C,
Z5.T1A.T2A.X1A.X2C, Z6.T1A.T2A.X1A.X2C,
Z1.T1B.T2A.X1A.X2C, Z2.T1B.T2A.X1A.X2C,
Z3.T1B.T2A.X1A.X2C, Z4.T1B.T2A.X1A.X2C,
Z5.T1B.T2A.X1A.X2C, Z6.T1B.T2A.X1A.X2C,
Z1.T1C.T2A.X1A.X2C, Z2.T1C.T2A.X1A.X2C,
Z3.T1C.T2A.X1A.X2C, Z4.T1C.T2A.X1A.X2C,
Z5.T1C.T2A.X1A.X2C, Z6.T1C.T2A.X1A.X2C,
Z1.T1D.T2A.X1A.X2C, Z2.T1D.T2A.X1A.X2C,
Z3.T1D.T2A.X1A.X2C, Z4.T1D.T2A.X1A.X2C,
Z5.T1D.T2A.X1A.X2C, Z6.T1D.T2A.X1A.X2C,
Z1.T1A.T2B.X1A.X2C, Z2.T1A.T2B.X1A.X2C,
Z3.T1A.T2B.X1A.X2C, Z4.T1A.T2B.X1A.X2C,
Z5.T1A.T2B.X1A.X2C, Z6.T1A.T2B.X1A.X2C,
Z1.T1B.T2B.X1A.X2C, Z2.T1B.T2B.X1A.X2C,
Z3.T1B.T2B.X1A.X2C, Z4.T1B.T2B.X1A.X2C,
Z5.T1B.T2B.X1A.X2C, Z6.T1B.T2B.X1A.X2C,
Z1.T1C.T2B.X1A.X2C, Z2.T1C.T2B.X1A.X2C,
Z3.T1C.T2B.X1A.X2C, Z4.T1C.T2B.X1A.X2C,
Z5.T1C.T2B.X1A.X2C, Z6.T1C.T2B.X1A.X2C,
Z1.T1D.T2B.X1A.X2C, Z2.T1D.T2B.X1A.X2C,
Z3.T1D.T2B.X1A.X2C, Z4.T1D.T2B.X1A.X2C,
Z5.T1D.T2B.X1A.X2C, Z6.T1D.T2B.X1A.X2C,
Z1.T1A.T2C.X1A.X2C, Z2.T1A.T2C.X1A.X2C,
Z3.T1A.T2C.X1A.X2C, Z4.T1A.T2C.X1A.X2C,
Z5.T1A.T2C.X1A.X2C, Z6.T1A.T2C.X1A.X2C,
Z1.T1B.T2C.X1A.X2C, Z2.T1B.T2C.X1A.X2C,
Z3.T1B.T2C.X1A.X2C, Z4.T1B.T2C.X1A.X2C,
Z5.T1B.T2C.X1A.X2C, Z6.T1B.T2C.X1A.X2C,
Z1.T1C.T2C.X1A.X2C, Z2.T1C.T2C.X1A.X2C,
Z3.T1C.T2C.X1A.X2C, Z4.T1C.T2C.X1A.X2C,
Z5.T1C.T2C.X1A.X2C, Z6.T1C.T2C.X1A.X2C,
Z1.T1D.T2C.X1A.X2C, Z2.T1D.T2C.X1A.X2C,
Z3.T1D.T2C.X1A.X2C, Z4.T1D.T2C.X1A.X2C,
Z5.T1D.T2C.X1A.X2C, Z6.T1D.T2C.X1A.X2C,
Z1.T1A.T2D.X1A.X2C, Z2.T1A.T2D.X1A.X2C,
Z3.T1A.T2D.X1A.X2C, Z4.T1A.T2D.X1A.X2C,
Z5.T1A.T2D.X1A.X2C, Z6.T1A.T2D.X1A.X2C,
Z1.T1B.T2D.X1A.X2C, Z2.T1B.T2D.X1A.X2C,
Z3.T1B.T2D.X1A.X2C, Z4.T1B.T2D.X1A.X2C,
Z5.T1B.T2D.X1A.X2C, Z6.T1B.T2D.X1A.X2C,
Z1.T1C.T2D.X1A.X2C, Z2.T1C.T2D.X1A.X2C,
Z3.T1C.T2D.X1A.X2C, Z4.T1C.T2D.X1A.X2C,
Z5.T1C.T2D.X1A.X2C, Z6.T1C.T2D.X1A.X2C,
Z1.T1D.T2D.X1A.X2C, Z2.T1D.T2D.X1A.X2C,
Z3.T1D.T2D.X1A.X2C, Z4.T1D.T2D.X1A.X2C,
Z5.T1D.T2D.X1A.X2C, Z6.T1D.T2D.X1A.X2C,
Z1.T1A.T2A.X1B.X2C, Z2.T1A.T2A.X1B.X2C,
Z3.T1A.T2A.X1B.X2C, Z4.T1A.T2A.X1B.X2C,
Z5.T1A.T2A.X1B.X2C, Z6.T1A.T2A.X1B.X2C,
Z1.T1B.T2A.X1B.X2C, Z2.T1B.T2A.X1B.X2C,
Z3.T1B.T2A.X1B.X2C, Z4.T1B.T2A.X1B.X2C,
Z5.T1B.T2A.X1B.X2C, Z6.T1B.T2A.X1B.X2C,
Z1.T1C.T2A.X1B.X2C, Z2.T1C.T2A.X1B.X2C,
Z3.T1C.T2A.X1B.X2C, Z4.T1C.T2A.X1B.X2C,
Z5.T1C.T2A.X1B.X2C, Z6.T1C.T2A.X1B.X2C,
Z1.T1D.T2A.X1B.X2C, Z2.T1D.T2A.X1B.X2C,
Z3.T1D.T2A.X1B.X2C, Z4.T1D.T2A.X1B.X2C,
Z5.T1D.T2A.X1B.X2C, Z6.T1D.T2A.X1B.X2C,
Z1.T1A.T2B.X1B.X2C, Z2.T1A.T2B.X1B.X2C,
Z3.T1A.T2B.X1B.X2C, Z4.T1A.T2B.X1B.X2C,
Z5.T1A.T2B.X1B.X2C, Z6.T1A.T2B.X1B.X2C,
Z1.T1B.T2B.X1B.X2C, Z2.T1B.T2B.X1B.X2C,
Z3.T1B.T2B.X1B.X2C, Z4.T1B.T2B.X1B.X2C,
Z5.T1B.T2B.X1B.X2C, Z6.T1B.T2B.X1B.X2C,
Z1.T1C.T2B.X1B.X2C, Z2.T1C.T2B.X1B.X2C,
Z3.T1C.T2B.X1B.X2C, Z4.T1C.T2B.X1B.X2C,
Z5.T1C.T2B.X1B.X2C, Z6.T1C.T2B.X1B.X2C,
Z1.T1D.T2B.X1B.X2C, Z2.T1D.T2B.X1B.X2C,
Z3.T1D.T2B.X1B.X2C, Z4.T1D.T2B.X1B.X2C,
Z5.T1D.T2B.X1B.X2C, Z6.T1D.T2B.X1B.X2C,
Z1.T1A.T2C.X1B.X2C, Z2.T1A.T2C.X1B.X2C,

TABLE 6-continued

List of Compound Structures of Formula II

Z3.T1A.T2C.X1B.X2C, Z4.T1A.T2C.X1B.X2C,
Z5.T1A.T2C.X1B.X2C, Z6.T1A.T2C.X1B.X2C,
Z1.T1B.T2C.X1B.X2C, Z2.T1B.T2C.X1B.X2C,
Z3.T1B.T2C.X1B.X2C, Z4.T1B.T2C.X1B.X2C,
Z5.T1B.T2C.X1B.X2C, Z6.T1B.T2C.X1B.X2C,
Z1.T1C.T2C.X1B.X2C, Z2.T1C.T2C.X1B.X2C,
Z3.T1C.T2C.X1B.X2C, Z4.T1C.T2C.X1B.X2C,
Z5.T1C.T2C.X1B.X2C, Z6.T1C.T2C.X1B.X2C,
Z1.T1D.T2C.X1B.X2C, Z2.T1D.T2C.X1B.X2C,
Z3.T1D.T2C.X1B.X2C, Z4.T1D.T2C.X1B.X2C,
Z5.T1D.T2C.X1B.X2C, Z6.T1D.T2C.X1B.X2C,
Z1.T1A.T2D.X1B.X2C, Z2.T1A.T2D.X1B.X2C,
Z3.T1A.T2D.X1B.X2C, Z4.T1A.T2D.X1B.X2C,
Z5.T1A.T2D.X1B.X2C, Z6.T1A.T2D.X1B.X2C,
Z1.T1B.T2D.X1B.X2C, Z2.T1B.T2D.X1B.X2C,
Z3.T1B.T2D.X1B.X2C, Z4.T1B.T2D.X1B.X2C,
Z5.T1B.T2D.X1B.X2C, Z6.T1B.T2D.X1B.X2C,
Z1.T1C.T2D.X1B.X2C, Z2.T1C.T2D.X1B.X2C,
Z3.T1C.T2D.X1B.X2C, Z4.T1C.T2D.X1B.X2C,
Z5.T1C.T2D.X1B.X2C, Z6.T1C.T2D.X1B.X2C,
Z1.T1D.T2D.X1B.X2C, Z2.T1D.T2D.X1B.X2C,
Z3.T1D.T2D.X1B.X2C, Z4.T1D.T2D.X1B.X2C,
Z5.T1D.T2D.X1B.X2C, Z6.T1D.T2D.X1B.X2C,
Z1.T1A.T2A.X1C.X2C, Z2.T1A.T2A.X1C.X2C,
Z3.T1A.T2A.X1C.X2C, Z4.T1A.T2A.X1C.X2C,
Z5.T1A.T2A.X1C.X2C, Z6.T1A.T2A.X1C.X2C,
Z1.T1B.T2A.X1C.X2C, Z2.T1B.T2A.X1C.X2C,
Z3.T1B.T2A.X1C.X2C, Z4.T1B.T2A.X1C.X2C,
Z5.T1B.T2A.X1C.X2C, Z6.T1B.T2A.X1C.X2C,
Z1.T1C.T2A.X1C.X2C, Z2.T1C.T2A.X1C.X2C,
Z3.T1C.T2A.X1C.X2C, Z4.T1C.T2A.X1C.X2C,
Z5.T1C.T2A.X1C.X2C, Z6.T1C.T2A.X1C.X2C,
Z1.T1D.T2A.X1C.X2C, Z2.T1D.T2A.X1C.X2C,
Z3.T1D.T2A.X1C.X2C, Z4.T1D.T2A.X1C.X2C,
Z5.T1D.T2A.X1C.X2C, Z6.T1D.T2A.X1C.X2C,
Z1.T1A.T2B.X1C.X2C, Z2.T1A.T2B.X1C.X2C,
Z3.T1A.T2B.X1C.X2C, Z4.T1A.T2B.X1C.X2C,
Z5.T1A.T2B.X1C.X2C, Z6.T1A.T2B.X1C.X2C,
Z1.T1B.T2B.X1C.X2C, Z2.T1B.T2B.X1C.X2C,
Z3.T1B.T2B.X1C.X2C, Z4.T1B.T2B.X1C.X2C,
Z5.T1B.T2B.X1C.X2C, Z6.T1B.T2B.X1C.X2C,
Z1.T1C.T2B.X1C.X2C, Z2.T1C.T2B.X1C.X2C,
Z3.T1C.T2B.X1C.X2C, Z4.T1C.T2B.X1C.X2C,
Z5.T1C.T2B.X1C.X2C, Z6.T1C.T2B.X1C.X2C,
Z1.T1D.T2B.X1C.X2C, Z2.T1D.T2B.X1C.X2C,
Z3.T1D.T2B.X1C.X2C, Z4.T1D.T2B.X1C.X2C,
Z5.T1D.T2B.X1C.X2C, Z6.T1D.T2B.X1C.X2C,
Z1.T1A.T2C.X1C.X2C, Z2.T1A.T2C.X1C.X2C,
Z3.T1A.T2C.X1C.X2C, Z4.T1A.T2C.X1C.X2C,
Z5.T1A.T2C.X1C.X2C, Z6.T1A.T2C.X1C.X2C,
Z1.T1B.T2C.X1C.X2C, Z2.T1B.T2C.X1C.X2C,
Z3.T1B.T2C.X1C.X2C, Z4.T1B.T2C.X1C.X2C,
Z5.T1B.T2C.X1C.X2C, Z6.T1B.T2C.X1C.X2C,
Z1.T1C.T2C.X1C.X2C, Z2.T1C.T2C.X1C.X2C,
Z3.T1C.T2C.X1C.X2C, Z4.T1C.T2C.X1C.X2C,
Z5.T1C.T2C.X1C.X2C, Z6.T1C.T2C.X1C.X2C,
Z1.T1D.T2C.X1C.X2C, Z2.T1D.T2C.X1C.X2C,
Z3.T1D.T2C.X1C.X2C, Z4.T1D.T2C.X1C.X2C,
Z5.T1D.T2C.X1C.X2C, Z6.T1D.T2C.X1C.X2C,
Z1.T1A.T2D.X1C.X2C, Z2.T1A.T2D.X1C.X2C,
Z3.T1A.T2D.X1C.X2C, Z4.T1A.T2D.X1C.X2C,
Z5.T1A.T2D.X1C.X2C, Z6.T1A.T2D.X1C.X2C,
Z1.T1B.T2D.X1C.X2C, Z2.T1B.T2D.X1C.X2C,
Z3.T1B.T2D.X1C.X2C, Z4.T1B.T2D.X1C.X2C,
Z5.T1B.T2D.X1C.X2C, Z6.T1B.T2D.X1C.X2C,
Z1.T1C.T2D.X1C.X2C, Z2.T1C.T2D.X1C.X2C,
Z3.T1C.T2D.X1C.X2C, Z4.T1C.T2D.X1C.X2C,
Z5.T1C.T2D.X1C.X2C, Z6.T1C.T2D.X1C.X2C,
Z1.T1D.T2D.X1C.X2C, Z2.T1D.T2D.X1C.X2C,
Z3.T1D.T2D.X1C.X2C, Z4.T1D.T2D.X1C.X2C,
Z5.T1D.T2D.X1C.X2C, Z6.T1D.T2D.X1C.X2C,
Z1.T1A.T2A.X1D.X2C, Z2.T1A.T2A.X1D.X2C,
Z3.T1A.T2A.X1D.X2C, Z4.T1A.T2A.X1D.X2C,
Z5.T1A.T2A.X1D.X2C, Z6.T1A.T2A.X1D.X2C,
Z1.T1B.T2A.X1D.X2C, Z2.T1B.T2A.X1D.X2C,
Z3.T1B.T2A.X1D.X2C, Z4.T1B.T2A.X1D.X2C,
Z5.T1B.T2A.X1D.X2C, Z6.T1B.T2A.X1D.X2C,
Z1.T1C.T2A.X1D.X2C, Z2.T1C.T2A.X1D.X2C,
Z3.T1C.T2A.X1D.X2C, Z4.T1C.T2A.X1D.X2C,
Z5.T1C.T2A.X1D.X2C, Z6.T1C.T2A.X1D.X2C,
Z1.T1D.T2A.X1D.X2C, Z2.T1D.T2A.X1D.X2C,
Z3.T1D.T2A.X1D.X2C, Z4.T1D.T2A.X1D.X2C,
Z5.T1D.T2A.X1D.X2C, Z6.T1D.T2A.X1D.X2C,
Z1.T1A.T2B.X1D.X2C, Z2.T1A.T2B.X1D.X2C,
Z3.T1A.T2B.X1D.X2C, Z4.T1A.T2B.X1D.X2C,
Z5.T1A.T2B.X1D.X2C, Z6.T1A.T2B.X1D.X2C,
Z1.T1B.T2B.X1D.X2C, Z2.T1B.T2B.X1D.X2C,
Z3.T1B.T2B.X1D.X2C, Z4.T1B.T2B.X1D.X2C,
Z5.T1B.T2B.X1D.X2C, Z6.T1B.T2B.X1D.X2C,
Z1.T1C.T2B.X1D.X2C, Z2.T1C.T2B.X1D.X2C,
Z3.T1C.T2B.X1D.X2C, Z4.T1C.T2B.X1D.X2C,
Z5.T1C.T2B.X1D.X2C, Z6.T1C.T2B.X1D.X2C,
Z1.T1D.T2B.X1D.X2C, Z2.T1D.T2B.X1D.X2C,
Z3.T1D.T2B.X1D.X2C, Z4.T1D.T2B.X1D.X2C,
Z5.T1D.T2B.X1D.X2C, Z6.T1D.T2B.X1D.X2C,
Z1.T1A.T2C.X1D.X2C, Z2.T1A.T2C.X1D.X2C,
Z3.T1A.T2C.X1D.X2C, Z4.T1A.T2C.X1D.X2C,
Z5.T1A.T2C.X1D.X2C, Z6.T1A.T2C.X1D.X2C,
Z1.T1B.T2C.X1D.X2C, Z2.T1B.T2C.X1D.X2C,
Z3.T1B.T2C.X1D.X2C, Z4.T1B.T2C.X1D.X2C,
Z5.T1B.T2C.X1D.X2C, Z6.T1B.T2C.X1D.X2C,
Z1.T1C.T2C.X1D.X2C, Z2.T1C.T2C.X1D.X2C,
Z3.T1C.T2C.X1D.X2C, Z4.T1C.T2C.X1D.X2C,
Z5.T1C.T2C.X1D.X2C, Z6.T1C.T2C.X1D.X2C,
Z1.T1D.T2C.X1D.X2C, Z2.T1D.T2C.X1D.X2C,
Z3.T1D.T2C.X1D.X2C, Z4.T1D.T2C.X1D.X2C,
Z5.T1D.T2C.X1D.X2C, Z6.T1D.T2C.X1D.X2C,
Z1.T1A.T2D.X1D.X2C, Z2.T1A.T2D.X1D.X2C,
Z3.T1A.T2D.X1D.X2C, Z4.T1A.T2D.X1D.X2C,
Z5.T1A.T2D.X1D.X2C, Z6.T1A.T2D.X1D.X2C,
Z1.T1B.T2D.X1D.X2C, Z2.T1B.T2D.X1D.X2C,
Z3.T1B.T2D.X1D.X2C, Z4.T1B.T2D.X1D.X2C,
Z5.T1B.T2D.X1D.X2C, Z6.T1B.T2D.X1D.X2C,
Z1.T1C.T2D.X1D.X2C, Z2.T1C.T2D.X1D.X2C,
Z3.T1C.T2D.X1D.X2C, Z4.T1C.T2D.X1D.X2C,
Z5.T1C.T2D.X1D.X2C, Z6.T1C.T2D.X1D.X2C,
Z1.T1D.T2D.X1D.X2C, Z2.T1D.T2D.X1D.X2C,
Z3.T1D.T2D.X1D.X2C, Z4.T1D.T2D.X1D.X2C,
Z5.T1D.T2D.X1D.X2C, Z6.T1D.T2D.X1D.X2C,
Z1.T1A.T2A.X1E.X2C, Z2.T1A.T2A.X1E.X2C,
Z3.T1A.T2A.X1E.X2C, Z4.T1A.T2A.X1E.X2C,
Z5.T1A.T2A.X1E.X2C, Z6.T1A.T2A.X1E.X2C,
Z1.T1B.T2A.X1E.X2C, Z2.T1B.T2A.X1E.X2C,
Z3.T1B.T2A.X1E.X2C, Z4.T1B.T2A.X1E.X2C,
Z5.T1B.T2A.X1E.X2C, Z6.T1B.T2A.X1E.X2C,
Z1.T1C.T2A.X1E.X2C, Z2.T1C.T2A.X1E.X2C,
Z3.T1C.T2A.X1E.X2C, Z4.T1C.T2A.X1E.X2C,
Z5.T1C.T2A.X1E.X2C, Z6.T1C.T2A.X1E.X2C,
Z1.T1D.T2A.X1E.X2C, Z2.T1D.T2A.X1E.X2C,
Z3.T1D.T2A.X1E.X2C, Z4.T1D.T2A.X1E.X2C,
Z5.T1D.T2A.X1E.X2C, Z6.T1D.T2A.X1E.X2C,
Z1.T1A.T2B.X1E.X2C, Z2.T1A.T2B.X1E.X2C,
Z3.T1A.T2B.X1E.X2C, Z4.T1A.T2B.X1E.X2C,
Z5.T1A.T2B.X1E.X2C, Z6.T1A.T2B.X1E.X2C,
Z1.T1B.T2B.X1E.X2C, Z2.T1B.T2B.X1E.X2C,
Z3.T1B.T2B.X1E.X2C, Z4.T1B.T2B.X1E.X2C,
Z5.T1B.T2B.X1E.X2C, Z6.T1B.T2B.X1E.X2C,
Z1.T1C.T2B.X1E.X2C, Z2.T1C.T2B.X1E.X2C,
Z3.T1C.T2B.X1E.X2C, Z4.T1C.T2B.X1E.X2C,
Z5.T1C.T2B.X1E.X2C, Z6.T1C.T2B.X1E.X2C,
Z1.T1D.T2B.X1E.X2C, Z2.T1D.T2B.X1E.X2C,
Z3.T1D.T2B.X1E.X2C, Z4.T1D.T2B.X1E.X2C,
Z5.T1D.T2B.X1E.X2C, Z6.T1D.T2B.X1E.X2C,
Z1.T1A.T2C.X1E.X2C, Z2.T1A.T2C.X1E.X2C,
Z3.T1A.T2C.X1E.X2C, Z4.T1A.T2C.X1E.X2C,
Z5.T1A.T2C.X1E.X2C, Z6.T1A.T2C.X1E.X2C,
Z1.T1B.T2C.X1E.X2C, Z2.T1B.T2C.X1E.X2C,
Z3.T1B.T2C.X1E.X2C, Z4.T1B.T2C.X1E.X2C,
Z5.T1B.T2C.X1E.X2C, Z6.T1B.T2C.X1E.X2C,
Z1.T1C.T2C.X1E.X2C, Z2.T1C.T2C.X1E.X2C,
Z3.T1C.T2C.X1E.X2C, Z4.T1C.T2C.X1E.X2C,
Z5.T1C.T2C.X1E.X2C, Z6.T1C.T2C.X1E.X2C,
Z1.T1D.T2C.X1E.X2C, Z2.T1D.T2C.X1E.X2C,
Z3.T1D.T2C.X1E.X2C, Z4.T1D.T2C.X1E.X2C,
Z5.T1D.T2C.X1E.X2C, Z6.T1D.T2C.X1E.X2C,
Z1.T1A.T2D.X1E.X2C, Z2.T1A.T2D.X1E.X2C,

TABLE 6-continued

List of Compound Structures of Formula II

Z3.T1A.T2D.X1E.X2C, Z4.T1A.T2D.X1E.X2C,
Z5.T1A.T2D.X1E.X2C, Z6.T1A.T2D.X1E.X2C,
Z1.T1B.T2D.X1E.X2C, Z2.T1B.T2D.X1E.X2C,
Z3.T1B.T2D.X1E.X2C, Z4.T1B.T2D.X1E.X2C,
Z5.T1B.T2D.X1E.X2C, Z6.T1B.T2D.X1E.X2C,
Z1.T1C.T2D.X1E.X2C, Z2.T1C.T2D.X1E.X2C,
Z3.T1C.T2D.X1E.X2C, Z4.T1C.T2D.X1E.X2C,
Z5.T1C.T2D.X1E.X2C, Z6.T1C.T2D.X1E.X2C,
Z1.T1D.T2D.X1E.X2C, Z2.T1D.T2D.X1E.X2C,
Z3.T1D.T2D.X1E.X2C, Z4.T1D.T2D.X1E.X2C,
Z5.T1D.T2D.X1E.X2C, Z6.T1D.T2D.X1E.X2C,
Z1.T1A.T2A.X1A.X2D, Z2.T1A.T2A.X1A.X2D,
Z3.T1A.T2A.X1A.X2D, Z4.T1A.T2A.X1A.X2D,
Z5.T1A.T2A.X1A.X2D, Z6.T1A.T2A.X1A.X2D,
Z1.T1B.T2A.X1A.X2D, Z2.T1B.T2A.X1A.X2D,
Z3.T1B.T2A.X1A.X2D, Z4.T1B.T2A.X1A.X2D,
Z5.T1B.T2A.X1A.X2D, Z6.T1B.T2A.X1A.X2D,
Z1.T1C.T2A.X1A.X2D, Z2.T1C.T2A.X1A.X2D,
Z3.T1C.T2A.X1A.X2D, Z4.T1C.T2A.X1A.X2D,
Z5.T1C.T2A.X1A.X2D, Z6.T1C.T2A.X1A.X2D,
Z1.T1D.T2A.X1A.X2D, Z2.T1D.T2A.X1A.X2D,
Z3.T1D.T2A.X1A.X2D, Z4.T1D.T2A.X1A.X2D,
Z5.T1D.T2A.X1A.X2D, Z6.T1D.T2A.X1A.X2D,
Z1.T1A.T2B.X1A.X2D, Z2.T1A.T2B.X1A.X2D,
Z3.T1A.T2B.X1A.X2D, Z4.T1A.T2B.X1A.X2D,
Z5.T1A.T2B.X1A.X2D, Z6.T1A.T2B.X1A.X2D,
Z1.T1B.T2B.X1A.X2D, Z2.T1B.T2B.X1A.X2D,
Z3.T1B.T2B.X1A.X2D, Z4.T1B.T2B.X1A.X2D,
Z5.T1B.T2B.X1A.X2D, Z6.T1B.T2B.X1A.X2D,
Z1.T1C.T2B.X1A.X2D, Z2.T1C.T2B.X1A.X2D,
Z3.T1C.T2B.X1A.X2D, Z4.T1C.T2B.X1A.X2D,
Z5.T1C.T2B.X1A.X2D, Z6.T1C.T2B.X1A.X2D,
Z1.T1D.T2B.X1A.X2D, Z2.T1D.T2B.X1A.X2D,
Z3.T1D.T2B.X1A.X2D, Z4.T1D.T2B.X1A.X2D,
Z5.T1D.T2B.X1A.X2D, Z6.T1D.T2B.X1A.X2D,
Z1.T1A.T2C.X1A.X2D, Z2.T1A.T2C.X1A.X2D,
Z3.T1A.T2C.X1A.X2D, Z4.T1A.T2C.X1A.X2D,
Z5.T1A.T2C.X1A.X2D, Z6.T1A.T2C.X1A.X2D,
Z1.T1B.T2C.X1A.X2D, Z2.T1B.T2C.X1A.X2D,
Z3.T1B.T2C.X1A.X2D, Z4.T1B.T2C.X1A.X2D,
Z5.T1B.T2C.X1A.X2D, Z6.T1B.T2C.X1A.X2D,
Z1.T1C.T2C.X1A.X2D, Z2.T1C.T2C.X1A.X2D,
Z3.T1C.T2C.X1A.X2D, Z4.T1C.T2C.X1A.X2D,
Z5.T1C.T2C.X1A.X2D, Z6.T1C.T2C.X1A.X2D,
Z1.T1D.T2C.X1A.X2D, Z2.T1D.T2C.X1A.X2D,
Z3.T1D.T2C.X1A.X2D, Z4.T1D.T2C.X1A.X2D,
Z5.T1D.T2C.X1A.X2D, Z6.T1D.T2C.X1A.X2D,
Z1.T1A.T2D.X1A.X2D, Z2.T1A.T2D.X1A.X2D,
Z3.T1A.T2D.X1A.X2D, Z4.T1A.T2D.X1A.X2D,
Z5.T1A.T2D.X1A.X2D, Z6.T1A.T2D.X1A.X2D,
Z1.T1B.T2D.X1A.X2D, Z2.T1B.T2D.X1A.X2D,
Z3.T1B.T2D.X1A.X2D, Z4.T1B.T2D.X1A.X2D,
Z5.T1B.T2D.X1A.X2D, Z6.T1B.T2D.X1A.X2D,
Z1.T1C.T2D.X1A.X2D, Z2.T1C.T2D.X1A.X2D,
Z3.T1C.T2D.X1A.X2D, Z4.T1C.T2D.X1A.X2D,
Z5.T1C.T2D.X1A.X2D, Z6.T1C.T2D.X1A.X2D,
Z1.T1D.T2D.X1A.X2D, Z2.T1D.T2D.X1A.X2D,
Z3.T1D.T2D.X1A.X2D, Z4.T1D.T2D.X1A.X2D,
Z5.T1D.T2D.X1A.X2D, Z6.T1D.T2D.X1A.X2D,
Z1.T1A.T2A.X1B.X2D, Z2.T1A.T2A.X1B.X2D,
Z3.T1A.T2A.X1B.X2D, Z4.T1A.T2A.X1B.X2D,
Z5.T1A.T2A.X1B.X2D, Z6.T1A.T2A.X1B.X2D,
Z1.T1B.T2A.X1B.X2D, Z2.T1B.T2A.X1B.X2D,
Z3.T1B.T2A.X1B.X2D, Z4.T1B.T2A.X1B.X2D,
Z5.T1B.T2A.X1B.X2D, Z6.T1B.T2A.X1B.X2D,
Z1.T1C.T2A.X1B.X2D, Z2.T1C.T2A.X1B.X2D,
Z3.T1C.T2A.X1B.X2D, Z4.T1C.T2A.X1B.X2D,
Z5.T1C.T2A.X1B.X2D, Z6.T1C.T2A.X1B.X2D,
Z1.T1D.T2A.X1B.X2D, Z2.T1D.T2A.X1B.X2D,
Z3.T1D.T2A.X1B.X2D, Z4.T1D.T2A.X1B.X2D,
Z5.T1D.T2A.X1B.X2D, Z6.T1D.T2A.X1B.X2D,
Z1.T1A.T2B.X1B.X2D, Z2.T1A.T2B.X1B.X2D,
Z3.T1A.T2B.X1B.X2D, Z4.T1A.T2B.X1B.X2D,
Z5.T1A.T2B.X1B.X2D, Z6.T1A.T2B.X1B.X2D,
Z1.T1B.T2B.X1B.X2D, Z2.T1B.T2B.X1B.X2D,
Z3.T1B.T2B.X1B.X2D, Z4.T1B.T2B.X1B.X2D,
Z5.T1B.T2B.X1B.X2D, Z6.T1B.T2B.X1B.X2D,
Z1.T1C.T2B.X1B.X2D, Z2.T1C.T2B.X1B.X2D,
Z3.T1C.T2B.X1B.X2D, Z4.T1C.T2B.X1B.X2D,
Z5.T1C.T2B.X1B.X2D, Z6.T1C.T2B.X1B.X2D,
Z1.T1D.T2B.X1B.X2D, Z2.T1D.T2B.X1B.X2D,
Z3.T1D.T2B.X1B.X2D, Z4.T1D.T2B.X1B.X2D,
Z5.T1D.T2B.X1B.X2D, Z6.T1D.T2B.X1B.X2D,
Z1.T1A.T2C.X1B.X2D, Z2.T1A.T2C.X1B.X2D,
Z3.T1A.T2C.X1B.X2D, Z4.T1A.T2C.X1B.X2D,
Z5.T1A.T2C.X1B.X2D, Z6.T1A.T2C.X1B.X2D,
Z1.T1B.T2C.X1B.X2D, Z2.T1B.T2C.X1B.X2D,
Z3.T1B.T2C.X1B.X2D, Z4.T1B.T2C.X1B.X2D,
Z5.T1B.T2C.X1B.X2D, Z6.T1B.T2C.X1B.X2D,
Z1.T1C.T2C.X1B.X2D, Z2.T1C.T2C.X1B.X2D,
Z3.T1C.T2C.X1B.X2D, Z4.T1C.T2C.X1B.X2D,
Z5.T1C.T2C.X1B.X2D, Z6.T1C.T2C.X1B.X2D,
Z1.T1D.T2C.X1B.X2D, Z2.T1D.T2C.X1B.X2D,
Z3.T1D.T2C.X1B.X2D, Z4.T1D.T2C.X1B.X2D,
Z5.T1D.T2C.X1B.X2D, Z6.T1D.T2C.X1B.X2D,
Z1.T1A.T2D.X1B.X2D, Z2.T1A.T2D.X1B.X2D,
Z3.T1A.T2D.X1B.X2D, Z4.T1A.T2D.X1B.X2D,
Z5.T1A.T2D.X1B.X2D, Z6.T1A.T2D.X1B.X2D,
Z1.T1B.T2D.X1B.X2D, Z2.T1B.T2D.X1B.X2D,
Z3.T1B.T2D.X1B.X2D, Z4.T1B.T2D.X1B.X2D,
Z5.T1B.T2D.X1B.X2D, Z6.T1B.T2D.X1B.X2D,
Z1.T1C.T2D.X1B.X2D, Z2.T1C.T2D.X1B.X2D,
Z3.T1C.T2D.X1B.X2D, Z4.T1C.T2D.X1B.X2D,
Z5.T1C.T2D.X1B.X2D, Z6.T1C.T2D.X1B.X2D,
Z1.T1D.T2D.X1B.X2D, Z2.T1D.T2D.X1B.X2D,
Z3.T1D.T2D.X1B.X2D, Z4.T1D.T2D.X1B.X2D,
Z5.T1D.T2D.X1B.X2D, Z6.T1D.T2D.X1B.X2D,
Z1.T1A.T2A.X1C.X2D, Z2.T1A.T2A.X1C.X2D,
Z3.T1A.T2A.X1C.X2D, Z4.T1A.T2A.X1C.X2D,
Z5.T1A.T2A.X1C.X2D, Z6.T1A.T2A.X1C.X2D,
Z1.T1B.T2A.X1C.X2D, Z2.T1B.T2A.X1C.X2D,
Z3.T1B.T2A.X1C.X2D, Z4.T1B.T2A.X1C.X2D,
Z5.T1B.T2A.X1C.X2D, Z6.T1B.T2A.X1C.X2D,
Z1.T1C.T2A.X1C.X2D, Z2.T1C.T2A.X1C.X2D,
Z3.T1C.T2A.X1C.X2D, Z4.T1C.T2A.X1C.X2D,
Z5.T1C.T2A.X1C.X2D, Z6.T1C.T2A.X1C.X2D,
Z1.T1D.T2A.X1C.X2D, Z2.T1D.T2A.X1C.X2D,
Z3.T1D.T2A.X1C.X2D, Z4.T1D.T2A.X1C.X2D,
Z5.T1D.T2A.X1C.X2D, Z6.T1D.T2A.X1C.X2D,
Z1.T1A.T2B.X1C.X2D, Z2.T1A.T2B.X1C.X2D,
Z3.T1A.T2B.X1C.X2D, Z4.T1A.T2B.X1C.X2D,
Z5.T1A.T2B.X1C.X2D, Z6.T1A.T2B.X1C.X2D,
Z1.T1B.T2B.X1C.X2D, Z2.T1B.T2B.X1C.X2D,
Z3.T1B.T2B.X1C.X2D, Z4.T1B.T2B.X1C.X2D,
Z5.T1B.T2B.X1C.X2D, Z6.T1B.T2B.X1C.X2D,
Z1.T1C.T2B.X1C.X2D, Z2.T1C.T2B.X1C.X2D,
Z3.T1C.T2B.X1C.X2D, Z4.T1C.T2B.X1C.X2D,
Z5.T1C.T2B.X1C.X2D, Z6.T1C.T2B.X1C.X2D,
Z1.T1D.T2B.X1C.X2D, Z2.T1D.T2B.X1C.X2D,
Z3.T1D.T2B.X1C.X2D, Z4.T1D.T2B.X1C.X2D,
Z5.T1D.T2B.X1C.X2D, Z6.T1D.T2B.X1C.X2D,
Z1.T1A.T2C.X1C.X2D, Z2.T1A.T2C.X1C.X2D,
Z3.T1A.T2C.X1C.X2D, Z4.T1A.T2C.X1C.X2D,
Z5.T1A.T2C.X1C.X2D, Z6.T1A.T2C.X1C.X2D,
Z1.T1B.T2C.X1C.X2D, Z2.T1B.T2C.X1C.X2D,
Z3.T1B.T2C.X1C.X2D, Z4.T1B.T2C.X1C.X2D,
Z5.T1B.T2C.X1C.X2D, Z6.T1B.T2C.X1C.X2D,
Z1.T1C.T2C.X1C.X2D, Z2.T1C.T2C.X1C.X2D,
Z3.T1C.T2C.X1C.X2D, Z4.T1C.T2C.X1C.X2D,
Z5.T1C.T2C.X1C.X2D, Z6.T1C.T2C.X1C.X2D,
Z1.T1D.T2C.X1C.X2D, Z2.T1D.T2C.X1C.X2D,
Z3.T1D.T2C.X1C.X2D, Z4.T1D.T2C.X1C.X2D,
Z5.T1D.T2C.X1C.X2D, Z6.T1D.T2C.X1C.X2D,
Z1.T1A.T2D.X1C.X2D, Z2.T1A.T2D.X1C.X2D,
Z3.T1A.T2D.X1C.X2D, Z4.T1A.T2D.X1C.X2D,
Z5.T1A.T2D.X1C.X2D, Z6.T1A.T2D.X1C.X2D,
Z1.T1B.T2D.X1C.X2D, Z2.T1B.T2D.X1C.X2D,
Z3.T1B.T2D.X1C.X2D, Z4.T1B.T2D.X1C.X2D,
Z5.T1B.T2D.X1C.X2D, Z6.T1B.T2D.X1C.X2D,
Z1.T1C.T2D.X1C.X2D, Z2.T1C.T2D.X1C.X2D,
Z3.T1C.T2D.X1C.X2D, Z4.T1C.T2D.X1C.X2D,
Z5.T1C.T2D.X1C.X2D, Z6.T1C.T2D.X1C.X2D,
Z1.T1D.T2D.X1C.X2D, Z2.T1D.T2D.X1C.X2D,
Z3.T1D.T2D.X1C.X2D, Z4.T1D.T2D.X1C.X2D,
Z5.T1D.T2D.X1C.X2D, Z6.T1D.T2D.X1C.X2D,
Z1.T1A.T2A.X1D.X2D, Z2.T1A.T2A.X1D.X2D,

TABLE 6-continued

List of Compound Structures of Formula II

Z3.T1A.T2A.X1D.X2D, Z4.T1A.T2A.X1D.X2D,
Z5.T1A.T2A.X1D.X2D, Z6.T1A.T2A.X1D.X2D,
Z1.T1B.T2A.X1D.X2D, Z2.T1B.T2A.X1D.X2D,
Z3.T1B.T2A.X1D.X2D, Z4.T1B.T2A.X1D.X2D,
Z5.T1B.T2A.X1D.X2D, Z6.T1B.T2A.X1D.X2D,
Z1.T1C.T2A.X1D.X2D, Z2.T1C.T2A.X1D.X2D,
Z3.T1C.T2A.X1D.X2D, Z4.T1C.T2A.X1D.X2D,
Z5.T1C.T2A.X1D.X2D, Z6.T1C.T2A.X1D.X2D,
Z1.T1D.T2A.X1D.X2D, Z2.T1D.T2A.X1D.X2D,
Z3.T1D.T2A.X1D.X2D, Z4.T1D.T2A.X1D.X2D,
Z5.T1D.T2A.X1D.X2D, Z6.T1D.T2A.X1D.X2D,
Z1.T1A.T2B.X1D.X2D, Z2.T1A.T2B.X1D.X2D,
Z3.T1A.T2B.X1D.X2D, Z4.T1A.T2B.X1D.X2D,
Z5.T1A.T2B.X1D.X2D, Z6.T1A.T2B.X1D.X2D,
Z1.T1B.T2B.X1D.X2D, Z2.T1B.T2B.X1D.X2D,
Z3.T1B.T2B.X1D.X2D, Z4.T1B.T2B.X1D.X2D,
Z5.T1B.T2B.X1D.X2D, Z6.T1B.T2B.X1D.X2D,
Z1.T1C.T2B.X1D.X2D, Z2.T1C.T2B.X1D.X2D,
Z3.T1C.T2B.X1D.X2D, Z4.T1C.T2B.X1D.X2D,
Z5.T1C.T2B.X1D.X2D, Z6.T1C.T2B.X1D.X2D,
Z1.T1D.T2B.X1D.X2D, Z2.T1D.T2B.X1D.X2D,
Z3.T1D.T2B.X1D.X2D, Z4.T1D.T2B.X1D.X2D,
Z5.T1D.T2B.X1D.X2D, Z6.T1D.T2B.X1D.X2D,
Z1.T1A.T2C.X1D.X2D, Z2.T1A.T2C.X1D.X2D,
Z3.T1A.T2C.X1D.X2D, Z4.T1A.T2C.X1D.X2D,
Z5.T1A.T2C.X1D.X2D, Z6.T1A.T2C.X1D.X2D,
Z1.T1B.T2C.X1D.X2D, Z2.T1B.T2C.X1D.X2D,
Z3.T1B.T2C.X1D.X2D, Z4.T1B.T2C.X1D.X2D,
Z5.T1B.T2C.X1D.X2D, Z6.T1B.T2C.X1D.X2D,
Z1.T1C.T2C.X1D.X2D, Z2.T1C.T2C.X1D.X2D,
Z3.T1C.T2C.X1D.X2D, Z4.T1C.T2C.X1D.X2D,
Z5.T1C.T2C.X1D.X2D, Z6.T1C.T2C.X1D.X2D,
Z1.T1D.T2C.X1D.X2D, Z2.T1D.T2C.X1D.X2D,
Z3.T1D.T2C.X1D.X2D, Z4.T1D.T2C.X1D.X2D,
Z5.T1D.T2C.X1D.X2D, Z6.T1D.T2C.X1D.X2D,
Z1.T1A.T2D.X1D.X2D, Z2.T1A.T2D.X1D.X2D,
Z3.T1A.T2D.X1D.X2D, Z4.T1A.T2D.X1D.X2D,
Z5.T1A.T2D.X1D.X2D, Z6.T1A.T2D.X1D.X2D,
Z1.T1B.T2D.X1D.X2D, Z2.T1B.T2D.X1D.X2D,
Z3.T1B.T2D.X1D.X2D, Z4.T1B.T2D.X1D.X2D,
Z5.T1B.T2D.X1D.X2D, Z6.T1B.T2D.X1D.X2D,
Z1.T1C.T2D.X1D.X2D, Z2.T1C.T2D.X1D.X2D,
Z3.T1C.T2D.X1D.X2D, Z4.T1C.T2D.X1D.X2D,
Z5.T1C.T2D.X1D.X2D, Z6.T1C.T2D.X1D.X2D,
Z1.T1D.T2D.X1D.X2D, Z2.T1D.T2D.X1D.X2D,
Z3.T1D.T2D.X1D.X2D, Z4.T1D.T2D.X1D.X2D,
Z5.T1D.T2D.X1D.X2D, Z6.T1D.T2D.X1D.X2D,
Z1.T1A.T2A.X1E.X2D, Z2.T1A.T2A.X1E.X2D,
Z3.T1A.T2A.X1E.X2D, Z4.T1A.T2A.X1E.X2D,
Z5.T1A.T2A.X1E.X2D, Z6.T1A.T2A.X1E.X2D,
Z1.T1B.T2A.X1E.X2D, Z2.T1B.T2A.X1E.X2D,
Z3.T1B.T2A.X1E.X2D, Z4.T1B.T2A.X1E.X2D,
Z5.T1B.T2A.X1E.X2D, Z6.T1B.T2A.X1E.X2D,
Z1.T1C.T2A.X1E.X2D, Z2.T1C.T2A.X1E.X2D,
Z3.T1C.T2A.X1E.X2D, Z4.T1C.T2A.X1E.X2D,
Z5.T1C.T2A.X1E.X2D, Z6.T1C.T2A.X1E.X2D,
Z1.T1D.T2A.X1E.X2D, Z2.T1D.T2A.X1E.X2D,
Z3.T1D.T2A.X1E.X2D, Z4.T1D.T2A.X1E.X2D,
Z5.T1D.T2A.X1E.X2D, Z6.T1D.T2A.X1E.X2D,
Z1.T1A.T2B.X1E.X2D, Z2.T1A.T2B.X1E.X2D,
Z3.T1A.T2B.X1E.X2D, Z4.T1A.T2B.X1E.X2D,
Z5.T1A.T2B.X1E.X2D, Z6.T1A.T2B.X1E.X2D,
Z1.T1B.T2B.X1E.X2D, Z2.T1B.T2B.X1E.X2D,
Z3.T1B.T2B.X1E.X2D, Z4.T1B.T2B.X1E.X2D,
Z5.T1B.T2B.X1E.X2D, Z6.T1B.T2B.X1E.X2D,
Z1.T1C.T2B.X1E.X2D, Z2.T1C.T2B.X1E.X2D,
Z3.T1C.T2B.X1E.X2D, Z4.T1C.T2B.X1E.X2D,
Z5.T1C.T2B.X1E.X2D, Z6.T1C.T2B.X1E.X2D,
Z1.T1D.T2B.X1E.X2D, Z2.T1D.T2B.X1E.X2D,
Z3.T1D.T2B.X1E.X2D, Z4.T1D.T2B.X1E.X2D,
Z5.T1D.T2B.X1E.X2D, Z6.T1D.T2B.X1E.X2D,
Z1.T1A.T2C.X1E.X2D, Z2.T1A.T2C.X1E.X2D,
Z3.T1A.T2C.X1E.X2D, Z4.T1A.T2C.X1E.X2D,
Z5.T1A.T2C.X1E.X2D, Z6.T1A.T2C.X1E.X2D,
Z1.T1B.T2C.X1E.X2D, Z2.T1B.T2C.X1E.X2D,
Z3.T1B.T2C.X1E.X2D, Z4.T1B.T2C.X1E.X2D,
Z5.T1B.T2C.X1E.X2D, Z6.T1B.T2C.X1E.X2D,
Z1.T1C.T2C.X1E.X2D, Z2.T1C.T2C.X1E.X2D,
Z3.T1C.T2C.X1E.X2D, Z4.T1C.T2C.X1E.X2D,
Z5.T1C.T2C.X1E.X2D, Z6.T1C.T2C.X1E.X2D,
Z1.T1D.T2C.X1E.X2D, Z2.T1D.T2C.X1E.X2D,
Z3.T1D.T2C.X1E.X2D, Z4.T1D.T2C.X1E.X2D,
Z5.T1D.T2C.X1E.X2D, Z6.T1D.T2C.X1E.X2D,
Z1.T1A.T2D.X1E.X2D, Z2.T1A.T2D.X1E.X2D,
Z3.T1A.T2D.X1E.X2D, Z4.T1A.T2D.X1E.X2D,
Z5.T1A.T2D.X1E.X2D, Z6.T1A.T2D.X1E.X2D,
Z1.T1B.T2D.X1E.X2D, Z2.T1B.T2D.X1E.X2D,
Z3.T1B.T2D.X1E.X2D, Z4.T1B.T2D.X1E.X2D,
Z5.T1B.T2D.X1E.X2D, Z6.T1B.T2D.X1E.X2D,
Z1.T1C.T2D.X1E.X2D, Z2.T1C.T2D.X1E.X2D,
Z3.T1C.T2D.X1E.X2D, Z4.T1C.T2D.X1E.X2D,
Z5.T1C.T2D.X1E.X2D, Z6.T1C.T2D.X1E.X2D,
Z1.T1D.T2D.X1E.X2D, Z2.T1D.T2D.X1E.X2D,
Z3.T1D.T2D.X1E.X2D, Z4.T1D.T2D.X1E.X2D,
Z5.T1D.T2D.X1E.X2D, Z6.T1D.T2D.X1E.X2D,
Z1.T1A.T2A.X1A.X2E, Z2.T1A.T2A.X1A.X2E,
Z3.T1A.T2A.X1A.X2E, Z4.T1A.T2A.X1A.X2E,
Z5.T1A.T2A.X1A.X2E, Z6.T1A.T2A.X1A.X2E,
Z1.T1B.T2A.X1A.X2E, Z2.T1B.T2A.X1A.X2E,
Z3.T1B.T2A.X1A.X2E, Z4.T1B.T2A.X1A.X2E,
Z5.T1B.T2A.X1A.X2E, Z6.T1B.T2A.X1A.X2E,
Z1.T1C.T2A.X1A.X2E, Z2.T1C.T2A.X1A.X2E,
Z3.T1C.T2A.X1A.X2E, Z4.T1C.T2A.X1A.X2E,
Z5.T1C.T2A.X1A.X2E, Z6.T1C.T2A.X1A.X2E,
Z1.T1D.T2A.X1A.X2E, Z2.T1D.T2A.X1A.X2E,
Z3.T1D.T2A.X1A.X2E, Z4.T1D.T2A.X1A.X2E,
Z5.T1D.T2A.X1A.X2E, Z6.T1D.T2A.X1A.X2E,
Z1.T1A.T2B.X1A.X2E, Z2.T1A.T2B.X1A.X2E,
Z3.T1A.T2B.X1A.X2E, Z4.T1A.T2B.X1A.X2E,
Z5.T1A.T2B.X1A.X2E, Z6.T1A.T2B.X1A.X2E,
Z1.T1B.T2B.X1A.X2E, Z2.T1B.T2B.X1A.X2E,
Z3.T1B.T2B.X1A.X2E, Z4.T1B.T2B.X1A.X2E,
Z5.T1B.T2B.X1A.X2E, Z6.T1B.T2B.X1A.X2E,
Z1.T1C.T2B.X1A.X2E, Z2.T1C.T2B.X1A.X2E,
Z3.T1C.T2B.X1A.X2E, Z4.T1C.T2B.X1A.X2E,
Z5.T1C.T2B.X1A.X2E, Z6.T1C.T2B.X1A.X2E,
Z1.T1D.T2B.X1A.X2E, Z2.T1D.T2B.X1A.X2E,
Z3.T1D.T2B.X1A.X2E, Z4.T1D.T2B.X1A.X2E,
Z5.T1D.T2B.X1A.X2E, Z6.T1D.T2B.X1A.X2E,
Z1.T1A.T2C.X1A.X2E, Z2.T1A.T2C.X1A.X2E,
Z3.T1A.T2C.X1A.X2E, Z4.T1A.T2C.X1A.X2E,
Z5.T1A.T2C.X1A.X2E, Z6.T1A.T2C.X1A.X2E,
Z1.T1B.T2C.X1A.X2E, Z2.T1B.T2C.X1A.X2E,
Z3.T1B.T2C.X1A.X2E, Z4.T1B.T2C.X1A.X2E,
Z5.T1B.T2C.X1A.X2E, Z6.T1B.T2C.X1A.X2E,
Z1.T1C.T2C.X1A.X2E, Z2.T1C.T2C.X1A.X2E,
Z3.T1C.T2C.X1A.X2E, Z4.T1C.T2C.X1A.X2E,
Z5.T1C.T2C.X1A.X2E, Z6.T1C.T2C.X1A.X2E,
Z1.T1D.T2C.X1A.X2E, Z2.T1D.T2C.X1A.X2E,
Z3.T1D.T2C.X1A.X2E, Z4.T1D.T2C.X1A.X2E,
Z5.T1D.T2C.X1A.X2E, Z6.T1D.T2C.X1A.X2E,
Z1.T1A.T2D.X1A.X2E, Z2.T1A.T2D.X1A.X2E,
Z3.T1A.T2D.X1A.X2E, Z4.T1A.T2D.X1A.X2E,
Z5.T1A.T2D.X1A.X2E, Z6.T1A.T2D.X1A.X2E,
Z1.T1B.T2D.X1A.X2E, Z2.T1B.T2D.X1A.X2E,
Z3.T1B.T2D.X1A.X2E, Z4.T1B.T2D.X1A.X2E,
Z5.T1B.T2D.X1A.X2E, Z6.T1B.T2D.X1A.X2E,
Z1.T1C.T2D.X1A.X2E, Z2.T1C.T2D.X1A.X2E,
Z3.T1C.T2D.X1A.X2E, Z4.T1C.T2D.X1A.X2E,
Z5.T1C.T2D.X1A.X2E, Z6.T1C.T2D.X1A.X2E,
Z1.T1D.T2D.X1A.X2E, Z2.T1D.T2D.X1A.X2E,
Z3.T1D.T2D.X1A.X2E, Z4.T1D.T2D.X1A.X2E,
Z5.T1D.T2D.X1A.X2E, Z6.T1D.T2D.X1A.X2E,
Z1.T1A.T2A.X1B.X2E, Z2.T1A.T2A.X1B.X2E,
Z3.T1A.T2A.X1B.X2E, Z4.T1A.T2A.X1B.X2E,
Z5.T1A.T2A.X1B.X2E, Z6.T1A.T2A.X1B.X2E,
Z1.T1B.T2A.X1B.X2E, Z2.T1B.T2A.X1B.X2E,
Z3.T1B.T2A.X1B.X2E, Z4.T1B.T2A.X1B.X2E,
Z5.T1B.T2A.X1B.X2E, Z6.T1B.T2A.X1B.X2E,
Z1.T1C.T2A.X1B.X2E, Z2.T1C.T2A.X1B.X2E,
Z3.T1C.T2A.X1B.X2E, Z4.T1C.T2A.X1B.X2E,
Z5.T1C.T2A.X1B.X2E, Z6.T1C.T2A.X1B.X2E,
Z1.T1D.T2A.X1B.X2E, Z2.T1D.T2A.X1B.X2E,
Z3.T1D.T2A.X1B.X2E, Z4.T1D.T2A.X1B.X2E,
Z5.T1D.T2A.X1B.X2E, Z6.T1D.T2A.X1B.X2E,
Z1.T1A.T2B.X1B.X2E, Z2.T1A.T2B.X1B.X2E,

TABLE 6-continued

List of Compound Structures of Formula II

Z3.T1A.T2B.X1B.X2E, Z4.T1A.T2B.X1B.X2E,
Z5.T1A.T2B.X1B.X2E, Z6.T1A.T2B.X1B.X2E,
Z1.T1B.T2B.X1B.X2E, Z2.T1B.T2B.X1B.X2E,
Z3.T1B.T2B.X1B.X2E, Z4.T1B.T2B.X1B.X2E,
Z5.T1B.T2B.X1B.X2E, Z6.T1B.T2B.X1B.X2E,
Z1.T1C.T2B.X1B.X2E, Z2.T1C.T2B.X1B.X2E,
Z3.T1C.T2B.X1B.X2E, Z4.T1C.T2B.X1B.X2E,
Z5.T1C.T2B.X1B.X2E, Z6.T1C.T2B.X1B.X2E,
Z1.T1D.T2B.X1B.X2E, Z2.T1D.T2B.X1B.X2E,
Z3.T1D.T2B.X1B.X2E, Z4.T1D.T2B.X1B.X2E,
Z5.T1D.T2B.X1B.X2E, Z6.T1D.T2B.X1B.X2E,
Z1.T1A.T2C.X1B.X2E, Z2.T1A.T2C.X1B.X2E,
Z3.T1A.T2C.X1B.X2E, Z4.T1A.T2C.X1B.X2E,
Z5.T1A.T2C.X1B.X2E, Z6.T1A.T2C.X1B.X2E,
Z1.T1B.T2C.X1B.X2E, Z2.T1B.T2C.X1B.X2E,
Z3.T1B.T2C.X1B.X2E, Z4.T1B.T2C.X1B.X2E,
Z5.T1B.T2C.X1B.X2E, Z6.T1B.T2C.X1B.X2E,
Z1.T1C.T2C.X1B.X2E, Z2.T1C.T2C.X1B.X2E,
Z3.T1C.T2C.X1B.X2E, Z4.T1C.T2C.X1B.X2E,
Z5.T1C.T2C.X1B.X2E, Z6.T1C.T2C.X1B.X2E,
Z1.T1D.T2C.X1B.X2E, Z2.T1D.T2C.X1B.X2E,
Z3.T1D.T2C.X1B.X2E, Z4.T1D.T2C.X1B.X2E,
Z5.T1D.T2C.X1B.X2E, Z6.T1D.T2C.X1B.X2E,
Z1.T1A.T2D.X1B.X2E, Z2.T1A.T2D.X1B.X2E,
Z3.T1A.T2D.X1B.X2E, Z4.T1A.T2D.X1B.X2E,
Z5.T1A.T2D.X1B.X2E, Z6.T1A.T2D.X1B.X2E,
Z1.T1B.T2D.X1B.X2E, Z2.T1B.T2D.X1B.X2E,
Z3.T1B.T2D.X1B.X2E, Z4.T1B.T2D.X1B.X2E,
Z5.T1B.T2D.X1B.X2E, Z6.T1B.T2D.X1B.X2E,
Z1.T1C.T2D.X1B.X2E, Z2.T1C.T2D.X1B.X2E,
Z3.T1C.T2D.X1B.X2E, Z4.T1C.T2D.X1B.X2E,
Z5.T1C.T2D.X1B.X2E, Z6.T1C.T2D.X1B.X2E,
Z1.T1D.T2D.X1B.X2E, Z2.T1D.T2D.X1B.X2E,
Z3.T1D.T2D.X1B.X2E, Z4.T1D.T2D.X1B.X2E,
Z5.T1D.T2D.X1B.X2E, Z6.T1D.T2D.X1B.X2E,
Z1.T1A.T2A.X1C.X2E, Z2.T1A.T2A.X1C.X2E,
Z3.T1A.T2A.X1C.X2E, Z4.T1A.T2A.X1C.X2E,
Z5.T1A.T2A.X1C.X2E, Z6.T1A.T2A.X1C.X2E,
Z1.T1B.T2A.X1C.X2E, Z2.T1B.T2A.X1C.X2E,
Z3.T1B.T2A.X1C.X2E, Z4.T1B.T2A.X1C.X2E,
Z5.T1B.T2A.X1C.X2E, Z6.T1B.T2A.X1C.X2E,
Z1.T1C.T2A.X1C.X2E, Z2.T1C.T2A.X1C.X2E,
Z3.T1C.T2A.X1C.X2E, Z4.T1C.T2A.X1C.X2E,
Z5.T1C.T2A.X1C.X2E, Z6.T1C.T2A.X1C.X2E,
Z1.T1D.T2A.X1C.X2E, Z2.T1D.T2A.X1C.X2E,
Z3.T1D.T2A.X1C.X2E, Z4.T1D.T2A.X1C.X2E,
Z5.T1D.T2A.X1C.X2E, Z6.T1D.T2A.X1C.X2E,
Z1.T1A.T2B.X1C.X2E, Z2.T1A.T2B.X1C.X2E,
Z3.T1A.T2B.X1C.X2E, Z4.T1A.T2B.X1C.X2E,
Z5.T1A.T2B.X1C.X2E, Z6.T1A.T2B.X1C.X2E,
Z1.T1B.T2B.X1C.X2E, Z2.T1B.T2B.X1C.X2E,
Z3.T1B.T2B.X1C.X2E, Z4.T1B.T2B.X1C.X2E,
Z5.T1B.T2B.X1C.X2E, Z6.T1B.T2B.X1C.X2E,
Z1.T1C.T2B.X1C.X2E, Z2.T1C.T2B.X1C.X2E,
Z3.T1C.T2B.X1C.X2E, Z4.T1C.T2B.X1C.X2E,
Z5.T1C.T2B.X1C.X2E, Z6.T1C.T2B.X1C.X2E,
Z1.T1D.T2B.X1C.X2E, Z2.T1D.T2B.X1C.X2E,
Z3.T1D.T2B.X1C.X2E, Z4.T1D.T2B.X1C.X2E,
Z5.T1D.T2B.X1C.X2E, Z6.T1D.T2B.X1C.X2E,
Z1.T1A.T2C.X1C.X2E, Z2.T1A.T2C.X1C.X2E,
Z3.T1A.T2C.X1C.X2E, Z4.T1A.T2C.X1C.X2E,
Z5.T1A.T2C.X1C.X2E, Z6.T1A.T2C.X1C.X2E,
Z1.T1B.T2C.X1C.X2E, Z2.T1B.T2C.X1C.X2E,
Z3.T1B.T2C.X1C.X2E, Z4.T1B.T2C.X1C.X2E,
Z5.T1B.T2C.X1C.X2E, Z6.T1B.T2C.X1C.X2E,
Z1.T1C.T2C.X1C.X2E, Z2.T1C.T2C.X1C.X2E,
Z3.T1C.T2C.X1C.X2E, Z4.T1C.T2C.X1C.X2E,
Z5.T1C.T2C.X1C.X2E, Z6.T1C.T2C.X1C.X2E,
Z1.T1D.T2C.X1C.X2E, Z2.T1D.T2C.X1C.X2E,
Z3.T1D.T2C.X1C.X2E, Z4.T1D.T2C.X1C.X2E,
Z5.T1D.T2C.X1C.X2E, Z6.T1D.T2C.X1C.X2E,
Z1.T1A.T2D.X1C.X2E, Z2.T1A.T2D.X1C.X2E,
Z3.T1A.T2D.X1C.X2E, Z4.T1A.T2D.X1C.X2E,
Z5.T1A.T2D.X1C.X2E, Z6.T1A.T2D.X1C.X2E,
Z1.T1B.T2D.X1C.X2E, Z2.T1B.T2D.X1C.X2E,
Z3.T1B.T2D.X1C.X2E, Z4.T1B.T2D.X1C.X2E,
Z5.T1B.T2D.X1C.X2E, Z6.T1B.T2D.X1C.X2E,
Z1.T1C.T2D.X1C.X2E, Z2.T1C.T2D.X1C.X2E,
Z3.T1C.T2D.X1C.X2E, Z4.T1C.T2D.X1C.X2E,
Z5.T1C.T2D.X1C.X2E, Z6.T1C.T2D.X1C.X2E,
Z1.T1D.T2D.X1C.X2E, Z2.T1D.T2D.X1C.X2E,
Z3.T1D.T2D.X1C.X2E, Z4.T1D.T2D.X1C.X2E,
Z5.T1D.T2D.X1C.X2E, Z6.T1D.T2D.X1C.X2E,
Z1.T1A.T2A.X1D.X2E, Z2.T1A.T2A.X1D.X2E,
Z3.T1A.T2A.X1D.X2E, Z4.T1A.T2A.X1D.X2E,
Z5.T1A.T2A.X1D.X2E, Z6.T1A.T2A.X1D.X2E,
Z1.T1B.T2A.X1D.X2E, Z2.T1B.T2A.X1D.X2E,
Z3.T1B.T2A.X1D.X2E, Z4.T1B.T2A.X1D.X2E,
Z5.T1B.T2A.X1D.X2E, Z6.T1B.T2A.X1D.X2E,
Z1.T1C.T2A.X1D.X2E, Z2.T1C.T2A.X1D.X2E,
Z3.T1C.T2A.X1D.X2E, Z4.T1C.T2A.X1D.X2E,
Z5.T1C.T2A.X1D.X2E, Z6.T1C.T2A.X1D.X2E,
Z1.T1D.T2A.X1D.X2E, Z2.T1D.T2A.X1D.X2E,
Z3.T1D.T2A.X1D.X2E, Z4.T1D.T2A.X1D.X2E,
Z5.T1D.T2A.X1D.X2E, Z6.T1D.T2A.X1D.X2E,
Z1.T1A.T2B.X1D.X2E, Z2.T1A.T2B.X1D.X2E,
Z3.T1A.T2B.X1D.X2E, Z4.T1A.T2B.X1D.X2E,
Z5.T1A.T2B.X1D.X2E, Z6.T1A.T2B.X1D.X2E,
Z1.T1B.T2B.X1D.X2E, Z2.T1B.T2B.X1D.X2E,
Z3.T1B.T2B.X1D.X2E, Z4.T1B.T2B.X1D.X2E,
Z5.T1B.T2B.X1D.X2E, Z6.T1B.T2B.X1D.X2E,
Z1.T1C.T2B.X1D.X2E, Z2.T1C.T2B.X1D.X2E,
Z3.T1C.T2B.X1D.X2E, Z4.T1C.T2B.X1D.X2E,
Z5.T1C.T2B.X1D.X2E, Z6.T1C.T2B.X1D.X2E,
Z1.T1D.T2B.X1D.X2E, Z2.T1D.T2B.X1D.X2E,
Z3.T1D.T2B.X1D.X2E, Z4.T1D.T2B.X1D.X2E,
Z5.T1D.T2B.X1D.X2E, Z6.T1D.T2B.X1D.X2E,
Z1.T1A.T2C.X1D.X2E, Z2.T1A.T2C.X1D.X2E,
Z3.T1A.T2C.X1D.X2E, Z4.T1A.T2C.X1D.X2E,
Z5.T1A.T2C.X1D.X2E, Z6.T1A.T2C.X1D.X2E,
Z1.T1B.T2C.X1D.X2E, Z2.T1B.T2C.X1D.X2E,
Z3.T1B.T2C.X1D.X2E, Z4.T1B.T2C.X1D.X2E,
Z5.T1B.T2C.X1D.X2E, Z6.T1B.T2C.X1D.X2E,
Z1.T1C.T2C.X1D.X2E, Z2.T1C.T2C.X1D.X2E,
Z3.T1C.T2C.X1D.X2E, Z4.T1C.T2C.X1D.X2E,
Z5.T1C.T2C.X1D.X2E, Z6.T1C.T2C.X1D.X2E,
Z1.T1D.T2C.X1D.X2E, Z2.T1D.T2C.X1D.X2E,
Z3.T1D.T2C.X1D.X2E, Z4.T1D.T2C.X1D.X2E,
Z5.T1D.T2C.X1D.X2E, Z6.T1D.T2C.X1D.X2E,
Z1.T1A.T2D.X1D.X2E, Z2.T1A.T2D.X1D.X2E,
Z3.T1A.T2D.X1D.X2E, Z4.T1A.T2D.X1D.X2E,
Z5.T1A.T2D.X1D.X2E, Z6.T1A.T2D.X1D.X2E,
Z1.T1B.T2D.X1D.X2E, Z2.T1B.T2D.X1D.X2E,
Z3.T1B.T2D.X1D.X2E, Z4.T1B.T2D.X1D.X2E,
Z5.T1B.T2D.X1D.X2E, Z6.T1B.T2D.X1D.X2E,
Z1.T1C.T2D.X1D.X2E, Z2.T1C.T2D.X1D.X2E,
Z3.T1C.T2D.X1D.X2E, Z4.T1C.T2D.X1D.X2E,
Z5.T1C.T2D.X1D.X2E, Z6.T1C.T2D.X1D.X2E,
Z1.T1D.T2D.X1D.X2E, Z2.T1D.T2D.X1D.X2E,
Z3.T1D.T2D.X1D.X2E, Z4.T1D.T2D.X1D.X2E,
Z5.T1D.T2D.X1D.X2E, Z6.T1D.T2D.X1D.X2E,
Z1.T1A.T2A.X1E.X2E, Z2.T1A.T2A.X1E.X2E,
Z3.T1A.T2A.X1E.X2E, Z4.T1A.T2A.X1E.X2E,
Z5.T1A.T2A.X1E.X2E, Z6.T1A.T2A.X1E.X2E,
Z1.T1B.T2A.X1E.X2E, Z2.T1B.T2A.X1E.X2E,
Z3.T1B.T2A.X1E.X2E, Z4.T1B.T2A.X1E.X2E,
Z5.T1B.T2A.X1E.X2E, Z6.T1B.T2A.X1E.X2E,
Z1.T1C.T2A.X1E.X2E, Z2.T1C.T2A.X1E.X2E,
Z3.T1C.T2A.X1E.X2E, Z4.T1C.T2A.X1E.X2E,
Z5.T1C.T2A.X1E.X2E, Z6.T1C.T2A.X1E.X2E,
Z1.T1D.T2A.X1E.X2E, Z2.T1D.T2A.X1E.X2E,
Z3.T1D.T2A.X1E.X2E, Z4.T1D.T2A.X1E.X2E,
Z5.T1D.T2A.X1E.X2E, Z6.T1D.T2A.X1E.X2E,
Z1.T1A.T2B.X1E.X2E, Z2.T1A.T2B.X1E.X2E,
Z3.T1A.T2B.X1E.X2E, Z4.T1A.T2B.X1E.X2E,
Z5.T1A.T2B.X1E.X2E, Z6.T1A.T2B.X1E.X2E,
Z1.T1B.T2B.X1E.X2E, Z2.T1B.T2B.X1E.X2E,
Z3.T1B.T2B.X1E.X2E, Z4.T1B.T2B.X1E.X2E,
Z5.T1B.T2B.X1E.X2E, Z6.T1B.T2B.X1E.X2E,
Z1.T1C.T2B.X1E.X2E, Z2.T1C.T2B.X1E.X2E,
Z3.T1C.T2B.X1E.X2E, Z4.T1C.T2B.X1E.X2E,
Z5.T1C.T2B.X1E.X2E, Z6.T1C.T2B.X1E.X2E,
Z1.T1D.T2B.X1E.X2E, Z2.T1D.T2B.X1E.X2E,
Z3.T1D.T2B.X1E.X2E, Z4.T1D.T2B.X1E.X2E,
Z5.T1D.T2B.X1E.X2E, Z6.T1D.T2B.X1E.X2E,
Z1.T1A.T2C.X1E.X2E, Z2.T1A.T2C.X1E.X2E,

TABLE 6-continued

List of Compound Structures of Formula II

Z3.T1A.T2C.X1E.X2E, Z4.T1A.T2C.X1E.X2E,
Z5.T1A.T2C.X1E.X2E, Z6.T1A.T2C.X1E.X2E,
Z1.T1B.T2C.X1E.X2E, Z2.T1B.T2C.X1E.X2E,
Z3.T1B.T2C.X1E.X2E, Z4.T1B.T2C.X1E.X2E,
Z5.T1B.T2C.X1E.X2E, Z6.T1B.T2C.X1E.X2E,
Z1.T1C.T2C.X1E.X2E, Z2.T1C.T2C.X1E.X2E,
Z3.T1C.T2C.X1E.X2E, Z4.T1C.T2C.X1E.X2E,
Z5.T1C.T2C.X1E.X2E, Z6.T1C.T2C.X1E.X2E,
Z1.T1D.T2C.X1E.X2E, Z2.T1D.T2C.X1E.X2E,
Z3.T1D.T2C.X1E.X2E, Z4.T1D.T2C.X1E.X2E,
Z5.T1D.T2C.X1E.X2E, Z6.T1D.T2C.X1E.X2E,
Z1.T1A.T2D.X1E.X2E, Z2.T1A.T2D.X1E.X2E,
Z3.T1A.T2D.X1E.X2E, Z4.T1A.T2D.X1E.X2E,
Z5.T1A.T2D.X1E.X2E, Z6.T1A.T2D.X1E.X2E,
Z1.T1B.T2D.X1E.X2E, Z2.T1B.T2D.X1E.X2E,
Z3.T1B.T2D.X1E.X2E, Z4.T1B.T2D.X1E.X2E,
Z5.T1B.T2D.X1E.X2E, Z6.T1B.T2D.X1E.X2E,
Z1.T1C.T2D.X1E.X2E, Z2.T1C.T2D.X1E.X2E,
Z3.T1C.T2D.X1E.X2E, Z4.T1C.T2D.X1E.X2E,
Z5.T1C.T2D.X1E.X2E, Z6.T1C.T2D.X1E.X2E,
Z1.T1D.T2D.X1E.X2E, Z2.T1D.T2D.X1E.X2E,
Z3.T1D.T2D.X1E.X2E, Z4.T1D.T2D.X1E.X2E,
Z5.T1D.T2D.X1E.X2E, and Z6.T1D.T2D.X1E.X2E.

In still another embodiment, selected compounds of Formula I are named below in tabular format (Table 12) as compounds of general Formula III (below):

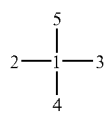

Formula III where 1, 2, 3, 4 and 5 are defined in Tables 7-11, below. Each compound is designated in tabular form by combining the "code" representing each structural moiety using the following syntax: 1.2.3.4.5. Thus, for example, 1a.2a.3a.4a.5a represents the following structure:

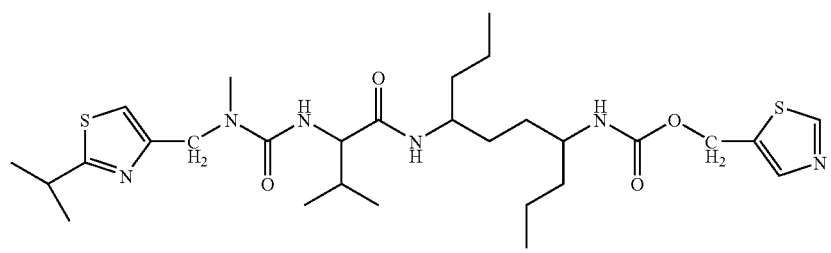

TABLE 7

"1" Structures

| Code | "1" Structure |
|---|---|
| 1a | ![structure] |
| 1b | ![structure] |
| 1c | ![structure] |
| 1d | ![structure] |
| 1e | ![structure] |
| 1f | ![structure] |
| 1g | ![structure] |

TABLE 7-continued
"1" Structures
| Code | "1" Structure |
|---|---|
| 1h | 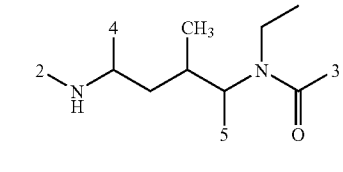 |
| 1i | 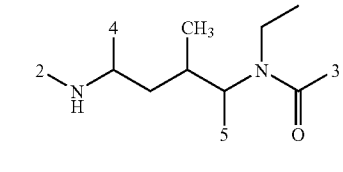 |
| 1j | 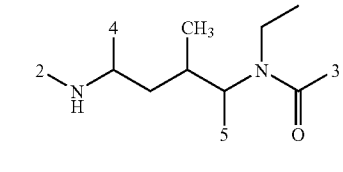 |
| 1k | 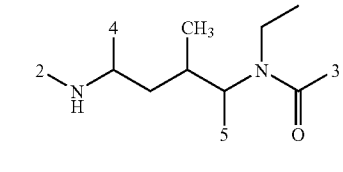 |
| 1l | 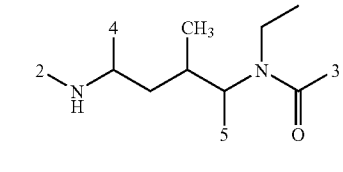 |
| 1m | 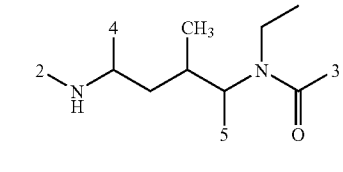 |
| 1n | 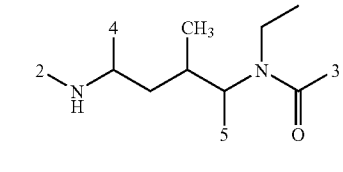 |
| 1o | 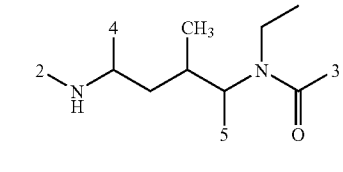 |
| 1p | 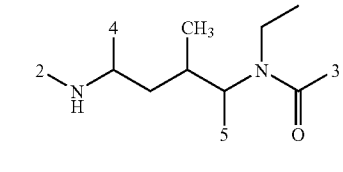 |
| 1q | 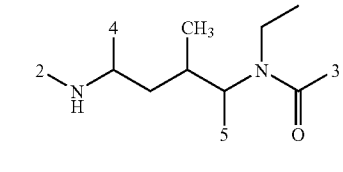 |
| 1r | 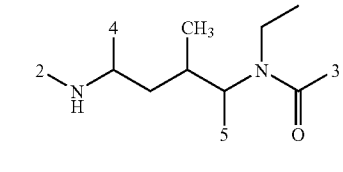 |
| 1s | 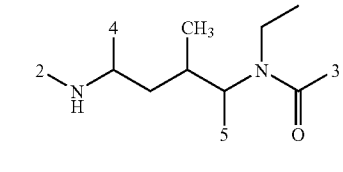 |
| 1t | 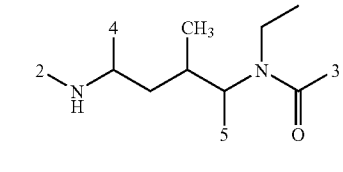 |
| 1u | 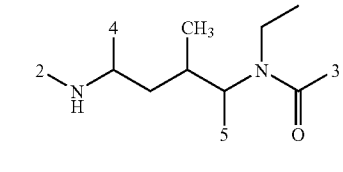 |
TABLE 8
"2" Structures
| Code | "2" Structure |
|---|---|
| 2a | 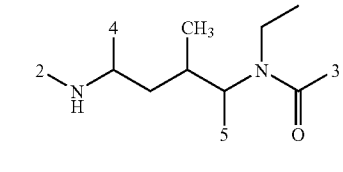 |
| 2b | 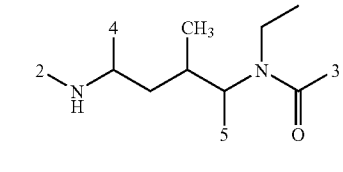 |
| 2c | 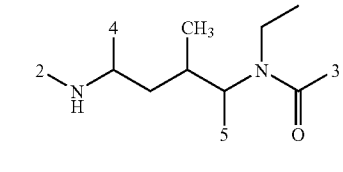 |

TABLE 8-continued
"2" Structures
| Code | "2" Structure |
|------|---------------|
| 2d | 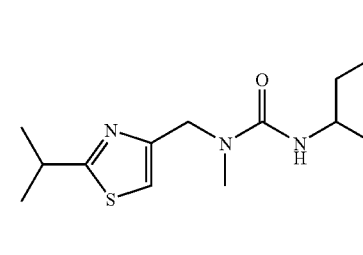 |
| 2e | |
| 2f | |
| 2g | |
| 2h | |
| 2i | |
| 2j | |
TABLE 8-continued
"2" Structures
| Code | "2" Structure |
|------|---------------|
| 2k | 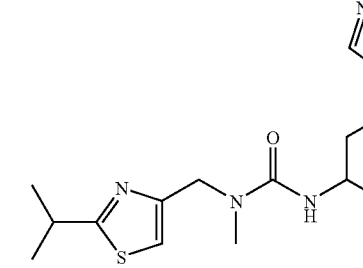 |
| 2l | |
| 2m | |
| 2n | |
| 2o | |
| 2p | |

TABLE 8-continued

"2" Structures

| Code | "2" Structure |
|------|---------------|
| 2q | (structure) |
| 2r | (structure) |
| 2s | (structure) |
| 2t | (structure) |
| 2u | (structure) |
| 2v | (structure) |
| 2w | (structure) |
| 2x | (structure) |
| 2y | (structure) |

TABLE 9

"3" Structures

| Code | "3" Structure |
|------|---------------|
| 3a | —O—CH2-(5-thiazolyl) |
| 3b | —O—CH2-(3-pyridyl) |
| 3c | —NH—CH2-(5-thiazolyl) |
| 3d | —NH—CH2-(3-pyridyl) |
| 3e | —N(CH3)—CH2-(5-thiazolyl) |
| 3f | —N(CH3)—CH2-(3-pyridyl) |
| 3g | —N(CH3)-(5-thiazolyl) |
| 3h | —N(CH3)-(3-pyridyl) |

TABLE 10

"4" Structures

| Code | "4" Structure |
|------|---------------|
| 4a | n-propyl |
| 4b | i-butyl |
| 4c | —CH$_2$-cyclohexyl |
| 4d | —CH$_2$-phenyl |
| 4e | —CH$_2$-(4-methoxyphenyl) |
| 4f | —CH$_2$-(3-fluorophenyl) |
| 4g | —CH$_2$-(4-pyridyl) |
| 4h | —CH$_2$-(3-pyridyl) |
| 4i | —CH$_2$-(2-pyridyl) |
| 4j | —CH$_2$CH$_2$-(4-morpholinyl) |

TABLE 10-continued

"4" Structures

| Code | "4" Structure |
|------|---------------|
| 4k | 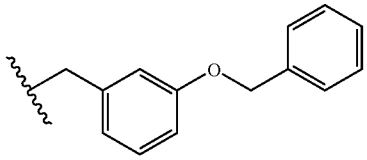 |
| 4l | 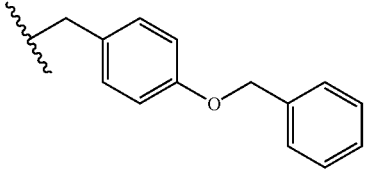 |
| 4m | 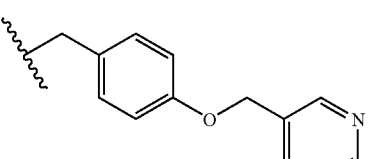 |
| 4n | 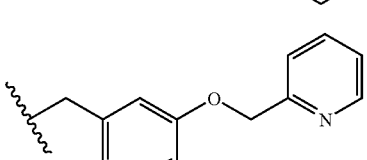 |
| 4o | 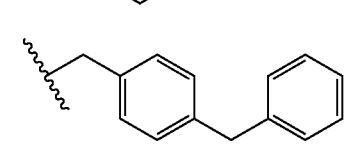 |
| 4p | 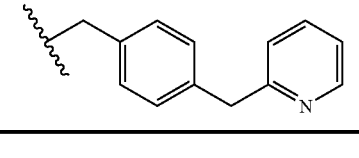 |

TABLE 11

"5" Structures

| Code | "5" Structure |
|------|---------------|
| 5a | n-propyl |
| 5b | i-butyl |
| 5c | —CH$_2$-cyclohexyl |
| 5d | —CH$_2$-phenyl |
| 5e | —CH$_2$-(4-methoxyphenyl) |
| 5f | —CH$_2$-(3-fluorophenyl) |
| 5g | —CH$_2$-(4-pyridyl) |
| 5h | —CH$_2$-(3-pyridyl) |
| 5i | —CH$_2$-(2-pyridyl) |
| 5j | —CH$_2$CH$_2$-(4-morpholinyl) |
| 5k | 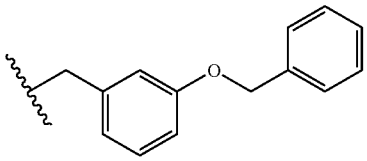 |

TABLE 11-continued

"5" Structures

| Code | "5" Structure |
|------|---------------|
| 5l | 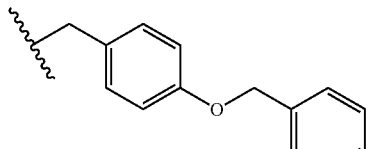 |
| 5m | 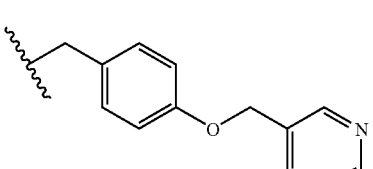 |
| 5n | 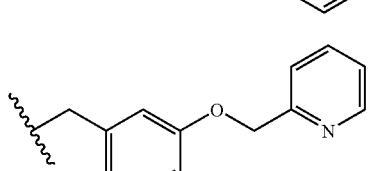 |
| 5o | 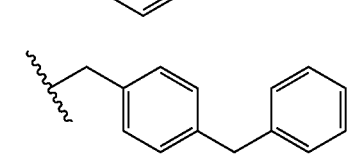 |

TABLE 12

List of Compound Structures of Formula III 1a.2a.3a.4a.5a., 1b.2a.3a.4a.5a., 1f.2a.3a.4a.5a., 1h.2a.3a.4a.5a., 1j.2a.3a.4a.5a., 1p.2a.3a.4a.5a., 1a.2b.3a.4a.5a., 1b.2b.3a.4a.5a., 1f.2b.3a.4a.5a., 1h.2b.3a.4a.5a., 1j.2b.3a.4a.5a., 1p.2b.3a.4a.5a., 1a.2e.3a.4a.5a., 1b.2e.3a.4a.5a., 1f.2e.3a.4a.5a., 1h.2e.3a.4a.5a., 1j.2e.3a.4a.5a., 1p.2e.3a.4a.5a., 1a.2f.3a.4a.5a., 1b.2f.3a.4a.5a., 1f.2f.3a.4a.5a., 1h.2f.3a.4a.5a., 1j.2f.3a.4a.5a., 1p.2f.3a.4a.5a., 1a.2i.3a.4a.5a., 1b.2i.3a.4a.5a., 1f.2i.3a.4a.5a., 1h.2i.3a.4a.5a., 1j.2i.3a.4a.5a., 1p.2i.3a.4a.5a., 1a.2m.3a.4a.5a., 1b.2m.3a.4a.5a., 1f.2m.3a.4a.5a., 1h.2m.3a.4a.5a., 1j.2m.3a.4a.5a., 1p.2m.3a.4a.5a., 1a.2o.3a.4a.5a., 1b.2o.3a.4a.5a., 1f.2o.3a.4a.5a., 1h.2o.3a.4a.5a., 1j.2o.3a.4a.5a., 1p.2o.3a.4a.5a., 1a.2u.3a.4a.5a., 1b.2u.3a.4a.5a., 1f.2u.3a.4a.5a., 1h.2u.3a.4a.5a., 1j.2u.3a.4a.5a., 1p.2u.3a.4a.5a., 1a.2y.3a.4a.5a., 1b.2y.3a.4a.5a., 1f.2y.3a.4a.5a., 1h.2y.3a.4a.5a., 1j.2y.3a.4a.5a., 1p.2y.3a.4a.5a., 1a.2a.3b.4a.5a., 1b.2a.3b.4a.5a., 1f.2a.3b.4a.5a., 1h.2a.3b.4a.5a., 1j.2a.3b.4a.5a., 1p.2a.3b.4a.5a., 1a.2b.3b.4a.5a., 1b.2b.3b.4a.5a., 1f.2b.3b.4a.5a., 1h.2b.3b.4a.5a., 1j.2b.3b.4a.5a., 1p.2b.3b.4a.5a., 1a.2e.3b.4a.5a., 1b.2e.3b.4a.5a., 1f.2e.3b.4a.5a., 1h.2e.3b.4a.5a., 1j.2e.3b.4a.5a., 1p.2e.3b.4a.5a., 1a.2f.3b.4a.5a., 1b.2f.3b.4a.5a., 1f.2f.3b.4a.5a., 1h.2f.3b.4a.5a., 1j.2f.3b.4a.5a., 1p.2f.3b.4a.5a., 1a.2i.3b.4a.5a., 1b.2i.3b.4a.5a., 1f.2i.3b.4a.5a., 1h.2i.3b.4a.5a., 1j.2i.3b.4a.5a., 1p.2i.3b.4a.5a., 1a.2m.3b.4a.5a., 1b.2m.3b.4a.5a., 1f.2m.3b.4a.5a., 1h.2m.3b.4a.5a., 1j.2m.3b.4a.5a., 1p.2m.3b.4a.5a., 1a.2o.3b.4a.5a., 1b.2o.3b.4a.5a., 1f.2o.3b.4a.5a., 1h.2o.3b.4a.5a., 1j.2o.3b.4a.5a., 1p.2o.3b.4a.5a., 1a.2u.3b.4a.5a., 1b.2u.3b.4a.5a., 1f.2u.3b.4a.5a., 1h.2u.3b.4a.5a., 1j.2u.3b.4a.5a., 1p.2u.3b.4a.5a., 1a.2y.3b.4a.5a., 1b.2y.3b.4a.5a., 1f.2y.3b.4a.5a., 1h.2y.3b.4a.5a., 1j.2y.3b.4a.5a., 1p.2y.3b.4a.5a., 1a.2a.3e.4a.5a., 1b.2a.3e.4a.5a., 1f.2a.3e.4a.5a., 1h.2a.3e.4a.5a., 1j.2a.3e.4a.5a., 1p.2a.3e.4a.5a., 1a.2b.3e.4a.5a., 1b.2b.3e.4a.5a., 1f.2b.3e.4a.5a., 1h.2b.3e.4a.5a., 1j.2b.3e.4a.5a., 1p.2b.3e.4a.5a., 1a.2e.3e.4a.5a., 1b.2e.3e.4a.5a., 1f.2e.3e.4a.5a., 1h.2e.3e.4a.5a., 1j.2e.3e.4a.5a., 1p.2e.3e.4a.5a., 1a.2f.3e.4a.5a., 1b.2f.3e.4a.5a., 1f.2f.3e.4a.5a., 1h.2f.3e.4a.5a., 1j.2f.3e.4a.5a., 1p.2f.3e.4a.5a., 1a.2i.3e.4a.5a., 1b.2i.3e.4a.5a., 1f.2i.3e.4a.5a., 1h.2i.3e.4a.5a., 1j.2i.3e.4a.5a., 1p.2i.3e.4a.5a., 1a.2m.3e.4a.5a., 1b.2m.3e.4a.5a., 1f.2m.3e.4a.5a., 1h.2m.3e.4a.5a., 1j.2m.3e.4a.5a., 1p.2m.3e.4a.5a.,

TABLE 12-continued

List of Compound Structures of Formula III 1a.2o.3e.4a.5a., 1b.2o.3e.4a.5a., 1f.2o.3e.4a.5a., 1h.2o.3e.4a.5a.,
1j.2o.3e.4a.5a., 1p.2o.3e.4a.5a., 1a.2u.3e.4a.5a., 1b.2u.3e.4a.5a.,
1f.2u.3e.4a.5a., 1h.2u.3e.4a.5a., 1j.2u.3e.4a.5a., 1p.2u.3e.4a.5a.,
1a.2y.3e.4a.5a., 1b.2y.3e.4a.5a., 1f.2y.3e.4a.5a., 1h.2y.3e.4a.5a.,
1j.2y.3e.4a.5a., 1p.2y.3e.4a.5a., 1a.2a.3g.4a.5a., 1b.2a.3g.4a.5a.,
1f.2a.3g.4a.5a., 1h.2a.3g.4a.5a., 1j.2a.3g.4a.5a., 1p.2a.3g.4a.5a.,
1a.2b.3g.4a.5a., 1b.2b.3g.4a.5a., 1f.2b.3g.4a.5a., 1h.2b.3g.4a.5a.,
1j.2b.3g.4a.5a., 1p.2b.3g.4a.5a., 1a.2e.3g.4a.5a., 1b.2e.3g.4a.5a.,
1f.2e.3g.4a.5a., 1h.2e.3g.4a.5a., 1j.2e.3g.4a.5a., 1p.2e.3g.4a.5a.,
1a.2f.3g.4a.5a., 1b.2f.3g.4a.5a., 1f.2f.3g.4a.5a., 1h.2f.3g.4a.5a.,
1j.2f.3g.4a.5a., 1p.2f.3g.4a.5a., 1a.2i.3g.4a.5a., 1b.2i.3g.4a.5a.,
1f.2i.3g.4a.5a., 1h.2i.3g.4a.5a., 1j.2i.3g.4a.5a., 1p.2i.3g.4a.5a.,
1a.2m.3g.4a.5a., 1b.2m.3g.4a.5a., 1f.2m.3g.4a.5a., 1h.2m.3g.4a.5a.,
1j.2m.3g.4a.5a., 1p.2m.3g.4a.5a., 1a.2o.3g.4a.5a., 1b.2o.3g.4a.5a.,
1f.2o.3g.4a.5a., 1h.2o.3g.4a.5a., 1j.2o.3g.4a.5a., 1p.2o.3g.4a.5a.,
1a.2u.3g.4a.5a., 1b.2u.3g.4a.5a., 1f.2u.3g.4a.5a., 1h.2u.3g.4a.5a.,
1j.2u.3g.4a.5a., 1p.2u.3g.4a.5a., 1a.2y.3g.4a.5a., 1b.2y.3g.4a.5a.,
1f.2y.3g.4a.5a., 1h.2y.3g.4a.5a., 1j.2y.3g.4a.5a., 1p.2y.3g.4a.5a.,
1a.2a.3a.4d.5a., 1b.2a.3a.4d.5a., 1f.2a.3a.4d.5a., 1h.2a.3a.4d.5a.,
1j.2a.3a.4d.5a., 1p.2a.3a.4d.5a., 1a.2b.3a.4d.5a., 1b.2b.3a.4d.5a.,
1f.2b.3a.4d.5a., 1h.2b.3a.4d.5a., 1j.2b.3a.4d.5a., 1p.2b.3a.4d.5a.,
1a.2e.3a.4d.5a., 1b.2e.3a.4d.5a., 1f.2e.3a.4d.5a., 1h.2e.3a.4d.5a.,
1j.2e.3a.4d.5a., 1p.2e.3a.4d.5a., 1a.2f.3a.4d.5a., 1b.2f.3a.4d.5a.,
1f.2f.3a.4d.5a., 1h.2f.3a.4d.5a., 1j.2f.3a.4d.5a., 1p.2f.3a.4d.5a.,
1a.2i.3a.4d.5a., 1b.2i.3a.4d.5a., 1f.2i.3a.4d.5a., 1h.2i.3a.4d.5a.,
1j.2i.3a.4d.5a., 1p.2i.3a.4d.5a., 1a.2m.3a.4d.5a., 1b.2m.3a.4d.5a.,
1f.2m.3a.4d.5a., 1h.2m.3a.4d.5a., 1j.2m.3a.4d.5a., 1p.2m.3a.4d.5a.,
1a.2o.3a.4d.5a., 1b.2o.3a.4d.5a., 1f.2o.3a.4d.5a., 1h.2o.3a.4d.5a.,
1j.2o.3a.4d.5a., 1p.2o.3a.4d.5a., 1a.2u.3a.4d.5a., 1b.2u.3a.4d.5a.,
1f.2u.3a.4d.5a., 1h.2u.3a.4d.5a., 1j.2u.3a.4d.5a., 1p.2u.3a.4d.5a.,
1a.2y.3a.4d.5a., 1b.2y.3a.4d.5a., 1f.2y.3a.4d.5a., 1h.2y.3a.4d.5a.,
1j.2y.3a.4d.5a., 1p.2y.3a.4d.5a., 1a.2a.3b.4d.5a., 1b.2a.3b.4d.5a.,
1f.2a.3b.4d.5a., 1h.2a.3b.4d.5a., 1j.2a.3b.4d.5a., 1p.2a.3b.4d.5a.,
1a.2b.3b.4d.5a., 1b.2b.3b.4d.5a., 1f.2b.3b.4d.5a., 1h.2b.3b.4d.5a.,
1j.2b.3b.4d.5a., 1p.2b.3b.4d.5a., 1a.2e.3b.4d.5a., 1b.2e.3b.4d.5a.,
1f.2e.3b.4d.5a., 1h.2e.3b.4d.5a., 1j.2e.3b.4d.5a., 1p.2e.3b.4d.5a.,
1a.2f.3b.4d.5a., 1b.2f.3b.4d.5a., 1f.2f.3b.4d.5a., 1h.2f.3b.4d.5a.,
1j.2f.3b.4d.5a., 1p.2f.3b.4d.5a., 1a.2i.3b.4d.5a., 1b.2i.3b.4d.5a.,
1f.2i.3b.4d.5a., 1h.2i.3b.4d.5a., 1j.2i.3b.4d.5a., 1p.2i.3b.4d.5a.,
1a.2m.3b.4d.5a., 1b.2m.3b.4d.5a., 1f.2m.3b.4d.5a., 1h.2m.3b.4d.5a.,
1j.2m.3b.4d.5a., 1p.2m.3b.4d.5a., 1a.2o.3b.4d.5a., 1b.2o.3b.4d.5a.,
1f.2o.3b.4d.5a., 1h.2o.3b.4d.5a., 1j.2o.3b.4d.5a., 1p.2o.3b.4d.5a.,
1a.2u.3b.4d.5a., 1b.2u.3b.4d.5a., 1f.2u.3b.4d.5a., 1h.2u.3b.4d.5a.,
1j.2u.3b.4d.5a., 1p.2u.3b.4d.5a., 1a.2y.3b.4d.5a., 1b.2y.3b.4d.5a.,
1f.2y.3b.4d.5a., 1h.2y.3b.4d.5a., 1j.2y.3b.4d.5a., 1p.2y.3b.4d.5a.,
1a.2a.3e.4d.5a., 1b.2a.3e.4d.5a., 1f.2a.3e.4d.5a., 1h.2a.3e.4d.5a.,
1j.2a.3e.4d.5a., 1p.2a.3e.4d.5a., 1a.2b.3e.4d.5a., 1b.2b.3e.4d.5a.,
1f.2b.3e.4d.5a., 1h.2b.3e.4d.5a., 1j.2b.3e.4d.5a., 1p.2b.3e.4d.5a.,
1a.2e.3e.4d.5a., 1b.2e.3e.4d.5a., 1f.2e.3e.4d.5a., 1h.2e.3e.4d.5a.,
1j.2e.3e.4d.5a., 1p.2e.3e.4d.5a., 1a.2f.3e.4d.5a., 1b.2f.3e.4d.5a.,
1f.2f.3e.4d.5a., 1h.2f.3e.4d.5a., 1j.2f.3e.4d.5a., 1p.2f.3e.4d.5a.,
1a.2i.3e.4d.5a., 1b.2i.3e.4d.5a., 1f.2i.3e.4d.5a., 1h.2i.3e.4d.5a.,
1j.2i.3e.4d.5a., 1p.2i.3e.4d.5a., 1a.2m.3e.4d.5a., 1b.2m.3e.4d.5a.,
1f.2m.3e.4d.5a., 1h.2m.3e.4d.5a., 1j.2m.3e.4d.5a., 1p.2m.3e.4d.5a.,
1a.2o.3e.4d.5a., 1b.2o.3e.4d.5a., 1f.2o.3e.4d.5a., 1h.2o.3e.4d.5a.,
1j.2o.3e.4d.5a., 1p.2o.3e.4d.5a., 1a.2u.3e.4d.5a., 1b.2u.3e.4d.5a.,
1f.2u.3e.4d.5a., 1h.2u.3e.4d.5a., 1j.2u.3e.4d.5a., 1p.2u.3e.4d.5a.,
1a.2y.3e.4d.5a., 1b.2y.3e.4d.5a., 1f.2y.3e.4d.5a., 1h.2y.3e.4d.5a.,
1j.2y.3e.4d.5a., 1p.2y.3e.4d.5a., 1a.2a.3g.4d.5a., 1b.2a.3g.4d.5a.,
1f.2a.3g.4d.5a., 1h.2a.3g.4d.5a., 1j.2a.3g.4d.5a., 1p.2a.3g.4d.5a.,
1a.2b.3g.4d.5a., 1b.2b.3g.4d.5a., 1f.2b.3g.4d.5a., 1h.2b.3g.4d.5a.,
1j.2b.3g.4d.5a., 1p.2b.3g.4d.5a., 1a.2e.3g.4d.5a., 1b.2e.3g.4d.5a.,
1f.2e.3g.4d.5a., 1h.2e.3g.4d.5a., 1j.2e.3g.4d.5a., 1p.2e.3g.4d.5a.,
1a.2f.3g.4d.5a., 1b.2f.3g.4d.5a., 1f.2f.3g.4d.5a., 1h.2f.3g.4d.5a.,
1j.2f.3g.4d.5a., 1p.2f.3g.4d.5a., 1a.2i.3g.4d.5a., 1b.2i.3g.4d.5a.,
1f.2i.3g.4d.5a., 1h.2i.3g.4d.5a., 1j.2i.3g.4d.5a., 1p.2i.3g.4d.5a.,
1a.2m.3g.4d.5a., 1b.2m.3g.4d.5a., 1f.2m.3g.4d.5a., 1h.2m.3g.4d.5a.,
1j.2m.3g.4d.5a., 1p.2m.3g.4d.5a., 1a.2o.3g.4d.5a., 1b.2o.3g.4d.5a.,
1f.2o.3g.4d.5a., 1h.2o.3g.4d.5a., 1j.2o.3g.4d.5a., 1p.2o.3g.4d.5a.,
1a.2u.3g.4d.5a., 1b.2u.3g.4d.5a., 1f.2u.3g.4d.5a., 1h.2u.3g.4d.5a.,
1j.2u.3g.4d.5a., 1p.2u.3g.4d.5a., 1a.2y.3g.4d.5a., 1b.2y.3g.4d.5a.,
1f.2y.3g.4d.5a., 1h.2y.3g.4d.5a., 1j.2y.3g.4d.5a., 1p.2y.3g.4d.5a.,
1a.2a.3a.4f.5a., 1b.2a.3a.4f.5a., 1f.2a.3a.4f.5a., 1h.2a.3a.4f.5a.,
1j.2a.3a.4f.5a., 1p.2a.3a.4f.5a., 1a.2b.3a.4f.5a., 1b.2b.3a.4f.5a.,
1f.2b.3a.4f.5a., 1h.2b.3a.4f.5a., 1j.2b.3a.4f.5a., 1p.2b.3a.4f.5a.,
1a.2e.3a.4f.5a., 1b.2e.3a.4f.5a., 1f.2e.3a.4f.5a., 1h.2e.3a.4f.5a.,
1j.2e.3a.4f.5a., 1p.2e.3a.4f.5a., 1a.2f.3a.4f.5a., 1b.2f.3a.4f.5a.,
1f.2f.3a.4f.5a., 1h.2f.3a.4f.5a., 1j.2f.3a.4f.5a., 1p.2f.3a.4f.5a.,
1a.2i.3a.4f.5a., 1b.2i.3a.4f.5a., 1f.2i.3a.4f.5a., 1h.2i.3a.4f.5a.,
1j.2i.3a.4f.5a., 1p.2i.3a.4f.5a., 1a.2m.3a.4f.5a., 1b.2m.3a.4f.5a.,
1f.2m.3a.4f.5a., 1h.2m.3a.4f.5a., 1j.2m.3a.4f.5a., 1p.2m.3a.4f.5a.,
1a.2o.3a.4f.5a., 1b.2o.3a.4f.5a., 1f.2o.3a.4f.5a., 1h.2o.3a.4f.5a.,
1j.2o.3a.4f.5a., 1p.2o.3a.4f.5a., 1a.2u.3a.4f.5a., 1b.2u.3a.4f.5a.,
1f.2u.3a.4f.5a., 1h.2u.3a.4f.5a., 1j.2u.3a.4f.5a., 1p.2u.3a.4f.5a.,
1a.2y.3a.4f.5a., 1b.2y.3a.4f.5a., 1f.2y.3a.4f.5a., 1h.2y.3a.4f.5a.,
1j.2y.3a.4f.5a., 1p.2y.3a.4f.5a., 1a.2a.3b.4f.5a., 1b.2a.3b.4f.5a.,
1f.2a.3b.4f.5a., 1h.2a.3b.4f.5a., 1j.2a.3b.4f.5a., 1p.2a.3b.4f.5a.,
1a.2b.3b.4f.5a., 1b.2b.3b.4f.5a., 1f.2b.3b.4f.5a., 1h.2b.3b.4f.5a.,
1j.2b.3b.4f.5a., 1p.2b.3b.4f.5a., 1a.2e.3b.4f.5a., 1b.2e.3b.4f.5a.,
1f.2e.3b.4f.5a., 1h.2e.3b.4f.5a., 1j.2e.3b.4f.5a., 1p.2e.3b.4f.5a.,
1a.2f.3b.4f.5a., 1b.2f.3b.4f.5a., 1f.2f.3b.4f.5a., 1h.2f.3b.4f.5a.,
1j.2f.3b.4f.5a., 1p.2f.3b.4f.5a., 1a.2i.3b.4f.5a., 1b.2i.3b.4f.5a.,
1f.2i.3b.4f.5a., 1h.2i.3b.4f.5a., 1j.2i.3b.4f.5a., 1p.2i.3b.4f.5a.,
1a.2m.3b.4f.5a., 1b.2m.3b.4f.5a., 1f.2m.3b.4f.5a., 1h.2m.3b.4f.5a.,
1j.2m.3b.4f.5a., 1p.2m.3b.4f.5a., 1a.2o.3b.4f.5a., 1b.2o.3b.4f.5a.,
1f.2o.3b.4f.5a., 1h.2o.3b.4f.5a., 1j.2o.3b.4f.5a., 1p.2o.3b.4f.5a.,
1a.2u.3b.4f.5a., 1b.2u.3b.4f.5a., 1f.2u.3b.4f.5a., 1h.2u.3b.4f.5a.,
1j.2u.3b.4f.5a., 1p.2u.3b.4f.5a., 1a.2y.3b.4f.5a., 1b.2y.3b.4f.5a.,
1f.2y.3b.4f.5a., 1h.2y.3b.4f.5a., 1j.2y.3b.4f.5a., 1p.2y.3b.4f.5a.,
1a.2a.3e.4f.5a., 1b.2a.3e.4f.5a., 1f.2a.3e.4f.5a., 1h.2a.3e.4f.5a.,
1j.2a.3e.4f.5a., 1p.2a.3e.4f.5a., 1a.2b.3e.4f.5a., 1b.2b.3e.4f.5a.,
1f.2b.3e.4f.5a., 1h.2b.3e.4f.5a., 1j.2b.3e.4f.5a., 1p.2b.3e.4f.5a.,
1a.2e.3e.4f.5a., 1b.2e.3e.4f.5a., 1f.2e.3e.4f.5a., 1h.2e.3e.4f.5a.,
1j.2e.3e.4f.5a., 1p.2e.3e.4f.5a., 1a.2f.3e.4f.5a., 1b.2f.3e.4f.5a.,
1f.2f.3e.4f.5a., 1h.2f.3e.4f.5a., 1j.2f.3e.4f.5a., 1p.2f.3e.4f.5a.,
1a.2i.3e.4f.5a., 1b.2i.3e.4f.5a., 1f.2i.3e.4f.5a., 1h.2i.3e.4f.5a.,
1j.2i.3e.4f.5a., 1p.2i.3e.4f.5a., 1a.2m.3e.4f.5a., 1b.2m.3e.4f.5a.,
1f.2m.3e.4f.5a., 1h.2m.3e.4f.5a., 1j.2m.3e.4f.5a., 1p.2m.3e.4f.5a.,
1a.2o.3e.4f.5a., 1b.2o.3e.4f.5a., 1f.2o.3e.4f.5a., 1h.2o.3e.4f.5a.,
1j.2o.3e.4f.5a., 1p.2o.3e.4f.5a., 1a.2u.3e.4f.5a., 1b.2u.3e.4f.5a.,
1f.2u.3e.4f.5a., 1h.2u.3e.4f.5a., 1j.2u.3e.4f.5a., 1p.2u.3e.4f.5a.,
1a.2y.3e.4f.5a., 1b.2y.3e.4f.5a., 1f.2y.3e.4f.5a., 1h.2y.3e.4f.5a.,
1j.2y.3e.4f.5a., 1p.2y.3e.4f.5a., 1a.2a.3g.4f.5a., 1b.2a.3g.4f.5a.,
1f.2a.3g.4f.5a., 1h.2a.3g.4f.5a., 1j.2a.3g.4f.5a., 1p.2a.3g.4f.5a.,
1a.2b.3g.4f.5a., 1b.2b.3g.4f.5a., 1f.2b.3g.4f.5a., 1h.2b.3g.4f.5a.,
1j.2b.3g.4f.5a., 1p.2b.3g.4f.5a., 1a.2e.3g.4f.5a., 1b.2e.3g.4f.5a.,
1f.2e.3g.4f.5a., 1h.2e.3g.4f.5a., 1j.2e.3g.4f.5a., 1p.2e.3g.4f.5a.,
1a.2f.3g.4f.5a., 1b.2f.3g.4f.5a., 1f.2f.3g.4f.5a., 1h.2f.3g.4f.5a.,
1j.2f.3g.4f.5a., 1p.2f.3g.4f.5a., 1a.2i.3g.4f.5a., 1b.2i.3g.4f.5a.,
1f.2i.3g.4f.5a., 1h.2i.3g.4f.5a., 1j.2i.3g.4f.5a., 1p.2i.3g.4f.5a.,
1a.2m.3g.4f.5a., 1b.2m.3g.4f.5a., 1f.2m.3g.4f.5a., 1h.2m.3g.4f.5a.,
1j.2m.3g.4f.5a., 1p.2m.3g.4f.5a., 1a.2o.3g.4f.5a., 1b.2o.3g.4f.5a.,
1f.2o.3g.4f.5a., 1h.2o.3g.4f.5a., 1j.2o.3g.4f.5a., 1p.2o.3g.4f.5a.,
1a.2u.3g.4f.5a., 1b.2u.3g.4f.5a., 1f.2u.3g.4f.5a., 1h.2u.3g.4f.5a.,
1j.2u.3g.4f.5a., 1p.2u.3g.4f.5a., 1a.2y.3g.4f.5a., 1b.2y.3g.4f.5a.,
1f.2y.3g.4f.5a., 1h.2y.3g.4f.5a., 1j.2y.3g.4f.5a., 1p.2y.3g.4f.5a.,
1a.2a.3a.4g.5a., 1b.2a.3a.4g.5a., 1f.2a.3a.4g.5a., 1h.2a.3a.4g.5a.,
1j.2a.3a.4g.5a., 1p.2a.3a.4g.5a., 1a.2b.3a.4g.5a., 1b.2b.3a.4g.5a.,
1f.2b.3a.4g.5a., 1h.2b.3a.4g.5a., 1j.2b.3a.4g.5a., 1p.2b.3a.4g.5a.,
1a.2e.3a.4g.5a., 1b.2e.3a.4g.5a., 1f.2e.3a.4g.5a., 1h.2e.3a.4g.5a.,
1j.2e.3a.4g.5a., 1p.2e.3a.4g.5a., 1a.2f.3a.4g.5a., 1b.2f.3a.4g.5a.,
1f.2f.3a.4g.5a., 1h.2f.3a.4g.5a., 1j.2f.3a.4g.5a., 1p.2f.3a.4g.5a.,
1a.2i.3a.4g.5a., 1b.2i.3a.4g.5a., 1f.2i.3a.4g.5a., 1h.2i.3a.4g.5a.,
1j.2i.3a.4g.5a., 1p.2i.3a.4g.5a., 1a.2m.3a.4g.5a., 1b.2m.3a.4g.5a.,
1f.2m.3a.4g.5a., 1h.2m.3a.4g.5a., 1j.2m.3a.4g.5a., 1p.2m.3a.4g.5a.,
1a.2o.3a.4g.5a., 1b.2o.3a.4g.5a., 1f.2o.3a.4g.5a., 1h.2o.3a.4g.5a.,
1j.2o.3a.4g.5a., 1p.2o.3a.4g.5a., 1a.2u.3a.4g.5a., 1b.2u.3a.4g.5a.,
1f.2u.3a.4g.5a., 1h.2u.3a.4g.5a., 1j.2u.3a.4g.5a., 1p.2u.3a.4g.5a.,
1a.2y.3a.4g.5a., 1b.2y.3a.4g.5a., 1f.2y.3a.4g.5a., 1h.2y.3a.4g.5a.,
1j.2y.3a.4g.5a., 1p.2y.3a.4g.5a., 1a.2a.3b.4g.5a., 1b.2a.3b.4g.5a.,
1f.2a.3b.4g.5a., 1h.2a.3b.4g.5a., 1j.2a.3b.4g.5a., 1p.2a.3b.4g.5a.,
1a.2b.3b.4g.5a., 1b.2b.3b.4g.5a., 1f.2b.3b.4g.5a., 1h.2b.3b.4g.5a.,
1j.2b.3b.4g.5a., 1p.2b.3b.4g.5a., 1a.2e.3b.4g.5a., 1b.2e.3b.4g.5a.,
1f.2e.3b.4g.5a., 1h.2e.3b.4g.5a., 1j.2e.3b.4g.5a., 1p.2e.3b.4g.5a.,
1a.2f.3b.4g.5a., 1b.2f.3b.4g.5a., 1f.2f.3b.4g.5a., 1h.2f.3b.4g.5a.,
1j.2f.3b.4g.5a., 1p.2f.3b.4g.5a., 1a.2i.3b.4g.5a., 1b.2i.3b.4g.5a.,
1f.2i.3b.4g.5a., 1h.2i.3b.4g.5a., 1j.2i.3b.4g.5a., 1p.2i.3b.4g.5a.,
1a.2m.3b.4g.5a., 1b.2m.3b.4g.5a., 1f.2m.3b.4g.5a., 1h.2m.3b.4g.5a.,
1j.2m.3b.4g.5a., 1p.2m.3b.4g.5a., 1a.2o.3b.4g.5a., 1b.2o.3b.4g.5a.,
1f.2o.3b.4g.5a., 1h.2o.3b.4g.5a., 1j.2o.3b.4g.5a., 1p.2o.3b.4g.5a.,
1a.2u.3b.4g.5a., 1b.2u.3b.4g.5a., 1f.2u.3b.4g.5a., 1h.2u.3b.4g.5a.,
1j.2u.3b.4g.5a., 1p.2u.3b.4g.5a., 1a.2y.3b.4g.5a., 1b.2y.3b.4g.5a.,
1f.2y.3b.4g.5a., 1h.2y.3b.4g.5a., 1j.2y.3b.4g.5a., 1p.2y.3b.4g.5a.,
1a.2a.3e.4g.5a., 1b.2a.3e.4g.5a., 1f.2a.3e.4g.5a., 1h.2a.3e.4g.5a.,
1j.2a.3e.4g.5a., 1p.2a.3e.4g.5a., 1a.2b.3e.4g.5a., 1b.2b.3e.4g.5a.,
1f.2b.3e.4g.5a., 1h.2b.3e.4g.5a., 1j.2b.3e.4g.5a., 1p.2b.3e.4g.5a.,

TABLE 12-continued

List of Compound Structures of Formula III 1a.2e.3e.4g.5a., 1b.2e.3e.4g.5a., 1f.2e.3e.4g.5a., 1h.2e.3e.4g.5a.,
1j.2e.3e.4g.5a., 1p.2e.3e.4g.5a., 1a.2f.3e.4g.5a., 1b.2f.3e.4g.5a.,
1f.2f.3e.4g.5a., 1h.2f.3e.4g.5a., 1j.2f.3e.4g.5a., 1p.2f.3e.4g.5a.,
1a.2i.3e.4g.5a., 1b.2i.3e.4g.5a., 1f.2i.3e.4g.5a., 1h.2i.3e.4g.5a.,
1j.2i.3e.4g.5a., 1p.2i.3e.4g.5a., 1a.2m.3e.4g.5a., 1b.2m.3e.4g.5a.,
1f.2m.3e.4g.5a., 1h.2m.3e.4g.5a., 1j.2m.3e.4g.5a., 1p.2m.3e.4g.5a.,
1a.2o.3e.4g.5a., 1b.2o.3e.4g.5a., 1f.2o.3e.4g.5a., 1h.2o.3e.4g.5a.,
1j.2o.3e.4g.5a., 1p.2o.3e.4g.5a., 1a.2u.3e.4g.5a., 1b.2u.3e.4g.5a.,
1f.2u.3e.4g.5a., 1h.2u.3e.4g.5a., 1j.2u.3e.4g.5a., 1p.2u.3e.4g.5a.,
1a.2y.3e.4g.5a., 1b.2y.3e.4g.5a., 1f.2y.3e.4g.5a., 1h.2y.3e.4g.5a.,
1j.2y.3e.4g.5a., 1p.2y.3e.4g.5a., 1a.2a.3g.4g.5a., 1b.2a.3g.4g.5a.,
1f.2a.3g.4g.5a., 1h.2a.3g.4g.5a., 1j.2a.3g.4g.5a., 1p.2a.3g.4g.5a.,
1a.2b.3g.4g.5a., 1b.2b.3g.4g.5a., 1f.2b.3g.4g.5a., 1h.2b.3g.4g.5a.,
1j.2b.3g.4g.5a., 1p.2b.3g.4g.5a., 1a.2e.3g.4g.5a., 1b.2e.3g.4g.5a.,
1f.2e.3g.4g.5a., 1h.2e.3g.4g.5a., 1j.2e.3g.4g.5a., 1p.2e.3g.4g.5a.,
1a.2f.3g.4g.5a., 1b.2f.3g.4g.5a., 1f.2f.3g.4g.5a., 1h.2f.3g.4g.5a.,
1j.2f.3g.4g.5a., 1p.2f.3g.4g.5a., 1a.2i.3g.4g.5a., 1b.2i.3g.4g.5a.,
1f.2i.3g.4g.5a., 1h.2i.3g.4g.5a., 1j.2i.3g.4g.5a., 1p.2i.3g.4g.5a.,
1a.2m.3g.4g.5a., 1b.2m.3g.4g.5a., 1f.2m.3g.4g.5a., 1h.2m.3g.4g.5a.,
1j.2m.3g.4g.5a., 1p.2m.3g.4g.5a., 1a.2o.3g.4g.5a., 1b.2o.3g.4g.5a.,
1f.2o.3g.4g.5a., 1h.2o.3g.4g.5a., 1j.2o.3g.4g.5a., 1p.2o.3g.4g.5a.,
1a.2u.3g.4g.5a., 1b.2u.3g.4g.5a., 1f.2u.3g.4g.5a., 1h.2u.3g.4g.5a.,
1j.2u.3g.4g.5a., 1p.2u.3g.4g.5a., 1a.2y.3g.4g.5a., 1b.2y.3g.4g.5a.,
1f.2y.3g.4g.5a., 1h.2y.3g.4g.5a., 1j.2y.3g.4g.5a., 1p.2y.3g.4g.5a.,
1a.2a.3a.4h.5a., 1b.2a.3a.4h.5a., 1f.2a.3a.4h.5a., 1h.2a.3a.4h.5a.,
1j.2a.3a.4h.5a., 1p.2a.3a.4h.5a., 1a.2b.3a.4h.5a., 1b.2b.3a.4h.5a.,
1f.2b.3a.4h.5a., 1h.2b.3a.4h.5a., 1j.2b.3a.4h.5a., 1p.2b.3a.4h.5a.,
1a.2e.3a.4h.5a., 1b.2e.3a.4h.5a., 1f.2e.3a.4h.5a., 1h.2e.3a.4h.5a.,
1j.2e.3a.4h.5a., 1p.2e.3a.4h.5a., 1a.2f.3a.4h.5a., 1b.2f.3a.4h.5a.,
1f.2f.3a.4h.5a., 1h.2f.3a.4h.5a., 1j.2f.3a.4h.5a., 1p.2f.3a.4h.5a.,
1a.2i.3a.4h.5a., 1b.2i.3a.4h.5a., 1f.2i.3a.4h.5a., 1h.2i.3a.4h.5a.,
1j.2i.3a.4h.5a., 1p.2i.3a.4h.5a., 1a.2m.3a.4h.5a., 1b.2m.3a.4h.5a.,
1f.2m.3a.4h.5a., 1h.2m.3a.4h.5a., 1j.2m.3a.4h.5a., 1p.2m.3a.4h.5a.,
1a.2o.3a.4h.5a., 1b.2o.3a.4h.5a., 1f.2o.3a.4h.5a., 1h.2o.3a.4h.5a.,
1j.2o.3a.4h.5a., 1p.2o.3a.4h.5a., 1a.2u.3a.4h.5a., 1b.2u.3a.4h.5a.,
1f.2u.3a.4h.5a., 1h.2u.3a.4h.5a., 1j.2u.3a.4h.5a., 1p.2u.3a.4h.5a.,
1a.2y.3a.4h.5a., 1b.2y.3a.4h.5a., 1f.2y.3a.4h.5a., 1h.2y.3a.4h.5a.,
1j.2y.3a.4h.5a., 1p.2y.3a.4h.5a., 1a.2a.3b.4h.5a., 1b.2a.3b.4h.5a.,
1f.2a.3b.4h.5a., 1h.2a.3b.4h.5a., 1j.2a.3b.4h.5a., 1p.2a.3b.4h.5a.,
1a.2b.3b.4h.5a., 1b.2b.3b.4h.5a., 1f.2b.3b.4h.5a., 1h.2b.3b.4h.5a.,
1j.2b.3b.4h.5a., 1p.2b.3b.4h.5a., 1a.2e.3b.4h.5a., 1b.2e.3b.4h.5a.,
1f.2e.3b.4h.5a., 1h.2e.3b.4h.5a., 1j.2e.3b.4h.5a., 1p.2e.3b.4h.5a.,
1a.2f.3b.4h.5a., 1b.2f.3b.4h.5a., 1f.2f.3b.4h.5a., 1h.2f.3b.4h.5a.,
1j.2f.3b.4h.5a., 1p.2f.3b.4h.5a., 1a.2i.3b.4h.5a., 1b.2i.3b.4h.5a.,
1f.2i.3b.4h.5a., 1h.2i.3b.4h.5a., 1j.2i.3b.4h.5a., 1p.2i.3b.4h.5a.,
1a.2m.3b.4h.5a., 1b.2m.3b.4h.5a., 1f.2m.3b.4h.5a., 1h.2m.3b.4h.5a.,
1j.2m.3b.4h.5a., 1p.2m.3b.4h.5a., 1a.2o.3b.4h.5a., 1b.2o.3b.4h.5a.,
1f.2o.3b.4h.5a., 1h.2o.3b.4h.5a., 1j.2o.3b.4h.5a., 1p.2o.3b.4h.5a.,
1a.2u.3b.4h.5a., 1b.2u.3b.4h.5a., 1f.2u.3b.4h.5a., 1h.2u.3b.4h.5a.,
1j.2u.3b.4h.5a., 1p.2u.3b.4h.5a., 1a.2y.3b.4h.5a., 1b.2y.3b.4h.5a.,
1f.2y.3b.4h.5a., 1h.2y.3b.4h.5a., 1j.2y.3b.4h.5a., 1p.2y.3b.4h.5a.,
1a.2a.3e.4h.5a., 1b.2a.3e.4h.5a., 1f.2a.3e.4h.5a., 1h.2a.3e.4h.5a.,
1j.2a.3e.4h.5a., 1p.2a.3e.4h.5a., 1a.2b.3e.4h.5a., 1b.2b.3e.4h.5a.,
1f.2b.3e.4h.5a., 1h.2b.3e.4h.5a., 1j.2b.3e.4h.5a., 1p.2b.3e.4h.5a.,
1a.2e.3e.4h.5a., 1b.2e.3e.4h.5a., 1f.2e.3e.4h.5a., 1h.2e.3e.4h.5a.,
1j.2e.3e.4h.5a., 1p.2e.3e.4h.5a., 1a.2f.3e.4h.5a., 1b.2f.3e.4h.5a.,
1f.2f.3e.4h.5a., 1h.2f.3e.4h.5a., 1j.2f.3e.4h.5a., 1p.2f.3e.4h.5a.,
1a.2i.3e.4h.5a., 1b.2i.3e.4h.5a., 1f.2i.3e.4h.5a., 1h.2i.3e.4h.5a.,
1j.2i.3e.4h.5a., 1p.2i.3e.4h.5a., 1a.2m.3e.4h.5a., 1b.2m.3e.4h.5a.,
1f.2m.3e.4h.5a., 1h.2m.3e.4h.5a., 1j.2m.3e.4h.5a., 1p.2m.3e.4h.5a.,
1a.2o.3e.4h.5a., 1b.2o.3e.4h.5a., 1f.2o.3e.4h.5a., 1h.2o.3e.4h.5a.,
1j.2o.3e.4h.5a., 1p.2o.3e.4h.5a., 1a.2u.3e.4h.5a., 1b.2u.3e.4h.5a.,
1f.2u.3e.4h.5a., 1h.2u.3e.4h.5a., 1j.2u.3e.4h.5a., 1p.2u.3e.4h.5a.,
1a.2y.3e.4h.5a., 1b.2y.3e.4h.5a., 1f.2y.3e.4h.5a., 1h.2y.3e.4h.5a.,
1j.2y.3e.4h.5a., 1p.2y.3e.4h.5a., 1a.2a.3g.4h.5a., 1b.2a.3g.4h.5a.,
1f.2a.3g.4h.5a., 1h.2a.3g.4h.5a., 1j.2a.3g.4h.5a., 1p.2a.3g.4h.5a.,
1a.2b.3g.4h.5a., 1b.2b.3g.4h.5a., 1f.2b.3g.4h.5a., 1h.2b.3g.4h.5a.,
1j.2b.3g.4h.5a., 1p.2b.3g.4h.5a., 1a.2e.3g.4h.5a., 1b.2e.3g.4h.5a.,
1f.2e.3g.4h.5a., 1h.2e.3g.4h.5a., 1j.2e.3g.4h.5a., 1p.2e.3g.4h.5a.,
1a.2f.3g.4h.5a., 1b.2f.3g.4h.5a., 1f.2f.3g.4h.5a., 1h.2f.3g.4h.5a.,
1j.2f.3g.4h.5a., 1p.2f.3g.4h.5a., 1a.2i.3g.4h.5a., 1b.2i.3g.4h.5a.,
1f.2i.3g.4h.5a., 1h.2i.3g.4h.5a., 1j.2i.3g.4h.5a., 1p.2i.3g.4h.5a.,
1a.2m.3g.4h.5a., 1b.2m.3g.4h.5a., 1f.2m.3g.4h.5a., 1h.2m.3g.4h.5a.,
1j.2m.3g.4h.5a., 1p.2m.3g.4h.5a., 1a.2o.3g.4h.5a., 1b.2o.3g.4h.5a.,
1f.2o.3g.4h.5a., 1h.2o.3g.4h.5a., 1j.2o.3g.4h.5a., 1p.2o.3g.4h.5a.,
1a.2u.3g.4h.5a., 1b.2u.3g.4h.5a., 1f.2u.3g.4h.5a., 1h.2u.3g.4h.5a.,
1j.2u.3g.4h.5a., 1p.2u.3g.4h.5a., 1a.2y.3g.4h.5a., 1b.2y.3g.4h.5a.,
1f.2y.3g.4h.5a., 1h.2y.3g.4h.5a., 1j.2y.3g.4h.5a., 1p.2y.3g.4h.5a., 1a.2a.3a.4i.5a., 1b.2a.3a.4i.5a., 1f.2a.3a.4i.5a., 1h.2a.3a.4i.5a.,
1j.2a.3a.4i.5a., 1p.2a.3a.4i.5a., 1a.2b.3a.4i.5a., 1b.2b.3a.4i.5a.,
1f.2b.3a.4i.5a., 1h.2b.3a.4i.5a., 1j.2b.3a.4i.5a., 1p.2b.3a.4i.5a.,
1a.2e.3a.4i.5a., 1b.2e.3a.4i.5a., 1f.2e.3a.4i.5a., 1h.2e.3a.4i.5a.,
1j.2e.3a.4i.5a., 1p.2e.3a.4i.5a., 1a.2f.3a.4i.5a., 1b.2f.3a.4i.5a.,
1f.2f.3a.4i.5a., 1h.2f.3a.4i.5a., 1j.2f.3a.4i.5a., 1p.2f.3a.4i.5a.,
1a.2i.3a.4i.5a., 1b.2i.3a.4i.5a., 1f.2i.3a.4i.5a., 1h.2i.3a.4i.5a.,
1j.2i.3a.4i.5a., 1p.2i.3a.4i.5a., 1a.2m.3a.4i.5a., 1b.2m.3a.4i.5a.,
1f.2m.3a.4i.5a., 1h.2m.3a.4i.5a., 1j.2m.3a.4i.5a., 1p.2m.3a.4i.5a.,
1a.2o.3a.4i.5a., 1b.2o.3a.4i.5a., 1f.2o.3a.4i.5a., 1h.2o.3a.4i.5a.,
1j.2o.3a.4i.5a., 1p.2o.3a.4i.5a., 1a.2u.3a.4i.5a., 1b.2u.3a.4i.5a.,
1f.2u.3a.4i.5a., 1h.2u.3a.4i.5a., 1j.2u.3a.4i.5a., 1p.2u.3a.4i.5a.,
1a.2y.3a.4i.5a., 1b.2y.3a.4i.5a., 1f.2y.3a.4i.5a., 1h.2y.3a.4i.5a.,
1j.2y.3a.4i.5a., 1p.2y.3a.4i.5a., 1a.2a.3b.4i.5a., 1b.2a.3b.4i.5a.,
1f.2a.3b.4i.5a., 1h.2a.3b.4i.5a., 1j.2a.3b.4i.5a., 1p.2a.3b.4i.5a.,
1a.2b.3b.4i.5a., 1b.2b.3b.4i.5a., 1f.2b.3b.4i.5a., 1h.2b.3b.4i.5a.,
1j.2b.3b.4i.5a., 1p.2b.3b.4i.5a., 1a.2e.3b.4i.5a., 1b.2e.3b.4i.5a.,
1f.2e.3b.4i.5a., 1h.2e.3b.4i.5a., 1j.2e.3b.4i.5a., 1p.2e.3b.4i.5a.,
1a.2f.3b.4i.5a., 1b.2f.3b.4i.5a., 1f.2f.3b.4i.5a., 1h.2f.3b.4i.5a.,
1j.2f.3b.4i.5a., 1p.2f.3b.4i.5a., 1a.2i.3b.4i.5a., 1b.2i.3b.4i.5a.,
1f.2i.3b.4i.5a., 1h.2i.3b.4i.5a., 1j.2i.3b.4i.5a., 1p.2i.3b.4i.5a.,
1a.2m.3b.4i.5a., 1b.2m.3b.4i.5a., 1f.2m.3b.4i.5a., 1h.2m.3b.4i.5a.,
1j.2m.3b.4i.5a., 1p.2m.3b.4i.5a., 1a.2o.3b.4i.5a., 1b.2o.3b.4i.5a.,
1f.2o.3b.4i.5a., 1h.2o.3b.4i.5a., 1j.2o.3b.4i.5a., 1p.2o.3b.4i.5a.,
1a.2u.3b.4i.5a., 1b.2u.3b.4i.5a., 1f.2u.3b.4i.5a., 1h.2u.3b.4i.5a.,
1j.2u.3b.4i.5a., 1p.2u.3b.4i.5a., 1a.2y.3b.4i.5a., 1b.2y.3b.4i.5a.,
1f.2y.3b.4i.5a., 1h.2y.3b.4i.5a., 1j.2y.3b.4i.5a., 1p.2y.3b.4i.5a.,
1a.2a.3e.4i.5a., 1b.2a.3e.4i.5a., 1f.2a.3e.4i.5a., 1h.2a.3e.4i.5a.,
1j.2a.3e.4i.5a., 1p.2a.3e.4i.5a., 1a.2b.3e.4i.5a., 1b.2b.3e.4i.5a.,
1f.2b.3e.4i.5a., 1h.2b.3e.4i.5a., 1j.2b.3e.4i.5a., 1p.2b.3e.4i.5a.,
1a.2e.3e.4i.5a., 1b.2e.3e.4i.5a., 1f.2e.3e.4i.5a., 1h.2e.3e.4i.5a.,
1j.2e.3e.4i.5a., 1p.2e.3e.4i.5a., 1a.2f.3e.4i.5a., 1b.2f.3e.4i.5a.,
1f.2f.3e.4i.5a., 1h.2f.3e.4i.5a., 1j.2f.3e.4i.5a., 1p.2f.3e.4i.5a.,
1a.2i.3e.4i.5a., 1b.2i.3e.4i.5a., 1f.2i.3e.4i.5a., 1h.2i.3e.4i.5a.,
1j.2i.3e.4i.5a., 1p.2i.3e.4i.5a., 1a.2m.3e.4i.5a., 1b.2m.3e.4i.5a.,
1f.2m.3e.4i.5a., 1h.2m.3e.4i.5a., 1j.2m.3e.4i.5a., 1p.2m.3e.4i.5a.,
1a.2o.3e.4i.5a., 1b.2o.3e.4i.5a., 1f.2o.3e.4i.5a., 1h.2o.3e.4i.5a.,
1j.2o.3e.4i.5a., 1p.2o.3e.4i.5a., 1a.2u.3e.4i.5a., 1b.2u.3e.4i.5a.,
1f.2u.3e.4i.5a., 1h.2u.3e.4i.5a., 1j.2u.3e.4i.5a., 1p.2u.3e.4i.5a.,
1a.2y.3e.4i.5a., 1b.2y.3e.4i.5a., 1f.2y.3e.4i.5a., 1h.2y.3e.4i.5a.,
1j.2y.3e.4i.5a., 1p.2y.3e.4i.5a., 1a.2a.3g.4i.5a., 1b.2a.3g.4i.5a.,
1f.2a.3g.4i.5a., 1h.2a.3g.4i.5a., 1j.2a.3g.4i.5a., 1p.2a.3g.4i.5a.,
1a.2b.3g.4i.5a., 1b.2b.3g.4i.5a., 1f.2b.3g.4i.5a., 1h.2b.3g.4i.5a.,
1j.2b.3g.4i.5a., 1p.2b.3g.4i.5a., 1a.2e.3g.4i.5a., 1b.2e.3g.4i.5a.,
1f.2e.3g.4i.5a., 1h.2e.3g.4i.5a., 1j.2e.3g.4i.5a., 1p.2e.3g.4i.5a.,
1a.2f.3g.4i.5a., 1b.2f.3g.4i.5a., 1f.2f.3g.4i.5a., 1h.2f.3g.4i.5a.,
1j.2f.3g.4i.5a., 1p.2f.3g.4i.5a., 1a.2i.3g.4i.5a., 1b.2i.3g.4i.5a.,
1f.2i.3g.4i.5a., 1h.2i.3g.4i.5a., 1j.2i.3g.4i.5a., 1p.2i.3g.4i.5a.,
1a.2m.3g.4i.5a., 1b.2m.3g.4i.5a., 1f.2m.3g.4i.5a., 1h.2m.3g.4i.5a.,
1j.2m.3g.4i.5a., 1p.2m.3g.4i.5a., 1a.2o.3g.4i.5a., 1b.2o.3g.4i.5a.,
1f.2o.3g.4i.5a., 1h.2o.3g.4i.5a., 1j.2o.3g.4i.5a., 1p.2o.3g.4i.5a.,
1a.2u.3g.4i.5a., 1b.2u.3g.4i.5a., 1f.2u.3g.4i.5a., 1h.2u.3g.4i.5a.,
1j.2u.3g.4i.5a., 1p.2u.3g.4i.5a., 1a.2y.3g.4i.5a., 1b.2y.3g.4i.5a.,
1f.2y.3g.4i.5a., 1h.2y.3g.4i.5a., 1j.2y.3g.4i.5a., 1p.2y.3g.4i.5a.,
1a.2a.3a.4a.5d., 1b.2a.3a.4a.5d., 1f.2a.3a.4a.5d., 1h.2a.3a.4a.5d.,
1j.2a.3a.4a.5d., 1p.2a.3a.4a.5d., 1a.2b.3a.4a.5d., 1b.2b.3a.4a.5d.,
1f.2b.3a.4a.5d., 1h.2b.3a.4a.5d., 1j.2b.3a.4a.5d., 1p.2b.3a.4a.5d.,
1a.2e.3a.4a.5d., 1b.2e.3a.4a.5d., 1f.2e.3a.4a.5d., 1h.2e.3a.4a.5d.,
1j.2e.3a.4a.5d., 1p.2e.3a.4a.5d., 1a.2f.3a.4a.5d., 1b.2f.3a.4a.5d.,
1f.2f.3a.4a.5d., 1h.2f.3a.4a.5d., 1j.2f.3a.4a.5d., 1p.2f.3a.4a.5d.,
1a.2i.3a.4a.5d., 1b.2i.3a.4a.5d., 1f.2i.3a.4a.5d., 1h.2i.3a.4a.5d.,
1j.2i.3a.4a.5d., 1p.2i.3a.4a.5d., 1a.2m.3a.4a.5d., 1b.2m.3a.4a.5d.,
1f.2m.3a.4a.5d., 1h.2m.3a.4a.5d., 1j.2m.3a.4a.5d., 1p.2m.3a.4a.5d.,
1a.2o.3a.4a.5d., 1b.2o.3a.4a.5d., 1f.2o.3a.4a.5d., 1h.2o.3a.4a.5d.,
1j.2o.3a.4a.5d., 1p.2o.3a.4a.5d., 1a.2u.3a.4a.5d., 1b.2u.3a.4a.5d.,
1f.2u.3a.4a.5d., 1h.2u.3a.4a.5d., 1j.2u.3a.4a.5d., 1p.2u.3a.4a.5d.,
1a.2y.3a.4a.5d., 1b.2y.3a.4a.5d., 1f.2y.3a.4a.5d., 1h.2y.3a.4a.5d.,
1j.2y.3a.4a.5d., 1p.2y.3a.4a.5d., 1a.2a.3b.4a.5d., 1b.2a.3b.4a.5d.,
1f.2a.3b.4a.5d., 1h.2a.3b.4a.5d., 1j.2a.3b.4a.5d., 1p.2a.3b.4a.5d.,
1a.2b.3b.4a.5d., 1b.2b.3b.4a.5d., 1f.2b.3b.4a.5d., 1h.2b.3b.4a.5d.,
1j.2b.3b.4a.5d., 1p.2b.3b.4a.5d., 1a.2e.3b.4a.5d., 1b.2e.3b.4a.5d.,
1f.2e.3b.4a.5d., 1h.2e.3b.4a.5d., 1j.2e.3b.4a.5d., 1p.2e.3b.4a.5d.,
1a.2f.3b.4a.5d., 1b.2f.3b.4a.5d., 1f.2f.3b.4a.5d., 1h.2f.3b.4a.5d.,
1j.2f.3b.4a.5d., 1p.2f.3b.4a.5d., 1a.2i.3b.4a.5d., 1b.2i.3b.4a.5d.,
1f.2i.3b.4a.5d., 1h.2i.3b.4a.5d., 1j.2i.3b.4a.5d., 1p.2i.3b.4a.5d.,
1a.2m.3b.4a.5d., 1b.2m.3b.4a.5d., 1f.2m.3b.4a.5d., 1h.2m.3b.4a.5d.,
1j.2m.3b.4a.5d., 1p.2m.3b.4a.5d., 1a.2o.3b.4a.5d., 1b.2o.3b.4a.5d.,
1f.2o.3b.4a.5d., 1h.2o.3b.4a.5d., 1j.2o.3b.4a.5d., 1p.2o.3b.4a.5d.,

TABLE 12-continued

List of Compound Structures of Formula III 1a.2u.3b.4a.5d., 1b.2u.3b.4a.5d., 1f.2u.3b.4a.5d., 1h.2u.3b.4a.5d.,
1j.2u.3b.4a.5d., 1p.2u.3b.4a.5d., 1a.2y.3b.4a.5d., 1b.2y.3b.4a.5d.,
1f.2y.3b.4a.5d., 1h.2y.3b.4a.5d., 1j.2y.3b.4a.5d., 1p.2y.3b.4a.5d.,
1a.2a.3e.4a.5d., 1b.2a.3e.4a.5d., 1f.2a.3e.4a.5d., 1h.2a.3e.4a.5d.,
1j.2a.3e.4a.5d., 1p.2a.3e.4a.5d., 1a.2b.3e.4a.5d., 1b.2b.3e.4a.5d.,
1f.2b.3e.4a.5d., 1h.2b.3e.4a.5d., 1j.2b.3e.4a.5d., 1p.2b.3e.4a.5d.,
1a.2e.3e.4a.5d., 1b.2e.3e.4a.5d., 1f.2e.3e.4a.5d., 1h.2e.3e.4a.5d.,
1j.2e.3e.4a.5d., 1p.2e.3e.4a.5d., 1a.2f.3e.4a.5d., 1b.2f.3e.4a.5d.,
1f.2f.3e.4a.5d., 1h.2f.3e.4a.5d., 1j.2f.3e.4a.5d., 1p.2f.3e.4a.5d.,
1a.2i.3e.4a.5d., 1b.2i.3e.4a.5d., 1f.2i.3e.4a.5d., 1h.2i.3e.4a.5d.,
1j.2i.3e.4a.5d., 1p.2i.3e.4a.5d., 1a.2m.3e.4a.5d., 1b.2m.3e.4a.5d.,
1f.2m.3e.4a.5d., 1h.2m.3e.4a.5d., 1j.2m.3e.4a.5d., 1p.2m.3e.4a.5d.,
1a.2o.3e.4a.5d., 1b.2o.3e.4a.5d., 1f.2o.3e.4a.5d., 1h.2o.3e.4a.5d.,
1j.2o.3e.4a.5d., 1p.2o.3e.4a.5d., 1a.2u.3e.4a.5d., 1b.2u.3e.4a.5d.,
1f.2u.3e.4a.5d., 1h.2u.3e.4a.5d., 1j.2u.3e.4a.5d., 1p.2u.3e.4a.5d.,
1a.2y.3e.4a.5d., 1b.2y.3e.4a.5d., 1f.2y.3e.4a.5d., 1h.2y.3e.4a.5d.,
1j.2y.3e.4a.5d., 1p.2y.3e.4a.5d., 1a.2a.3g.4a.5d., 1b.2a.3g.4a.5d.,
1f.2a.3g.4a.5d., 1h.2a.3g.4a.5d., 1j.2a.3g.4a.5d., 1p.2a.3g.4a.5d.,
1a.2b.3g.4a.5d., 1b.2b.3g.4a.5d., 1f.2b.3g.4a.5d., 1h.2b.3g.4a.5d.,
1j.2b.3g.4a.5d., 1p.2b.3g.4a.5d., 1a.2e.3g.4a.5d., 1b.2e.3g.4a.5d.,
1f.2e.3g.4a.5d., 1h.2e.3g.4a.5d., 1j.2e.3g.4a.5d., 1p.2e.3g.4a.5d.,
1a.2f.3g.4a.5d., 1b.2f.3g.4a.5d., 1f.2f.3g.4a.5d., 1h.2f.3g.4a.5d.,
1j.2f.3g.4a.5d., 1p.2f.3g.4a.5d., 1a.2i.3g.4a.5d., 1b.2i.3g.4a.5d.,
1f.2i.3g.4a.5d., 1h.2i.3g.4a.5d., 1j.2i.3g.4a.5d., 1p.2i.3g.4a.5d.,
1a.2m.3g.4a.5d., 1b.2m.3g.4a.5d., 1f.2m.3g.4a.5d., 1h.2m.3g.4a.5d.,
1j.2m.3g.4a.5d., 1p.2m.3g.4a.5d., 1a.2o.3g.4a.5d., 1b.2o.3g.4a.5d.,
1f.2o.3g.4a.5d., 1h.2o.3g.4a.5d., 1j.2o.3g.4a.5d., 1p.2o.3g.4a.5d.,
1a.2u.3g.4a.5d., 1b.2u.3g.4a.5d., 1f.2u.3g.4a.5d., 1h.2u.3g.4a.5d.,
1j.2u.3g.4a.5d., 1p.2u.3g.4a.5d., 1a.2y.3g.4a.5d., 1b.2y.3g.4a.5d.,
1f.2y.3g.4a.5d., 1h.2y.3g.4a.5d., 1j.2y.3g.4a.5d., 1p.2y.3g.4a.5d.,
1a.2a.3a.4d.5d., 1b.2a.3a.4d.5d., 1f.2a.3a.4d.5d., 1h.2a.3a.4d.5d.,
1j.2a.3a.4d.5d., 1p.2a.3a.4d.5d., 1a.2b.3a.4d.5d., 1b.2b.3a.4d.5d.,
1f.2b.3a.4d.5d., 1h.2b.3a.4d.5d., 1j.2b.3a.4d.5d., 1p.2b.3a.4d.5d.,
1a.2e.3a.4d.5d., 1b.2e.3a.4d.5d., 1f.2e.3a.4d.5d., 1h.2e.3a.4d.5d.,
1j.2e.3a.4d.5d., 1p.2e.3a.4d.5d., 1a.2f.3a.4d.5d., 1b.2f.3a.4d.5d.,
1f.2f.3a.4d.5d., 1h.2f.3a.4d.5d., 1j.2f.3a.4d.5d., 1p.2f.3a.4d.5d.,
1a.2i.3a.4d.5d., 1b.2i.3a.4d.5d., 1f.2i.3a.4d.5d., 1h.2i.3a.4d.5d.,
1j.2i.3a.4d.5d., 1p.2i.3a.4d.5d., 1a.2m.3a.4d.5d., 1b.2m.3a.4d.5d.,
1f.2m.3a.4d.5d., 1h.2m.3a.4d.5d., 1j.2m.3a.4d.5d., 1p.2m.3a.4d.5d.,
1a.2o.3a.4d.5d., 1b.2o.3a.4d.5d., 1f.2o.3a.4d.5d., 1h.2o.3a.4d.5d.,
1j.2o.3a.4d.5d., 1p.2o.3a.4d.5d., 1a.2u.3a.4d.5d., 1b.2u.3a.4d.5d.,
1f.2u.3a.4d.5d., 1h.2u.3a.4d.5d., 1j.2u.3a.4d.5d., 1p.2u.3a.4d.5d.,
1a.2y.3a.4d.5d., 1b.2y.3a.4d.5d., 1f.2y.3a.4d.5d., 1h.2y.3a.4d.5d.,
1j.2y.3a.4d.5d., 1p.2y.3a.4d.5d., 1a.2a.3b.4d.5d., 1b.2a.3b.4d.5d.,
1f.2a.3b.4d.5d., 1h.2a.3b.4d.5d., 1j.2a.3b.4d.5d., 1p.2a.3b.4d.5d.,
1a.2b.3b.4d.5d., 1b.2b.3b.4d.5d., 1f.2b.3b.4d.5d., 1h.2b.3b.4d.5d.,
1j.2b.3b.4d.5d., 1p.2b.3b.4d.5d., 1a.2e.3b.4d.5d., 1b.2e.3b.4d.5d.,
1f.2e.3b.4d.5d., 1h.2e.3b.4d.5d., 1j.2e.3b.4d.5d., 1p.2e.3b.4d.5d.,
1a.2f.3b.4d.5d., 1b.2f.3b.4d.5d., 1f.2f.3b.4d.5d., 1h.2f.3b.4d.5d.,
1j.2f.3b.4d.5d., 1p.2f.3b.4d.5d., 1a.2i.3b.4d.5d., 1b.2i.3b.4d.5d.,
1f.2i.3b.4d.5d., 1h.2i.3b.4d.5d., 1j.2i.3b.4d.5d., 1p.2i.3b.4d.5d.,
1a.2m.3b.4d.5d., 1b.2m.3b.4d.5d., 1f.2m.3b.4d.5d., 1h.2m.3b.4d.5d.,
1j.2m.3b.4d.5d., 1p.2m.3b.4d.5d., 1a.2o.3b.4d.5d., 1b.2o.3b.4d.5d.,
1f.2o.3b.4d.5d., 1h.2o.3b.4d.5d., 1j.2o.3b.4d.5d., 1p.2o.3b.4d.5d.,
1a.2u.3b.4d.5d., 1b.2u.3b.4d.5d., 1f.2u.3b.4d.5d., 1h.2u.3b.4d.5d.,
1j.2u.3b.4d.5d., 1p.2u.3b.4d.5d., 1a.2y.3b.4d.5d., 1b.2y.3b.4d.5d.,
1f.2y.3b.4d.5d., 1h.2y.3b.4d.5d., 1j.2y.3b.4d.5d., 1p.2y.3b.4d.5d.,
1a.2a.3e.4d.5d., 1b.2a.3e.4d.5d., 1f.2a.3e.4d.5d., 1h.2a.3e.4d.5d.,
1j.2a.3e.4d.5d., 1p.2a.3e.4d.5d., 1a.2b.3e.4d.5d., 1b.2b.3e.4d.5d.,
1f.2b.3e.4d.5d., 1h.2b.3e.4d.5d., 1j.2b.3e.4d.5d., 1p.2b.3e.4d.5d.,
1a.2e.3e.4d.5d., 1b.2e.3e.4d.5d., 1f.2e.3e.4d.5d., 1h.2e.3e.4d.5d.,
1j.2e.3e.4d.5d., 1p.2e.3e.4d.5d., 1a.2f.3e.4d.5d., 1b.2f.3e.4d.5d.,
1f.2f.3e.4d.5d., 1h.2f.3e.4d.5d., 1j.2f.3e.4d.5d., 1p.2f.3e.4d.5d.,
1a.2i.3e.4d.5d., 1b.2i.3e.4d.5d., 1f.2i.3e.4d.5d., 1h.2i.3e.4d.5d.,
1j.2i.3e.4d.5d., 1p.2i.3e.4d.5d., 1a.2m.3e.4d.5d., 1b.2m.3e.4d.5d.,
1f.2m.3e.4d.5d., 1h.2m.3e.4d.5d., 1j.2m.3e.4d.5d., 1p.2m.3e.4d.5d.,
1a.2o.3e.4d.5d., 1b.2o.3e.4d.5d., 1f.2o.3e.4d.5d., 1h.2o.3e.4d.5d.,
1j.2o.3e.4d.5d., 1p.2o.3e.4d.5d., 1a.2u.3e.4d.5d., 1b.2u.3e.4d.5d.,
1f.2u.3e.4d.5d., 1h.2u.3e.4d.5d., 1j.2u.3e.4d.5d., 1p.2u.3e.4d.5d.,
1a.2y.3e.4d.5d., 1b.2y.3e.4d.5d., 1f.2y.3e.4d.5d., 1h.2y.3e.4d.5d.,
1j.2y.3e.4d.5d., 1p.2y.3e.4d.5d., 1a.2a.3g.4d.5d., 1b.2a.3g.4d.5d.,
1f.2a.3g.4d.5d., 1h.2a.3g.4d.5d., 1j.2a.3g.4d.5d., 1p.2a.3g.4d.5d.,
1a.2b.3g.4d.5d., 1b.2b.3g.4d.5d., 1f.2b.3g.4d.5d., 1h.2b.3g.4d.5d.,
1j.2b.3g.4d.5d., 1p.2b.3g.4d.5d., 1a.2e.3g.4d.5d., 1b.2e.3g.4d.5d.,
1f.2e.3g.4d.5d., 1h.2e.3g.4d.5d., 1j.2e.3g.4d.5d., 1p.2e.3g.4d.5d.,
1a.2f.3g.4d.5d., 1b.2f.3g.4d.5d., 1f.2f.3g.4d.5d., 1h.2f.3g.4d.5d.,
1j.2f.3g.4d.5d., 1p.2f.3g.4d.5d., 1a.2i.3g.4d.5d., 1b.2i.3g.4d.5d.,
1f.2i.3g.4d.5d., 1h.2i.3g.4d.5d., 1j.2i.3g.4d.5d., 1p.2i.3g.4d.5d.,
1a.2m.3g.4d.5d., 1b.2m.3g.4d.5d., 1f.2m.3g.4d.5d., 1h.2m.3g.4d.5d.,
1j.2m.3g.4d.5d., 1p.2m.3g.4d.5d., 1a.2o.3g.4d.5d., 1b.2o.3g.4d.5d.,
1f.2o.3g.4d.5d., 1h.2o.3g.4d.5d., 1j.2o.3g.4d.5d., 1p.2o.3g.4d.5d.,
1a.2u.3g.4d.5d., 1b.2u.3g.4d.5d., 1f.2u.3g.4d.5d., 1h.2u.3g.4d.5d.,
1j.2u.3g.4d.5d., 1p.2u.3g.4d.5d., 1a.2y.3g.4d.5d., 1b.2y.3g.4d.5d.,
1f.2y.3g.4d.5d., 1h.2y.3g.4d.5d., 1j.2y.3g.4d.5d., 1p.2y.3g.4d.5d.,
1a.2a.3a.4f.5d., 1b.2a.3a.4f.5d., 1f.2a.3a.4f.5d., 1h.2a.3a.4f.5d.,
1j.2a.3a.4f.5d., 1p.2a.3a.4f.5d., 1a.2b.3a.4f.5d., 1b.2b.3a.4f.5d.,
1f.2b.3a.4f.5d., 1h.2b.3a.4f.5d., 1j.2b.3a.4f.5d., 1p.2b.3a.4f.5d.,
1a.2e.3a.4f.5d., 1b.2e.3a.4f.5d., 1f.2e.3a.4f.5d., 1h.2e.3a.4f.5d.,
1j.2e.3a.4f.5d., 1p.2e.3a.4f.5d., 1a.2f.3a.4f.5d., 1b.2f.3a.4f.5d.,
1f.2f.3a.4f.5d., 1h.2f.3a.4f.5d., 1j.2f.3a.4f.5d., 1p.2f.3a.4f.5d.,
1a.2i.3a.4f.5d., 1b.2i.3a.4f.5d., 1f.2i.3a.4f.5d., 1h.2i.3a.4f.5d.,
1j.2i.3a.4f.5d., 1p.2i.3a.4f.5d., 1a.2m.3a.4f.5d., 1b.2m.3a.4f.5d.,
1f.2m.3a.4f.5d., 1h.2m.3a.4f.5d., 1j.2m.3a.4f.5d., 1p.2m.3a.4f.5d.,
1a.2o.3a.4f.5d., 1b.2o.3a.4f.5d., 1f.2o.3a.4f.5d., 1h.2o.3a.4f.5d.,
1j.2o.3a.4f.5d., 1p.2o.3a.4f.5d., 1a.2u.3a.4f.5d., 1b.2u.3a.4f.5d.,
1f.2u.3a.4f.5d., 1h.2u.3a.4f.5d., 1j.2u.3a.4f.5d., 1p.2u.3a.4f.5d.,
1a.2y.3a.4f.5d., 1b.2y.3a.4f.5d., 1f.2y.3a.4f.5d., 1h.2y.3a.4f.5d.,
1j.2y.3a.4f.5d., 1p.2y.3a.4f.5d., 1a.2a.3b.4f.5d., 1b.2a.3b.4f.5d.,
1f.2a.3b.4f.5d., 1h.2a.3b.4f.5d., 1j.2a.3b.4f.5d., 1p.2a.3b.4f.5d.,
1a.2b.3b.4f.5d., 1b.2b.3b.4f.5d., 1f.2b.3b.4f.5d., 1h.2b.3b.4f.5d.,
1j.2b.3b.4f.5d., 1p.2b.3b.4f.5d., 1a.2e.3b.4f.5d., 1b.2e.3b.4f.5d.,
1f.2e.3b.4f.5d., 1h.2e.3b.4f.5d., 1j.2e.3b.4f.5d., 1p.2e.3b.4f.5d.,
1a.2f.3b.4f.5d., 1b.2f.3b.4f.5d., 1f.2f.3b.4f.5d., 1h.2f.3b.4f.5d.,
1j.2f.3b.4f.5d., 1p.2f.3b.4f.5d., 1a.2i.3b.4f.5d., 1b.2i.3b.4f.5d.,
1f.2i.3b.4f.5d., 1h.2i.3b.4f.5d., 1j.2i.3b.4f.5d., 1p.2i.3b.4f.5d.,
1a.2m.3b.4f.5d., 1b.2m.3b.4f.5d., 1f.2m.3b.4f.5d., 1h.2m.3b.4f.5d.,
1j.2m.3b.4f.5d., 1p.2m.3b.4f.5d., 1a.2o.3b.4f.5d., 1b.2o.3b.4f.5d.,
1f.2o.3b.4f.5d., 1h.2o.3b.4f.5d., 1j.2o.3b.4f.5d., 1p.2o.3b.4f.5d.,
1a.2u.3b.4f.5d., 1b.2u.3b.4f.5d., 1f.2u.3b.4f.5d., 1h.2u.3b.4f.5d.,
1j.2u.3b.4f.5d., 1p.2u.3b.4f.5d., 1a.2y.3b.4f.5d., 1b.2y.3b.4f.5d.,
1f.2y.3b.4f.5d., 1h.2y.3b.4f.5d., 1j.2y.3b.4f.5d., 1p.2y.3b.4f.5d.,
1a.2a.3e.4f.5d., 1b.2a.3e.4f.5d., 1f.2a.3e.4f.5d., 1h.2a.3e.4f.5d.,
1j.2a.3e.4f.5d., 1p.2a.3e.4f.5d., 1a.2b.3e.4f.5d., 1b.2b.3e.4f.5d.,
1f.2b.3e.4f.5d., 1h.2b.3e.4f.5d., 1j.2b.3e.4f.5d., 1p.2b.3e.4f.5d.,
1a.2e.3e.4f.5d., 1b.2e.3e.4f.5d., 1f.2e.3e.4f.5d., 1h.2e.3e.4f.5d.,
1j.2e.3e.4f.5d., 1p.2e.3e.4f.5d., 1a.2f.3e.4f.5d., 1b.2f.3e.4f.5d.,
1f.2f.3e.4f.5d., 1h.2f.3e.4f.5d., 1j.2f.3e.4f.5d., 1p.2f.3e.4f.5d.,
1a.2i.3e.4f.5d., 1b.2i.3e.4f.5d., 1f.2i.3e.4f.5d., 1h.2i.3e.4f.5d.,
1j.2i.3e.4f.5d., 1p.2i.3e.4f.5d., 1a.2m.3e.4f.5d., 1b.2m.3e.4f.5d.,
1f.2m.3e.4f.5d., 1h.2m.3e.4f.5d., 1j.2m.3e.4f.5d., 1p.2m.3e.4f.5d.,
1a.2o.3e.4f.5d., 1b.2o.3e.4f.5d., 1f.2o.3e.4f.5d., 1h.2o.3e.4f.5d.,
1j.2o.3e.4f.5d., 1p.2o.3e.4f.5d., 1a.2u.3e.4f.5d., 1b.2u.3e.4f.5d.,
1f.2u.3e.4f.5d., 1h.2u.3e.4f.5d., 1j.2u.3e.4f.5d., 1p.2u.3e.4f.5d.,
1a.2y.3e.4f.5d., 1b.2y.3e.4f.5d., 1f.2y.3e.4f.5d., 1h.2y.3e.4f.5d.,
1j.2y.3e.4f.5d., 1p.2y.3e.4f.5d., 1a.2a.3g.4f.5d., 1b.2a.3g.4f.5d.,
1f.2a.3g.4f.5d., 1h.2a.3g.4f.5d., 1j.2a.3g.4f.5d., 1p.2a.3g.4f.5d.,
1a.2b.3g.4f.5d., 1b.2b.3g.4f.5d., 1f.2b.3g.4f.5d., 1h.2b.3g.4f.5d.,
1j.2b.3g.4f.5d., 1p.2b.3g.4f.5d., 1a.2e.3g.4f.5d., 1b.2e.3g.4f.5d.,
1f.2e.3g.4f.5d., 1h.2e.3g.4f.5d., 1j.2e.3g.4f.5d., 1p.2e.3g.4f.5d.,
1a.2f.3g.4f.5d., 1b.2f.3g.4f.5d., 1f.2f.3g.4f.5d., 1h.2f.3g.4f.5d.,
1j.2f.3g.4f.5d., 1p.2f.3g.4f.5d., 1a.2i.3g.4f.5d., 1b.2i.3g.4f.5d.,
1f.2i.3g.4f.5d., 1h.2i.3g.4f.5d., 1j.2i.3g.4f.5d., 1p.2i.3g.4f.5d.,
1a.2m.3g.4f.5d., 1b.2m.3g.4f.5d., 1f.2m.3g.4f.5d., 1h.2m.3g.4f.5d.,
1j.2m.3g.4f.5d., 1p.2m.3g.4f.5d., 1a.2o.3g.4f.5d., 1b.2o.3g.4f.5d.,
1f.2o.3g.4f.5d., 1h.2o.3g.4f.5d., 1j.2o.3g.4f.5d., 1p.2o.3g.4f.5d.,
1a.2u.3g.4f.5d., 1b.2u.3g.4f.5d., 1f.2u.3g.4f.5d., 1h.2u.3g.4f.5d.,
1j.2u.3g.4f.5d., 1p.2u.3g.4f.5d., 1a.2y.3g.4f.5d., 1b.2y.3g.4f.5d.,
1f.2y.3g.4f.5d., 1h.2y.3g.4f.5d., 1j.2y.3g.4f.5d., 1p.2y.3g.4f.5d.,
1a.2a.3a.4g.5d., 1b.2a.3a.4g.5d., 1f.2a.3a.4g.5d., 1h.2a.3a.4g.5d.,
1j.2a.3a.4g.5d., 1p.2a.3a.4g.5d., 1a.2b.3a.4g.5d., 1b.2b.3a.4g.5d.,
1f.2b.3a.4g.5d., 1h.2b.3a.4g.5d., 1j.2b.3a.4g.5d., 1p.2b.3a.4g.5d.,
1a.2e.3a.4g.5d., 1b.2e.3a.4g.5d., 1f.2e.3a.4g.5d., 1h.2e.3a.4g.5d.,
1j.2e.3a.4g.5d., 1p.2e.3a.4g.5d., 1a.2f.3a.4g.5d., 1b.2f.3a.4g.5d.,
1f.2f.3a.4g.5d., 1h.2f.3a.4g.5d., 1j.2f.3a.4g.5d., 1p.2f.3a.4g.5d.,
1a.2i.3a.4g.5d., 1b.2i.3a.4g.5d., 1f.2i.3a.4g.5d., 1h.2i.3a.4g.5d.,
1j.2i.3a.4g.5d., 1p.2i.3a.4g.5d., 1a.2m.3a.4g.5d., 1b.2m.3a.4g.5d.,
1f.2m.3a.4g.5d., 1h.2m.3a.4g.5d., 1j.2m.3a.4g.5d., 1p.2m.3a.4g.5d.,
1a.2o.3a.4g.5d., 1b.2o.3a.4g.5d., 1f.2o.3a.4g.5d., 1h.2o.3a.4g.5d.,
1j.2o.3a.4g.5d., 1p.2o.3a.4g.5d., 1a.2u.3a.4g.5d., 1b.2u.3a.4g.5d.,
1f.2u.3a.4g.5d., 1h.2u.3a.4g.5d., 1j.2u.3a.4g.5d., 1p.2u.3a.4g.5d.,
1a.2y.3a.4g.5d., 1b.2y.3a.4g.5d., 1f.2y.3a.4g.5d., 1h.2y.3a.4g.5d.,
1j.2y.3a.4g.5d., 1p.2y.3a.4g.5d., 1a.2a.3b.4g.5d., 1b.2a.3b.4g.5d.,
1f.2a.3b.4g.5d., 1h.2a.3b.4g.5d., 1j.2a.3b.4g.5d., 1p.2a.3b.4g.5d.,
1a.2b.3b.4g.5d., 1b.2b.3b.4g.5d., 1f.2b.3b.4g.5d., 1h.2b.3b.4g.5d.,
1j.2b.3b.4g.5d., 1p.2b.3b.4g.5d., 1a.2e.3b.4g.5d., 1b.2e.3b.4g.5d.,
1f.2e.3b.4g.5d., 1h.2e.3b.4g.5d., 1j.2e.3b.4g.5d., 1p.2e.3b.4g.5d.,

TABLE 12-continued

List of Compound Structures of Formula III 1a.2f.3b.4g.5d., 1b.2f.3b.4g.5d., 1f.2f.3b.4g.5d., 1h.2f.3b.4g.5d.,
1j.2f.3b.4g.5d., 1p.2f.3b.4g.5d., 1a.2i.3b.4g.5d., 1b.2i.3b.4g.5d.,
1f.2i.3b.4g.5d., 1h.2i.3b.4g.5d., 1j.2i.3b.4g.5d., 1p.2i.3b.4g.5d.,
1a.2m.3b.4g.5d., 1b.2m.3b.4g.5d., 1f.2m.3b.4g.5d., 1h.2m.3b.4g.5d.,
1j.2m.3b.4g.5d., 1p.2m.3b.4g.5d., 1a.2o.3b.4g.5d., 1b.2o.3b.4g.5d.,
1f.2o.3b.4g.5d., 1h.2o.3b.4g.5d., 1j.2o.3b.4g.5d., 1p.2o.3b.4g.5d.,
1a.2u.3b.4g.5d., 1b.2u.3b.4g.5d., 1f.2u.3b.4g.5d., 1h.2u.3b.4g.5d.,
1j.2u.3b.4g.5d., 1p.2u.3b.4g.5d., 1a.2y.3b.4g.5d., 1b.2y.3b.4g.5d.,
1f.2y.3b.4g.5d., 1h.2y.3b.4g.5d., 1j.2y.3b.4g.5d., 1p.2y.3b.4g.5d.,
1a.2a.3e.4g.5d., 1b.2a.3e.4g.5d., 1f.2a.3e.4g.5d., 1h.2a.3e.4g.5d.,
1j.2a.3e.4g.5d., 1p.2a.3e.4g.5d., 1a.2b.3e.4g.5d., 1b.2b.3e.4g.5d.,
1f.2b.3e.4g.5d., 1h.2b.3e.4g.5d., 1j.2b.3e.4g.5d., 1p.2b.3e.4g.5d.,
1a.2e.3e.4g.5d., 1b.2e.3e.4g.5d., 1f.2e.3e.4g.5d., 1h.2e.3e.4g.5d.,
1j.2e.3e.4g.5d., 1p.2e.3e.4g.5d., 1a.2f.3e.4g.5d., 1b.2f.3e.4g.5d.,
1f.2f.3e.4g.5d., 1h.2f.3e.4g.5d., 1j.2f.3e.4g.5d., 1p.2f.3e.4g.5d.,
1a.2i.3e.4g.5d., 1b.2i.3e.4g.5d., 1f.2i.3e.4g.5d., 1h.2i.3e.4g.5d.,
1j.2i.3e.4g.5d., 1p.2i.3e.4g.5d., 1a.2m.3e.4g.5d., 1b.2m.3e.4g.5d.,
1f.2m.3e.4g.5d., 1h.2m.3e.4g.5d., 1j.2m.3e.4g.5d., 1p.2m.3e.4g.5d.,
1a.2o.3e.4g.5d., 1b.2o.3e.4g.5d., 1f.2o.3e.4g.5d., 1h.2o.3e.4g.5d.,
1j.2o.3e.4g.5d., 1p.2o.3e.4g.5d., 1a.2u.3e.4g.5d., 1b.2u.3e.4g.5d.,
1f.2u.3e.4g.5d., 1h.2u.3e.4g.5d., 1j.2u.3e.4g.5d., 1p.2u.3e.4g.5d.,
1a.2y.3e.4g.5d., 1b.2y.3e.4g.5d., 1f.2y.3e.4g.5d., 1h.2y.3e.4g.5d.,
1j.2y.3e.4g.5d., 1p.2y.3e.4g.5d., 1a.2a.3g.4g.5d., 1b.2a.3g.4g.5d.,
1f.2a.3g.4g.5d., 1h.2a.3g.4g.5d., 1j.2a.3g.4g.5d., 1p.2a.3g.4g.5d.,
1a.2b.3g.4g.5d., 1b.2b.3g.4g.5d., 1f.2b.3g.4g.5d., 1h.2b.3g.4g.5d.,
1j.2b.3g.4g.5d., 1p.2b.3g.4g.5d., 1a.2e.3g.4g.5d., 1b.2e.3g.4g.5d.,
1f.2e.3g.4g.5d., 1h.2e.3g.4g.5d., 1j.2e.3g.4g.5d., 1p.2e.3g.4g.5d.,
1a.2f.3g.4g.5d., 1b.2f.3g.4g.5d., 1f.2f.3g.4g.5d., 1h.2f.3g.4g.5d.,
1j.2f.3g.4g.5d., 1p.2f.3g.4g.5d., 1a.2i.3g.4g.5d., 1b.2i.3g.4g.5d.,
1f.2i.3g.4g.5d., 1h.2i.3g.4g.5d., 1j.2i.3g.4g.5d., 1p.2i.3g.4g.5d.,
1a.2m.3g.4g.5d., 1b.2m.3g.4g.5d., 1f.2m.3g.4g.5d., 1h.2m.3g.4g.5d.,
1j.2m.3g.4g.5d., 1p.2m.3g.4g.5d., 1a.2o.3g.4g.5d., 1b.2o.3g.4g.5d.,
1f.2o.3g.4g.5d., 1h.2o.3g.4g.5d., 1j.2o.3g.4g.5d., 1p.2o.3g.4g.5d.,
1a.2u.3g.4g.5d., 1b.2u.3g.4g.5d., 1f.2u.3g.4g.5d., 1h.2u.3g.4g.5d.,
1j.2u.3g.4g.5d., 1p.2u.3g.4g.5d., 1a.2y.3g.4g.5d., 1b.2y.3g.4g.5d.,
1f.2y.3g.4g.5d., 1h.2y.3g.4g.5d., 1j.2y.3g.4g.5d., 1p.2y.3g.4g.5d.,
1a.2a.3a.4h.5d., 1b.2a.3a.4h.5d., 1f.2a.3a.4h.5d., 1h.2a.3a.4h.5d.,
1j.2a.3a.4h.5d., 1p.2a.3a.4h.5d., 1a.2b.3a.4h.5d., 1b.2b.3a.4h.5d.,
1f.2b.3a.4h.5d., 1h.2b.3a.4h.5d., 1j.2b.3a.4h.5d., 1p.2b.3a.4h.5d.,
1a.2e.3a.4h.5d., 1b.2e.3a.4h.5d., 1f.2e.3a.4h.5d., 1h.2e.3a.4h.5d.,
1j.2e.3a.4h.5d., 1p.2e.3a.4h.5d., 1a.2f.3a.4h.5d., 1b.2f.3a.4h.5d.,
1f.2f.3a.4h.5d., 1h.2f.3a.4h.5d., 1j.2f.3a.4h.5d., 1p.2f.3a.4h.5d.,
1a.2i.3a.4h.5d., 1b.2i.3a.4h.5d., 1f.2i.3a.4h.5d., 1h.2i.3a.4h.5d.,
1j.2i.3a.4h.5d., 1p.2i.3a.4h.5d., 1a.2m.3a.4h.5d., 1b.2m.3a.4h.5d.,
1f.2m.3a.4h.5d., 1h.2m.3a.4h.5d., 1j.2m.3a.4h.5d., 1p.2m.3a.4h.5d.,
1a.2o.3a.4h.5d., 1b.2o.3a.4h.5d., 1f.2o.3a.4h.5d., 1h.2o.3a.4h.5d.,
1j.2o.3a.4h.5d., 1p.2o.3a.4h.5d., 1a.2u.3a.4h.5d., 1b.2u.3a.4h.5d.,
1f.2u.3a.4h.5d., 1h.2u.3a.4h.5d., 1j.2u.3a.4h.5d., 1p.2u.3a.4h.5d.,
1a.2y.3a.4h.5d., 1b.2y.3a.4h.5d., 1f.2y.3a.4h.5d., 1h.2y.3a.4h.5d.,
1j.2y.3a.4h.5d., 1p.2y.3a.4h.5d., 1a.2a.3b.4h.5d., 1b.2a.3b.4h.5d.,
1f.2a.3b.4h.5d., 1h.2a.3b.4h.5d., 1j.2a.3b.4h.5d., 1p.2a.3b.4h.5d.,
1a.2b.3b.4h.5d., 1b.2b.3b.4h.5d., 1f.2b.3b.4h.5d., 1h.2b.3b.4h.5d.,
1j.2b.3b.4h.5d., 1p.2b.3b.4h.5d., 1a.2e.3b.4h.5d., 1b.2e.3b.4h.5d.,
1f.2e.3b.4h.5d., 1h.2e.3b.4h.5d., 1j.2e.3b.4h.5d., 1p.2e.3b.4h.5d.,
1a.2f.3b.4h.5d., 1b.2f.3b.4h.5d., 1f.2f.3b.4h.5d., 1h.2f.3b.4h.5d.,
1j.2f.3b.4h.5d., 1p.2f.3b.4h.5d., 1a.2i.3b.4h.5d., 1b.2i.3b.4h.5d.,
1f.2i.3b.4h.5d., 1h.2i.3b.4h.5d., 1j.2i.3b.4h.5d., 1p.2i.3b.4h.5d.,
1a.2m.3b.4h.5d., 1b.2m.3b.4h.5d., 1f.2m.3b.4h.5d., 1h.2m.3b.4h.5d.,
1j.2m.3b.4h.5d., 1p.2m.3b.4h.5d., 1a.2o.3b.4h.5d., 1b.2o.3b.4h.5d.,
1f.2o.3b.4h.5d., 1h.2o.3b.4h.5d., 1j.2o.3b.4h.5d., 1p.2o.3b.4h.5d.,
1a.2u.3b.4h.5d., 1b.2u.3b.4h.5d., 1f.2u.3b.4h.5d., 1h.2u.3b.4h.5d.,
1j.2u.3b.4h.5d., 1p.2u.3b.4h.5d., 1a.2y.3b.4h.5d., 1b.2y.3b.4h.5d.,
1f.2y.3b.4h.5d., 1h.2y.3b.4h.5d., 1j.2y.3b.4h.5d., 1p.2y.3b.4h.5d.,
1a.2a.3e.4h.5d., 1b.2a.3e.4h.5d., 1f.2a.3e.4h.5d., 1h.2a.3e.4h.5d.,
1j.2a.3e.4h.5d., 1p.2a.3e.4h.5d., 1a.2b.3e.4h.5d., 1b.2b.3e.4h.5d.,
1f.2b.3e.4h.5d., 1h.2b.3e.4h.5d., 1j.2b.3e.4h.5d., 1p.2b.3e.4h.5d.,
1a.2e.3e.4h.5d., 1b.2e.3e.4h.5d., 1f.2e.3e.4h.5d., 1h.2e.3e.4h.5d.,
1j.2e.3e.4h.5d., 1p.2e.3e.4h.5d., 1a.2f.3e.4h.5d., 1b.2f.3e.4h.5d.,
1f.2f.3e.4h.5d., 1h.2f.3e.4h.5d., 1j.2f.3e.4h.5d., 1p.2f.3e.4h.5d.,
1a.2i.3e.4h.5d., 1b.2i.3e.4h.5d., 1f.2i.3e.4h.5d., 1h.2i.3e.4h.5d.,
1j.2i.3e.4h.5d., 1p.2i.3e.4h.5d., 1a.2m.3e.4h.5d., 1b.2m.3e.4h.5d.,
1f.2m.3e.4h.5d., 1h.2m.3e.4h.5d., 1j.2m.3e.4h.5d., 1p.2m.3e.4h.5d.,
1a.2o.3e.4h.5d., 1b.2o.3e.4h.5d., 1f.2o.3e.4h.5d., 1h.2o.3e.4h.5d.,
1j.2o.3e.4h.5d., 1p.2o.3e.4h.5d., 1a.2u.3e.4h.5d., 1b.2u.3e.4h.5d.,
1f.2u.3e.4h.5d., 1h.2u.3e.4h.5d., 1j.2u.3e.4h.5d., 1p.2u.3e.4h.5d.,
1a.2y.3e.4h.5d., 1b.2y.3e.4h.5d., 1f.2y.3e.4h.5d., 1h.2y.3e.4h.5d.,
1j.2y.3e.4h.5d., 1p.2y.3e.4h.5d., 1a.2a.3g.4h.5d., 1b.2a.3g.4h.5d.,
1f.2a.3g.4h.5d., 1h.2a.3g.4h.5d., 1j.2a.3g.4h.5d., 1p.2a.3g.4h.5d., 1a.2b.3g.4h.5d., 1b.2b.3g.4h.5d., 1f.2b.3g.4h.5d., 1h.2b.3g.4h.5d.,
1j.2b.3g.4h.5d., 1p.2b.3g.4h.5d., 1a.2e.3g.4h.5d., 1b.2e.3g.4h.5d.,
1f.2e.3g.4h.5d., 1h.2e.3g.4h.5d., 1j.2e.3g.4h.5d., 1p.2e.3g.4h.5d.,
1a.2f.3g.4h.5d., 1b.2f.3g.4h.5d., 1f.2f.3g.4h.5d., 1h.2f.3g.4h.5d.,
1j.2f.3g.4h.5d., 1p.2f.3g.4h.5d., 1a.2i.3g.4h.5d., 1b.2i.3g.4h.5d.,
1f.2i.3g.4h.5d., 1h.2i.3g.4h.5d., 1j.2i.3g.4h.5d., 1p.2i.3g.4h.5d.,
1a.2m.3g.4h.5d., 1b.2m.3g.4h.5d., 1f.2m.3g.4h.5d., 1h.2m.3g.4h.5d.,
1j.2m.3g.4h.5d., 1p.2m.3g.4h.5d., 1a.2o.3g.4h.5d., 1b.2o.3g.4h.5d.,
1f.2o.3g.4h.5d., 1h.2o.3g.4h.5d., 1j.2o.3g.4h.5d., 1p.2o.3g.4h.5d.,
1a.2u.3g.4h.5d., 1b.2u.3g.4h.5d., 1f.2u.3g.4h.5d., 1h.2u.3g.4h.5d.,
1j.2u.3g.4h.5d., 1p.2u.3g.4h.5d., 1a.2y.3g.4h.5d., 1b.2y.3g.4h.5d.,
1f.2y.3g.4h.5d., 1h.2y.3g.4h.5d., 1j.2y.3g.4h.5d., 1p.2y.3g.4h.5d.,
1a.2a.3a.4i.5d., 1b.2a.3a.4i.5d., 1f.2a.3a.4i.5d., 1h.2a.3a.4i.5d.,
1j.2a.3a.4i.5d., 1p.2a.3a.4i.5d., 1a.2b.3a.4i.5d., 1b.2b.3a.4i.5d.,
1f.2b.3a.4i.5d., 1h.2b.3a.4i.5d., 1j.2b.3a.4i.5d., 1p.2b.3a.4i.5d.,
1a.2e.3a.4i.5d., 1b.2e.3a.4i.5d., 1f.2e.3a.4i.5d., 1h.2e.3a.4i.5d.,
1j.2e.3a.4i.5d., 1p.2e.3a.4i.5d., 1a.2f.3a.4i.5d., 1b.2f.3a.4i.5d.,
1f.2f.3a.4i.5d., 1h.2f.3a.4i.5d., 1j.2f.3a.4i.5d., 1p.2f.3a.4i.5d.,
1a.2i.3a.4i.5d., 1b.2i.3a.4i.5d., 1f.2i.3a.4i.5d., 1h.2i.3a.4i.5d.,
1j.2i.3a.4i.5d., 1p.2i.3a.4i.5d., 1a.2m.3a.4i.5d., 1b.2m.3a.4i.5d.,
1f.2m.3a.4i.5d., 1h.2m.3a.4i.5d., 1j.2m.3a.4i.5d., 1p.2m.3a.4i.5d.,
1a.2o.3a.4i.5d., 1b.2o.3a.4i.5d., 1f.2o.3a.4i.5d., 1h.2o.3a.4i.5d.,
1j.2o.3a.4i.5d., 1p.2o.3a.4i.5d., 1a.2u.3a.4i.5d., 1b.2u.3a.4i.5d.,
1f.2u.3a.4i.5d., 1h.2u.3a.4i.5d., 1j.2u.3a.4i.5d., 1p.2u.3a.4i.5d.,
1a.2y.3a.4i.5d., 1b.2y.3a.4i.5d., 1f.2y.3a.4i.5d., 1h.2y.3a.4i.5d.,
1j.2y.3a.4i.5d., 1p.2y.3a.4i.5d., 1a.2a.3b.4i.5d., 1b.2a.3b.4i.5d.,
1f.2a.3b.4i.5d., 1h.2a.3b.4i.5d., 1j.2a.3b.4i.5d., 1p.2a.3b.4i.5d.,
1a.2b.3b.4i.5d., 1b.2b.3b.4i.5d., 1f.2b.3b.4i.5d., 1h.2b.3b.4i.5d.,
1j.2b.3b.4i.5d., 1p.2b.3b.4i.5d., 1a.2e.3b.4i.5d., 1b.2e.3b.4i.5d.,
1f.2e.3b.4i.5d., 1h.2e.3b.4i.5d., 1j.2e.3b.4i.5d., 1p.2e.3b.4i.5d.,
1a.2f.3b.4i.5d., 1b.2f.3b.4i.5d., 1f.2f.3b.4i.5d., 1h.2f.3b.4i.5d.,
1j.2f.3b.4i.5d., 1p.2f.3b.4i.5d., 1a.2i.3b.4i.5d., 1b.2i.3b.4i.5d.,
1f.2i.3b.4i.5d., 1h.2i.3b.4i.5d., 1j.2i.3b.4i.5d., 1p.2i.3b.4i.5d.,
1a.2m.3b.4i.5d., 1b.2m.3b.4i.5d., 1f.2m.3b.4i.5d., 1h.2m.3b.4i.5d.,
1j.2m.3b.4i.5d., 1p.2m.3b.4i.5d., 1a.2o.3b.4i.5d., 1b.2o.3b.4i.5d.,
1f.2o.3b.4i.5d., 1h.2o.3b.4i.5d., 1j.2o.3b.4i.5d., 1p.2o.3b.4i.5d.,
1a.2u.3b.4i.5d., 1b.2u.3b.4i.5d., 1f.2u.3b.4i.5d., 1h.2u.3b.4i.5d.,
1j.2u.3b.4i.5d., 1p.2u.3b.4i.5d., 1a.2y.3b.4i.5d., 1b.2y.3b.4i.5d.,
1f.2y.3b.4i.5d., 1h.2y.3b.4i.5d., 1j.2y.3b.4i.5d., 1p.2y.3b.4i.5d.,
1a.2a.3e.4i.5d., 1b.2a.3e.4i.5d., 1f.2a.3e.4i.5d., 1h.2a.3e.4i.5d.,
1j.2a.3e.4i.5d., 1p.2a.3e.4i.5d., 1a.2b.3e.4i.5d., 1b.2b.3e.4i.5d.,
1f.2b.3e.4i.5d., 1h.2b.3e.4i.5d., 1j.2b.3e.4i.5d., 1p.2b.3e.4i.5d.,
1a.2e.3e.4i.5d., 1b.2e.3e.4i.5d., 1f.2e.3e.4i.5d., 1h.2e.3e.4i.5d.,
1j.2e.3e.4i.5d., 1p.2e.3e.4i.5d., 1a.2f.3e.4i.5d., 1b.2f.3e.4i.5d.,
1f.2f.3e.4i.5d., 1h.2f.3e.4i.5d., 1j.2f.3e.4i.5d., 1p.2f.3e.4i.5d.,
1a.2i.3e.4i.5d., 1b.2i.3e.4i.5d., 1f.2i.3e.4i.5d., 1h.2i.3e.4i.5d.,
1j.2i.3e.4i.5d., 1p.2i.3e.4i.5d., 1a.2m.3e.4i.5d., 1b.2m.3e.4i.5d.,
1f.2m.3e.4i.5d., 1h.2m.3e.4i.5d., 1j.2m.3e.4i.5d., 1p.2m.3e.4i.5d.,
1a.2o.3e.4i.5d., 1b.2o.3e.4i.5d., 1f.2o.3e.4i.5d., 1h.2o.3e.4i.5d.,
1j.2o.3e.4i.5d., 1p.2o.3e.4i.5d., 1a.2u.3e.4i.5d., 1b.2u.3e.4i.5d.,
1f.2u.3e.4i.5d., 1h.2u.3e.4i.5d., 1j.2u.3e.4i.5d., 1p.2u.3e.4i.5d.,
1a.2y.3e.4i.5d., 1b.2y.3e.4i.5d., 1f.2y.3e.4i.5d., 1h.2y.3e.4i.5d.,
1j.2y.3e.4i.5d., 1p.2y.3e.4i.5d., 1a.2a.3g.4i.5d., 1b.2a.3g.4i.5d.,
1f.2a.3g.4i.5d., 1h.2a.3g.4i.5d., 1j.2a.3g.4i.5d., 1p.2a.3g.4i.5d.,
1a.2b.3g.4i.5d., 1b.2b.3g.4i.5d., 1f.2b.3g.4i.5d., 1h.2b.3g.4i.5d.,
1j.2b.3g.4i.5d., 1p.2b.3g.4i.5d., 1a.2e.3g.4i.5d., 1b.2e.3g.4i.5d.,
1f.2e.3g.4i.5d., 1h.2e.3g.4i.5d., 1j.2e.3g.4i.5d., 1p.2e.3g.4i.5d.,
1a.2f.3g.4i.5d., 1b.2f.3g.4i.5d., 1f.2f.3g.4i.5d., 1h.2f.3g.4i.5d.,
1j.2f.3g.4i.5d., 1p.2f.3g.4i.5d., 1a.2i.3g.4i.5d., 1b.2i.3g.4i.5d.,
1f.2i.3g.4i.5d., 1h.2i.3g.4i.5d., 1j.2i.3g.4i.5d., 1p.2i.3g.4i.5d.,
1a.2m.3g.4i.5d., 1b.2m.3g.4i.5d., 1f.2m.3g.4i.5d., 1h.2m.3g.4i.5d.,
1j.2m.3g.4i.5d., 1p.2m.3g.4i.5d., 1a.2o.3g.4i.5d., 1b.2o.3g.4i.5d.,
1f.2o.3g.4i.5d., 1h.2o.3g.4i.5d., 1j.2o.3g.4i.5d., 1p.2o.3g.4i.5d.,
1a.2u.3g.4i.5d., 1b.2u.3g.4i.5d., 1f.2u.3g.4i.5d., 1h.2u.3g.4i.5d.,
1j.2u.3g.4i.5d., 1p.2u.3g.4i.5d., 1a.2y.3g.4i.5d., 1b.2y.3g.4i.5d.,
1f.2y.3g.4i.5d., 1h.2y.3g.4i.5d., 1j.2y.3g.4i.5d., 1p.2y.3g.4i.5d.,
1a.2a.3a.4a.5f., 1b.2a.3a.4a.5f., 1f.2a.3a.4a.5f., 1h.2a.3a.4a.5f.,
1j.2a.3a.4a.5f., 1p.2a.3a.4a.5f., 1a.2b.3a.4a.5f., 1b.2b.3a.4a.5f.,
1f.2b.3a.4a.5f., 1h.2b.3a.4a.5f., 1j.2b.3a.4a.5f., 1p.2b.3a.4a.5f.,
1a.2e.3a.4a.5f., 1b.2e.3a.4a.5f., 1f.2e.3a.4a.5f., 1h.2e.3a.4a.5f.,
1j.2e.3a.4a.5f., 1p.2e.3a.4a.5f., 1a.2f.3a.4a.5f., 1b.2f.3a.4a.5f.,
1f.2f.3a.4a.5f., 1h.2f.3a.4a.5f., 1j.2f.3a.4a.5f., 1p.2f.3a.4a.5f.,
1a.2i.3a.4a.5f., 1b.2i.3a.4a.5f., 1f.2i.3a.4a.5f., 1h.2i.3a.4a.5f.,
1j.2i.3a.4a.5f., 1p.2i.3a.4a.5f., 1a.2m.3a.4a.5f., 1b.2m.3a.4a.5f.,
1f.2m.3a.4a.5f., 1h.2m.3a.4a.5f., 1j.2m.3a.4a.5f., 1p.2m.3a.4a.5f.,
1a.2o.3a.4a.5f., 1b.2o.3a.4a.5f., 1f.2o.3a.4a.5f., 1h.2o.3a.4a.5f.,
1j.2o.3a.4a.5f., 1p.2o.3a.4a.5f., 1a.2u.3a.4a.5f., 1b.2u.3a.4a.5f.,
1f.2u.3a.4a.5f., 1h.2u.3a.4a.5f., 1j.2u.3a.4a.5f., 1p.2u.3a.4a.5f., TABLE 12-continued List of Compound Structures of Formula III 1a.2y.3a.4a.5f., 1b.2y.3a.4a.5f., 1f.2y.3a.4a.5f., 1h.2y.3a.4a.5f.,
1j.2y.3a.4a.5f., 1p.2y.3a.4a.5f., 1a.2a.3b.4a.5f., 1b.2a.3b.4a.5f.,
1f.2a.3b.4a.5f., 1h.2a.3b.4a.5f., 1j.2a.3b.4a.5f., 1p.2a.3b.4a.5f.,
1a.2b.3b.4a.5f., 1b.2b.3b.4a.5f., 1f.2b.3b.4a.5f., 1h.2b.3b.4a.5f.,
1j.2b.3b.4a.5f., 1p.2b.3b.4a.5f., 1a.2e.3b.4a.5f., 1b.2e.3b.4a.5f.,
1f.2e.3b.4a.5f., 1h.2e.3b.4a.5f., 1j.2e.3b.4a.5f., 1p.2e.3b.4a.5f.,
1a.2f.3b.4a.5f., 1b.2f.3b.4a.5f., 1f.2f.3b.4a.5f., 1h.2f.3b.4a.5f.,
1j.2f.3b.4a.5f., 1p.2f.3b.4a.5f., 1a.2i.3b.4a.5f., 1b.2i.3b.4a.5f.,
1f.2i.3b.4a.5f., 1h.2i.3b.4a.5f., 1j.2i.3b.4a.5f., 1p.2i.3b.4a.5f.,
1a.2m.3b.4a.5f., 1b.2m.3b.4a.5f., 1f.2m.3b.4a.5f., 1h.2m.3b.4a.5f.,
1j.2m.3b.4a.5f., 1p.2m.3b.4a.5f., 1a.2o.3b.4a.5f., 1b.2o.3b.4a.5f.,
1f.2o.3b.4a.5f., 1h.2o.3b.4a.5f., 1j.2o.3b.4a.5f., 1p.2o.3b.4a.5f.,
1a.2u.3b.4a.5f., 1b.2u.3b.4a.5f., 1f.2u.3b.4a.5f., 1h.2u.3b.4a.5f.,
1j.2u.3b.4a.5f., 1p.2u.3b.4a.5f., 1a.2y.3b.4a.5f., 1b.2y.3b.4a.5f.,
1f.2y.3b.4a.5f., 1h.2y.3b.4a.5f., 1j.2y.3b.4a.5f., 1p.2y.3b.4a.5f.,
1a.2a.3e.4a.5f., 1b.2a.3e.4a.5f., 1f.2a.3e.4a.5f., 1h.2a.3e.4a.5f.,
1j.2a.3e.4a.5f., 1p.2a.3e.4a.5f., 1a.2b.3e.4a.5f., 1b.2b.3e.4a.5f.,
1f.2b.3e.4a.5f., 1h.2b.3e.4a.5f., 1j.2b.3e.4a.5f., 1p.2b.3e.4a.5f.,
1a.2e.3e.4a.5f., 1b.2e.3e.4a.5f., 1f.2e.3e.4a.5f., 1h.2e.3e.4a.5f.,
1j.2e.3e.4a.5f., 1p.2e.3e.4a.5f., 1a.2f.3e.4a.5f., 1b.2f.3e.4a.5f.,
1f.2f.3e.4a.5f., 1h.2f.3e.4a.5f., 1j.2f.3e.4a.5f., 1p.2f.3e.4a.5f.,
1a.2i.3e.4a.5f., 1b.2i.3e.4a.5f., 1f.2i.3e.4a.5f., 1h.2i.3e.4a.5f.,
1j.2i.3e.4a.5f., 1p.2i.3e.4a.5f., 1a.2m.3e.4a.5f., 1b.2m.3e.4a.5f.,
1f.2m.3e.4a.5f., 1h.2m.3e.4a.5f., 1j.2m.3e.4a.5f., 1p.2m.3e.4a.5f.,
1a.2o.3e.4a.5f., 1b.2o.3e.4a.5f., 1f.2o.3e.4a.5f., 1h.2o.3e.4a.5f.,
1j.2o.3e.4a.5f., 1p.2o.3e.4a.5f., 1a.2u.3e.4a.5f., 1b.2u.3e.4a.5f.,
1f.2u.3e.4a.5f., 1h.2u.3e.4a.5f., 1j.2u.3e.4a.5f., 1p.2u.3e.4a.5f.,
1a.2y.3e.4a.5f., 1b.2y.3e.4a.5f., 1f.2y.3e.4a.5f., 1h.2y.3e.4a.5f.,
1j.2y.3e.4a.5f., 1p.2y.3e.4a.5f., 1a.2a.3g.4a.5f., 1b.2a.3g.4a.5f.,
1f.2a.3g.4a.5f., 1h.2a.3g.4a.5f., 1j.2a.3g.4a.5f., 1p.2a.3g.4a.5f.,
1a.2b.3g.4a.5f., 1b.2b.3g.4a.5f., 1f.2b.3g.4a.5f., 1h.2b.3g.4a.5f.,
1j.2b.3g.4a.5f., 1p.2b.3g.4a.5f., 1a.2e.3g.4a.5f., 1b.2e.3g.4a.5f.,
1f.2e.3g.4a.5f., 1h.2e.3g.4a.5f., 1j.2e.3g.4a.5f., 1p.2e.3g.4a.5f.,
1a.2f.3g.4a.5f., 1b.2f.3g.4a.5f., 1f.2f.3g.4a.5f., 1h.2f.3g.4a.5f.,
1j.2f.3g.4a.5f., 1p.2f.3g.4a.5f., 1a.2i.3g.4a.5f., 1b.2i.3g.4a.5f.,
1f.2i.3g.4a.5f., 1h.2i.3g.4a.5f., 1j.2i.3g.4a.5f., 1p.2i.3g.4a.5f.,
1a.2m.3g.4a.5f., 1b.2m.3g.4a.5f., 1f.2m.3g.4a.5f., 1h.2m.3g.4a.5f.,
1j.2m.3g.4a.5f., 1p.2m.3g.4a.5f., 1a.2o.3g.4a.5f., 1b.2o.3g.4a.5f.,
1f.2o.3g.4a.5f., 1h.2o.3g.4a.5f., 1j.2o.3g.4a.5f., 1p.2o.3g.4a.5f.,
1a.2u.3g.4a.5f., 1b.2u.3g.4a.5f., 1f.2u.3g.4a.5f., 1h.2u.3g.4a.5f.,
1j.2u.3g.4a.5f., 1p.2u.3g.4a.5f., 1a.2y.3g.4a.5f., 1b.2y.3g.4a.5f.,
1f.2y.3g.4a.5f., 1h.2y.3g.4a.5f., 1j.2y.3g.4a.5f., 1p.2y.3g.4a.5f.,
1a.2a.3a.4d.5f., 1b.2a.3a.4d.5f., 1f.2a.3a.4d.5f., 1h.2a.3a.4d.5f.,
1j.2a.3a.4d.5f., 1p.2a.3a.4d.5f., 1a.2b.3a.4d.5f., 1b.2b.3a.4d.5f.,
1f.2b.3a.4d.5f., 1h.2b.3a.4d.5f., 1j.2b.3a.4d.5f., 1p.2b.3a.4d.5f.,
1a.2e.3a.4d.5f., 1b.2e.3a.4d.5f., 1f.2e.3a.4d.5f., 1h.2e.3a.4d.5f.,
1j.2e.3a.4d.5f., 1p.2e.3a.4d.5f., 1a.2f.3a.4d.5f., 1b.2f.3a.4d.5f.,
1f.2f.3a.4d.5f., 1h.2f.3a.4d.5f., 1j.2f.3a.4d.5f., 1p.2f.3a.4d.5f.,
1a.2i.3a.4d.5f., 1b.2i.3a.4d.5f., 1f.2i.3a.4d.5f., 1h.2i.3a.4d.5f.,
1j.2i.3a.4d.5f., 1p.2i.3a.4d.5f., 1a.2m.3a.4d.5f., 1b.2m.3a.4d.5f.,
1f.2m.3a.4d.5f., 1h.2m.3a.4d.5f., 1j.2m.3a.4d.5f., 1p.2m.3a.4d.5f.,
1a.2o.3a.4d.5f., 1b.2o.3a.4d.5f., 1f.2o.3a.4d.5f., 1h.2o.3a.4d.5f.,
1j.2o.3a.4d.5f., 1p.2o.3a.4d.5f., 1a.2u.3a.4d.5f., 1b.2u.3a.4d.5f.,
1f.2u.3a.4d.5f., 1h.2u.3a.4d.5f., 1j.2u.3a.4d.5f., 1p.2u.3a.4d.5f.,
1a.2y.3a.4d.5f., 1b.2y.3a.4d.5f., 1f.2y.3a.4d.5f., 1h.2y.3a.4d.5f.,
1j.2y.3a.4d.5f., 1p.2y.3a.4d.5f., 1a.2a.3b.4d.5f., 1b.2a.3b.4d.5f.,
1f.2a.3b.4d.5f., 1h.2a.3b.4d.5f., 1j.2a.3b.4d.5f., 1p.2a.3b.4d.5f.,
1a.2b.3b.4d.5f., 1b.2b.3b.4d.5f., 1f.2b.3b.4d.5f., 1h.2b.3b.4d.5f.,
1j.2b.3b.4d.5f., 1p.2b.3b.4d.5f., 1a.2e.3b.4d.5f., 1b.2e.3b.4d.5f.,
1f.2e.3b.4d.5f., 1h.2e.3b.4d.5f., 1j.2e.3b.4d.5f., 1p.2e.3b.4d.5f.,
1a.2f.3b.4d.5f., 1b.2f.3b.4d.5f., 1f.2f.3b.4d.5f., 1h.2f.3b.4d.5f.,
1j.2f.3b.4d.5f., 1p.2f.3b.4d.5f., 1a.2i.3b.4d.5f., 1b.2i.3b.4d.5f.,
1f.2i.3b.4d.5f., 1h.2i.3b.4d.5f., 1j.2i.3b.4d.5f., 1p.2i.3b.4d.5f.,
1a.2m.3b.4d.5f., 1b.2m.3b.4d.5f., 1f.2m.3b.4d.5f., 1h.2m.3b.4d.5f.,
1j.2m.3b.4d.5f., 1p.2m.3b.4d.5f., 1a.2o.3b.4d.5f., 1b.2o.3b.4d.5f.,
1f.2o.3b.4d.5f., 1h.2o.3b.4d.5f., 1j.2o.3b.4d.5f., 1p.2o.3b.4d.5f.,
1a.2u.3b.4d.5f., 1b.2u.3b.4d.5f., 1f.2u.3b.4d.5f., 1h.2u.3b.4d.5f.,
1j.2u.3b.4d.5f., 1p.2u.3b.4d.5f., 1a.2y.3b.4d.5f., 1b.2y.3b.4d.5f.,
1f.2y.3b.4d.5f., 1h.2y.3b.4d.5f., 1j.2y.3b.4d.5f., 1p.2y.3b.4d.5f.,
1a.2a.3e.4d.5f., 1b.2a.3e.4d.5f., 1f.2a.3e.4d.5f., 1h.2a.3e.4d.5f.,
1j.2a.3e.4d.5f., 1p.2a.3e.4d.5f., 1a.2b.3e.4d.5f., 1b.2b.3e.4d.5f.,
1f.2b.3e.4d.5f., 1h.2b.3e.4d.5f., 1j.2b.3e.4d.5f., 1p.2b.3e.4d.5f.,
1a.2e.3e.4d.5f., 1b.2e.3e.4d.5f., 1f.2e.3e.4d.5f., 1h.2e.3e.4d.5f.,
1j.2e.3e.4d.5f., 1p.2e.3e.4d.5f., 1a.2f.3e.4d.5f., 1b.2f.3e.4d.5f.,
1f.2f.3e.4d.5f., 1h.2f.3e.4d.5f., 1j.2f.3e.4d.5f., 1p.2f.3e.4d.5f.,
1a.2i.3e.4d.5f., 1b.2i.3e.4d.5f., 1f.2i.3e.4d.5f., 1h.2i.3e.4d.5f.,
1j.2i.3e.4d.5f., 1p.2i.3e.4d.5f., 1a.2m.3e.4d.5f., 1b.2m.3e.4d.5f.,
1f.2m.3e.4d.5f., 1h.2m.3e.4d.5f., 1j.2m.3e.4d.5f., 1p.2m.3e.4d.5f.,
1a.2o.3e.4d.5f., 1b.2o.3e.4d.5f., 1f.2o.3e.4d.5f., 1h.2o.3e.4d.5f.,
1j.2o.3e.4d.5f., 1p.2o.3e.4d.5f., 1a.2u.3e.4d.5f., 1b.2u.3e.4d.5f.,
1f.2u.3e.4d.5f., 1h.2u.3e.4d.5f., 1j.2u.3e.4d.5f., 1p.2u.3e.4d.5f.,
1a.2y.3e.4d.5f., 1b.2y.3e.4d.5f., 1f.2y.3e.4d.5f., 1h.2y.3e.4d.5f.,
1j.2y.3e.4d.5f., 1p.2y.3e.4d.5f., 1a.2a.3g.4d.5f., 1b.2a.3g.4d.5f.,
1f.2a.3g.4d.5f., 1h.2a.3g.4d.5f., 1j.2a.3g.4d.5f., 1p.2a.3g.4d.5f.,
1a.2b.3g.4d.5f., 1b.2b.3g.4d.5f., 1f.2b.3g.4d.5f., 1h.2b.3g.4d.5f.,
1j.2b.3g.4d.5f., 1p.2b.3g.4d.5f., 1a.2e.3g.4d.5f., 1b.2e.3g.4d.5f.,
1f.2e.3g.4d.5f., 1h.2e.3g.4d.5f., 1j.2e.3g.4d.5f., 1p.2e.3g.4d.5f.,
1a.2f.3g.4d.5f., 1b.2f.3g.4d.5f., 1f.2f.3g.4d.5f., 1h.2f.3g.4d.5f.,
1j.2f.3g.4d.5f., 1p.2f.3g.4d.5f., 1a.2i.3g.4d.5f., 1b.2i.3g.4d.5f.,
1f.2i.3g.4d.5f., 1h.2i.3g.4d.5f., 1j.2i.3g.4d.5f., 1p.2i.3g.4d.5f.,
1a.2m.3g.4d.5f., 1b.2m.3g.4d.5f., 1f.2m.3g.4d.5f., 1h.2m.3g.4d.5f.,
1j.2m.3g.4d.5f., 1p.2m.3g.4d.5f., 1a.2o.3g.4d.5f., 1b.2o.3g.4d.5f.,
1f.2o.3g.4d.5f., 1h.2o.3g.4d.5f., 1j.2o.3g.4d.5f., 1p.2o.3g.4d.5f.,
1a.2u.3g.4d.5f., 1b.2u.3g.4d.5f., 1f.2u.3g.4d.5f., 1h.2u.3g.4d.5f.,
1j.2u.3g.4d.5f., 1p.2u.3g.4d.5f., 1a.2y.3g.4d.5f., 1b.2y.3g.4d.5f.,
1f.2y.3g.4d.5f., 1h.2y.3g.4d.5f., 1j.2y.3g.4d.5f., 1p.2y.3g.4d.5f.,
1a.2a.3a.4f.5f., 1b.2a.3a.4f.5f., 1f.2a.3a.4f.5f., 1h.2a.3a.4f.5f.,
1j.2a.3a.4f.5f., 1p.2a.3a.4f.5f., 1a.2b.3a.4f.5f., 1b.2b.3a.4f.5f.,
1f.2b.3a.4f.5f., 1h.2b.3a.4f.5f., 1j.2b.3a.4f.5f., 1p.2b.3a.4f.5f.,
1a.2e.3a.4f.5f., 1b.2e.3a.4f.5f., 1f.2e.3a.4f.5f., 1h.2e.3a.4f.5f.,
1j.2e.3a.4f.5f., 1p.2e.3a.4f.5f., 1a.2f.3a.4f.5f., 1b.2f.3a.4f.5f.,
1f.2f.3a.4f.5f., 1h.2f.3a.4f.5f., 1j.2f.3a.4f.5f., 1p.2f.3a.4f.5f.,
1a.2i.3a.4f.5f., 1b.2i.3a.4f.5f., 1f.2i.3a.4f.5f., 1h.2i.3a.4f.5f.,
1j.2i.3a.4f.5f., 1p.2i.3a.4f.5f., 1a.2m.3a.4f.5f., 1b.2m.3a.4f.5f.,
1f.2m.3a.4f.5f., 1h.2m.3a.4f.5f., 1j.2m.3a.4f.5f., 1p.2m.3a.4f.5f.,
1a.2o.3a.4f.5f., 1b.2o.3a.4f.5f., 1f.2o.3a.4f.5f., 1h.2o.3a.4f.5f.,
1j.2o.3a.4f.5f., 1p.2o.3a.4f.5f., 1a.2u.3a.4f.5f., 1b.2u.3a.4f.5f.,
1f.2u.3a.4f.5f., 1h.2u.3a.4f.5f., 1j.2u.3a.4f.5f., 1p.2u.3a.4f.5f.,
1a.2y.3a.4f.5f., 1b.2y.3a.4f.5f., 1f.2y.3a.4f.5f., 1h.2y.3a.4f.5f.,
1j.2y.3a.4f.5f., 1p.2y.3a.4f.5f., 1a.2a.3b.4f.5f., 1b.2a.3b.4f.5f.,
1f.2a.3b.4f.5f., 1h.2a.3b.4f.5f., 1j.2a.3b.4f.5f., 1p.2a.3b.4f.5f.,
1a.2b.3b.4f.5f., 1b.2b.3b.4f.5f., 1f.2b.3b.4f.5f., 1h.2b.3b.4f.5f.,
1j.2b.3b.4f.5f., 1p.2b.3b.4f.5f., 1a.2e.3b.4f.5f., 1b.2e.3b.4f.5f.,
1f.2e.3b.4f.5f., 1h.2e.3b.4f.5f., 1j.2e.3b.4f.5f., 1p.2e.3b.4f.5f.,
1a.2f.3b.4f.5f., 1b.2f.3b.4f.5f., 1f.2f.3b.4f.5f., 1h.2f.3b.4f.5f.,
1j.2f.3b.4f.5f., 1p.2f.3b.4f.5f., 1a.2i.3b.4f.5f., 1b.2i.3b.4f.5f.,
1f.2i.3b.4f.5f., 1h.2i.3b.4f.5f., 1j.2i.3b.4f.5f., 1p.2i.3b.4f.5f.,
1a.2m.3b.4f.5f., 1b.2m.3b.4f.5f., 1f.2m.3b.4f.5f., 1h.2m.3b.4f.5f.,
1j.2m.3b.4f.5f., 1p.2m.3b.4f.5f., 1a.2o.3b.4f.5f., 1b.2o.3b.4f.5f.,
1f.2o.3b.4f.5f., 1h.2o.3b.4f.5f., 1j.2o.3b.4f.5f., 1p.2o.3b.4f.5f.,
1a.2u.3b.4f.5f., 1b.2u.3b.4f.5f., 1f.2u.3b.4f.5f., 1h.2u.3b.4f.5f.,
1j.2u.3b.4f.5f., 1p.2u.3b.4f.5f., 1a.2y.3b.4f.5f., 1b.2y.3b.4f.5f.,
1f.2y.3b.4f.5f., 1h.2y.3b.4f.5f., 1j.2y.3b.4f.5f., 1p.2y.3b.4f.5f.,
1a.2a.3e.4f.5f., 1b.2a.3e.4f.5f., 1f.2a.3e.4f.5f., 1h.2a.3e.4f.5f.,
1j.2a.3e.4f.5f., 1p.2a.3e.4f.5f., 1a.2b.3e.4f.5f., 1b.2b.3e.4f.5f.,
1f.2b.3e.4f.5f., 1h.2b.3e.4f.5f., 1j.2b.3e.4f.5f., 1p.2b.3e.4f.5f.,
1a.2e.3e.4f.5f., 1b.2e.3e.4f.5f., 1f.2e.3e.4f.5f., 1h.2e.3e.4f.5f.,
1j.2e.3e.4f.5f., 1p.2e.3e.4f.5f., 1a.2f.3e.4f.5f., 1b.2f.3e.4f.5f.,
1f.2f.3e.4f.5f., 1h.2f.3e.4f.5f., 1j.2f.3e.4f.5f., 1p.2f.3e.4f.5f.,
1a.2i.3e.4f.5f., 1b.2i.3e.4f.5f., 1f.2i.3e.4f.5f., 1h.2i.3e.4f.5f.,
1j.2i.3e.4f.5f., 1p.2i.3e.4f.5f., 1a.2m.3e.4f.5f., 1b.2m.3e.4f.5f.,
1f.2m.3e.4f.5f., 1h.2m.3e.4f.5f., 1j.2m.3e.4f.5f., 1p.2m.3e.4f.5f.,
1a.2o.3e.4f.5f., 1b.2o.3e.4f.5f., 1f.2o.3e.4f.5f., 1h.2o.3e.4f.5f.,
1j.2o.3e.4f.5f., 1p.2o.3e.4f.5f., 1a.2u.3e.4f.5f., 1b.2u.3e.4f.5f.,
1f.2u.3e.4f.5f., 1h.2u.3e.4f.5f., 1j.2u.3e.4f.5f., 1p.2u.3e.4f.5f.,
1a.2y.3e.4f.5f., 1b.2y.3e.4f.5f., 1f.2y.3e.4f.5f., 1h.2y.3e.4f.5f.,
1j.2y.3e.4f.5f., 1p.2y.3e.4f.5f., 1a.2a.3g.4f.5f., 1b.2a.3g.4f.5f.,
1f.2a.3g.4f.5f., 1h.2a.3g.4f.5f., 1j.2a.3g.4f.5f., 1p.2a.3g.4f.5f.,
1a.2b.3g.4f.5f., 1b.2b.3g.4f.5f., 1f.2b.3g.4f.5f., 1h.2b.3g.4f.5f.,
1j.2b.3g.4f.5f., 1p.2b.3g.4f.5f., 1a.2e.3g.4f.5f., 1b.2e.3g.4f.5f.,
1f.2e.3g.4f.5f., 1h.2e.3g.4f.5f., 1j.2e.3g.4f.5f., 1p.2e.3g.4f.5f.,
1a.2f.3g.4f.5f., 1b.2f.3g.4f.5f., 1f.2f.3g.4f.5f., 1h.2f.3g.4f.5f.,
1j.2f.3g.4f.5f., 1p.2f.3g.4f.5f., 1a.2i.3g.4f.5f., 1b.2i.3g.4f.5f.,
1f.2i.3g.4f.5f., 1h.2i.3g.4f.5f., 1j.2i.3g.4f.5f., 1p.2i.3g.4f.5f.,
1a.2m.3g.4f.5f., 1b.2m.3g.4f.5f., 1f.2m.3g.4f.5f., 1h.2m.3g.4f.5f.,
1j.2m.3g.4f.5f., 1p.2m.3g.4f.5f., 1a.2o.3g.4f.5f., 1b.2o.3g.4f.5f.,
1f.2o.3g.4f.5f., 1h.2o.3g.4f.5f., 1j.2o.3g.4f.5f., 1p.2o.3g.4f.5f.,
1a.2u.3g.4f.5f., 1b.2u.3g.4f.5f., 1f.2u.3g.4f.5f., 1h.2u.3g.4f.5f.,
1j.2u.3g.4f.5f., 1p.2u.3g.4f.5f., 1a.2y.3g.4f.5f., 1b.2y.3g.4f.5f.,
1f.2y.3g.4f.5f., 1h.2y.3g.4f.5f., 1j.2y.3g.4f.5f., 1p.2y.3g.4f.5f.,
1a.2a.3a.4g.5f., 1b.2a.3a.4g.5f., 1f.2a.3a.4g.5f., 1h.2a.3a.4g.5f.,
1j.2a.3a.4g.5f., 1p.2a.3a.4g.5f., 1a.2b.3a.4g.5f., 1b.2b.3a.4g.5f.,
1f.2b.3a.4g.5f., 1h.2b.3a.4g.5f., 1j.2b.3a.4g.5f., 1p.2b.3a.4g.5f.,
1a.2e.3a.4g.5f., 1b.2e.3a.4g.5f., 1f.2e.3a.4g.5f., 1h.2e.3a.4g.5f.,
1j.2e.3a.4g.5f., 1p.2e.3a.4g.5f., 1a.2f.3a.4g.5f., 1b.2f.3a.4g.5f.,
1f.2f.3a.4g.5f., 1h.2f.3a.4g.5f., 1j.2f.3a.4g.5f., 1p.2f.3a.4g.5f.,

TABLE 12-continued

List of Compound Structures of Formula III 1a.2i.3a.4g.5f., 1b.2i.3a.4g.5f., 1f.2i.3a.4g.5f., 1h.2i.3a.4g.5f.,
1j.2i.3a.4g.5f., 1p.2i.3a.4g.5f., 1a.2m.3a.4g.5f., 1b.2m.3a.4g.5f.,
1f.2m.3a.4g.5f., 1h.2m.3a.4g.5f., 1j.2m.3a.4g.5f., 1p.2m.3a.4g.5f.,
1a.2o.3a.4g.5f., 1b.2o.3a.4g.5f., 1f.2o.3a.4g.5f., 1h.2o.3a.4g.5f.,
1j.2o.3a.4g.5f., 1p.2o.3a.4g.5f., 1a.2u.3a.4g.5f., 1b.2u.3a.4g.5f.,
1f.2u.3a.4g.5f., 1h.2u.3a.4g.5f., 1j.2u.3a.4g.5f., 1p.2u.3a.4g.5f.,
1a.2y.3a.4g.5f., 1b.2y.3a.4g.5f., 1f.2y.3a.4g.5f., 1h.2y.3a.4g.5f.,
1j.2y.3a.4g.5f., 1p.2y.3a.4g.5f., 1a.2a.3b.4g.5f., 1b.2a.3b.4g.5f.,
1f.2a.3b.4g.5f., 1h.2a.3b.4g.5f., 1j.2a.3b.4g.5f., 1p.2a.3b.4g.5f.,
1a.2b.3b.4g.5f., 1b.2b.3b.4g.5f., 1f.2b.3b.4g.5f., 1h.2b.3b.4g.5f.,
1j.2b.3b.4g.5f., 1p.2b.3b.4g.5f., 1a.2e.3b.4g.5f., 1b.2e.3b.4g.5f.,
1f.2e.3b.4g.5f., 1h.2e.3b.4g.5f., 1j.2e.3b.4g.5f., 1p.2e.3b.4g.5f.,
1a.2f.3b.4g.5f., 1b.2f.3b.4g.5f., 1f.2f.3b.4g.5f., 1h.2f.3b.4g.5f.,
1j.2f.3b.4g.5f., 1p.2f.3b.4g.5f., 1a.2i.3b.4g.5f., 1b.2i.3b.4g.5f.,
1f.2i.3b.4g.5f., 1h.2i.3b.4g.5f., 1j.2i.3b.4g.5f., 1p.2i.3b.4g.5f.,
1a.2m.3b.4g.5f., 1b.2m.3b.4g.5f., 1f.2m.3b.4g.5f., 1h.2m.3b.4g.5f.,
1j.2m.3b.4g.5f., 1p.2m.3b.4g.5f., 1a.2o.3b.4g.5f., 1b.2o.3b.4g.5f.,
1f.2o.3b.4g.5f., 1h.2o.3b.4g.5f., 1j.2o.3b.4g.5f., 1p.2o.3b.4g.5f.,
1a.2u.3b.4g.5f., 1b.2u.3b.4g.5f., 1f.2u.3b.4g.5f., 1h.2u.3b.4g.5f.,
1j.2u.3b.4g.5f., 1p.2u.3b.4g.5f., 1a.2y.3b.4g.5f., 1b.2y.3b.4g.5f.,
1f.2y.3b.4g.5f., 1h.2y.3b.4g.5f., 1j.2y.3b.4g.5f., 1p.2y.3b.4g.5f.,
1a.2a.3e.4g.5f., 1b.2a.3e.4g.5f., 1f.2a.3e.4g.5f., 1h.2a.3e.4g.5f.,
1j.2a.3e.4g.5f., 1p.2a.3e.4g.5f., 1a.2b.3e.4g.5f., 1b.2b.3e.4g.5f.,
1f.2b.3e.4g.5f., 1h.2b.3e.4g.5f., 1j.2b.3e.4g.5f., 1p.2b.3e.4g.5f.,
1a.2e.3e.4g.5f., 1b.2e.3e.4g.5f., 1f.2e.3e.4g.5f., 1h.2e.3e.4g.5f.,
1j.2e.3e.4g.5f., 1p.2e.3e.4g.5f., 1a.2f.3e.4g.5f., 1b.2f.3e.4g.5f.,
1f.2f.3e.4g.5f., 1h.2f.3e.4g.5f., 1j.2f.3e.4g.5f., 1p.2f.3e.4g.5f.,
1a.2i.3e.4g.5f., 1b.2i.3e.4g.5f., 1f.2i.3e.4g.5f., 1h.2i.3e.4g.5f.,
1j.2i.3e.4g.5f., 1p.2i.3e.4g.5f., 1a.2m.3e.4g.5f., 1b.2m.3e.4g.5f.,
1f.2m.3e.4g.5f., 1h.2m.3e.4g.5f., 1j.2m.3e.4g.5f., 1p.2m.3e.4g.5f.,
1a.2o.3e.4g.5f., 1b.2o.3e.4g.5f., 1f.2o.3e.4g.5f., 1h.2o.3e.4g.5f.,
1j.2o.3e.4g.5f., 1p.2o.3e.4g.5f., 1a.2u.3e.4g.5f., 1b.2u.3e.4g.5f.,
1f.2u.3e.4g.5f., 1h.2u.3e.4g.5f., 1j.2u.3e.4g.5f., 1p.2u.3e.4g.5f.,
1a.2y.3e.4g.5f., 1b.2y.3e.4g.5f., 1f.2y.3e.4g.5f., 1h.2y.3e.4g.5f.,
1j.2y.3e.4g.5f., 1p.2y.3e.4g.5f., 1a.2a.3g.4g.5f., 1b.2a.3g.4g.5f.,
1f.2a.3g.4g.5f., 1h.2a.3g.4g.5f., 1j.2a.3g.4g.5f., 1p.2a.3g.4g.5f.,
1a.2b.3g.4g.5f., 1b.2b.3g.4g.5f., 1f.2b.3g.4g.5f., 1h.2b.3g.4g.5f.,
1j.2b.3g.4g.5f., 1p.2b.3g.4g.5f., 1a.2e.3g.4g.5f., 1b.2e.3g.4g.5f.,
1f.2e.3g.4g.5f., 1h.2e.3g.4g.5f., 1j.2e.3g.4g.5f., 1p.2e.3g.4g.5f.,
1a.2f.3g.4g.5f., 1b.2f.3g.4g.5f., 1f.2f.3g.4g.5f., 1h.2f.3g.4g.5f.,
1j.2f.3g.4g.5f., 1p.2f.3g.4g.5f., 1a.2i.3g.4g.5f., 1b.2i.3g.4g.5f.,
1f.2i.3g.4g.5f., 1h.2i.3g.4g.5f., 1j.2i.3g.4g.5f., 1p.2i.3g.4g.5f.,
1a.2m.3g.4g.5f., 1b.2m.3g.4g.5f., 1f.2m.3g.4g.5f., 1h.2m.3g.4g.5f.,
1j.2m.3g.4g.5f., 1p.2m.3g.4g.5f., 1a.2o.3g.4g.5f., 1b.2o.3g.4g.5f.,
1f.2o.3g.4g.5f., 1h.2o.3g.4g.5f., 1j.2o.3g.4g.5f., 1p.2o.3g.4g.5f.,
1a.2u.3g.4g.5f., 1b.2u.3g.4g.5f., 1f.2u.3g.4g.5f., 1h.2u.3g.4g.5f.,
1j.2u.3g.4g.5f., 1p.2u.3g.4g.5f., 1a.2y.3g.4g.5f., 1b.2y.3g.4g.5f.,
1f.2y.3g.4g.5f., 1h.2y.3g.4g.5f., 1j.2y.3g.4g.5f., 1p.2y.3g.4g.5f.,
1a.2a.3a.4h.5f., 1b.2a.3a.4h.5f., 1f.2a.3a.4h.5f., 1h.2a.3a.4h.5f.,
1j.2a.3a.4h.5f., 1p.2a.3a.4h.5f., 1a.2b.3a.4h.5f., 1b.2b.3a.4h.5f.,
1f.2b.3a.4h.5f., 1h.2b.3a.4h.5f., 1j.2b.3a.4h.5f., 1p.2b.3a.4h.5f.,
1a.2e.3a.4h.5f., 1b.2e.3a.4h.5f., 1f.2e.3a.4h.5f., 1h.2e.3a.4h.5f.,
1j.2e.3a.4h.5f., 1p.2e.3a.4h.5f., 1a.2f.3a.4h.5f., 1b.2f.3a.4h.5f.,
1f.2f.3a.4h.5f., 1h.2f.3a.4h.5f., 1j.2f.3a.4h.5f., 1p.2f.3a.4h.5f.,
1a.2i.3a.4h.5f., 1b.2i.3a.4h.5f., 1f.2i.3a.4h.5f., 1h.2i.3a.4h.5f.,
1j.2i.3a.4h.5f., 1p.2i.3a.4h.5f., 1a.2m.3a.4h.5f., 1b.2m.3a.4h.5f.,
1f.2m.3a.4h.5f., 1h.2m.3a.4h.5f., 1j.2m.3a.4h.5f., 1p.2m.3a.4h.5f.,
1a.2o.3a.4h.5f., 1b.2o.3a.4h.5f., 1f.2o.3a.4h.5f., 1h.2o.3a.4h.5f.,
1j.2o.3a.4h.5f., 1p.2o.3a.4h.5f., 1a.2u.3a.4h.5f., 1b.2u.3a.4h.5f.,
1f.2u.3a.4h.5f., 1h.2u.3a.4h.5f., 1j.2u.3a.4h.5f., 1p.2u.3a.4h.5f.,
1a.2y.3a.4h.5f., 1b.2y.3a.4h.5f., 1f.2y.3a.4h.5f., 1h.2y.3a.4h.5f.,
1j.2y.3a.4h.5f., 1p.2y.3a.4h.5f., 1a.2a.3b.4h.5f., 1b.2a.3b.4h.5f.,
1f.2a.3b.4h.5f., 1h.2a.3b.4h.5f., 1j.2a.3b.4h.5f., 1p.2a.3b.4h.5f.,
1a.2b.3b.4h.5f., 1b.2b.3b.4h.5f., 1f.2b.3b.4h.5f., 1h.2b.3b.4h.5f.,
1j.2b.3b.4h.5f., 1p.2b.3b.4h.5f., 1a.2e.3b.4h.5f., 1b.2e.3b.4h.5f.,
1f.2e.3b.4h.5f., 1h.2e.3b.4h.5f., 1j.2e.3b.4h.5f., 1p.2e.3b.4h.5f.,
1a.2f.3b.4h.5f., 1b.2f.3b.4h.5f., 1f.2f.3b.4h.5f., 1h.2f.3b.4h.5f.,
1j.2f.3b.4h.5f., 1p.2f.3b.4h.5f., 1a.2i.3b.4h.5f., 1b.2i.3b.4h.5f.,
1f.2i.3b.4h.5f., 1h.2i.3b.4h.5f., 1j.2i.3b.4h.5f., 1p.2i.3b.4h.5f.,
1a.2m.3b.4h.5f., 1b.2m.3b.4h.5f., 1f.2m.3b.4h.5f., 1h.2m.3b.4h.5f.,
1j.2m.3b.4h.5f., 1p.2m.3b.4h.5f., 1a.2o.3b.4h.5f., 1b.2o.3b.4h.5f.,
1f.2o.3b.4h.5f., 1h.2o.3b.4h.5f., 1j.2o.3b.4h.5f., 1p.2o.3b.4h.5f.,
1a.2u.3b.4h.5f., 1b.2u.3b.4h.5f., 1f.2u.3b.4h.5f., 1h.2u.3b.4h.5f.,
1j.2u.3b.4h.5f., 1p.2u.3b.4h.5f., 1a.2y.3b.4h.5f., 1b.2y.3b.4h.5f.,
1f.2y.3b.4h.5f., 1h.2y.3b.4h.5f., 1j.2y.3b.4h.5f., 1p.2y.3b.4h.5f.,
1a.2a.3e.4h.5f., 1b.2a.3e.4h.5f., 1f.2a.3e.4h.5f., 1h.2a.3e.4h.5f.,
1j.2a.3e.4h.5f., 1p.2a.3e.4h.5f., 1a.2b.3e.4h.5f., 1b.2b.3e.4h.5f.,
1f.2b.3e.4h.5f., 1h.2b.3e.4h.5f., 1j.2b.3e.4h.5f., 1p.2b.3e.4h.5f.,
1a.2e.3e.4h.5f., 1b.2e.3e.4h.5f., 1f.2e.3e.4h.5f., 1h.2e.3e.4h.5f.,
1j.2e.3e.4h.5f., 1p.2e.3e.4h.5f., 1a.2f.3e.4h.5f., 1b.2f.3e.4h.5f.,
1f.2f.3e.4h.5f., 1h.2f.3e.4h.5f., 1j.2f.3e.4h.5f., 1p.2f.3e.4h.5f.,
1a.2i.3e.4h.5f., 1b.2i.3e.4h.5f., 1f.2i.3e.4h.5f., 1h.2i.3e.4h.5f.,
1j.2i.3e.4h.5f., 1p.2i.3e.4h.5f., 1a.2m.3e.4h.5f., 1b.2m.3e.4h.5f.,
1f.2m.3e.4h.5f., 1h.2m.3e.4h.5f., 1j.2m.3e.4h.5f., 1p.2m.3e.4h.5f.,
1a.2o.3e.4h.5f., 1b.2o.3e.4h.5f., 1f.2o.3e.4h.5f., 1h.2o.3e.4h.5f.,
1j.2o.3e.4h.5f., 1p.2o.3e.4h.5f., 1a.2u.3e.4h.5f., 1b.2u.3e.4h.5f.,
1f.2u.3e.4h.5f., 1h.2u.3e.4h.5f., 1j.2u.3e.4h.5f., 1p.2u.3e.4h.5f.,
1a.2y.3e.4h.5f., 1b.2y.3e.4h.5f., 1f.2y.3e.4h.5f., 1h.2y.3e.4h.5f.,
1j.2y.3e.4h.5f., 1p.2y.3e.4h.5f., 1a.2a.3g.4h.5f., 1b.2a.3g.4h.5f.,
1f.2a.3g.4h.5f., 1h.2a.3g.4h.5f., 1j.2a.3g.4h.5f., 1p.2a.3g.4h.5f.,
1a.2b.3g.4h.5f., 1b.2b.3g.4h.5f., 1f.2b.3g.4h.5f., 1h.2b.3g.4h.5f.,
1j.2b.3g.4h.5f., 1p.2b.3g.4h.5f., 1a.2e.3g.4h.5f., 1b.2e.3g.4h.5f.,
1f.2e.3g.4h.5f., 1h.2e.3g.4h.5f., 1j.2e.3g.4h.5f., 1p.2e.3g.4h.5f.,
1a.2f.3g.4h.5f., 1b.2f.3g.4h.5f., 1f.2f.3g.4h.5f., 1h.2f.3g.4h.5f.,
1j.2f.3g.4h.5f., 1p.2f.3g.4h.5f., 1a.2i.3g.4h.5f., 1b.2i.3g.4h.5f.,
1f.2i.3g.4h.5f., 1h.2i.3g.4h.5f., 1j.2i.3g.4h.5f., 1p.2i.3g.4h.5f.,
1a.2m.3g.4h.5f., 1b.2m.3g.4h.5f., 1f.2m.3g.4h.5f., 1h.2m.3g.4h.5f.,
1j.2m.3g.4h.5f., 1p.2m.3g.4h.5f., 1a.2o.3g.4h.5f., 1b.2o.3g.4h.5f.,
1f.2o.3g.4h.5f., 1h.2o.3g.4h.5f., 1j.2o.3g.4h.5f., 1p.2o.3g.4h.5f.,
1a.2u.3g.4h.5f., 1b.2u.3g.4h.5f., 1f.2u.3g.4h.5f., 1h.2u.3g.4h.5f.,
1j.2u.3g.4h.5f., 1p.2u.3g.4h.5f., 1a.2y.3g.4h.5f., 1b.2y.3g.4h.5f.,
1f.2y.3g.4h.5f., 1h.2y.3g.4h.5f., 1j.2y.3g.4h.5f., 1p.2y.3g.4h.5f.,
1a.2a.3a.4i.5f., 1b.2a.3a.4i.5f., 1f.2a.3a.4i.5f., 1h.2a.3a.4i.5f.,
1j.2a.3a.4i.5f., 1p.2a.3a.4i.5f., 1a.2b.3a.4i.5f., 1b.2b.3a.4i.5f.,
1f.2b.3a.4i.5f., 1h.2b.3a.4i.5f., 1j.2b.3a.4i.5f., 1p.2b.3a.4i.5f.,
1a.2e.3a.4i.5f., 1b.2e.3a.4i.5f., 1f.2e.3a.4i.5f., 1h.2e.3a.4i.5f.,
1j.2e.3a.4i.5f., 1p.2e.3a.4i.5f., 1a.2f.3a.4i.5f., 1b.2f.3a.4i.5f.,
1f.2f.3a.4i.5f., 1h.2f.3a.4i.5f., 1j.2f.3a.4i.5f., 1p.2f.3a.4i.5f.,
1a.2i.3a.4i.5f., 1b.2i.3a.4i.5f., 1f.2i.3a.4i.5f., 1h.2i.3a.4i.5f.,
1j.2i.3a.4i.5f., 1p.2i.3a.4i.5f., 1a.2m.3a.4i.5f., 1b.2m.3a.4i.5f.,
1f.2m.3a.4i.5f., 1h.2m.3a.4i.5f., 1j.2m.3a.4i.5f., 1p.2m.3a.4i.5f.,
1a.2o.3a.4i.5f., 1b.2o.3a.4i.5f., 1f.2o.3a.4i.5f., 1h.2o.3a.4i.5f.,
1j.2o.3a.4i.5f., 1p.2o.3a.4i.5f., 1a.2u.3a.4i.5f., 1b.2u.3a.4i.5f.,
1f.2u.3a.4i.5f., 1h.2u.3a.4i.5f., 1j.2u.3a.4i.5f., 1p.2u.3a.4i.5f.,
1a.2y.3a.4i.5f., 1b.2y.3a.4i.5f., 1f.2y.3a.4i.5f., 1h.2y.3a.4i.5f.,
1j.2y.3a.4i.5f., 1p.2y.3a.4i.5f., 1a.2a.3b.4i.5f., 1b.2a.3b.4i.5f.,
1f.2a.3b.4i.5f., 1h.2a.3b.4i.5f., 1j.2a.3b.4i.5f., 1p.2a.3b.4i.5f.,
1a.2b.3b.4i.5f., 1b.2b.3b.4i.5f., 1f.2b.3b.4i.5f., 1h.2b.3b.4i.5f.,
1j.2b.3b.4i.5f., 1p.2b.3b.4i.5f., 1a.2e.3b.4i.5f., 1b.2e.3b.4i.5f.,
1f.2e.3b.4i.5f., 1h.2e.3b.4i.5f., 1j.2e.3b.4i.5f., 1p.2e.3b.4i.5f.,
1a.2f.3b.4i.5f., 1b.2f.3b.4i.5f., 1f.2f.3b.4i.5f., 1h.2f.3b.4i.5f.,
1j.2f.3b.4i.5f., 1p.2f.3b.4i.5f., 1a.2i.3b.4i.5f., 1b.2i.3b.4i.5f.,
1f.2i.3b.4i.5f., 1h.2i.3b.4i.5f., 1j.2i.3b.4i.5f., 1p.2i.3b.4i.5f.,
1a.2m.3b.4i.5f., 1b.2m.3b.4i.5f., 1f.2m.3b.4i.5f., 1h.2m.3b.4i.5f.,
1j.2m.3b.4i.5f., 1p.2m.3b.4i.5f., 1a.2o.3b.4i.5f., 1b.2o.3b.4i.5f.,
1f.2o.3b.4i.5f., 1h.2o.3b.4i.5f., 1j.2o.3b.4i.5f., 1p.2o.3b.4i.5f.,
1a.2u.3b.4i.5f., 1b.2u.3b.4i.5f., 1f.2u.3b.4i.5f., 1h.2u.3b.4i.5f.,
1j.2u.3b.4i.5f., 1p.2u.3b.4i.5f., 1a.2y.3b.4i.5f., 1b.2y.3b.4i.5f.,
1f.2y.3b.4i.5f., 1h.2y.3b.4i.5f., 1j.2y.3b.4i.5f., 1p.2y.3b.4i.5f.,
1a.2a.3e.4i.5f., 1b.2a.3e.4i.5f., 1f.2a.3e.4i.5f., 1h.2a.3e.4i.5f.,
1j.2a.3e.4i.5f., 1p.2a.3e.4i.5f., 1a.2b.3e.4i.5f., 1b.2b.3e.4i.5f.,
1f.2b.3e.4i.5f., 1h.2b.3e.4i.5f., 1j.2b.3e.4i.5f., 1p.2b.3e.4i.5f.,
1a.2e.3e.4i.5f., 1b.2e.3e.4i.5f., 1f.2e.3e.4i.5f., 1h.2e.3e.4i.5f.,
1j.2e.3e.4i.5f., 1p.2e.3e.4i.5f., 1a.2f.3e.4i.5f., 1b.2f.3e.4i.5f.,
1f.2f.3e.4i.5f., 1h.2f.3e.4i.5f., 1j.2f.3e.4i.5f., 1p.2f.3e.4i.5f.,
1a.2i.3e.4i.5f., 1b.2i.3e.4i.5f., 1f.2i.3e.4i.5f., 1h.2i.3e.4i.5f.,
1j.2i.3e.4i.5f., 1p.2i.3e.4i.5f., 1a.2m.3e.4i.5f., 1b.2m.3e.4i.5f.,
1f.2m.3e.4i.5f., 1h.2m.3e.4i.5f., 1j.2m.3e.4i.5f., 1p.2m.3e.4i.5f.,
1a.2o.3e.4i.5f., 1b.2o.3e.4i.5f., 1f.2o.3e.4i.5f., 1h.2o.3e.4i.5f.,
1j.2o.3e.4i.5f., 1p.2o.3e.4i.5f., 1a.2u.3e.4i.5f., 1b.2u.3e.4i.5f.,
1f.2u.3e.4i.5f., 1h.2u.3e.4i.5f., 1j.2u.3e.4i.5f., 1p.2u.3e.4i.5f.,
1a.2y.3e.4i.5f., 1b.2y.3e.4i.5f., 1f.2y.3e.4i.5f., 1h.2y.3e.4i.5f.,
1j.2y.3e.4i.5f., 1p.2y.3e.4i.5f., 1a.2a.3g.4i.5f., 1b.2a.3g.4i.5f.,
1f.2a.3g.4i.5f., 1h.2a.3g.4i.5f., 1j.2a.3g.4i.5f., 1p.2a.3g.4i.5f.,
1a.2b.3g.4i.5f., 1b.2b.3g.4i.5f., 1f.2b.3g.4i.5f., 1h.2b.3g.4i.5f.,
1j.2b.3g.4i.5f., 1p.2b.3g.4i.5f., 1a.2e.3g.4i.5f., 1b.2e.3g.4i.5f.,
1f.2e.3g.4i.5f., 1h.2e.3g.4i.5f., 1j.2e.3g.4i.5f., 1p.2e.3g.4i.5f.,
1a.2f.3g.4i.5f., 1b.2f.3g.4i.5f., 1f.2f.3g.4i.5f., 1h.2f.3g.4i.5f.,
1j.2f.3g.4i.5f., 1p.2f.3g.4i.5f., 1a.2i.3g.4i.5f., 1b.2i.3g.4i.5f.,
1f.2i.3g.4i.5f., 1h.2i.3g.4i.5f., 1j.2i.3g.4i.5f., 1p.2i.3g.4i.5f.,
1a.2m.3g.4i.5f., 1b.2m.3g.4i.5f., 1f.2m.3g.4i.5f., 1h.2m.3g.4i.5f.,
1j.2m.3g.4i.5f., 1p.2m.3g.4i.5f., 1a.2o.3g.4i.5f., 1b.2o.3g.4i.5f.,
1f.2o.3g.4i.5f., 1h.2o.3g.4i.5f., 1j.2o.3g.4i.5f., 1p.2o.3g.4i.5f.,
1a.2u.3g.4i.5f., 1b.2u.3g.4i.5f., 1f.2u.3g.4i.5f., 1h.2u.3g.4i.5f.,
1j.2u.3g.4i.5f., 1p.2u.3g.4i.5f., 1a.2y.3g.4i.5f., 1b.2y.3g.4i.5f.,
1f.2y.3g.4i.5f., 1h.2y.3g.4i.5f., 1j.2y.3g.4i.5f., 1p.2y.3g.4i.5f.,

TABLE 12-continued

List of Compound Structures of Formula III 1a.2a.3a.4a.5g., 1b.2a.3a.4a.5g., 1f.2a.3a.4a.5g., 1h.2a.3a.4a.5g.,
1j.2a.3a.4a.5g., 1p.2a.3a.4a.5g., 1a.2b.3a.4a.5g., 1b.2b.3a.4a.5g.,
1f.2b.3a.4a.5g., 1h.2b.3a.4a.5g., 1j.2b.3a.4a.5g., 1p.2b.3a.4a.5g.,
1a.2e.3a.4a.5g., 1b.2e.3a.4a.5g., 1f.2e.3a.4a.5g., 1h.2e.3a.4a.5g.,
1j.2e.3a.4a.5g., 1p.2e.3a.4a.5g., 1a.2f.3a.4a.5g., 1b.2f.3a.4a.5g.,
1f.2f.3a.4a.5g., 1h.2f.3a.4a.5g., 1j.2f.3a.4a.5g., 1p.2f.3a.4a.5g.,
1a.2i.3a.4a.5g., 1b.2i.3a.4a.5g., 1f.2i.3a.4a.5g., 1h.2i.3a.4a.5g.,
1j.2i.3a.4a.5g., 1p.2i.3a.4a.5g., 1a.2m.3a.4a.5g., 1b.2m.3a.4a.5g.,
1f.2m.3a.4a.5g., 1h.2m.3a.4a.5g., 1j.2m.3a.4a.5g., 1p.2m.3a.4a.5g.,
1a.2o.3a.4a.5g., 1b.2o.3a.4a.5g., 1f.2o.3a.4a.5g., 1h.2o.3a.4a.5g.,
1j.2o.3a.4a.5g., 1p.2o.3a.4a.5g., 1a.2u.3a.4a.5g., 1b.2u.3a.4a.5g.,
1f.2u.3a.4a.5g., 1h.2u.3a.4a.5g., 1j.2u.3a.4a.5g., 1p.2u.3a.4a.5g.,
1a.2y.3a.4a.5g., 1b.2y.3a.4a.5g., 1f.2y.3a.4a.5g., 1h.2y.3a.4a.5g.,
1j.2y.3a.4a.5g., 1p.2y.3a.4a.5g., 1a.2a.3b.4a.5g., 1b.2a.3b.4a.5g.,
1f.2a.3b.4a.5g., 1h.2a.3b.4a.5g., 1j.2a.3b.4a.5g., 1p.2a.3b.4a.5g.,
1a.2b.3b.4a.5g., 1b.2b.3b.4a.5g., 1f.2b.3b.4a.5g., 1h.2b.3b.4a.5g.,
1j.2b.3b.4a.5g., 1p.2b.3b.4a.5g., 1a.2e.3b.4a.5g., 1b.2e.3b.4a.5g.,
1f.2e.3b.4a.5g., 1h.2e.3b.4a.5g., 1j.2e.3b.4a.5g., 1p.2e.3b.4a.5g.,
1a.2f.3b.4a.5g., 1b.2f.3b.4a.5g., 1f.2f.3b.4a.5g., 1h.2f.3b.4a.5g.,
1j.2f.3b.4a.5g., 1p.2f.3b.4a.5g., 1a.2i.3b.4a.5g., 1b.2i.3b.4a.5g.,
1f.2i.3b.4a.5g., 1h.2i.3b.4a.5g., 1j.2i.3b.4a.5g., 1p.2i.3b.4a.5g.,
1a.2m.3b.4a.5g., 1b.2m.3b.4a.5g., 1f.2m.3b.4a.5g., 1h.2m.3b.4a.5g.,
1j.2m.3b.4a.5g., 1p.2m.3b.4a.5g., 1a.2o.3b.4a.5g., 1b.2o.3b.4a.5g.,
1f.2o.3b.4a.5g., 1h.2o.3b.4a.5g., 1j.2o.3b.4a.5g., 1p.2o.3b.4a.5g.,
1a.2u.3b.4a.5g., 1b.2u.3b.4a.5g., 1f.2u.3b.4a.5g., 1h.2u.3b.4a.5g.,
1j.2u.3b.4a.5g., 1p.2u.3b.4a.5g., 1a.2y.3b.4a.5g., 1b.2y.3b.4a.5g.,
1f.2y.3b.4a.5g., 1h.2y.3b.4a.5g., 1j.2y.3b.4a.5g., 1p.2y.3b.4a.5g.,
1a.2a.3e.4a.5g., 1b.2a.3e.4a.5g., 1f.2a.3e.4a.5g., 1h.2a.3e.4a.5g.,
1j.2a.3e.4a.5g., 1p.2a.3e.4a.5g., 1a.2b.3e.4a.5g., 1b.2b.3e.4a.5g.,
1f.2b.3e.4a.5g., 1h.2b.3e.4a.5g., 1j.2b.3e.4a.5g., 1p.2b.3e.4a.5g.,
1a.2e.3e.4a.5g., 1b.2e.3e.4a.5g., 1f.2e.3e.4a.5g., 1h.2e.3e.4a.5g.,
1j.2e.3e.4a.5g., 1p.2e.3e.4a.5g., 1a.2f.3e.4a.5g., 1b.2f.3e.4a.5g.,
1f.2f.3e.4a.5g., 1h.2f.3e.4a.5g., 1j.2f.3e.4a.5g., 1p.2f.3e.4a.5g.,
1a.2i.3e.4a.5g., 1b.2i.3e.4a.5g., 1f.2i.3e.4a.5g., 1h.2i.3e.4a.5g.,
1j.2i.3e.4a.5g., 1p.2i.3e.4a.5g., 1a.2m.3e.4a.5g., 1b.2m.3e.4a.5g.,
1f.2m.3e.4a.5g., 1h.2m.3e.4a.5g., 1j.2m.3e.4a.5g., 1p.2m.3e.4a.5g.,
1a.2o.3e.4a.5g., 1b.2o.3e.4a.5g., 1f.2o.3e.4a.5g., 1h.2o.3e.4a.5g.,
1j.2o.3e.4a.5g., 1p.2o.3e.4a.5g., 1a.2u.3e.4a.5g., 1b.2u.3e.4a.5g.,
1f.2u.3e.4a.5g., 1h.2u.3e.4a.5g., 1j.2u.3e.4a.5g., 1p.2u.3e.4a.5g.,
1a.2y.3e.4a.5g., 1b.2y.3e.4a.5g., 1f.2y.3e.4a.5g., 1h.2y.3e.4a.5g.,
1j.2y.3e.4a.5g., 1p.2y.3e.4a.5g., 1a.2a.3g.4a.5g., 1b.2a.3g.4a.5g.,
1f.2a.3g.4a.5g., 1h.2a.3g.4a.5g., 1j.2a.3g.4a.5g., 1p.2a.3g.4a.5g.,
1a.2b.3g.4a.5g., 1b.2b.3g.4a.5g., 1f.2b.3g.4a.5g., 1h.2b.3g.4a.5g.,
1j.2b.3g.4a.5g., 1p.2b.3g.4a.5g., 1a.2e.3g.4a.5g., 1b.2e.3g.4a.5g.,
1f.2e.3g.4a.5g., 1h.2e.3g.4a.5g., 1j.2e.3g.4a.5g., 1p.2e.3g.4a.5g.,
1a.2f.3g.4a.5g., 1b.2f.3g.4a.5g., 1f.2f.3g.4a.5g., 1h.2f.3g.4a.5g.,
1j.2f.3g.4a.5g., 1p.2f.3g.4a.5g., 1a.2i.3g.4a.5g., 1b.2i.3g.4a.5g.,
1f.2i.3g.4a.5g., 1h.2i.3g.4a.5g., 1j.2i.3g.4a.5g., 1p.2i.3g.4a.5g.,
1a.2m.3g.4a.5g., 1b.2m.3g.4a.5g., 1f.2m.3g.4a.5g., 1h.2m.3g.4a.5g.,
1j.2m.3g.4a.5g., 1p.2m.3g.4a.5g., 1a.2o.3g.4a.5g., 1b.2o.3g.4a.5g.,
1f.2o.3g.4a.5g., 1h.2o.3g.4a.5g., 1j.2o.3g.4a.5g., 1p.2o.3g.4a.5g.,
1a.2u.3g.4a.5g., 1b.2u.3g.4a.5g., 1f.2u.3g.4a.5g., 1h.2u.3g.4a.5g.,
1j.2u.3g.4a.5g., 1p.2u.3g.4a.5g., 1a.2y.3g.4a.5g., 1b.2y.3g.4a.5g.,
1f.2y.3g.4a.5g., 1h.2y.3g.4a.5g., 1j.2y.3g.4a.5g., 1p.2y.3g.4a.5g.,
1a.2a.3a.4d.5g., 1b.2a.3a.4d.5g., 1f.2a.3a.4d.5g., 1h.2a.3a.4d.5g.,
1j.2a.3a.4d.5g., 1p.2a.3a.4d.5g., 1a.2b.3a.4d.5g., 1b.2b.3a.4d.5g.,
1f.2b.3a.4d.5g., 1h.2b.3a.4d.5g., 1j.2b.3a.4d.5g., 1p.2b.3a.4d.5g.,
1a.2e.3a.4d.5g., 1b.2e.3a.4d.5g., 1f.2e.3a.4d.5g., 1h.2e.3a.4d.5g.,
1j.2e.3a.4d.5g., 1p.2e.3a.4d.5g., 1a.2f.3a.4d.5g., 1b.2f.3a.4d.5g.,
1f.2f.3a.4d.5g., 1h.2f.3a.4d.5g., 1j.2f.3a.4d.5g., 1p.2f.3a.4d.5g.,
1a.2i.3a.4d.5g., 1b.2i.3a.4d.5g., 1f.2i.3a.4d.5g., 1h.2i.3a.4d.5g.,
1j.2i.3a.4d.5g., 1p.2i.3a.4d.5g., 1a.2m.3a.4d.5g., 1b.2m.3a.4d.5g.,
1f.2m.3a.4d.5g., 1h.2m.3a.4d.5g., 1j.2m.3a.4d.5g., 1p.2m.3a.4d.5g.,
1a.2o.3a.4d.5g., 1b.2o.3a.4d.5g., 1f.2o.3a.4d.5g., 1h.2o.3a.4d.5g.,
1j.2o.3a.4d.5g., 1p.2o.3a.4d.5g., 1a.2u.3a.4d.5g., 1b.2u.3a.4d.5g.,
1f.2u.3a.4d.5g., 1h.2u.3a.4d.5g., 1j.2u.3a.4d.5g., 1p.2u.3a.4d.5g.,
1a.2y.3a.4d.5g., 1b.2y.3a.4d.5g., 1f.2y.3a.4d.5g., 1h.2y.3a.4d.5g.,
1j.2y.3a.4d.5g., 1p.2y.3a.4d.5g., 1a.2a.3b.4d.5g., 1b.2a.3b.4d.5g.,
1f.2a.3b.4d.5g., 1h.2a.3b.4d.5g., 1j.2a.3b.4d.5g., 1p.2a.3b.4d.5g.,
1a.2b.3b.4d.5g., 1b.2b.3b.4d.5g., 1f.2b.3b.4d.5g., 1h.2b.3b.4d.5g.,
1j.2b.3b.4d.5g., 1p.2b.3b.4d.5g., 1a.2e.3b.4d.5g., 1b.2e.3b.4d.5g.,
1f.2e.3b.4d.5g., 1h.2e.3b.4d.5g., 1j.2e.3b.4d.5g., 1p.2e.3b.4d.5g.,
1a.2f.3b.4d.5g., 1b.2f.3b.4d.5g., 1f.2f.3b.4d.5g., 1h.2f.3b.4d.5g.,
1j.2f.3b.4d.5g., 1p.2f.3b.4d.5g., 1a.2i.3b.4d.5g., 1b.2i.3b.4d.5g.,
1f.2i.3b.4d.5g., 1h.2i.3b.4d.5g., 1j.2i.3b.4d.5g., 1p.2i.3b.4d.5g.,
1a.2m.3b.4d.5g., 1b.2m.3b.4d.5g., 1f.2m.3b.4d.5g., 1h.2m.3b.4d.5g.,
1j.2m.3b.4d.5g., 1p.2m.3b.4d.5g., 1a.2o.3b.4d.5g., 1b.2o.3b.4d.5g.,
1f.2o.3b.4d.5g., 1h.2o.3b.4d.5g., 1j.2o.3b.4d.5g., 1p.2o.3b.4d.5g.,
1a.2u.3b.4d.5g., 1b.2u.3b.4d.5g., 1f.2u.3b.4d.5g., 1h.2u.3b.4d.5g.,
1j.2u.3b.4d.5g., 1p.2u.3b.4d.5g., 1a.2y.3b.4d.5g., 1b.2y.3b.4d.5g.,
1f.2y.3b.4d.5g., 1h.2y.3b.4d.5g., 1j.2y.3b.4d.5g., 1p.2y.3b.4d.5g.,
1a.2a.3e.4d.5g., 1b.2a.3e.4d.5g., 1f.2a.3e.4d.5g., 1h.2a.3e.4d.5g.,
1j.2a.3e.4d.5g., 1p.2a.3e.4d.5g., 1a.2b.3e.4d.5g., 1b.2b.3e.4d.5g.,
1f.2b.3e.4d.5g., 1h.2b.3e.4d.5g., 1j.2b.3e.4d.5g., 1p.2b.3e.4d.5g.,
1a.2e.3e.4d.5g., 1b.2e.3e.4d.5g., 1f.2e.3e.4d.5g., 1h.2e.3e.4d.5g.,
1j.2e.3e.4d.5g., 1p.2e.3e.4d.5g., 1a.2f.3e.4d.5g., 1b.2f.3e.4d.5g.,
1f.2f.3e.4d.5g., 1h.2f.3e.4d.5g., 1j.2f.3e.4d.5g., 1p.2f.3e.4d.5g.,
1a.2i.3e.4d.5g., 1b.2i.3e.4d.5g., 1f.2i.3e.4d.5g., 1h.2i.3e.4d.5g.,
1j.2i.3e.4d.5g., 1p.2i.3e.4d.5g., 1a.2m.3e.4d.5g., 1b.2m.3e.4d.5g.,
1f.2m.3e.4d.5g., 1h.2m.3e.4d.5g., 1j.2m.3e.4d.5g., 1p.2m.3e.4d.5g.,
1a.2o.3e.4d.5g., 1b.2o.3e.4d.5g., 1f.2o.3e.4d.5g., 1h.2o.3e.4d.5g.,
1j.2o.3e.4d.5g., 1p.2o.3e.4d.5g., 1a.2u.3e.4d.5g., 1b.2u.3e.4d.5g.,
1f.2u.3e.4d.5g., 1h.2u.3e.4d.5g., 1j.2u.3e.4d.5g., 1p.2u.3e.4d.5g.,
1a.2y.3e.4d.5g., 1b.2y.3e.4d.5g., 1f.2y.3e.4d.5g., 1h.2y.3e.4d.5g.,
1j.2y.3e.4d.5g., 1p.2y.3e.4d.5g., 1a.2a.3g.4d.5g., 1b.2a.3g.4d.5g.,
1f.2a.3g.4d.5g., 1h.2a.3g.4d.5g., 1j.2a.3g.4d.5g., 1p.2a.3g.4d.5g.,
1a.2b.3g.4d.5g., 1b.2b.3g.4d.5g., 1f.2b.3g.4d.5g., 1h.2b.3g.4d.5g.,
1j.2b.3g.4d.5g., 1p.2b.3g.4d.5g., 1a.2e.3g.4d.5g., 1b.2e.3g.4d.5g.,
1f.2e.3g.4d.5g., 1h.2e.3g.4d.5g., 1j.2e.3g.4d.5g., 1p.2e.3g.4d.5g.,
1a.2f.3g.4d.5g., 1b.2f.3g.4d.5g., 1f.2f.3g.4d.5g., 1h.2f.3g.4d.5g.,
1j.2f.3g.4d.5g., 1p.2f.3g.4d.5g., 1a.2i.3g.4d.5g., 1b.2i.3g.4d.5g.,
1f.2i.3g.4d.5g., 1h.2i.3g.4d.5g., 1j.2i.3g.4d.5g., 1p.2i.3g.4d.5g.,
1a.2m.3g.4d.5g., 1b.2m.3g.4d.5g., 1f.2m.3g.4d.5g., 1h.2m.3g.4d.5g.,
1j.2m.3g.4d.5g., 1p.2m.3g.4d.5g., 1a.2o.3g.4d.5g., 1b.2o.3g.4d.5g.,
1f.2o.3g.4d.5g., 1h.2o.3g.4d.5g., 1j.2o.3g.4d.5g., 1p.2o.3g.4d.5g.,
1a.2u.3g.4d.5g., 1b.2u.3g.4d.5g., 1f.2u.3g.4d.5g., 1h.2u.3g.4d.5g.,
1j.2u.3g.4d.5g., 1p.2u.3g.4d.5g., 1a.2y.3g.4d.5g., 1b.2y.3g.4d.5g.,
1f.2y.3g.4d.5g., 1h.2y.3g.4d.5g., 1j.2y.3g.4d.5g., 1p.2y.3g.4d.5g.,
1a.2a.3a.4f.5g., 1b.2a.3a.4f.5g., 1f.2a.3a.4f.5g., 1h.2a.3a.4f.5g.,
1j.2a.3a.4f.5g., 1p.2a.3a.4f.5g., 1a.2b.3a.4f.5g., 1b.2b.3a.4f.5g.,
1f.2b.3a.4f.5g., 1h.2b.3a.4f.5g., 1j.2b.3a.4f.5g., 1p.2b.3a.4f.5g.,
1a.2e.3a.4f.5g., 1b.2e.3a.4f.5g., 1f.2e.3a.4f.5g., 1h.2e.3a.4f.5g.,
1j.2e.3a.4f.5g., 1p.2e.3a.4f.5g., 1a.2f.3a.4f.5g., 1b.2f.3a.4f.5g.,
1f.2f.3a.4f.5g., 1h.2f.3a.4f.5g., 1j.2f.3a.4f.5g., 1p.2f.3a.4f.5g.,
1a.2i.3a.4f.5g., 1b.2i.3a.4f.5g., 1f.2i.3a.4f.5g., 1h.2i.3a.4f.5g.,
1j.2i.3a.4f.5g., 1p.2i.3a.4f.5g., 1a.2m.3a.4f.5g., 1b.2m.3a.4f.5g.,
1f.2m.3a.4f.5g., 1h.2m.3a.4f.5g., 1j.2m.3a.4f.5g., 1p.2m.3a.4f.5g.,
1a.2o.3a.4f.5g., 1b.2o.3a.4f.5g., 1f.2o.3a.4f.5g., 1h.2o.3a.4f.5g.,
1j.2o.3a.4f.5g., 1p.2o.3a.4f.5g., 1a.2u.3a.4f.5g., 1b.2u.3a.4f.5g.,
1f.2u.3a.4f.5g., 1h.2u.3a.4f.5g., 1j.2u.3a.4f.5g., 1p.2u.3a.4f.5g.,
1a.2y.3a.4f.5g., 1b.2y.3a.4f.5g., 1f.2y.3a.4f.5g., 1h.2y.3a.4f.5g.,
1j.2y.3a.4f.5g., 1p.2y.3a.4f.5g., 1a.2a.3b.4f.5g., 1b.2a.3b.4f.5g.,
1f.2a.3b.4f.5g., 1h.2a.3b.4f.5g., 1j.2a.3b.4f.5g., 1p.2a.3b.4f.5g.,
1a.2b.3b.4f.5g., 1b.2b.3b.4f.5g., 1f.2b.3b.4f.5g., 1h.2b.3b.4f.5g.,
1j.2b.3b.4f.5g., 1p.2b.3b.4f.5g., 1a.2e.3b.4f.5g., 1b.2e.3b.4f.5g.,
1f.2e.3b.4f.5g., 1h.2e.3b.4f.5g., 1j.2e.3b.4f.5g., 1p.2e.3b.4f.5g.,
1a.2f.3b.4f.5g., 1b.2f.3b.4f.5g., 1f.2f.3b.4f.5g., 1h.2f.3b.4f.5g.,
1j.2f.3b.4f.5g., 1p.2f.3b.4f.5g., 1a.2i.3b.4f.5g., 1b.2i.3b.4f.5g.,
1f.2i.3b.4f.5g., 1h.2i.3b.4f.5g., 1j.2i.3b.4f.5g., 1p.2i.3b.4f.5g.,
1a.2m.3b.4f.5g., 1b.2m.3b.4f.5g., 1f.2m.3b.4f.5g., 1h.2m.3b.4f.5g.,
1j.2m.3b.4f.5g., 1p.2m.3b.4f.5g., 1a.2o.3b.4f.5g., 1b.2o.3b.4f.5g.,
1f.2o.3b.4f.5g., 1h.2o.3b.4f.5g., 1j.2o.3b.4f.5g., 1p.2o.3b.4f.5g.,
1a.2u.3b.4f.5g., 1b.2u.3b.4f.5g., 1f.2u.3b.4f.5g., 1h.2u.3b.4f.5g.,
1j.2u.3b.4f.5g., 1p.2u.3b.4f.5g., 1a.2y.3b.4f.5g., 1b.2y.3b.4f.5g.,
1f.2y.3b.4f.5g., 1h.2y.3b.4f.5g., 1j.2y.3b.4f.5g., 1p.2y.3b.4f.5g.,
1a.2a.3e.4f.5g., 1b.2a.3e.4f.5g., 1f.2a.3e.4f.5g., 1h.2a.3e.4f.5g.,
1j.2a.3e.4f.5g., 1p.2a.3e.4f.5g., 1a.2b.3e.4f.5g., 1b.2b.3e.4f.5g.,
1f.2b.3e.4f.5g., 1h.2b.3e.4f.5g., 1j.2b.3e.4f.5g., 1p.2b.3e.4f.5g.,
1a.2e.3e.4f.5g., 1b.2e.3e.4f.5g., 1f.2e.3e.4f.5g., 1h.2e.3e.4f.5g.,
1j.2e.3e.4f.5g., 1p.2e.3e.4f.5g., 1a.2f.3e.4f.5g., 1b.2f.3e.4f.5g.,
1f.2f.3e.4f.5g., 1h.2f.3e.4f.5g., 1j.2f.3e.4f.5g., 1p.2f.3e.4f.5g.,
1a.2i.3e.4f.5g., 1b.2i.3e.4f.5g., 1f.2i.3e.4f.5g., 1h.2i.3e.4f.5g.,
1j.2i.3e.4f.5g., 1p.2i.3e.4f.5g., 1a.2m.3e.4f.5g., 1b.2m.3e.4f.5g.,
1f.2m.3e.4f.5g., 1h.2m.3e.4f.5g., 1j.2m.3e.4f.5g., 1p.2m.3e.4f.5g.,
1a.2o.3e.4f.5g., 1b.2o.3e.4f.5g., 1f.2o.3e.4f.5g., 1h.2o.3e.4f.5g.,
1j.2o.3e.4f.5g., 1p.2o.3e.4f.5g., 1a.2u.3e.4f.5g., 1b.2u.3e.4f.5g.,
1f.2u.3e.4f.5g., 1h.2u.3e.4f.5g., 1j.2u.3e.4f.5g., 1p.2u.3e.4f.5g.,
1a.2y.3e.4f.5g., 1b.2y.3e.4f.5g., 1f.2y.3e.4f.5g., 1h.2y.3e.4f.5g.,
1j.2y.3e.4f.5g., 1p.2y.3e.4f.5g., 1a.2a.3g.4f.5g., 1b.2a.3g.4f.5g.,
1f.2a.3g.4f.5g., 1h.2a.3g.4f.5g., 1j.2a.3g.4f.5g., 1p.2a.3g.4f.5g.,
1a.2b.3g.4f.5g., 1b.2b.3g.4f.5g., 1f.2b.3g.4f.5g., 1h.2b.3g.4f.5g.,
1j.2b.3g.4f.5g., 1p.2b.3g.4f.5g., 1a.2e.3g.4f.5g., 1b.2e.3g.4f.5g.,
1f.2e.3g.4f.5g., 1h.2e.3g.4f.5g., 1j.2e.3g.4f.5g., 1p.2e.3g.4f.5g.,
1a.2f.3g.4f.5g., 1b.2f.3g.4f.5g., 1f.2f.3g.4f.5g., 1h.2f.3g.4f.5g.,
1j.2f.3g.4f.5g., 1p.2f.3g.4f.5g., 1a.2i.3g.4f.5g., 1b.2i.3g.4f.5g.,
1f.2i.3g.4f.5g., 1h.2i.3g.4f.5g., 1j.2i.3g.4f.5g., 1p.2i.3g.4f.5g.,

TABLE 12-continued

List of Compound Structures of Formula III 1a.2m.3g.4f.5g., 1b.2m.3g.4f.5g., 1f.2m.3g.4f.5g., 1h.2m.3g.4f.5g.,
1j.2m.3g.4f.5g., 1p.2m.3g.4f.5g., 1a.2o.3g.4f.5g., 1b.2o.3g.4f.5g.,
1f.2o.3g.4f.5g., 1h.2o.3g.4f.5g., 1j.2o.3g.4f.5g., 1p.2o.3g.4f.5g.,
1a.2u.3g.4f.5g., 1b.2u.3g.4f.5g., 1f.2u.3g.4f.5g., 1h.2u.3g.4f.5g.,
1j.2u.3g.4f.5g., 1p.2u.3g.4f.5g., 1a.2y.3g.4f.5g., 1b.2y.3g.4f.5g.,
1f.2y.3g.4f.5g., 1h.2y.3g.4f.5g., 1j.2y.3g.4f.5g., 1p.2y.3g.4f.5g.,
1a.2a.3a.4g.5g., 1b.2a.3a.4g.5g., 1f.2a.3a.4g.5g., 1h.2a.3a.4g.5g.,
1j.2a.3a.4g.5g., 1p.2a.3a.4g.5g., 1a.2b.3a.4g.5g., 1b.2b.3a.4g.5g.,
1f.2b.3a.4g.5g., 1h.2b.3a.4g.5g., 1j.2b.3a.4g.5g., 1p.2b.3a.4g.5g.,
1a.2e.3a.4g.5g., 1b.2e.3a.4g.5g., 1f.2e.3a.4g.5g., 1h.2e.3a.4g.5g.,
1j.2e.3a.4g.5g., 1p.2e.3a.4g.5g., 1a.2f.3a.4g.5g., 1b.2f.3a.4g.5g.,
1f.2f.3a.4g.5g., 1h.2f.3a.4g.5g., 1j.2f.3a.4g.5g., 1p.2f.3a.4g.5g.,
1a.2i.3a.4g.5g., 1b.2i.3a.4g.5g., 1f.2i.3a.4g.5g., 1h.2i.3a.4g.5g.,
1j.2i.3a.4g.5g., 1p.2i.3a.4g.5g., 1a.2m.3a.4g.5g., 1b.2m.3a.4g.5g.,
1f.2m.3a.4g.5g., 1h.2m.3a.4g.5g., 1j.2m.3a.4g.5g., 1p.2m.3a.4g.5g.,
1a.2o.3a.4g.5g., 1b.2o.3a.4g.5g., 1f.2o.3a.4g.5g., 1h.2o.3a.4g.5g.,
1j.2o.3a.4g.5g., 1p.2o.3a.4g.5g., 1a.2u.3a.4g.5g., 1b.2u.3a.4g.5g.,
1f.2u.3a.4g.5g., 1h.2u.3a.4g.5g., 1j.2u.3a.4g.5g., 1p.2u.3a.4g.5g.,
1a.2y.3a.4g.5g., 1b.2y.3a.4g.5g., 1f.2y.3a.4g.5g., 1h.2y.3a.4g.5g.,
1j.2y.3a.4g.5g., 1p.2y.3a.4g.5g., 1a.2a.3b.4g.5g., 1b.2a.3b.4g.5g.,
1f.2a.3b.4g.5g., 1h.2a.3b.4g.5g., 1j.2a.3b.4g.5g., 1p.2a.3b.4g.5g.,
1a.2b.3b.4g.5g., 1b.2b.3b.4g.5g., 1f.2b.3b.4g.5g., 1h.2b.3b.4g.5g.,
1j.2b.3b.4g.5g., 1p.2b.3b.4g.5g., 1a.2e.3b.4g.5g., 1b.2e.3b.4g.5g.,
1f.2e.3b.4g.5g., 1h.2e.3b.4g.5g., 1j.2e.3b.4g.5g., 1p.2e.3b.4g.5g.,
1a.2f.3b.4g.5g., 1b.2f.3b.4g.5g., 1f.2f.3b.4g.5g., 1h.2f.3b.4g.5g.,
1j.2f.3b.4g.5g., 1p.2f.3b.4g.5g., 1a.2i.3b.4g.5g., 1b.2i.3b.4g.5g.,
1f.2i.3b.4g.5g., 1h.2i.3b.4g.5g., 1j.2i.3b.4g.5g., 1p.2i.3b.4g.5g.,
1a.2m.3b.4g.5g., 1b.2m.3b.4g.5g., 1f.2m.3b.4g.5g., 1h.2m.3b.4g.5g.,
1j.2m.3b.4g.5g., 1p.2m.3b.4g.5g., 1a.2o.3b.4g.5g., 1b.2o.3b.4g.5g.,
1f.2o.3b.4g.5g., 1h.2o.3b.4g.5g., 1j.2o.3b.4g.5g., 1p.2o.3b.4g.5g.,
1a.2u.3b.4g.5g., 1b.2u.3b.4g.5g., 1f.2u.3b.4g.5g., 1h.2u.3b.4g.5g.,
1j.2u.3b.4g.5g., 1p.2u.3b.4g.5g., 1a.2y.3b.4g.5g., 1b.2y.3b.4g.5g.,
1f.2y.3b.4g.5g., 1h.2y.3b.4g.5g., 1j.2y.3b.4g.5g., 1p.2y.3b.4g.5g.,
1a.2a.3e.4g.5g., 1b.2a.3e.4g.5g., 1f.2a.3e.4g.5g., 1h.2a.3e.4g.5g.,
1j.2a.3e.4g.5g., 1p.2a.3e.4g.5g., 1a.2b.3e.4g.5g., 1b.2b.3e.4g.5g.,
1f.2b.3e.4g.5g., 1h.2b.3e.4g.5g., 1j.2b.3e.4g.5g., 1p.2b.3e.4g.5g.,
1a.2e.3e.4g.5g., 1b.2e.3e.4g.5g., 1f.2e.3e.4g.5g., 1h.2e.3e.4g.5g.,
1j.2e.3e.4g.5g., 1p.2e.3e.4g.5g., 1a.2f.3e.4g.5g., 1b.2f.3e.4g.5g.,
1f.2f.3e.4g.5g., 1h.2f.3e.4g.5g., 1j.2f.3e.4g.5g., 1p.2f.3e.4g.5g.,
1a.2i.3e.4g.5g., 1b.2i.3e.4g.5g., 1f.2i.3e.4g.5g., 1h.2i.3e.4g.5g.,
1j.2i.3e.4g.5g., 1p.2i.3e.4g.5g., 1a.2m.3e.4g.5g., 1b.2m.3e.4g.5g.,
1f.2m.3e.4g.5g., 1h.2m.3e.4g.5g., 1j.2m.3e.4g.5g., 1p.2m.3e.4g.5g.,
1a.2o.3e.4g.5g., 1b.2o.3e.4g.5g., 1f.2o.3e.4g.5g., 1h.2o.3e.4g.5g.,
1j.2o.3e.4g.5g., 1p.2o.3e.4g.5g., 1a.2u.3e.4g.5g., 1b.2u.3e.4g.5g.,
1f.2u.3e.4g.5g., 1h.2u.3e.4g.5g., 1j.2u.3e.4g.5g., 1p.2u.3e.4g.5g.,
1a.2y.3e.4g.5g., 1b.2y.3e.4g.5g., 1f.2y.3e.4g.5g., 1h.2y.3e.4g.5g.,
1j.2y.3e.4g.5g., 1p.2y.3e.4g.5g., 1a.2a.3g.4g.5g., 1b.2a.3g.4g.5g.,
1f.2a.3g.4g.5g., 1h.2a.3g.4g.5g., 1j.2a.3g.4g.5g., 1p.2a.3g.4g.5g.,
1a.2b.3g.4g.5g., 1b.2b.3g.4g.5g., 1f.2b.3g.4g.5g., 1h.2b.3g.4g.5g.,
1j.2b.3g.4g.5g., 1p.2b.3g.4g.5g., 1a.2e.3g.4g.5g., 1b.2e.3g.4g.5g.,
1f.2e.3g.4g.5g., 1h.2e.3g.4g.5g., 1j.2e.3g.4g.5g., 1p.2e.3g.4g.5g.,
1a.2f.3g.4g.5g., 1b.2f.3g.4g.5g., 1f.2f.3g.4g.5g., 1h.2f.3g.4g.5g.,
1j.2f.3g.4g.5g., 1p.2f.3g.4g.5g., 1a.2i.3g.4g.5g., 1b.2i.3g.4g.5g.,
1f.2i.3g.4g.5g., 1h.2i.3g.4g.5g., 1j.2i.3g.4g.5g., 1p.2i.3g.4g.5g.,
1a.2m.3g.4g.5g., 1b.2m.3g.4g.5g., 1f.2m.3g.4g.5g., 1h.2m.3g.4g.5g.,
1j.2m.3g.4g.5g., 1p.2m.3g.4g.5g., 1a.2o.3g.4g.5g., 1b.2o.3g.4g.5g.,
1f.2o.3g.4g.5g., 1h.2o.3g.4g.5g., 1j.2o.3g.4g.5g., 1p.2o.3g.4g.5g.,
1a.2u.3g.4g.5g., 1b.2u.3g.4g.5g., 1f.2u.3g.4g.5g., 1h.2u.3g.4g.5g.,
1j.2u.3g.4g.5g., 1p.2u.3g.4g.5g., 1a.2y.3g.4g.5g., 1b.2y.3g.4g.5g.,
1f.2y.3g.4g.5g., 1h.2y.3g.4g.5g., 1j.2y.3g.4g.5g., 1p.2y.3g.4g.5g.,
1a.2a.3a.4h.5g., 1b.2a.3a.4h.5g., 1f.2a.3a.4h.5g., 1h.2a.3a.4h.5g.,
1j.2a.3a.4h.5g., 1p.2a.3a.4h.5g., 1a.2b.3a.4h.5g., 1b.2b.3a.4h.5g.,
1f.2b.3a.4h.5g., 1h.2b.3a.4h.5g., 1j.2b.3a.4h.5g., 1p.2b.3a.4h.5g.,
1a.2e.3a.4h.5g., 1b.2e.3a.4h.5g., 1f.2e.3a.4h.5g., 1h.2e.3a.4h.5g.,
1j.2e.3a.4h.5g., 1p.2e.3a.4h.5g., 1a.2f.3a.4h.5g., 1b.2f.3a.4h.5g.,
1f.2f.3a.4h.5g., 1h.2f.3a.4h.5g., 1j.2f.3a.4h.5g., 1p.2f.3a.4h.5g.,
1a.2i.3a.4h.5g., 1b.2i.3a.4h.5g., 1f.2i.3a.4h.5g., 1h.2i.3a.4h.5g.,
1j.2i.3a.4h.5g., 1p.2i.3a.4h.5g., 1a.2m.3a.4h.5g., 1b.2m.3a.4h.5g.,
1f.2m.3a.4h.5g., 1h.2m.3a.4h.5g., 1j.2m.3a.4h.5g., 1p.2m.3a.4h.5g.,
1a.2o.3a.4h.5g., 1b.2o.3a.4h.5g., 1f.2o.3a.4h.5g., 1h.2o.3a.4h.5g.,
1j.2o.3a.4h.5g., 1p.2o.3a.4h.5g., 1a.2u.3a.4h.5g., 1b.2u.3a.4h.5g.,
1f.2u.3a.4h.5g., 1h.2u.3a.4h.5g., 1j.2u.3a.4h.5g., 1p.2u.3a.4h.5g.,
1a.2y.3a.4h.5g., 1b.2y.3a.4h.5g., 1f.2y.3a.4h.5g., 1h.2y.3a.4h.5g.,
1j.2y.3a.4h.5g., 1p.2y.3a.4h.5g., 1a.2a.3b.4h.5g., 1b.2a.3b.4h.5g.,
1f.2a.3b.4h.5g., 1h.2a.3b.4h.5g., 1j.2a.3b.4h.5g., 1p.2a.3b.4h.5g.,
1a.2b.3b.4h.5g., 1b.2b.3b.4h.5g., 1f.2b.3b.4h.5g., 1h.2b.3b.4h.5g.,
1j.2b.3b.4h.5g., 1p.2b.3b.4h.5g., 1a.2e.3b.4h.5g., 1b.2e.3b.4h.5g.,
1f.2e.3b.4h.5g., 1h.2e.3b.4h.5g., 1j.2e.3b.4h.5g., 1p.2e.3b.4h.5g.,
1a.2f.3b.4h.5g., 1b.2f.3b.4h.5g., 1f.2f.3b.4h.5g., 1h.2f.3b.4h.5g.,
1j.2f.3b.4h.5g., 1p.2f.3b.4h.5g., 1a.2i.3b.4h.5g., 1b.2i.3b.4h.5g.,
1f.2i.3b.4h.5g., 1h.2i.3b.4h.5g., 1j.2i.3b.4h.5g., 1p.2i.3b.4h.5g.,
1a.2m.3b.4h.5g., 1b.2m.3b.4h.5g., 1f.2m.3b.4h.5g., 1h.2m.3b.4h.5g.,
1j.2m.3b.4h.5g., 1p.2m.3b.4h.5g., 1a.2o.3b.4h.5g., 1b.2o.3b.4h.5g.,
1f.2o.3b.4h.5g., 1h.2o.3b.4h.5g., 1j.2o.3b.4h.5g., 1p.2o.3b.4h.5g.,
1a.2u.3b.4h.5g., 1b.2u.3b.4h.5g., 1f.2u.3b.4h.5g., 1h.2u.3b.4h.5g.,
1j.2u.3b.4h.5g., 1p.2u.3b.4h.5g., 1a.2y.3b.4h.5g., 1b.2y.3b.4h.5g.,
1f.2y.3b.4h.5g., 1h.2y.3b.4h.5g., 1j.2y.3b.4h.5g., 1p.2y.3b.4h.5g.,
1a.2a.3e.4h.5g., 1b.2a.3e.4h.5g., 1f.2a.3e.4h.5g., 1h.2a.3e.4h.5g.,
1j.2a.3e.4h.5g., 1p.2a.3e.4h.5g., 1a.2b.3e.4h.5g., 1b.2b.3e.4h.5g.,
1f.2b.3e.4h.5g., 1h.2b.3e.4h.5g., 1j.2b.3e.4h.5g., 1p.2b.3e.4h.5g.,
1a.2e.3e.4h.5g., 1b.2e.3e.4h.5g., 1f.2e.3e.4h.5g., 1h.2e.3e.4h.5g.,
1j.2e.3e.4h.5g., 1p.2e.3e.4h.5g., 1a.2f.3e.4h.5g., 1b.2f.3e.4h.5g.,
1f.2f.3e.4h.5g., 1h.2f.3e.4h.5g., 1j.2f.3e.4h.5g., 1p.2f.3e.4h.5g.,
1a.2i.3e.4h.5g., 1b.2i.3e.4h.5g., 1f.2i.3e.4h.5g., 1h.2i.3e.4h.5g.,
1j.2i.3e.4h.5g., 1p.2i.3e.4h.5g., 1a.2m.3e.4h.5g., 1b.2m.3e.4h.5g.,
1f.2m.3e.4h.5g., 1h.2m.3e.4h.5g., 1j.2m.3e.4h.5g., 1p.2m.3e.4h.5g.,
1a.2o.3e.4h.5g., 1b.2o.3e.4h.5g., 1f.2o.3e.4h.5g., 1h.2o.3e.4h.5g.,
1j.2o.3e.4h.5g., 1p.2o.3e.4h.5g., 1a.2u.3e.4h.5g., 1b.2u.3e.4h.5g.,
1f.2u.3e.4h.5g., 1h.2u.3e.4h.5g., 1j.2u.3e.4h.5g., 1p.2u.3e.4h.5g.,
1a.2y.3e.4h.5g., 1b.2y.3e.4h.5g., 1f.2y.3e.4h.5g., 1h.2y.3e.4h.5g.,
1j.2y.3e.4h.5g., 1p.2y.3e.4h.5g., 1a.2a.3g.4h.5g., 1b.2a.3g.4h.5g.,
1f.2a.3g.4h.5g., 1h.2a.3g.4h.5g., 1j.2a.3g.4h.5g., 1p.2a.3g.4h.5g.,
1a.2b.3g.4h.5g., 1b.2b.3g.4h.5g., 1f.2b.3g.4h.5g., 1h.2b.3g.4h.5g.,
1j.2b.3g.4h.5g., 1p.2b.3g.4h.5g., 1a.2e.3g.4h.5g., 1b.2e.3g.4h.5g.,
1f.2e.3g.4h.5g., 1h.2e.3g.4h.5g., 1j.2e.3g.4h.5g., 1p.2e.3g.4h.5g.,
1a.2f.3g.4h.5g., 1b.2f.3g.4h.5g., 1f.2f.3g.4h.5g., 1h.2f.3g.4h.5g.,
1j.2f.3g.4h.5g., 1p.2f.3g.4h.5g., 1a.2i.3g.4h.5g., 1b.2i.3g.4h.5g.,
1f.2i.3g.4h.5g., 1h.2i.3g.4h.5g., 1j.2i.3g.4h.5g., 1p.2i.3g.4h.5g.,
1a.2m.3g.4h.5g., 1b.2m.3g.4h.5g., 1f.2m.3g.4h.5g., 1h.2m.3g.4h.5g.,
1j.2m.3g.4h.5g., 1p.2m.3g.4h.5g., 1a.2o.3g.4h.5g., 1b.2o.3g.4h.5g.,
1f.2o.3g.4h.5g., 1h.2o.3g.4h.5g., 1j.2o.3g.4h.5g., 1p.2o.3g.4h.5g.,
1a.2u.3g.4h.5g., 1b.2u.3g.4h.5g., 1f.2u.3g.4h.5g., 1h.2u.3g.4h.5g.,
1j.2u.3g.4h.5g., 1p.2u.3g.4h.5g., 1a.2y.3g.4h.5g., 1b.2y.3g.4h.5g.,
1f.2y.3g.4h.5g., 1h.2y.3g.4h.5g., 1j.2y.3g.4h.5g., 1p.2y.3g.4h.5g.,
1a.2a.3a.4i.5g., 1b.2a.3a.4i.5g., 1f.2a.3a.4i.5g., 1h.2a.3a.4i.5g.,
1j.2a.3a.4i.5g., 1p.2a.3a.4i.5g., 1a.2b.3a.4i.5g., 1b.2b.3a.4i.5g.,
1f.2b.3a.4i.5g., 1h.2b.3a.4i.5g., 1j.2b.3a.4i.5g., 1p.2b.3a.4i.5g.,
1a.2e.3a.4i.5g., 1b.2e.3a.4i.5g., 1f.2e.3a.4i.5g., 1h.2e.3a.4i.5g.,
1j.2e.3a.4i.5g., 1p.2e.3a.4i.5g., 1a.2f.3a.4i.5g., 1b.2f.3a.4i.5g.,
1f.2f.3a.4i.5g., 1h.2f.3a.4i.5g., 1j.2f.3a.4i.5g., 1p.2f.3a.4i.5g.,
1a.2i.3a.4i.5g., 1b.2i.3a.4i.5g., 1f.2i.3a.4i.5g., 1h.2i.3a.4i.5g.,
1j.2i.3a.4i.5g., 1p.2i.3a.4i.5g., 1a.2m.3a.4i.5g., 1b.2m.3a.4i.5g.,
1f.2m.3a.4i.5g., 1h.2m.3a.4i.5g., 1j.2m.3a.4i.5g., 1p.2m.3a.4i.5g.,
1a.2o.3a.4i.5g., 1b.2o.3a.4i.5g., 1f.2o.3a.4i.5g., 1h.2o.3a.4i.5g.,
1j.2o.3a.4i.5g., 1p.2o.3a.4i.5g., 1a.2u.3a.4i.5g., 1b.2u.3a.4i.5g.,
1f.2u.3a.4i.5g., 1h.2u.3a.4i.5g., 1j.2u.3a.4i.5g., 1p.2u.3a.4i.5g.,
1a.2y.3a.4i.5g., 1b.2y.3a.4i.5g., 1f.2y.3a.4i.5g., 1h.2y.3a.4i.5g.,
1j.2y.3a.4i.5g., 1p.2y.3a.4i.5g., 1a.2a.3b.4i.5g., 1b.2a.3b.4i.5g.,
1f.2a.3b.4i.5g., 1h.2a.3b.4i.5g., 1j.2a.3b.4i.5g., 1p.2a.3b.4i.5g.,
1a.2b.3b.4i.5g., 1b.2b.3b.4i.5g., 1f.2b.3b.4i.5g., 1h.2b.3b.4i.5g.,
1j.2b.3b.4i.5g., 1p.2b.3b.4i.5g., 1a.2e.3b.4i.5g., 1b.2e.3b.4i.5g.,
1f.2e.3b.4i.5g., 1h.2e.3b.4i.5g., 1j.2e.3b.4i.5g., 1p.2e.3b.4i.5g.,
1a.2f.3b.4i.5g., 1b.2f.3b.4i.5g., 1f.2f.3b.4i.5g., 1h.2f.3b.4i.5g.,
1j.2f.3b.4i.5g., 1p.2f.3b.4i.5g., 1a.2i.3b.4i.5g., 1b.2i.3b.4i.5g.,
1f.2i.3b.4i.5g., 1h.2i.3b.4i.5g., 1j.2i.3b.4i.5g., 1p.2i.3b.4i.5g.,
1a.2m.3b.4i.5g., 1b.2m.3b.4i.5g., 1f.2m.3b.4i.5g., 1h.2m.3b.4i.5g.,
1j.2m.3b.4i.5g., 1p.2m.3b.4i.5g., 1a.2o.3b.4i.5g., 1b.2o.3b.4i.5g.,
1f.2o.3b.4i.5g., 1h.2o.3b.4i.5g., 1j.2o.3b.4i.5g., 1p.2o.3b.4i.5g.,
1a.2u.3b.4i.5g., 1b.2u.3b.4i.5g., 1f.2u.3b.4i.5g., 1h.2u.3b.4i.5g.,
1j.2u.3b.4i.5g., 1p.2u.3b.4i.5g., 1a.2y.3b.4i.5g., 1b.2y.3b.4i.5g.,
1f.2y.3b.4i.5g., 1h.2y.3b.4i.5g., 1j.2y.3b.4i.5g., 1p.2y.3b.4i.5g.,
1a.2a.3e.4i.5g., 1b.2a.3e.4i.5g., 1f.2a.3e.4i.5g., 1h.2a.3e.4i.5g.,
1j.2a.3e.4i.5g., 1p.2a.3e.4i.5g., 1a.2b.3e.4i.5g., 1b.2b.3e.4i.5g.,
1f.2b.3e.4i.5g., 1h.2b.3e.4i.5g., 1j.2b.3e.4i.5g., 1p.2b.3e.4i.5g.,
1a.2e.3e.4i.5g., 1b.2e.3e.4i.5g., 1f.2e.3e.4i.5g., 1h.2e.3e.4i.5g.,
1j.2e.3e.4i.5g., 1p.2e.3e.4i.5g., 1a.2f.3e.4i.5g., 1b.2f.3e.4i.5g.,
1f.2f.3e.4i.5g., 1h.2f.3e.4i.5g., 1j.2f.3e.4i.5g., 1p.2f.3e.4i.5g.,
1a.2i.3e.4i.5g., 1b.2i.3e.4i.5g., 1f.2i.3e.4i.5g., 1h.2i.3e.4i.5g.,
1j.2i.3e.4i.5g., 1p.2i.3e.4i.5g., 1a.2m.3e.4i.5g., 1b.2m.3e.4i.5g.,
1f.2m.3e.4i.5g., 1h.2m.3e.4i.5g., 1j.2m.3e.4i.5g., 1p.2m.3e.4i.5g.,
1a.2o.3e.4i.5g., 1b.2o.3e.4i.5g., 1f.2o.3e.4i.5g., 1h.2o.3e.4i.5g.,
1j.2o.3e.4i.5g., 1p.2o.3e.4i.5g., 1a.2u.3e.4i.5g., 1b.2u.3e.4i.5g.,
1f.2u.3e.4i.5g., 1h.2u.3e.4i.5g., 1j.2u.3e.4i.5g., 1p.2u.3e.4i.5g.,
1a.2y.3e.4i.5g., 1b.2y.3e.4i.5g., 1f.2y.3e.4i.5g., 1h.2y.3e.4i.5g.,
1j.2y.3e.4i.5g., 1p.2y.3e.4i.5g., 1a.2a.3g.4i.5g., 1b.2a.3g.4i.5g.,
1f.2a.3g.4i.5g., 1h.2a.3g.4i.5g., 1j.2a.3g.4i.5g., 1p.2a.3g.4i.5g.,

TABLE 12-continued

List of Compound Structures of Formula III 1a.2b.3g.4i.5g., 1b.2b.3g.4i.5g., 1f.2b.3g.4i.5g., 1h.2b.3g.4i.5g.,
1j.2b.3g.4i.5g., 1p.2b.3g.4i.5g., 1a.2e.3g.4i.5g., 1b.2e.3g.4i.5g.,
1f.2e.3g.4i.5g., 1h.2e.3g.4i.5g., 1j.2e.3g.4i.5g., 1p.2e.3g.4i.5g.,
1a.2f.3g.4i.5g., 1b.2f.3g.4i.5g., 1f.2f.3g.4i.5g., 1h.2f.3g.4i.5g.,
1j.2f.3g.4i.5g., 1p.2f.3g.4i.5g., 1a.2i.3g.4i.5g., 1b.2i.3g.4i.5g.,
1f.2i.3g.4i.5g., 1h.2i.3g.4i.5g., 1j.2i.3g.4i.5g., 1p.2i.3g.4i.5g.,
1a.2m.3g.4i.5g., 1b.2m.3g.4i.5g., 1f.2m.3g.4i.5g., 1h.2m.3g.4i.5g.,
1j.2m.3g.4i.5g., 1p.2m.3g.4i.5g., 1a.2o.3g.4i.5g., 1b.2o.3g.4i.5g.,
1f.2o.3g.4i.5g., 1h.2o.3g.4i.5g., 1j.2o.3g.4i.5g., 1p.2o.3g.4i.5g.,
1a.2u.3g.4i.5g., 1b.2u.3g.4i.5g., 1f.2u.3g.4i.5g., 1h.2u.3g.4i.5g.,
1j.2u.3g.4i.5g., 1p.2u.3g.4i.5g., 1a.2y.3g.4i.5g., 1b.2y.3g.4i.5g.,
1f.2y.3g.4i.5g., 1h.2y.3g.4i.5g., 1j.2y.3g.4i.5g., 1p.2y.3g.4i.5g.,
1a.2a.3a.4a.5h., 1b.2a.3a.4a.5h., 1f.2a.3a.4a.5h., 1h.2a.3a.4a.5h.,
1j.2a.3a.4a.5h., 1p.2a.3a.4a.5h., 1a.2b.3a.4a.5h., 1b.2b.3a.4a.5h.,
1f.2b.3a.4a.5h., 1h.2b.3a.4a.5h., 1j.2b.3a.4a.5h., 1p.2b.3a.4a.5h.,
1a.2e.3a.4a.5h., 1b.2e.3a.4a.5h., 1f.2e.3a.4a.5h., 1h.2e.3a.4a.5h.,
1j.2e.3a.4a.5h., 1p.2e.3a.4a.5h., 1a.2f.3a.4a.5h., 1b.2f.3a.4a.5h.,
1f.2f.3a.4a.5h., 1h.2f.3a.4a.5h., 1j.2f.3a.4a.5h., 1p.2f.3a.4a.5h.,
1a.2i.3a.4a.5h., 1b.2i.3a.4a.5h., 1f.2i.3a.4a.5h., 1h.2i.3a.4a.5h.,
1j.2i.3a.4a.5h., 1p.2i.3a.4a.5h., 1a.2m.3a.4a.5h., 1b.2m.3a.4a.5h.,
1f.2m.3a.4a.5h., 1h.2m.3a.4a.5h., 1j.2m.3a.4a.5h., 1p.2m.3a.4a.5h.,
1a.2o.3a.4a.5h., 1b.2o.3a.4a.5h., 1f.2o.3a.4a.5h., 1h.2o.3a.4a.5h.,
1j.2o.3a.4a.5h., 1p.2o.3a.4a.5h., 1a.2u.3a.4a.5h., 1b.2u.3a.4a.5h.,
1f.2u.3a.4a.5h., 1h.2u.3a.4a.5h., 1j.2u.3a.4a.5h., 1p.2u.3a.4a.5h.,
1a.2y.3a.4a.5h., 1b.2y.3a.4a.5h., 1f.2y.3a.4a.5h., 1h.2y.3a.4a.5h.,
1j.2y.3a.4a.5h., 1p.2y.3a.4a.5h., 1a.2a.3b.4a.5h., 1b.2a.3b.4a.5h.,
1f.2a.3b.4a.5h., 1h.2a.3b.4a.5h., 1j.2a.3b.4a.5h., 1p.2a.3b.4a.5h.,
1a.2b.3b.4a.5h., 1b.2b.3b.4a.5h., 1f.2b.3b.4a.5h., 1h.2b.3b.4a.5h.,
1j.2b.3b.4a.5h., 1p.2b.3b.4a.5h., 1a.2e.3b.4a.5h., 1b.2e.3b.4a.5h.,
1f.2e.3b.4a.5h., 1h.2e.3b.4a.5h., 1j.2e.3b.4a.5h., 1p.2e.3b.4a.5h.,
1a.2f.3b.4a.5h., 1b.2f.3b.4a.5h., 1f.2f.3b.4a.5h., 1h.2f.3b.4a.5h.,
1j.2f.3b.4a.5h., 1p.2f.3b.4a.5h., 1a.2i.3b.4a.5h., 1b.2i.3b.4a.5h.,
1f.2i.3b.4a.5h., 1h.2i.3b.4a.5h., 1j.2i.3b.4a.5h., 1p.2i.3b.4a.5h.,
1a.2m.3b.4a.5h., 1b.2m.3b.4a.5h., 1f.2m.3b.4a.5h., 1h.2m.3b.4a.5h.,
1j.2m.3b.4a.5h., 1p.2m.3b.4a.5h., 1a.2o.3b.4a.5h., 1b.2o.3b.4a.5h.,
1f.2o.3b.4a.5h., 1h.2o.3b.4a.5h., 1j.2o.3b.4a.5h., 1p.2o.3b.4a.5h.,
1a.2u.3b.4a.5h., 1b.2u.3b.4a.5h., 1f.2u.3b.4a.5h., 1h.2u.3b.4a.5h.,
1j.2u.3b.4a.5h., 1p.2u.3b.4a.5h., 1a.2y.3b.4a.5h., 1b.2y.3b.4a.5h.,
1f.2y.3b.4a.5h., 1h.2y.3b.4a.5h., 1j.2y.3b.4a.5h., 1p.2y.3b.4a.5h.,
1a.2a.3e.4a.5h., 1b.2a.3e.4a.5h., 1f.2a.3e.4a.5h., 1h.2a.3e.4a.5h.,
1j.2a.3e.4a.5h., 1p.2a.3e.4a.5h., 1a.2b.3e.4a.5h., 1b.2b.3e.4a.5h.,
1f.2b.3e.4a.5h., 1h.2b.3e.4a.5h., 1j.2b.3e.4a.5h., 1p.2b.3e.4a.5h.,
1a.2e.3e.4a.5h., 1b.2e.3e.4a.5h., 1f.2e.3e.4a.5h., 1h.2e.3e.4a.5h.,
1j.2e.3e.4a.5h., 1p.2e.3e.4a.5h., 1a.2f.3e.4a.5h., 1b.2f.3e.4a.5h.,
1f.2f.3e.4a.5h., 1h.2f.3e.4a.5h., 1j.2f.3e.4a.5h., 1p.2f.3e.4a.5h.,
1a.2i.3e.4a.5h., 1b.2i.3e.4a.5h., 1f.2i.3e.4a.5h., 1h.2i.3e.4a.5h.,
1j.2i.3e.4a.5h., 1p.2i.3e.4a.5h., 1a.2m.3e.4a.5h., 1b.2m.3e.4a.5h.,
1f.2m.3e.4a.5h., 1h.2m.3e.4a.5h., 1j.2m.3e.4a.5h., 1p.2m.3e.4a.5h.,
1a.2o.3e.4a.5h., 1b.2o.3e.4a.5h., 1f.2o.3e.4a.5h., 1h.2o.3e.4a.5h.,
1j.2o.3e.4a.5h., 1p.2o.3e.4a.5h., 1a.2u.3e.4a.5h., 1b.2u.3e.4a.5h.,
1f.2u.3e.4a.5h., 1h.2u.3e.4a.5h., 1j.2u.3e.4a.5h., 1p.2u.3e.4a.5h.,
1a.2y.3e.4a.5h., 1b.2y.3e.4a.5h., 1f.2y.3e.4a.5h., 1h.2y.3e.4a.5h.,
1j.2y.3e.4a.5h., 1p.2y.3e.4a.5h., 1a.2a.3g.4a.5h., 1b.2a.3g.4a.5h.,
1f.2a.3g.4a.5h., 1h.2a.3g.4a.5h., 1j.2a.3g.4a.5h., 1p.2a.3g.4a.5h.,
1a.2b.3g.4a.5h., 1b.2b.3g.4a.5h., 1f.2b.3g.4a.5h., 1h.2b.3g.4a.5h.,
1j.2b.3g.4a.5h., 1p.2b.3g.4a.5h., 1a.2e.3g.4a.5h., 1b.2e.3g.4a.5h.,
1f.2e.3g.4a.5h., 1h.2e.3g.4a.5h., 1j.2e.3g.4a.5h., 1p.2e.3g.4a.5h.,
1a.2f.3g.4a.5h., 1b.2f.3g.4a.5h., 1f.2f.3g.4a.5h., 1h.2f.3g.4a.5h.,
1j.2f.3g.4a.5h., 1p.2f.3g.4a.5h., 1a.2i.3g.4a.5h., 1b.2i.3g.4a.5h.,
1f.2i.3g.4a.5h., 1h.2i.3g.4a.5h., 1j.2i.3g.4a.5h., 1p.2i.3g.4a.5h.,
1a.2m.3g.4a.5h., 1b.2m.3g.4a.5h., 1f.2m.3g.4a.5h., 1h.2m.3g.4a.5h.,
1j.2m.3g.4a.5h., 1p.2m.3g.4a.5h., 1a.2o.3g.4a.5h., 1b.2o.3g.4a.5h.,
1f.2o.3g.4a.5h., 1h.2o.3g.4a.5h., 1j.2o.3g.4a.5h., 1p.2o.3g.4a.5h.,
1a.2u.3g.4a.5h., 1b.2u.3g.4a.5h., 1f.2u.3g.4a.5h., 1h.2u.3g.4a.5h.,
1j.2u.3g.4a.5h., 1p.2u.3g.4a.5h., 1a.2y.3g.4a.5h., 1b.2y.3g.4a.5h.,
1f.2y.3g.4a.5h., 1h.2y.3g.4a.5h., 1j.2y.3g.4a.5h., 1p.2y.3g.4a.5h.,
1a.2a.3a.4d.5h., 1b.2a.3a.4d.5h., 1f.2a.3a.4d.5h., 1h.2a.3a.4d.5h.,
1j.2a.3a.4d.5h., 1p.2a.3a.4d.5h., 1a.2b.3a.4d.5h., 1b.2b.3a.4d.5h.,
1f.2b.3a.4d.5h., 1h.2b.3a.4d.5h., 1j.2b.3a.4d.5h., 1p.2b.3a.4d.5h.,
1a.2e.3a.4d.5h., 1b.2e.3a.4d.5h., 1f.2e.3a.4d.5h., 1h.2e.3a.4d.5h.,
1j.2e.3a.4d.5h., 1p.2e.3a.4d.5h., 1a.2f.3a.4d.5h., 1b.2f.3a.4d.5h.,
1f.2f.3a.4d.5h., 1h.2f.3a.4d.5h., 1j.2f.3a.4d.5h., 1p.2f.3a.4d.5h.,
1a.2i.3a.4d.5h., 1b.2i.3a.4d.5h., 1f.2i.3a.4d.5h., 1h.2i.3a.4d.5h.,
1j.2i.3a.4d.5h., 1p.2i.3a.4d.5h., 1a.2m.3a.4d.5h., 1b.2m.3a.4d.5h.,
1f.2m.3a.4d.5h., 1h.2m.3a.4d.5h., 1j.2m.3a.4d.5h., 1p.2m.3a.4d.5h.,
1a.2o.3a.4d.5h., 1b.2o.3a.4d.5h., 1f.2o.3a.4d.5h., 1h.2o.3a.4d.5h.,
1j.2o.3a.4d.5h., 1p.2o.3a.4d.5h., 1a.2u.3a.4d.5h., 1b.2u.3a.4d.5h.,
1f.2u.3a.4d.5h., 1h.2u.3a.4d.5h., 1j.2u.3a.4d.5h., 1p.2u.3a.4d.5h.,
1a.2y.3a.4d.5h., 1b.2y.3a.4d.5h., 1f.2y.3a.4d.5h., 1h.2y.3a.4d.5h.,
1j.2y.3a.4d.5h., 1p.2y.3a.4d.5h., 1a.2a.3b.4d.5h., 1b.2a.3b.4d.5h.,
1f.2a.3b.4d.5h., 1h.2a.3b.4d.5h., 1j.2a.3b.4d.5h., 1p.2a.3b.4d.5h.,
1a.2b.3b.4d.5h., 1b.2b.3b.4d.5h., 1f.2b.3b.4d.5h., 1h.2b.3b.4d.5h.,
1j.2b.3b.4d.5h., 1p.2b.3b.4d.5h., 1a.2e.3b.4d.5h., 1b.2e.3b.4d.5h.,
1f.2e.3b.4d.5h., 1h.2e.3b.4d.5h., 1j.2e.3b.4d.5h., 1p.2e.3b.4d.5h.,
1a.2f.3b.4d.5h., 1b.2f.3b.4d.5h., 1f.2f.3b.4d.5h., 1h.2f.3b.4d.5h.,
1j.2f.3b.4d.5h., 1p.2f.3b.4d.5h., 1a.2i.3b.4d.5h., 1b.2i.3b.4d.5h.,
1f.2i.3b.4d.5h., 1h.2i.3b.4d.5h., 1j.2i.3b.4d.5h., 1p.2i.3b.4d.5h.,
1a.2m.3b.4d.5h., 1b.2m.3b.4d.5h., 1f.2m.3b.4d.5h., 1h.2m.3b.4d.5h.,
1j.2m.3b.4d.5h., 1p.2m.3b.4d.5h., 1a.2o.3b.4d.5h., 1b.2o.3b.4d.5h.,
1f.2o.3b.4d.5h., 1h.2o.3b.4d.5h., 1j.2o.3b.4d.5h., 1p.2o.3b.4d.5h.,
1a.2u.3b.4d.5h., 1b.2u.3b.4d.5h., 1f.2u.3b.4d.5h., 1h.2u.3b.4d.5h.,
1j.2u.3b.4d.5h., 1p.2u.3b.4d.5h., 1a.2y.3b.4d.5h., 1b.2y.3b.4d.5h.,
1f.2y.3b.4d.5h., 1h.2y.3b.4d.5h., 1j.2y.3b.4d.5h., 1p.2y.3b.4d.5h.,
1a.2a.3e.4d.5h., 1b.2a.3e.4d.5h., 1f.2a.3e.4d.5h., 1h.2a.3e.4d.5h.,
1j.2a.3e.4d.5h., 1p.2a.3e.4d.5h., 1a.2b.3e.4d.5h., 1b.2b.3e.4d.5h.,
1f.2b.3e.4d.5h., 1h.2b.3e.4d.5h., 1j.2b.3e.4d.5h., 1p.2b.3e.4d.5h.,
1a.2e.3e.4d.5h., 1b.2e.3e.4d.5h., 1f.2e.3e.4d.5h., 1h.2e.3e.4d.5h.,
1j.2e.3e.4d.5h., 1p.2e.3e.4d.5h., 1a.2f.3e.4d.5h., 1b.2f.3e.4d.5h.,
1f.2f.3e.4d.5h., 1h.2f.3e.4d.5h., 1j.2f.3e.4d.5h., 1p.2f.3e.4d.5h.,
1a.2i.3e.4d.5h., 1b.2i.3e.4d.5h., 1f.2i.3e.4d.5h., 1h.2i.3e.4d.5h.,
1j.2i.3e.4d.5h., 1p.2i.3e.4d.5h., 1a.2m.3e.4d.5h., 1b.2m.3e.4d.5h.,
1f.2m.3e.4d.5h., 1h.2m.3e.4d.5h., 1j.2m.3e.4d.5h., 1p.2m.3e.4d.5h.,
1a.2o.3e.4d.5h., 1b.2o.3e.4d.5h., 1f.2o.3e.4d.5h., 1h.2o.3e.4d.5h.,
1j.2o.3e.4d.5h., 1p.2o.3e.4d.5h., 1a.2u.3e.4d.5h., 1b.2u.3e.4d.5h.,
1f.2u.3e.4d.5h., 1h.2u.3e.4d.5h., 1j.2u.3e.4d.5h., 1p.2u.3e.4d.5h.,
1a.2y.3e.4d.5h., 1b.2y.3e.4d.5h., 1f.2y.3e.4d.5h., 1h.2y.3e.4d.5h.,
1j.2y.3e.4d.5h., 1p.2y.3e.4d.5h., 1a.2a.3g.4d.5h., 1b.2a.3g.4d.5h.,
1f.2a.3g.4d.5h., 1h.2a.3g.4d.5h., 1j.2a.3g.4d.5h., 1p.2a.3g.4d.5h.,
1a.2b.3g.4d.5h., 1b.2b.3g.4d.5h., 1f.2b.3g.4d.5h., 1h.2b.3g.4d.5h.,
1j.2b.3g.4d.5h., 1p.2b.3g.4d.5h., 1a.2e.3g.4d.5h., 1b.2e.3g.4d.5h.,
1f.2e.3g.4d.5h., 1h.2e.3g.4d.5h., 1j.2e.3g.4d.5h., 1p.2e.3g.4d.5h.,
1a.2f.3g.4d.5h., 1b.2f.3g.4d.5h., 1f.2f.3g.4d.5h., 1h.2f.3g.4d.5h.,
1j.2f.3g.4d.5h., 1p.2f.3g.4d.5h., 1a.2i.3g.4d.5h., 1b.2i.3g.4d.5h.,
1f.2i.3g.4d.5h., 1h.2i.3g.4d.5h., 1j.2i.3g.4d.5h., 1p.2i.3g.4d.5h.,
1a.2m.3g.4d.5h., 1b.2m.3g.4d.5h., 1f.2m.3g.4d.5h., 1h.2m.3g.4d.5h.,
1j.2m.3g.4d.5h., 1p.2m.3g.4d.5h., 1a.2o.3g.4d.5h., 1b.2o.3g.4d.5h.,
1f.2o.3g.4d.5h., 1h.2o.3g.4d.5h., 1j.2o.3g.4d.5h., 1p.2o.3g.4d.5h.,
1a.2u.3g.4d.5h., 1b.2u.3g.4d.5h., 1f.2u.3g.4d.5h., 1h.2u.3g.4d.5h.,
1j.2u.3g.4d.5h., 1p.2u.3g.4d.5h., 1a.2y.3g.4d.5h., 1b.2y.3g.4d.5h.,
1f.2y.3g.4d.5h., 1h.2y.3g.4d.5h., 1j.2y.3g.4d.5h., 1p.2y.3g.4d.5h.,
1a.2a.3a.4f.5h., 1b.2a.3a.4f.5h., 1f.2a.3a.4f.5h., 1h.2a.3a.4f.5h.,
1j.2a.3a.4f.5h., 1p.2a.3a.4f.5h., 1a.2b.3a.4f.5h., 1b.2b.3a.4f.5h.,
1f.2b.3a.4f.5h., 1h.2b.3a.4f.5h., 1j.2b.3a.4f.5h., 1p.2b.3a.4f.5h.,
1a.2e.3a.4f.5h., 1b.2e.3a.4f.5h., 1f.2e.3a.4f.5h., 1h.2e.3a.4f.5h.,
1j.2e.3a.4f.5h., 1p.2e.3a.4f.5h., 1a.2f.3a.4f.5h., 1b.2f.3a.4f.5h.,
1f.2f.3a.4f.5h., 1h.2f.3a.4f.5h., 1j.2f.3a.4f.5h., 1p.2f.3a.4f.5h.,
1a.2i.3a.4f.5h., 1b.2i.3a.4f.5h., 1f.2i.3a.4f.5h., 1h.2i.3a.4f.5h.,
1j.2i.3a.4f.5h., 1p.2i.3a.4f.5h., 1a.2m.3a.4f.5h., 1b.2m.3a.4f.5h.,
1f.2m.3a.4f.5h., 1h.2m.3a.4f.5h., 1j.2m.3a.4f.5h., 1p.2m.3a.4f.5h.,
1a.2o.3a.4f.5h., 1b.2o.3a.4f.5h., 1f.2o.3a.4f.5h., 1h.2o.3a.4f.5h.,
1j.2o.3a.4f.5h., 1p.2o.3a.4f.5h., 1a.2u.3a.4f.5h., 1b.2u.3a.4f.5h.,
1f.2u.3a.4f.5h., 1h.2u.3a.4f.5h., 1j.2u.3a.4f.5h., 1p.2u.3a.4f.5h.,
1a.2y.3a.4f.5h., 1b.2y.3a.4f.5h., 1f.2y.3a.4f.5h., 1h.2y.3a.4f.5h.,
1j.2y.3a.4f.5h., 1p.2y.3a.4f.5h., 1a.2a.3b.4f.5h., 1b.2a.3b.4f.5h.,
1f.2a.3b.4f.5h., 1h.2a.3b.4f.5h., 1j.2a.3b.4f.5h., 1p.2a.3b.4f.5h.,
1a.2b.3b.4f.5h., 1b.2b.3b.4f.5h., 1f.2b.3b.4f.5h., 1h.2b.3b.4f.5h.,
1j.2b.3b.4f.5h., 1p.2b.3b.4f.5h., 1a.2e.3b.4f.5h., 1b.2e.3b.4f.5h.,
1f.2e.3b.4f.5h., 1h.2e.3b.4f.5h., 1j.2e.3b.4f.5h., 1p.2e.3b.4f.5h.,
1a.2f.3b.4f.5h., 1b.2f.3b.4f.5h., 1f.2f.3b.4f.5h., 1h.2f.3b.4f.5h.,
1j.2f.3b.4f.5h., 1p.2f.3b.4f.5h., 1a.2i.3b.4f.5h., 1b.2i.3b.4f.5h.,
1f.2i.3b.4f.5h., 1h.2i.3b.4f.5h., 1j.2i.3b.4f.5h., 1p.2i.3b.4f.5h.,
1a.2m.3b.4f.5h., 1b.2m.3b.4f.5h., 1f.2m.3b.4f.5h., 1h.2m.3b.4f.5h.,
1j.2m.3b.4f.5h., 1p.2m.3b.4f.5h., 1a.2o.3b.4f.5h., 1b.2o.3b.4f.5h.,
1f.2o.3b.4f.5h., 1h.2o.3b.4f.5h., 1j.2o.3b.4f.5h., 1p.2o.3b.4f.5h.,
1a.2u.3b.4f.5h., 1b.2u.3b.4f.5h., 1f.2u.3b.4f.5h., 1h.2u.3b.4f.5h.,
1j.2u.3b.4f.5h., 1p.2u.3b.4f.5h., 1a.2y.3b.4f.5h., 1b.2y.3b.4f.5h.,
1f.2y.3b.4f.5h., 1h.2y.3b.4f.5h., 1j.2y.3b.4f.5h., 1p.2y.3b.4f.5h.,
1a.2a.3e.4f.5h., 1b.2a.3e.4f.5h., 1f.2a.3e.4f.5h., 1h.2a.3e.4f.5h.,
1j.2a.3e.4f.5h., 1p.2a.3e.4f.5h., 1a.2b.3e.4f.5h., 1b.2b.3e.4f.5h.,
1f.2b.3e.4f.5h., 1h.2b.3e.4f.5h., 1j.2b.3e.4f.5h., 1p.2b.3e.4f.5h.,
1a.2e.3e.4f.5h., 1b.2e.3e.4f.5h., 1f.2e.3e.4f.5h., 1h.2e.3e.4f.5h.,
1j.2e.3e.4f.5h., 1p.2e.3e.4f.5h., 1a.2f.3e.4f.5h., 1b.2f.3e.4f.5h.,
1f.2f.3e.4f.5h., 1h.2f.3e.4f.5h., 1j.2f.3e.4f.5h., 1p.2f.3e.4f.5h,
1a.2i.3e.4f.5h., 1b.2i.3e.4f.5h., 1f.2i.3e.4f.5h., 1h.2i.3e.4f.5h.,
1j.2i.3e.4f.5h., 1p.2i.3e.4f.5h., 1a.2m.3e.4f.5h., 1b.2m.3e.4f.5h.,
1f.2m.3e.4f.5h., 1h.2m.3e.4f.5h., 1j.2m.3e.4f.5h., 1p.2m.3e.4f.5h.,

TABLE 12-continued

List of Compound Structures of Formula III 1a.2o.3e.4f.5h., 1b.2o.3e.4f.5h., 1f.2o.3e.4f.5h., 1h.2o.3e.4f.5h., 1j.2o.3e.4f.5h., 1p.2o.3e.4f.5h., 1a.2u.3e.4f.5h., 1b.2u.3e.4f.5h., 1f.2u.3e.4f.5h., 1h.2u.3e.4f.5h., 1j.2u.3e.4f.5h., 1p.2u.3e.4f.5h., 1a.2y.3e.4f.5h., 1b.2y.3e.4f.5h., 1f.2y.3e.4f.5h., 1h.2y.3e.4f.5h., 1j.2y.3e.4f.5h., 1p.2y.3e.4f.5h., 1a.2a.3g.4f.5h., 1b.2a.3g.4f.5h., 1f.2a.3g.4f.5h., 1h.2a.3g.4f.5h., 1j.2a.3g.4f.5h., 1p.2a.3g.4f.5h., 1a.2b.3g.4f.5h., 1b.2b.3g.4f.5h., 1f.2b.3g.4f.5h., 1h.2b.3g.4f.5h., 1j.2b.3g.4f.5h., 1p.2b.3g.4f.5h., 1a.2e.3g.4f.5h., 1b.2e.3g.4f.5h., 1f.2e.3g.4f.5h., 1h.2e.3g.4f.5h., 1j.2e.3g.4f.5h., 1p.2e.3g.4f.5h., 1a.2f.3g.4f.5h., 1b.2f.3g.4f.5h., 1f.2f.3g.4f.5h., 1h.2f.3g.4f.5h., 1j.2f.3g.4f.5h., 1p.2f.3g.4f.5h., 1a.2i.3g.4f.5h., 1b.2i.3g.4f.5h., 1f.2i.3g.4f.5h., 1h.2i.3g.4f.5h., 1j.2i.3g.4f.5h., 1p.2i.3g.4f.5h., 1a.2m.3g.4f.5h., 1b.2m.3g.4f.5h., 1f.2m.3g.4f.5h., 1h.2m.3g.4f.5h., 1j.2m.3g.4f.5h., 1p.2m.3g.4f.5h., 1a.2o.3g.4f.5h., 1b.2o.3g.4f.5h., 1f.2o.3g.4f.5h., 1h.2o.3g.4f.5h., 1j.2o.3g.4f.5h., 1p.2o.3g.4f.5h., 1a.2u.3g.4f.5h., 1b.2u.3g.4f.5h., 1f.2u.3g.4f.5h., 1h.2u.3g.4f.5h., 1j.2u.3g.4f.5h., 1p.2u.3g.4f.5h., 1a.2y.3g.4f.5h., 1b.2y.3g.4f.5h., 1f.2y.3g.4f.5h., 1h.2y.3g.4f.5h., 1j.2y.3g.4f.5h., 1p.2y.3g.4f.5h., 1a.2a.3a.4g.5h., 1b.2a.3a.4g.5h., 1f.2a.3a.4g.5h., 1h.2a.3a.4g.5h., 1j.2a.3a.4g.5h., 1p.2a.3a.4g.5h., 1a.2b.3a.4g.5h., 1b.2b.3a.4g.5h., 1f.2b.3a.4g.5h., 1h.2b.3a.4g.5h., 1j.2b.3a.4g.5h., 1p.2b.3a.4g.5h., 1a.2e.3a.4g.5h., 1b.2e.3a.4g.5h., 1f.2e.3a.4g.5h., 1h.2e.3a.4g.5h., 1j.2e.3a.4g.5h., 1p.2e.3a.4g.5h., 1a.2f.3a.4g.5h., 1b.2f.3a.4g.5h., 1f.2f.3a.4g.5h., 1h.2f.3a.4g.5h., 1j.2f.3a.4g.5h., 1p.2f.3a.4g.5h., 1a.2i.3a.4g.5h., 1b.2i.3a.4g.5h., 1f.2i.3a.4g.5h., 1h.2i.3a.4g.5h., 1j.2i.3a.4g.5h., 1p.2i.3a.4g.5h., 1a.2m.3a.4g.5h., 1b.2m.3a.4g.5h., 1f.2m.3a.4g.5h., 1h.2m.3a.4g.5h., 1j.2m.3a.4g.5h., 1p.2m.3a.4g.5h., 1a.2o.3a.4g.5h., 1b.2o.3a.4g.5h., 1f.2o.3a.4g.5h., 1h.2o.3a.4g.5h., 1j.2o.3a.4g.5h., 1p.2o.3a.4g.5h., 1a.2u.3a.4g.5h., 1b.2u.3a.4g.5h., 1f.2u.3a.4g.5h., 1h.2u.3a.4g.5h., 1j.2u.3a.4g.5h., 1p.2u.3a.4g.5h., 1a.2y.3a.4g.5h., 1b.2y.3a.4g.5h., 1f.2y.3a.4g.5h., 1h.2y.3a.4g.5h., 1j.2y.3a.4g.5h., 1p.2y.3a.4g.5h., 1a.2a.3b.4g.5h., 1b.2a.3b.4g.5h., 1f.2a.3b.4g.5h., 1h.2a.3b.4g.5h., 1j.2a.3b.4g.5h., 1p.2a.3b.4g.5h., 1a.2b.3b.4g.5h., 1b.2b.3b.4g.5h., 1f.2b.3b.4g.5h., 1h.2b.3b.4g.5h., 1j.2b.3b.4g.5h., 1p.2b.3b.4g.5h., 1a.2e.3b.4g.5h., 1b.2e.3b.4g.5h., 1f.2e.3b.4g.5h., 1h.2e.3b.4g.5h., 1j.2e.3b.4g.5h., 1p.2e.3b.4g.5h., 1a.2f.3b.4g.5h., 1b.2f.3b.4g.5h., 1f.2f.3b.4g.5h., 1h.2f.3b.4g.5h., 1j.2f.3b.4g.5h., 1p.2f.3b.4g.5h., 1a.2i.3b.4g.5h., 1b.2i.3b.4g.5h., 1f.2i.3b.4g.5h., 1h.2i.3b.4g.5h., 1j.2i.3b.4g.5h., 1p.2i.3b.4g.5h., 1a.2m.3b.4g.5h., 1b.2m.3b.4g.5h., 1f.2m.3b.4g.5h., 1h.2m.3b.4g.5h., 1j.2m.3b.4g.5h., 1p.2m.3b.4g.5h., 1a.2o.3b.4g.5h., 1b.2o.3b.4g.5h., 1f.2o.3b.4g.5h., 1h.2o.3b.4g.5h., 1j.2o.3b.4g.5h., 1p.2o.3b.4g.5h., 1a.2u.3b.4g.5h., 1b.2u.3b.4g.5h., 1f.2u.3b.4g.5h., 1h.2u.3b.4g.5h., 1j.2u.3b.4g.5h., 1p.2u.3b.4g.5h., 1a.2y.3b.4g.5h., 1b.2y.3b.4g.5h., 1f.2y.3b.4g.5h., 1h.2y.3b.4g.5h., 1j.2y.3b.4g.5h., 1p.2y.3b.4g.5h., 1a.2a.3e.4g.5h., 1b.2a.3e.4g.5h., 1f.2a.3e.4g.5h., 1h.2a.3e.4g.5h., 1j.2a.3e.4g.5h., 1p.2a.3e.4g.5h., 1a.2b.3e.4g.5h., 1b.2b.3e.4g.5h., 1f.2b.3e.4g.5h., 1h.2b.3e.4g.5h., 1j.2b.3e.4g.5h., 1p.2b.3e.4g.5h., 1a.2e.3e.4g.5h., 1b.2e.3e.4g.5h., 1f.2e.3e.4g.5h., 1h.2e.3e.4g.5h., 1j.2e.3e.4g.5h., 1p.2e.3e.4g.5h., 1a.2f.3e.4g.5h., 1b.2f.3e.4g.5h., 1f.2f.3e.4g.5h., 1h.2f.3e.4g.5h., 1j.2f.3e.4g.5h., 1p.2f.3e.4g.5h., 1a.2i.3e.4g.5h., 1b.2i.3e.4g.5h., 1f.2i.3e.4g.5h., 1h.2i.3e.4g.5h., 1j.2i.3e.4g.5h., 1p.2i.3e.4g.5h., 1a.2m.3e.4g.5h., 1b.2m.3e.4g.5h., 1f.2m.3e.4g.5h., 1h.2m.3e.4g.5h., 1j.2m.3e.4g.5h., 1p.2m.3e.4g.5h., 1a.2o.3e.4g.5h., 1b.2o.3e.4g.5h., 1f.2o.3e.4g.5h., 1h.2o.3e.4g.5h., 1j.2o.3e.4g.5h., 1p.2o.3e.4g.5h., 1a.2u.3e.4g.5h., 1b.2u.3e.4g.5h., 1f.2u.3e.4g.5h., 1h.2u.3e.4g.5h., 1j.2u.3e.4g.5h., 1p.2u.3e.4g.5h., 1a.2y.3e.4g.5h., 1b.2y.3e.4g.5h., 1f.2y.3e.4g.5h., 1h.2y.3e.4g.5h., 1j.2y.3e.4g.5h., 1p.2y.3e.4g.5h., 1a.2a.3g.4g.5h., 1b.2a.3g.4g.5h., 1f.2a.3g.4g.5h., 1h.2a.3g.4g.5h., 1j.2a.3g.4g.5h., 1p.2a.3g.4g.5h., 1a.2b.3g.4g.5h., 1b.2b.3g.4g.5h., 1f.2b.3g.4g.5h., 1h.2b.3g.4g.5h., 1j.2b.3g.4g.5h., 1p.2b.3g.4g.5h., 1a.2e.3g.4g.5h., 1b.2e.3g.4g.5h., 1f.2e.3g.4g.5h., 1h.2e.3g.4g.5h., 1j.2e.3g.4g.5h., 1p.2e.3g.4g.5h., 1a.2f.3g.4g.5h., 1b.2f.3g.4g.5h., 1f.2f.3g.4g.5h., 1h.2f.3g.4g.5h., 1j.2f.3g.4g.5h., 1p.2f.3g.4g.5h., 1a.2i.3g.4g.5h., 1b.2i.3g.4g.5h., 1f.2i.3g.4g.5h., 1h.2i.3g.4g.5h., 1j.2i.3g.4g.5h., 1p.2i.3g.4g.5h., 1a.2m.3g.4g.5h., 1b.2m.3g.4g.5h., 1f.2m.3g.4g.5h., 1h.2m.3g.4g.5h., 1j.2m.3g.4g.5h., 1p.2m.3g.4g.5h., 1a.2o.3g.4g.5h., 1b.2o.3g.4g.5h., 1f.2o.3g.4g.5h., 1h.2o.3g.4g.5h., 1j.2o.3g.4g.5h., 1p.2o.3g.4g.5h., 1a.2u.3g.4g.5h., 1b.2u.3g.4g.5h., 1f.2u.3g.4g.5h., 1h.2u.3g.4g.5h., 1j.2u.3g.4g.5h., 1p.2u.3g.4g.5h., 1a.2y.3g.4g.5h., 1b.2y.3g.4g.5h., 1f.2y.3g.4g.5h., 1h.2y.3g.4g.5h., 1j.2y.3g.4g.5h., 1p.2y.3g.4g.5h., 1a.2a.3a.4h.5h., 1b.2a.3a.4h.5h., 1f.2a.3a.4h.5h., 1h.2a.3a.4h.5h., 1j.2a.3a.4h.5h., 1p.2a.3a.4h.5h., 1a.2b.3a.4h.5h., 1b.2b.3a.4h.5h., 1f.2b.3a.4h.5h., 1h.2b.3a.4h.5h., 1j.2b.3a.4h.5h., 1p.2b.3a.4h.5h., 1a.2e.3a.4h.5h., 1b.2e.3a.4h.5h., 1f.2e.3a.4h.5h., 1h.2e.3a.4h.5h., 1j.2e.3a.4h.5h., 1p.2e.3a.4h.5h., 1a.2f.3a.4h.5h., 1b.2f.3a.4h.5h., 1f.2f.3a.4h.5h., 1h.2f.3a.4h.5h., 1j.2f.3a.4h.5h., 1p.2f.3a.4h.5h., 1a.2i.3a.4h.5h., 1b.2i.3a.4h.5h., 1f.2i.3a.4h.5h., 1h.2i.3a.4h.5h., 1j.2i.3a.4h.5h., 1p.2i.3a.4h.5h., 1a.2m.3a.4h.5h., 1b.2m.3a.4h.5h., 1f.2m.3a.4h.5h., 1h.2m.3a.4h.5h., 1j.2m.3a.4h.5h., 1p.2m.3a.4h.5h., 1a.2o.3a.4h.5h., 1b.2o.3a.4h.5h., 1f.2o.3a.4h.5h., 1h.2o.3a.4h.5h., 1j.2o.3a.4h.5h., 1p.2o.3a.4h.5h., 1a.2u.3a.4h.5h., 1b.2u.3a.4h.5h., 1f.2u.3a.4h.5h., 1h.2u.3a.4h.5h., 1j.2u.3a.4h.5h., 1p.2u.3a.4h.5h., 1a.2y.3a.4h.5h., 1b.2y.3a.4h.5h., 1f.2y.3a.4h.5h., 1h.2y.3a.4h.5h., 1j.2y.3a.4h.5h., 1p.2y.3a.4h.5h., 1a.2a.3b.4h.5h., 1b.2a.3b.4h.5h., 1f.2a.3b.4h.5h., 1h.2a.3b.4h.5h., 1j.2a.3b.4h.5h., 1p.2a.3b.4h.5h., 1a.2b.3b.4h.5h., 1b.2b.3b.4h.5h., 1f.2b.3b.4h.5h., 1h.2b.3b.4h.5h., 1j.2b.3b.4h.5h., 1p.2b.3b.4h.5h., 1a.2e.3b.4h.5h., 1b.2e.3b.4h.5h., 1f.2e.3b.4h.5h., 1h.2e.3b.4h.5h., 1j.2e.3b.4h.5h., 1p.2e.3b.4h.5h., 1a.2f.3b.4h.5h., 1b.2f.3b.4h.5h., 1f.2f.3b.4h.5h., 1h.2f.3b.4h.5h., 1j.2f.3b.4h.5h., 1p.2f.3b.4h.5h., 1a.2i.3b.4h.5h., 1b.2i.3b.4h.5h., 1f.2i.3b.4h.5h., 1h.2i.3b.4h.5h., 1j.2i.3b.4h.5h., 1p.2i.3b.4h.5h., 1a.2m.3b.4h.5h., 1b.2m.3b.4h.5h., 1f.2m.3b.4h.5h., 1h.2m.3b.4h.5h., 1j.2m.3b.4h.5h., 1p.2m.3b.4h.5h., 1a.2o.3b.4h.5h., 1b.2o.3b.4h.5h., 1f.2o.3b.4h.5h., 1h.2o.3b.4h.5h., 1j.2o.3b.4h.5h., 1p.2o.3b.4h.5h., 1a.2u.3b.4h.5h., 1b.2u.3b.4h.5h., 1f.2u.3b.4h.5h., 1h.2u.3b.4h.5h., 1j.2u.3b.4h.5h., 1p.2u.3b.4h.5h., 1a.2y.3b.4h.5h., 1b.2y.3b.4h.5h., 1f.2y.3b.4h.5h., 1h.2y.3b.4h.5h., 1j.2y.3b.4h.5h., 1p.2y.3b.4h.5h., 1a.2a.3e.4h.5h., 1b.2a.3e.4h.5h., 1f.2a.3e.4h.5h., 1h.2a.3e.4h.5h., 1j.2a.3e.4h.5h., 1p.2a.3e.4h.5h., 1a.2b.3e.4h.5h., 1b.2b.3e.4h.5h., 1f.2b.3e.4h.5h., 1h.2b.3e.4h.5h., 1j.2b.3e.4h.5h., 1p.2b.3e.4h.5h., 1a.2e.3e.4h.5h., 1b.2e.3e.4h.5h., 1f.2e.3e.4h.5h., 1h.2e.3e.4h.5h., 1j.2e.3e.4h.5h., 1p.2e.3e.4h.5h., 1a.2f.3e.4h.5h., 1b.2f.3e.4h.5h., 1f.2f.3e.4h.5h., 1h.2f.3e.4h.5h., 1j.2f.3e.4h.5h., 1p.2f.3e.4h.5h., 1a.2i.3e.4h.5h., 1b.2i.3e.4h.5h., 1f.2i.3e.4h.5h., 1h.2i.3e.4h.5h., 1j.2i.3e.4h.5h., 1p.2i.3e.4h.5h., 1a.2m.3e.4h.5h., 1b.2m.3e.4h.5h., 1f.2m.3e.4h.5h., 1h.2m.3e.4h.5h., 1j.2m.3e.4h.5h., 1p.2m.3e.4h.5h., 1a.2o.3e.4h.5h., 1b.2o.3e.4h.5h., 1f.2o.3e.4h.5h., 1h.2o.3e.4h.5h., 1j.2o.3e.4h.5h., 1p.2o.3e.4h.5h., 1a.2u.3e.4h.5h., 1b.2u.3e.4h.5h., 1f.2u.3e.4h.5h., 1h.2u.3e.4h.5h., 1j.2u.3e.4h.5h., 1p.2u.3e.4h.5h., 1a.2y.3e.4h.5h., 1b.2y.3e.4h.5h., 1f.2y.3e.4h.5h., 1h.2y.3e.4h.5h., 1j.2y.3e.4h.5h., 1p.2y.3e.4h.5h., 1a.2a.3g.4h.5h., 1b.2a.3g.4h.5h., 1f.2a.3g.4h.5h., 1h.2a.3g.4h.5h., 1j.2a.3g.4h.5h., 1p.2a.3g.4h.5h., 1a.2b.3g.4h.5h., 1b.2b.3g.4h.5h., 1f.2b.3g.4h.5h., 1h.2b.3g.4h.5h., 1j.2b.3g.4h.5h., 1p.2b.3g.4h.5h., 1a.2e.3g.4h.5h., 1b.2e.3g.4h.5h., 1f.2e.3g.4h.5h., 1h.2e.3g.4h.5h., 1j.2e.3g.4h.5h., 1p.2e.3g.4h.5h., 1a.2f.3g.4h.5h., 1b.2f.3g.4h.5h., 1f.2f.3g.4h.5h., 1h.2f.3g.4h.5h., 1j.2f.3g.4h.5h., 1p.2f.3g.4h.5h., 1a.2i.3g.4h.5h., 1b.2i.3g.4h.5h., 1f.2i.3g.4h.5h., 1h.2i.3g.4h.5h., 1j.2i.3g.4h.5h., 1p.2i.3g.4h.5h., 1a.2m.3g.4h.5h., 1b.2m.3g.4h.5h., 1f.2m.3g.4h.5h., 1h.2m.3g.4h.5h., 1j.2m.3g.4h.5h., 1p.2m.3g.4h.5h., 1a.2o.3g.4h.5h., 1b.2o.3g.4h.5h., 1f.2o.3g.4h.5h., 1h.2o.3g.4h.5h., 1j.2o.3g.4h.5h., 1p.2o.3g.4h.5h., 1a.2u.3g.4h.5h., 1b.2u.3g.4h.5h., 1f.2u.3g.4h.5h., 1h.2u.3g.4h.5h., 1j.2u.3g.4h.5h., 1p.2u.3g.4h.5h., 1a.2y.3g.4h.5h., 1b.2y.3g.4h.5h., 1f.2y.3g.4h.5h., 1h.2y.3g.4h.5h., 1j.2y.3g.4h.5h., 1p.2y.3g.4h.5h., 1a.2a.3a.4i.5h., 1b.2a.3a.4i.5h., 1f.2a.3a.4i.5h., 1h.2a.3a.4i.5h., 1j.2a.3a.4i.5h., 1p.2a.3a.4i.5h., 1a.2b.3a.4i.5h., 1b.2b.3a.4i.5h., 1f.2b.3a.4i.5h., 1h.2b.3a.4i.5h., 1j.2b.3a.4i.5h., 1p.2b.3a.4i.5h., 1a.2e.3a.4i.5h., 1b.2e.3a.4i.5h., 1f.2e.3a.4i.5h., 1h.2e.3a.4i.5h., 1j.2e.3a.4i.5h., 1p.2e.3a.4i.5h., 1a.2f.3a.4i.5h., 1b.2f.3a.4i.5h., 1f.2f.3a.4i.5h., 1h.2f.3a.4i.5h., 1j.2f.3a.4i.5h., 1p.2f.3a.4i.5h., 1a.2i.3a.4i.5h., 1b.2i.3a.4i.5h., 1f.2i.3a.4i.5h., 1h.2i.3a.4i.5h., 1j.2i.3a.4i.5h., 1p.2i.3a.4i.5h., 1a.2m.3a.4i.5h., 1b.2m.3a.4i.5h., 1f.2m.3a.4i.5h., 1h.2m.3a.4i.5h., 1j.2m.3a.4i.5h., 1p.2m.3a.4i.5h., 1a.2o.3a.4i.5h., 1b.2o.3a.4i.5h., 1f.2o.3a.4i.5h., 1h.2o.3a.4i.5h., 1j.2o.3a.4i.5h., 1p.2o.3a.4i.5h., 1a.2u.3a.4i.5h., 1b.2u.3a.4i.5h., 1f.2u.3a.4i.5h., 1h.2u.3a.4i.5h., 1j.2u.3a.4i.5h., 1p.2u.3a.4i.5h., 1a.2y.3a.4i.5h., 1b.2y.3a.4i.5h., 1f.2y.3a.4i.5h., 1h.2y.3a.4i.5h., 1j.2y.3a.4i.5h., 1p.2y.3a.4i.5h., 1a.2a.3b.4i.5h., 1b.2a.3b.4i.5h., 1f.2a.3b.4i.5h., 1h.2a.3b.4i.5h., 1j.2a.3b.4i.5h., 1p.2a.3b.4i.5h., 1a.2b.3b.4i.5h., 1b.2b.3b.4i.5h., 1f.2b.3b.4i.5h., 1h.2b.3b.4i.5h., 1j.2b.3b.4i.5h., 1p.2b.3b.4i.5h., 1a.2e.3b.4i.5h., 1b.2e.3b.4i.5h., 1f.2e.3b.4i.5h., 1h.2e.3b.4i.5h., 1j.2e.3b.4i.5h., 1p.2e.3b.4i.5h., 1a.2f.3b.4i.5h., 1b.2f.3b.4i.5h., 1f.2f.3b.4i.5h., 1h.2f.3b.4i.5h., 1j.2f.3b.4i.5h., 1p.2f.3b.4i.5h., 1a.2i.3b.4i.5h., 1b.2i.3b.4i.5h., 1f.2i.3b.4i.5h., 1h.2i.3b.4i.5h., 1j.2i.3b.4i.5h., 1p.2i.3b.4i.5h., 1a.2m.3b.4i.5h., 1b.2m.3b.4i.5h., 1f.2m.3b.4i.5h., 1h.2m.3b.4i.5h., 1j.2m.3b.4i.5h., 1p.2m.3b.4i.5h., 1a.2o.3b.4i.5h., 1b.2o.3b.4i.5h., 1f.2o.3b.4i.5h., 1h.2o.3b.4i.5h., 1j.2o.3b.4i.5h., 1p.2o.3b.4i.5h., 1a.2u.3b.4i.5h., 1b.2u.3b.4i.5h., 1f.2u.3b.4i.5h., 1h.2u.3b.4i.5h., 1j.2u.3b.4i.5h., 1p.2u.3b.4i.5h., 1a.2y.3b.4i.5h., 1b.2y.3b.4i.5h., 1f.2y.3b.4i.5h., 1h.2y.3b.4i.5h., 1j.2y.3b.4i.5h., 1p.2y.3b.4i.5h., 1a.2a.3e.4i.5h., 1b.2a.3e.4i.5h., 1f.2a.3e.4i.5h., 1h.2a.3e.4i.5h., 1j.2a.3e.4i.5h., 1p.2a.3e.4i.5h., 1a.2b.3e.4i.5h., 1b.2b.3e.4i.5h., 1f.2b.3e.4i.5h., 1h.2b.3e.4i.5h., 1j.2b.3e.4i.5h., 1p.2b.3e.4i.5h.,

TABLE 12-continued

List of Compound Structures of Formula III 1a.2e.3e.4i.5h., 1b.2e.3e.4i.5h., 1f.2e.3e.4i.5h., 1h.2e.3e.4i.5h.,
1j.2e.3e.4i.5h., 1p.2e.3e.4i.5h., 1a.2f.3e.4i.5h., 1b.2f.3e.4i.5h.,
1f.2f.3e.4i.5h., 1h.2f.3e.4i.5h., 1j.2f.3e.4i.5h., 1p.2f.3e.4i.5h.,
1a.2i.3e.4i.5h., 1b.2i.3e.4i.5h., 1f.2i.3e.4i.5h., 1h.2i.3e.4i.5h.,
1j.2i.3e.4i.5h., 1p.2i.3e.4i.5h., 1a.2m.3e.4i.5h., 1b.2m.3e.4i.5h.,
1f.2m.3e.4i.5h., 1h.2m.3e.4i.5h., 1j.2m.3e.4i.5h., 1p.2m.3e.4i.5h.,
1a.2o.3e.4i.5h., 1b.2o.3e.4i.5h., 1f.2o.3e.4i.5h., 1h.2o.3e.4i.5h.,
1j.2o.3e.4i.5h., 1p.2o.3e.4i.5h., 1a.2u.3e.4i.5h., 1b.2u.3e.4i.5h.,
1f.2u.3e.4i.5h., 1h.2u.3e.4i.5h., 1j.2u.3e.4i.5h., 1p.2u.3e.4i.5h.,
1a.2y.3e.4i.5h., 1b.2y.3e.4i.5h., 1f.2y.3e.4i.5h., 1h.2y.3e.4i.5h.,
1j.2y.3e.4i.5h., 1p.2y.3e.4i.5h., 1a.2a.3g.4i.5h., 1b.2a.3g.4i.5h.,
1f.2a.3g.4i.5h., 1h.2a.3g.4i.5h., 1j.2a.3g.4i.5h., 1p.2a.3g.4i.5h.,
1a.2b.3g.4i.5h., 1b.2b.3g.4i.5h., 1f.2b.3g.4i.5h., 1h.2b.3g.4i.5h.,
1j.2b.3g.4i.5h., 1p.2b.3g.4i.5h., 1a.2e.3g.4i.5h., 1b.2e.3g.4i.5h.,
1f.2e.3g.4i.5h., 1h.2e.3g.4i.5h., 1j.2e.3g.4i.5h., 1p.2e.3g.4i.5h.,
1a.2f.3g.4i.5h., 1b.2f.3g.4i.5h., 1f.2f.3g.4i.5h., 1h.2f.3g.4i.5h.,
1j.2f.3g.4i.5h., 1p.2f.3g.4i.5h., 1a.2i.3g.4i.5h., 1b.2i.3g.4i.5h.,
1f.2i.3g.4i.5h., 1h.2i.3g.4i.5h., 1j.2i.3g.4i.5h., 1p.2i.3g.4i.5h.,
1a.2m.3g.4i.5h., 1b.2m.3g.4i.5h., 1f.2m.3g.4i.5h., 1h.2m.3g.4i.5h.,
1j.2m.3g.4i.5h., 1p.2m.3g.4i.5h., 1a.2o.3g.4i.5h., 1b.2o.3g.4i.5h.,
1f.2o.3g.4i.5h., 1h.2o.3g.4i.5h., 1j.2o.3g.4i.5h., 1p.2o.3g.4i.5h.,
1a.2u.3g.4i.5h., 1b.2u.3g.4i.5h., 1f.2u.3g.4i.5h., 1h.2u.3g.4i.5h.,
1j.2u.3g.4i.5h., 1p.2u.3g.4i.5h., 1a.2y.3g.4i.5h., 1b.2y.3g.4i.5h.,
1f.2y.3g.4i.5h., 1h.2y.3g.4i.5h., 1j.2y.3g.4i.5h., 1p.2y.3g.4i.5h.,
1a.2a.3a.4a.5i., 1b.2a.3a.4a.5i., 1f.2a.3a.4a.5i., 1h.2a.3a.4a.5i.,
1j.2a.3a.4a.5i., 1p.2a.3a.4a.5i., 1a.2b.3a.4a.5i., 1b.2b.3a.4a.5i.,
1f.2b.3a.4a.5i., 1h.2b.3a.4a.5i., 1j.2b.3a.4a.5i., 1p.2b.3a.4a.5i.,
1a.2e.3a.4a.5i., 1b.2e.3a.4a.5i., 1f.2e.3a.4a.5i., 1h.2e.3a.4a.5i.,
1j.2e.3a.4a.5i., 1p.2e.3a.4a.5i., 1a.2f.3a.4a.5i., 1b.2f.3a.4a.5i.,
1f.2f.3a.4a.5i., 1h.2f.3a.4a.5i., 1j.2f.3a.4a.5i., 1p.2f.3a.4a.5i.,
1a.2i.3a.4a.5i., 1b.2i.3a.4a.5i., 1f.2i.3a.4a.5i., 1h.2i.3a.4a.5i.,
1j.2i.3a.4a.5i., 1p.2i.3a.4a.5i., 1a.2m.3a.4a.5i., 1b.2m.3a.4a.5i.,
1f.2m.3a.4a.5i., 1h.2m.3a.4a.5i., 1j.2m.3a.4a.5i., 1p.2m.3a.4a.5i.,
1a.2o.3a.4a.5i., 1b.2o.3a.4a.5i., 1f.2o.3a.4a.5i., 1h.2o.3a.4a.5i.,
1j.2o.3a.4a.5i., 1p.2o.3a.4a.5i., 1a.2u.3a.4a.5i., 1b.2u.3a.4a.5i.,
1f.2u.3a.4a.5i., 1h.2u.3a.4a.5i., 1j.2u.3a.4a.5i., 1p.2u.3a.4a.5i.,
1a.2y.3a.4a.5i., 1b.2y.3a.4a.5i., 1f.2y.3a.4a.5i., 1h.2y.3a.4a.5i.,
1j.2y.3a.4a.5i., 1p.2y.3a.4a.5i., 1a.2a.3b.4a.5i., 1b.2a.3b.4a.5i.,
1f.2a.3b.4a.5i., 1h.2a.3b.4a.5i., 1j.2a.3b.4a.5i., 1p.2a.3b.4a.5i.,
1a.2b.3b.4a.5i., 1b.2b.3b.4a.5i., 1f.2b.3b.4a.5i., 1h.2b.3b.4a.5i.,
1j.2b.3b.4a.5i., 1p.2b.3b.4a.5i., 1a.2e.3b.4a.5i., 1b.2e.3b.4a.5i.,
1f.2e.3b.4a.5i., 1h.2e.3b.4a.5i., 1j.2e.3b.4a.5i., 1p.2e.3b.4a.5i.,
1a.2f.3b.4a.5i., 1b.2f.3b.4a.5i., 1f.2f.3b.4a.5i., 1h.2f.3b.4a.5i.,
1j.2f.3b.4a.5i., 1p.2f.3b.4a.5i., 1a.2i.3b.4a.5i., 1b.2i.3b.4a.5i.,
1f.2i.3b.4a.5i., 1h.2i.3b.4a.5i., 1j.2i.3b.4a.5i., 1p.2i.3b.4a.5i.,
1a.2m.3b.4a.5i., 1b.2m.3b.4a.5i., 1f.2m.3b.4a.5i., 1h.2m.3b.4a.5i.,
1j.2m.3b.4a.5i., 1p.2m.3b.4a.5i., 1a.2o.3b.4a.5i., 1b.2o.3b.4a.5i.,
1f.2o.3b.4a.5i., 1h.2o.3b.4a.5i., 1j.2o.3b.4a.5i., 1p.2o.3b.4a.5i.,
1a.2u.3b.4a.5i., 1b.2u.3b.4a.5i., 1f.2u.3b.4a.5i., 1h.2u.3b.4a.5i.,
1j.2u.3b.4a.5i., 1p.2u.3b.4a.5i., 1a.2y.3b.4a.5i., 1b.2y.3b.4a.5i.,
1f.2y.3b.4a.5i., 1h.2y.3b.4a.5i., 1j.2y.3b.4a.5i., 1p.2y.3b.4a.5i.,
1a.2a.3e.4a.5i., 1b.2a.3e.4a.5i., 1f.2a.3e.4a.5i., 1h.2a.3e.4a.5i.,
1j.2a.3e.4a.5i., 1p.2a.3e.4a.5i., 1a.2b.3e.4a.5i., 1b.2b.3e.4a.5i.,
1f.2b.3e.4a.5i., 1h.2b.3e.4a.5i., 1j.2b.3e.4a.5i., 1p.2b.3e.4a.5i.,
1a.2e.3e.4a.5i., 1b.2e.3e.4a.5i., 1f.2e.3e.4a.5i., 1h.2e.3e.4a.5i.,
1j.2e.3e.4a.5i., 1p.2e.3e.4a.5i., 1a.2f.3e.4a.5i., 1b.2f.3e.4a.5i.,
1f.2f.3e.4a.5i., 1h.2f.3e.4a.5i., 1j.2f.3e.4a.5i., 1p.2f.3e.4a.5i.,
1a.2i.3e.4a.5i., 1b.2i.3e.4a.5i., 1f.2i.3e.4a.5i., 1h.2i.3e.4a.5i.,
1j.2i.3e.4a.5i., 1p.2i.3e.4a.5i., 1a.2m.3e.4a.5i., 1b.2m.3e.4a.5i.,
1f.2m.3e.4a.5i., 1h.2m.3e.4a.5i., 1j.2m.3e.4a.5i., 1p.2m.3e.4a.5i.,
1a.2o.3e.4a.5i., 1b.2o.3e.4a.5i., 1f.2o.3e.4a.5i., 1h.2o.3e.4a.5i.,
1j.2o.3e.4a.5i., 1p.2o.3e.4a.5i., 1a.2u.3e.4a.5i., 1b.2u.3e.4a.5i.,
1f.2u.3e.4a.5i., 1h.2u.3e.4a.5i., 1j.2u.3e.4a.5i., 1p.2u.3e.4a.5i.,
1a.2y.3e.4a.5i., 1b.2y.3e.4a.5i., 1f.2y.3e.4a.5i., 1h.2y.3e.4a.5i.,
1j.2y.3e.4a.5i., 1p.2y.3e.4a.5i., 1a.2a.3g.4a.5i., 1b.2a.3g.4a.5i.,
1f.2a.3g.4a.5i., 1h.2a.3g.4a.5i., 1j.2a.3g.4a.5i., 1p.2a.3g.4a.5i.,
1a.2b.3g.4a.5i., 1b.2b.3g.4a.5i., 1f.2b.3g.4a.5i., 1h.2b.3g.4a.5i.,
1j.2b.3g.4a.5i., 1p.2b.3g.4a.5i., 1a.2e.3g.4a.5i., 1b.2e.3g.4a.5i.,
1f.2e.3g.4a.5i., 1h.2e.3g.4a.5i., 1j.2e.3g.4a.5i., 1p.2e.3g.4a.5i.,
1a.2f.3g.4a.5i., 1b.2f.3g.4a.5i., 1f.2f.3g.4a.5i., 1h.2f.3g.4a.5i.,
1j.2f.3g.4a.5i., 1p.2f.3g.4a.5i., 1a.2i.3g.4a.5i., 1b.2i.3g.4a.5i.,
1f.2i.3g.4a.5i., 1h.2i.3g.4a.5i., 1j.2i.3g.4a.5i., 1p.2i.3g.4a.5i.,
1a.2m.3g.4a.5i., 1b.2m.3g.4a.5i., 1f.2m.3g.4a.5i., 1h.2m.3g.4a.5i.,
1j.2m.3g.4a.5i., 1p.2m.3g.4a.5i., 1a.2o.3g.4a.5i., 1b.2o.3g.4a.5i.,
1f.2o.3g.4a.5i., 1h.2o.3g.4a.5i., 1j.2o.3g.4a.5i., 1p.2o.3g.4a.5i.,
1a.2u.3g.4a.5i., 1b.2u.3g.4a.5i., 1f.2u.3g.4a.5i., 1h.2u.3g.4a.5i.,
1j.2u.3g.4a.5i., 1p.2u.3g.4a.5i., 1a.2y.3g.4a.5i., 1b.2y.3g.4a.5i.,
1f.2y.3g.4a.5i., 1h.2y.3g.4a.5i., 1j.2y.3g.4a.5i., 1p.2y.3g.4a.5i.,
1a.2a.3a.4d.5i., 1b.2a.3a.4d.5i., 1f.2a.3a.4d.5i., 1h.2a.3a.4d.5i.,
1j.2a.3a.4d.5i., 1p.2a.3a.4d.5i., 1a.2b.3a.4d.5i., 1b.2b.3a.4d.5i.,
1f.2b.3a.4d.5i., 1h.2b.3a.4d.5i., 1j.2b.3a.4d.5i., 1p.2b.3a.4d.5i.,
1a.2e.3a.4d.5i., 1b.2e.3a.4d.5i., 1f.2e.3a.4d.5i., 1h.2e.3a.4d.5i.,
1j.2e.3a.4d.5i., 1p.2e.3a.4d.5i., 1a.2f.3a.4d.5i., 1b.2f.3a.4d.5i.,
1f.2f.3a.4d.5i., 1h.2f.3a.4d.5i., 1j.2f.3a.4d.5i., 1p.2f.3a.4d.5i.,
1a.2i.3a.4d.5i., 1b.2i.3a.4d.5i., 1f.2i.3a.4d.5i., 1h.2i.3a.4d.5i.,
1j.2i.3a.4d.5i., 1p.2i.3a.4d.5i., 1a.2m.3a.4d.5i., 1b.2m.3a.4d.5i.,
1f.2m.3a.4d.5i., 1h.2m.3a.4d.5i., 1j.2m.3a.4d.5i., 1p.2m.3a.4d.5i.,
1a.2o.3a.4d.5i., 1b.2o.3a.4d.5i., 1f.2o.3a.4d.5i., 1h.2o.3a.4d.5i.,
1j.2o.3a.4d.5i., 1p.2o.3a.4d.5i., 1a.2u.3a.4d.5i., 1b.2u.3a.4d.5i.,
1f.2u.3a.4d.5i., 1h.2u.3a.4d.5i., 1j.2u.3a.4d.5i., 1p.2u.3a.4d.5i.,
1a.2y.3a.4d.5i., 1b.2y.3a.4d.5i., 1f.2y.3a.4d.5i., 1h.2y.3a.4d.5i.,
1j.2y.3a.4d.5i., 1p.2y.3a.4d.5i., 1a.2a.3b.4d.5i., 1b.2a.3b.4d.5i.,
1f.2a.3b.4d.5i., 1h.2a.3b.4d.5i., 1j.2a.3b.4d.5i., 1p.2a.3b.4d.5i.,
1a.2b.3b.4d.5i., 1b.2b.3b.4d.5i., 1f.2b.3b.4d.5i., 1h.2b.3b.4d.5i.,
1j.2b.3b.4d.5i., 1p.2b.3b.4d.5i., 1a.2e.3b.4d.5i., 1b.2e.3b.4d.5i.,
1f.2e.3b.4d.5i., 1h.2e.3b.4d.5i., 1j.2e.3b.4d.5i., 1p.2e.3b.4d.5i.,
1a.2f.3b.4d.5i., 1b.2f.3b.4d.5i., 1f.2f.3b.4d.5i., 1h.2f.3b.4d.5i.,
1j.2f.3b.4d.5i., 1p.2f.3b.4d.5i., 1a.2i.3b.4d.5i., 1b.2i.3b.4d.5i.,
1f.2i.3b.4d.5i., 1h.2i.3b.4d.5i., 1j.2i.3b.4d.5i., 1p.2i.3b.4d.5i.,
1a.2m.3b.4d.5i., 1b.2m.3b.4d.5i., 1f.2m.3b.4d.5i., 1h.2m.3b.4d.5i.,
1j.2m.3b.4d.5i., 1p.2m.3b.4d.5i., 1a.2o.3b.4d.5i., 1b.2o.3b.4d.5i.,
1f.2o.3b.4d.5i., 1h.2o.3b.4d.5i., 1j.2o.3b.4d.5i., 1p.2o.3b.4d.5i.,
1a.2u.3b.4d.5i., 1b.2u.3b.4d.5i., 1f.2u.3b.4d.5i., 1h.2u.3b.4d.5i.,
1j.2u.3b.4d.5i., 1p.2u.3b.4d.5i., 1a.2y.3b.4d.5i., 1b.2y.3b.4d.5i.,
1f.2y.3b.4d.5i., 1h.2y.3b.4d.5i., 1j.2y.3b.4d.5i., 1p.2y.3b.4d.5i.,
1a.2a.3e.4d.5i., 1b.2a.3e.4d.5i., 1f.2a.3e.4d.5i., 1h.2a.3e.4d.5i.,
1j.2a.3e.4d.5i., 1p.2a.3e.4d.5i., 1a.2b.3e.4d.5i., 1b.2b.3e.4d.5i.,
1f.2b.3e.4d.5i., 1h.2b.3e.4d.5i., 1j.2b.3e.4d.5i., 1p.2b.3e.4d.5i.,
1a.2e.3e.4d.5i., 1b.2e.3e.4d.5i., 1f.2e.3e.4d.5i., 1h.2e.3e.4d.5i.,
1j.2e.3e.4d.5i., 1p.2e.3e.4d.5i., 1a.2f.3e.4d.5i., 1b.2f.3e.4d.5i.,
1f.2f.3e.4d.5i., 1h.2f.3e.4d.5i., 1j.2f.3e.4d.5i., 1p.2f.3e.4d.5i.,
1a.2i.3e.4d.5i., 1b.2i.3e.4d.5i., 1f.2i.3e.4d.5i., 1h.2i.3e.4d.5i.,
1j.2i.3e.4d.5i., 1p.2i.3e.4d.5i., 1a.2m.3e.4d.5i., 1b.2m.3e.4d.5i.,
1f.2m.3e.4d.5i., 1h.2m.3e.4d.5i., 1j.2m.3e.4d.5i., 1p.2m.3e.4d.5i.,
1a.2o.3e.4d.5i., 1b.2o.3e.4d.5i., 1f.2o.3e.4d.5i., 1h.2o.3e.4d.5i.,
1j.2o.3e.4d.5i., 1p.2o.3e.4d.5i., 1a.2u.3e.4d.5i., 1b.2u.3e.4d.5i.,
1f.2u.3e.4d.5i., 1h.2u.3e.4d.5i., 1j.2u.3e.4d.5i., 1p.2u.3e.4d.5i.,
1a.2y.3e.4d.5i., 1b.2y.3e.4d.5i., 1f.2y.3e.4d.5i., 1h.2y.3e.4d.5i.,
1j.2y.3e.4d.5i., 1p.2y.3e.4d.5i., 1a.2a.3g.4d.5i., 1b.2a.3g.4d.5i.,
1f.2a.3g.4d.5i., 1h.2a.3g.4d.5i., 1j.2a.3g.4d.5i., 1p.2a.3g.4d.5i.,
1a.2b.3g.4d.5i., 1b.2b.3g.4d.5i., 1f.2b.3g.4d.5i., 1h.2b.3g.4d.5i.,
1j.2b.3g.4d.5i., 1p.2b.3g.4d.5i., 1a.2e.3g.4d.5i., 1b.2e.3g.4d.5i.,
1f.2e.3g.4d.5i., 1h.2e.3g.4d.5i., 1j.2e.3g.4d.5i., 1p.2e.3g.4d.5i.,
1a.2f.3g.4d.5i., 1b.2f.3g.4d.5i., 1f.2f.3g.4d.5i., 1h.2f.3g.4d.5i.,
1j.2f.3g.4d.5i., 1p.2f.3g.4d.5i., 1a.2i.3g.4d.5i., 1b.2i.3g.4d.5i.,
1f.2i.3g.4d.5i., 1h.2i.3g.4d.5i., 1j.2i.3g.4d.5i., 1p.2i.3g.4d.5i.,
1a.2m.3g.4d.5i., 1b.2m.3g.4d.5i., 1f.2m.3g.4d.5i., 1h.2m.3g.4d.5i.,
1j.2m.3g.4d.5i., 1p.2m.3g.4d.5i., 1a.2o.3g.4d.5i., 1b.2o.3g.4d.5i.,
1f.2o.3g.4d.5i., 1h.2o.3g.4d.5i., 1j.2o.3g.4d.5i., 1p.2o.3g.4d.5i.,
1a.2u.3g.4d.5i., 1b.2u.3g.4d.5i., 1f.2u.3g.4d.5i., 1h.2u.3g.4d.5i.,
1j.2u.3g.4d.5i., 1p.2u.3g.4d.5i., 1a.2y.3g.4d.5i., 1b.2y.3g.4d.5i.,
1f.2y.3g.4d.5i., 1h.2y.3g.4d.5i., 1j.2y.3g.4d.5i., 1p.2y.3g.4d.5i.,
1a.2a.3a.4f.5i., 1b.2a.3a.4f.5i., 1f.2a.3a.4f.5i., 1h.2a.3a.4f.5i.,
1j.2a.3a.4f.5i., 1p.2a.3a.4f.5i., 1a.2b.3a.4f.5i., 1b.2b.3a.4f.5i.,
1f.2b.3a.4f.5i., 1h.2b.3a.4f.5i., 1j.2b.3a.4f.5i., 1p.2b.3a.4f.5i.,
1a.2e.3a.4f.5i., 1b.2e.3a.4f.5i., 1f.2e.3a.4f.5i., 1h.2e.3a.4f.5i.,
1j.2e.3a.4f.5i., 1p.2e.3a.4f.5i., 1a.2f.3a.4f.5i., 1b.2f.3a.4f.5i.,
1f.2f.3a.4f.5i., 1h.2f.3a.4f.5i., 1j.2f.3a.4f.5i., 1p.2f.3a.4f.5i.,
1a.2i.3a.4f.5i., 1b.2i.3a.4f.5i., 1f.2i.3a.4f.5i., 1h.2i.3a.4f.5i.,
1j.2i.3a.4f.5i., 1p.2i.3a.4f.5i., 1a.2m.3a.4f.5i., 1b.2m.3a.4f.5i.,
1f.2m.3a.4f.5i., 1h.2m.3a.4f.5i., 1j.2m.3a.4f.5i., 1p.2m.3a.4f.5i.,
1a.2o.3a.4f.5i., 1b.2o.3a.4f.5i., 1f.2o.3a.4f.5i., 1h.2o.3a.4f.5i.,
1j.2o.3a.4f.5i., 1p.2o.3a.4f.5i., 1a.2u.3a.4f.5i., 1b.2u.3a.4f.5i.,
1f.2u.3a.4f.5i., 1h.2u.3a.4f.5i., 1j.2u.3a.4f.5i., 1p.2u.3a.4f.5i.,
1a.2y.3a.4f.5i., 1b.2y.3a.4f.5i., 1f.2y.3a.4f.5i., 1h.2y.3a.4f.5i.,
1j.2y.3a.4f.5i., 1p.2y.3a.4f.5i., 1a.2a.3b.4f.5i., 1b.2a.3b.4f.5i.,
1f.2a.3b.4f.5i., 1h.2a.3b.4f.5i., 1j.2a.3b.4f.5i., 1p.2a.3b.4f.5i.,
1a.2b.3b.4f.5i., 1b.2b.3b.4f.5i., 1f.2b.3b.4f.5i., 1h.2b.3b.4f.5i.,
1j.2b.3b.4f.5i., 1p.2b.3b.4f.5i., 1a.2e.3b.4f.5i., 1b.2e.3b.4f.5i.,
1f.2e.3b.4f.5i., 1h.2e.3b.4f.5i., 1j.2e.3b.4f.5i., 1p.2e.3b.4f.5i.,
1a.2f.3b.4f.5i., 1b.2f.3b.4f.5i., 1f.2f.3b.4f.5i., 1h.2f.3b.4f.5i.,
1j.2f.3b.4f.5i., 1p.2f.3b.4f.5i., 1a.2i.3b.4f.5i., 1b.2i.3b.4f.5i.,
1f.2i.3b.4f.5i., 1h.2i.3b.4f.5i., 1j.2i.3b.4f.5i., 1p.2i.3b.4f.5i.,
1a.2m.3b.4f.5i., 1b.2m.3b.4f.5i., 1f.2m.3b.4f.5i., 1h.2m.3b.4f.5i.,
1j.2m.3b.4f.5i., 1p.2m.3b.4f.5i., 1a.2o.3b.4f.5i., 1b.2o.3b.4f.5i.,
1f.2o.3b.4f.5i., 1h.2o.3b.4f.5i., 1j.2o.3b.4f.5i., 1p.2o.3b.4f.5i.,

TABLE 12-continued

List of Compound Structures of Formula III 1a.2u.3b.4f.5i., 1b.2u.3b.4f.5i., 1f.2u.3b.4f.5i., 1h.2u.3b.4f.5i.,
1j.2u.3b.4f.5i., 1p.2u.3b.4f.5i., 1a.2y.3b.4f.5i., 1b.2y.3b.4f.5i.,
1f.2y.3b.4f.5i., 1h.2y.3b.4f.5i., 1j.2y.3b.4f.5i., 1p.2y.3b.4f.5i.,
1a.2a.3e.4f.5i., 1b.2a.3e.4f.5i., 1f.2a.3e.4f.5i., 1h.2a.3e.4f.5i.,
1j.2a.3e.4f.5i., 1p.2a.3e.4f.5i., 1a.2b.3e.4f.5i., 1b.2b.3e.4f.5i.,
1f.2b.3e.4f.5i., 1h.2b.3e.4f.5i., 1j.2b.3e.4f.5i., 1p.2b.3e.4f.5i.,
1a.2e.3e.4f.5i., 1b.2e.3e.4f.5i., 1f.2e.3e.4f.5i., 1h.2e.3e.4f.5i.,
1j.2e.3e.4f.5i., 1p.2e.3e.4f.5i., 1a.2f.3e.4f.5i., 1b.2f.3e.4f.5i.,
1f.2f.3e.4f.5i., 1h.2f.3e.4f.5i., 1j.2f.3e.4f.5i., 1p.2f.3e.4f.5i.,
1a.2i.3e.4f.5i., 1b.2i.3e.4f.5i., 1f.2i.3e.4f.5i., 1h.2i.3e.4f.5i.,
1j.2i.3e.4f.5i., 1p.2i.3e.4f.5i., 1a.2m.3e.4f.5i., 1b.2m.3e.4f.5i.,
1f.2m.3e.4f.5i., 1h.2m.3e.4f.5i., 1j.2m.3e.4f.5i., 1p.2m.3e.4f.5i.,
1a.2o.3e.4f.5i., 1b.2o.3e.4f.5i., 1f.2o.3e.4f.5i., 1h.2o.3e.4f.5i.,
1j.2o.3e.4f.5i., 1p.2o.3e.4f.5i., 1a.2u.3e.4f.5i., 1b.2u.3e.4f.5i.,
1f.2u.3e.4f.5i., 1h.2u.3e.4f.5i., 1j.2u.3e.4f.5i., 1p.2u.3e.4f.5i.,
1a.2y.3e.4f.5i., 1b.2y.3e.4f.5i., 1f.2y.3e.4f.5i., 1h.2y.3e.4f.5i.,
1j.2y.3e.4f.5i., 1p.2y.3e.4f.5i., 1a.2a.3g.4f.5i., 1b.2a.3g.4f.5i.,
1f.2a.3g.4f.5i., 1h.2a.3g.4f.5i., 1j.2a.3g.4f.5i., 1p.2a.3g.4f.5i.,
1a.2b.3g.4f.5i., 1b.2b.3g.4f.5i., 1f.2b.3g.4f.5i., 1h.2b.3g.4f.5i.,
1j.2b.3g.4f.5i., 1p.2b.3g.4f.5i., 1a.2e.3g.4f.5i., 1b.2e.3g.4f.5i.,
1f.2e.3g.4f.5i., 1h.2e.3g.4f.5i., 1j.2e.3g.4f.5i., 1p.2e.3g.4f.5i.,
1a.2f.3g.4f.5i., 1b.2f.3g.4f.5i., 1f.2f.3g.4f.5i., 1h.2f.3g.4f.5i.,
1j.2f.3g.4f.5i., 1p.2f.3g.4f.5i., 1a.2i.3g.4f.5i., 1b.2i.3g.4f.5i.,
1f.2i.3g.4f.5i., 1h.2i.3g.4f.5i., 1j.2i.3g.4f.5i., 1p.2i.3g.4f.5i.,
1a.2m.3g.4f.5i., 1b.2m.3g.4f.5i., 1f.2m.3g.4f.5i., 1h.2m.3g.4f.5i.,
1j.2m.3g.4f.5i., 1p.2m.3g.4f.5i., 1a.2o.3g.4f.5i., 1b.2o.3g.4f.5i.,
1f.2o.3g.4f.5i., 1h.2o.3g.4f.5i., 1j.2o.3g.4f.5i., 1p.2o.3g.4f.5i.,
1a.2u.3g.4f.5i., 1b.2u.3g.4f.5i., 1f.2u.3g.4f.5i., 1h.2u.3g.4f.5i.,
1j.2u.3g.4f.5i., 1p.2u.3g.4f.5i., 1a.2y.3g.4f.5i., 1b.2y.3g.4f.5i.,
1f.2y.3g.4f.5i., 1h.2y.3g.4f.5i., 1j.2y.3g.4f.5i., 1p.2y.3g.4f.5i.,
1a.2a.3a.4g.5i., 1b.2a.3a.4g.5i., 1f.2a.3a.4g.5i., 1h.2a.3a.4g.5i.,
1j.2a.3a.4g.5i., 1p.2a.3a.4g.5i., 1a.2b.3a.4g.5i., 1b.2b.3a.4g.5i.,
1f.2b.3a.4g.5i., 1h.2b.3a.4g.5i., 1j.2b.3a.4g.5i., 1p.2b.3a.4g.5i.,
1a.2e.3a.4g.5i., 1b.2e.3a.4g.5i., 1f.2e.3a.4g.5i., 1h.2e.3a.4g.5i.,
1j.2e.3a.4g.5i., 1p.2e.3a.4g.5i., 1a.2f.3a.4g.5i., 1b.2f.3a.4g.5i.,
1f.2f.3a.4g.5i., 1h.2f.3a.4g.5i., 1j.2f.3a.4g.5i., 1p.2f.3a.4g.5i.,
1a.2i.3a.4g.5i., 1b.2i.3a.4g.5i., 1f.2i.3a.4g.5i., 1h.2i.3a.4g.5i.,
1j.2i.3a.4g.5i., 1p.2i.3a.4g.5i., 1a.2m.3a.4g.5i., 1b.2m.3a.4g.5i.,
1f.2m.3a.4g.5i., 1h.2m.3a.4g.5i., 1j.2m.3a.4g.5i., 1p.2m.3a.4g.5i.,
1a.2o.3a.4g.5i., 1b.2o.3a.4g.5i., 1f.2o.3a.4g.5i., 1h.2o.3a.4g.5i.,
1j.2o.3a.4g.5i., 1p.2o.3a.4g.5i., 1a.2u.3a.4g.5i., 1b.2u.3a.4g.5i.,
1f.2u.3a.4g.5i., 1h.2u.3a.4g.5i., 1j.2u.3a.4g.5i., 1p.2u.3a.4g.5i.,
1a.2y.3a.4g.5i., 1b.2y.3a.4g.5i., 1f.2y.3a.4g.5i., 1h.2y.3a.4g.5i.,
1j.2y.3a.4g.5i., 1p.2y.3a.4g.5i., 1a.2a.3b.4g.5i., 1b.2a.3b.4g.5i.,
1f.2a.3b.4g.5i., 1h.2a.3b.4g.5i., 1j.2a.3b.4g.5i., 1p.2a.3b.4g.5i.,
1a.2b.3b.4g.5i., 1b.2b.3b.4g.5i., 1f.2b.3b.4g.5i., 1h.2b.3b.4g.5i.,
1j.2b.3b.4g.5i., 1p.2b.3b.4g.5i., 1a.2e.3b.4g.5i., 1b.2e.3b.4g.5i.,
1f.2e.3b.4g.5i., 1h.2e.3b.4g.5i., 1j.2e.3b.4g.5i., 1p.2e.3b.4g.5i.,
1a.2f.3b.4g.5i., 1b.2f.3b.4g.5i., 1f.2f.3b.4g.5i., 1h.2f.3b.4g.5i.,
1j.2f.3b.4g.5i., 1p.2f.3b.4g.5i., 1a.2i.3b.4g.5i., 1b.2i.3b.4g.5i.,
1f.2i.3b.4g.5i., 1h.2i.3b.4g.5i., 1j.2i.3b.4g.5i., 1p.2i.3b.4g.5i.,
1a.2m.3b.4g.5i., 1b.2m.3b.4g.5i., 1f.2m.3b.4g.5i., 1h.2m.3b.4g.5i.,
1j.2m.3b.4g.5i., 1p.2m.3b.4g.5i., 1a.2o.3b.4g.5i., 1b.2o.3b.4g.5i.,
1f.2o.3b.4g.5i., 1h.2o.3b.4g.5i., 1j.2o.3b.4g.5i., 1p.2o.3b.4g.5i.,
1a.2u.3b.4g.5i., 1b.2u.3b.4g.5i., 1f.2u.3b.4g.5i., 1h.2u.3b.4g.5i.,
1j.2u.3b.4g.5i., 1p.2u.3b.4g.5i., 1a.2y.3b.4g.5i., 1b.2y.3b.4g.5i.,
1f.2y.3b.4g.5i., 1h.2y.3b.4g.5i., 1j.2y.3b.4g.5i., 1p.2y.3b.4g.5i.,
1a.2a.3e.4g.5i., 1b.2a.3e.4g.5i., 1f.2a.3e.4g.5i., 1h.2a.3e.4g.5i.,
1j.2a.3e.4g.5i., 1p.2a.3e.4g.5i., 1a.2b.3e.4g.5i., 1b.2b.3e.4g.5i.,
1f.2b.3e.4g.5i., 1h.2b.3e.4g.5i., 1j.2b.3e.4g.5i., 1p.2b.3e.4g.5i.,
1a.2e.3e.4g.5i., 1b.2e.3e.4g.5i., 1f.2e.3e.4g.5i., 1h.2e.3e.4g.5i.,
1j.2e.3e.4g.5i., 1p.2e.3e.4g.5i., 1a.2f.3e.4g.5i., 1b.2f.3e.4g.5i.,
1f.2f.3e.4g.5i., 1h.2f.3e.4g.5i., 1j.2f.3e.4g.5i., 1p.2f.3e.4g.5i.,
1a.2i.3e.4g.5i., 1b.2i.3e.4g.5i., 1f.2i.3e.4g.5i., 1h.2i.3e.4g.5i.,
1j.2i.3e.4g.5i., 1p.2i.3e.4g.5i., 1a.2m.3e.4g.5i., 1b.2m.3e.4g.5i.,
1f.2m.3e.4g.5i., 1h.2m.3e.4g.5i., 1j.2m.3e.4g.5i., 1p.2m.3e.4g.5i.,
1a.2o.3e.4g.5i., 1b.2o.3e.4g.5i., 1f.2o.3e.4g.5i., 1h.2o.3e.4g.5i.,
1j.2o.3e.4g.5i., 1p.2o.3e.4g.5i., 1a.2u.3e.4g.5i., 1b.2u.3e.4g.5i.,
1f.2u.3e.4g.5i., 1h.2u.3e.4g.5i., 1j.2u.3e.4g.5i., 1p.2u.3e.4g.5i.,
1a.2y.3e.4g.5i., 1b.2y.3e.4g.5i., 1f.2y.3e.4g.5i., 1h.2y.3e.4g.5i.,
1j.2y.3e.4g.5i., 1p.2y.3e.4g.5i., 1a.2a.3g.4g.5i., 1b.2a.3g.4g.5i.,
1f.2a.3g.4g.5i., 1h.2a.3g.4g.5i., 1j.2a.3g.4g.5i., 1p.2a.3g.4g.5i.,
1a.2b.3g.4g.5i., 1b.2b.3g.4g.5i., 1f.2b.3g.4g.5i., 1h.2b.3g.4g.5i.,
1j.2b.3g.4g.5i., 1p.2b.3g.4g.5i., 1a.2e.3g.4g.5i., 1b.2e.3g.4g.5i.,
1f.2e.3g.4g.5i., 1h.2e.3g.4g.5i., 1j.2e.3g.4g.5i., 1p.2e.3g.4g.5i.,
1a.2f.3g.4g.5i., 1b.2f.3g.4g.5i., 1f.2f.3g.4g.5i., 1h.2f.3g.4g.5i.,
1j.2f.3g.4g.5i., 1p.2f.3g.4g.5i., 1a.2i.3g.4g.5i., 1b.2i.3g.4g.5i.,
1f.2i.3g.4g.5i., 1h.2i.3g.4g.5i., 1j.2i.3g.4g.5i., 1p.2i.3g.4g.5i.,
1a.2m.3g.4g.5i., 1b.2m.3g.4g.5i., 1f.2m.3g.4g.5i., 1h.2m.3g.4g.5i.,
1j.2m.3g.4g.5i., 1p.2m.3g.4g.5i., 1a.2o.3g.4g.5i., 1b.2o.3g.4g.5i.,
1f.2o.3g.4g.5i., 1h.2o.3g.4g.5i., 1j.2o.3g.4g.5i., 1p.2o.3g.4g.5i.,
1a.2u.3g.4g.5i., 1b.2u.3g.4g.5i., 1f.2u.3g.4g.5i., 1h.2u.3g.4g.5i.,
1j.2u.3g.4g.5i., 1p.2u.3g.4g.5i., 1a.2y.3g.4g.5i., 1b.2y.3g.4g.5i.,
1f.2y.3g.4g.5i., 1h.2y.3g.4g.5i., 1j.2y.3g.4g.5i., 1p.2y.3g.4g.5i.,
1a.2a.3a.4h.5i., 1b.2a.3a.4h.5i., 1f.2a.3a.4h.5i., 1h.2a.3a.4h.5i.,
1j.2a.3a.4h.5i., 1p.2a.3a.4h.5i., 1a.2b.3a.4h.5i., 1b.2b.3a.4h.5i.,
1f.2b.3a.4h.5i., 1h.2b.3a.4h.5i., 1j.2b.3a.4h.5i., 1p.2b.3a.4h.5i.,
1a.2e.3a.4h.5i., 1b.2e.3a.4h.5i., 1f.2e.3a.4h.5i., 1h.2e.3a.4h.5i.,
1j.2e.3a.4h.5i., 1p.2e.3a.4h.5i., 1a.2f.3a.4h.5i., 1b.2f.3a.4h.5i.,
1f.2f.3a.4h.5i., 1h.2f.3a.4h.5i., 1j.2f.3a.4h.5i., 1p.2f.3a.4h.5i.,
1a.2i.3a.4h.5i., 1b.2i.3a.4h.5i., 1f.2i.3a.4h.5i., 1h.2i.3a.4h.5i.,
1j.2i.3a.4h.5i., 1p.2i.3a.4h.5i., 1a.2m.3a.4h.5i., 1b.2m.3a.4h.5i.,
1f.2m.3a.4h.5i., 1h.2m.3a.4h.5i., 1j.2m.3a.4h.5i., 1p.2m.3a.4h.5i.,
1a.2o.3a.4h.5i., 1b.2o.3a.4h.5i., 1f.2o.3a.4h.5i., 1h.2o.3a.4h.5i.,
1j.2o.3a.4h.5i., 1p.2o.3a.4h.5i., 1a.2u.3a.4h.5i., 1b.2u.3a.4h.5i.,
1f.2u.3a.4h.5i., 1h.2u.3a.4h.5i., 1j.2u.3a.4h.5i., 1p.2u.3a.4h.5i.,
1a.2y.3a.4h.5i., 1b.2y.3a.4h.5i., 1f.2y.3a.4h.5i., 1h.2y.3a.4h.5i.,
1j.2y.3a.4h.5i., 1p.2y.3a.4h.5i., 1a.2a.3b.4h.5i., 1b.2a.3b.4h.5i.,
1f.2a.3b.4h.5i., 1h.2a.3b.4h.5i., 1j.2a.3b.4h.5i., 1p.2a.3b.4h.5i.,
1a.2b.3b.4h.5i., 1b.2b.3b.4h.5i., 1f.2b.3b.4h.5i., 1h.2b.3b.4h.5i.,
1j.2b.3b.4h.5i., 1p.2b.3b.4h.5i., 1a.2e.3b.4h.5i., 1b.2e.3b.4h.5i.,
1f.2e.3b.4h.5i., 1h.2e.3b.4h.5i., 1j.2e.3b.4h.5i., 1p.2e.3b.4h.5i.,
1a.2f.3b.4h.5i., 1b.2f.3b.4h.5i., 1f.2f.3b.4h.5i., 1h.2f.3b.4h.5i.,
1j.2f.3b.4h.5i., 1p.2f.3b.4h.5i., 1a.2i.3b.4h.5i., 1b.2i.3b.4h.5i.,
1f.2i.3b.4h.5i., 1h.2i.3b.4h.5i., 1j.2i.3b.4h.5i., 1p.2i.3b.4h.5i.,
1a.2m.3b.4h.5i., 1b.2m.3b.4h.5i., 1f.2m.3b.4h.5i., 1h.2m.3b.4h.5i.,
1j.2m.3b.4h.5i., 1p.2m.3b.4h.5i., 1a.2o.3b.4h.5i., 1b.2o.3b.4h.5i.,
1f.2o.3b.4h.5i., 1h.2o.3b.4h.5i., 1j.2o.3b.4h.5i., 1p.2o.3b.4h.5i.,
1a.2u.3b.4h.5i., 1b.2u.3b.4h.5i., 1f.2u.3b.4h.5i., 1h.2u.3b.4h.5i.,
1j.2u.3b.4h.5i., 1p.2u.3b.4h.5i., 1a.2y.3b.4h.5i., 1b.2y.3b.4h.5i.,
1f.2y.3b.4h.5i., 1h.2y.3b.4h.5i., 1j.2y.3b.4h.5i., 1p.2y.3b.4h.5i.,
1a.2a.3e.4h.5i., 1b.2a.3e.4h.5i., 1f.2a.3e.4h.5i., 1h.2a.3e.4h.5i.,
1j.2a.3e.4h.5i., 1p.2a.3e.4h.5i., 1a.2b.3e.4h.5i., 1b.2b.3e.4h.5i.,
1f.2b.3e.4h.5i., 1h.2b.3e.4h.5i., 1j.2b.3e.4h.5i., 1p.2b.3e.4h.5i.,
1a.2e.3e.4h.5i., 1b.2e.3e.4h.5i., 1f.2e.3e.4h.5i., 1h.2e.3e.4h.5i.,
1j.2e.3e.4h.5i., 1p.2e.3e.4h.5i., 1a.2f.3e.4h.5i., 1b.2f.3e.4h.5i.,
1f.2f.3e.4h.5i., 1h.2f.3e.4h.5i., 1j.2f.3e.4h.5i., 1p.2f.3e.4h.5i.,
1a.2i.3e.4h.5i., 1b.2i.3e.4h.5i., 1f.2i.3e.4h.5i., 1h.2i.3e.4h.5i.,
1j.2i.3e.4h.5i., 1p.2i.3e.4h.5i., 1a.2m.3e.4h.5i., 1b.2m.3e.4h.5i.,
1f.2m.3e.4h.5i., 1h.2m.3e.4h.5i., 1j.2m.3e.4h.5i., 1p.2m.3e.4h.5i.,
1a.2o.3e.4h.5i., 1b.2o.3e.4h.5i., 1f.2o.3e.4h.5i., 1h.2o.3e.4h.5i.,
1j.2o.3e.4h.5i., 1p.2o.3e.4h.5i., 1a.2u.3e.4h.5i., 1b.2u.3e.4h.5i.,
1f.2u.3e.4h.5i., 1h.2u.3e.4h.5i., 1j.2u.3e.4h.5i., 1p.2u.3e.4h.5i.,
1a.2y.3e.4h.5i., 1b.2y.3e.4h.5i., 1f.2y.3e.4h.5i., 1h.2y.3e.4h.5i.,
1j.2y.3e.4h.5i., 1p.2y.3e.4h.5i., 1a.2a.3g.4h.5i., 1b.2a.3g.4h.5i.,
1f.2a.3g.4h.5i., 1h.2a.3g.4h.5i., 1j.2a.3g.4h.5i., 1p.2a.3g.4h.5i.,
1a.2b.3g.4h.5i., 1b.2b.3g.4h.5i., 1f.2b.3g.4h.5i., 1h.2b.3g.4h.5i.,
1j.2b.3g.4h.5i., 1p.2b.3g.4h.5i., 1a.2e.3g.4h.5i., 1b.2e.3g.4h.5i.,
1f.2e.3g.4h.5i., 1h.2e.3g.4h.5i., 1j.2e.3g.4h.5i., 1p.2e.3g.4h.5i.,
1a.2f.3g.4h.5i., 1b.2f.3g.4h.5i., 1f.2f.3g.4h.5i., 1h.2f.3g.4h.5i.,
1j.2f.3g.4h.5i., 1p.2f.3g.4h.5i., 1a.2i.3g.4h.5i., 1b.2i.3g.4h.5i.,
1f.2i.3g.4h.5i., 1h.2i.3g.4h.5i., 1j.2i.3g.4h.5i., 1p.2i.3g.4h.5i.,
1a.2m.3g.4h.5i., 1b.2m.3g.4h.5i., 1f.2m.3g.4h.5i., 1h.2m.3g.4h.5i.,
1j.2m.3g.4h.5i., 1p.2m.3g.4h.5i., 1a.2o.3g.4h.5i., 1b.2o.3g.4h.5i.,
1f.2o.3g.4h.5i., 1h.2o.3g.4h.5i., 1j.2o.3g.4h.5i., 1p.2o.3g.4h.5i.,
1a.2u.3g.4h.5i., 1b.2u.3g.4h.5i., 1f.2u.3g.4h.5i., 1h.2u.3g.4h.5i.,
1j.2u.3g.4h.5i., 1p.2u.3g.4h.5i., 1a.2y.3g.4h.5i., 1b.2y.3g.4h.5i.,
1f.2y.3g.4h.5i., 1h.2y.3g.4h.5i., 1j.2y.3g.4h.5i., 1p.2y.3g.4h.5i.,
1a.2a.3a.4i.5i., 1b.2a.3a.4i.5i., 1f.2a.3a.4i.5i., 1h.2a.3a.4i.5i.,
1j.2a.3a.4i.5i., 1p.2a.3a.4i.5i., 1a.2b.3a.4i.5i., 1b.2b.3a.4i.5i.,
1f.2b.3a.4i.5i., 1h.2b.3a.4i.5i., 1j.2b.3a.4i.5i., 1p.2b.3a.4i.5i.,
1a.2e.3a.4i.5i., 1b.2e.3a.4i.5i., 1f.2e.3a.4i.5i., 1h.2e.3a.4i.5i.,
1j.2e.3a.4i.5i., 1p.2e.3a.4i.5i., 1a.2f.3a.4i.5i., 1b.2f.3a.4i.5i.,
1f.2f.3a.4i.5i., 1h.2f.3a.4i.5i., 1j.2f.3a.4i.5i., 1p.2f.3a.4i.5i.,
1a.2i.3a.4i.5i., 1b.2i.3a.4i.5i., 1f.2i.3a.4i.5i., 1h.2i.3a.4i.5i.,
1j.2i.3a.4i.5i., 1p.2i.3a.4i.5i., 1a.2m.3a.4i.5i., 1b.2m.3a.4i.5i.,
1f.2m.3a.4i.5i., 1h.2m.3a.4i.5i., 1j.2m.3a.4i.5i., 1p.2m.3a.4i.5i.,
1a.2o.3a.4i.5i., 1b.2o.3a.4i.5i., 1f.2o.3a.4i.5i., 1h.2o.3a.4i.5i.,
1j.2o.3a.4i.5i., 1p.2o.3a.4i.5i., 1a.2u.3a.4i.5i., 1b.2u.3a.4i.5i.,
1f.2u.3a.4i.5i., 1h.2u.3a.4i.5i., 1j.2u.3a.4i.5i., 1p.2u.3a.4i.5i.,
1a.2y.3a.4i.5i., 1b.2y.3a.4i.5i., 1f.2y.3a.4i.5i., 1h.2y.3a.4i.5i.,
1j.2y.3a.4i.5i., 1p.2y.3a.4i.5i., 1a.2a.3b.4i.5i., 1b.2a.3b.4i.5i.,
1f.2a.3b.4i.5i., 1h.2a.3b.4i.5i., 1j.2a.3b.4i.5i., 1p.2a.3b.4i.5i.,
1a.2b.3b.4i.5i., 1b.2b.3b.4i.5i., 1f.2b.3b.4i.5i., 1h.2b.3b.4i.5i.,
1j.2b.3b.4i.5i., 1p.2b.3b.4i.5i., 1a.2e.3b.4i.5i., 1b.2e.3b.4i.5i.,
1f.2e.3b.4i.5i., 1h.2e.3b.4i.5i., 1j.2e.3b.4i.5i., 1p.2e.3b.4i.5i.,

TABLE 12-continued

List of Compound Structures of Formula III 1a.2f.3b.4i.5i., 1b.2f.3b.4i.5i., 1f.2f.3b.4i.5i., 1h.2f.3b.4i.5i.,
1j.2f.3b.4i.5i., 1p.2f.3b.4i.5i., 1a.2i.3b.4i.5i., 1b.2i.3b.4i.5i.,
1f.2i.3b.4i.5i., 1h.2i.3b.4i.5i., 1j.2i.3b.4i.5i., 1p.2i.3b.4i.5i.,
1a.2m.3b.4i.5i., 1b.2m.3b.4i.5i., 1f.2m.3b.4i.5i., 1h.2m.3b.4i.5i.,
1j.2m.3b.4i.5i., 1p.2m.3b.4i.5i., 1a.2o.3b.4i.5i., 1b.2o.3b.4i.5i.,
1f.2o.3b.4i.5i., 1h.2o.3b.4i.5i., 1j.2o.3b.4i.5i., 1p.2o.3b.4i.5i.,
1a.2u.3b.4i.5i., 1b.2u.3b.4i.5i., 1f.2u.3b.4i.5i., 1h.2u.3b.4i.5i.,
1j.2u.3b.4i.5i., 1p.2u.3b.4i.5i., 1a.2y.3b.4i.5i., 1b.2y.3b.4i.5i.,
1f.2y.3b.4i.5i., 1h.2y.3b.4i.5i., 1j.2y.3b.4i.5i., 1p.2y.3b.4i.5i.,
1a.2a.3e.4i.5i., 1b.2a.3e.4i.5i., 1f.2a.3e.4i.5i., 1h.2a.3e.4i.5i.,
1j.2a.3e.4i.5i., 1p.2a.3e.4i.5i., 1a.2b.3e.4i.5i., 1b.2b.3e.4i.5i.,
1f.2b.3e.4i.5i., 1h.2b.3e.4i.5i., 1j.2b.3e.4i.5i., 1p.2b.3e.4i.5i.,
1a.2e.3e.4i.5i., 1b.2e.3e.4i.5i., 1f.2e.3e.4i.5i., 1h.2e.3e.4i.5i.,
1j.2e.3e.4i.5i., 1p.2e.3e.4i.5i., 1a.2f.3e.4i.5i., 1b.2f.3e.4i.5i.,
1f.2f.3e.4i.5i., 1h.2f.3e.4i.5i., 1j.2f.3e.4i.5i., 1p.2f.3e.4i.5i.,
1a.2i.3e.4i.5i., 1b.2i.3e.4i.5i., 1f.2i.3e.4i.5i., 1h.2i.3e.4i.5i.,
1j.2i.3e.4i.5i., 1p.2i.3e.4i.5i., 1a.2m.3e.4i.5i., 1b.2m.3e.4i.5i.,
1f.2m.3e.4i.5i., 1h.2m.3e.4i.5i., 1j.2m.3e.4i.5i., 1p.2m.3e.4i.5i.,
1a.2o.3e.4i.5i., 1b.2o.3e.4i.5i., 1f.2o.3e.4i.5i., 1h.2o.3e.4i.5i.,
1j.2o.3e.4i.5i., 1p.2o.3e.4i.5i., 1a.2u.3e.4i.5i., 1b.2u.3e.4i.5i.,
1f.2u.3e.4i.5i., 1h.2u.3e.4i.5i., 1j.2u.3e.4i.5i., 1p.2u.3e.4i.5i.,
1a.2y.3e.4i.5i., 1b.2y.3e.4i.5i., 1f.2y.3e.4i.5i., 1h.2y.3e.4i.5i.,
1j.2y.3e.4i.5i., 1p.2y.3e.4i.5i., 1a.2a.3g.4i.5i., 1b.2a.3g.4i.5i.,
1f.2a.3g.4i.5i., 1h.2a.3g.4i.5i., 1j.2a.3g.4i.5i., 1p.2a.3g.4i.5i.,
1a.2b.3g.4i.5i., 1b.2b.3g.4i.5i., 1f.2b.3g.4i.5i., 1h.2b.3g.4i.5i.,
1j.2b.3g.4i.5i., 1p.2b.3g.4i.5i., 1a.2e.3g.4i.5i., 1b.2e.3g.4i.5i.,
1f.2e.3g.4i.5i., 1h.2e.3g.4i.5i., 1j.2e.3g.4i.5i., 1p.2e.3g.4i.5i.,
1a.2f.3g.4i.5i., 1b.2f.3g.4i.5i., 1f.2f.3g.4i.5i., 1h.2f.3g.4i.5i.,
1j.2f.3g.4i.5i., 1p.2f.3g.4i.5i., 1a.2i.3g.4i.5i., 1b.2i.3g.4i.5i.,
1f.2i.3g.4i.5i., 1h.2i.3g.4i.5i., 1j.2i.3g.4i.5i., 1p.2i.3g.4i.5i.,
1a.2m.3g.4i.5i., 1b.2m.3g.4i.5i., 1f.2m.3g.4i.5i., 1h.2m.3g.4i.5i.,
1j.2m.3g.4i.5i., 1p.2m.3g.4i.5i., 1a.2o.3g.4i.5i., 1b.2o.3g.4i.5i.,
1f.2o.3g.4i.5i., 1h.2o.3g.4i.5i., 1j.2o.3g.4i.5i., 1p.2o.3g.4i.5i.,
1a.2u.3g.4i.5i., 1b.2u.3g.4i.5i., 1f.2u.3g.4i.5i., 1h.2u.3g.4i.5i.,
1j.2u.3g.4i.5i., 1p.2u.3g.4i.5i., 1a.2y.3g.4i.5i., 1b.2y.3g.4i.5i.,
1f.2y.3g.4i.5i., 1h.2y.3g.4i.5i., 1j.2y.3g.4i.5i., and 1p.2y.3g.4i.5i.

In one embodiment, the present application provides compounds according to Formula IV:

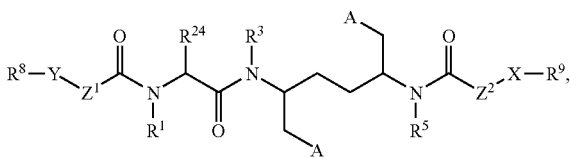

Formula IV or a pharmaceutically acceptable salt, solvate, and/or ester thereof, wherein:

each A is independently aryl or heterocyclyl;

$Z^1$ and $Z^2$ are each independently —O— or —N($R^7$)—;

X and Y are each independently aryl, arylalkyl, heterocyclyl, or heterocyclylalkyl;

$R^1$, $R^3$, and $R^5$ are each independently selected from the group consisting of H, alkyl, substituted alkyl, arylalkyl, and substituted arylalkyl;

each $R^7$ is independently selected from the group consisting of H, alkyl, substituted alkyl, heteroalkyl, substituted heteroalkyl, carbocyclyl, substituted carbocyclyl, heterocyclyl, and substituted heterocyclyl;

$R^8$ and $R^9$ are each one or more substituents independently selected from the group consisting of H, alkyl, halogen, aryl, heterocyclyl, and CN; and $R^{24}$ is selected from the group consisting of -alkylene-$NR^5$—C(O)—$R^{25}$, -alkylene-C(O)—$NR^5$—$R^{26}$, -alkylene-N($R^{27})_2$, —$CH_2$-heterocyclyl, and substituted —$CH_2$-heterocyclyl;

$R^{25}$ is alkyl, heterocyclylalkyl, or substituted heterocyclylalkyl;

$R^{26}$ is a substituted or unsubstituted heterocyclyl; or $R^5$ and $R^{26}$ together with the nitrogen atom to which they are both shown attached, form a substituted or unsubstituted bicyclic heterocyclyl;

each $R^{27}$ is independently a substituted alkyl which may be the same or different; or each $R^{27}$, together with the nitrogen atom to which they are both shown attached, form a substituted or unsubstituted bicyclic heterocyclyl;

with the following provisos:

(i) when X and Y are both thiazolylmethyl, $Z^1$ is —N($R^7$)—, $Z^2$ is —O—, each A is phenyl, and $R^{24}$ is —$CH_2CH_2$—$NR^5$—C(O)-alkyl, then each $R^8$ and $R^9$ are H; and (ii) when X and Y are both thiazolylmethyl, $Z^1$ is —N($R^7$)—, $Z^2$ is —O—, each A is phenyl, and $R^{24}$ is —$CH_2$—C(O)—$NR^5$-pyridyl or —$CH_2$—C(O)—$NR^5$-pyrrolidinyl, then $R^5$ is alkyl, substituted alkyl, arylalkyl, or substituted arylalkyl; and (iii) when X and Y are both thiazolylmethyl, $Z^1$ is —N($R^7$)—, $Z^2$ is —O—, each A is phenyl, and $R^{24}$ is substituted or unsubstituted —$CH_2$-heterocyclyl, then said substituted or unsubstituted —$CH_2$-heterocyclyl is not pyridylmethyl, pyrazolylmethyl, imidazolidine-2,4-ione-5-yl-methyl, imidazolylmethyl, or morpholinylmethyl.

In one embodiment of the compounds of Formula IV, each A is independently aryl, substituted aryl, heterocyclyl, or substituted heterocyclyl. When A is aryl, said aryl includes any aryl defined or exemplified herein. When A is heterocyclyl, said heterocyclyl includes any heterocyclyl defined or exemplified herein.

In still another embodiment of the compounds of Formula IV, each A is substituted or unsubstituted aryl, wherein aryl is any aryl defined or exemplified herein, and, when present, the substituents on said aryl include one or more of any substituents defined or exemplified herein. In a particular embodiment, each A is phenyl. In another particular embodiment, each A is unsubstituted phenyl.

In still another embodiment of the compounds of Formula IV, each A is substituted or unsubstituted heterocyclyl, wherein heterocyclyl is any heterocyclyl defined or exemplified herein, and, when present, the substituents on said heterocyclyl include one or more of any substituents defined or exemplified herein.

In still another embodiment of the compounds of Formula IV, one A is substituted or unsubstituted aryl and the other A is substituted or unsubstituted heterocyclyl, wherein aryl is any aryl defined or exemplified herein, and the substituents on said aryl are any substituents defined and exemplified herein, and wherein heterocyclyl is any heterocyclyl defined or exemplified herein, and the substituents on said heterocyclyl are any substituents defined and exemplified herein. In a particular embodiment, one A is phenyl.

In still another embodiment of the compounds of Formula IV, $Z^1$ is —O— or —N($R^7$)—. When $Z^1$ is —N($R^7$)—, $R^7$ is H, alkyl, substituted alkyl, heteroalkyl, substituted heteroalkyl, carbocyclyl, substituted carbocyclyl, heterocyclyl, or substituted heterocyclyl, wherein alkyl, substituted alkyl, heteroalkyl, substituted heteroalkyl, carbocyclyl, substituted carbocyclyl, heterocyclyl, and substituted heterocyclyl are any alkyl, substituted alkyl, heteroalkyl, substituted heteroalkyl, carbocyclyl, substituted carbocyclyl, heterocyclyl, or substituted heterocyclyl defined or exemplified herein.

In still another embodiment of the compounds of Formula IV, $Z^2$ is —O— or —N($R^7$)—. When $Z^1$ is —N($R^7$)—, $R^7$ is H, alkyl, substituted alkyl, heteroalkyl, substituted heteroalkyl, carbocyclyl, substituted carbocyclyl, heterocyclyl, or substituted heterocyclyl, wherein alkyl, substituted alkyl, heteroalkyl, substituted heteroalkyl, carbocyclyl, substituted carbocyclyl, heterocyclyl, and substituted heterocyclyl are any alkyl, substituted alkyl, heteroalkyl, substituted heteroalkyl, carbocyclyl, substituted carbocyclyl, heterocyclyl, or substituted heterocyclyl defined or exemplified herein.

In still another embodiment of the compounds of Formula IV, $Z^1$ and $Z^2$ are the same, e.g., $Z^1$ and $Z^2$ are both —O—, or $Z^1$ and $Z^2$ are both —N($R^7$)—, wherein $R^7$ is H, alkyl, substituted alkyl, heteroalkyl, substituted heteroalkyl, carbocyclyl, substituted carbocyclyl, heterocyclyl, or substituted heterocyclyl, wherein alkyl, substituted alkyl, heteroalkyl, substituted heteroalkyl, carbocyclyl, substituted carbocyclyl, heterocyclyl, and substituted heterocyclyl are any alkyl, substituted alkyl, heteroalkyl, substituted heteroalkyl, carbocyclyl, substituted carbocyclyl, heterocyclyl, or substituted heterocyclyl defined or exemplified herein.

In still another embodiment of the compounds of Formula IV, $Z^1$ and $Z^2$ are different, e.g. $Z^1$ is —O— and $Z^2$ is —N($R^7$)—, $Z^1$ is —N($R^7$)— and $Z^2$ is —O—, or $Z^1$ and $Z^2$ are both —N($R^7$)— but in $Z^1$ the $R^7$ is different from the $R^7$ in $Z^2$. When either $Z^1$ or $Z^2$ is —N($R^7$)—, $R^7$ is H, alkyl, or substituted alkyl, wherein alkyl or substituted alkyl are any alkyl or substituted alkyl defined or exemplified herein.

In still another embodiment of the compounds of Formula IV, Y is aryl or arylalkyl, wherein aryl and arylalkyl are any aryl or arylalkyl defined or exemplified herein.

In still another embodiment of the compounds of Formula IV, Y is heterocyclyl or heterocyclylalkyl, wherein heterocyclyl and heterocyclylalkyl are any heterocyclyl or heterocyclylalkyl defined or exemplified herein. In a particular embodiment, Y is heteroarylalkyl; e.g. thiazolylmethyl (e.g., 4- or 5-thiazolylmethyl).

In still another embodiment of the compounds of Formula IV, X is aryl or arylalkyl, wherein aryl and arylalkyl are any aryl or arylalkyl defined or exemplified herein.

In still another embodiment of the compounds of Formula IV, X is heterocyclyl or heterocyclylalkyl, wherein heterocyclyl and heterocyclylalkyl are any heterocyclyl or heterocyclylalkyl defined or exemplified herein. In a particular embodiment, X is heteroarylalkyl, e.g. thiazolylmethyl (e.g., 5-thiazolylmethyl).

In still another embodiment of the compounds of Formula IV, X and Y are the same, e.g., the same heterocyclylalkyl. In a particular embodiment, X and Y are both thiazolylmethyl (e.g., both are 5-thiazolylmethyl, or one of X and Y is 5-thiazolylmethyl and the other is 4-thiazolylmethyl).

In still another embodiment of the compounds of Formula IV, X and Y are different. For example, X and Y are different heterocyclyls, X and Y are different heterocyclylalkyls, X is heterocyclyl and Y is heterocyclylalkyl, or X is heterocyclylalkyl and Y is heterocyclyl, wherein heterocyclyl and heterocyclylalkyl are any heterocyclyl or heterocyclylalkyl defined or exemplified herein; X is arylalkyl and Y is heterocyclylalkyl, or X is heterocyclylalkyl and Y is arylalkyl; X and Y are different arylalkyls; X is arylalkyl and Y is aryl, or X is aryl and Y is arylalkyl.

In still another embodiment of the compounds of Formula IV, $R^1$, $R^3$, and $R^5$ are each independently H, alkyl, or substituted alkyl, wherein alkyl and substituted alkyl include any of the alkyl or substituted alkyls defined or disclosed herein.

In still another embodiment of the compounds of Formula IV, $R^1$, $R^3$, and $R^5$ are each the same. In a particular embodiment $R^1$, $R^3$, and $R^5$ are each H. In another particular embodiment $R^1$, $R^3$, and $R^5$ are each alkyl, e.g. one of the alkyl groups defined or disclosed herein. In another particular embodiment $R^1$, $R^3$, and $R^5$ are each arylalkyl, e.g. one of the arylalkyl groups defined or disclosed herein.

In still another embodiment of the compounds of Formula IV, $R^1$, $R^3$, and $R^5$ are each different.

In still another embodiment of the compounds of Formula IV, one of $R^1$, $R^3$, and $R^5$ is different from the other two groups. For example, $R^1$ is H while $R^3$ and $R^5$ are each alkyl.

In still another embodiment of the compounds of Formula IV, $R^8$ and $R^9$ are each one or more substituents independently selected from the group consisting of H, alkyl, substituted alkyl, halogen, aryl, substituted aryl, heterocyclyl, substituted heterocyclyl, and —CN, wherein when $R^8$ or $R^9$ are alkyl, substituted alkyl, halogen, aryl, substituted aryl, heterocyclyl, or substituted heterocyclyl, said alkyl, substituted alkyl, halogen, aryl, substituted aryl, heterocyclyl, or substituted heterocyclyl are any such groups defined or disclosed herein.

In still another embodiment of the compounds of Formula IV, $R^8$ and $R^9$ are the same. In a particular embodiment $R^8$ and $R^9$ are both H.

In still another embodiment of the compounds of Formula IV, $R^8$ and $R^9$ are different. In a particular embodiment, $R^8$ is alkyl (e.g., isopropyl) and $R^9$ is H.

In still another embodiment of the compounds of Formula IV, Y is arylalkyl and $R^8$ is H. In a particular embodiment, Y is benzyl and $R^8$ is H.

In still another embodiment of the compounds of Formula IV, Y is heterocyclylalkyl and $R^8$ is H. In a particular embodiment, Y is heteroarylalkyl (e.g., thiazolylmethyl) and $R^8$ is H.

In still another embodiment of the compounds of Formula IV, Y is heterocyclylalkyl and $R^8$ is alkyl. In a particular embodiment, Y is heteroarylalkyl (e.g., thiazolylmethyl) and $R^8$ is alkyl. In another particular embodiment, Y is heteroarylalkyl and $R^8$ is $C_{1-4}$ alkyl (e.g., isopropyl).

In still another embodiment of the compounds of Formula IV, X is heterocyclyl or heterocyclylalkyl and $R^9$ is H. In a particular embodiment, X is heterocyclylalkyl (e.g., thiazolylmethyl) and $R^9$ is H.

In still another embodiment of the compounds of Formula IV, X is heterocyclyl or heterocyclylalkyl and $R^9$ is alkyl. In a particular embodiment, X is heterocyclylalkyl (e.g., thiazolylmethyl) and $R^9$ is alkyl. In another particular embodiment, X is heterocyclylalkyl and $R^9$ is $C_{1-4}$ alkyl.

In still another embodiment of the compounds of Formula IV, $R^8$—Y is aryl or arylalkyl and $R^7$ is H. In another particular embodiment, $R^8$—Y is aryl or arylalkyl and $R^7$ is alkyl, e.g., substituted or unsubstituted $C_{1-4}$ alkyl.

In still another embodiment of the compounds of Formula V, $R^8$—Y is heterocyclyl or heterocyclylalkyl and $R^7$ is H. In another embodiment, $R^8$—Y is heterocyclyl or heterocyclylalkyl and $R^7$ is alkyl, e.g., substituted or unsubstituted $C_{1-4}$ alkyl. In a particular embodiment, $R^8$—Y is unsubstituted thiazolyl and $R^7$ is H. In another particular embodiment, $R^8$—Y is unsubstituted thiazolyl and $R^7$ is alkyl, e.g., substituted or unsubstituted $C_{1-4}$ alkyl. In another particular embodiment, Y is thiazolyl, $R^8$ is isopropyl, and $R^7$ is $C_{1-4}$ alkyl.

In still another embodiment of the compounds of Formula IV, $R^8$—Y is heterocyclyl or heterocyclylalkyl and $R^7$ is H. In a particular embodiment, $R^8$—Y is unsubstituted thiazolyl and $R^7$ is H. In another particular embodiment, Y is thiazolyl, $R^8$ is isopropyl, and $R^7$ is H.

In still another embodiment of the compounds of Formula IV, $R^{24}$ is -alkylene-$NR^5C(O)$—$R^{25}$, wherein $R^{25}$ is any alkyl, heterocyclylalkyl, or substituted heteroalkyl defined or exemplified herein, with the proviso that when X and Y are both thiazolylmethyl, $Z^1$ is —N($R^7$)—, $Z^2$ is —O—, each A is phenyl, and $R^{24}$ is —CH$_2$CH$_2$—NR$^5$—C(O)-alkyl, then each $R^8$ and $R^9$ are H. In another embodiment, $R^{24}$ is —(CH$_2$)$_{1-4}$NHC(O)—R$^{25}$. In another embodiment, $R^{24}$ is —(CH$_2$)$_2$NHC(O)-alkyl. In another embodiment, $R^{24}$ is —(CH$_2$)$_2$NHC(O)-heteroalkyl. In another embodiment, $R^{24}$ is —(CH$_2$)$_2$NHC(O)-aminoalkyl. In another embodiment, $R^{24}$ is (CH$_2$)$_2$NHC(O)-heterocyclylalkyl.

In still another embodiment of the compounds of Formula IV, $R^{24}$ is —(CH$_2$)$_2$NHC(O)-alkyl, $Z^1$ is —N($R^7$)—, $Z^2$ is —O—, and X and Y are both thiazolylmethyl.

In still another embodiment of the compounds of Formula IV, $R^{24}$ is -alkylene-C(O)NR$^5$R$^{26}$, wherein $R^{26}$ is any substituted or unsubstituted heterocyclyl defined or exemplified herein, with the proviso that when when X and Y are both thiazolylmethyl, $Z^1$ is —N($R^7$)—, $Z^2$ is —O—, each A is phenyl, and $R^{24}$ is —CH$_2$—C(O)—NR$^5$-pyridyl or —CH$_2$—C(O)—NR$^5$-pyrrolidinyl, then $R^5$ is alkyl, substituted alkyl, arylalkyl, or substituted arylalkyl. In another embodiment, $R^{24}$ is —(CH$_2$)$_{1-4}$C(O)NR$^5$R$^{26}$. In another embodiment, $R^{24}$ is —CH$_2$C(O)NR$^5$R$^{26}$. In another $R^5$ and $R^{26}$, together with the nitrogen atom to which they are both shown attached, form a substituted or unsubstituted bicyclic heterocyclyl. In a particular embodiment, the bicyclic heterocyclyl contains 1-4 nitrogen atoms. In another particular embodiment, the bicyclic heterocyclyl contains one aromatic ring. In another particular embodiment, the bicyclic heterocyclyl is substituted (e.g., —CF$_3$ or —CH$_3$).

In still another embodiment of the compounds of Formula IV, $R^{24}$ is —CH$_2$C(O)NR$^5$R$^{26}$, $Z^1$ is —N($R^7$)—, $Z^2$ is —O—, and X and Y are both thiazolylmethyl.

In still another embodiment of the compounds of Formula IV, $R^{24}$ is -alkylene-N(R$^{27}$)$_2$ wherein each $R^{27}$ is independently a substituted alkyl which may be the same or different; or each $R^{27}$, together with the nitrogen atom to which they are both shown attached, form a substituted or unsubstituted bicyclic heterocyclyl. In another embodiment, $R^{24}$ is —(CH$_2$)$_{1-4}$N(R$^{27}$)$_2$. In another embodiment, $R^{24}$ is —(CH$_2$)$_2$N(R$^{27}$)$_2$. In another embodiment, each $R^{27}$ is independently hydroxyalkyl or alkoxyalkyl. In another embodiment, each $R^{27}$, together with the nitrogen atom to which they are both shown attached, form a substituted or unsubstituted bicyclic heterocyclyl. In a particular embodiment, the bicyclic heterocyclyl contains 1-4 nitrogen atoms. In another particular embodiment, the bicyclic heterocyclyl contains one aromatic ring. In another particular embodiment, the bicyclic heterocyclyl is substituted (e.g., —CF$_3$ or —CH$_3$).

In another embodiment, $R^{24}$ is —(CH$_2$)$_2$N(R$^{27}$)$_2$, $Z^1$ is —N($R^7$)—, $Z^2$ is —O—, and X and Y are both thiazolylmethyl.

In still another embodiment of the compounds of Formula IV, $R^{24}$ is substituted or unsubstituted -alkylene-heterocyclyl, wherein heterocyclyl is any heterocyclyl defined or exemplified herein, with the provisos that when X and Y are both thiazolylmethyl, $Z^1$ is —N($R^7$)—, $Z^2$ is —O—, each A is phenyl, and $R^{24}$ is substituted or unsubstituted —CH$_2$-heterocyclyl, then the substituted or unsubstituted —CH$_2$-heterocyclyl is not pyridylmethyl, pyrazolylmethyl, imidazolidine-2,4-dione-5-yl-methyl imidazolylmethyl, or morpholinylmethyl. In another embodiment, $R^{24}$ is —CH$_2$-heteroaryl. In another embodiment, $R^{24}$ is —CH$_2$-heteroaryl. In a particular embodiment, the methylene of $R^{24}$ is bonded to a carbon atom of the heterocyclyl ring. In another embodiment, the heterocyclyl moiety is monocyclic. In another embodiment, the heterocyclyl moiety is bicyclic. In another embodiment, the heterocyclyl moiety contains from 1-2 heteroatoms selected from the group consisting of N and S.

In still another embodiment $R^{24}$ is —CH$_2$-heterocyclyl, $Z^1$ is —N($R^7$)—, $Z^2$ is —O—, and X and Y are both thiazolylmethyl.

In still another embodiment of the compounds of Formula IV, A is aryl; $R^{24}$ is -alkylene-NHC(O)-alkyl; $Z^1$ is —N($R^7$)—; $Z^2$ is —O—; and X and Y are both thiazolylmethyl.

In still another embodiment of the compounds of Formula IV, A is phenyl; $R^{24}$ is —(CH$_2$)$_2$NHC(O)-alkyl; $Z^1$ is —N($R^7$)—; $Z^2$ is —O—; and X and Y are both thiazolylmethyl.

In still another embodiment of the compounds of Formula IV, A is aryl; $R^{24}$ is -alkylene-C(O)NR$^5$R$^{26}$; $Z^1$ is —N($R^7$)—; $Z^2$ is —O—; and X and Y are both thiazolylmethyl.

In still another embodiment of the compounds of Formula IV, A is phenyl; $R^{24}$ is —CH$_2$C(O)NR$^5$R$^{26}$; $Z^1$ is —N($R^7$)—; $Z^2$ is —; and X and Y are both thiazolylmethyl.

In still another embodiment of the compounds of Formula IV, A is aryl; $R^{24}$ is -alkylene-N(R$^{27}$)$_2$; $Z^1$ is —N($R^7$)—; $Z^2$ is —O—; and X and Y are both thiazolylmethyl.

In still another embodiment of the compounds of Formula IV, A is phenyl; $R^{24}$ is —(CH$_2$)$_2$N(R$^{27}$)$_2$; $Z^1$ is —N($R^7$)—; $Z^2$ is —O—; and X and Y are both thiazolylmethyl.

In still another embodiment of the compounds of Formula IV, A is phenyl; $R^{24}$ is —CH$_2$-heteroaryl; $Z^1$ is —N($R^7$)—; $Z^2$ is —O—; and X and Y are both thiazolylmethyl.

In another embodiment, the compounds of Formula IV have the following general Formula IVA:

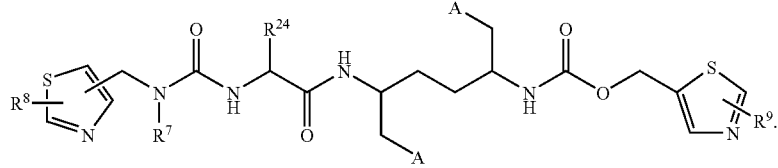

Formula IVA

In another embodiment of the compounds of Formula IVA, $R^{24}$ is —(CH$_2$)$_2$NHC(O)-alkyl. In a particular embodiment, each A is phenyl.

In another embodiment of the compounds of Formula IVA, $R^{24}$ is —CH$_2$C(O)NR$^5$R$^{26}$. In a particular embodiment, each A is phenyl.

In another embodiment of the compounds of Formula IVA, $R^{24}$ is —(CH$_2$)$_2$N(R$^{27}$)$_2$. In a particular embodiment, each A is phenyl.

In another embodiment of the compounds of Formula IVA, $R^{24}$ is substituted or unsubstituted —CH$_2$-heteroaryl. In a particular embodiment, each A is phenyl.

In another embodiment, the compounds of Formula IV have the following general Formula IVB:

Formula IVB

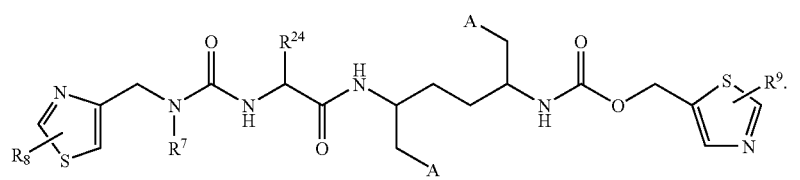

In another embodiment of the compounds of Formula IVB, $R^{24}$ is —$(CH_2)_2NHC(O)$-alkyl. In a particular embodiment, each A is phenyl.

In another embodiment of the compounds of Formula IVB, $R^{24}$ is —$CH_2C(O)NR^5R^{26}$. In a particular embodiment, each A is phenyl.

In another embodiment of the compounds of Formula IVB, $R^{24}$ is —$(CH_2)_2N(R^{27})_2$. In a particular embodiment, each A is phenyl.

In another embodiment of the compounds of Formula IVB, $R^{24}$ is —$CH_2$-heteroaryl. In a particular embodiment, each A is phenyl.

In another embodiment, the compounds of Formula IV have the following general Formula IVC:

Formula IVC

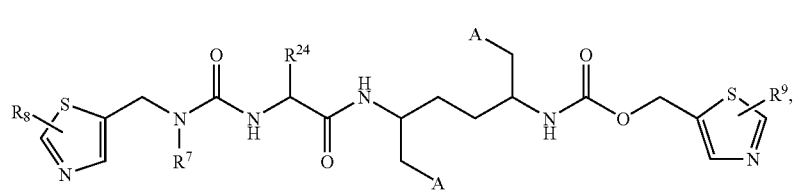

In another embodiment of the compounds of Formula IVC, $R^{24}$ is —$(CH_2)_2NHC(O)$-alkyl. In a particular embodiment, each A is phenyl.

In another embodiment of the compounds of Formula IVC, $R^{24}$ is —$CH_2C(O)NR^5R^{26}$. In a particular embodiment, each A is phenyl.

In another embodiment of the compounds of Formula IVC, $R^{24}$ is —$(CH_2)_2N(R^{27})_2$. In a particular embodiment, each A is phenyl.

In another embodiment of the compounds of Formula IVC, $R^{24}$ is —$CH_2$-heteroaryl. In a particular embodiment, each A is phenyl.

In another embodiment, the compounds of Formula IV have one of the following structures:

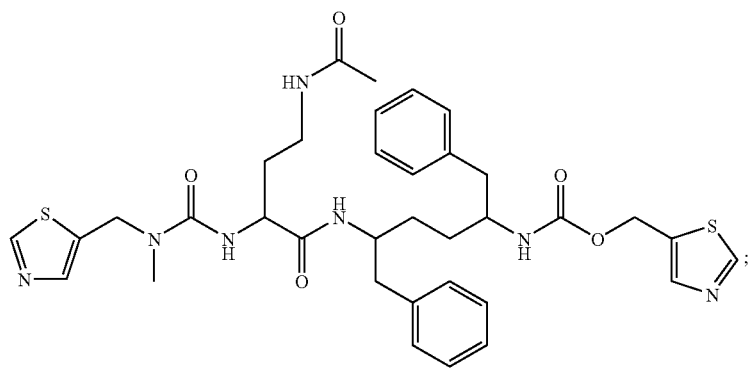

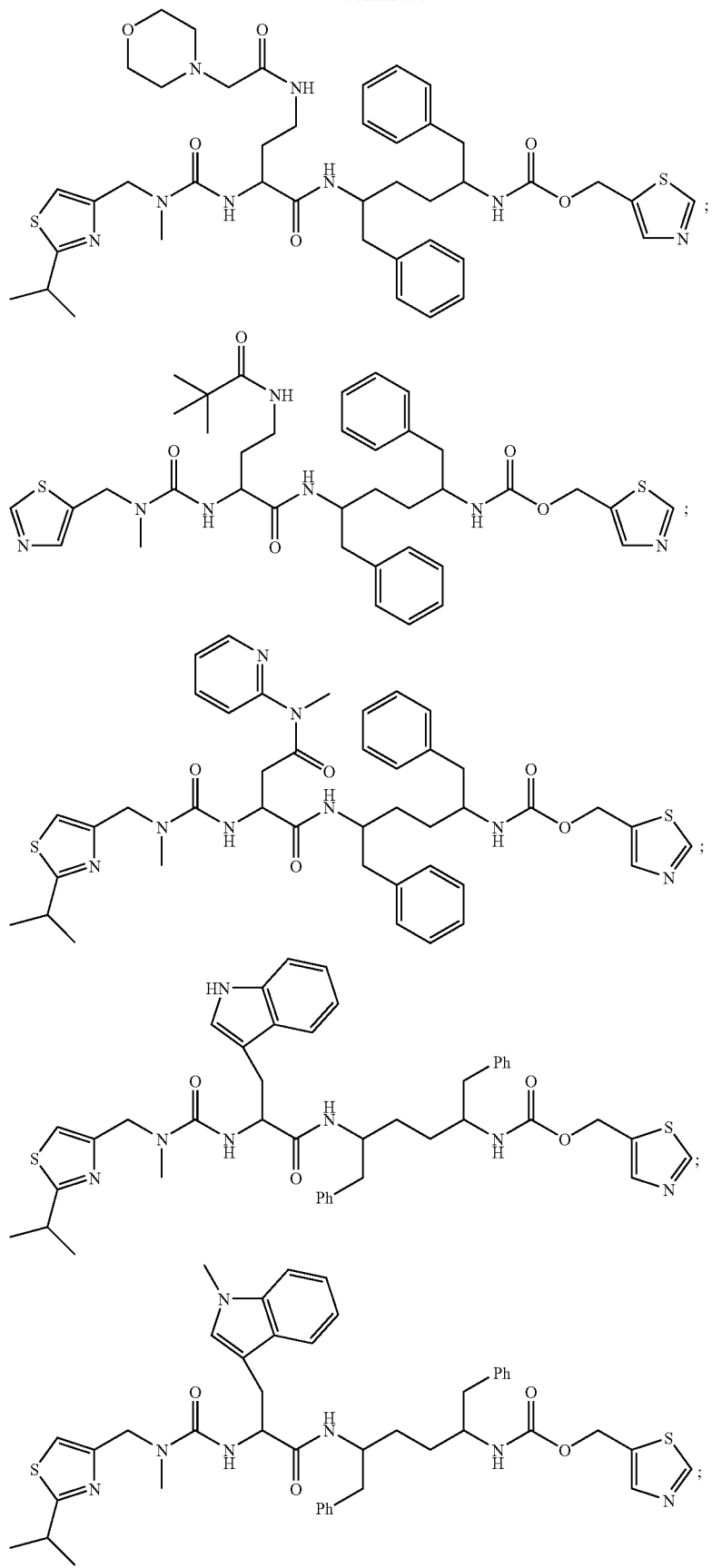

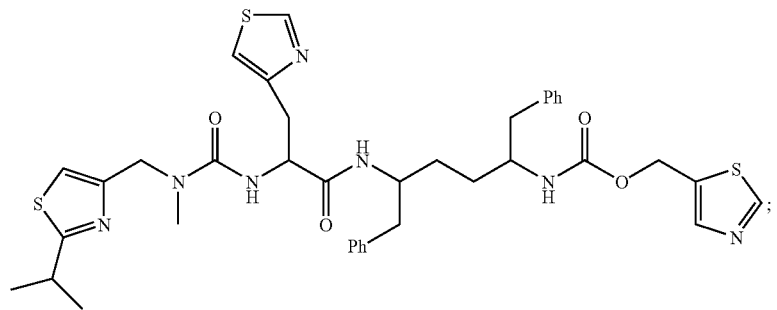
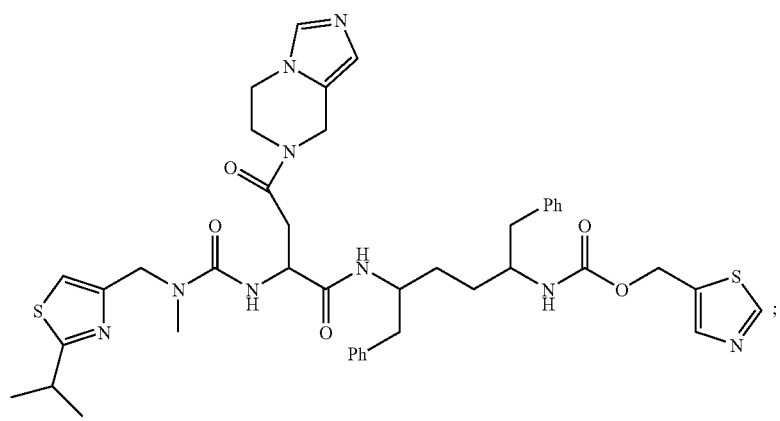
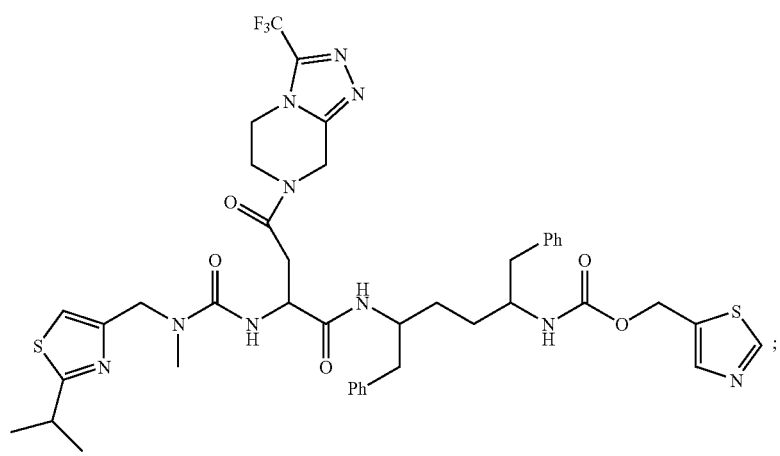
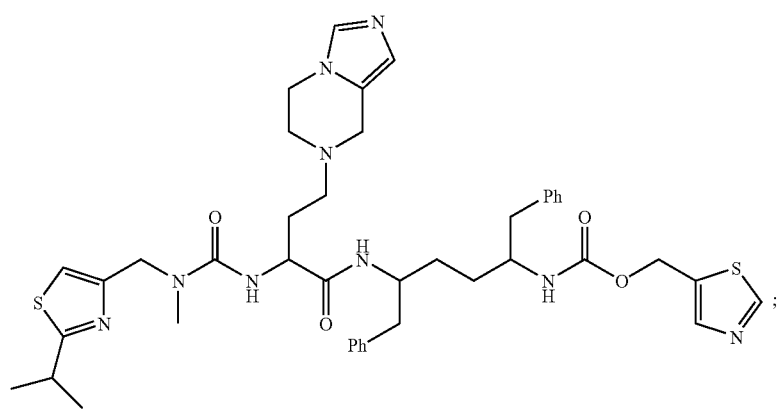

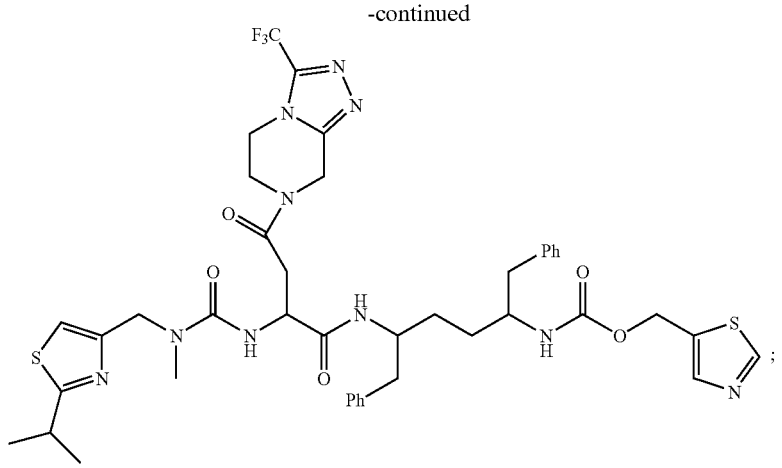
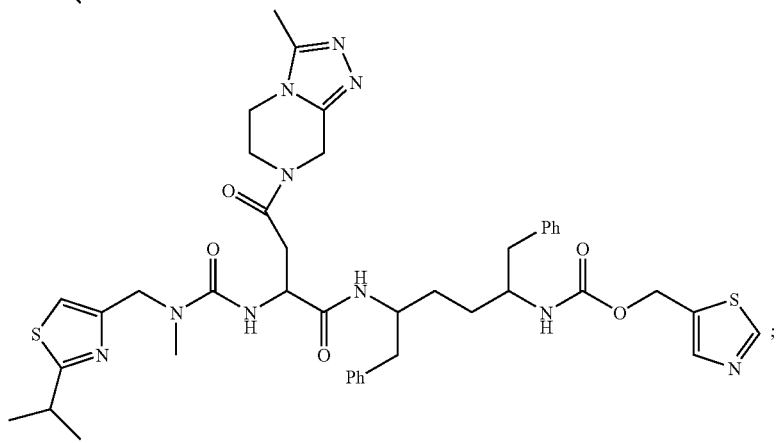
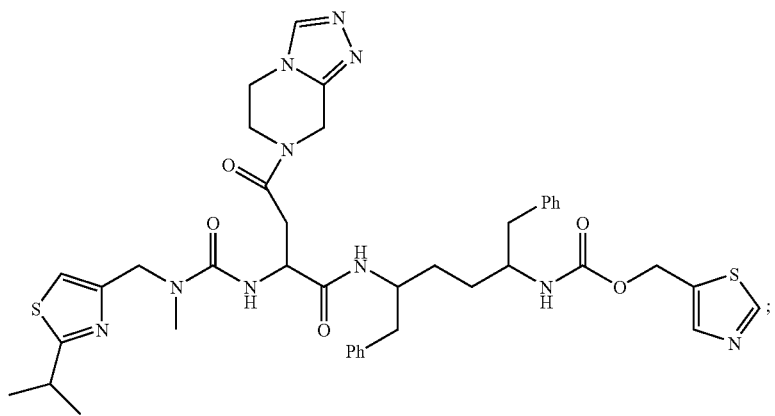
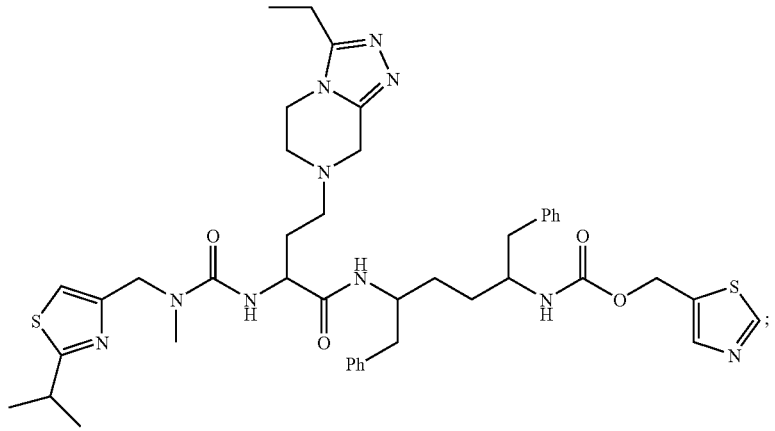

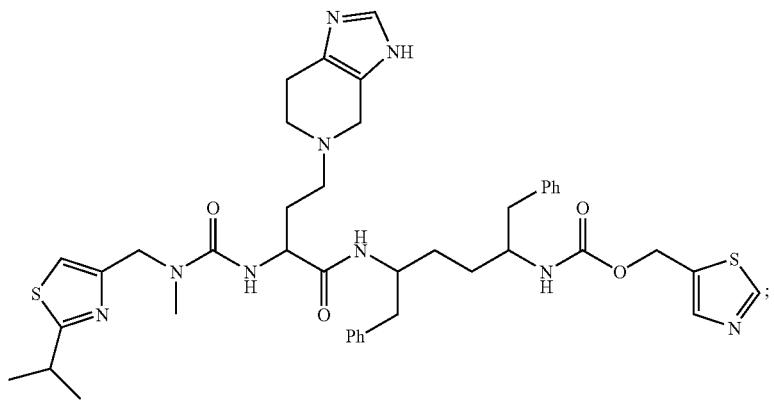
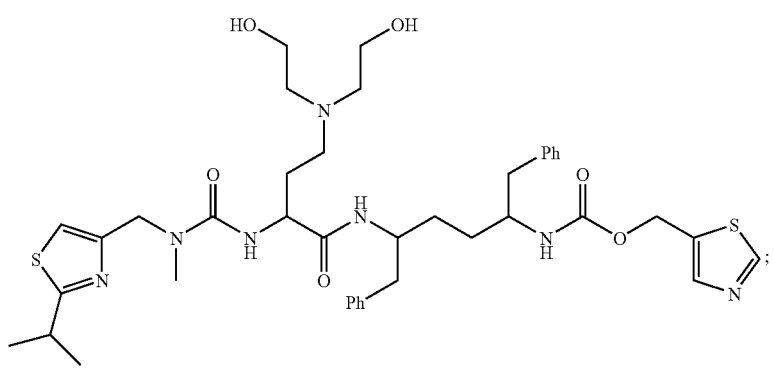
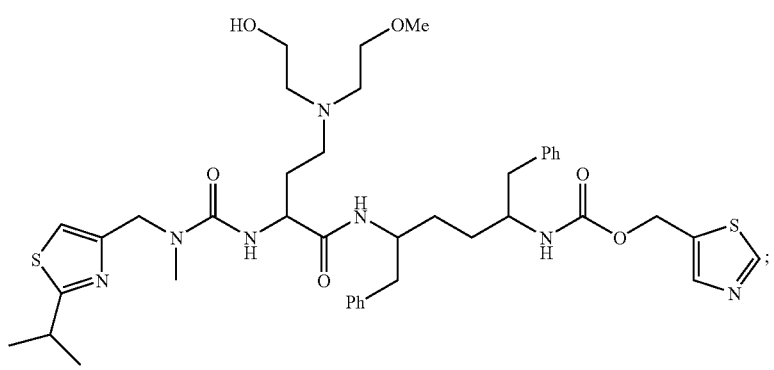
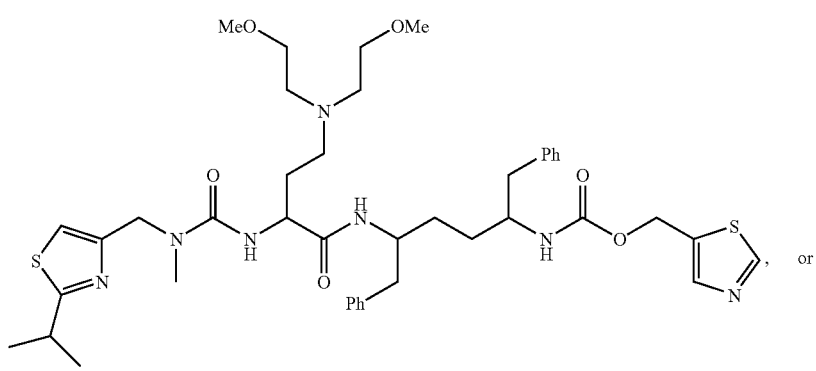
a pharmaceutically acceptable salt, solvate, ester, or a stereoisomer or mixture of stereoisomers thereof.
In another embodiment, the present application provides for a compound having the following structure:

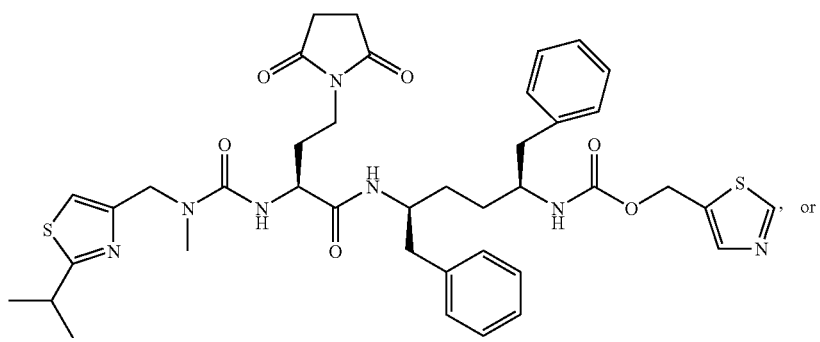 or a pharmaceutically acceptable salt, solvate, ester, or a stereoisomer or mixture of stereoisomers thereof.

In still yet another embodiment, the compound of the present invention has an inhibition activity against P450 at a level equal to or better than the inhibition activity of a compound as represented by an $IC_{50}$ of less than about 2000 nM, less than about 1500 nM, less than about 1000 nM, less than about 900 nM, less than about 800 nM, less than about 700 nM, less than about 650 nM, less than about 600 nM, less than about 550 nM, less than about 500 nM, less than about 400 nM, less than about 350 nM, less than about 300 nM, less than about 250 nM, less than about 200 nM, less than about 100 nM, or less than about 50 nM.

In still yet another embodiment, the compound of the present invention has an inhibition activity against an isozyme of P450, e.g., 3A in a range represented by $IC_{50}$ from about 2000 nM to about 100 nM, from about 1000 nM to about 100 nM, from about 900 nM to about 200 nM, from about 800 nM to about 300 nM, from about 700 nM to about 200 nM, from about 600 nM to about 200 nM, from about 500 nM to about 200 nM, from about 700 nM to about 300 nM, from about 600 nM to about 300 nM, from about 700 nM to about 400 nM, from about 600 nM to about 400 nM, from about 400 nM to about 100 nM, from about 300 nM to about 100 nM, or from about 600 nM to about 150 nM.

In still yet another embodiment, the compound of the present invention has an inhibition activity against P450 at a level equal to or better than the inhibition activity of a compound as represented by an $IC_{50}$ of less than about 2000 nM, less than about 1500 nM, less than about 1000 nM, less than about 900 nM, less than about 800 nM, less than about 700 nM, less than about 650 nM, less than about 600 nM, less than about 550 nM, less than about 500 nM, less than about 400 nM, less than about 350 nM, less than about 300 nM, less than about 250 nM, less than about 200 nM, less than about 100 nM, or less than about 50 nM, provided that such compound also does not substantially exhibit biological activities other than its inhibition activity against P450. For example, the compound of the present invention can have a reduced or not significant activity of protease inhibition, including without any limitation a level of protease inhibition as represented by HIV $EC_{50}$ of greater than about 1000 nM, greater than about 900 nM, greater than about 800 nM, greater than about 700 nM, greater than about 600 nM, greater than about 500 nM, greater than about 400 nM, greater than about 300 nM, greater than about 200 nM, greater than about 100 nM, greater than about 50 nM, greater than about 40 nM, greater than about 30 nM, greater than about 20 nM, greater than about 10 nM, greater than about 5 nM, or greater than about 1 nM.

In yet another embodiment, the compound of the present invention has an inhibition activity specifically against one or more isozymes of P450 including without limitation 1A2, 2B6, 2C8, 2C19, 2C9, 2D6, 2E1, and 3A4, 5, 7, etc.

In yet another embodiment, the compound of the present invention has an inhibition activity specifically against an isozyme of P450 that is involved in metabolizing anti-viral drugs, e.g., indinavir, nelfinavir, ritonavir, saquinavir etc.

In still yet another embodiment, the compound of the present invention has an inhibition activity specifically against one or more isozymes of P450, but not the other(s). For example, the compound of the present invention can have an inhibition activity specifically against P450 3A, but a reduced, insubstantial, or minimum inhibition activity against another isozyme of P450, e.g., P450 2C9.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, e.g. a compound of the present invention, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation.

These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 μm (including particle sizes in a range between 0.1 and 500 μm in increments such as 0.5 μm, 1 μm, 30 μm, 35 μm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients provided by the present invention the formulations of this invention may include other agents conventional in the art having regard to the type of formulation in question, for example those suitable for oral administration may include flavoring agents.

The invention further provides veterinary compositions comprising at least one active ingredient, e.g., a compound of the present invention together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 100 mg/kg body weight per day, for example from about 0.01 to about 10 mg/kg body weight per day, from about 0.01 to about 5 mg/kg body weight per day, or from about 0.05 to about 0.5 mg/kg body weight per day. For example, the daily candidate dose for an adult human of approximately 70 kg body weight will range from 1 mg to 1000 mg, or between 5 mg and 500 mg, and may take the form of single or multiple doses.

In yet another embodiment, the present application discloses pharmaceutical compositions comprising a compound of the present invention, or a pharmaceutically acceptable salt, solvate, and/or ester thereof, and a pharmaceutically acceptable carrier or excipient.

In yet another embodiment, the present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or excipient.

According to the present invention, the therapeutic agent used in combination with the compound of the present invention can be any agent having a therapeutic effect when used in combination with the compound of the present invention. For example, the therapeutic agent used in combination with the compound of the present invention can be any agent that is accessible to oxidative metabolism by cytochrome P450 enzymes, especially cytochrome P450 monooxygenase, e.g., 1A2, 2B6, 2C8, 2C19, 2C9, 2D6, 2E1, 3A4,5,7, etc.

In another example, the therapeutic agent used in combination with the compound of the present invention can be any anti-viral agent, e.g., anti-HIV, anti-HCV, etc., anti-bacterial agent, anti-fungal agent, immuno-modulator, e.g., immuno-suppressant, anti-neoplastic agent, chemotherapeutic agent, agents useful for treating cardiovascular conditions, neurological conditions, etc.

In yet another example, the therapeutic agent used in combination with the compound of the present invention can be any proton pump inhibitor, anti-epileptics, NSAID, oral hypoglycemic agent, angiotensin II, sulfonylureas, beta blocker, antidepressant, antipsychotics, or anesthetics, or a combination thereof.

In yet another example, the therapeutic agent used in combination with the compound of the present invention can be any 1) macrolide antibiotics, e.g., clarithromycin, erythromycin, telithromycin, 2) anti-arrhythmics, e.g., quinidine=>3-OH, 3) benzodiazepines, e.g., alprazolam, diazepam=>3OH, midazolam, triazolam, 4) immune modulators, e.g., cyclosporine, tacrolimus (FK506), 5) HIV antivirals, e.g., indinavir, nelfinavir, ritonavir, saquinavir, 6) prokinetic, e.g., cisapride, 7) antihistamines, e.g., astemizole, chlorpheniramine, terfenadine, 8) calcium channel blockers, e.g., amlodipine, diltiazem, felodipine, lercanidipine, nifedipine, nisoldipine, nitrendipine, verapamil, 9) HMG CoA reductase inhibitors, e.g., atorvastatin, cerivastatin, lovastatin, simvastatin, or 10) steroid 6beta-OH, e.g., estradiol, hydrocortisone, progesterone, testosterone.

In still yet another example, the therapeutic agent used in combination with the compound of the present invention can be any alfentanil, aprepitant, aripiprazole, buspirone, cafergot, caffeine, TMU, cilostazol, cocaine, codeine-N-demethylation, dapsone, dextromethorphan, docetaxel, domperidone, eplernone, fentanyl, finasteride, gleevec, haloperidol, irinotecan, LAAM, lidocaine, methadone, nateglinide, ondensetron, pimozide, propranolol, quetiapene, quinine, salmeterol, sildenafil, sirolimus, tamoxifen, taxol, terfenadine, trazodone, vincristine, zaleplon, or zolpidem or a combination thereof.

In one embodiment, the present application discloses pharmaceutical compositions comprising a compound of the present invention, or a pharmaceutically acceptable salt, solvate, and/or ester thereof, in combination with at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, non-nucleoside inhibitors of HCV, CCR5 inhibitors, and combinations thereof, and a pharmaceutically acceptable carrier or excipient.

In another embodiment, the present application provides pharmaceutical compositions comprising a compound of the present invention, or a pharmaceutically acceptable salt, solvate, and/or ester thereof, in combination with at least one additional therapeutic agent selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, capravirine, emivirine, delaviridine, efavirenz, nevirapine, (+) calanolide A, etravirine, GW5634, DPC-083, DPC-961, DPC-963, MIV-150, TMC-120, zidovudine, emtricitabine, didanosine, stavudine, zalcitabine, lamivudine, abacavir, amdoxovir, elvucitabine, alovudine, MIV-210, Racivir (±-FTC), D-d4FC, AVX754, tenofovir disoproxil fumarate, adefovir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, L-870810, benzimidazole derivatives, benzo-1,2,4-thiadiazine derivatives, phenylalanine derivatives, aplaviroc, vicriviroc, and maraviroc, cyclosporine, FK-506, rapamycin, taxol, taxotere, clarithromycin, A-77003, A-80987, MK-639, saquinavir, VX-478, AG1343, DMP-323, XM-450, BILA 2011 BS, BILA 1096 BS, BILA 2185 BS, BMS 186,318, LB71262, SC-52151, SC-629 (N,N-dimethylglycyl-N-(2-hydroxy-3-(((4-methoxyphenyl)sulphonyl)(2-methylpropyl)amino)-1-(phenylmethyl)propyl)-3-methyl-L-valinamide), KNI-272, CGP 53437, CGP 57813 and U-103017 and a pharmaceutically acceptable carrier or excipient.

In yet another embodiment, the present application provides a combination pharmaceutical agent comprising:

a) a first pharmaceutical composition comprising a compound of the present invention, or a pharmaceutically acceptable salt, solvate, or ester thereof; and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

In one embodiment, the compounds of the present invention can be used alone, e.g., for inhibiting cytochrome P450 monooxygenase. In another embodiment, the compounds of the present invention are used in combination with other active therapeutic ingredients or agents. Preferably, the other active therapeutic ingredients or agents are metabolized or accessible to the oxidative metabolism by cytochrome P450 enzymes, e.g., monooxygenase enzymes such as 1A2, 2B6, 2C8, 2C19, 2C9, 2D6, 2E1, 3A4,5,7, etc.

Combinations of the compounds of the present invention are typically selected based on the condition to be treated, cross-reactivities of ingredients and pharmaco-properties of the combination. For example, when treating an infection (e.g., HIV or HCV), the compositions of the invention are combined with anti-infective agents (such as those described herein).

In one embodiment, non-limiting examples of suitable combinations include combinations of one or more compounds of the present invention with one or more anti-viral agents, e.g., anti-HIV, anti-HCV, etc., anti-bacterial agents, anti-fungal agents, immuno-modulators, e.g., immunosuppressant, anti-neoplastic agents, chemotherapeutic agents, agents useful for treating cardiovascular conditions, neurological conditions, etc.

In another embodiment, non-limiting examples of suitable combinations include combinations of one or more compounds of the present invention with one or more proton pump inhibitors, anti-epileptics, NSAIDs, oral hypoglycemic agents, angiotensin II, sulfonylureas, beta blockers, antidepressants, antipsychotics, or anesthetics, or a combination thereof.

In yet another embodiment, non-limiting examples of suitable combinations include combinations of one or more compounds of the present invention with one or more 1) macrolide antibiotics, e.g., clarithromycin, erythromycin, telithromycin, 2) anti-arrhythmics, e.g., quinidine=>3-OH, 3) benzodiazepines, e.g., alprazolam, diazepam=>3OH, midazolam, triazolam, 4) immune modulators, e.g., cyclosporine, tacrolimus (FK506), 5) HIV antivirals, e.g., indinavir, nelfinavir, ritonavir, saquinavir, 6) prokinetic, e.g., cisapride, 7) antihistamines, e.g., astemizole, chlorpheniramine, terfenadine, 8) calcium channel blockers, e.g., amlodipine, diltiazem, felodipine, lercanidipine, nifedipine, nisoldipine, nitrendipine, verapamil, 9) HMG CoA reductase inhibitors, e.g., atorvastatin, cerivastatin, lovastatin, simvastatin, or 10) steroid 6beta-OH, e.g., estradiol, hydrocortisone, progesterone, testosterone.

In still yet another embodiment, non-limiting examples of suitable combinations include combinations of one or more compounds of the present invention with one or more compounds selected from the group consisting of alfentanil, aprepitant, aripiprazole, buspirone, cafergot, caffeine=>TMU, cilostazol, cocaine, codeine-N-demethylation, dapsone, dextromethorphan, docetaxel, domperidone, eplernone, fentanyl, finasteride, gleevec, haloperidol, irinotecan, LAAM, lidocaine, methadone, nateglinide, odanestron, pimozide, propranolol, quetiapene, quinine, salmeterol, sildenafil, sirolimus, tamoxifen, taxol, terfenadine, trazodone, vincristine, zaleplon, and zolpidem or a combination thereof.

In one embodiment, non-limiting examples of suitable combinations include combinations of one or more compounds of the present invention with one or more HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, CCR8 inhibitors, entry inhibitors, RNase H inhibitors, maturation inhibitors, and other drugs for treating HIV.

More specifically, one or more compounds of the present invention may be combined with one or more compounds selected from the group consisting of: (1) HIV protease inhibitors, e.g., amprenavir (Agenerase), atazanavir (Reyataz), fosamprenavir (Lexiva), indinavir (Crixivan), lopinavir, ritonavir (norvir), nelfinavir (Viracept), saquinavir (Invirase), tipranavir (Aptivus), brecanavir, darunavir (Prezista), TMC-126, TMC-114, mozenavir (DMP-450), JE-2147 (AG1776), L-756423, RO0334649, KNI-272, DPC-681, DPC-684, DG17, GS-8374, MK-8122 (PPL-100), DG35, and AG 1859, SPI-256, TMC 52390, PL-337, SM-322377, SM-309515, GRL-02031, CRS-074, CRS-075, KB-98, and A-790742; (2) HIV non-nucleoside inhibitors of reverse transcriptase, e.g., capravirine, emivirine, delaviridine (Rescriptor), efavirenz (Sustiva), nevirapine (Viramune), (+)-calanolide A, calanolide B, etravirine (Intelence), GW5634, DPC-083, DPC-961, DPC-963, MIV-150, MIV-160, MIV-170, dapivirine (TMC-120), rilpivirine (TMC-278), BILR 355 BS, VRX 840773, UK-453061, and RDEA806, RDEA 427, RDEA 640, IDX 899, ANX-201 (Thiovir), R-1206, LOC-dd, IQP-0410 (SJ-3366), YM-215389, YM-228855, CMX-052, and CMX-182; (3) HIV nucleoside inhibitors of reverse transcriptase, e.g., zidovudine (Retrovir), emtricitabine (Emtriva), didanosine (Videx), stavudine (Zerit), zalcitabine (Hivid), lamivudine (Epivir), abacavir (Ziagen), amdoxovir, elvucitabine (ACH 126443), alovudine (MIV-310), MIV-210, racivir (racemic FTC, PSI-5004), D-d4FC, phosphazide, fozivudine tidoxil, apricitibine (AVX754, SPD-754), GS-7340, KP-1461, AVX756, OBP-601, dioxolane thymine, TMC-254072, INK-20, PPI-801, PPI-802, MIV-410, 4'-Ed4T, B-108, and fosalvudine tidoxil (HDP 99.0003); (4) HIV nucleotide inhibitors of reverse transcriptase, e.g., tenofovir disoproxil fumarate (Viread), and adefovir dipivoxil; (5) HIV integrase inhibitors, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, raltegravir (Isentress, MK-0518), elvitegravir (GS-9137), BMS-538158, GSK364735C, BMS-707035, MK-2048, GSK-349572 (S-349572), GSK-265744 (S-265744), GSK-247303 (S-247303), S-1360 (GW810871), 1,5-DCQA, INH-001, INT-349, V-165, RIN-25, BFX-1001, BFX-1002, BFX-1003, RSC-1838, BCH-33040, and BA 011; (6) gp41 inhibitors, e.g., enfuvirtide (Fuzeon), sifuvirtide, MPI-451936, FB006M, A-329029, and TRI-1144; (7) CXCR4 inhibitors, e.g., AMD-070, KRH-3955 (CS-3955), AMD-9370, AMD-3451, RPI-MN, MSX-122, and POL-2438; (8) entry inhibitors, e.g., SP01A, PA-161, SPC3, TNX-355, DES6, SP-10, SP-03, CT-319, and CT-32; (9) gp120 inhibitors, e.g., BMS-488043 and its prodrugs, BlockAide/CR, KPC-2, and MNLP62; (10) G6PD and NADH-oxidase inhibitors, e.g., immunitin; (11) CCR5 inhibitors, e.g., aplaviroc, nifeviroc, vicriviroc (SCH-417690), maraviroc (Selzentry), PRO-140, PRO-542, INCB15050, INCB9471, PF-232798, SCH-532706, GSK-706769, TAK-652, TAK-220, ESN-196, RO-1752, ZM-688523, AMD-887, YM-370749, NIBR-1282, SCH-350634, ZM-688523, and CCR5 mAb004; (12) CCR8 inhibitors, e.g., ZK-756326; (13) RNase H inhibitors, e.g., ODN-93, and ODN-112; (14) maturation inhibitors, e.g., bevirimat (PA-457), PA-040, MPC-9055 (vicecon, MPI-49839), ACH-100703, ACH-100706; and (15) other drugs for treating HIV, e.g., REP 9, SP-01A, TNX-355, DES6, ODN-93, ODN-112, VGV-1, Ampligen, HRG214, Cytolin, VGX-410, VGX-820, KD-247, AMZ 0026, CYT 99007, A-221 HIV, HPH-116, DEBIO-025, BAY 50-4798, MDX010 (ipilimumab), PBS 119, BIT-225, UBT-8147, ITI-367, AFX-400, BL-1050, GRN-139951, GRN-140665, AX-38679, RGB-340638, PPI-367, and ALG 889.

It is also contemplated that the compounds of the present invention can be used with any other active therapeutic agent or ingredient which is appreciably metabolized by cytochrome P450 monooxygenase enzymes, e.g. cytochrome P450 monooxygenase 3A, thereby reducing the amount or rate at which the other active therapeutic agent or ingredient is metabolized, whereby the pharmacokinetics of the other active therapeutic agent or ingredient is improved. Such improvements can include elevating the blood plasma levels of the other therapeutic agent or ingredient or maintaining a more therapeutically effective blood plasma level of the other therapeutic active agent or ingredient—compared to blood plasma levels of the other therapeutic agent or ingredient administered without the compound of the present invention.

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In yet another embodiment, the present application provides a method for improving the pharmacokinetics of a drug which is metabolized by cytochrome P450 monooxygenase, comprising administering to a patient treated with said drug, a therapeutically effective amount of a compound of the present invention, or a pharmaceutically acceptable salt, solvate, and/or ester thereof.

In yet another embodiment, the present application provides a method for improving the pharmacokinetics of a drug which is metabolized by cytochrome P450 monooxygenase, comprising administering to a patient treated with said drug, a therapeutically effective amount of a combination comprising said drug and a compound of the present invention, or a pharmaceutically acceptable salt, solvate, and/or ester thereof.

In yet another embodiment, the present application provides a method for improving the pharmacokinetics of a drug which is metabolized by cytochrome P450 monooxygenase 3A, comprising administering to a patient treated with said drug, a therapeutically effective amount of a compound of the present invention, or a pharmaceutically acceptable salt, solvate, and/or ester thereof.

In yet another embodiment, the present application provides a method for increasing blood plasma levels of a drug which is metabolized by cytochrome P450 monooxygenase, comprising administering to a patient treated with said drug, a therapeutically effective amount of a compound of the present invention, or a pharmaceutically acceptable salt, solvate, and/or ester thereof.

In yet another embodiment, the present application provides a method for increasing blood plasma levels of a drug which is metabolized by cytochrome P450 monooxygenase, comprising administering to a patient treated with said drug, a therapeutically effective amount of a combination comprising said drug and a compound of the present invention, or a pharmaceutically acceptable salt, solvate, and/or ester thereof.

In yet another embodiment, the present application provides a method for increasing blood plasma levels of a drug which is metabolized by cytochrome P450 monooxygenase 3A, comprising administering to a patient treated with said drug, a therapeutically effective amount of a compound of the present invention, or a pharmaceutically acceptable salt, solvate, and/or ester thereof.

In yet another embodiment, the present application provides a method for increasing blood plasma levels of a drug which is metabolized by cytochrome P450 monooxygenase, comprising administering to a patient treated with said drug, a therapeutically effective amount of a compound of the present invention, or a pharmaceutically acceptable salt, solvate, and/or ester thereof, and wherein the amount of the compound of the present invention administered is effective to inhibit cytochrome P450 monooxygenase.

In yet another embodiment, the present application provides a method for inhibiting cytochrome P450 monooxygenase in a patient comprising administering to a patient in need thereof an amount of a compound of the present invention, or a pharmaceutically acceptable salt, solvate, and/or ester thereof, effective to inhibit cytochrome P450 monooxygenase.

In yet another embodiment, the present application provides a method for inhibiting cytochrome P450 monooxygenase 3A in a patient comprising administering to a patient in need thereof an amount of a compound of the present invention, or a pharmaceutically acceptable salt, solvate, and/or ester thereof, effective to inhibit cytochrome P450 monooxygenase 3A.

In yet another embodiment, the present application provides a method for inhibiting cytochrome P450 monooxygenase comprising contacting cytochrome P450 monooxygenase with an amount of a compound of the present invention, or a pharmaceutically acceptable salt, solvate, and/or ester thereof, effective to inhibit cytochrome P450 monooxygenase.

In yet another embodiment, the present application provides a method for inhibiting cytochrome P450 monooxygenase 3A comprising contacting cytochrome P450 monooxygenase 3A with an amount of a compound of the present invention, or a pharmaceutically acceptable salt, solvate, and/or ester thereof, effective to inhibit cytochrome P450 monooxygenase 3A.

In yet another embodiment, the present application provides a method for treating an HIV infection comprising administering to a patient in need thereof a therapeutically effective amount of a compound of the present invention, or a pharmaceutically acceptable salt, solvate, and/or ester thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, CCR8 inhibitors, RNase H inhibitors, maturation inhibitors, other drugs for treating HIV, and rmixtures thereof.

In yet another embodiment, the present application provides a method for treating an HIV infection comprising administering to a patient in need thereof a therapeutically effective amount of a compound of the present invention, or a pharmaceutically acceptable salt, solvate, and/or ester thereof, in combination with a therapeutically effective amount of one or more additional therapeutic agents selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, DG17, GS-8374, MK-8122 (PPL-100), DG35, AG 1859, SPI-256, TMC 52390, PL-337, SM-322377, SM-309515, GRL-02031, CRS-074, CRS-075, KB-98, and A-790742; capravirine, emivirine, delaviridine, efavirenz, nevirapine, (+) calanolide A, calanolide B, etravirine, GW5634, DPC-083, DPC-961, DPC-963, MIV-150, MIV-160, TMC-120 (dapiravine), TMC-278 (rilpivirene), BILR 355 BS, VRX 840773, UK-453061, RDEA806, RDEA806, RDEA 427, RDEA 640, IDX 899, ANX-201, R-1206, LOC-dd, IQP-0410 (SJ-3366), YM-215389, YM-228855, CMX-052, and CMX-182; zidovudine, emtricitabine, didanosine, stavudine, zalcitabine, lamivudine, abacavir, amdoxovir, elvucitabine, alovudine, MIV-210, racivir (±-FTC), D-d4FC, phosphazide, fozivudine tidoxil, apricitibine (AVX754), GS-7340, KP-1461, OBP-601, dioxolane thymine, TMC-254072, INK-20, PPI-801, PPI-802, MIV-410, 4'-Ed4T, B-108, and fosalvudine tidoxil (formerly HDP 99.0003); tenofovir, disoproxil fumarate, and adefovir dipivoxil; curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, L-870810, MK-0518 (raltegravir), elvitegravir (GS-9137), GSK-349572 (S-349572), GSK-265744 (S-265744), GSK-247303 (S-247303), S-1360 (GW810871), 1,5-DCQA, INH-001, INT-349, V-165, RIN-25, BFX-1001, BFX-1002, BFX-1003, RSC-1838, BCH-33040BMS-538158, GSK364735C, BMS-707035, MK-2048, and BA 011; enfuvirtide, sifuvirtide, MPI-451936, FB006M, Z-329029, and TRI-1144; AMD-070, KRH-3955 (CS-3955), AMD-9370, AMD-3451, RPI-MN, MSX-122, and POL-2438; SP01A, PA-161, SPC3, TNX-355, DES6, SP-10, SP-03, CT-319, and CT-326; BMS-488043, prodrugs of BMS-488043, BlockAide/CR, KPC-2, and MNLP62; immunitin; aplaviroc, nifeviroc, vicriviroc (SCH-417690), maraviroc, PRO-140, PRO-542, INCB15050, INCB9471, PF-232798, SCH-532706, GSK-706769, TAK-652, TAK-220, ESN-196, RO-1752, ZM-688523, AMD-887, YM-370749, NIBR-1282, SCH-350634, ZM-688523, and CCR5 mAb004; ZK-756326, ODN-93 or ODN-112, bevirimat (PA-457), PA-040, MPC-9055 (vicecon, MPI-49839), ACH-100703, and ACH-100706; BAS-100, SPI-452, PF-419-4477, TMC-41629, and roxythromycin, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX010 (ipilimumab), PBS 119, BIT-225, UBT-8147, ITI-367, AFX-400, BL-1050, GRN-139951, GRN-140665, AX-38679, RGB-340638, PPI-367, and ALG 889.

In yet another embodiment, the present application provides a method for treating an HcV infection comprising administering to a patient in need thereof a therapeutically effective amount of a compound of the present invention, or a pharmaceutically acceptable salt, solvate, and/or ester thereof, in combination with a therapeutically effective amount of one or more additional therapeutic agents selected from the group consisting of interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophilin inhibitors, HCV IRES inhibitors, and other drugs for treating HCV.

In yet another embodiment, the present application provides a method for treating an HCV infection comprising administering to a patient in need thereof a therapeutically effective amount of a compound of the present invention, or a pharmaceutically acceptable salt, solvate, and/or ester thereof, in combination with a therapeutically effective amount of one or more additional therapeutic agents selected from the group consisting of pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha-2b XL, BLX-883 (Locteron), DA-3021, glycosylated interferon alpha-2b (AVI-005), PEG-Infergen, PEGylated interferon lambda-1 (PEGylated IL-29), and belerofon; (2) ribavirin and its analogs, e.g., ribavirin (Rebetol, Copegus), and taribavirin (Viramidine); (3) HCV NS3 protease inhibitors, e.g., boceprevir (SCH-503034, SCH-7), telaprevir (VX-950), TMC435350, BI-1335, BI-1230, MK-7009, VBY-376, VX-500, BMS-790052, BMS-605339, PHX-1766, AS-101, YH-5258, YH5530, YH5531, and ITMN-191; (4) alpha-glucosidase 1 inhibitors, e.g., celgosivir (MX-3253), Miglitol, and UT-231B; (5) hepatoprotectants, e.g., IDN-6556, ME 3738, LB-84451, silibilin, and MitoQ; (6) nucleoside or nucleotide inhibitors of HCV NS5B polymerase, e.g., R1626, R7128 (R4048), IDX184, IDX-102, BCX-4678, valopicitabine (NM-283), and MK-0608; (7) non-nucleoside inhibitors of HCV NS5B polymerase, e.g., PF-868554, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190; (8) HCV NS5A inhibitors, e.g., AZD-2836 (A-831), and A-689; (9) TLR-7 agonists, e.g., ANA-975, and SM-360320; (10) cyclophilin inhibitors, e.g., DEBIO-025, SCY-635, and NIM811; (11) HCV IRES inhibitors, e.g., MCI-067; and (12) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, and VX-497 (merimepodib).

In still yet another embodiment, the present application provides for the use of a compound of the present invention, or a pharmaceutically acceptable salt, solvate, and/or ester thereof, for the preparation of a medicament for inhibiting cytochrome P450 monooxygenase in a patient.

In still yet another embodiment, the present application provides for the use of a compound of the present invention, or a pharmaceutically acceptable salt, solvate, and/or ester thereof, for the preparation of a medicament for treating an HIV infection.

In still yet another embodiment, the present application provides for the use of a compound of the present invention, or a pharmaceutically acceptable salt, solvate, and/or ester thereof, for the preparation of a medicament for increasing blood plasma levels of the drug which is metabolized by cytochrome P450 monooxygenase.

In still yet another embodiment, the present application provides for the use of a compound of the present invention, or a pharmaceutically acceptable salt, solvate, and/or ester thereof, for the preparation of a medicament for improving the pharmacokinetics of a drug which is metabolized by cytochrome P450 monooxygenase.

EXAMPLES

Preparation of Example A

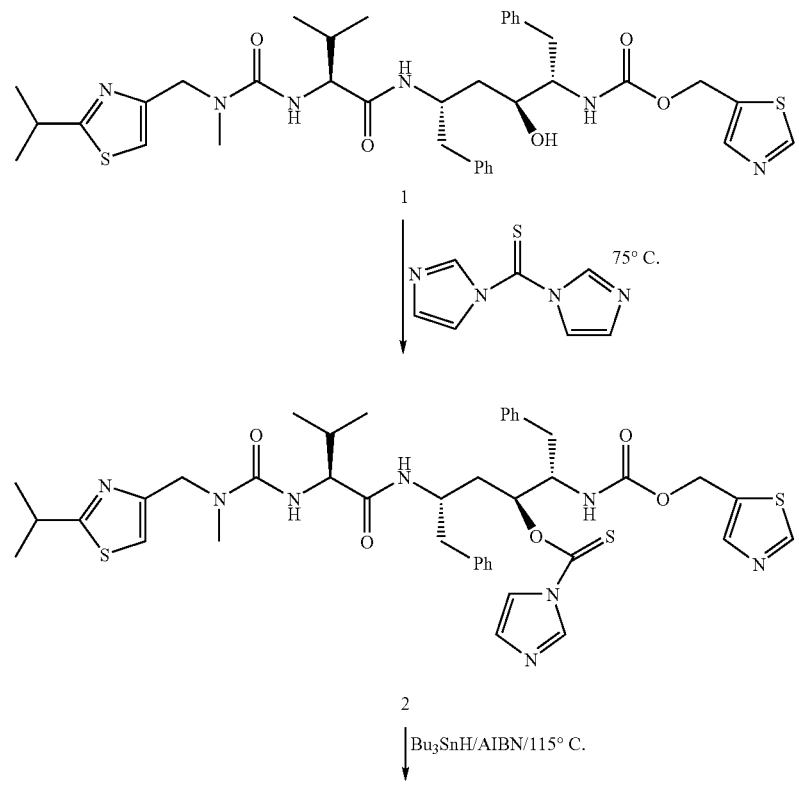

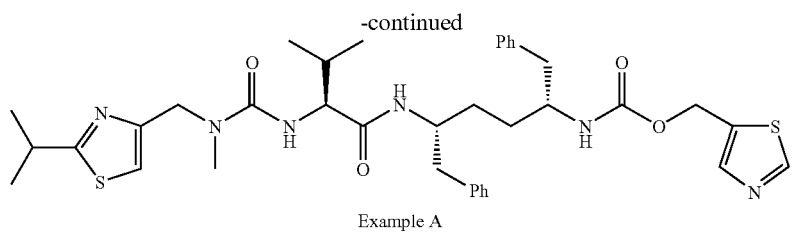
Example A

Compound 2

To a solution of Compound 1 (ritonavir) (1.8 g, 2.5 mmol) in 1,2-dichloroethane (15 mL) was added 1,1'-thiocarbonyldiimidazole (890 mg, 5.0 mmol). The mixture was heated at 75° C. for 6 hours and cooled to 25° C. Evaporation under reduced pressure gave a white solid. Purification by flash column chromatography (stationary phase: silica gel; eluent: EtOAc) gave Compound 2 (1.6 g). m/z: 831.1 (M+H)$^+$.

Example A

To the refluxing solution of tributyltin hydride (0.78 mL, 2.9 mmol) in toluene (130 mL) was added a solution of Compound 2 (1.6 g, 1.9 mmol) and 2,2'-azobisisobutyronitrile (31 mg, 0.19 mmol) in toluene (30 mL) over 30 minutes. The mixture was heated at 115° C. for 6 hours and cooled to 25° C. Toluene was removed under reduced pressure. Purification by flash column chromatography (stationary phase: silica gel; eluent: hexane/EtOAc=1/10) gave Example A (560 mg). m/z: 705.2 (M+H)$^+$. $^1$H-NMR (CDCl$_3$) δ 8.79 (1H, s), 7.82 (1H, s), 7.26-7.05 (10H, m), 6.98 (1H, s), 6.28 (1H, m), 6.03 (1H, m), 5.27 (1H, m), 5.23 (2H, s), 4.45-4.22 (2H, m), 4.17 (1H, m), 3.98 (1H, m), 3.75 (1H, m), 3.25 (1H, m), 2.91 (3H, s), 2.67 (4H, m), 2.36 (1H, m), 1.6-1.2 (10H, m), 0.85 (6H, m).

Example B

To a solution of Compound 1 (ritonavir) (98 mg, 0.136 mmol) in dichloromethane (4 mL) was added Dess-Martin periodinane (61 mg, 0.143 mmol). The mixture was stirred at room temperature for 6 hours. The mixture was then partitioned between dichloromethane and brine, the dichloromethane layer was separated, dried and evaporated to dryness. Purification with CombiFlash® (stationary phase: silica gel; eluent: 40-80% EtOAc/Hexane gradient) gave Example B as a white solid. Example B was further purified by trituration with MeOH/hexane to give 83 mg of a white solid. m/z: 719 (M+H)$^+$.

Preparation of Example C

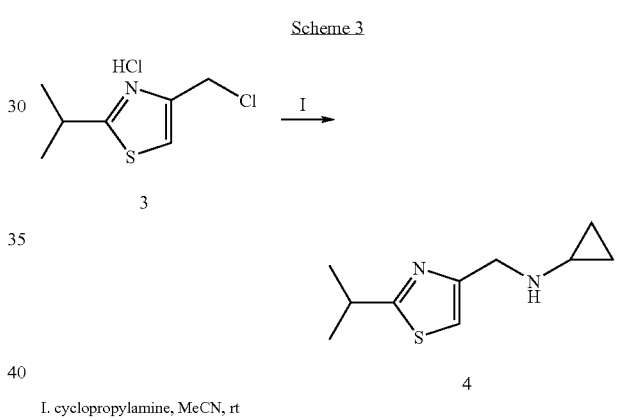

I. cyclopropylamine, MeCN, rt

Preparation of Example B

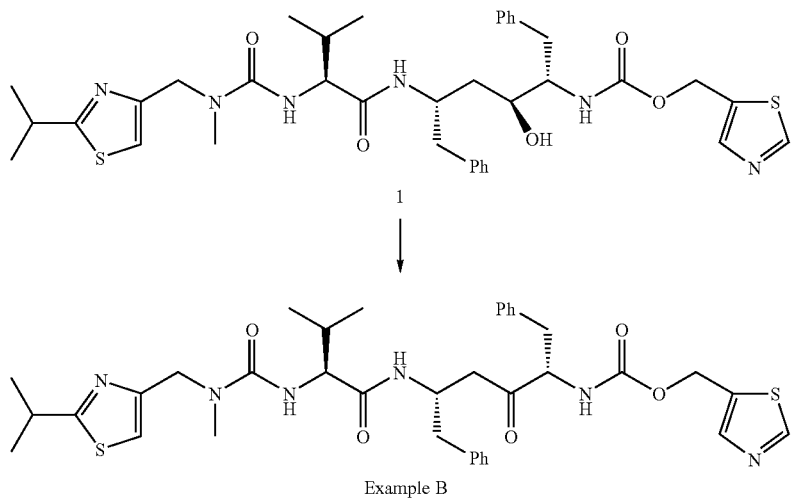

Example B

151

Compound 3

Compound 3 was prepared according to the procedures of J. Med. Chem. 1998, 41, 602, herein incorporated by reference in its entirety for all purposes.

Compound 4

A flask was charged with cyclopropylamine (8.2 mL, 117.8 mmol) at room temperature. A solution of Compound 3 (1 g, 4.71 mmol) in MeCN (8.5 mL) was added dropwise over 5 min. to produce a clear yellow solution that was allowed to stand at room temperature overnight. Volatiles were removed in vacuo, and the resulting residue was purified via silica gel chromatography (gradient elution, 0 to 50% EtOAc/hexane) to afford 0.65 g (70%) of 4 as a yellow liquid (LC/MS m/z 197 (M+H)$^+$; 218 (M+Na)$^+$).

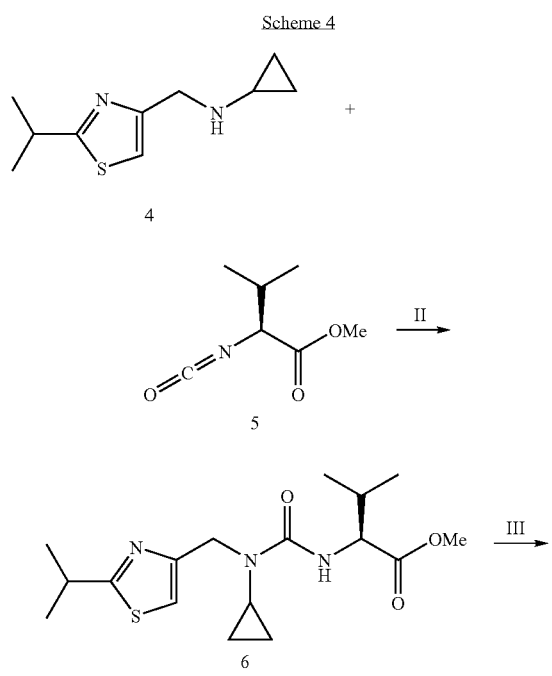

152

-continued

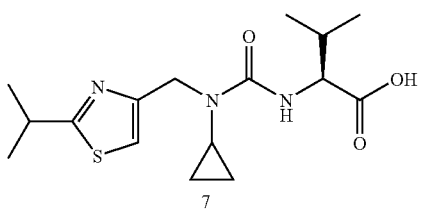

II. rt, DCM; III. 1M LiOH, THF/H$_2$O

Compound 5

Compound 5 was purchased from Aldrich or alternatively prepared according to the procedures of J. Org. Chem. 1994, 59, 1937, herein incorporated by reference in its entirety for all purposes.

Compound 6

To a solution of Compound 4 in DCM (3 mL) at room temperature was added 5 (0.1 mL, 0.695 mmol). The resulting clear solution was allowed to stand at room temperature for 2 h. The solvent was removed in vacuo, and the residue was chromatographed directly using silica gel chromatography (gradient elution, 0 to 50% EtOAc/hexane) to produce 0.218 g (89%) of 6 (LC/MS m/z 354 (M+H)$^+$; 729 (2M+Na)$^+$) as a colorless glass.

Compound 7

Compound 6 was taken up in THF (5 mL) at room temperature, and LiOH (1 M in H$_2$O) was added. The resulting reaction mixture was then stirred vigorously for 1.5 h. The reaction mixture was acidified with 1 M HCl to a pH of 3 (monitored using pH test strips). The acidified reaction mixture was then extracted several times with EtOAc. The combined organic phases were washed with brine, dried over anhydrous Na$_2$SO$_4$, and concentrated in vacuo to produce 0.20 g (quantitative yield) of 7 (LC/MS m/z 340 (M+H)$^+$) as a colorless film. This material was used without further purification.

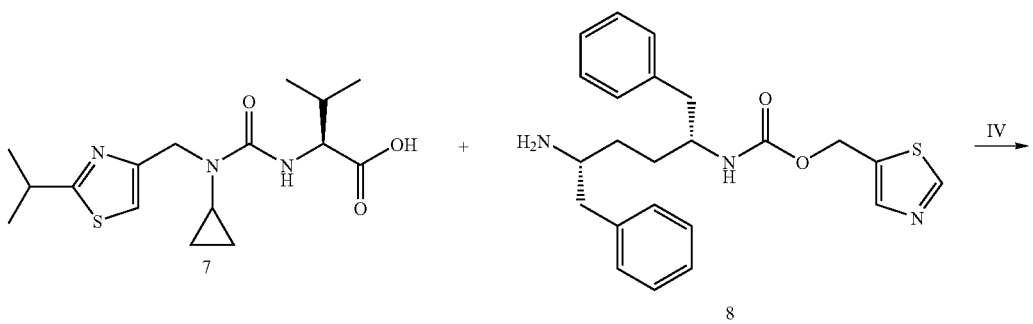

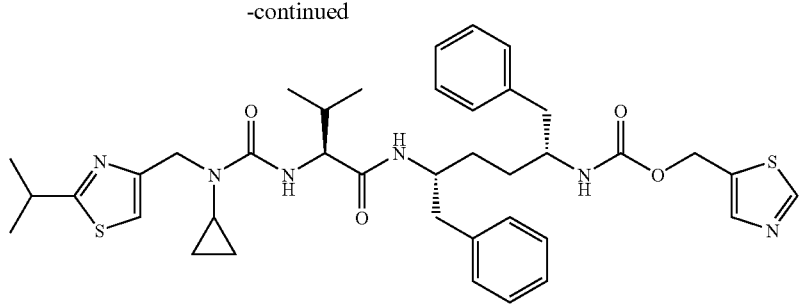

IV. EDC, HOBt, DIPEA, THF

Example C

Example C

Compounds 7 (0.034 g, 0.100 mmol) and 8, (0.034 g, 0.083 mmol) were diluted in THF (2 mL) at room temperature. To the resulting solution were added N,N-diisopropylethylamine (0.022 mL, 0.125 mmol), EDC (0.018 mL, 0.099 mmol) and HOBt (0.013 g, 0.099 mmol). The solution was then allowed to stand overnight at room temperature. The solvent was removed in vacuo and the residue was taken up in MeCN (0.5 mL) and passed through an Acrodisc LC13 PVDF filter (0.45 mM) prior to purification by preparatory HPLC to afford 0.043 g (71%) of Example C as a fluffy white solid.

($^1$H-NMR (300 MHz, CDCl$_3$) δ 8.79 (s, 1H); 7.82 (s, 1H); 7.27-7.02 (m, 10H); 6.81 (s, 1H); 5.97 (br d, J=8.7 Hz, 1H); 5.76 (br d, J=7.2 Hz, 1H); 5.21 (dt, J=7.5, 12.6 Hz, 2H); 5.02, br d, J=8.4 Hz, 1H); 4.58 (s, 2H); 4.16 (m, 1H); 3.99 (br t, J=6.6 Hz, 1H); 3.79 (m, 1H); 3.27 (pent, J=6.6 Hz, 1H); 2.85-2.50 (m, 3H); 2.23 (m, 1H); 1.82 (br s, 2H); 1.60-1.22 (m, 4H); 1.36 (d, J=6.6 Hz, 6H); 0.91 (d, J=6.6 Hz, 3H); 0.90-0.7 (m, 4H); 0.80 (d, J=6.6 Hz, 3H); LC/MS m/z 731 (M$^+$)).

Preparation of Examples D-I

Scheme 6

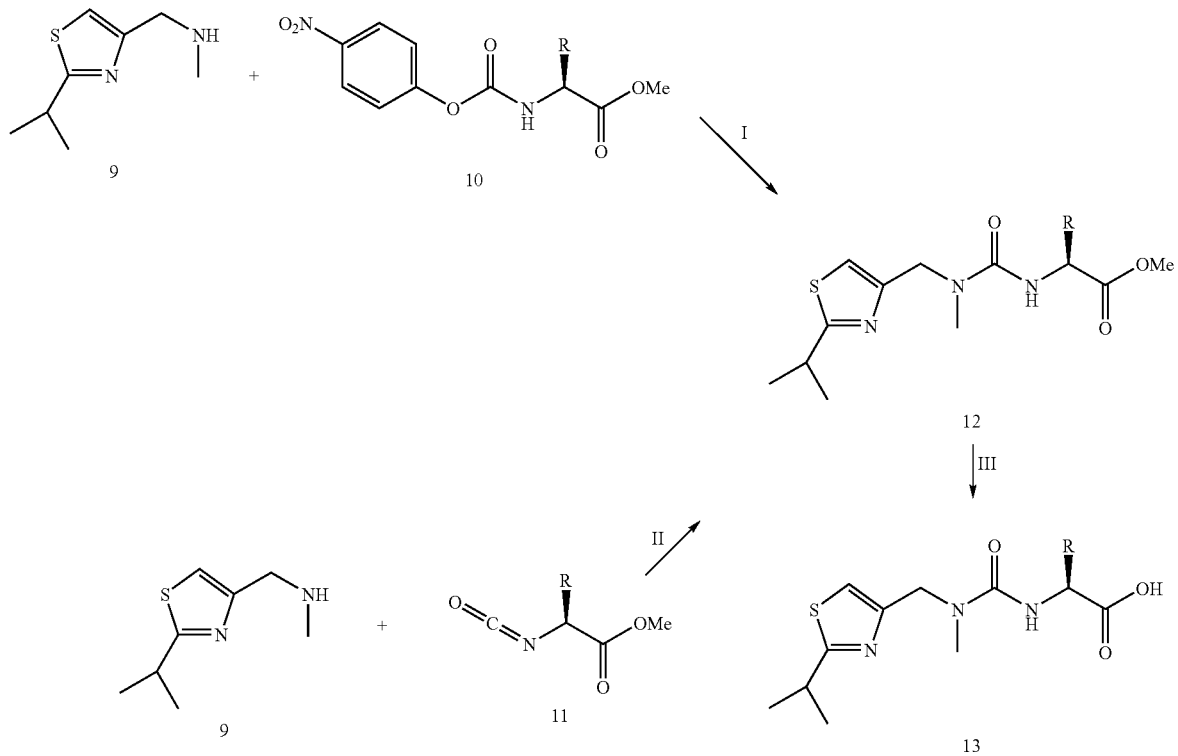

I. Et$_3$N/DMAP/THF/65° C.; II. CH$_2$Cl$_2$/25° C.;
III. a. NaOH/dioxane/H$_2$O; b. HCl a: R = H
b: R = CH$_3$
c: R = CH$_2$CH$_3$
d: R = CH$_2$OBn
e: R = CH(O-t-Bu)CH$_3$
f: R = CH(OH)CH$_3$ Compound 9

Compound 9 was prepared according to the procedures of J. Med. Chem. 1998, 41, 602.

Compound 10

The structures of Compound 10 were prepared according to the procedures of J. Med. Chem. 1998, 41, 602.

Compound 11

The structures of Compound 11 were purchased from Aldrich or prepared according to the procedures of J. Org. Chem. 1994, 59, 1937.

Compound 12

Method 1: To a solution of Compound 9 (0.8 mmol) in THF (2 mL) was added a carbamate of Compound 10 (0.6 mmol), followed by DMAP (16 mg) and triethylamine (0.25 mL). The resulting mixture was heated at 70° C. for two hours and diluted with EtOAc. The organic phase was separated, and washed sequentially with saturated aqueous $Na_2CO_3$, water, and brine, then concentrated under reduced pressure. Purification of the residue by flash column chromatography (silica gel, 1/1-1/3 hexanes/EtOAc gradient) gave compounds of Structure 12.

Method 2: To a solution of Compound 9 (2.4 mmol) in $CH_2Cl_2$ (2 mL) was added an isocyanate of Compound 11 (2 mmol). The resulting mixture was stirred for 4 hours and concentrated. Purification of the residue by flash column chromatography (silica gel, hexane/EtOAc 1/1-1/3) gave structures of Compound 12.

Compound 13

To a solution of structures of Compound 12 (1.8 mmol) in dioxane (8 mL) and water (8 mL) was added sodium hydroxide (3.6 mmol). The resulting reaction mixture was stirred for 1 hour and acidified with HCl in dioxane (3.6 mmol). The reaction mixture was extracted with EtOAc and the organic phase was dried with anhydrous $MgSO_4$. Concentration of the dried organic phase gave structures of Compound 13.

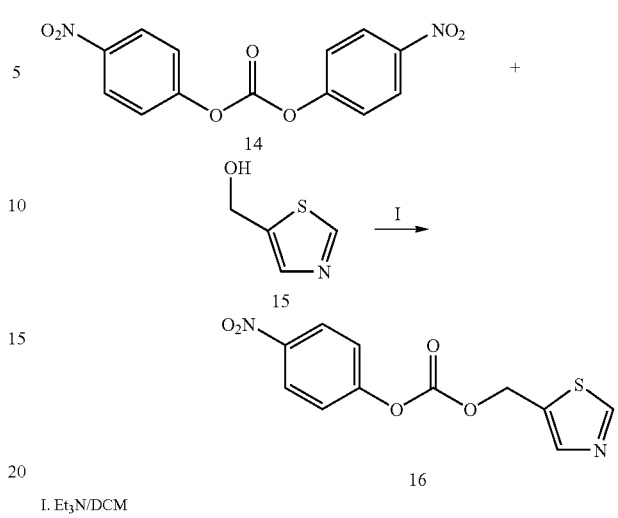

Scheme 7

I. $Et_3N/DCM$

Compound 16

To a solution of Compound 15 (obtained commercially from Molekula) (17 mmol) in DCM (40 mL) was added Compound 14 (19 mmol), followed by triethylamine (26 mmol). The resulting reaction mixture was stirred for 12 hour and concentrated under reduced pressure. The reaction mixture was diluted with EtOAc and washed sequentially with saturated aqueous $Na_2CO_3$, water, and brine. The solvent was removed under reduced pressure. Purification of the residue by flash column chromatography (silica gel, eluent: hexanes/EtOAc 1/1) gave Compound 16 (4.7 g).

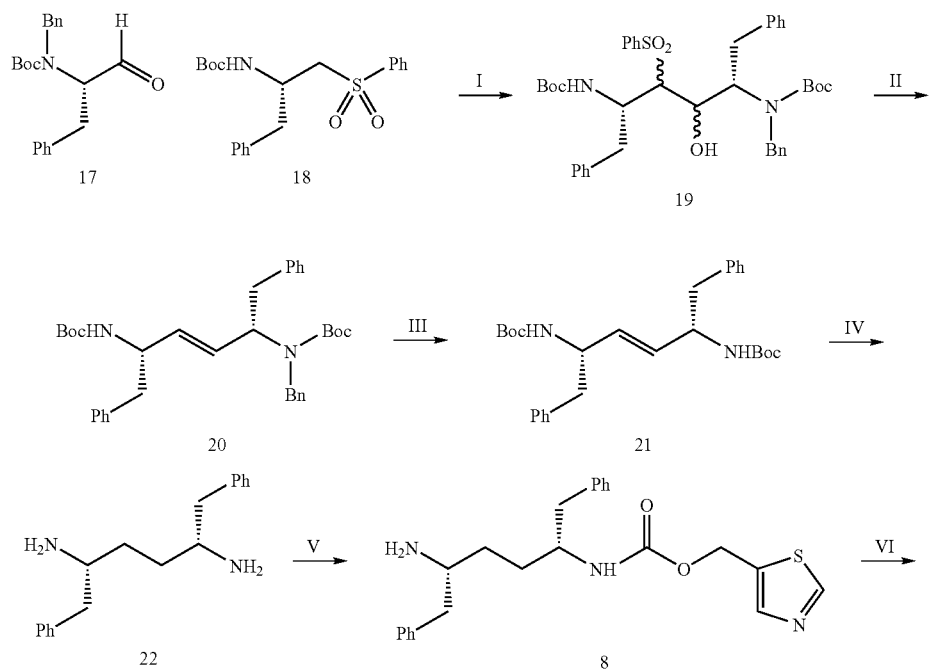

Scheme 8

-continued

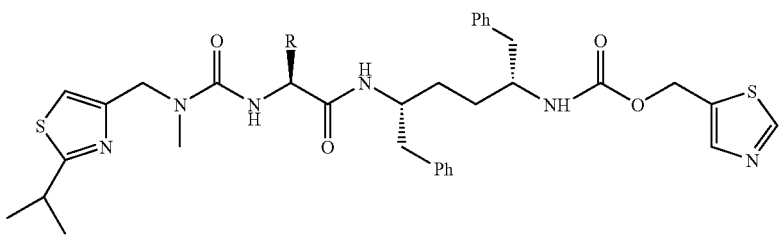

Examples:
D: R = H
E: R = CH₃
F: R = CH₂CH₃
G: R = CH₂OBn
H: R = CH(O-t-Bu)CH₃
I: R = CH(OH)CH₃

I. a. n-BuLi/-78° C.; b.i-Bu₂Al(OMe); II. a. Ac₂O/pyridine; b. Na-Hg/MeOH/THF;
III. Na/NH₃/-33° C.; IV. a. H₂/10%Pd/C.; b. TFA/DCM; V. 16/Et₃N;
VI. acid of structure 13/EDC/HOBt Compound 17

Compound 17 was prepared according to the procedures of Tetrahedron 1997, 53, 4769, herein incorporated by reference in its entirety for all purposes.

Compound 18

Compound 18 was prepared according to the procedures of J. Org. Chem. 1987, 52, 3759, herein incorporated by reference in its entirety for all purposes.

Compound 19

A suspension of Compound 18 (7.4 mmol) in THF (200 mL) was heated under reflux until a clear solution was obtained. The solution was cooled to −78° C. and n-butyl-lithium (14.8 mmol) was added dropwise to provide a solution of the dianion of sulfone 18.

To a DIBAL-H solution (7.8 mmol) at 0° C. was added a solution of MeOH (7.8 mmol) in THF (5 mL). The mixture was stirred for 5 minutes and cooled to −78° C. A solution of Compound 17 (6.6 mmol) in THF (5 mL) was added to the above DIBAL-H/MeOH solution, and the resulting reaction mixture was stirred for another 5 minutes. The resulting solution of aldehyde complexes was transferred to solution of the dianion of sulfone 18. The resulting mixture was stirred at −78° C. for 30 minutes, quenched with an aqueous solution of NH₄Cl, and warmed to 25° C. The mixture was then extracted with EtOAc, and concentrated to give Compound 19 as a mixture of diastereomers. (m/z 737.3 (M+Na)⁺.

Compound 20

To a solution of Compound 19 in DCM (20 mL) was added Ac₂O (1.5 mL), followed by pyridine (3 mL). The resulting mixture was stirred for 12 hours and concentrated. The concentrate was dissolved in MeOH (30 mL) and cooled to 0° C. NaH₂PO₄ (4.9 g) was added to the solution, followed by freshly prepared Na—Hg (6%, 6 g). The resulting mixture was warmed to 25° C. and stirred for 12 hours. Water (50 mL) was then added, and the mixture was filtered and concentrated. The concentrate was diluted with EtOAc and washed with brine. The organic phase was concentrated. Purification by flash column chromatography (silica gel, eluent: hexanes/EtOAc=10/1) gave Compound 20 (1.4 g).

Compound 21

To liquid ammonia (25 mL) at −33° C. was added a solution of Compound 20 (1.4 g) in THF (2.5 mL). Sodium was slowly added until the blue color of the solution persisted. The resulting mixture was stirred for 1 hour. Solid NH₄Cl (6 g) was then added slowly, the mixture was warmed to 25° C. and the ammonia was evaporated. The mixture was diluted with EtOAc, and washed sequentially with water and brine. The solvent was removed under reduced pressure. Purification of the resulting residue by flash column chromatography (silica gel, eluent: hexanes/EtOAc=5/1) gave Compound 21 (1.15 g).

Compound 22

A mixture of Compound 21 (1.15 g) and 10% Pd/C (160 mg) in MeOH (20 mL) was hydrogenated for 12 hours. CELITE was added and the resulting mixture was stirred for 5 minutes. The mixture was then filtered and concentrated to give an intermediate (1 g). The intermediate (700 mg) was dissolved in DCM (20 mL) and TFA (4 mL), and the resulting mixture was stirred for 4 hours, then concentrated under reduced pressure. The concentrated mixture was diluted with EtOAc, and washed sequentially with saturated aqueous Na₂CO₃, water, and brine. Concentration of the washed EtOAc mixture gave Compound 22 (420 mg).

Compound 8

To a solution of Compound 22 (1.57 mmol) in CH₃CN (16 mL) was added Compound 16 (1.57 mmol), followed by diisopropylethylamine (3.14 mmol). The resulting mixture was stirred for 12 hours. The mixture was then diluted with EtOAc, and washed sequentially with saturated aqueous Na₂CO₃, water and brine. Purification by reverse-phase HPLC (Phenomenex Synergi® Comb-HTS column, eluent: 25%-100% CH₃CN in water) gave Compound 8 (460 mg).

Example D

To the solution of Compound 13a (R=H, 0.08 mmol) and Compound 8 (0.06 mmol) in THF (1 mL) were added HOBt (15 mg), EDC (26 mg), and disopropylethylamine (0.25 mL). The mixture was stirred for 12 hours and concentrated. Purification by reverse phase HPLC (Phenomenex Synergi® Comb-HTS column, eluent: 25%-100% CH₃CN in water) gave Example D (27 mg). m/z 663.1 (M+H)⁺. ¹H-NMR (CDCl₃) δ 8.79 (1H, s), 7.83 (1H, s), 7.25-7.04 (10H, m), 6.98 (1H, s), 6.25 (1H, m), 5.25 (3H, m), 4.40 (2H, s), 4.12 (1H, m), 3.8 (3H, m), 3.22 (1H, m), 2.95 (3H, s), 2.70 (4H, m), 1.60 (4H, m), 1.26 (6H, d, J=7 Hz).

Example E

Example E was prepared following the procedure for Example D (30 mg), except that Compound 13b was used instead of Compound 13a. m/z 677.1 (M+H)$^+$.

Example F

Compound F was prepared following the procedure for Example D (40 mg), except that Compound 13c was used instead of Compound 13a. m/z 691.2 (M+H)$^+$. $^1$H-NMR (CDCl$_3$) δ 8.80 (1H, s), 7.83 (1H, s), 7.25-7.06 (10H, m), 6.98 (1H, s), 6.35 (1H, m), 6.23 (1H, m), 5.24 (2H, s), 5.12 (1H, m), 4.34 (2H, s), 4.10 (2H, m), 3.78 (1H, m), 3.23 (1H, m), 2.90 (3H, s), 2.68 (4H, m), 1.90 (2H, m), 1.7-1.4 (4H, m), 1.36 (6H, d, J=7.0 Hz), 0.90 (3H, t, J=7.3 Hz)

Example G

Example G was prepared following the procedure for Example D (84 mg), except that Compound 13d was used instead of Compound 13a. m/z 783.2 (M+H)$^+$.

Example H

Example H was prepared following the procedure for Example D (90 mg), except that Compound 13e was used instead of Compound 13a. m/z 763.2 (M+H)$^+$.

Example I

Example H (24 mg) was dissolved in TFA (2 mL) and the mixture was stirred for 12 hours, then concentrated, Purification by reverse phase HPLC (Phenomenex Synergi® Comb-HTS column, eluent: 25%-100% CH$_3$CN in water) gave Example I (14 mg). m/z 707.2 (M+H)$^+$. $^1$H-NMR (CDCl$_3$) δ 8.82 (1H, s), 7.85 (1H, s), 7.26-7.04 (10H, m), 7.0 (1H, s), 5.25 (2H, s), 4.86 (1H, m), 4.56 (1H, m), 4.37 (2H, m), 4.13 (1H, m), 4.06 (1H, m), 3.86 (1H, m), 3.32 (1H, m), 2.99 (3H, s), 2.8-2.6 (4H, m), 1.6-1.4 (4H, m), 1.37 (6H, m), 1.15 (3H, m).

Preparation of Example J

Scheme 9

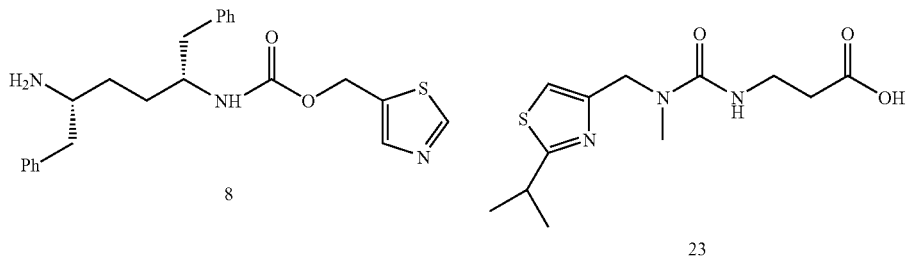

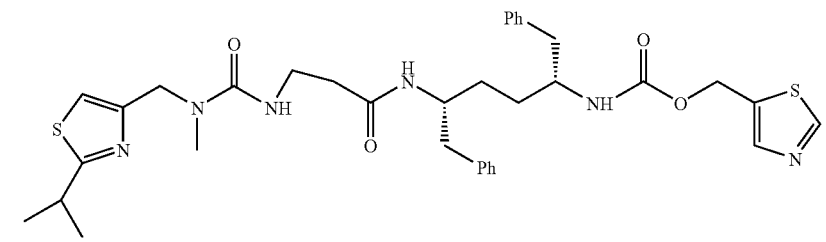

Example J

Example J

Compound 23 was prepared following the procedure for Compound 13, with the exception that methyl 3-isocyanatopropionate was used instead of Compound 11.

Example J was prepared following the procedure for Example D (37 mg), except that Compound 23 was used instead of Compound 13a. m/z 677.2 (M+H)$^+$.

Preparation of Example K

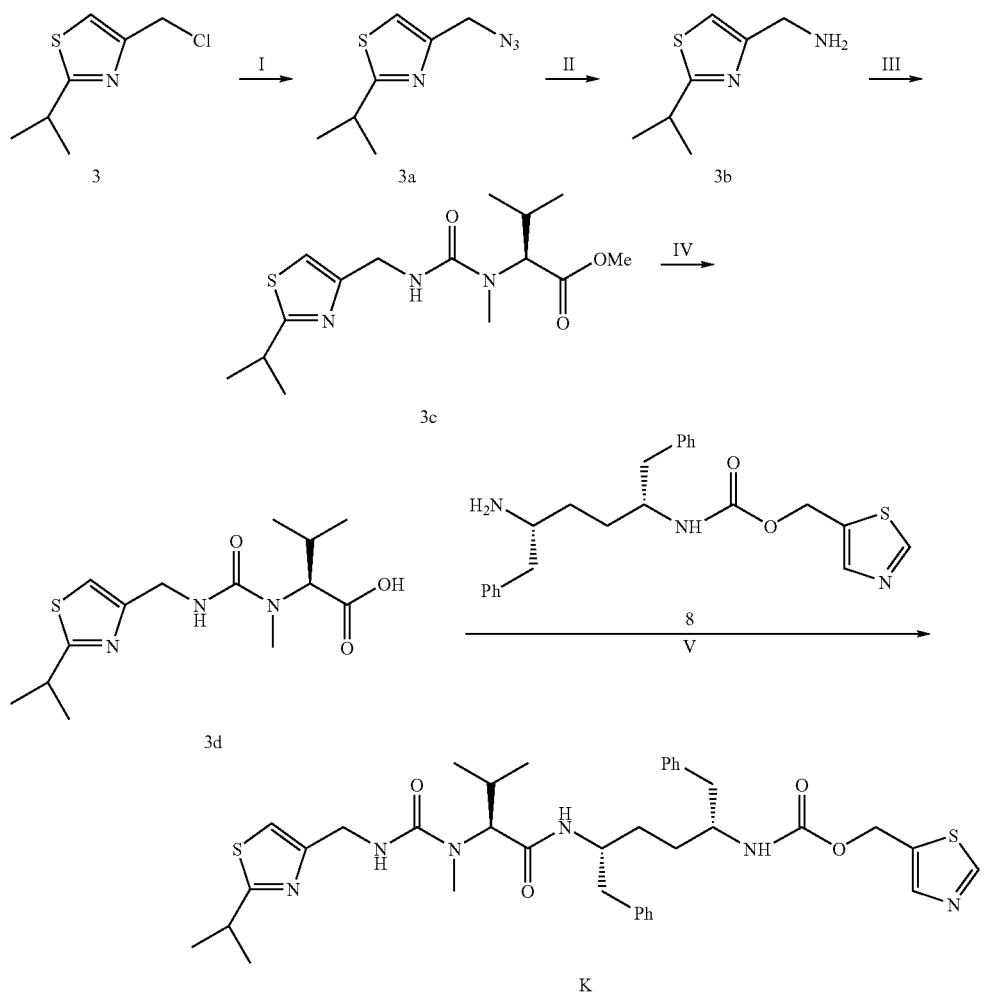

1. NaN₃/DMF; II. PPh₃/H₂O; III. a. Cl₃COCOOCCl₃; b. HCl——NH₂CHiPrCO₂Et;
IV. a. NaOH; b. HCl; V. EDC/HOBt/compound 8

Example K

Compound 5a

Compound 5a was prepared following the literature procedure of Synthesis 823, 1976, herein incorporated by reference in its entirety for all purposes.

Compound 5b

To the solution of Compound 5a (700 mg, 3.9 mmol) in THF (10 mL) was added water (69 μL, 3.9 mmol), followed by triphenylphosphine (1.06 g, 4.0 mmol). The mixture was stirred for 12 hours. Solvents were removed and the mixture was dried to give Compound 5b, which was used for next step without further purification.

Compound 5c

To a solution of triphosgene (110 mg, 0.37 mmol) in CH₂Cl₂ (2 mL) at 0° C. was added a solution of Compound 5b (1 mmol) and iPrNEt₂ (0.38 mL, 2.2 mmol) in CH₂Cl₂ (3.5 mL) over 30 minutes period. The mixture was stirred for 30 minutes, and a solution of amino N-methyl leucine methyl ester HCl salt (182 mg, 1 mmol) and iPrNEt₂ (0.34 mL, 2.2 mmol) in CH₂Cl₂ (2 mL) was added. The mixture was stirred for 12 hours, and diluted with EtOAc. The solution was washed with sat. Na₂CO₃ (2×), water (2×), and brine, and dried over Na₂SO₄. Concentration and purification with silica gel flash column gave Compound 5c (300 mg).

Compound 5d

Compound 5d was prepared following the procedure for Compound 13, with the exception that Compound 5c was used instead of Compound 12.

Example K

Example K was prepared following the procedure for Example D (7 mg), except that Compound 5d was used instead of Compound 13a. m/z 705.2 (M+H)⁺. ¹H-NMR (CDCl₃) δ 8.8 (1H, m), 7.86 (1H, s), 7.26-6.8 (11H, m), 6.10 (1H, m), 5.5-5.10 (4H, m), 4.46 (2H, m), 4.2-3.75 (3H, m), 3.25 (1H, m), 2.82/2.4 (3H), 2.8-2.5 (4H, m), 2.17 (1H, m), 1.7-1.2 (10H, m), 0.8 (6H, m).

Preparation of Example L

Scheme 11

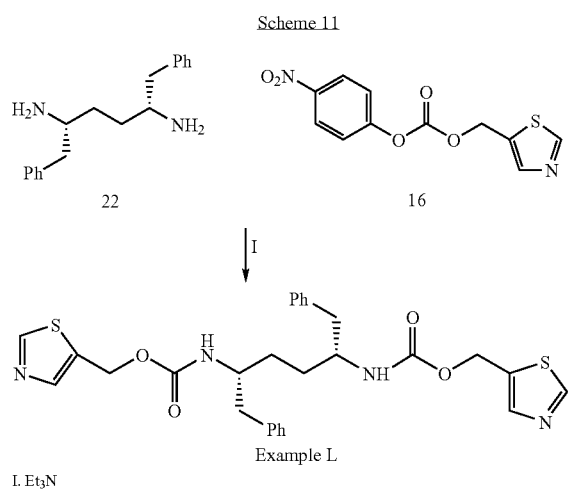

Example L

I. Et₃N

Example L

To a solution of Compound 22 (1.57 mmol) in CH₃CN (16 mL) was added Compound 16 (3.14 mmol), followed by triethylamine (4.71 mmol). The resulting mixture was stirred for 12 hours. The reaction mixture was diluted with EtOAc and washed sequentially with saturated aqueous $Na_2CO_3$, water, and brine. The solvent was removed under reduced pressure. Purification of the residue by flash column chromatography (silica gel, eluent: hexanes/EtOAc=1/1) gave Example L (460 mg). m/z 551.2 (M+H)⁺. ¹H-NMR (CDCl₃) δ 8.81 (2H, s), 7.85 (2H, s), 7.26-7.0 (10H, m), 5.24 (4H, s), 4.50 (2H, m), 3.87 (2H, m), 2.73 (4H, m), 1.4-1.2 (4H, m).

Alternate Preparation of Compound 22

Scheme 12

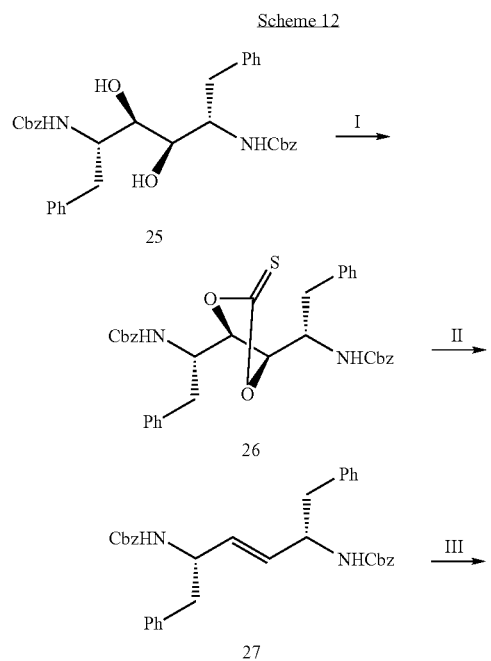

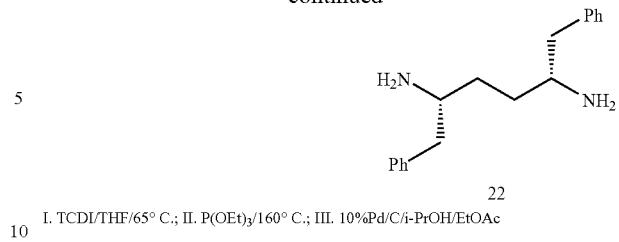

I. TCDI/THF/65° C.; II. P(OEt)₃/160° C.; III. 10%Pd/C/i-PrOH/EtOAc

Compound 25

Compound 25 was prepared following the literature procedure described in J. Org. Chem. 1996, 61, 444 (herein incorporated by reference in its entirety), except that the L-isomer was prepared instead of the D-isomer.

Compound 26

A mixture of Compound 25 (7.4 g) and 1,1'-thiocarbonyldiimidazole (4.5 g) in THF (260 mL) was heated at 65° C. for 54 hours. Solvent was removed from the mixture under reduced pressure. Purification by flash column chromatography (silica gel, hexanes/EtOAc=1/1) gave Compound 26 (7.33 g).

Compound 27

The mixture of Compound 26 (7.3 g) and triethylphosphite (100 mL) was heated at 160° C. for 4 hours. Excess reagents were removed under reduced pressure. Purification by flash column chromatography (silica gel, hexanes/EtOAc=3/1) gave Compound 27 (5 g).

Compound 22

A mixture of Compound 27 (250 mg) in i-PrOH/EtOAc (5 mL/5 mL) was hydrogenated for 14 hours in the presence of 10% Pd/C (75 mg). CELITE was added to the mixture, and the mixture was stirred for 5 minutes. Filtration and evaporation of solvents gave Compound 22 (116 mg).

The skilled practitioner will recognize that the procedure outlined in Scheme 12 can be used to prepare a variety of 1,4-substituted 1,4-diamines analogous to Compound 22. For example, an amine-protected 2,3-dihydroxy-1,4-diamine analogous to Compound 25 can be prepared:

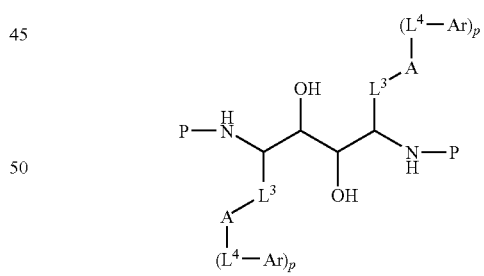

Analogs of Compound 25 wherein L³, A, Ar, and P are as defined herein, and protecting group "P" is any amine protecting group described in described in *Protective Groups in Organic Synthesis*, Theodora W. Greene and Peter G. M. Wuts (John Wiley & Sons, Inc., New York, 1999, ISBN 0-471-16019-9), which is herein incorporated by reference in its entirety for all purposes. The analogs of Compound 25 can then be transformed, according to the methods outlined in Scheme 12, to form analogs of Compound 26:

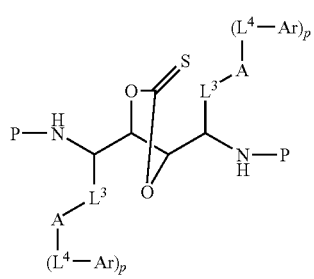

Analogs of Compound 26;

analogs of Compound 27:

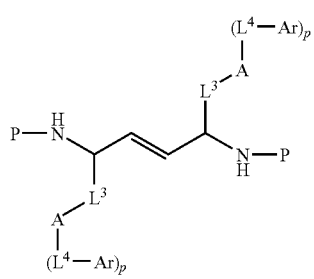

Analogs of Compound 27; and analogs of Compound 22:

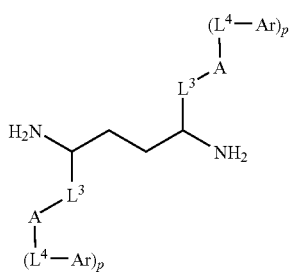

Analogs of Compound 22

Preparation of Examples M and N

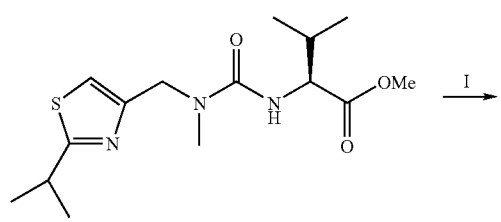

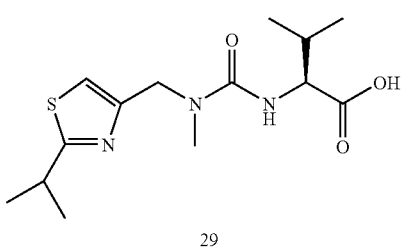

I. a. LiOH, THF/H$_2$O, 25° C.; b. HCl

Compound 29

Compound 28 was prepared using a procedure similar to that used to prepare Compound 6 (described in Scheme 4) except that Compound 9 was used instead of Compound 4.

To a solution of Compound 28 (0.757 g, 2.31 mmol) in THF (9 mL) at room temperature was added freshly prepared 1M LiOH (4.6 mL, 4.6 mmol). After 1.5 h, 1 M HCl (7 mL, 7 mmol) was added and the reaction mixture extracted thoroughly with EtOAc (5×15 mL). The combined organic layers were dried over anhydrous Na$_2$SO$_4$ and the volatiles removed in vacuo to afford 0.677 g (93%) of Compound 29 as a colorless glassy solid (LC/MS m/z 314.0 (M+H)$^+$) that was used in the following procedures without further purification.

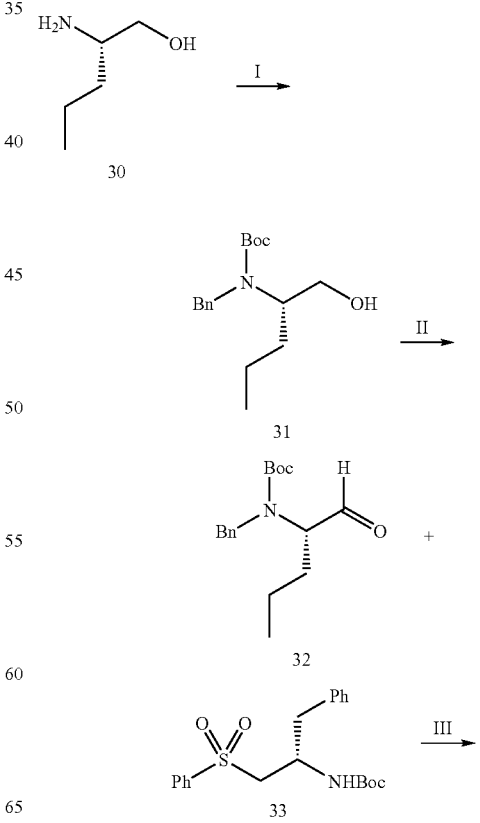

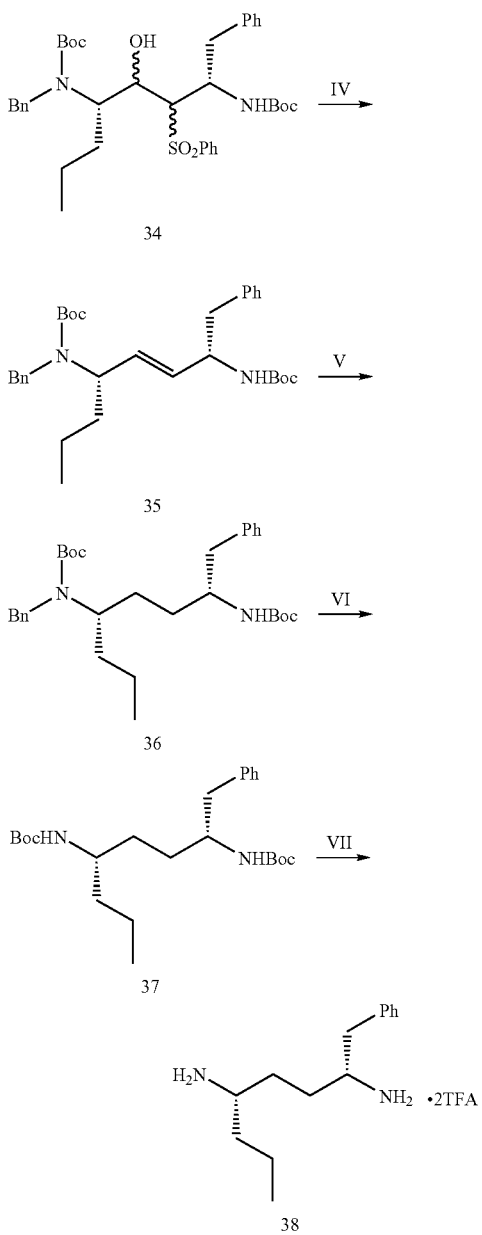

I. a. PhCHO, MeOH; b. NaBH₄; c. Boc₂O, THF/H₂O. II. Pyr·SO₃, Et₃N, DMSO 0° C. III. n-BuLi, MeOAl(i-Bu)₂, THF, -78° C. IV. a. Ac₂O, pyr, CH₂Cl₂, b. 6% Na/Hg, Na₂HPO₄, MeOH. V. H₂, 10% Pd/C, MeOH. VI. Na/NH₃, THF, -35° C. VII. 20% TFA/DCM.

Compound 30

Compound 30 was purchased from Aldrich Chemical Co., and used without further purification.

Compound 31

To a solution of Compound 30 (8.25 g, 80 mmol) in MeOH (50 mL), was added benzaldehyde (8.1 mL, 80 mmol) and the resulting solution was allowed to stir at room temperature. After 2 h, the reaction mixture was cooled to 0° C. and NaBH₄ (3.33 g, 88 mmol) was added in portions. After allowing the reaction mixture to warm to room temperature over 2 h, glacial acetic acid (2 mL) was added. The resulting viscous solution was concentrated in vacuo. EtOAc and H₂O (50 mL each) were added and the aqueous phase was extracted with EtOAc. The combined organic phases were washed with saturated NaHCO₃, brine, and concentrated in vacuo. The resulting material was taken up in THF (25 mL) and H₂O (25 mL) at room temperature and Boc₂O (15.1 g, 69.2 mmol) was added to produce an opaque suspension that was stirred vigorously for 2 h at room temperature. THF was removed in vacuo, and the aqueous layer was extracted with EtOAc. The combined organic layers were washed with brine and dried over anhydrous MgSO₄ and concentrated in vacuo. Chromatography on SiO₂ (3/1 Hex/EtOAC) afforded 18.5 g (79%) of Compound 31 as a colorless oil (LC/MS m/z 293.9 (M+H)⁺.

Compound 32

Compound 31 (5.95 g, 20.3 mmol) and Et₃N (9.9 mL, 71 mmol) were diluted in DMSO (65 mL) and allowed to age at room temperature for 30 min before cooling to 0° C. Pyridine·SO₃ was added in one portion and the reaction mixture was maintained at 5° C. to prevent freezing. After 45 min, the reaction mixture was poured into ice water and extracted with EtOAc. The combined organic layers were washed with saturated NaHCO₃, H₂O, and dried over anhydrous MgSO₄ prior to concentration in vacuo (bath temperature 25° C.) to produce 4.39 g (74%) of Compound 32 as a clear, yellow colored oil that was used without further purification. ¹H-NMR (CDCl₃, 300 MHz) δ (major rotamer) 9.36 (br s, 1H); 5.01 (d, J=15 Hz, 1H); 4.12 (d, J=15 Hz, 1H); 3.45 (m, 1H); 2.04-1.88 (m, 1H); 1.80-1.58 (m, 1H); 1.54-1.20 (m, 2H); 1.47 (s, 9H); 0.91 (t, J=7.2 Hz, 3H). (minor rotamer) 9.46 (br s, 1H); 4.71 (d, J=15 Hz, 1H); 4.20 (d, J=15 Hz, 1H); 3.78 (m, 1H); 2.04-1.88 (m, 1H); 1.80-1.58 (m, 1H); 1.54-1.20 (m, 2H); 1.47 (s, 9H); 0.91 (t, J=7.2 Hz, 3H)

Compound 34

A suspension of Compound 33 (6.23 g, 16.6 mmol) in THF (500 mL) was heated under reflux until a homogeneous solution was obtained. The solution was cooled to -78° C. and 1.6M n-BuLi (19.7 mL, 31.5 mmol) was introduced to produce a clear yellow solution. Meanwhile, DIBAL-OMe was prepared by dilution of DIBAL-H (1M in hexanes, 18.1 mL, 18.1 mmol) in THF (8 mL) and cooling to 0° C. prior to addition of MeOH (0.73 mL, 18.1 mmol). This solution was allowed to age while Compound 32 (4.39 g, 15.1 mmol) was diluted in THF (15 mL) and cooled to -78° C. The DIBAL-OMe solution was cannulated to the solution of Compound 32 and allowed to age for 5 min prior to cannulation to the sulfur dianion solution. The resulting clear yellow solution was allowed to age at -78° C. for 1 h. The reaction was quenched by addition of saturated NH₄Cl (100 mL) at -78° C. and allowed to warm to room temperature. Water was added until all precipitated solids were dissolved and the layers separated. The THF layer was concentrated in vacuo while the aqueous layer was extracted with EtOAc. The recombined organic layers were washed with brine, and the resulting emulsion was treated with solid NaOH until homogeneous bilayers resulted. The aqueous layer was extracted with EtOAc and the combined organics dried over anhydrous Na₂SO₄. Concentration in vacuo produced 9.57 g (95%) of Compound 34 as an amorphous white solid (LC/MS m/z: 689.3 (M+Na)⁺) that was used in the following procedures without further purification.

Compound 35

Crude Compound 34 was suspended in CH₂Cl₂ (65 mL) followed by addition of pyridine (6.7 mL, 83 mmol) and acetic anhydride (3.5 mL, 36.5 mmol). The resulting solution was allowed to age at room temperature overnight. MeOH (6 mL) was added and after 10 min, the reaction was poured into brine. Addition of water produced a bilayer that was separated and the aqueous phase was repeatedly extracted with CH₂Cl₂. The combined organic layers were dried over anhydrous MgSO₄ and concentrated in vacuo to produce 8.95 g (88%) of a white solid that was immediately taken up in MeOH (100 mL). Na$_2$HPO$_4$ (11.4 g, 80.3 mmol) was added and the resulting slurry was cooled to 0° C. prior to addition of Na—Hg (6%, 14.5 g, 37.8 mmol) in portions. After aging at room temperature overnight, H$_2$O (30 mL) was added and the reaction was filtered through a celite pad. MeOH was removed in vacuo and the aqueous residue was extracted with EtOAc. The combined organic layers were washed with brine, dried over anhydrous MgSO$_4$ and concentrated in vacuo to a yellow oil that was purified by chromatography on SiO$_2$ (0-15% EtOAc/hexanes) to afford 2.14 g (34%) of Compound 35 as a colorless oil (LC/MS m/z: 531.2 (M+Na)$^+$).

Compound 36

Compound 35 (1.73 g, 3.4 mmol) was diluted in MeOH (7.5 mL) and 10% Pd/C (0.36 g, 0.34 mmol) was added. The atmosphere was replaced with a H$_2$ balloon and the reaction mixture allowed to age at room temperature. After 2 h, the reaction mixture was filtered through a pad of celite, the filtrate was washed several times with MeOH, and the combined organic layers were concentrated in vacuo to afford 1.45 g (83%) of Compound 36 as a colorless oil (LC/MS m/z: 533.2 (M+Na)$^+$) that was used in the following procedures without further purification.

Compound 37

Compound 36 (0.528 g, 1.03 mmol) was diluted in THF (3 mL) and added to liquefied ammonia (approx. 20 mL) at −35° C. Small pieces of Na were added until a blue color persisted. After 1.5 h, solid NH$_4$Cl was added in portions until the remaining Na was destroyed and the ammonia was allowed to escape at ambient temperature. Water and EtOAc (20 mL each) were added, and the aqueous layer was extracted with EtOAc. The combined organic layers were washed with brine, dried over Na$_2$SO$_4$ and concentrated in vacuo to afford 0.395 g (91%) of Compound 37 as an amorphous white solid that was used without further purification in the following procedures (LC/MS m/z: 421.1 (M+H)$^+$; 443.2 (M+Na)$^+$).

Compound 38

Compound 37 (0.362 g, 0.861 mmol) was diluted in CH$_2$Cl$_2$ (3.2 mL). Trifluoroacetic acid (0.8 mL) was added and the clear solution was allowed to age overnight. Following concentration in vacuo, the residue was azeotroped with toluene several times to remove residual TFA. 0.382 g (99%) of the bis-trifluoroacetate salt of Compound 38 was collected as a colorless oil that was used without further purification (LC/MS m/z: 221.1 (M+H)$^+$).

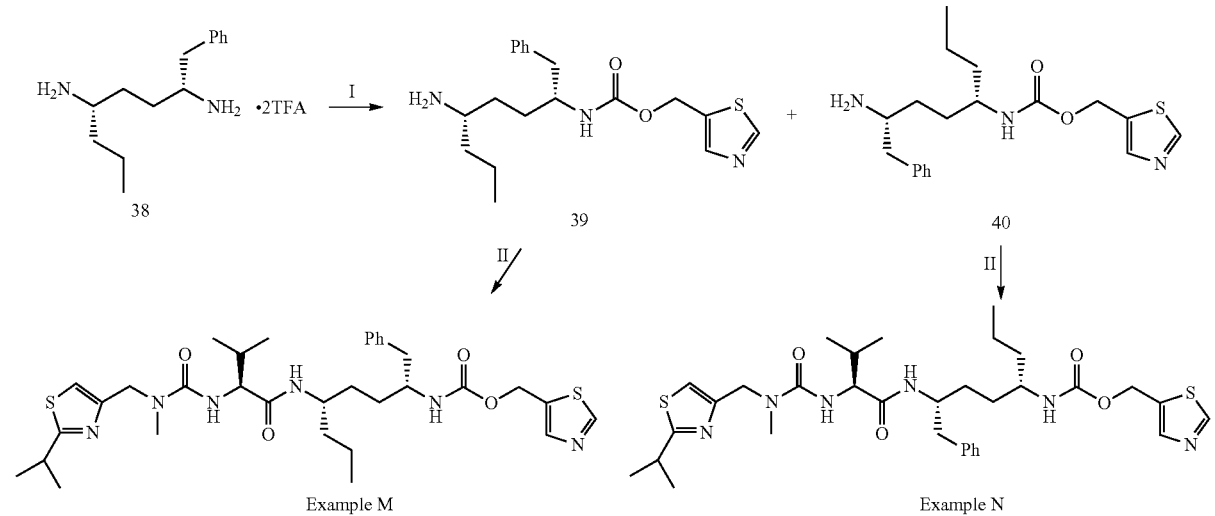

Scheme 15

I. carbonate 16, DIPEA, MeCN; II. acid 29, EDC, HOBt, DIPEA, THF

Compounds 39 and 40

Compound 38 (0.382 g, 0.852 mmol) was diluted in MeCN (10 mL) and N,N-diisopropylethylamine (0.60 mL, 3.41 mmol) was added, followed by a solution of Compound 16 in MeCN (1.5 mL). The clear, yellow solution was allowed to age at room temperature for 4 h and the volatiles were removed in vacuo. The residue was taken up in a 3/1 CHCl$_3$/IPA (v/v, 13 mL) and treated with saturated Na$_2$CO$_3$ (3 mL). The resulting suspension was diluted with H$_2$O (3 mL), and the aqueous phase thoroughly extracted with 3/1 CHCl$_3$/IPA. The combined organic layers were dried over a 3/2 (w/w) mixture of anhydrous Na$_2$SO$_4$/anhydrous Na$_2$CO$_3$ and concentrated in vacuo. Chromatography on SiO$_2$ (0-20% MeOH/CH$_2$Cl$_2$) afforded 0.043 g (14%) of Compound 39 as a colorless film (LC/MS m/z: 362.1 (M+H)$^+$) and 0.105 g (34%) of Compound 40 as a colorless film (LC/MS m/z: 362.1 (M+H)$^+$).

Example M

A flask was charged with Compound 39 (0.048 g, 0.133 mmol) and Compound 29 was added as a 0.2 M solution in THF (0.8 mL, 0.160 mmol). THF (1 mL) was added, followed by DIPEA (0.026 mL, 0.145 mmol), HOBt (0.022 g, 0.160 mmol) and finally EDC (0.028 mL, 0.160 mmol). The clear, colorless solution was allowed to age overnight. Volatiles were removed in vacuo and the residue chromatographed on SiO$_2$ (0-20% MeOH/CH$_2$Cl$_2$). Fractions containing the desired compound were concentrated in vacuo and submitted to preparatory LC/MS purification to afford 0.018 g (20%) of Example M as a colorless film LC/MS m/z: 657.2 (M+H)$^+$; $^1$H-NMR (CDCl$_3$, 300 MHz) δ 8.95 (s, 1H); 7.88 (br s, 1H); 7.27-7.04 (m, 5H); 7.04 (s, 1H); 6.60-6.20 (m, 2H); 5.22 (m, 2H); 5.12 (d, J=9.3 Hz, 1H); 4.50 (m, 2H); 4.01 (br s, 1H); 3.83 (m, 2H); 3.38 (m, 1H); 3.10-2.94 (m, 3H); 2.74 (m, 2H);

2.23 (m, 1H); 1.64-1.15 (m, 8H); 1.40 (d, J=6.9 Hz, 6H); 0.96 (m, 6H); 0.83 (t, J=6.9 Hz, 3H).

Example N

Example N was prepared using procedures similar to those used to prepare Example M, using the following reagents: Compound 40 (0.055 g, 0.152 mmol); Compound 29 (0.92 mL of 0.2 M THF solution, 0.183 mmol); THF (1 mL); DIPEA (0.040 mL, 0.228 mmol); HOBt (0.025 g, 0.182 mmol); EDC (0.032 mL, 0.182 mmol). 0.087 g (87%) of Example N was isolated as a colorless film (LC/MS m/z: 657.2 (M+H)+; 1H-NMR CDCl3, 300 MHz) δ 8.84 (s, 1H); 7.86 (s, 1H); 7.27-7.04 (m, 5H); 7.04 (s, 1H); 6.28 (br s, 1H); 6.12 (br s, 1H); 5.25 (m, 2H); 5.11 (d, J=9.0 Hz, 1H); 4.62-4.32 (m, 2H); 4.19 (m, 1H); 4.01 (br s, 1H); 3.53 (m, 1H); 3.10-2.90 (m, 3H); 2.72 (d, J=6.0 Hz, 2H); 2.29 (m, 1H); 1.65-1.18 (m, 8H); 1.39 (d, J=6.9 Hz, 6H); 1.00-0.78 (m, 9H).

Preparation of Examples O and P

Scheme 16

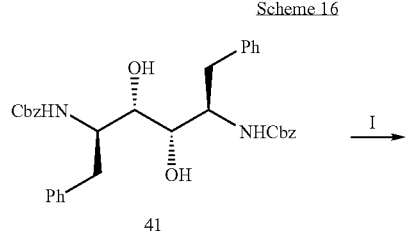

41

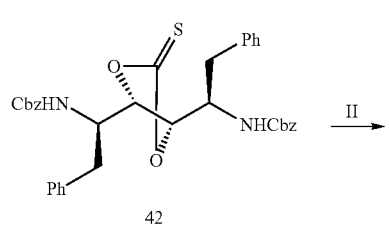

42

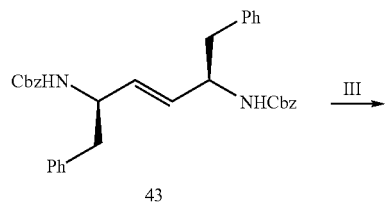

43

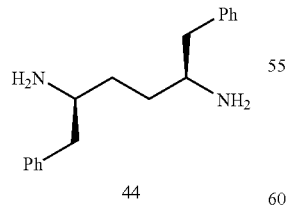

44

I. TCDI/THF/65° C.; II. P(OEt)3/160° C.; III. H2, 10% Pd/C.

Compound 41

Compound 41 was prepared following the procedure described in J. Org. Chem. 1996, 61, 444-450.

Compound 42

A mixture of Compound 41 (1.73 g, 3 mmol) and 1,1'-thiocarbonyldiimidazole (1.14 g, 6.1 mmol) in THF (60 mL) was heated at 65° C. for 72 hours. Solvent was removed under reduced pressure. The mixture was diluted with EtOAc, and washed successively with 1N HCl, water, and brine, and dried over MgSO4. Purification by flash column chromatography (silica gel, hexanes/EtOAc=1/1) gave Compound 42 (980 mg). m/z: 611.1 (M+H)+.

Compound 43

A mixture of Compound 42 (980 mg) and triethyl phosphite (10 mL) was heated at 160° C. for 14 hours. The excess reagents were removed under reduced pressure. Recrystallization from a mixture of hexanes (11 mL) and EtOAc (3.6 mL) gave Compound 57 (580 mg). m/z: 557.3 (M+Na)+.

Compound 44

A mixture of Compound 43 (580 mg) in i-PrOH/EtOAc (12 mL/12 mL) was hydrogenated under high pressure (100 psi) for 24 hours in the presence of 10% Pd/C (200 mg). Celite was added and the mixture was stirred for 5 minutes. Filtration and evaporation gave Compound 44 (285 mg). m/z: 269.1 (M+H)+.

The skilled practitioner will recognize that the procedure outlined in Scheme 16 can be used to prepare a variety of 1,4-substituted 1,4-diamines analogous to Compound 44. For example, an amine-protected 2,3-dihydroxy-1,4-diamine analogous to Compound 41 can be prepared:

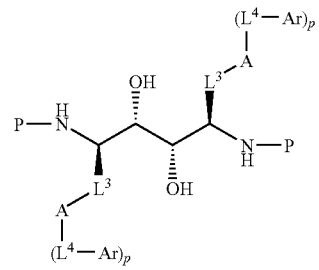

Analogs of Compound 41 wherein $L^3$, A, Ar, and P are as defined herein, and protecting group "P" is any amine protecting group described in described in *Protective Groups in Organic Synthesis*, Theodora W. Greene and Peter G. M. Wuts (John Wiley & Sons, Inc., New York, 1999, ISBN 0-471-16019-9). The analogs of Compound 41 can then be transformed, according to the methods outlined in Scheme 16, to form analogs of Compound 42:

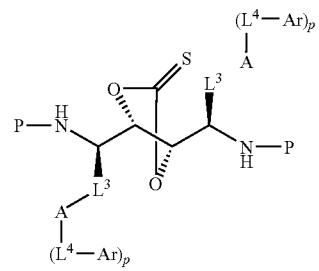

Analogs of Compound 42

Analogs of Compound 43

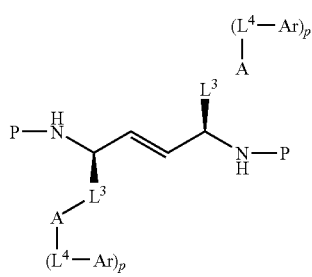

Analogs of Compound 43; and

Analogs of Compound 44

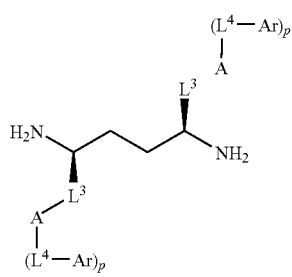

Analogs of Compound 44

It will also be recognized that stereochemical configurations other than those shown (i.e., enantiomers or diasteriomers) can be prepared by the selection of analogs of Compound 41 having the appropriate stereochemical configuration at the chiral centers.

Scheme 17

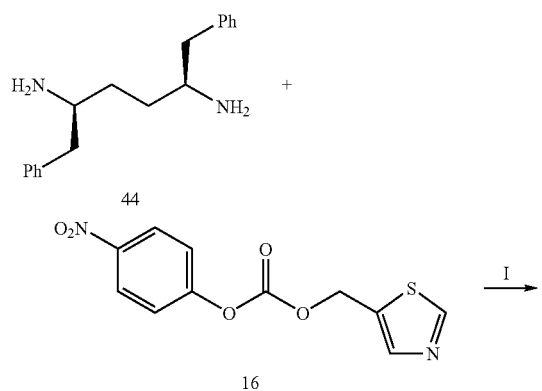

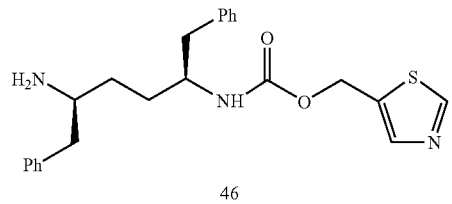

I. Et₃N/CH₃CN

Compound 46

To the solution of Compound 45 (950 mg, 3.5 mmol) in CH₃CN (36 mL) at 0° C. was added Compound 16 (892 mg, 3.2 mmol), followed by diisopropylethylamine (1.2 mL, 7 mmol). The mixture was stirred for 12 hours at 25° C. The mixture was diluted with EtOAc, and washed successively with saturated Na₂CO₃, water, and brine. Purification by flash column chromatography (silica gel, 100% EtOAc to CH₂Cl₂/MeOH=4/1) gave Compound 46 (770 mg). m/z: 410.1 (M+H)⁺.

The skilled practitioner will recognize that the procedure outlined in Scheme 17 can be used to prepare a variety of compounds analogous to Compound 46. For example, 1,4-diamines analogous to Compound 44 can be prepared as discussed above:

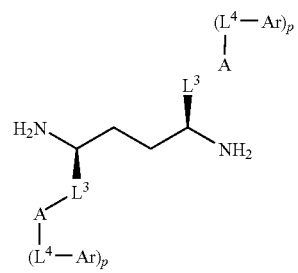

Analogs of Compound 44

The analogs of Compound 44 can then be reacted with analogs of Compound 16:

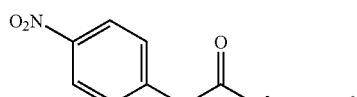

Analogs of Compound 16

(wherein Z², X, and R⁹ are as defined herein) to form analogs of Compound 46:

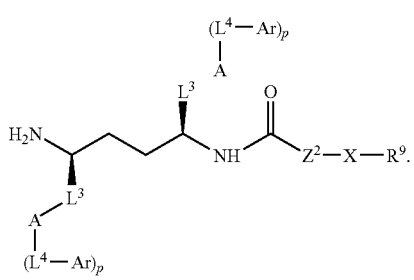

It will also be recognized that stereochemical configurations other than those shown (i.e., enantiomers or diasteriomers) can be prepared by the selection of analogs of Compound 44 having the appropriate stereochemical configuration at the chiral centers.

mixture was stirred for 14 hours. Purification by flash column chromatography (hexanes/EtOAc=1/1.5) gave Compound 48 (242 mg). m/z: 372.1 (M+H)$^+$.

Compound 49

To a solution of Compound 48 (240 mg, 0.65 mmol) in dioxane (4 mL) and water (4 mL) was added sodium hydroxide (40 mg, 1 mmol). The mixture was stirred for 1 hour and acidified with 4 N HCl in dioxane (0.25 mL, 1 mmol). The mixture was extracted with EtOAc and organic phase was dried with MgSO$_4$. Concentration gave Compound 49 (200 mg). m/z: 356.2 (M–H)$^+$.

Example O

To a solution of corresponding acid 49 (30 mg, 0.08 mmol) and Compound 46 (22 mg, 0.05 mmol) in THF (1 mL) were

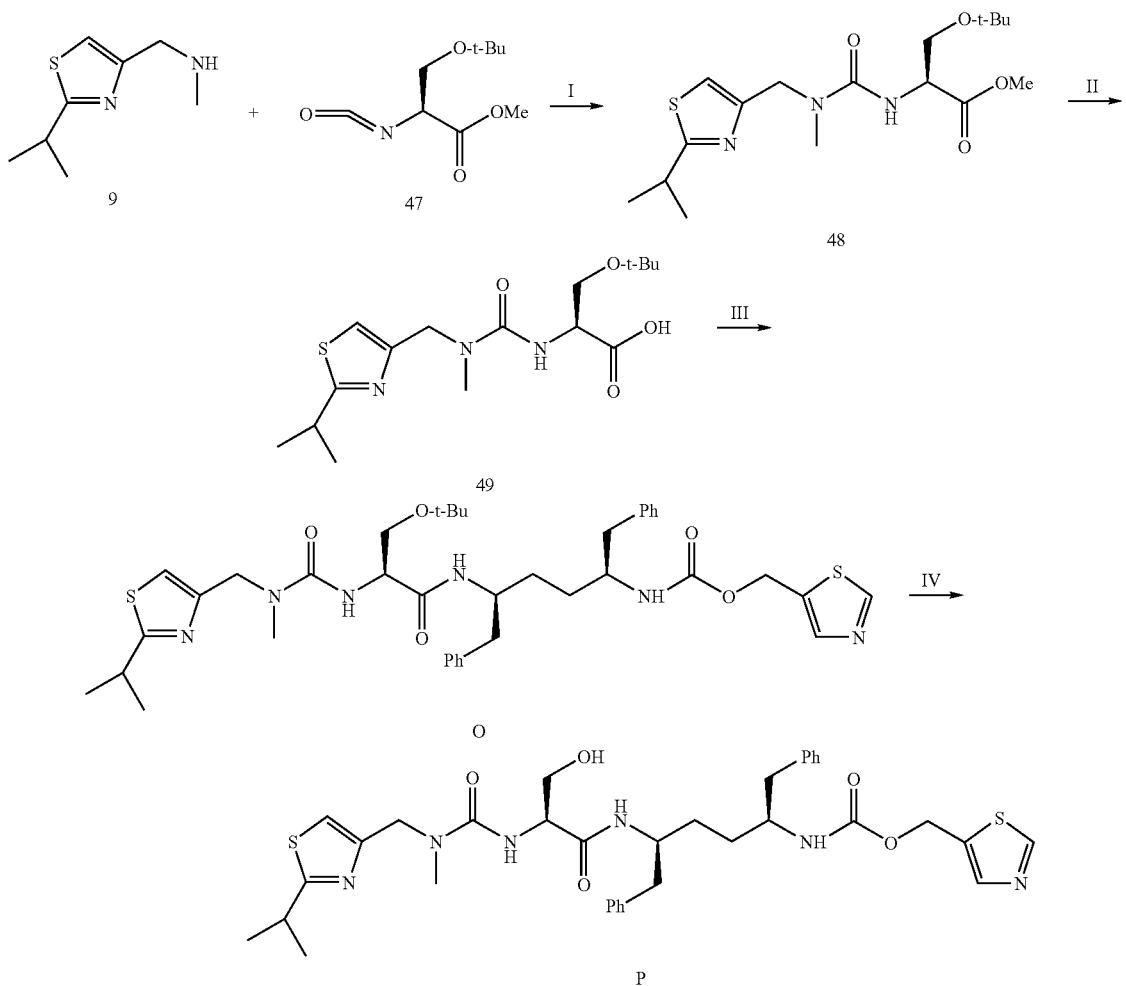

I. CH$_2$Cl$_2$/25° C.; II. a. NaOH/dioxane/H$_2$O; b. HCl; III. amine 46/EDC/HOBt; IV. a. TFA; b. NaOH Compound 47

Compound 47 is commercially available from TCI.

Compound 48

To a solution of Compound 9 (500 mg, 3 mmol) in CH$_2$Cl$_2$ (3 mL) was added Compound 47 (500 mg, 2.5 mmol). The added HOBt (15 mg, 0.11 mmol), EDC (20 μL, 0.11 mmol), and disopropylethylamine (0.2 mL). The mixture was stirred for 12 hours and concentrated. Purification by flash column chromatography (hexanes/EtOAc=1/5 to 0/100) gave Example O (17 mg). m/z: 749.3 (M+H)$^+$.

Example P

To Example O (17 mg) was added TFA (2 mL). The mixture was stirred for 3 hours and concentrated. The mixture was diluted with THF (2 mL) and 1.0 N NaOH solution was added until pH 11. The mixture was stirred for 10 minutes, and extracted with EtOAc. The organic phase was washed with water and brine. Purification by flash column chromatography (EtOAc) gave Example P (12 mg). $^1$H-NMR (CDCl$_3$) δ 8.76 (1H, s), 7.79 (1H, s), 7.25-6.9 (11H, m), 6.51 (1H, broad), 5.42 (1H, m), 5.18 (2H, m), 4.42 (2H, m), 4.22 (1H, m), 4.10 (1H, m), 3.95 (1H, m), 3.79 (1H, m), 3.58 (1H, m), 3.23 (1H, m), 2.93 (3H, s), 2.9-2.5 (4H, m), 1.6-1.2 (10H, m); m/z: 693.2 (M+H)$^+$.

Preparation of Examples Q, R, and S

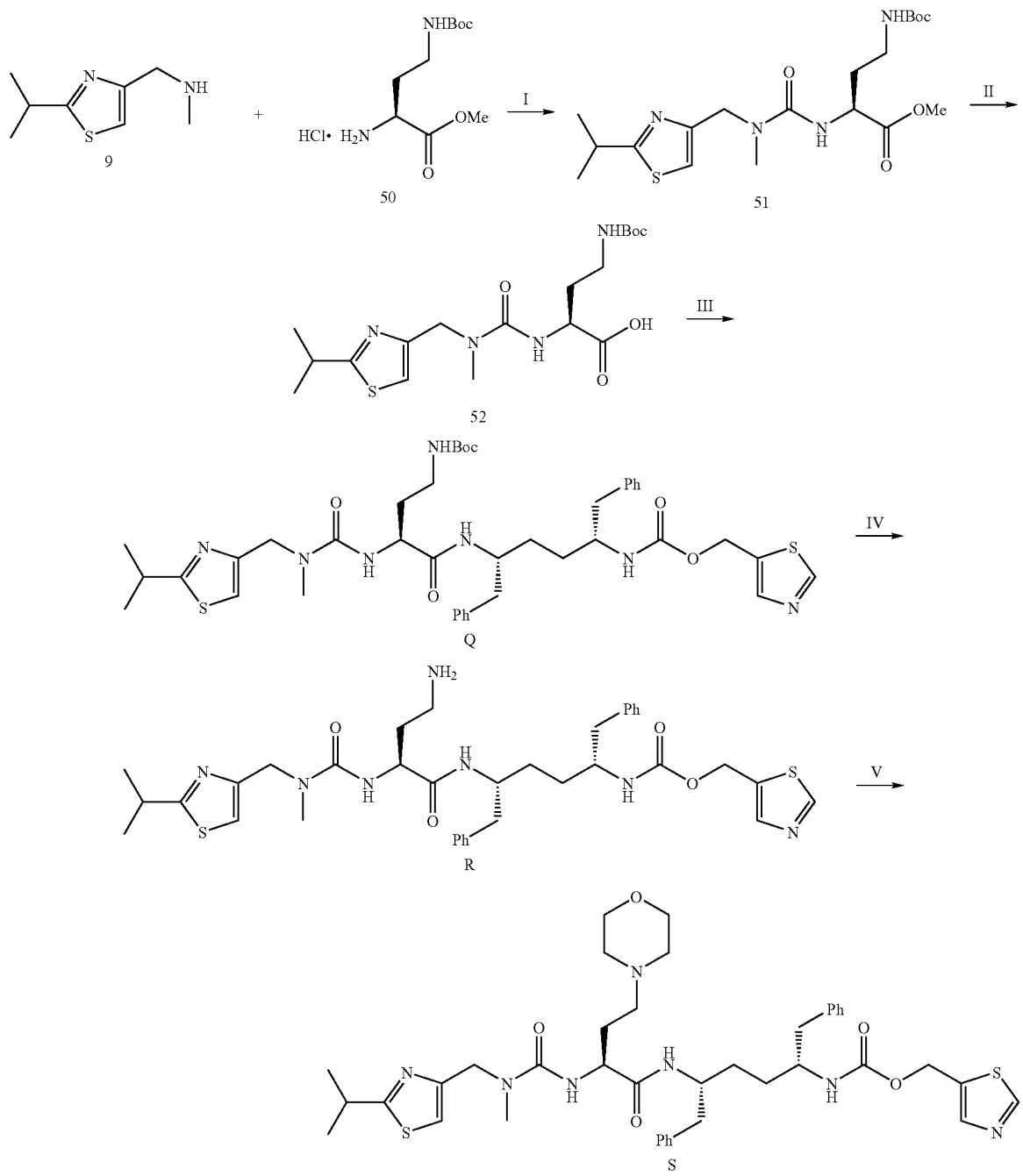

I. CDI, DIPEA, CH$_2$Cl$_2$; II. LiOH, THF/H$_2$O;
III. Cmpd. 8, DIPEA, EDC, HOBt, THF;
IV.a. HCl/dioxane; b. Na$_2$CO$_3$; V.
(BrCH$_2$CH$_2$)$_2$O, NaHCO$_3$, DMF Compound 50

Compound 50 is commercially available from Chem Impex International, and used without further purification.

Compound 51

Compound 50 (7.0 g, 26.0 mmol) was dissolved in $CH_2Cl_2$ (330 mL) and 1,1-carbonyldiimidazole (4.22 g, 26.0 mmol) was added, followed by i-Pr2NEt (19 mL, 104 mmol). The solution was stirred at 25° C. for 12 hours. Compound 9 (4.44 g, 26.0 mmol) was dissolved in 20 mL of $CH_2Cl_2$ and added to the reaction mixture. The solution was stirred at 25° C. for 7 hours. The solvent was removed in vacuo and the residue was diluted with ethyl acetate and washed with water and brine. The organic layers were dried ($Na_2SO_4$), filtered, and evaporated. Purification by Combiflash® (stationary phase: silica gel; eluent: 66-100% EtOAc/Hexane gradient) gave Compound 51 (7.34 g). m/z: 429.0 $(M+H)^+$.

Compound 52

Compound 51 (7.34 g, 17.13 mmol) was dissolved in THF (90 mL) and 1M aqueous LiOH (35 mL) was added. The mixture was stirred at 25° C. for 0.5 hour. The reaction was quenched with 1M HCl (51 mL) and the mixture was adjusted to pH 2. The mixture was extracted with ethyl acetate. The organic layers were dried over $Na_2SO_4$, filtered, and evaporated to provide Compound 52 (7.00 g). The recovered Compound 52 was used in the next step without further purification. m/z: 415.0 $(M+H)^+$.

The skilled practitioner will recognize that the procedure outlined in Scheme 19 can be used to prepare a variety of compounds analogous to Compounds 51 and 52. For example, amines analogous to Compound 9 can be reacted with the appropriate amino ester analogous to Compound 50:

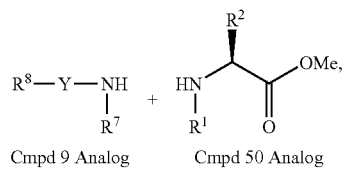

Cmpd 9 Analog    Cmpd 50 Analog to form compounds analogous to Compound 51, which are further reacted to form compounds analogous to Compound 52:

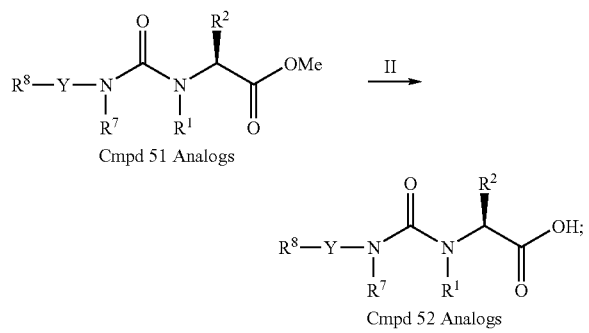

Cmpd 51 Analogs

Cmpd 52 Analogs wherein $R^1$, $R^2$, $R^7$, $R^8$ and Y are as defined herein.

It will also be recognized that stereochemical configurations other than those shown (i.e., enantiomers or diasteriomers) can be prepared by the selection of analogs of Compound 50 having the appropriate stereochemical configuration at the chiral center.

Example Q

Compound 52 (2.57 g, 6.21 mmol) was dissolved in THF (67 mL). Compound 8 (2.10 g, 5.13 mmol) was added, followed by HOBt (1.04 g, 7.70 mmol), i-Pr2NEt (3.67 mL, 20.52 mmol), and EDC (1.82 mL, 10.26 mmol). The mixture was stirred at 25° C. for 12 hours. The solvent was removed under reduced pressure. The residue was diluted with ethyl acetate and washed sequentially with saturated aqueous $Na_2CO_3$, water, and brine. The organic phase was dried over $Na_2SO_4$, filtered, and evaporated. Purification by flash column chromatography (stationary phase: silica gel; eluent: 5% iPrOH/$CH_2Cl_2$) gave Example Q (3.02 g). m/z: 806.2 $(M+H)^+$.

Example R

Example Q (3.02 g, 3.74 mmol) was suspended in 4.0 N HCl/dioxane solution (30 mL) and stirred at 25° C. for 3 hours. Solvent was removed under reduced pressure and $Et_2O$ was poured into the reaction mixture. The resulting suspension was stirred vigorously for 1.5 hours. The solid was allowed to settle and the ether layer was decanted. Washing of the precipitate with $Et_2O$ was repeated two more times. The product was dried in vacuo to afford a white solid (3.18 g, quantitative yield). Saturated aqueous $Na_2CO_3$ solution was added to above solid (3.18 g) with stirring until solid disappeared. The aqueous solution was extracted with ethyl acetate. The organic phases were dried over $Na_2SO_4$, filtered, and evaporated to afford Example R as a yellow foam (2.44 g, 81%). The recovered Example R was used without further purification in the next step. m/z: 706.1 $(M+H)^+$.

Example S

Method I

Example R (1.00 g, 1.42 mmol) was dissolved in DMF (20 mL) and bromoethyl ether (196 μL, 1.56 mmol) was added dropwise, followed by $NaHCO_3$ (0.239 g, 2.84 mmol). The reaction mixture was stirred at 25° C. for 2 hours. The solution was heated to 65° C. and stirred for 12 hours. The solvent was removed under reduced pressure. The residue was diluted with EtOAc and washed sequentially with water and brine. The organic phase was dried over $Na_2SO_4$ filtered, and evaporated. Purification by reverse-phase HPLC (Phenomenex Synergi® Comb-HTS column, eluent: 5-95% $CH_3CN$/water) gave Compound 70 (580 mg, 53%). $^1H$ NMR ($CDCl_3$) δ 8.98 (s, 1H); 7.90 (s, 1H); 7.75 (m, 1H); 7.40-7.00 (m, 11H), 6.55 (br s, 1H); 5.58 (m, 1H); 5.28, 5.19 ($d_{AB}$, J=14 Hz, 2H); 4.70-4.37 (m, 3H); 3.99 (m, 5H); 3.76 (br s, 1H); 3.65-3.30 (m, 3H); 2.97 (m, 5H); 2.90-2.60 (m, 6H); 2.28 (br s, 1H); 1.91 (br s, 1H); 1.60-1.30 (m, 10H). m/z: 776.2 $(M+H)^+$ Method II Scheme 20

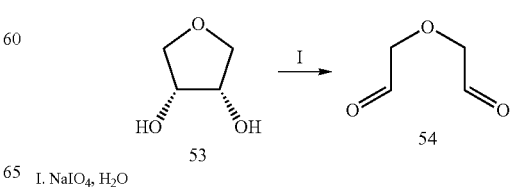

I. $NaIO_4$, $H_2O$

Compound 54

Compound 54 was prepared following the procedure described in J. Med. Chem. 1993, 36, 1384 (herein incorporated by reference in its entirety for all purposes).

To solution of Compound 53 (0.550 g, 5.28 mmol) (Sigma-Aldrich) in H₂O (8.8 mL) at 0° C. was added NaIO₄ (1.016 g, 4.75 mmol). The mixture was allowed to slowly warm to 25° C. and stirred for 12 hours. Solid NaHCO₃ was added to the reaction mixture until pH 7. CHCl₃ (16 mL) was added and the mixture was allowed to stir for 5 minutes. The mixture was filtered and the solid was washed with CHCl₃ (6 mL). The combined H₂O/CHCl₃ solution was used directly in the next step without further purification.

Scheme 21

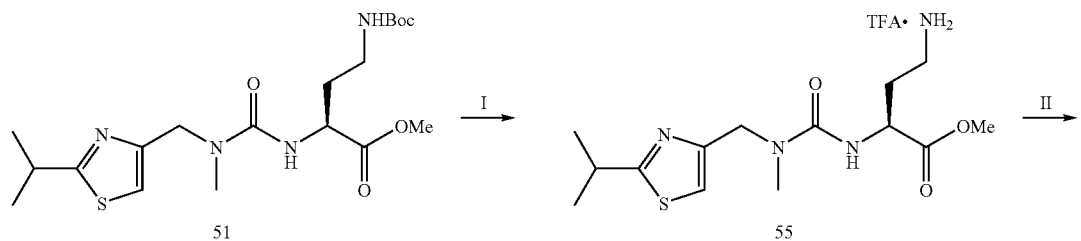

I. NaBH₃CN/CH₃CN/H₂O

Example S

To a solution of Example R (70 mg, 0.1 mmol) in CH₃CN (5 mL) was added sodium cyanoborohydride (50 mg) in water (5 mL). To the above mixture was added a solution of dialdehyde Compound 54 (0.6 mmol) in CHCl₃/H₂O) (4 mL/1 mL). The mixture was stirred for 12 hours, and basified with saturated Na₂CO₃ solution. The mixture was extracted with EtOAc, and organic phase was washed with water and brine, and dried over Na₂SO₄. Purification by reverse-phase HPLC (Phenomenex Synergi® Comb-HTS column) gave Example S (57 mg).

Method III

Scheme 22

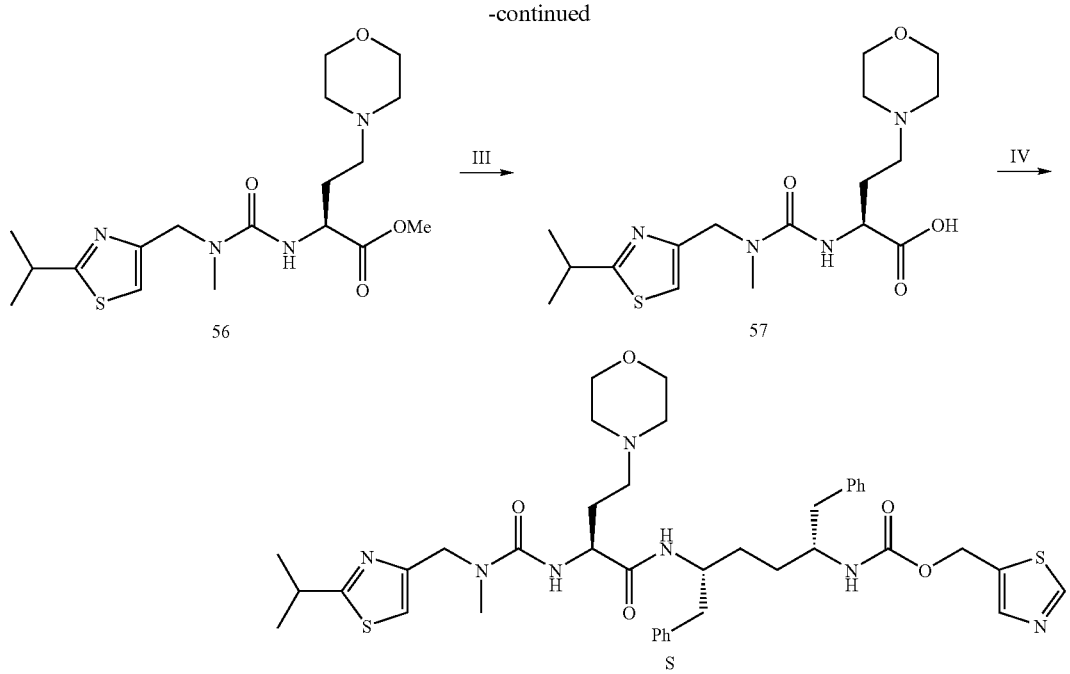

I. TFA, CH$_2$Cl$_2$; II. Cmpd 54, NaBH$_3$CN, H$_2$O/CH$_3$CN; III. LiOH, THF/H$_2$O; IV. amine Cmpd 8, DIPEA, EDC, HOBt, THF Compound 55

Compound 51 (0.28 g, 0.66 mmol) was dissolved in CH$_2$Cl$_2$ (4 mL) and TFA (1 mL) was added dropwise. The reaction was allowed to stir at 25° C. for 1 hour. The solvent was removed under reduced pressure to afford Compound 55 (0.39 g). m/z: 329.0 (M+H)$^+$.

Compound 56

To a solution of Compound 55 (0.39 g, 0.89 mmol) in CH$_3$CN (45 mL) was added NaBH$_3$CN (0.45 g, 7.12 mmol) and H$_2$O (45 mL). A solution of Compound 54 (0.55 g, 5.34 mmol) in CHCl$_3$/H$_2$O (40 mL) was added. The mixture was stirred at 25° C. for 12 hours. The reaction mixture was made basic with saturated aqueous Na$_2$CO$_3$ and extracted sequentially with ethyl acetate and dichloromethane. The combined organic layers were washed sequentially with H$_2$O and brine, dried over Na$_2$SO$_4$, filtered, and evaporated. Purification by Combiflash® (stationary phase: silica gel; eluent: 0-10% MeOH/CH$_2$Cl$_2$ gradient) gave Compound 56 (0.17 g). m/z: 399.1 (M+H)$^+$.

Compound 57

Compound 56 (377 mg, 0.95 mmol) was dissolved in THF (4 mL) and 1M aqueous LiOH (1.90 mL) was added. The mixture was stirred at 25° C. for 1 hour. The reaction was neutralized with 1M HCl. THF was removed under reduced pressure and the aqueous solution was lyophilized to afford Compound 57 (365 mg). The material was used directly in the next step without further purification. m/z: 385.1 (M+H)$^+$.

Example S

Example S (185 mg, 57%) was prepared following the same procedure as for Example Q, except that Compound 57 (160 mg, 0.42 mmol) was used instead of Compound 52. mass m/z: 776.2 (M+H)$^+$.

The skilled practitioner will recognize that the procedure outlined in Scheme 22 can be used to prepare a variety of compounds analogous to Compounds 55-57:

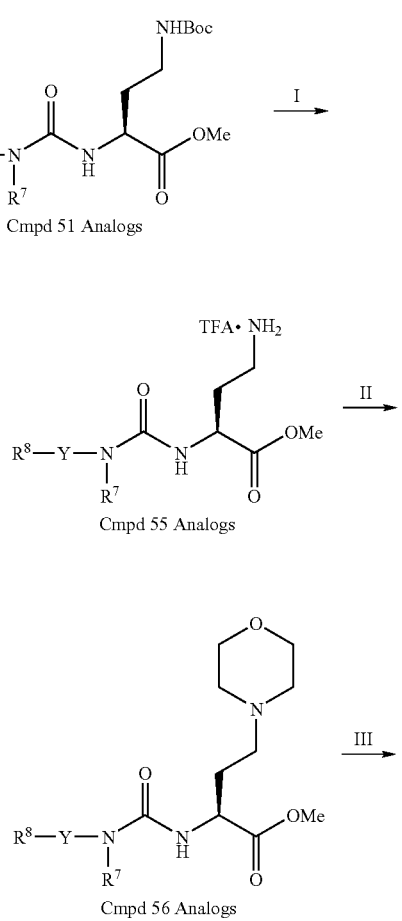

-continued

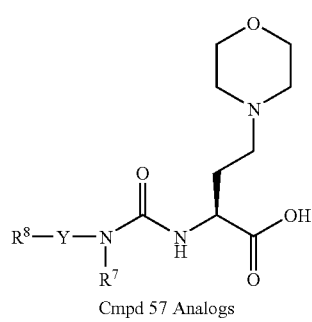

Cmpd 57 Analogs

I. TFA, CH$_2$Cl$_2$; II. Ex. R, NaBH$_3$CN, H$_2$O/CH$_3$CN; III. LiOH, THF/H$_2$O wherein R$^7$, R$^8$ and Y are as defined herein.

It will also be recognized that stereochemical configurations other than those shown (i.e., enantiomers or diasteriomers) can be prepared by the selection of analogs of Compound 51 having the appropriate stereochemical configuration at the chiral center.

Method IV

Scheme 23

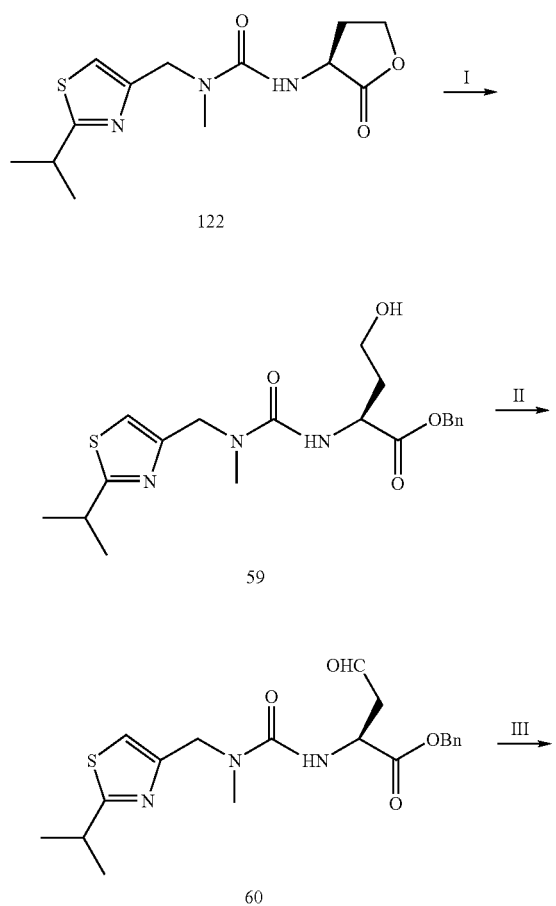

-continued

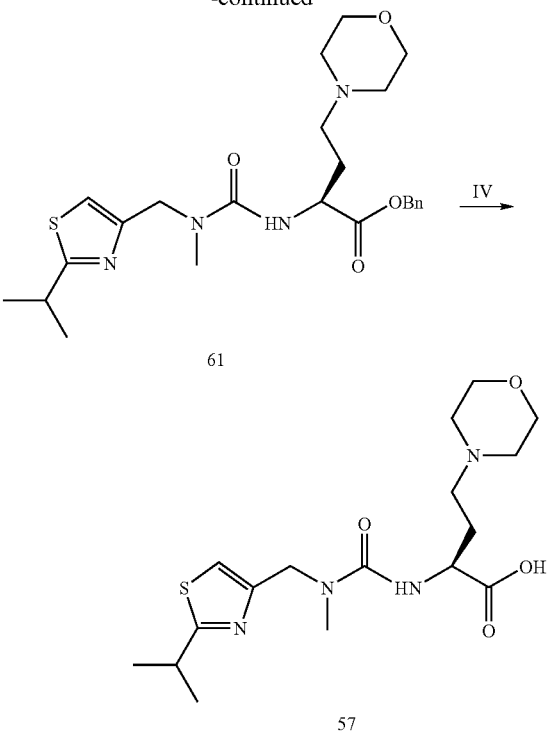

I. a. NaOH/H$_2$O; b. BnBr; II. SO$_3$/pyridine; III. morpholine/NaBH(OAc)$_3$;
IV. a. NaOH; b. HCl Compound 59

To a solution of Compound 122 (33 g, 112 mmol) (see Scheme 69) in ethanol (366 mL) at 0° C. was added a solution of sodium hydroxide (4.7 g, 117 mmol) in water (62 mL). The mixture was stirred for one hour at 25° C., and solvents were removed under reduced pressure. The mixture was coevaporated with ethanol (3×400 mL), and dried at 60° C. for two hours under high vacuum to give a white solid. To the solution of above solid in DMF (180 mL) was added benzyl bromide (16.2 mL, 136 mmol). The mixture was stirred for 16 hours under darkness, and was quenched with water (300 mL). The mixture was extracted with EtOAc (4×300 mL). The combined organic phase was washed with water (5×) and brine, and dried over Na$_2$SO$_4$. Concentration gave Compound 59 (48 g), which was used in the next step without further purification.

Compound 60

A mixture of Compound 59 (33 g, 74 mmol) in DMSO (225 mL) and Et$_3$N (36 mL) was stirred for 30 minutes. The mixture was cooled to 0-10° C., SO$_3$-pyridine (45 g) was added, and the stirring was continued for 60 minutes. Ice (300 g) was added, and the mixture was stirred for 30 minutes. EtOAc (300 mL) was added and sat. Na$_2$CO$_3$ was added until pH was 9-10. The organic phase was separated from the aqueous phase, and the aqueous phase was extracted with EtOAc (2×300 ml). The combined organic phases were washed with sat Na$_2$CO$_3$ (2×), water (3×), and brine. The mixture was dried over Na$_2$SO$_4$ and concentrated to give Compound 60 (32 g), which was used directly in next step without further purification.

Compound 61

To a solution of Compound 60 (32 g) in CH$_3$CN (325 mL) was added morpholine (12.9 mL, 148 mmol), with a water bath around the reaction vessel, followed by HOAc (8.9 mL, 148 mmol), and NaBH(OAc)$_3$ (47 g, 222 mmol). The mixture was stirred for 12 hours. CH₃CN was removed under reduced pressure, and the mixture was diluted with EtOAc (300 mL). Sat. Na₂CO₃ was added until the pH was 9~10 C. The organic phase was separated from the aqueous phase, and the aqueous phase was extracted with EtOAc (2×300 mL). The combined organic phases were washed with sat Na₂CO₃ (2×), water (1×), and brine (1×). The mixture was dried over Na₂SO₄. The resulting residue was concentrated and purified by silica gel column chromatography (EtoAc to DCM/iPrOH=10/1) to give Compound 61 (30 g).

Compound 57

To a solution of Compound 61 (26.5 g, 56 mmol) in ethanol (160 mL) at 0° C. was added a solution of sodium hydroxide (2.5 g, 62 mmol) in water (30 mL). The mixture was stirred for one hour at 25° C., and solvents were removed under reduced pressure. The mixture was diluted with water (200 mL), and was washed with CH₂Cl₂ (6×100 mL). The water phase was acidified with 12 N HCl (5.2 mL), and was dried under reduced pressure to give Compound 57 (22 g).

Example S

Compound 57 was converted to Example S using the procedure described in Method III, above.

Preparation of Compounds T and U 3.90 (m, 4H); 3.78 (m, 1H); 3.38 (m, 2H); 3.20-2.50 (m, 8H); 1.95 (s, 4H); 1.82 (m, 2H); 1.41 (m, 6H).

Method II

Saturated aqueous Na₂CO₃ solution was added to the hydrochloride salt of Example R (3.18 g, 3.46 mmol) while stirring until the solid disappeared. The aqueous solution was extracted with ethyl acetate. The organic phases were dried over Na₂SO₄, filtered, and evaporated to afford Example R as a yellow foam (2.44 g, 81%). This material was used without further purification in the next step. m/z: 706.1 (M+H)⁺.

Example R (300 mg, 0.43 mmol) was dissolved in THF (5.5 mL). Acetic acid (37 μL, 0.64 mmol) was added, followed by HOBt (85 mg, 0.64 mmol), iPr₂NEt (304 μL, 1.70 mmol), and EDC (151 μL, 0.85 mmol). The reaction mixture was allowed to stir at 25° C. for 12 hours. The solvent was removed under reduced pressure. The residue was diluted with EtOAc and washed sequentially with saturated aqueous Na₂CO₃, water, and brine. The organic phase was dried over Na₂SO₄, filtered, and evaporated. Purification by Combiflash® (stationary phase: silica gel; eluent: 10% MeOH/CH₂Cl₂) gave Example T (249 mg, 77%). m/z: 748.2 (M+H)⁺.

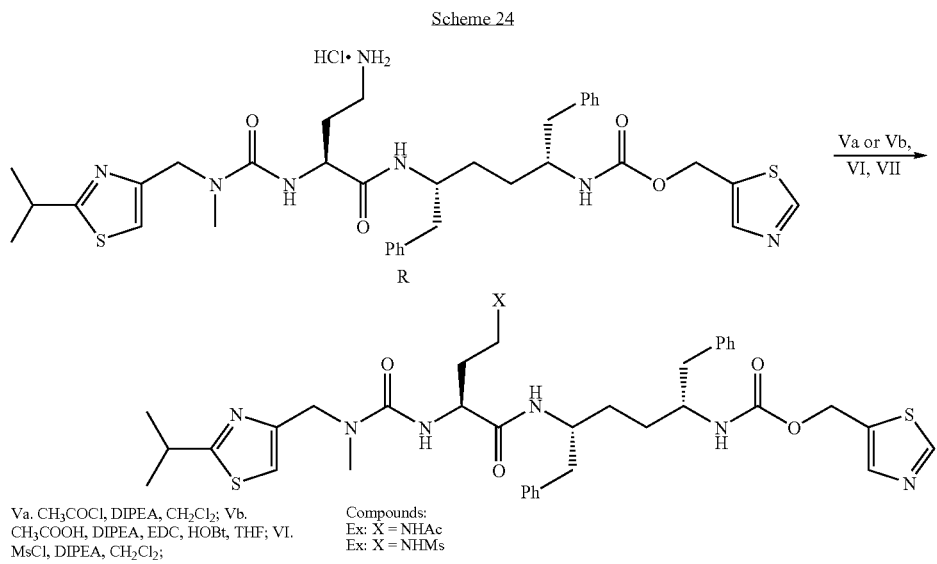

Scheme 24

Va. CH₃COCl, DIPEA, CH₂Cl₂; Vb. CH₃COOH, DIPEA, EDC, HOBt, THF; VI. MsCl, DIPEA, CH₂Cl₂;

Compounds:
Ex: X = NHAc
Ex: X = NHMs

Example T

Example U

Method I

The hydrochloride salt of Example R (100 mg, 0.13 mmol) was suspended in CH₂Cl₂ (2 mL) and dissolved by addition of iPr₂NEt (69 μL). Acetyl chloride (11 μL) was added dropwise and the mixture was allowed to stir at 25° C. for 4 hours. The solvent was removed in vacuo. Purification of the residue by flash column chromatography (stationary phase: silica gel; eluent: 8% iPrOH/CH₂Cl₂) gave Example T (39 mg, 40%). m/z: 748.2 (M+H)⁺. ¹H NMR (CDCl₃) δ 8.85 (s, 1H); 7.87 (s, 1H); 7.73 (s, 1H); 7.40-7.00 (m, 13H); 6.45 (br s, 1H); 5.70 (m, 1H); 5.32, 5.22 (d$_{AB}$, J=13 Hz, 2H); 4.51 (s, 2H); 4.20-

Example R (100 mg, 0.13 mmol) was suspended in CH₂Cl₂ (2 mL) and dissolved by addition of iPr₂NEt (69 μL). Methanesulfonyl chloride (12 μL) was added dropwise and the mixture was allowed to stir at 25° C. for 4 hours. The solvent was removed in vacuo. Purification of the residue by flash column chromatography (stationary phase: silica gel; eluent: 8% iPrOH/CH₂Cl₂) gave Example U (55 mg, 54%). m/z: 784.2 (M+H)⁺. ¹H NMR (CDCl₃) δ 8.90 (s, 1H); 7.88 (s, 1H); 7.40-7.00 (m, 12H); 6.54 (br s, 1H); 6.19 (br s, 1H); 5.25 (s, 2H); 4.53 (s, 2H); 4.38 (m, 1H); 4.12 (m, 1H); 3.79 (m, 1H); 3.79 (m, 1H); 3.48 (m, 1H); 2.99 (s, 3H); 2.90 (m, 3H); 2.73 (m, 6H); 2.00 (m, 1H); 1.79 (m, 1H); 1.60-1.18 (m, 10H).

Preparation of Examples V, W, X and Y

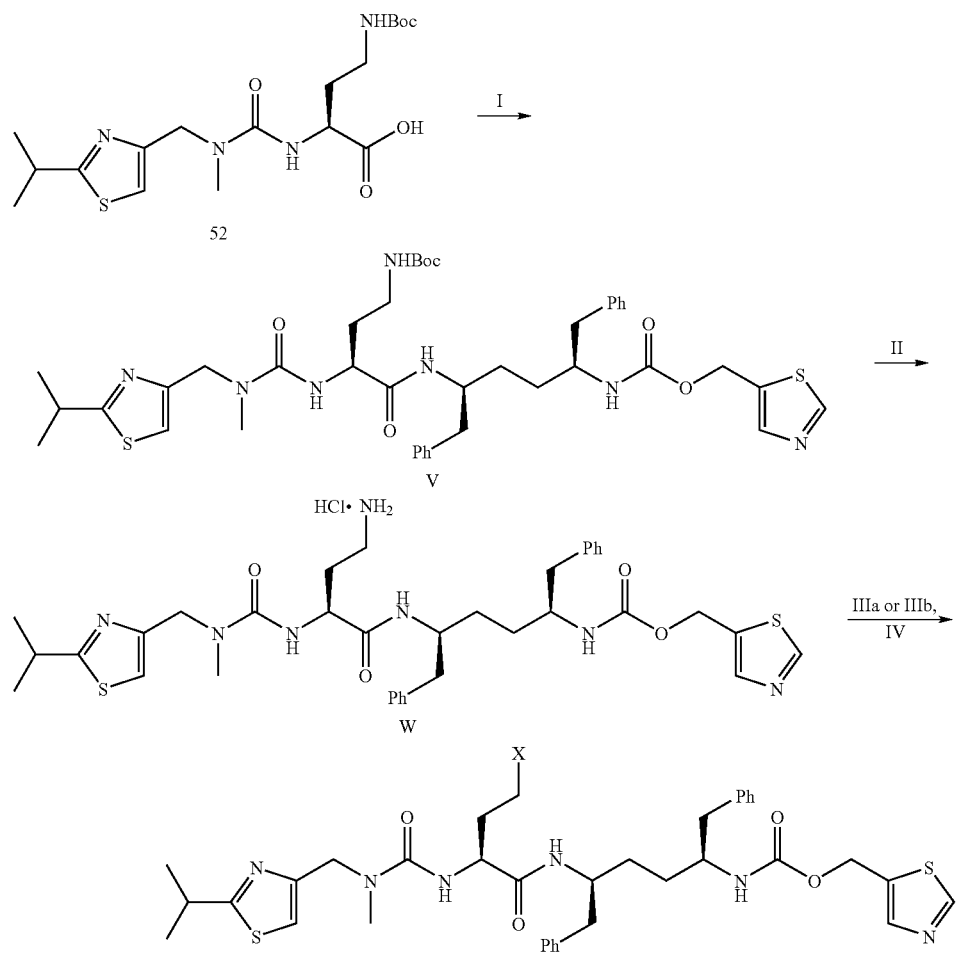

I. Cmpd. 46, DIPEA, EDC, HOBt, THF;
II. HCl/dioxane; IIIa. CH₃COCl, DIPEA, CH₂Cl₂; IIIb. CH₃COOH, DIPEA, EDC, HOBt, THF; IV. MsCl, DIPEA, CH₂Cl₂

Compounds:
Ex. X: X = NHAc
Ex. Y: X = NHMs

Example V

Example V (692 mg) was prepared following the same procedure used for preparing Example Q, except that Compound 46 was used instead of Compound 8. m/z: 806.2 (M+H)⁺.

Example W

Example W (770 mg, quantitative yield) was prepared following the same procedure for Example R except that Example V was used instead of Example Q. m/z: 706.2 (M+H)⁺. $^1$H NMR (CD$_3$OD) δ 9.86 (s, 1H); 8.23 (s, 1H); 7.66 (s, 1H); 7.40-7.00 (m, 10H); 5.29, 5.17 (d$_{AB}$, J=13 Hz, 2H); 4.80-4.60 (m, 2H); 4.18 (s, 2H); 4.26 (m, 2H); 3.67 (br s, 1H); 3.55 (m, 2H); 3.03 (m, 3H); 2.90-2.60 (m, 8H); 2.53 (s, 2H); 2.00-1.80 (m, 2H); 1.85-1.30 (m, 10H).

Compound 59
Method I

Example X (107 mg, 55%) was prepared following the Method I procedure for Example T except that Example W was used instead of Example R. m/z: 748.2 (M+H)⁺. $^1$H NMR (CDCl$_3$) δ 8.80 (s, 1H); 7.85 (s, 1H); 7.40 (m, 1H); 7.38-7.00 (m, 10H), 6.94 (s, 1H); 6.30 (m, 2H); 5.75 (m, 1H); 5.30, 5.23 (d$_{AB}$, J=13 Hz, 2H); 4.54, 4.46 (d$_{AB}$, J=8 Hz, 2H); 4.20-3.90 (m, 2H); 3.74 (br s, 1H); 3.46 (br s, 1H); 3.28 (m, 1H); 2.98 (s, 3H); 2.83 (m, 3H); 2.72 (m, 1H); 2.62 (m, 1H); 2.05-1.20 (m, 15H).

Method II

Example X (205 mg, 65%) was prepared following the Method II procedure for Example T except that Example W was used instead of Example R. m/z: 748.2 (M+H)⁺.

Example Y

Example Y (106 mg, 50%) was prepared following the same procedure for Example U, except that Example W was used instead of Example R. m/z: 784.2 (M+H)+. 1H NMR (CDCl3) δ 8.81 (s, 1H); 7.85 (s, 1H); 7.40-7.05 (m, 10H); 6.98 (s, 1H); 6.22 (br s, 1H); 5.78 (s, 1H); 5.25 (m, 4H); 4.29 (m, 2H); 4.33 (br s, 1H); 4.12 (br s, 1H); 3.77 (br s, 1H); 3.10 (br s, 1H); 2.98 (s, 3H); 2.90 (s, 3H); 2.73 (m, 6H); 2.00-1.20 (m, 12H).

Preparation of Examples Z-AD

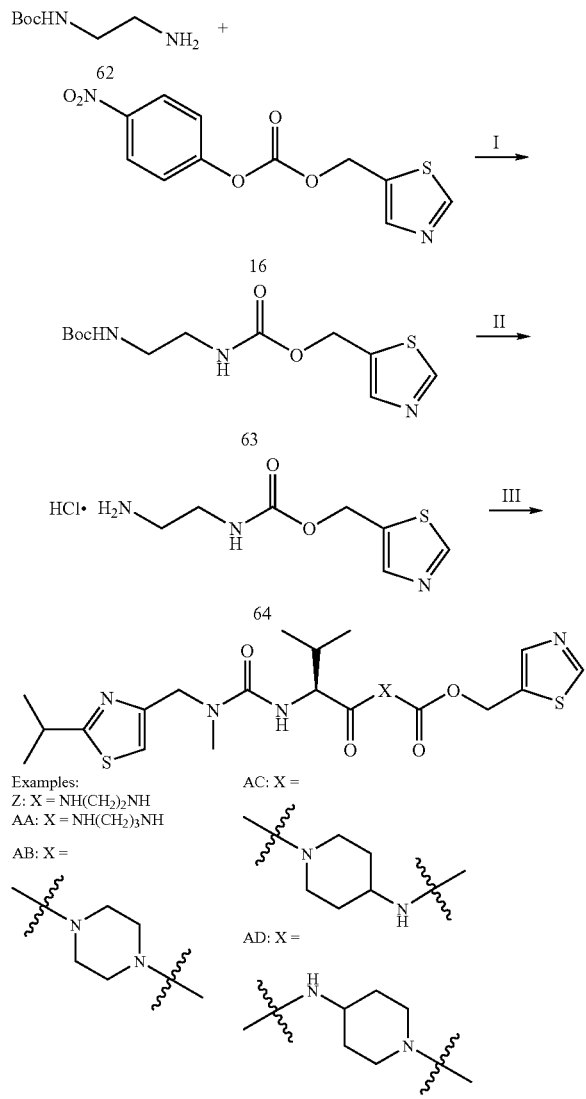

I. DIPEA, CH3CN; II. HCl/dioxane, EtOAc; III. acid 29, DIPEA, EDC, HOBt, THF

Compound 62

Tert-butyl 2-aminoethylcarbamate (62) is commercially available from Aldrich, and was used without further purification.

Compound 63

To a solution of Compound 62 (2.0 mmol) in CH3CN (15 mL) was added Compound 16 (1.82 mmol), followed by the addition of N,N-diisopropylethylamine (0.61 mL). The mixture was stirred at 25° C. for 12 hours. The solvent was removed in vacuo, and the residue was diluted with ethyl acetate and washed sequentially with saturated aqueous Na2CO3, water, and brine. The organic layers were dried with Na2SO4, filtered, and evaporated. Purification by Combiflash® (stationary phase: silica gel; eluent: 25-100% EtOAc/hexane gradient) gave Compound 63. m/z: 301.9 (M+H)+.

Compound 64

To a solution of Compound 63 (1.05 mmol) in EtOAc (3 mL) was added 4N HCl/dioxane solution (1.1 mL). The mixture was allowed to stir at 25° C. for 12 hours. The solvent was removed under reduced pressure, and Compound 64 was obtained as a white powder. This material was used in the next step without further purification. m/z: 216.0 (M+H)+.

Example Z

Compound 64 (70 mg, 0.29 mmol) was dissolved in THF (2.2 mL). Compound 29 (91 mg, 0.29 mmol) was added to the reaction flask as a 1.0M solution in THF, followed by HOBt (59 mg, 0.44 mmol), N,N-diisopropylethylamine (207 μL, 1.16 mmol), and EDC (103 μL, 0.58 mmol). The reaction was allowed to stir for 12 hours at 25° C. and concentrated under reduced pressure. The residue was diluted with EtOAc and washed sequentially with saturated aqueous Na2CO3, water, and brine. The organic layers were dried with Na2SO4, filtered, and evaporated. Purification by Combiflash® (stationary phase: silica gel; eluent: 0-10% MeOH/CH2Cl2 gradient) gave Example Z (54 mg, 38%). m/z: 497.1 (M+H)+. 1H NMR (CDCl3) δ 8.78 (s, 1H); 7.83 (s, 1H); 6.99 (s, 1H); 6.80 (br s, 1H); 6.22 (br s, 1H); 5.87 (br s, 1H); 5.25 (s, 2H); 4.43 (s, 2H); 3.97 (m, 1H); 3.34 (m, 4H); 2.95 (s, 3H); 2.22 (m, 2H); 1.38 (d, J=7 Hz, 6H); 0.97 (d, J=7 Hz, 6H).

Example AA

Example AA was prepared following the procedures for steps I-III (Scheme 20) for Example Z, with the exception that tert-butyl 3-aminopropylcarbamate was used instead of tert-butyl 2-aminoethylcarbamate (Compound 62). After Combiflash® purification, 38 mg (34%) of Example AA was obtained. m/z: 511.1 (M+H)+. 1H NMR (CDCl3) δ 8.78 (s, 1H); 7.84 (s, 1H); 6.96 (s, 2H); 6.17 (br s, 1H); 5.80 (m, 1H); 5.26 (m, 2H); 4.44 (s, 2H); 4.09 (m, 1H); 3.40-3.10 (m, 5H); 2.97 (s, 3H); 2.20 (m, 1H); 1.60 (m, 2H); 1.36 (d, J=7 Hz, 6H); 0.96 (d, J=7 Hz, 6H).

Example AB

Example AB was prepared following the procedures for steps I-III (Scheme 20) for Example Z, with the exception that tert-butyl 1-piperazinecarboxylate was used instead of tert-butyl 2-aminoethylcarbamate (Compound 62). After Combiflash® purification, 64 mg (45%) of Example AB was obtained. m/z: 523.1 (M+H)+. 1H NMR (CDCl3) δ 8.82 (s, 1H); 7.89 (s, 1H); 6.96 (s, 1H); 5.93 (br s, 1H); 5.35 (s, 2H); 4.62 (m, 1H); 4.50 (m, 2H); 3.80-3.40 (m, 8H); 3.34 (m, 1H); 3.00 (s, 3H); 1.97 (m, 1H); 1.40 (d, J=7 Hz, 6H); 0.96, 0.93 (d, J=7 Hz, 6H).

Example AC

Example AC was prepared following the procedures for steps I-III (Scheme 20) for Example Z, with the exception that tert-butyl 4-amino-1-piperidinecarboxylate was used instead of tert-butyl 2-aminoethylcarbamate (Compound 62). After Combiflash® purification, 60 mg (44%) of Example AC was obtained. m/z: 537.1 (M+H)+. 1H NMR (CDCl3) δ 8.82 (s, 1H); 7.87 (s, 1H); 6.97 (s, 1H); 5.82 (br s, 1H); 5.30 (m, 3H);

4.80-4.40 (m, 5H); 4.03 (m, 1H); 3.72 (br s, 1H); 3.34 (m, 1H); 3.18 (m, 1H); 3.01 (s, 3H); 2.79 (m, 1H); 2.20-1.90 (m, 4H); 1.40 (d, J=7 Hz, 6H); 0.97, 0.90 (d, J=7 Hz, 6H).

Example AD

Example AD was prepared following the procedures I-III for Example Z, with the exception that tert-butyl 4-piperidinylcarbamate was used instead of tert-butyl 2-aminoethylcarbamate (Compound 62). After Combiflash® purification, 49 mg (36%) of Example AD was obtained. m/z: 537.1 (M+H)$^+$. $^1$H NMR (CDCl$_3$) δ 8.82 (s, 1H); 7.87 (s, 1H); 7.01 (s, 1H); 6.33 (br s, 1H); 6.11 (br s, 1H); 5.32 (s, 2H); 4.47 (s, 2H); 4.20-3.80 (m, 4H); 3.35 (m, 1H); 3.10-2.80 (m, 6H); 2.21 (m, 2H); 1.90 (m, 2H); 1.40 (d, J=7 Hz, 6H); 0.97 (d, J=7 Hz, 6H).

Preparation of Examples AE-AG

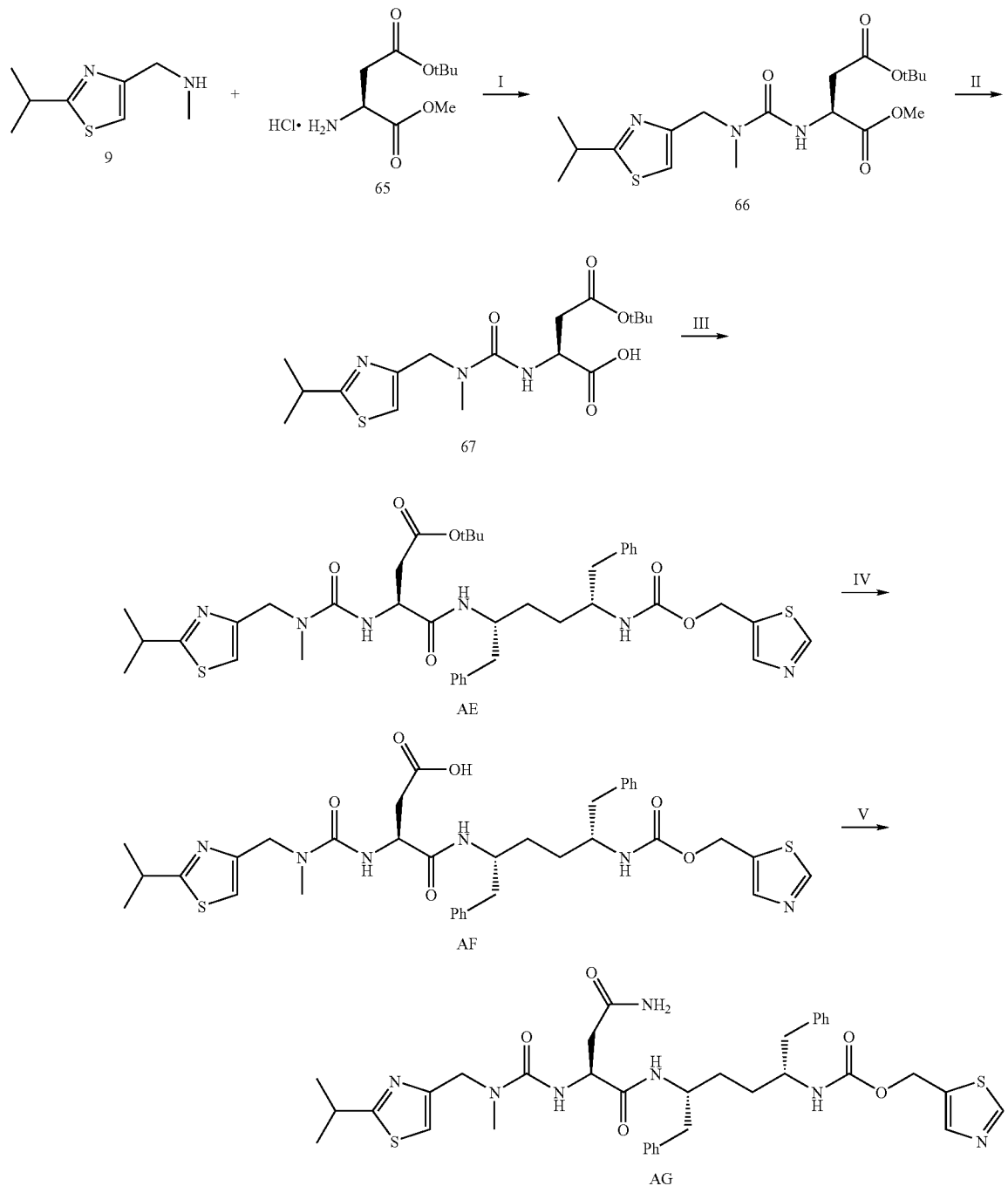

I. CDI, DIPEA, CH$_2$Cl$_2$; II. NaOH, THF/H$_2$O; III. Cmpd. 8, DIPEA, EDC, HOBt, THF; IV. neat TFA; V. (Boc)$_2$O, NH$_4$HCO$_3$, pyridine, dioxane, DMF Compound 65

Compound 65 is commercially available from Chem Impex International, and was used without further purification.

Compound 66

Compound 65 (956 mg, 4.0 mmol) was dissolved in CH$_2$Cl$_2$ (45 mL) and 1,1-carbonyldiimidazole (648 mg, 4.0 mmol) was added, followed by i-Pr2NEt (2.8 mL, 16 mmol). The solution was stirred at 25° C. for 12 hours. Compound 9 (679 mg, 4.0 mmol) was dissolved in CH$_2$Cl$_2$ (5 mL) and added to the reaction. The mixture was allowed to stir for 5 hours. Then, the solvent was removed under reduced pressure. The residue was diluted with ethyl acetate and filtered through celite. The ethyl acetate was then removed in vacuo. Purification by flash column chromatography (stationary phase: silica gel; eluent: EtOAc) gave Compound 66 (841 mg). m/z: 400.0 (M+H)$^+$.

Compound 67

Compound 66 (841 mg, 2.11 mmol) was dissolved in THF (9 mL) and 2N aqueous NaOH was added. The solution was stirred at 25° C. for 2 hours. The reaction was adjusted to pH 2 with 1N HCl. The mixture was extracted with ethyl acetate, dried over Na$_2$SO$_4$, filtered, and evaporated. Compound 67 (772 mg) was used directly in the next step without further purification. m/z: 386.0 (M+H)$^+$.

Example AE

Compound 67 (569 mg, 1.48 mmol) was dissolved in THF (17 mL). Compound 8 (970 mg, 2.37 mmol) was added, followed by HOBt (300 mg, 2.22 mmol), i-Pr2NEt (1.06 mL, 5.92 mmol), and EDC (0.52 mL, 2.96 mmol). The mixture was stirred at 25° C. for 36 hours. The solvent was removed under reduced pressure. The resulting residue was diluted with ethyl acetate and washed sequentially with saturated aqueous Na$_2$CO$_3$, water, and brine. The organic phase was dried over Na$_2$SO$_4$, filtered, and evaporated. Purification by flash column chromatography (stationary phase: silica gel; eluent: 8% iPrOH/CH$_2$Cl$_2$) gave Example AE (3.02 g). m/z: 777.2 (M+H)$^+$.

Example AF

Example AE (100 mg, 0.13 mmol) was dissolved in neat TFA (3 mL). The mixture was stirred at 25° C. for 2 hours. The solvent was removed under reduced pressure. Purification by reverse-phase HPLC (Phenomenex Synergi® Comb-HTS column, eluent: 5-95% CH$_3$CN/H$_2$O gradient) gave Example AF (20 mg, 21%). m/z: 721.2 (M+H)$^+$. $^1$H NMR (CDCl$_3$) δ 8.92 (s, 1H); 7.91 (s, 1H); 7.40-7.00 (m, 11H); 6.41 (br s, 1H); 6.12 (br s, 1H); 5.40-5.00 (m, 3H); 4.70-4.50 (m, 3H); 4.05 (br s, 1H); 3.81 (br s, 1H); 3.51 (br s, 1H); 2.97 (s, 3H); 2.90-2.60 (m, 6H); 1.41 (d, J=7 Hz, 10H).

Example AG

Example AF (70 mg, 0.10 mmol) was dissolved in dioxane (0.5 mL). DMF (83 µL), pyridine (25 µL, 0.29 mmol), di-tert-butyldicarbonate (27 mg, 0.13 mmol), and ammonium bicarbonate (15 mg, 0.19 mmol) were added. The mixture was stirred at 25° C. for 48 hours, then diluted with ethyl acetate and washed sequentially with water and brine. The organic phase was dried over Na$_2$SO$_4$, filtered, and evaporated. Purification by reverse-phase HPLC (Phenomenex Synergi® Comb-HTS column, eluent: 5-95% CH$_3$CN/H$_2$O gradient) gave Example AG (35 mg, 50%). $^1$H NMR (CDCl$_3$) δ 8.80 (s, 1H); 7.84 (s, 1H); 7.40-7.00 (m, 10H); 7.08 (s, 1H); 6.83 (m, 1H); 6.65 (m, 1H); 5.40-5.10 (m, 4H); 4.60-4.40 (m, 3H); 4.06 (m, 1H); 3.79 (m, 1H); 3.36 (m, 1H); 2.97 (s, 3H); 2.90-2.60 (m, 6H); 2.45 (m, 1H); 1.70-1.20 (m, 10H).

Preparation of Compounds 68 and 69

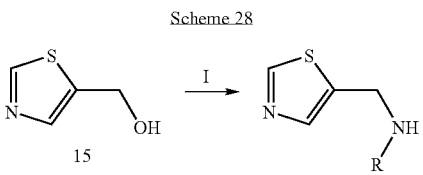

Scheme 28

68: R = methyl
69: R = cyclopropyl

I. a. MsCl, TEA, CH$_3$CN; b. MeNH$_2$/H$_2$O; c. cyclopropyl amine

Compound 15

Compound 15 is commercially available from Molekula, and was used without further purification.

Compound 68

Compound 15 (6.81 g, 59.1 mmol) was dissolved in CH$_3$CN (340 mL) and methanesulfonyl chloride (7.03 mL, 65.1 mmol) was added, followed by triethylamine (9.03 mL, 65.1 mmol). After the mixture was stirred for 20 min, 40% wt. methylamine/water (516 mL) was added to the reaction mixture. The solution was stirred for 12 hours at 25° C. Solvent was removed under reduced pressure and the residue was partitioned between saturated aqueous Na$_2$CO$_3$ and CH$_2$Cl$_2$. The organic phase was separated, dried over Na$_2$SO$_4$, filtered, and evaporated. Purification by flash chromatography (stationary phase: silica gel; eluent: 0-10% MeOH/CH$_2$Cl$_2$ gradient) gave Compound 68 (5.07 g). m/z: 128.9 (M+H)$^+$.

Compound 69

Compound 15 (10.0 g, 80 mmol) was dissolved in CH$_3$CN (500 mL) and methanesulfonyl chloride (7.0 mL, 88 mmol) was added, followed by triethylamine (12.3 mL, 88 mmol). After the mixture was stirred for 2 h, cyclopropylamine (140 mL, 2000 mmol) in CH$_3$CN (500 mL) was added to the reaction mixture. The solution was stirred for 36 hours at 25° C. Solvent was removed under reduced pressure and the slurry was partitioned between saturated aqueous Na$_2$CO$_3$ and 3:1 CH$_2$Cl$_2$:i-PrOH. The organic phase was separated, dried over Na$_2$SO$_4$, filtered, and evaporated. Compound 69 (12.81 g) was used in the next step without further purification. m/z: 155.0 (M+H)$^+$.

Preparation of Examples AH and AI

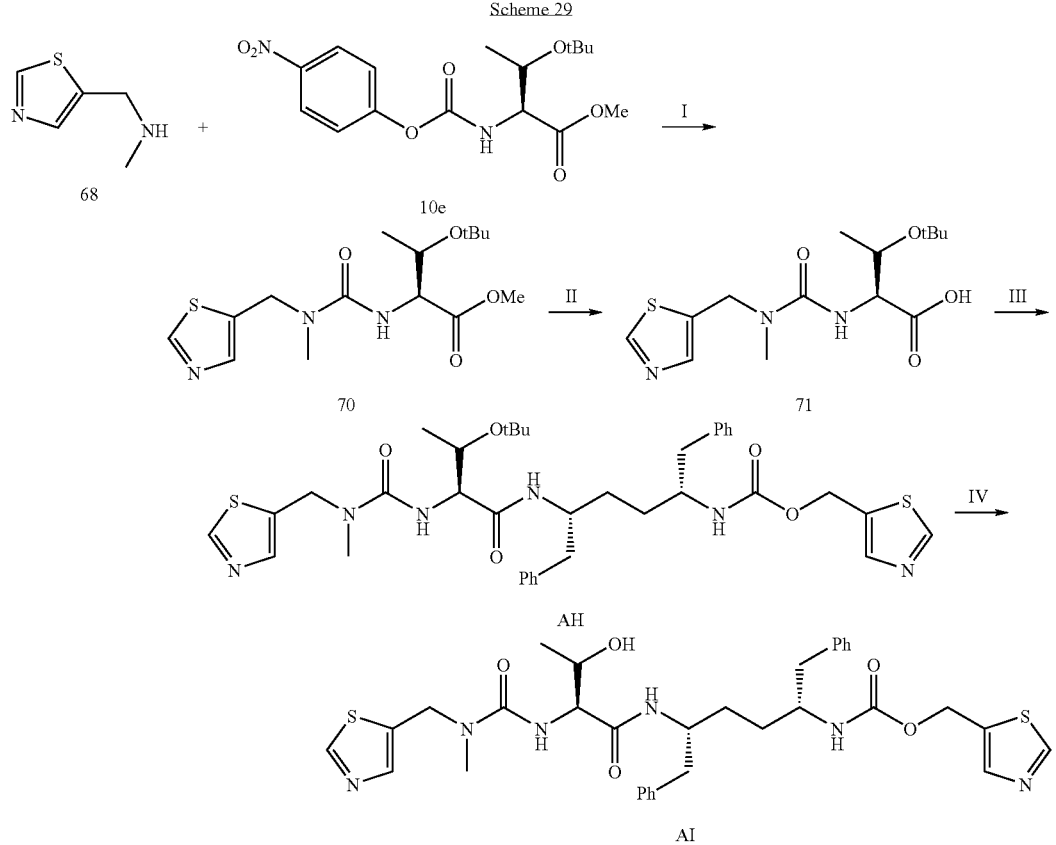

I. DIPEA, CH₂Cl₂; II. LiOH, THF/H₂O; III. Cmpd. 8, HOBt, EDC, DIPEA, THF; IV. a. neat TFA; b. NaOH, THF, H₂O Compound 70

Compound 68 (1.00 g, 7.80 mmol) was dissolved in THF (25 mL) and Compound 10e (2.51 g, 7.09 mmol) was added, followed by N,N-dimethaminopyridine (200 mg, 1.63 mmol), and triethylamine (4.34 mL, 31.2 mmol). The mixture was allowed to stir at 60° C. for 6 hours. Solvent was removed under reduced pressure. The residue was diluted with ethyl acetate and washed sequentially with saturated aqueous Na$_2$CO$_3$, H$_2$O, and brine. The organic layer was dried over Na$_2$SO$_4$, filtered, and evaporated. The resulting residue was purified by Combiflash® (stationary phase: silica gel; eluent: 20-100% EtOAc/Hexane gradient) to give Compound 70 (2.14 g). m/z: 343.9 (M+H)$^+$.

Compound 71

Compound 70 (2.14 g, 6.23 mmol) was dissolved in THF (25 mL) and 1M aqueous LiOH (12.5 mL) was added. The mixture was stirred at 25° C. for 2 hours. The reaction was quenched with 1M HCl (15 mL) and the mixture was adjusted to pH 2. The mixture was extracted with ethyl acetate. The organic layers were dried over Na$_2$SO$_4$, filtered, and evaporated to provide Compound 71 (1.96 g). This material was used in the next step without further purification. m/z: 330.0 (M+H)$^+$.

Example AH

Compound 71 (43 mg, 0.13 mmol) was dissolved in THF (1.5 mL). Compound 8 (50 mg, 0.12 mmol) was added, followed by HOBt (24 mg, 0.18 mmol), iPr$_2$NEt (86 μL, 0.48 mmol), and EDC (42 μL, 0.24 mmol). The mixture was stirred at 25° C. for 12 hours. The solvent was removed under reduced pressure, and the resulting residue was diluted with ethyl acetate and washed sequentially with saturated aqueous Na$_2$CO$_3$, water, and brine. The organic phase was dried over Na$_2$SO$_4$, filtered, and evaporated. Purification by flash column chromatography (stationary phase: silica gel; eluent: 1-10% MeOH/CH$_2$Cl$_2$ gradient) gave Example AH (66 mg). m/z: 721.2 (M+H)$^+$.

Compound AI

Example AH (66 mg, 0.09 mmol) was dissolved in TFA and allowed to stir at 25° C. for 3 hours. The solvent was removed under reduced pressure and the residue was diluted with THF (3 mL) and 2N aqueous NaOH was added until pH 12. The mixture was allowed to stir for 20 min and extracted with EtOAc. The organic layer was washed sequentially with water and brine, dried over Na$_2$SO$_4$, filtered, and evaporated. Purification by flash chromatography (stationary phase: silica gel; eluent: 0-20% i-PrOH/CH$_2$Cl$_2$ gradient) gave Example AI (71 mg, 97%). m/z: 665.2 (M+H)$^+$. $^1$H NMR (CDCl$_3$) δ 8.84 (s, 1H); 8.80 (s, 1H); 7.85 (s, 1H); 7.79 (s, 1H); 7.40-7.00 (m, 10H); 6.69 (m, 1H); 5.34 (m, 1H); 5.24 (s, 2H); 4.86 (m, 2H); 4.73, 4.59 (d$_{AB}$, J=16 Hz, 2H); 4.30 (s, 1H); 4.15 (m, 2H); 3.86 (br s, 1H); 2.88 (s, 3H); 2.85-2.60 (m, 4H); 2.01 (s, 1H); 1.58 (s, 2H); 1.44 (s, 2H); 1.09 (d, J=6 Hz, 3H).

Preparation of Examples AJ and AK

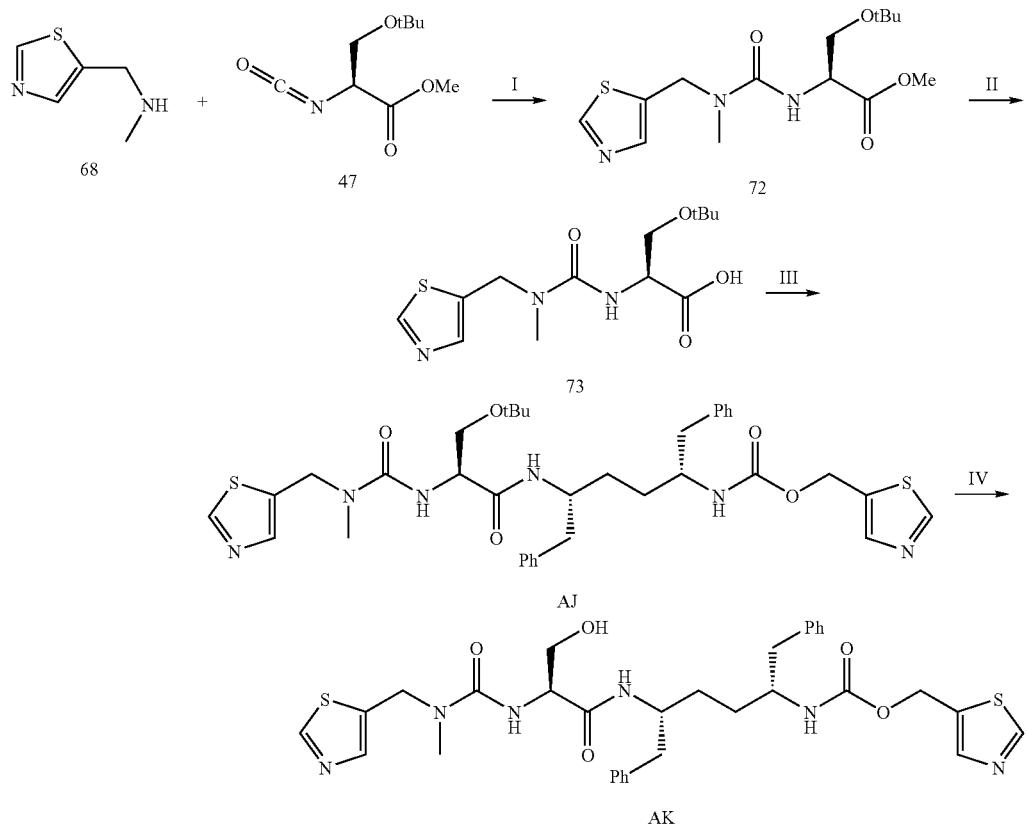

I. DIPEA, CH$_2$Cl$_2$; II. LiOH, THF/H$_2$O; III. Cmpd. 8, HOBt, EDC, DIPEA, THF; IV. a. neat TFA; b. NaOH, THF, H$_2$O Compound 47

Compound 47 is commercially available from TCI America, and was used without further purification.

Compound 72

Compound 72 was prepared following procedure for Compound 48 (Method II), except that Compound 68 was used instead of Compound 9.

Compound 73

Compound 73 was prepared following procedure for Compound 49, except that Compound 72 was used instead of Compound 48.

Example AJ

Example AJ (70 mg) was prepared following the same procedure used to prepare Example AH, with the exception that Compound 73 (41 mg, 0.13 mmol) was used instead of Compound 71. m/z: 707.2 (M+H)$^+$.

Example AK

Example AK (43 mg, 67%) was prepared following the same procedure used to prepare Example AI, with the exception that Example AJ (70 g, 0.10 mmol) was used instead of Example AH. m/z: 651.2 (M+H)$^+$. $^1$H NMR (CDCl$_3$) δ 8.83 (s, 2H); 7.84 (s, 1H); 7.79 (s, 1H); 7.40-7.00 (m, 10H); 6.65 (br s, 1H); 5.47 (br s, 1H); 5.24 (s, 2H); 4.90 (m, 1H); 4.82-4.50 (m, 2H); 4.30-4.00 (m, 3H); 3.84 (br s, 1H); 3.49 (m, 1H); 2.87 (s, 3H); 2.75 (br s, 5H); 1.60-1.20 (m, 4H).

Preparation of Examples AL and AM

Scheme 31

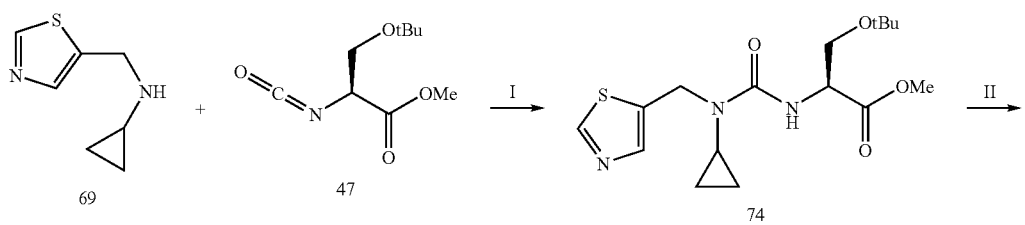

-continued

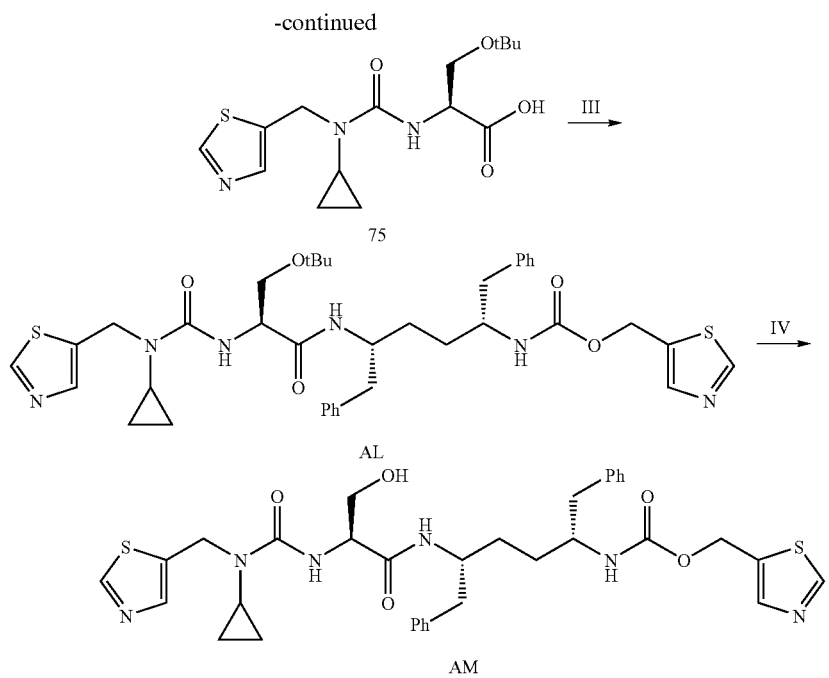

I. DIPEA, CH₂Cl₂; II. LiOH, THF/H₂O; III. Cmpd. 8, HOBt, EDC, DIPEA, THF; IV. a. neat TFA; b. NaOH, THF, H₂O Compound 74

Compound 69 (1.56 g, 10.1 mmol) was dissolved in CH₂Cl₂ (10 mL). Compound 47 (1.7 g, 8.5 mmol) in CH₂Cl₂ (20 mL) was added, followed by iPr₂NEt (3.02 mL, 16.9 mmol). The reaction was stirred at 25° C. for 12 hours. The solvent was removed under reduced pressure. The residue was diluted with ethyl acetate and washed sequentially with water and brine, dried over Na₂SO₄, filtered, and evaporated. Purification by Combiflash® (stationary phase: silica gel; eluent: 50-100% EtOAc/hexane gradient) gave Compound 74 (2.92 g). m/z: 356.0 (M+H)⁺.

Compound 75

Compound 74 (0.97 mmol) was taken up in THF (3 mL) and treated with freshly prepared 1M LiOH (2 mmol) and stirred vigorously for 1 h. The reaction was quenched with 1M HCl (2.5 mmol) and extracted with ETOAc (3×15 mL). The combined organics were washed with brine (25 mL), dried over anhydrous Na₂SO₄ and concentrated in vacuo to produce 0.331 g (quant) of Compound 75 as a colorless film (m/z 342.0 (M+H)⁺).

Example AL

Example AL (2.20 g) was prepared following the same procedure used to prepare Example AH, with the exception that Compound 75 (2.00 g, 4.88 mmol) was used instead of Compound 71. m/z: 733.2 (M+H)⁺.

Example AM

Example AM (1.88 g, 92%) was prepared following the same procedure used to prepare Example AI, with the exception that Example AL (2.20 g, 3.01 mmol) was used instead of Example AH. m/z: 677.2 (M+H)⁺. ¹H NMR (CDCl₃) δ 8.79 (s, 1H); 8.72 (s, 1H); 7.82 (s, 1H); 7.77 (s, 1H); 7.40-7.00 (m, 10H); 6.59 (m, 1H); 6.31 (m, 1H); 5.23 (s, 2H); 5.00 (m, 1H); 4.72, 4.60 (d$_{AB}$, J=15 Hz, 2H); 4.18 (s, 2H); 4.03 (m, 1H); 3.84 (br s, 1H); 3.48 (m, 1H); 2.85-2.60 (m, 4H); 2.37 (br s, 2H); 1.58 (s, 2H); 1.41 (s, 2H); 0.93 (m, 2H); 0.76 (m, 2H).

Scheme 32

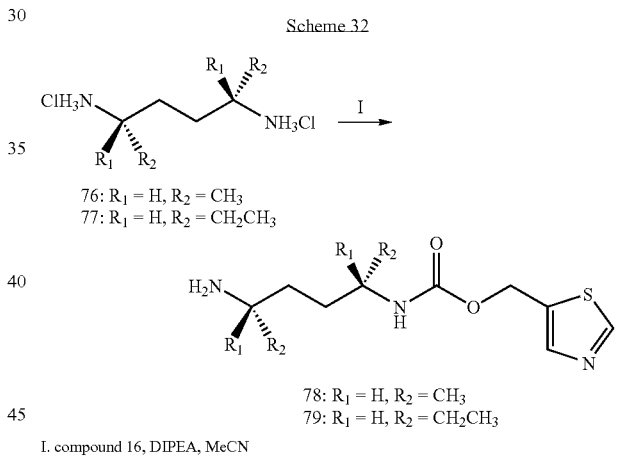

I. compound 16, DIPEA, MeCN

Compound 76

Compound 76 (m/z 117.0 (M+H)⁺ of diamine) was prepared using a procedure similar to that used to prepare Compound 25 (described in Scheme 7) except that CBZ-L-alininol was used instead of CBZ-D-phenylalininol and Step III was performed with 1 M HCl added.

Compound 77

Compound 77 (m/z 145.0 (M+H)⁺ of diamine) was prepared using a procedure similar to that used to prepare Compound 76 except that (S)-(+)-2-CBZ-amino-1-butanol was used instead of CBZ-D-phenylalininol.

Compound 78

Compound 76 (7.93 mmol) is added to a solution of NaOH (16.7 mmol) in H₂O (5 mL) that is cooled to 0° C. and diluted with MeCN (40 mL). DIPEA is added (2.1 mL, 11.9 mmol). Compound 16 (7.9 mmol) is taken up in MeCN (40 mL) and added to the reaction solution dropwise via an addition funnel over 1 h. The resulting solution is allowed to warm to room temperature overnight. The solvent is removed in vacuo and the residue taken up in 3/1 CHCl₃/IPA (50 mL). The resulting solution is washed with sat. Na₂CO₃ (50 mL) and water is added until the aqueous layer is homogeneous. The aqueous layer is extracted with 3/1 CHCl₃/IPA (3×25 mL). The combined organics are washed with saturated Na₂CO₃ (50 mL), water (50 mL) and brine (50 mL) and are dried over anhydrous Na₂SO₄. The solvent is removed in vacuo and the residue purified by column chromatography on SiO₂ (100% EtOAc, then 0 to 20% MeOH/DCM) to produce 0.63 g (31%) of 78 as an off-white solid. (m/z 258.0 (M+H)⁺).

Compound 79

Compound 79 (m/z 286.1 (M+H)⁺) was prepared following the procedure for Compound 78 except that Compound 77 was used instead of Compound 76.

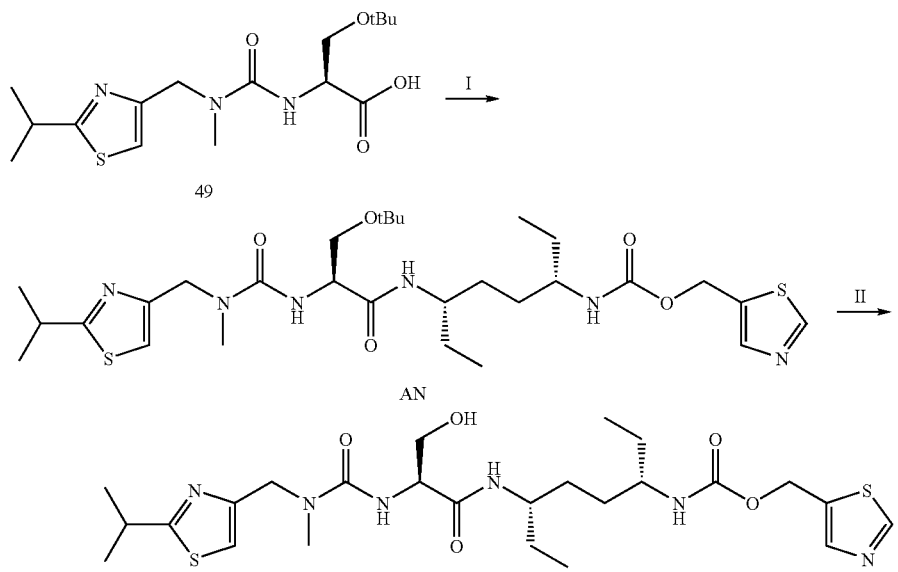

I. Cmpd. 79, HOBt, EDC, DIPEA, THF; II. a. neat TFA; b. NaOH, THF, H₂O

Example AN

Example AN (68 mg) was prepared following the same procedure used to prepare Example AH, with the exceptions that Compound 49 (68 mg, 0.19 mmol) was used instead of Compound 71, and Compound 79 (50 mg, 0.18 mmol) was used instead of Compound 8. m/z: 625.2 (M+H)⁺.

Example AO

Example AO (66 mg, 76%) was prepared following the same procedure used to prepare Example AI, with the exception that Example AN (43 mg, 0.13 mmol) was used instead of Example AH. m/z: 569.2 (M+H)⁺. ¹H NMR (CDCl₃) δ 8.85 (s, 1H); 7.89 (s, 1H); 7.08 (s, 1H); 6.81 (m, 1H); 5.29 (s, 2H); 4.87 (m, 1H); 4.63, 4.48 (d$_{AB}$, J=16 Hz, 2H); 4.31 (m, 1H); 4.11 (m, 1H); 3.76 (m, 2H); 3.44 (m, 2H); 3.02 (m, 4H); 1.60-1.20 (m, 14H); 1.00-0.70 (m, 6H).

Preparation of Examples AP and AQ

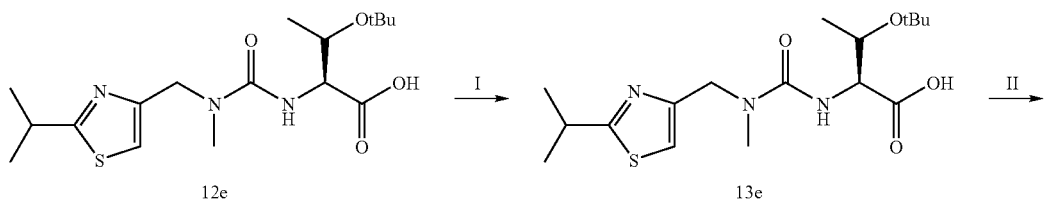

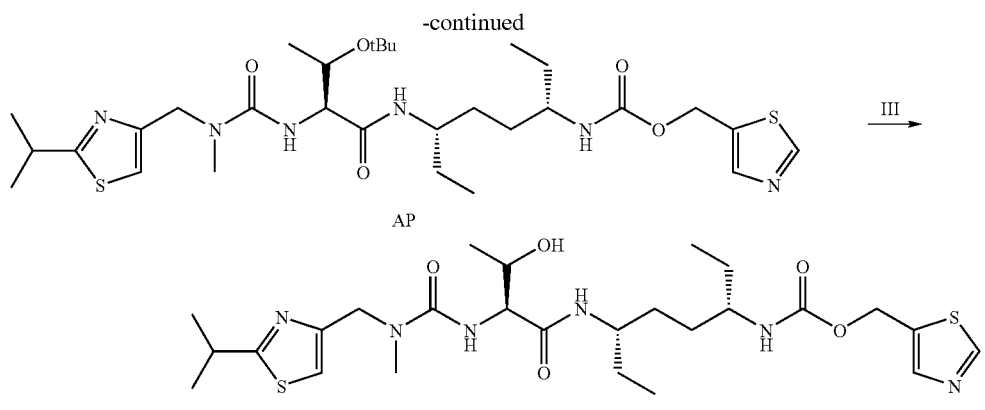

AP

AQ

I. LiOH, THF/H₂O; II. Cmpd. 79, HOBt, EDC, DIPEA, THF; III. a. neat TFA; b. NaOH, THF, H₂O Compound 13d Compound 13e (1.39 g) was prepared following the same procedure used to prepare Compound 71, with the exception that Compound 12e (1.53 g, 3.97 mmol) was used instead of Compound 70 m/z: 372.0 (M+H)⁺.

Example AP

Example AP (87 mg) was prepared following the same procedure used to prepare Example AH, with the exception that Compound 13e (71 mg, 0.19 mmol) was used instead of Compound 71, and Compound 79 (50 mg, 0.18 mmol) was used instead of Compound 8. m/z: 639.2 (M+H)⁺.

Compound AQ

Example AQ (61 mg, 76%) was prepared following the same procedure used to prepare Example AI, with the exception that Example AP (87 mg, 0.14 mmol) was used instead of Example AH. m/z: 583.2 (M+H)⁺. ¹H NMR (CDCl₃) δ 8.81 (s, 1H); 7.87 (s, 1H); 7.01 (s, 1H); 6.87 (m, 1H); 6.52 (s, 1H); 5.28 (m, 2H); 4.47 (m, 1H); 4.59, 4.43 (d$_{AB}$, J=16 Hz, 2H); 4.45 (m, 1H); 4.17 (br s, 1H); 3.75 (br s, 1H); 3.52 (br s, 1H); 3.35 (br s, 1H); 3.01 (m, 3H); 2.07 (br s, 1H); 1.60-1.10 (m, 17H); 1.00-0.70 (m, 6H).

Preparation of Example AR

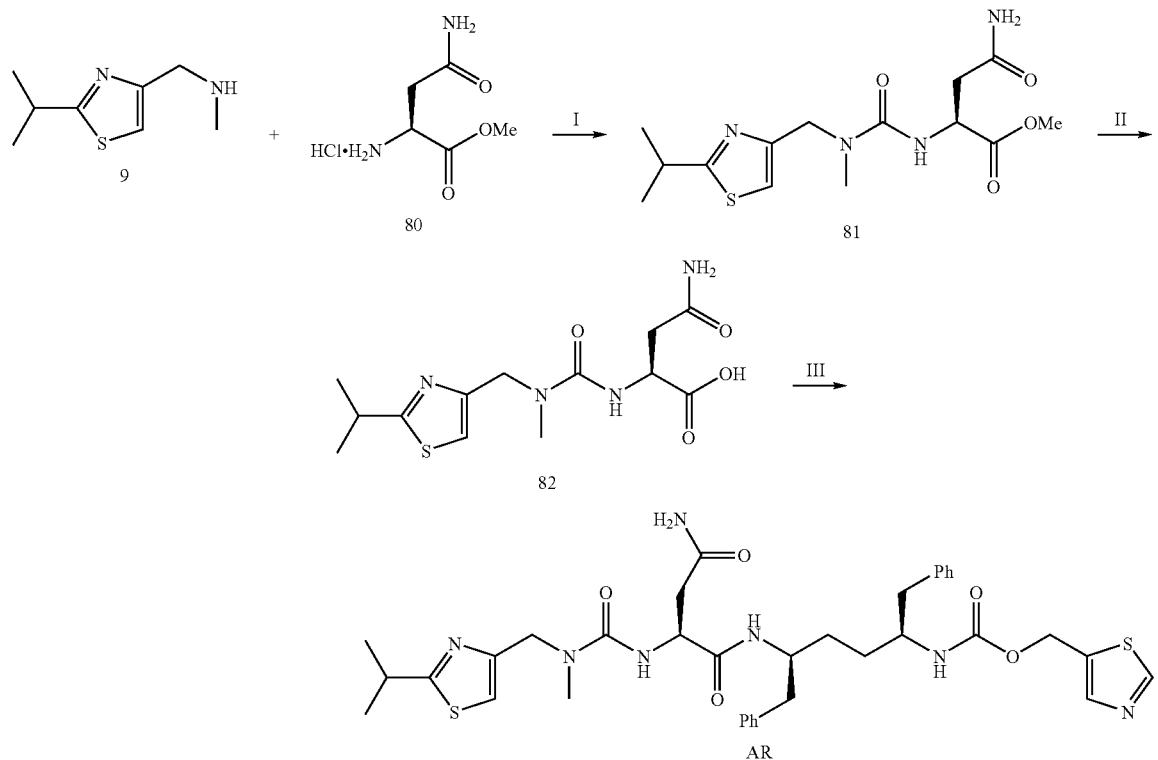

I. CDI, DIPEA, CH₂Cl₂; II. LiOH, THF/H₂O; III. Cmpd. 46, DIPEA, EDC, HOBt, THF

Compound 80

Compound 80 is commercially available from Chem Impex International, and was used without further purification.

Compound 81

Compound 80 (2.0 g, 11.0 mmol) was dissolved in CH$_2$Cl$_2$ (170 mL) and 1,1-carbonyldiimidazole (1.78 g, 11.0 mmol) was added, followed by iPr$_2$NEt (7.83 mL, 43.8 mmol). The solution was allowed to stir at 25° C. for 12 hours. Compound 9 (1.86 g, 11.0 mmol) was dissolved in 20 mL of CH$_2$Cl$_2$ and added to the reaction mixture. The solution was stirred at 25° C. for 12 hours. The solvent was removed in vacuo and the residue was diluted with ethyl acetate and washed water and brine. The organic layers were dried over Na$_2$SO$_4$, filtered, and evaporated. Purification by Combiflash® (stationary phase: silica gel; eluent: 66-100% EtOAc/Hexane gradient) gave Compound 81 (0.252 mg). m/z: 343.0 (M+H)$^+$.

Compound 82

Compound 82 (0.252 g, 0.74 mmol) was dissolved in THF (4 mL) and 1M aqueous LiOH (1.48 mL) was added. The mixture was stirred at 25° C. for 3 hours. The reaction was quenched with 1M HCl (2 mL) and the mixture was adjusted to pH 2. The mixture was extracted with ethyl acetate. The organic layers were dried over Na$_2$SO$_4$, filtered, and evaporated to afford Compound 82 (0.18 g). This material was used in the next step without further purification. m/z: 329.1 (M+H)$^+$.

Example AR

Compound 82 (182 mg, 0.55 mmol) was dissolved in THF (7.15 mL). Compound 46 (225 mg, 0.55 mmol) was added, followed by HOBt (112 mg, 0.83 mmol), iPr$_2$NEt (393 µL, 2.20 mmol), and EDC (194 µL, 1.10 mmol). The mixture was stirred at 25° C. for 12 hours. The solvent was removed under reduced pressure. The residue was diluted ethyl acetate and washed sequentially with saturated aqueous Na$_2$CO$_3$, water, and brine. The organic phase was dried over Na$_2$SO$_4$, filtered, and evaporated. Purification by flash column chromatography (stationary phase: silica gel; eluent: 5-10% MeOH/CH$_2$Cl$_2$ gradient) gave Example AR (208 mg, 53%). m/z: 720.2 (M+H)$^+$. $^1$H NMR (CDCl$_3$) δ 8.80 (s, 1H); 7.84 (s, 1H); 7.40-7.00 (m, 10H); 6.97 (s, 1H); 6.83 (m, 1H); 6.65 (br s, 1H); 5.99 (m, 1H); 5.40-5.10 (m, 4H); 4.52 (m, 3H); 4.06 (m, 1H); 3.79 (m, 1H); 3.34 (m, 1H); 2.97 (s, 3H); 2.90-2.60 (m, 5H); 2.50-2.40 (br s, 1H); 1.80-1.20 (m, 10H).

Preparation of Example AS

Scheme 36

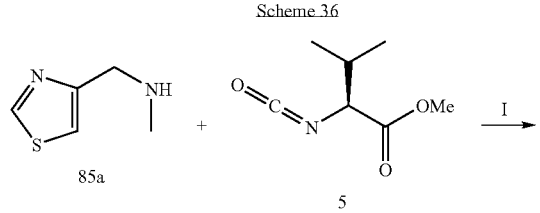

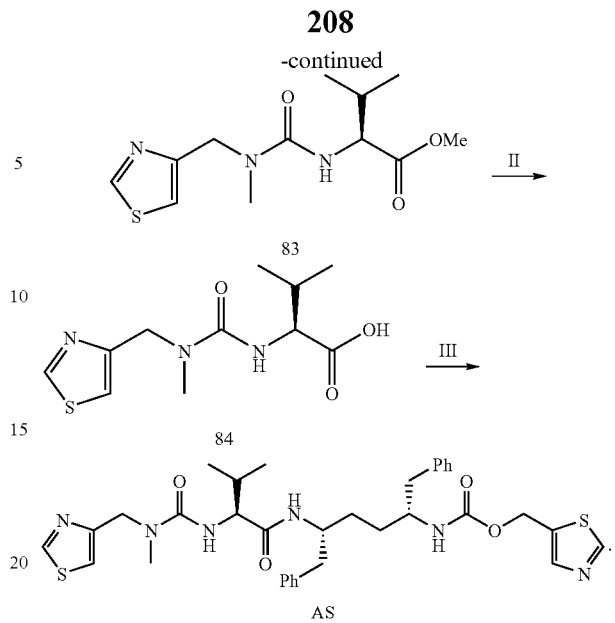

I. DIPEA, CH$_2$Cl$_2$; II. LiOH, THF/H$_2$O; III. Cmpd. 8, HOBt, EDC, DIPEA, THF Compound 85a Compound 85a was prepared following the same procedure as Compound 4, except that 4-chloromethylthiazole (purchased from TCI America) was used instead of Compound 3, and methylamine was used instead of isopropylamine.

Compound 83

To compound 85a (0.40 g, 3.12 mmol) in CH$_2$Cl$_2$ (9 mL) was added N,N-diisopropylethylamine (1.04 mL, 5.85 mmol), followed by Compound 5 (280 µL, 1.95 mmol). The reaction mixture was stirred for 3.5 hours at 25° C. Solvent was removed under reduced pressure. Purification by Combiflash® (stationary phase: silica gel; eluent: 90-100% EtOAc/Hexane gradient) gave Compound 83 (0.51 g). m/z: 286.0 (M+H)$^+$.

Compound 84

Compound 83 (0.51 g, 1.77 mmol) was dissolved in THF (10 mL) and 1M aqueous LiOH (3.54 mL) was added. The mixture was stirred at 25° C. for 2 hours. The reaction was quenched with 1M HCl (4.8 mL) and the mixture was adjusted to pH 2. The mixture was extracted with ethyl acetate. The organic layers were dried over Na$_2$SO$_4$, filtered, and evaporated to afford Compound 84 (0.430 g). This material was used in the next step without further purification. m/z: 272.0 (M+H)$^+$.

Example AS

Compound 84 (150 mg, 0.55 mmol) was dissolved in THF (7.15 mL). Compound 8 (225 mg, 0.55 mmol) was added, followed by HOBt (112 mg, 0.83 mmol), iPr$_2$NEt (393 µL, 2.20 mmol), and EDC (198 µL, 1.11 mmol). The mixture was stirred at 25° C. for 12 hours. The solvent was removed under reduced pressure. The residue was diluted ethyl acetate and washed sequentially with saturated aqueous Na$_2$CO$_3$, water, and brine. The organic phase was dried over Na$_2$SO$_4$, filtered, and evaporated. Purification by flash column chromatography (stationary phase: silica gel; eluent: 7% i-PrOH/CH$_2$Cl$_2$) gave Example AS (219 mg, 60%). m/z: 663.1 (M+H)$^+$. $^1$H NMR (CDCl$_3$) δ 8.87 (s, 1H); 8.76 (s, 1H); 7.84 (s, 1H); 7.40-7.00 (m, 10H); 6.22 (br s, 1H); 5.73 (br s, 1H); 5.22 (m, 2H); 4.50 (m, 2H); 4.16 (br s, 1H); 4.05 (br s, 1H); 3.75 (m, 1H); 2.93 (s, 3H); 2.90-2.60 (m, 5H); 2.90 (m, 1H); 2.31 (m, 1H); 1.60-1.30 (m, 4H); 1.00-0.80 (m, 6H).

Preparation of Example AT

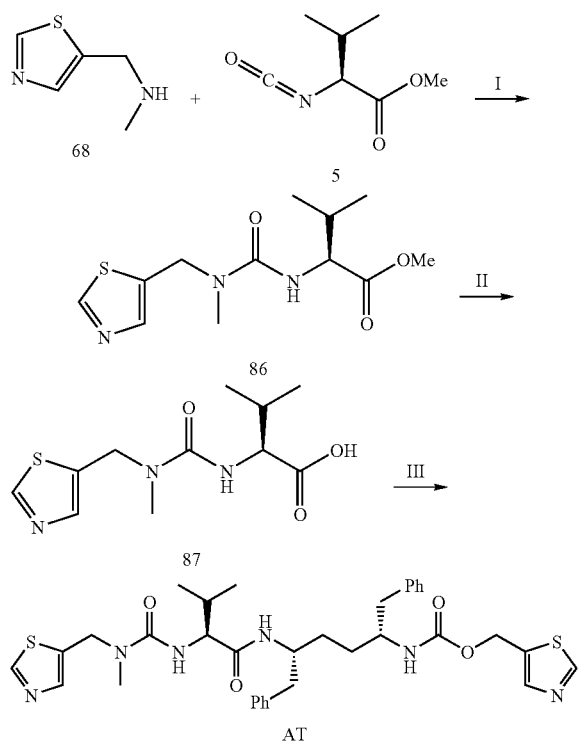

I. DIPEA, CH₂Cl₂; II. LiOH, THF/H₂O; III. Cmpd 8, HOBt, EDC, DIPEA, THF

Compound 87

Compound 87 (386 mg) was prepared from Compound 86 following the same procedure used to prepare Compound 7 from Compound 6, except that Compound 68 was used was used instead of Compound 4. m/z 286.0 (M+H)⁺

Preparation of Example AU

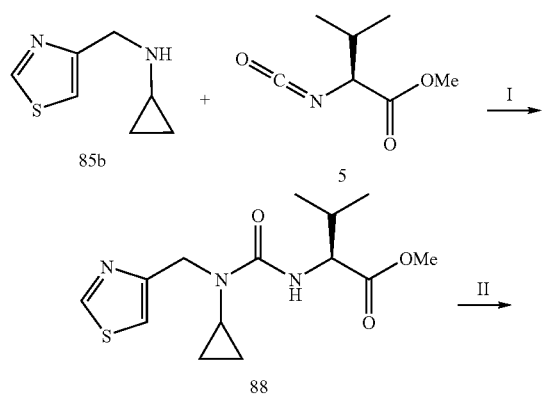

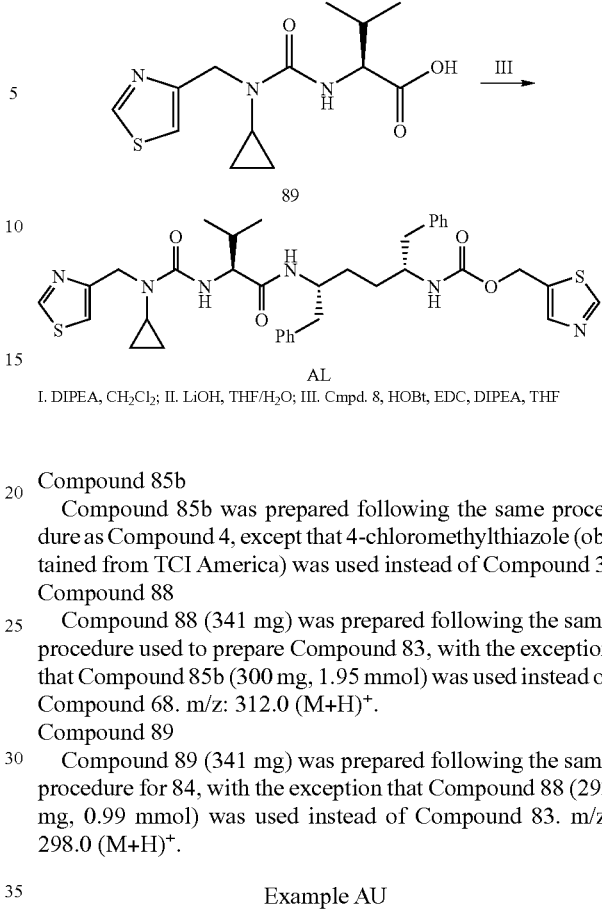

I. DIPEA, CH₂Cl₂; II. LiOH, THF/H₂O; III. Cmpd. 8, HOBt, EDC, DIPEA, THF

Compound 85b

Compound 85b was prepared following the same procedure as Compound 4, except that 4-chloromethylthiazole (obtained from TCI America) was used instead of Compound 3.

Compound 88

Compound 88 (341 mg) was prepared following the same procedure used to prepare Compound 83, with the exception that Compound 85b (300 mg, 1.95 mmol) was used instead of Compound 68. m/z: 312.0 (M+H)⁺.

Compound 89

Compound 89 (341 mg) was prepared following the same procedure for 84, with the exception that Compound 88 (293 mg, 0.99 mmol) was used instead of Compound 83. m/z: 298.0 (M+H)⁺.

Example AU

Example AU (226 mg, 64%) was prepared following the same procedure used to prepare Example AS, with the exception that Compound 89 (150 mg, 0.51 mmol) was used instead of Compound 84. m/z: 689.1 (M+H)⁺. ¹H NMR (CDCl₃) δ 8.87 (s, 1H); 8.74 (s, 1H); 7.83 (s, 1H); 7.40-7.00 (m, 10H); 6.21 (m, 1H); 5.73 (m, 1H); 5.29 (m, 1H); 5.17 (m, 2H); 4.88 (d, J=16 Hz, 1H); 4.47 (d, J=16 Hz, 1H); 4.18 (m, 1H); 3.75 (br s, 1H); 2.90-2.60 (m, 6H); 2.51 (br s, 1H); 2.31 (m, 1H); 1.60-1.30 (m, 4H); 1.00-0.80 (m, 10H).

Preparation of Example AV

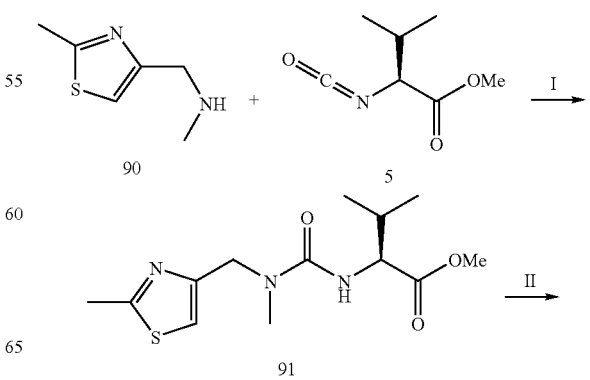

211
-continued

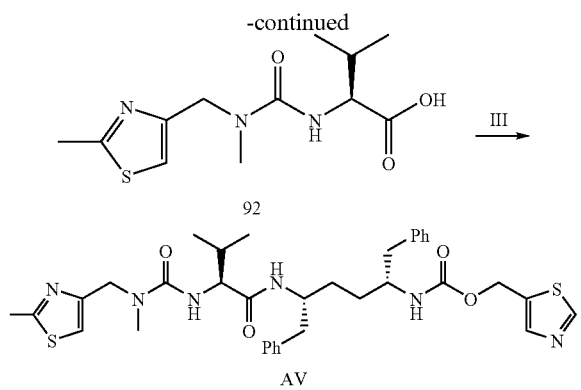

I. DIPEA, CH₂Cl₂; II. LiOH, THF/H₂O; III. Cmpd. 8, HOBt, EDC, DIPEA, THF

Compound 90

Compound 90 (190 mg) was prepared following the procedure used to prepare Compound 4, except that 4-(chloromethyl)-2-methylthiazole was used instead of Compound 3. m/z 141.1 (M–H)

212

Compound 91

Compound 91 (400 mg) was prepared following the same procedure used to prepare Compound 6 except that Compound 90 was used instead of Compound 4. m/z 300.0 $(M+H)^+$ Compound 92

Compound 92 (188 mg) was prepared following the same procedure as Compound 7 except that Compound 91 was used instead of Compound 6. m/z 284.0 $(M-H)^-$ Example AV Example AV (107 mg) was prepared following the procedure used to prepare Example C, except Compound 92 was used instead of Compound 7. $^1$H NMR (CDCl$_3$) δ 8.76 (s, 1H), 7.78 (s, 1H), 7.27-7.07 (m, 10H), 6.93 (s, 1H), 6.25 (m, 2H), 5.39 (m, 1H), 5.19 (m, 2H), 4.37-4.32 (m, 2H), 4.06 (m, 1H), 3.81 (br s, 1H), 2.83 (m, 4H), 2.65 (br s, 7H), 2.28-2.22 (m, 1H), 1.51-1.37 (m, 4H), 0.82 (m, 6H): m/z 677.2 $(M+H)^+$ Preparation of Example AW

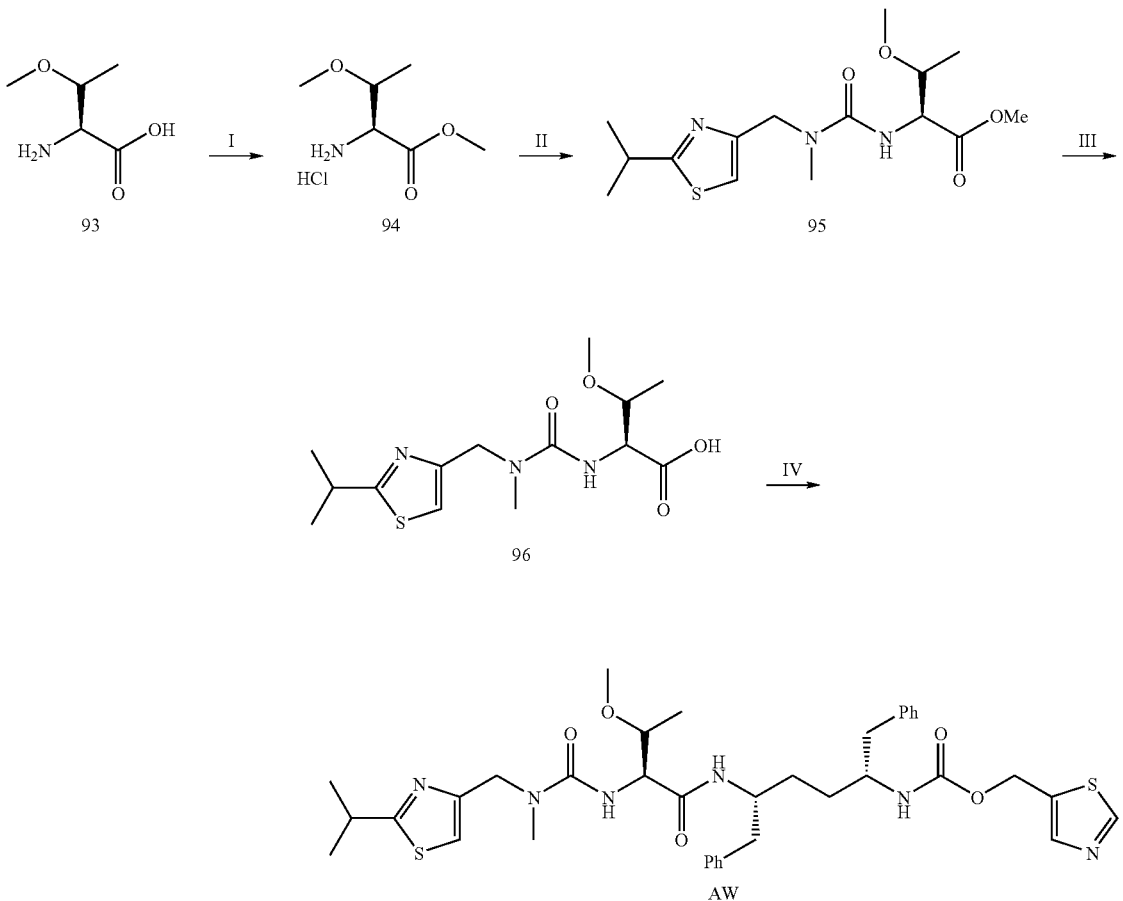

I. SOCl₂/MeOH; II. DIPEA, CH₂Cl₂, CDI; III. LiOH, THF/H₂O; IV. Cmpd 8, HOBt, EDC, IPEA, THF Compound 93

Compound 93 is commercially available from TCI, and was used without further purification.

Compound 94

To a solution of Compound 93 (500 mg, 3.76 mmol) in methanol (20 mL) was added thionyl chloride (0.5 mL, 6.6 mmol) dropwise. The mixture was stirred at 60° C. for 20 minutes, and concentrated in vacuo to gave Compound 94.

Compound 95

To a stirred solution of Compound 94 (3.7 mmol) and diisopropylethylamine (1.4 mL, 8.3 mmol) in dichloromethane (50 mL) was added CDI (609 mg, 3.7 mmol). The mixture was stirred for 12 hours. Compound 9 was added, and the mixture was stirred for 12 additional hours. Concentration and purification by flash column chromatography (0-100%: EtOAc/hexane) gave Compound 95 (100 mg). m/z 344.3 (M+H)$^+$ Compound 96

Compound 96 (39 mg) was prepared following the same procedure used to prepare Compound 7 except that Compound 95 was used instead of Compound 6. m/z 328.3 (M−H)$^−$ Example AW Example AW (107 mg) was prepared following the procedure for Example C, except that Compound 96 was used instead of Compound 7. $^1$H NMR (CDCl$_3$) δ 8.79 (s, 1H), 7.82 (s, 1H), 7.27-7.09 (m, 10H), 6.95 (s, 1H), 6.23 (m, 1H), 6.14 (s, 1H), 5.22 (s, 3H), 4.45 (m, 2H), 4.35-4.0 (m, 3H), 3.8 (m, 1H), 3.6 (m, 1H), 3.25 (s, 3H), 3.21 (m, 2H), 2.95 (s, 3H), 2.8-2.6 (m, 4H), 2.0-1.4 (m, 4H), 1.25 (m, 4H), 1.05 (m, 4H): m/z 721.3 (M+H)$^+$ Preparation of Examples AX and AY Example AX To a solution of Example I (650 mg, 1.00 mmol) in DMSO (3.5 mL) was added triethylamine (0.5 mL). The mixture was stirred for 30 minutes. Pyridine SO$_3$ was added to the mixture at 5° C. then stirred for 60 minutes. The mixture was poured on to ice-water, then stirred for 30 minutes. The mixture was diluted with EtOAc and washed with water, sat. NaHCO$_3$, and brine. Concentration gave Example AX. m/z 705.2 (M+H)$^+$ Example AY To a stirred solution of Example AX (70 mg, 0.099 mmol) and methylamine (1.5 mL, 2M) in MeOH (1.5 mL) was added AcOH (119 mg, 1.99 mmol). The mixture was stirred for 2 hours. NaBH(OAC)$_3$ (94 mg) was added, and the mixture was stirred for 2 hours. Concentration and purification by prep. HPLC gave Example AY (30 mg). $^1$H NMR (CDCl$_3$) δ 8.79 (s, 1H), 7.82 (s, 1H), 7.27-7.09 (m, 10H), 6.95 (s, 1H), 6.23 (m, 1H), 6.14 (s, 1H), 5.22 (s, 2H), 4.45 (m, 1H), 4.35-4.0 (m, 4H), 3.8 (m, 1H), 3.6 (m, 1H), 3.21 (m, 1H), 2.95 (s, 3H), 2.93 (s, 3H), 2.8-2.6 (m, 4H), 2.0-1.4 (m, 4H), 1.25 (m, 4H), 1.05 (m, 4H): m/z 720.3 (M+H)$^+$

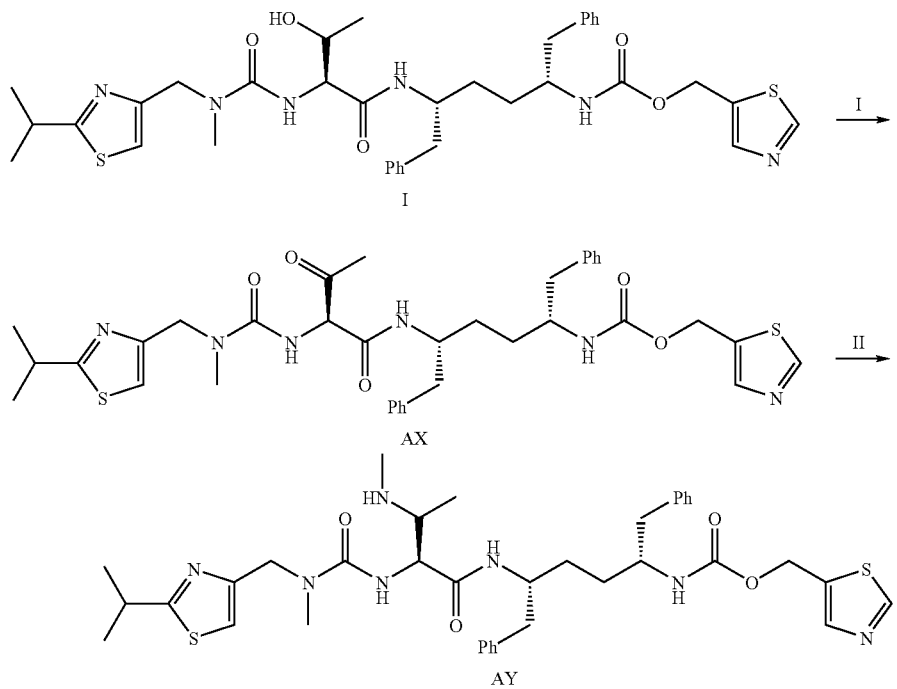

Scheme 41

I. DMSO, Et$_3$N, SO$_3$ pyridine: II. NaBH(OAc)$_3$, AcOH, Methylamine/MeOH

Preparation of Example AZ
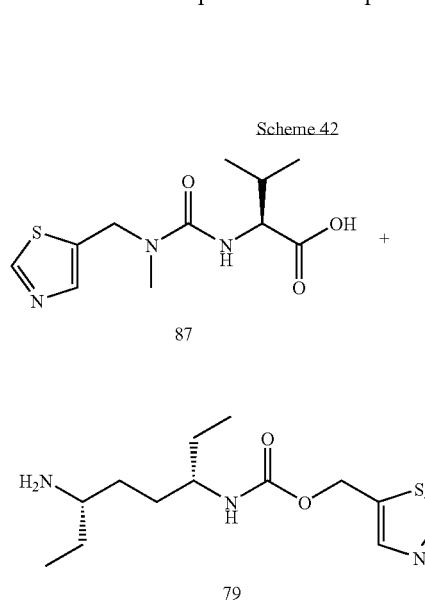
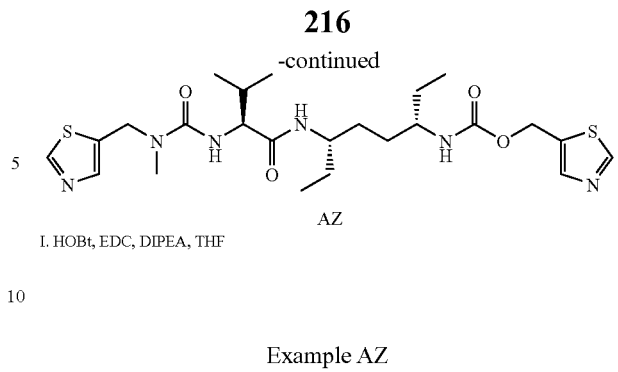
I. HOBt, EDC, DIPEA, THF
Example AZ
Compound AZ (61 mg) was prepared following the procedure for Example C, except that Compound 87 was used instead of Compound 7 and Compound 79 was used instead of Compound 8. $^1$H NMR (CDCl$_3$) δ 8.77 (s, 1H), 8.72 (s, 1H), 7.78 (s, 1H), 7.71 (s, 1H), 6.23 (d, 1H), 5.28-5.24 (m, 2H), 4.85 (d, 1H), 4.71-4.57 (m, 2H), 4.08-4.03 (m, 1H), 3.78 (br s, 1H), 3.51 (br s, 1H), 2.87 (s, 3H), 2.33 (br s, 1H), 2.13-2.06 (m, 1H), 1.49-1.33 (m, 8H), 0.93-0.80 (m, 12H): m/z 539.2 (M+H)$^+$
Preparation of Examples BA and BB
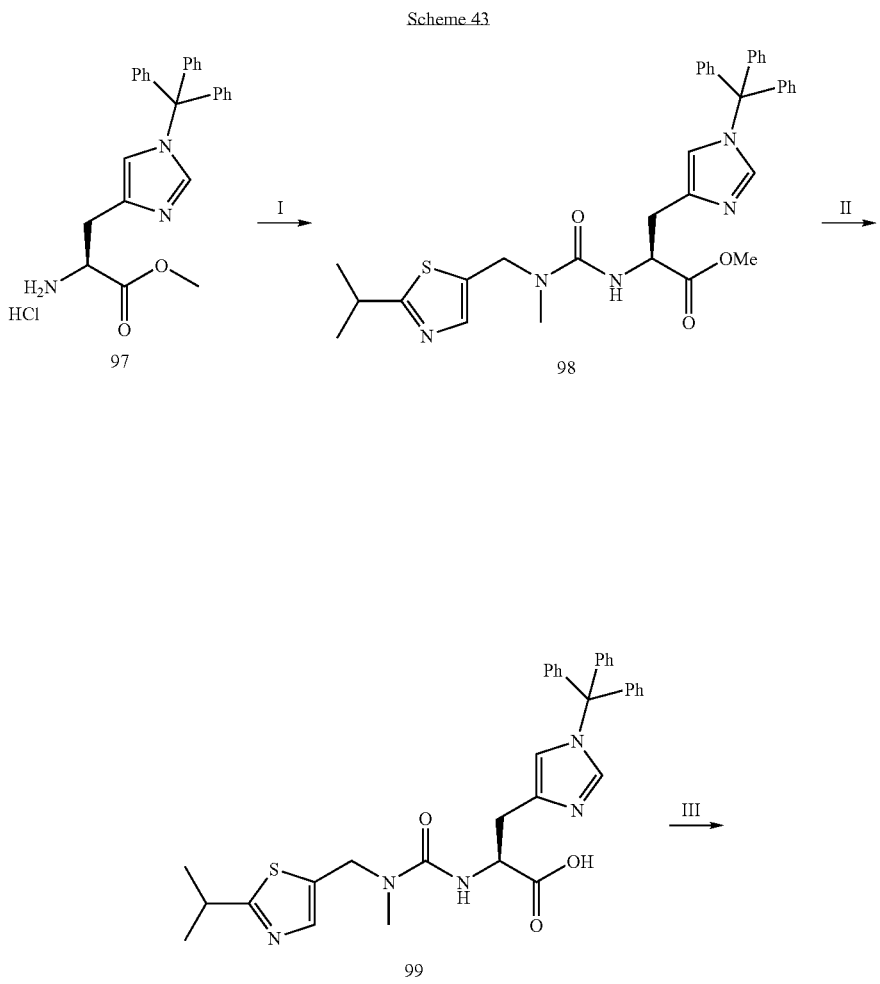

-continued

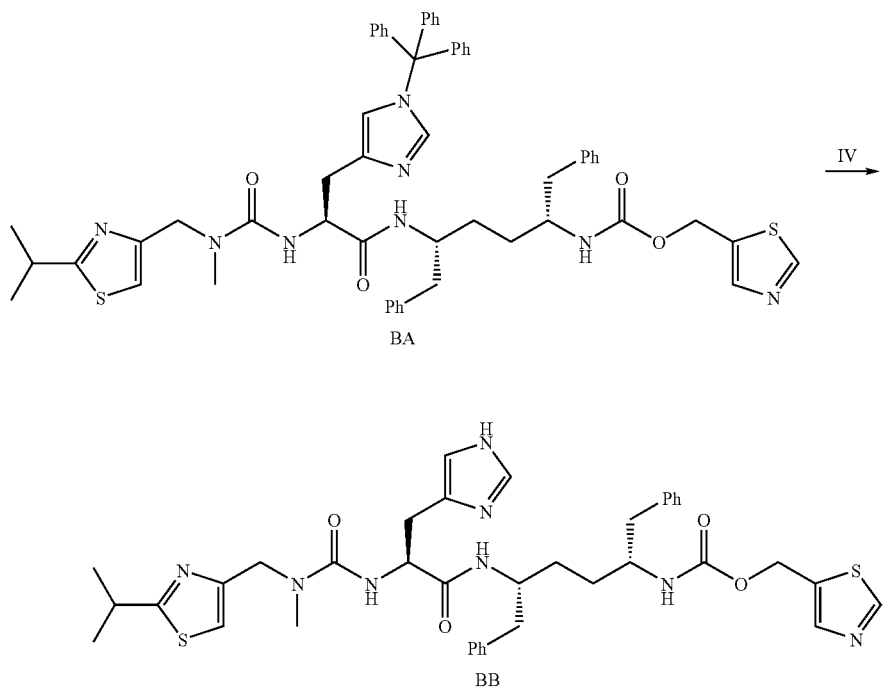

I. a. CDI/iPr₂NEt; b. Compound 9; II.a. NaOH/THF/H₂O; b. HCl;
III. Cmpd 8/EDC/HOBt, IPEA, THF: IV. EtSiH, TFA Compound 97

Compound 97 is commercially available from TCI, and was used as received.

Compound 98

To a stirred solution of Compound 97 (1 g, 2.2 mmol) and diisopropylethylamine (1.6 mL, 8.9 mmol) in dichloromethane (26 mL) was added CDI (362 mg, 2.2 mmol). The mixture was stirred for 12 hours. Compound 9 was added, and the mixture was stirred for 12 additional hours. Concentration and purification by flash column chromatography (0-8%: MeOH/DCM) gave Compound 98 (1.2 g). m/z 608.1 (M+H)⁺

Compound 99

Compound 99 (1.2 g) was prepared following the same procedure used to prepare Compound 67, with the exception that Compound 98 was used instead of Compound 66. m/z 592.2 (M−H)⁻

Example BA

Example BA (111 mg) was prepared following the procedure used to prepare Example C, except that Compound 99 was used instead of Compound 7. m/z 986.1 (M+H)⁺

Example BB

To a stirred solution of Example BA (111 mg, 0.113 mmol) and TFA (1.4 mL) was added Et₃SiH (0.1 mL). The mixture was stirred for 60 minutes, then concentrated and partitioned with EtOAc and sat. NaHCO₃, followed by extraction with EtOAc (2×) and drying over Na₂SO₄. Concentration and purification by flash column chromatography (0-15%: MeOH/DCM) gave Example BB (50 mg). ¹H-NMR (CDCl₃) δ 8.75 (s, 1H), 7.79 (s, 1H), 7.42 (s, 1H), 7.22-7.12 (m, 9H), 6.99-6.96 (m, 2H), 6.86 (s, 1H), 6.71 (m, 2H), 5.51 (br s, 1H), 5.17 (m, 2H), 4.57-4.52 (m, 1H), 4.39-4.35 (m, 2H), 4.07 (m, 1H), 3.74 (br s 1H), 3.28-3.19 (m, 1H,), 3.09-2.76 (m, 6H), 3.65-2.58 (m, 3H), 1.49 (m, 2H), 1.36-1.20 (m, 8H); m/z 743.2 (M+H)⁺

Preparation of Example BC

Scheme 44

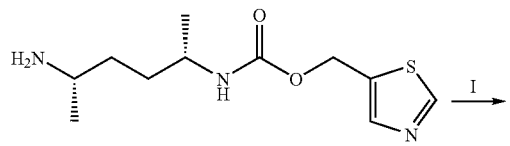

78

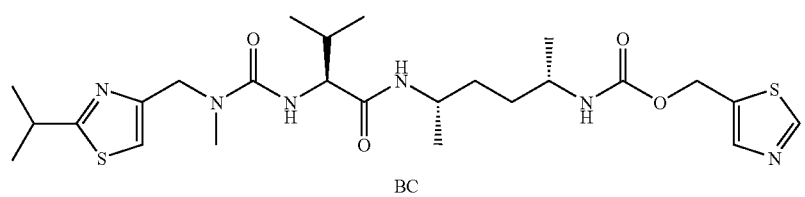

BC

I. HOBt, EDC, DIPEA, THF, Cmpd 29

Example BC

Example BC (95 mg) was prepared following the procedure used to prepare Example C, except that Compound 29 was used instead of Compound 7, and Compound 78 was used instead of Compound 8. $^1$H NMR (CDCl$_3$) δ 8.75 (s, 1H), 7.80 (s, 1H), 6.93 (s, 1H), 6.28 (d, 1H), 6.18 (m, 1H), 5.26-5.21 (m, 3H), 4.47-4.30 (m, 2H), 4.11-4.00 (m, 1H), 3.91 (br s, 1H), 3.59 (br s, 1H), 3.28 (m, 1H), 2.97-2.90 (m, 3H), 2.26-2.19 (m, 1H), 1.39-1.24 (m, 10H), 1.09-1.01 (m, 6H), 0.94-0.86 (m, 6H): m/z 553.1 (M+H)$^+$

Preparation of Examples BD and BE was used instead of Compound 7, and Compound 78 was used instead of amine 8. m/z 611.1 (M+H)$^+$

Example BE

Example BD (148 mg, 0.242 mmol) was dissolved in TFA (3 mL) and allowed to stir at 25° C. for 3 hours. The solvent was removed under reduced pressure and the residue was diluted with THF (3 mL) and 2N aqueous NaOH was added until pH 10. The mixture was allowed to stir for 20 min and extracted with EtOAc. The organic layer was washed sequentially with water and brine, dried over Na$_2$SO$_4$, filtered, and evaporated. Purification by flash chromatography (0-10% MeOH/CH$_2$Cl$_2$) gave Example BE (109 mg). $^1$H NMR

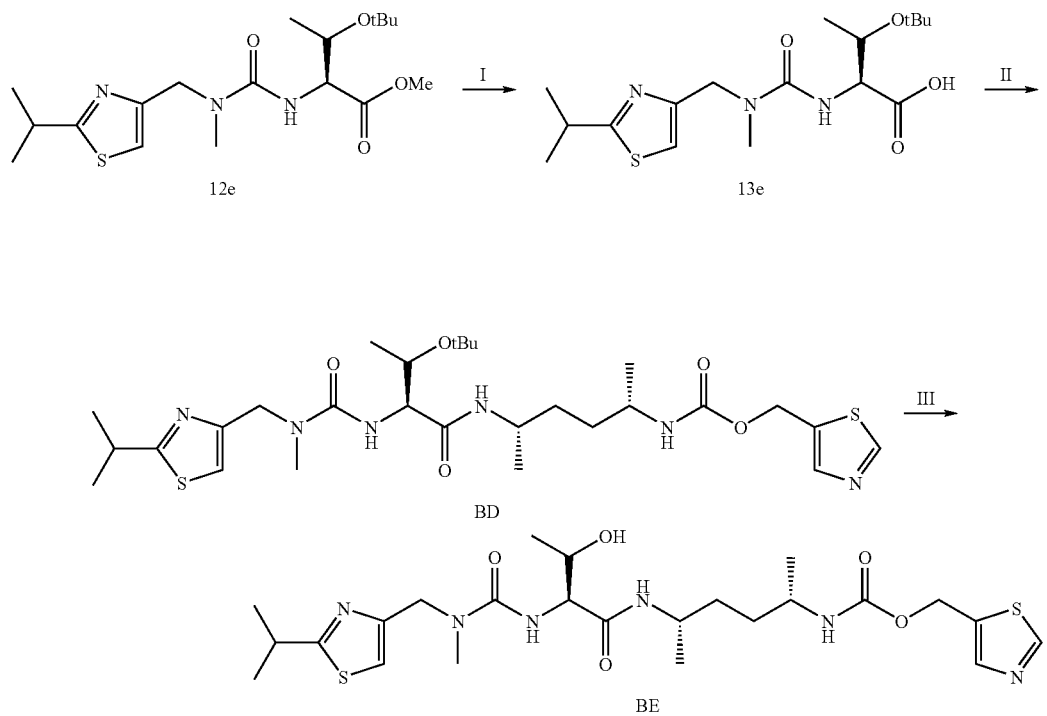

Scheme 45

BD

BE

I. LiOH, THF/H$_2$O; II. Cmpd. 78, HOBT, EDC, DIPEA, THF;
III. a. neat TFA; b. NaOH, THF, H$_2$O

Example BD

Example BD (148 mg) was prepared following the procedure used to prepare Example C, except that Compound 13e (CDCl$_3$) δ 8.75 (s, 1H), 7.80 (s, 1H), 6.97-6.94 (d, 1H), 6.90 (s, 1H), 6.32 (br s, 1H), 5.26-5.22 (m, 2H), 5.12 (d, 1H), 4.51-4.39 (m, 3H), 4.25-4.22 (m, 2H), 3.87 (br s, 1H), 3.62 (br s, 1H), 3.27-3.18 (m, 1H), 2.94 (s, 3H), 1.41-1.31 (m, 10H), 1.13-1.00 (m, 9H). m/z: 555.1 (M+H)$^+$.

Preparation of Example BF

Scheme 46

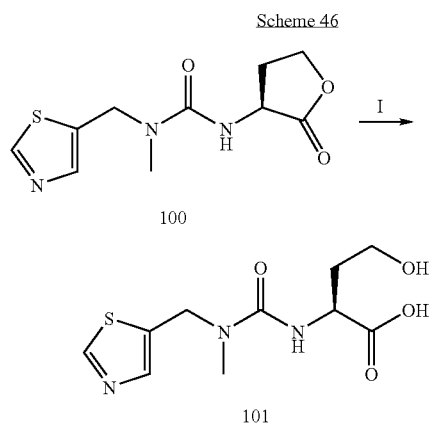

I. LiOH, THF/H₂O; II. Cmpd. 8, HOBt, EDC, DIPEA, THF

Compound 100

Compound 100 was prepared using the same method used to prepare Compound 122, except that Compound 9 was replaced with Compound 68 (see Scheme 70).

Compound 101

Compound 100 (108 mg, 0.423 mmol) was dissolved in THF (2 mL), then 847 µL of 1 M LiOH/H₂O was added. After stirring overnight, 843 µL of 1 N HCl was added. Concentration gave Compound 101.

Example BF

Example BF (24 mg) was prepared following the procedure used to prepare Example C, except that Compound 101 was used instead of Compound 7. $^1$H NMR (CDCl$_3$) δ 8.77 (s, 1H), 8.73 (s, 1H), 7.80 (s, 1H), 7.74 (s, 1H), 7.27-7.10 (m, 10H), 6.55-6.52 (d, 1H), 5.84 (d, 1H), 5.21-5.19 (m, 3H), 4.77-4.53 (m, 2H), 4.39 (br s, 1H), 4.11-3.99 (m, 2H), 3.81 (br s, 1H), 3.58 (m, 2H), 2.86 (s, 3H), 2.81-1.72 (m, 5H), 2.04 (m, 1H), 1.85 (m, 1H), 1.66-1.37 (m, 6H): m/z 665.2 (M+H)$^+$

Preparation of Example BG

Scheme 47

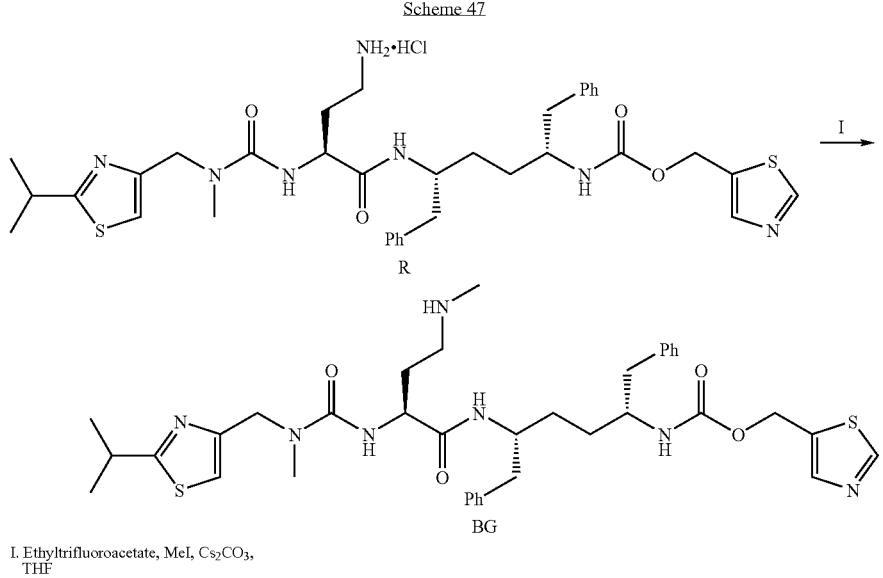

I. Ethyltrifluoroacetate, MeI, Cs₂CO₃, THF

Example BG

Example R (102 mg, 0.137 mmol) was dissolved in THF (2 mL), then 2 mL of ethyltrifluoroactate was added. Then 1.3 eq of MeI and excess Cs₂CO₃ were added. After stirring for 1 day, the mixture was partitioned with EtOAc and sat. Na₂CO₃, extracted with EtOAc (2x), and dried over Na₂SO₄. Purification by flash chromatography (0-20% MeOH/CH₂C2) gave Example BG (6.5 mg). $^1$H NMR (CD$_3$OD) δ 9.94 (s, 1H), 8.27 (s, 1H), 7.73 (s, 1H), 7.30-7.10 (m, 10H), 5.29, 5.17 (d 2H), 4.72 (s, 3H), 4.29 (m, 1H), 4.15 (br s, 1H), 3.83 (br s, 1H), 3.61 (m, 2H), 3.07 (s, 3H), 2.93 (m, 2H), 2.82-2.70 (m, 4H), 2.68-2.58 (m, 2H), 2.42 (s, 3H), 2.05 (m, 2H), 1.70-1.40 (m, 10H). m/z: 720.2. (M+H)$^+$.

Preparation of Example BH

Scheme 48

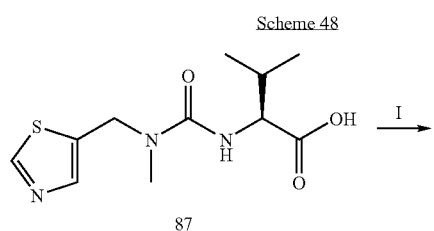
87

I ⟶

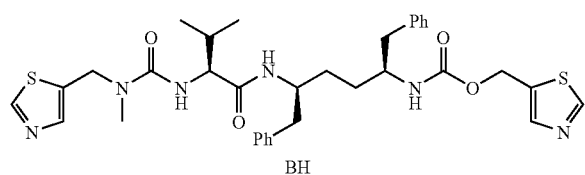
BH

I. amine 59, HOBt, EDC, DIPEA, THF

Example BH

Example BH (78 mg) was prepared following the procedure used to prepare Example C, except that Compound 87 was used instead of Compound 7, and Compound 46 was used instead of Compound 8. $^1$H NMR (CDCl$_3$) 8.73 (s, 1H), 8.68 (s, 1H), 7.76 (s, 1H), 7.68 (s, 1H), 7.18-7.09 (m, 10H), 6.26 (m, 1H), 5.76 (m, 1H), 5.22-5.18 (m, 4H), 4.71-4.65 (d, 1H), 4.46-4.40 (d, 1H), 4.11-4.04 (m, 2H), 3.81 (br s, 1H), 3.14 (br s, 1H), 2.83 (s, 3H), 2.76-2.52 (m, 4H), 1.88 (m, 1H), 1.51-1.37 (m, 2H), 0.73-0.69 (m, 6H) m/z 663.2 (M+H)$^+$

Preparation of Examples BI and BJ

Scheme 49

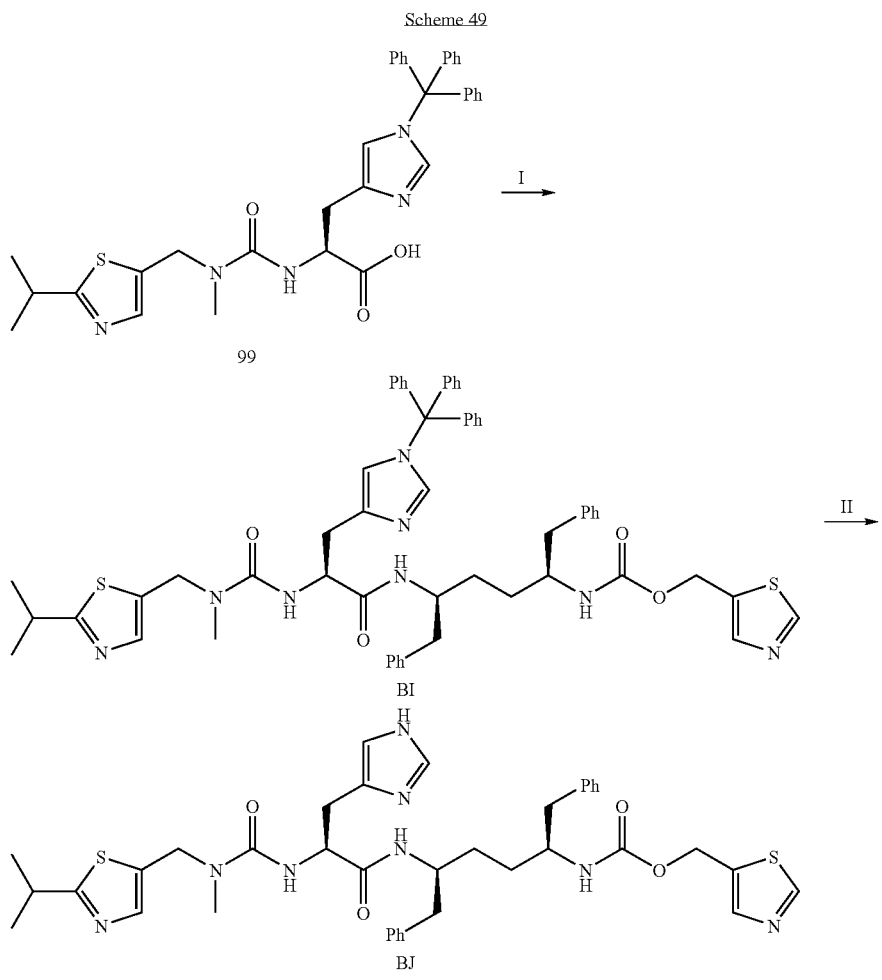

I. Cmpd. 46/EDC/HOBt, IPEA, THF; II. Et$_3$SiH, TFA

Example BI

Example BI (1.78 g) was prepared following the procedure used to prepare Example C, except that Compound 99 was used instead of Compound 7, and Compound 46 was used instead of Compound 8. m/z 986.1 (M+H)$^+$

Example BJ

Example BJ (728 mg) was prepared following the procedure used to prepare Example BB, except that Example BI was used instead of Example BA. $^1$H-NMR (CDCl3) δ 8.75

(s, 1H), 7.79 (s, 1H), 7.42 (s, 1H), 7.22-7.12 (m, 9H), 6.99-6.96 (m, 2H), 6.86 (s, 1H), 6.71 (m, 2H), 5.51 (br s, 1H), 5.17 (m, 2H), 4.57-4.52 (m, 1H), 4.39-4.35 (m, 2H), 4.07 (m, 1H), 3.74 (br s 1H), 3.28-3.19 (m, 1H,), 3.09-2.76 (m, 6H), 3.65-2.58 (m, 3H), 1.49 (m, 2H), 1.36-1.20 (m, 8H); m/z 743.2 (M+H)$^+$ and concentrated to provide 0.282 g (86%) of Compound 104 as an amorphous white powder that was used with further purification $^1$H-NMR (CDCl$_3$, 300 MHz): δ 7.06 (s, 1H); 4.37 (s, 1H); 3.28 (p, J=6.9 Hz, 1H); 3.00 (s, 3H); 1.62 (s, 6H); 1.39 (d, J=6.9 Hz, 6H).

Preparation of Compounds 104-115

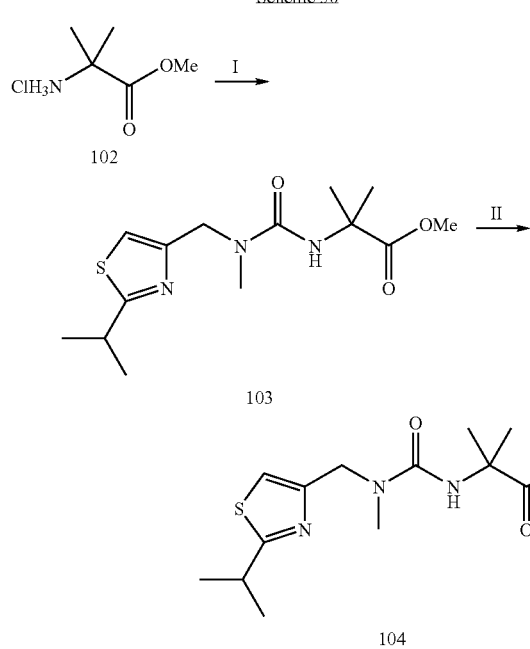

103

104

I. a. CDI, DIPEA, MeCN; b. Cmpd. 9, MeCN. II 1M LiOH, THF.

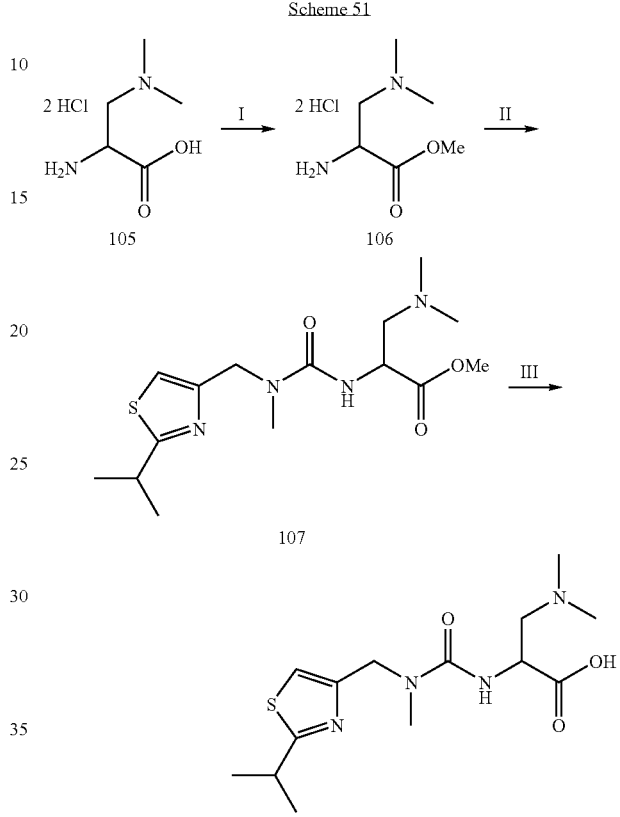

108

I. HCl, MeOH; II. a. CDI, DIPEA, MeCN; b. Cmpd. 9, MeCN. III. 1M LiOH, THF.

Compound 102

Compound 102 is commercially available from Aldrich Chemical Co., and was used without further purification.

Compound 103

Compound 102 (5.5 mmol) was suspended in MeCN (55 mL) and DIPEA (8.25 mmol) was added. Carbonyl diimidazole (5.5 mmol) was diluted in MeCN (20 mL) and the solution added slowly to the reaction mixture over 45 min. The resulting mixture was allowed to age overnight. Compound 9 (5.5 mmol) was diluted in MeCN (10 mL) and treated with DIPEA (8.25 mmol) before being added to the reaction mixture, which was then allowed to age overnight. The volatiles were removed in vacuo and the residue taken up in EtOAc (50 mL) and washed with 1M HCl (50 mL). The layers were separated and the aqueous layer extracted with EtOAc (3×50 mL). The combined organic layers were washed with sat. Na$_2$CO$_3$ until the pH of the washes was ~pH 8. A brine wash (30 mL) was followed by drying over anhydrous MgSO$_4$. Following concentration in vacuo, the residue was purified on SiO$_2$ (0-65% EtOAc/hex) to provide 0.340 g (20%) of Compound 103 as an amorphous white solid (m/z 314.0 (M+H)$^+$).

Compound 104

Compound 103 (1.1 mmol) was diluted in THF (5 mL) and treated with freshly prepared 1M LiOH (2.2 mmol). The biphasic reaction was stirred vigorously for 2 h before being quenched with 1M HCl (3 mmol). The reaction was extracted with EtOAc (5×15 mL) and the combined organics were washed with brine (30 mL), dried over anhydrous Na$_2$SO$_4$ Compound 105

Compound 105 is commercially available from Aldrich Chemical Co., and was used without further purification.

Compound 106

Racemic Compound 105 (12.2 mmol) was diluted in MeOH (100 mL). HCl/dioxane solution (4M, 25 mmol) was added and the solution was refluxed overnight. Volatiles were removed in vacuo to produce 2.60 g (97%) of Compound 106 as a racemic mixture. The foamy white solid was used without further purification (m/z 147.0 (M+H)$^+$).

Compound 107

Compound 106 (5 mmol) was diluted in MeCN (65 mL) and treated with DIPEA (25 mmol). The resulting solution was added slowly via addition funnel to a solution of CDI (5 mmol) in MeCN (30 mL) and allowed to age overnight. Compound 9 (5 mmol) and DIPEA (3 mmol) were added to the reaction solution which was allowed to age overnight. The volatiles were removed in vacuo and the residue was taken up in EtOAc and sat. Na$_2$CO$_3$ (30 mL each). The aqueous layer was extracted with EtOAc (3×25 mL) and the combined organics were washed with brine (50 mL) and dried over anhydrous MgSO$_4$. Following concentration in vacuo, purification by column chromatography on SiO$_2$ (0-10% MeOH/DCM) provided 0.36 g (21%) of racemic Compound 107 as a yellow oil (m/z 343.1 (M+H)$^+$).

Compound 108

Compound 107 (1.05 mmol) was taken up in THF (5 mL) and treated with freshly prepared 1M LiOH solution (2.1 mmol). The solution was stirred vigorously for 2 h and quenched with 1M HCl (2.1 mmol). The volatiles were removed in vacuo, and the resulting oil was azeotroped with toluene until a quantitative yield of racemic Compound 107 was produced as an amorphous white solid that was used without further purification (m/z 329.1 (M+H)$^+$).

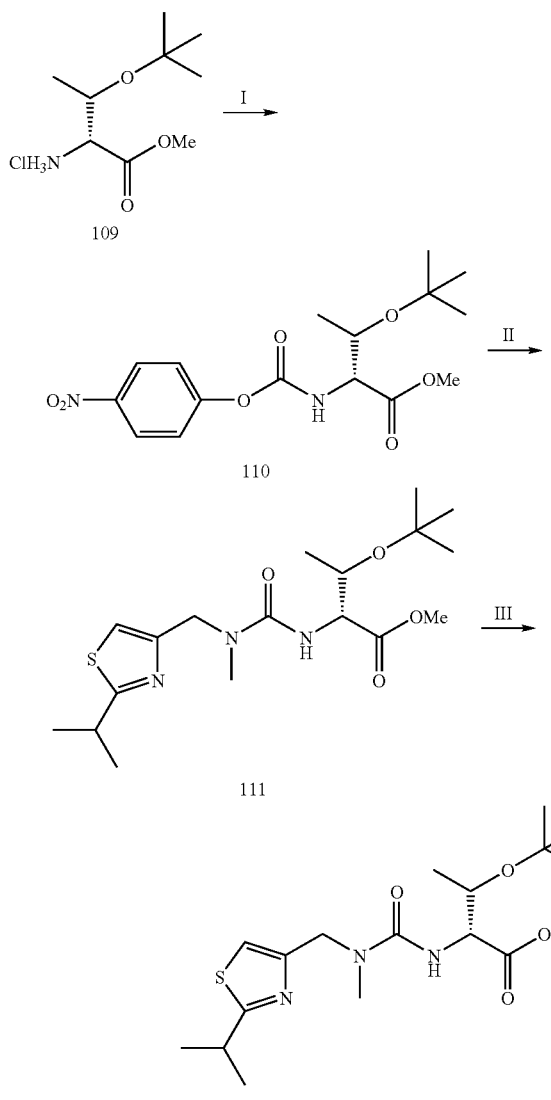

I. p-O$_2$NC$_6$H$_4$O(CO)Cl, NMM, DCM, 0° C. to rt; II. Cmpd. 9, Et$_3$N, DMAP, THF, 70° C.; III. 1M LiOH, THF Compound 109

Compound 109 is commercially available from Bachem, and was used as received.

Compound 110

Compound 109 (4.1 mmol) was diluted in DCM (5 mL) and treated with N-methylmorpholine (8.2 mmol). This solution was added slowly to a DCM (5 mL) solution of 4-nitrophenyl chloroformate (4.1 mmol) at 0° C. The reaction was then allowed to warm to room temperature overnight. The volatiles were removed in vacuo and the residue was taken up in EtOAc and sat. Na$_2$CO$_3$. The aqueous layer was extracted with EtOAc (3×10 mL) and the combined organics were washed with brine (30 mL) prior to being dried over anhydrous Na$_2$SO$_4$. Following concentration in vacuo, the residue was purified by column chromatography on SiO$_2$ (0-25% EtOAc/Hex) to produce 0.75 g (51%) of Compound 110 as an amorphous white solid (m/z 354.8 (M+H)$^+$).

Compound 111

Compound 110 (1.1 mmol) was diluted in THF (3.5 mL). Compound 9 (1.4 mmol) was diluted in THF (3 mL), treated with Et$_3$N (2.8 mmol) and transferred to the reaction solution. DMAP (0.11 mmol) was added and the reaction was heated to 70° C. for 2 h. After cooling to room temperature, EtOAc (10 mL) and sat. Na$_2$CO$_3$ were added. The aqueous phase was extracted with EtOAc (3×10 mL) and the combined organics were washed with sat. Na$_2$CO$_3$, H$_2$O, and brine (15 mL each). After drying over anhydrous MgSO$_4$, volatiles were removed in vacuo and the residue was purified by column chromatography on SiO$_2$ (0-50% EA/hex) to produce 0.346 g (82%) of Compound III (m/z 386.0 (M+H)$^+$).

Compound 112

Compound 111 (0.88 mmol) was taken up in THF (4 mL) and treated with freshly prepared 1M LiOH (1.8 mmol). The reaction mixture was stirred vigorously for 1.5 h and quenched with 1M HCl (2.5 mmol). The reaction mixture was extracted with EtOAc (3×10 mL), and the combined organics were washed with brine (30 mL) and dried over anhydrous Na$_2$SO$_4$. Concentration in vacuo produced 0.300 g (92%) of Compound 112 as a colorless film that was used without further purification (m/z 372.0 (M+H)$^+$).

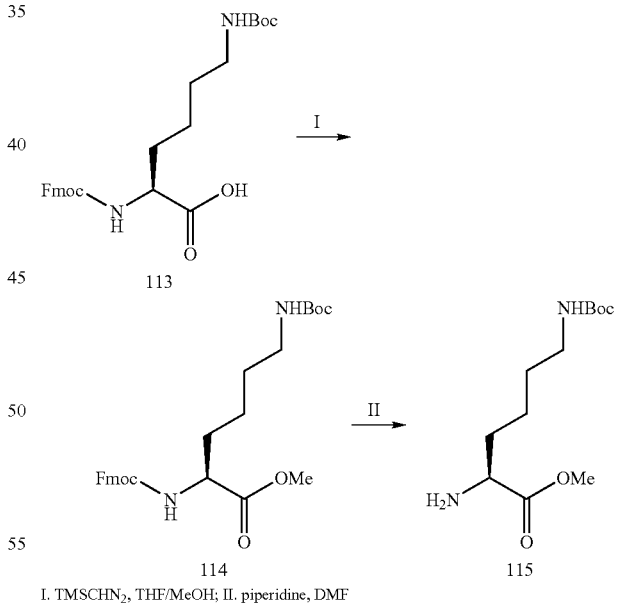

I. TMSCHN$_2$, THF/MeOH; II. piperidine, DMF

Compound 113

Compound 113 is commercially available from Chem-Impex, and was used without further purification.

Compound 114

Compound 113 (3.2 mmol) was diluted in THF (15 mL). TMSCHN$_2$ (3.2 mmol) was added slowly, followed by MeOH (5 mL). The solution rapidly became colorless, and heavy evolution of gas was observed. After aging overnight, the volatiles were removed in vacuo and the residue purified by column chromatography on SiO₂ (0-50% EtOAc/hex) to produce 0.805 g (52%) of Compound 114 (m/z 505.2 (M+Na)⁺).

Compound 115

Compound 114 (1.7 mmol) was diluted in DMF (4 mL) and piperidine (1 mL) was added. After 30 min, the volatiles were removed in vacuo and the residue was purified by column chromatography on SiO₂ (0-5% MeOH/DCM) to provide 0.414 (94%) of Compound 115 as an amorphous white solid (m/z 261.0 (M+H)⁺).

Preparation of Example BK

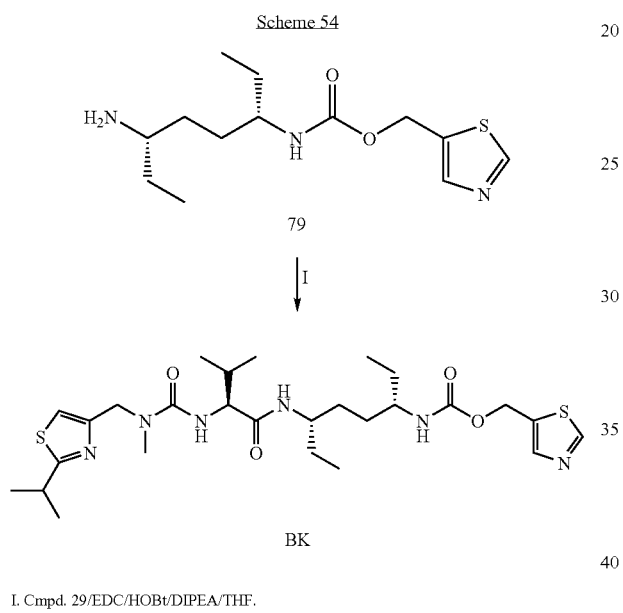

Compound BK

Compound 79 (0.70 mmol) and Compound 29 (0.91 mmol) were combined in THF (7 mL). HOBt (0.91 mmol), DIPEA (1.05 mmol) and EDC (0.91 mmol) were added consecutively at room temperature and the reaction was allowed to age overnight. The volatiles were removed in vacuo and the residue taken up in 3/1 CHCl₃/IPA and sat. Na₂CO₃ (15 mL each). The aqueous layer was extracted with 3/1 CHCl₃/IPA (3×10 mL) and the combined organics were washed with sat. Na₂CO₃, water, and brine (15 mL each). Following drying over anhydrous MgSO₄, the volatiles were removed in vacuo and the residue was purified by column chromatography on SiO₂ (0-10% MeOH/DCM) to produce 8.5 mg (2%) of Compound BK m/z 581.2 (M+H)⁺; ¹H-NMR (CDCl₃, 300 MHz): δ 8.91 (s, 1H); 7.89 (s, 1H); 7.15 (s, 1H); 6.52-6.0 (br m, 2H); 5.26 (s, 2H); 5.18 (br d, J=8.1 Hz, 1H); 4.55 (s, 2H); 4.06 (br s, 1H); 3.79 (br s, 1H); 3.48 (m, 2H); 3.09 (s, 3H, minor rotamer); 3.01 (s, 3H, major rotamer); 2.34 (m, 1H); 1.60-1.30 (m, 8H); 1.42 (d, J=6.9 Hz, 6H); 0.98 (t, J=7.2 Hz, 6H); 0.86 (m, 6H).

Preparation of Example BL

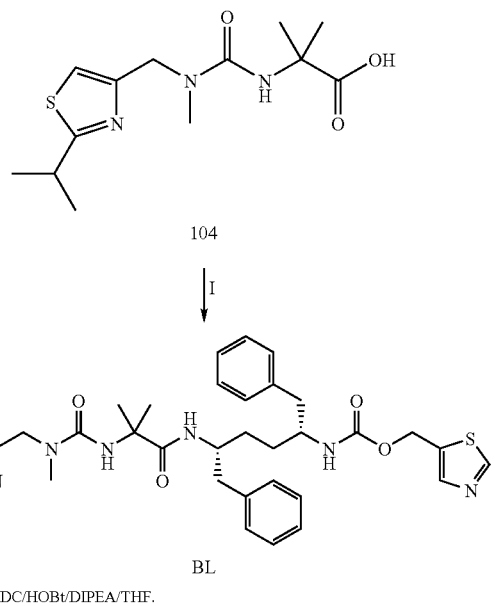

Example BL

Example BL was prepared in a similar fashion to Example BK using Compound 104 (0.26 mmol) and Compound 8 (0.29 mmol) to produce 0.087 g (64%) of Example BL as an amorphous white solid m/z 691.3 (M+H)⁺; ¹H-NMR (CDCl₃, 300 MHz): δ 8.82 (s, 1H); 7.82 (s, 1H); 7.30-7.10 (m, 11H); 7.06 (s, 1H); 6.54 (d, J=9.6 Hz, 1H); 5.89 (d, J=8.4 Hz, 1H); 5.22 (s, 1H); 5.07 (m, 1H); 4.45 (AB d, J=16.5 Hz, 1H); 4.37 (AB d, J=15.6 Hz, 1H); 4.07 (m, 1H); 3.68 (m, 1H); 3.40 (m, 1H); 3.06 (s, 3H, minor rotamer); 2.89 (s, 3H, major rotamer); 2.90-2.54 (m, 4H); 1.60-1.25 (m, 16H).

Preparation of Example BMA and BMB

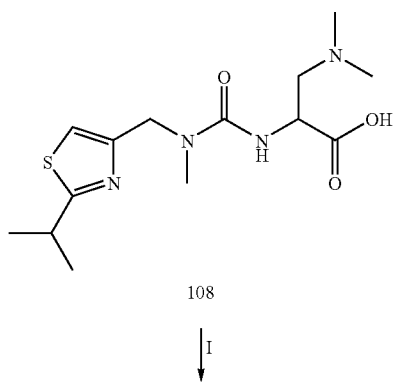

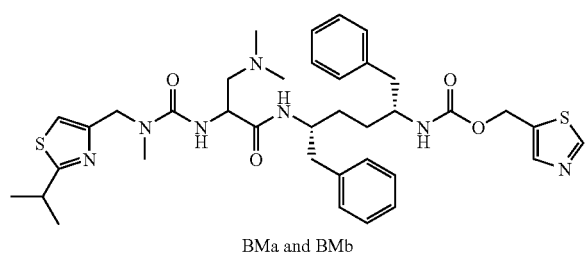

BMa and BMb

I. Cmpd. 8/EDC/HOBt/DIPEA/THF.

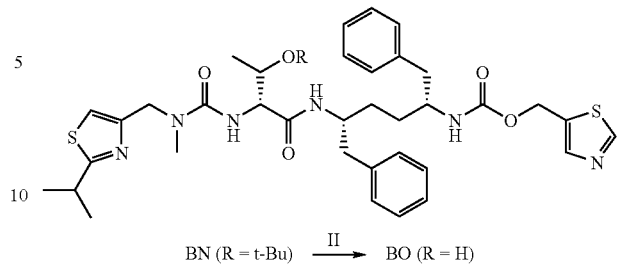

BN (R = t-Bu) —II→ BO (R = H)

I. Cmpd. 8/EDC/HOBt/DIPEA/THF; II. TFA, 1M NaOH.

Examples BMA and BMB

Examples BMA and BMB were prepared in a similar fashion to Compound BK using racemic Compound 108 (0.36 mmol) and Compound 8 (0.28 mmol). The enantiomeric products were separated by preparatory HPLC (Chiralcel OD-H (250×4.6 mm, 70:30 Heptane/IPA, 30 min) to produce 0.008 g (4%) of enantiomer BMa (HPLC $R_T$=11.71 min) m/z 720.3 (M+H)$^+$; $^1$H-NMR (CDCl$_3$, 300 MHz): δ 8.73 (s, 1H); 7.78 (s, 1H); 7.41 (br s, 1H); 7.30-7.00 (m, 11H); 6.94 (s, 1H); 5.40 (br s, 1H); 5.18 (br s, 2H); 4.56 (AB d, J=15 Hz, 1H); 4.48 (AB d, J=16 Hz, 1H); 4.39 (br s, 1H); 4.05 (br s, 1H); 3.73 (br s, 1H); 3.25 (s, 3H, minor rotamer); 3.23 (m, 1H); 2.98 (s, 3H, major rotamer); 2.82-2.30 (m, 10H); 1.60-1.20 (m, 6H); 1.32 (d, J=7 Hz, 6H) and 0.010 g (5%) of enantiomer BMb (HPLC $R_T$=15.41 min). (m/z 720.3 (M+H)$^+$; $^1$H-NMR (CDCl$_3$, 300 MHz): δ 8.78 (s, 1H); 7.83 (s, 1H); 7.38 (br d, J=8 Hz, 1H); 7.30-7.7.05 (m, 11H); 7.02 (s, 1H); 5.52 (d, J=9 Hz, 1H); 5.25 (AB d, J=13 Hz, 1H); 5.21 (AB d, J=13 Hz, 1H); 4.85-4.62 (m, 2H); 4.44 (d, J=16 Hz, 1H); 3.99 (br s, 1H); 3.78 (br s, 1H); 3.37 (br s, 3H, minor rotamer); 3.26 (m, 1H); 3.07 (s, 3H, major rotamer); 2.77 (s, 6H); 2.86-2.60 (m, 4H); 1.6-1.3 (m, 6H); 1.35 (d, J=7 Hz, 6H).

Preparation of Examples BN and BO

Example BP

Example BN was prepared in a similar fashion to Example BK using Compound 112 (0.78 mmol) and Compound 8 (0.60 mmol) to produce 0.227 g (50%) of Compound BN as colorless film. (m/z 763.3 (M+H)$^+$).

Example BO

Example BO was prepared in a similar fashion to Example AM using Example BN (0.29 mmol) to produce 0.149 g (72%) of Example BO as an amorphous white solid. (m/z 707.3 (M+H)$^+$; $^1$H-NMR (CDCl$_3$, 300 MHz): δ 8.82 (s, 1H); 7.84 (s, 1H); 7.26-7.03 (m, 11H); 6.99 (s, 1H); 6.69 (d, J=9.6, 1H); 6.42 (br s, 1H); 5.47 (br d, J=8.7 Hz, 1H); 5.27 (AB d, J=13 Hz, 1H); 5.22 (AB d, J=13 Hz, 1H); 4.55 (AB d, J=16 Hz, 1H); 4.43 (AB d, J=16 Hz, 1H); 4.18 (m, 1H); 4.00 (m, 2H); 3.72 (br s, 1H); 2.25 (m, 1H); 2.99 (s, 3H); 2.84-2.60 (m, 3H); 2.54-2.42 (m, 1H); 1.64-1.12 (m, 4H); 1.37 (d, J=7 Hz, 6H); 1.11 (d, J=6 Hz, 3H).

Preparation of Examples BP-BR

Scheme 57

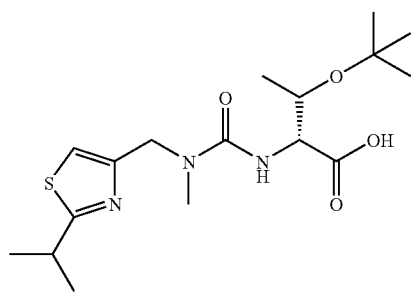

112

↓I

Scheme 58

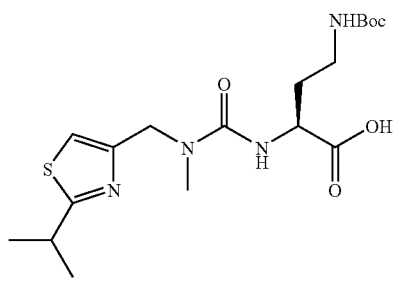

52

↓I

233

-continued

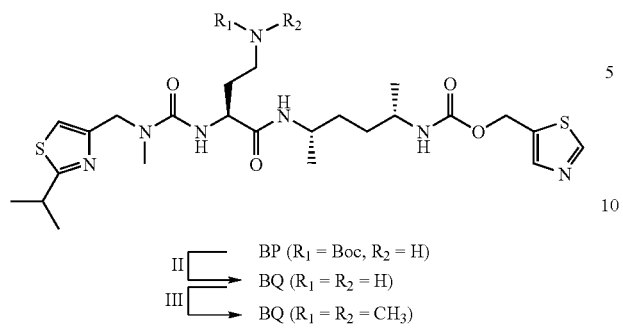

BP (R₁ = Boc, R₂ = H)
II⌐→ BQ (R₁ = R₂ = H)
III⌐→ BQ (R₁ = R₂ = CH₃)

I. Cmpd. 78/EDC/HOBt/DIPEA/THF; II. 4M HCl/dioxane; III. HCHO, NaHB(OAc)₃, MeOH

Example BP

Example BP was prepared in a similar fashion to Example BK using Compound 52 (0.22 mmol) and Compound 78 (0.20 mmol) to produce 0.091 g (71%) of Example BP as colorless film (m/z 654.2 $(M+H)^+$).

Example BQ

Example BQ (0.14 mmol) was treated with 4M HCl in dioxane (2 mL) to produce a white precipitate within 5 min. The solvents were removed, and the solid was taken up in MeOH. Concentration in vacuo afforded 0.083 g (99%) of the HCl salt of Example BQ as a colorless film (m/z 554.1 $(M+H)^+$; ¹H-NMR (CD₃OD, 300 MHz): δ 10.03 (s, 1H); 8.41 (s, 1H); 7.81 (s, 1H); 5.48 (s, 2H, minor rotamer); 5.35 (s, 2H, major rotamer); 4.74 (s, 2H); 4.34 (br s, 1H); 3.90 (br s, 1H); 3.78-3.54 (m, 2H); 3.20-2.98 (m, 5H); 2.20 (br s, 1H); 2.07 (br s, 1H); 1.60-1.4 (m, 10H); 1.12 (m, 6H).

Example BR

Example BQ (0.11 mmol) was taken up in MeOH (1.5 mL). Formaldehyde (37% in H₂O, 13.4 mmol) was added and aged 10 min. NaHB(OAc)₃ (0.324 mmol) was added, and the reaction mixture was allowed to age at room temperature overnight. More formaldehyde (13.4 mmol) and NaHB(OAc)₃ (0.324 mmol) were added and allowed to age an additional 6 h at room temperature. The solvents were removed in vacuo and the product was isolated by preparatory HPLC to produce 0.058 g (77%) of the TFA salt of Example BR as an amorphous solid. m/z 582.3 $(M+H)^+$; ¹H-NMR (CD₃OD, 300 MHz): δ 9.07 (s, 1H); 7.91 (s, 1H); 7.25 (s, 1H); 5.47 (s, 2H, minor rotamer); 5.28 (s, 2H, major rotamer); 4.59 (AB d, J=16 Hz, 1H); 4.53 (AB d, J=16 Hz, 1H); 4.31 (dd, J=9.2, 5 Hz, 1H); 3.88 (m, 1H); 3.59 (m, 1H); 3.32 (m, 1H); 3.20 (m, 2H); 2.98 (s, 3H); 2.89 (br s, 6H); 2.23 (m, 1H); 2.00 (m, 1H); 1.44 (m, 4H); 1.37 (d, J=7 Hz, 6H); 1.10 (m, 6H).

234

Preparation of Examples BS and BT

Scheme 59

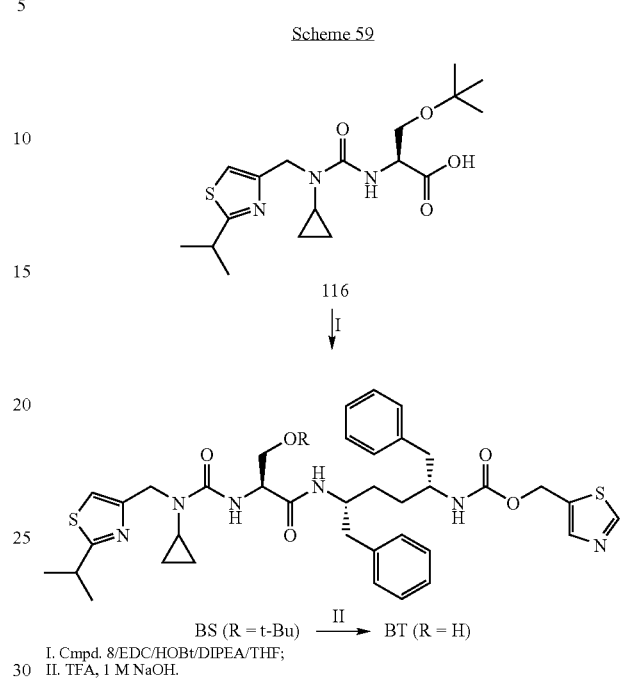

BS (R = t-Bu) →ᴵᴵ BT (R = H)

I. Cmpd. 8/EDC/HOBt/DIPEA/THF;
II. TFA, 1 M NaOH.

Compound 116

Compound 116 was prepared in a similar fashion to Compound 75 using Compound 4 (0.76 mmol) and Compound 47 (0.64 mmol) to produce 0.218 g (90%) of Compound 116 as a foamy white solid (m/z 384.1 $(M+H)^+$).

Example BS

Example BS was prepared in a similar fashion to Example BK using Compound 116 (0.28 mmol) and Compound 8 (0.25 mmol) to produce 0.139 g (72%) of Example BS as a colorless film (m/z 775.3 $(M+H)^+$).

Example BT

Example BT was prepared in a similar fashion to Example AM using Example BU (0.18 mmol) to produce 0.080 g (62%) of Example BT as an amorphous white solid. m/z 719.3 $(M+H)^+$; ¹H-NMR (CDCl₃, 300 MHz): δ 8.79 (s, 1H); 7.82 (s, 1H); 7.27-7.0 (m, 10H); 6.98-6.82 (m, 1H); 6.85 (s, 1H); 6.44 (br s, 1H); 5.30 (s, 2H, minor rotamer); 5.22 (s, 2H, major rotamer); 5.04 (br s, 1H); 4.62 (AB d, J=15 Hz, 1H); 4.54 (AB d, J=15 Hz, 1H); 4.27 (br s, 1H); 4.11 (br s, 1H); 3.97 (br d, J=10 Hz, 1H); 3.82, br s, 1H); 3.57 (br s, 1H); 3.40-3.10 (m, 2H); 2.80-2.60 (m, 4H); 2.55 (m, 1H); 1.54 (m, 2H); 1.46-1.30 (m, 2H); 1.35 (d, J=7 Hz, 6H); 0.94-0.72 (m, 4H).

Preparation of Examples BU and BV

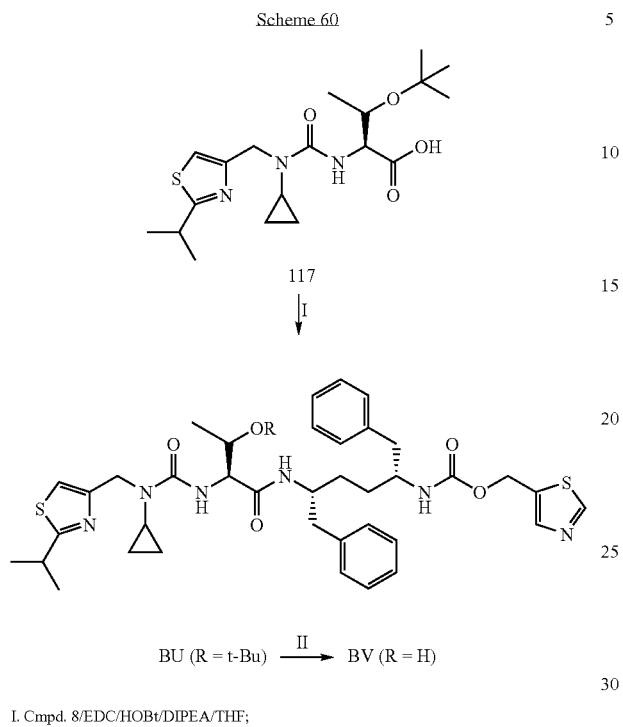

Scheme 60

117

BU (R = t-Bu) →II→ BV (R = H)

I. Cmpd. 8/EDC/HOBt/DIPEA/THF;
II. TFA, 1 M NaOH.

Compound 117

Compound 117 was prepared in a similar fashion to Compound 13d except that Compound 4 (1.5 mmol) and the L-enantiomer of Compound 10d (1.15 mmol) were used to ultimately produce 0.328 g (88%) of Compound 190 as a foamy white solid (m/z 398.1 (M+H)$^+$).

Example BU

Example BU was prepared in a similar fashion to Example AL using Compound 117 (0.33 mmol) and Compound 8 (0.30 mmol) to produce 0.196 g (84%) of Example BU as an amorphous white solid (m/z 789.3 (M+H)$^+$).

Example BV

Example BV was prepared in a similar fashion to Example AM using Example BU (0.29 mmol) to produce 0.140 g (77%) of Example BV as an amorphous white solid. m/z 733.3 (M+H)$^+$; $^1$H-NMR (CDCl$_3$, 300 MHz): δ 8.80 (s, 1H); 7.84 (s, 1H); 7.27-7.10 (m, 10H); 6.70-6.10 (m, 1H); 6.86 (s, 1H); 6.20 (br d, J=7 Hz, 1H); 5.24 (s, 2H); 4.81 (br d, J=7 Hz, 1H); 4.82 (s, 2H); 4.34 (br d, J=7 Hz, 1H); 4.16 (br s, 1H); 4.07 (br d, J=6 Hz, 1H); 3.86 (br s, 1H); 3.38 (br s, 1H); 2.69 (m, 6H); 1.62-1.50 (m, 2H); 1.50-1.34 (m, 2H); 1.38 (m, 6H); 1.13 (d, J=6 Hz, 3H); 0.98-0.76 (m, 4H).

Preparation of Examples BW and BX

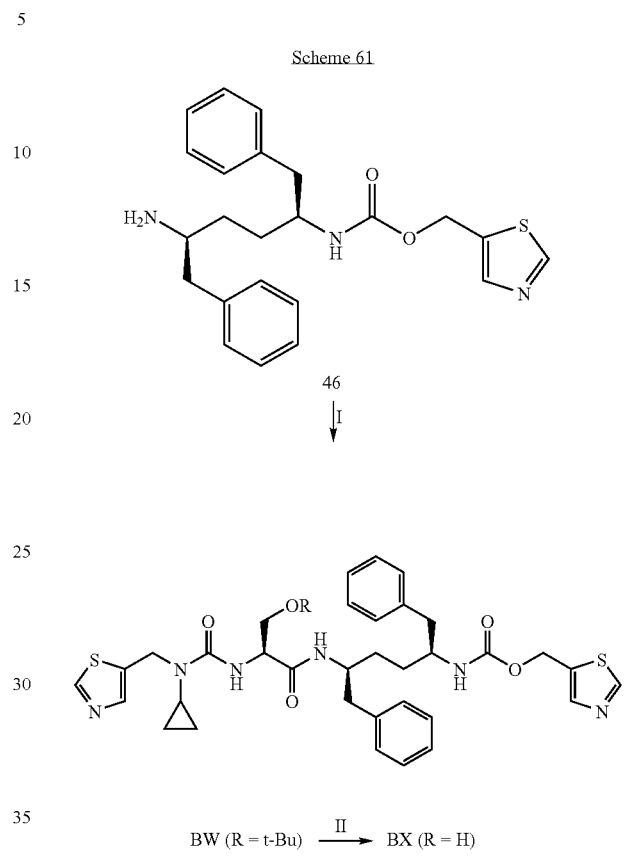

Scheme 61

46

BW (R = t-Bu) →II→ BX (R = H)

I. Cmpd. 75/EDC/HOBt/DIPEA/THF;
II. TFA, 1 M NaOH.

Example BW

Example BW was prepared in a similar fashion to Example BK using Compound 75 (0.27 mmol) and Compound 46 (0.24 mmol) to provide 0.154 g (86%) of Example BW as an amorphous white solid (m/z 733.3 (M+H)$^+$).

Example BX

Example BX was prepared in a similar fashion to Example AM using Example BW (0.21 mmol) to provide 0.091 g (98%) of the TFA salt of Example BX as an amorphous white solid. m/z 677.5 (M+H)$^+$; $^1$H-NMR (CDCl$_3$, 300 MHz): δ 8.83 (s, 1H); 8.77 (s, 1H); 7.84 (s, 1H); 7.77 (s, 1H); 7.27-7.00 (m, 10H); 6.62 (d, J=9 Hz, 1H); 6.44 (d, J=6 Hz, 1H); 5.35 (d, J=10 Hz, 1H); 5.24 (s, 2H); 4.69 (AB d, J=15 Hz, 1H); 4.62 (AB d, J=16 Hz, 1H); 4.14 (br m, 2H); 3.96-3.78 (m, 2H); 3.51 (dd, J=11, 4.5 Hz, 1H); 3.38 (br s, 1H); 2.82-2.58 (m, 4H); 2.41 (m, 1H); 1.70-1.24 (m, 4H); 1.20-0.88 (m, 2H); 0.88-0.54 (m, 2H).

237
Preparation of Examples BY and BZ

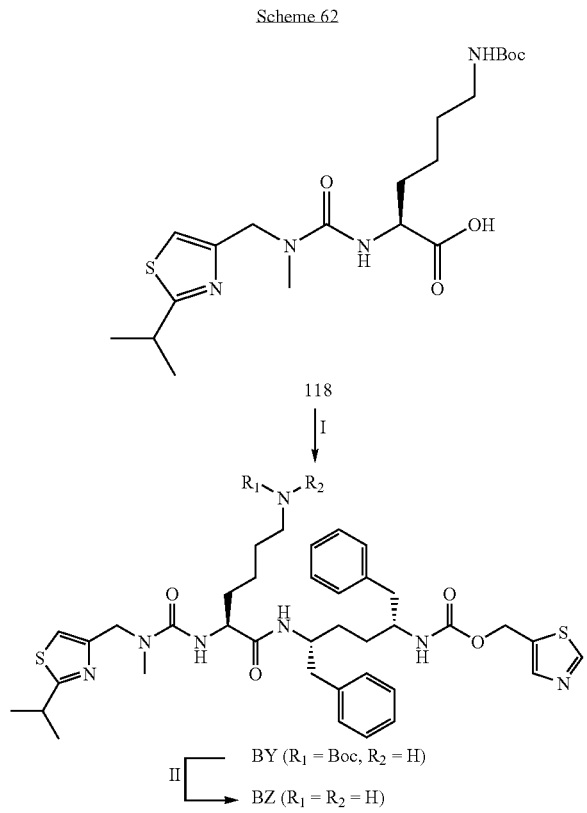

I. Cmpd. 8/EDC/HOBt/DIPEA/THF;
II. TFA, 4 M HCl/dioxane.

Compound 118

Compound 118 was prepared in a similar fashion to Compound 104 except that Compound 115 (0.40 mmol) was used instead of Compound 102, which was reacted with Compound 9 (0.48 mmol) to ultimately provide 0.075 g (89%) of Compound 118 as a foamy white solid (m/z 443.4 $(M+H)^+$).

Example BY

Example BY was prepared in a similar fashion to Example BM using Compound 118 (0.17 mmol) and Compound 8 (0.15 mmol) to produce 0.079 g (62%) of Example BY as an amorphous white solid (m/z 834.3 $(M+H)^+$).

Example BZ

Example BZ was prepared in a similar fashion to Example BQ using Example BY (0.095 mmol) to provide 0.082 g (99%) of the HCl salt of Example BZ as an amorphous white solid m/z 734.2 $(M+H)^+$; $^1$H-NMR (DMSO-$d_6$, 300 MHz): δ 8.08 (s, 1H); 7.86 (br m, 3H); 7.58 (d, j=9 Hz, 1H); 7.25-7.00 (m, 11H); 6.32 (br s, 1H); 5.16 (s, 2H); 4.99 (br m, 4H); 4.48 (AB d, J=15 Hz, 1H); 4.43 (AB d, J=15 Hz, 1H); 4.02 (m, 1H); 3.89 (m, 1H); 3.63 (m, 1H); 3.22 (hep, J=7 Hz, 1H); 2.87 (s, 3H); 2.76-2.56 (m, 4H); 1.58-1.15 (m, 10H); 1.29 (d, J=7 Hz, 6H).

238
Preparation of Example CA

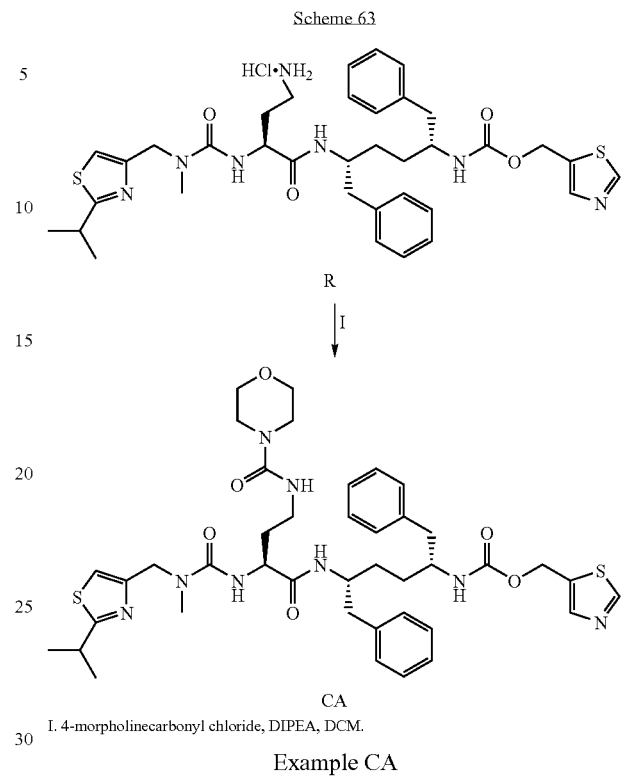

I. 4-morpholinecarbonyl chloride, DIPEA, DCM.

Example CA

Example R (0.11 mmol) was diluted in DCM (1 mL) and treated with 4-morpholinecarbonyl chloride (0.13 mmol) and DIPEA (0.16 mmol). After 2 h, volatiles were removed in vacuo and the residue was purified by column chromatography on $SiO_2$ (0-20% MeOH/DCM) to afford 0.068 g (76%) of Example CA as an amorphous white solid m/z 819.1 $(M+H)^+$; $^1$H-NMR (CDCl$_3$, 300 MHz): δ 8.82 (s, 1H); 7.85 (s, 1H); 7.27-7.07 (m, 12H); 6.94 (s, 1H); 6.26 (br s, 1H); 5.73 (d, J=8 Hz, 1H); 5.28 (AB d, J=13 Hz, 1H); 5.22 (AB d, J=13 Hz, 1H); 4.50 (AB d, J=16 Hz, 1H); 4.44 (AB d, J=16 Hz, 1H); 4.17 (m, 1H); 3.98 (br s, 1H) 3.76 (br s, 1H); 3.68 (br s, 1H); 3.60 (m, 4H); 3.40 (m, 2H); 3.32 (m, 4H); 2.97 (s, 3H); 2.87 (dd, J=13, 5 Hz, 2H); 2.73, (m, 2H); 2.57 (m, 2H); 1.79 (m, 2H); 1.60-1.20 (m, 6H); 1.37 (d, J=7 Hz, 6H).

Preparation of Compound CB

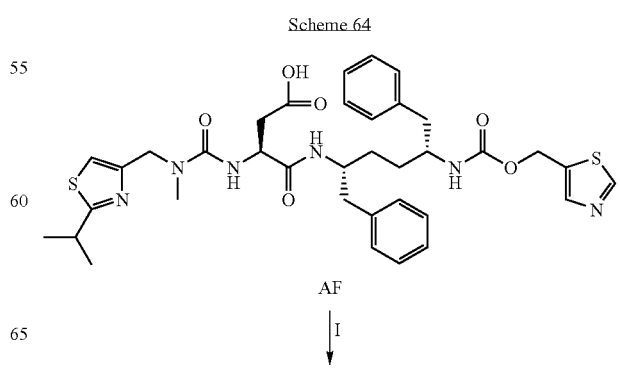

Preparation of Compound CC

Scheme 65

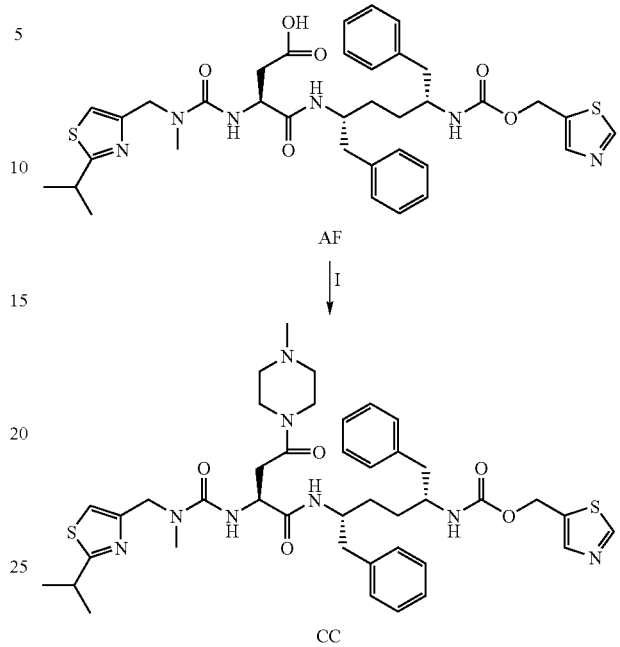

Example CB

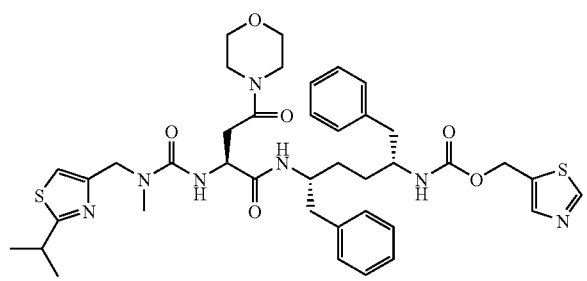

I. morpholine, EDC, HOBt, THF.

Example CB

Example AF (0.15 mmol) was diluted in THF (1 mL) and treated with morpholine (0.61 mmol), HOBt (0.18 mmol) and finally EDC (0.18 mmol). The reaction mixture was allowed to age overnight. The reaction mixture was then diluted in EtOAc and sat. $Na_2CO_3$. The aqueous layer was extracted with EtOAc and the combined organic layers were washed with brine, dried over anhydrous $MgSO_4$ and concentrated in vacuo. The resulting residue was purified via preparatory HPLC to provide 0.024 g (20%) of Example CB as an amorphous white solid. m/z 790.4 $(M+H)^+$; 1H-NMR ($CDCl_3$, 300 MHz): δ 8.81 (s, 1H); 7.84 (s, 1H); 7.27-7.10 (m, 10H); 6.96 (s, 1H); 6.78 (d, J=8 Hz, 1H); 6.67 (s, 1H); 5.36 (d, J=9 Hz, 1H); 5.27 (AB d, J=13 Hz, 1H); 5.20 (AB d, J=13 Hz, 1H); 4.59 (s, 1H); 4.51 (s, 2H); 4.02 (m, 1H); 3.80-3.30 (m, 10H); 2.98 (s, 3H); 2.90-2.45 (m, 6H); 1.52 (m, 2H); 1.39 (d, J=7 Hz, 6H); 1.32 (m, 2H).

I. N-methylpiperazine, EDC, HOBt, DIPEA, THF.

Example CC

Example CC was prepared in a similar fashion to Example CB except that N-methylpiperazine (0.16 mmol) was reacted with Compound AF (0.10 mmol) instead of morpholine and DIPEA (0.19 mmol) was added to produce 0.009 g (11%) of Example CC as an amorphous white solid m/z 803.4 $(M+H)^+$; $^1$H-NMR ($CDCl_3$, 300 MHz): δ 8.80 (s, 1H); 7.84 (s, 1H); 7.27-7.10 (m, 11H); 6.91 (s, 1H); 6.78 (m, 2H); 5.27 (AB d, J=13 Hz, 1H); 5.21 (AB d, J=13 Hz, 1H); 4.59 (m, 1H); 4.49 (AB d, J=16 Hz, 4.44 (AB d, J=16 Hz, 1H); 4.01 (m, 1H); 3.90-3.40 (m, 4H); 3.27 (hep, J=7 Hz, 1H); 3.10-2.90 (m, 1H); 2.97 (s, 3H); 2.90-2.30 (m, 11H); 1.60-1.25 (m, 6H); 1.37 (d, J=7 Hz, 6H).

Preparation of Example CD

Scheme 66

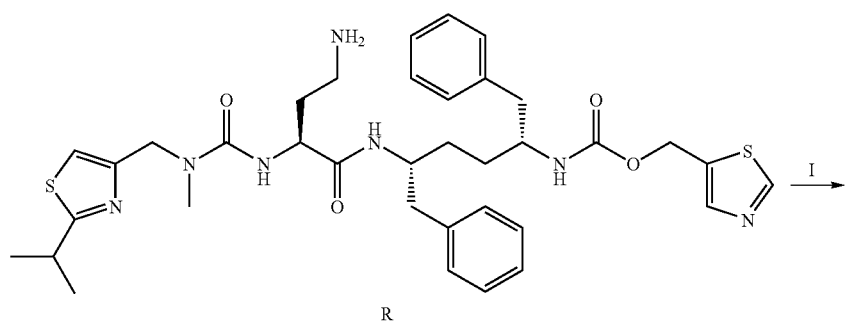

R

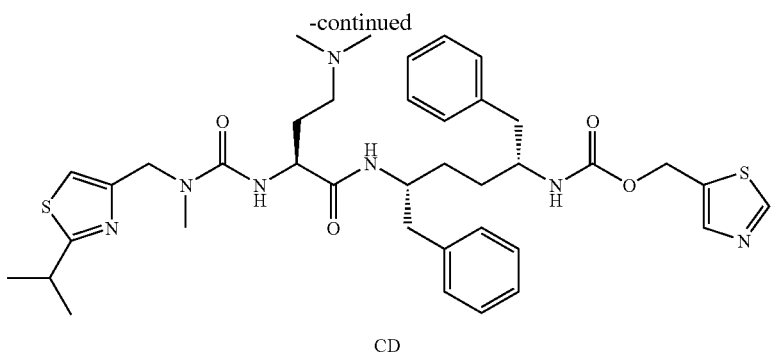

CD

I. HCHO/NaBH(OAc)₃/MeOH

Example CD

To a solution of Example R (30.5 mg, 0.043 mmol) in methanol (1.5 mL) was added formaldehyde (1 mL, 37% in H₂O). After stirring for 10 minutes, NaBH(OAc)₃ (49 mg, 0.23 mmol) was added and the resulting mixture was stirred for 10 h. The reaction was monitored with LC/MS. When LC/MS indicated the absence of starting material Example R, the reaction mixture was evaporated to dryness, and filtered through a cotton plug. The crude product was then purified through CombiFlash (10% MeOH/CH₂Cl₂) to give 29.7 mg of Example CD $^1$H-NMR (CDCl₃, 500 MHz): δ 8.78 (s, 1H); 7.83 (s, 1H); 7.12-7.22 (m, 10H); 6.85 (s, 1H); 5.83 (d, 1H, J=8.5 Hz ), 5.23 ($d_{AB}$, 2H, J=13.1 Hz); 4.49 ($d_{AB}$, 2H, J=16.5 Hz); 4.29 (m, 1H); 4.15 (m, 1H); 3.75 (m, 1H); 3.30 (m, 1H); 2.93 (s, 3H); 2.87 (dd, 1H, J1=5.5 Hz, J2=13.5 Hz); 2.72 (m, 2H); 2.66 (dd, J1=7.3 Hz, J2=13.3 Hz), 2.47 (br s, 1H), 2.36 (br s, 1H), 2.23 (s, 6H), 1.91 (m, 2H), 1.56 (m, 2H), 1.40 (m, 2H), 1.40 (d, 6H, J=6.8 Hz). m/z 734 (M+H)⁺; 756 (M+Na)⁺;

Preparation of Example CE

Scheme 67

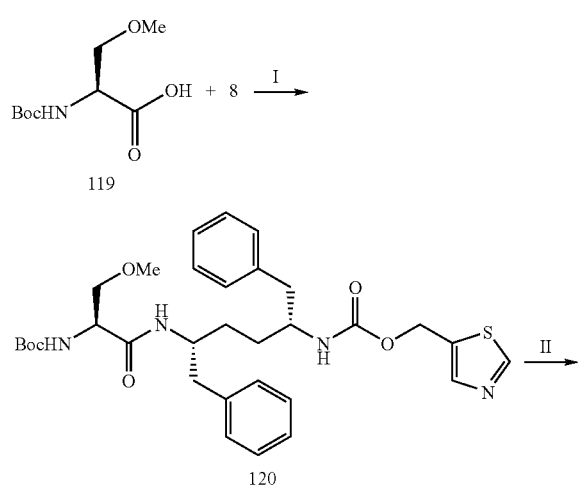

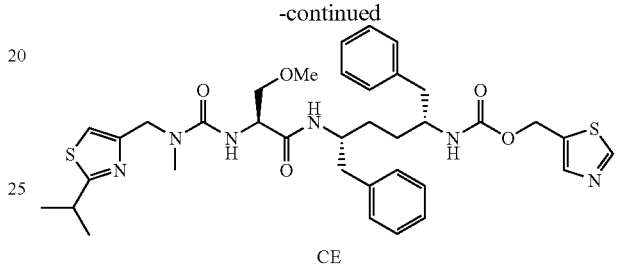

CE

I. EDC, HOBt, iPr₂NEt, THF
II. a. HCl;/dioxane; b. CDI, iPr₂NEt, Compound 9, CH₂Cl₂

Compound 119

Compound 119 is commercially available from Aldrich, and was used as received.

Compound 120

A mixture of Compound 119 (200 mg, 0.91 mmol), Compound 8 (373.7 mg, 0.91 mmol), EDC (212 mg, 1.37 mmol), HOBt (160.3 mg, 1.19 mmol) and iPr₂NEt (794.7 μL, 4.56 mmol) in THF was stirred for 10 h at room temperature. The mixture was then evaporated to a small volume and purified by CombiFlash (eluted with 1 to 10% MeOH/CH₂Cl₂). The fractions containing the target Compounds were collected and re-purified by CombiFlash (40-100% EtOAc/hexanes) to give 449 mg of Compound 120 as oil. (m/z 611.0 (M+H)⁺).

Example CE

Compound 120 (449 mg, 0.74 mmol) was treated with HCl/dioxane (3 mL). The resulting mixture was evaporated to dryness and lyophilized to provide 373.6 mg of a white solid.

To a solution of the above white compound (52.5 mg, 0.096 mmol) in CH₂Cl₂ (10 mL) was added Compound 9 (19.8 mg, 0.096 mmol), CDI (15.6 mg, 0.096 mmol) followed by iPr₂NEt (33.4 μL, 0.192 mmol). The mixture was stirred for 20 h before it was evaporated to dryness. The mixture was added CH₂Cl₂, then filtered through a cotton plug. The filtrate was evaporated to dryness and purified with CombiFlash. The fractions with Example CE was collected and re-purified on the TLC to give 15.1 mg of Example CE. $^1$H-NMR (CDCl₃, 300 MHz): δ 8.79 (s, 1H); 7.82 (s, 1H); 7.09-7.27 (m, 10H), 6.94 (s, 1H); 6.25 (d, 2H, J=8.7 Hz); 5.23 (s, 2H); 5.17 (br s, 1H); 4.43 ($d_{AB}$, 2H, J=16.5 Hz); 4.29 (m, 1H); 4.13 (m, 1H); 3.76 (m, 2H); 3.48 (m, 1H); 3.29 (s, 3H); 3.25 (m, 1H), 2.94 (s, 3H), 2.65-2.82 (m, 4H), 1.75 (m, 2H), 1.54 (m, 2H), 1.39 (d, 5H, J=6.9 Hz). m/z 707 (M+H)⁺; 729 (M+Na)⁺.

Preparation of Example CF

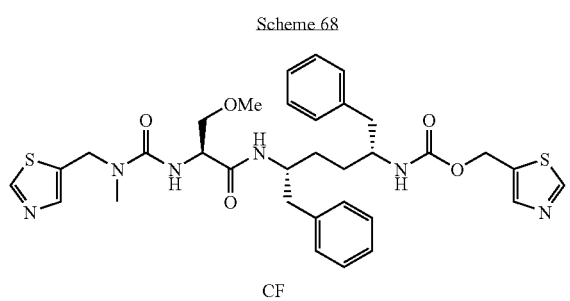

Example CF

Example CF was prepared using the same method as Example CE, except that Compound 9 was replaced with Compound 68. $^1$H-NMR (CDCl$_3$, 300 MHz): δ 8.79 (s, 1H); 8.74 (s, 1H), 7.81 (s, 1H), 7.73 (s, 1H); 7.12-7.27 (m, 10H); 6.15 (d, 1H, J=8.7 Hz), 5.39 (d, 1H, J=6.8 Hz); 5.21 (s, 2H); 5.06 (d, J=9.1 Hz, 1H); 4.64 (d$_{AB}$, 2H, J=15.5 Hz); 4.28 (m, 1H); 4.134 (m, 1H), 3.79 (m, 1H), 3.70 (m, 1H); 3.34 (m, 1H); 3.28 (s, 3H); 2.87 (s, 3H); 2.72 (m, 4H); 1.57 (m, 2H); 1.50 (m, 2H). m/z 665.2 (M+H)$^+$; 687.3 (M+Na)$^+$.

Preparation of Compound CG

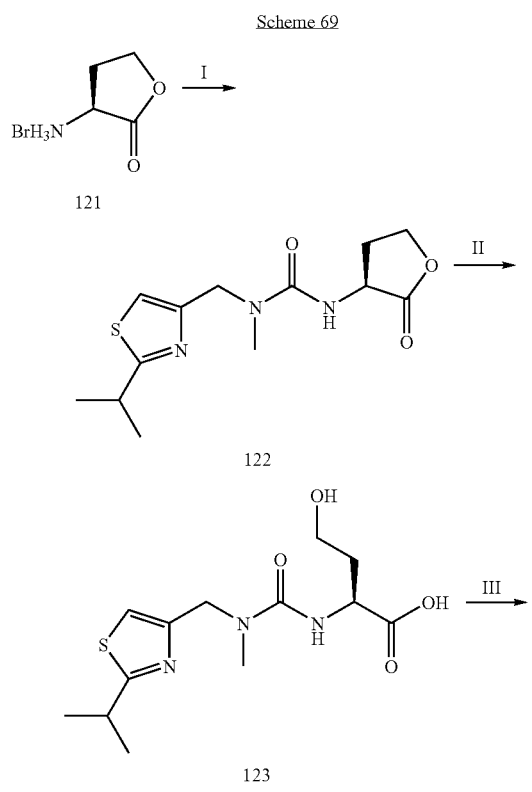

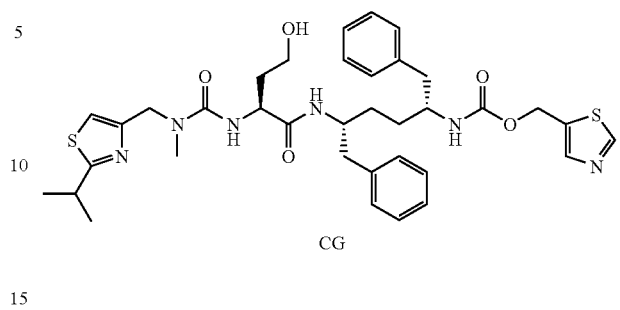

I. a. CDI, DIPEA, MeCN; b. compound 9, MeCN.
II. 1 M LiOH, THF.
III. EDCl, HOBt, iPr2NEt, compound 8

Compound 121

Compound 121 is commercially available from Aldrich, and was used as received.

Compound 122

To a suspension of Compound 121 (2.05 g, 11.3 mmol) in CH$_2$Cl$_2$ (40 mL) was added. iPr$_2$NEt (5.87 mL, 33.9 mmol) followed by CDI (1.86 g, 11.3 mmol). The resulting mixture was stirred at room temperature for 6 h, then Compound 9 (2.33 g, 11.3 mmol) was added. The resulting mixture was stirred for another 10 h before it was evaporated to dryness. The mixture was re-dissolved in CH$_2$Cl$_2$ and the solid was removed by filtration. The filtrate was evaporated to dryness and purified by CombiFlash (eluted with 20-80% EtOAc/hexanes) to give 3.2 g of Compound 122 as a pale yellow oil. m/z 298.0 (M+H)$^+$.

Compound 123

To a solution of Compound 122 (3.2 g, 10.8 mmol) in THF (100 mL) was added freshly prepared 1M LiOH (10.8 mmol). The biphasic reaction was stirred vigorously at room temperature for 16 h before being quenched with 1M HCl. The pH of the mixture was adjusted to 2.5-3, and then evaporated to a small volume. The mixture was partitioned between CH$_2$Cl$_2$ and brine (50 mL), the aqueous layer was separated and extracted with CH$_2$Cl$_2$ twice. The combined CH$_2$Cl$_2$ layers were dried over anhydrous Na$_2$SO$_4$ and concentrated to give 3.37 g of Compound 123 a pale yellow oil that is used with further purification. m/z 316.0 (M+H)$^+$, 338 (M+Na)$^+$;

Example CG

Example CG was prepared following the same procedure for Example C instead that Compound 123 was used instead of Compound 7. $^1$H-NMR (CDCl$_3$, 500 MHz): δ 8.80 (s, 1H); 7.83 (s, 1H), 7.11-7.26 (m, 10H), 6.96 (s, 1H); 7.12-7.27 (m, 10H); 6.52 (br s, 1H); 6.40 (br s, 1H); 5.23 (s, 2H); 5.20 (m, 1H), 4.44 (d$_{AB}$, 2H, J=15.5 Hz), 4.39 (m, 1H), 4.11 (m, 1H), 3.80 (m, 1H), 3.61 (m, 2H), 3.28 (sep, 1H, J=7.0 Hz); 2.94 (s, 3H); 2.79 (dd, 1H, J1=6.1 Hz, J2=13.4 Hz); 2.71 (m, 3H); 1.93 (m, 1H), 1.71 (m, 1H), 1.54 (m, 1H), 1.38 (d, 6H, J=7.0 Hz) 1.37 (m, 1H). m/z 707.3 (M+H)$^+$), 729.2 (M+Na)$^+$.

245
Preparation of Compound 100
Scheme 70
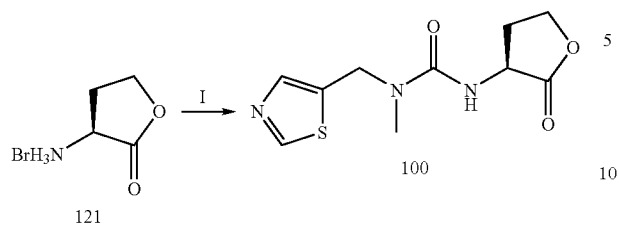
121
I. a. CDI, DIPEA, MeCN;
246
Compound 100 was prepared using the same method used to prepare Compound 122, except that Compound 9 was replaced with Compound 68.
Preparation of Example CH
Scheme 71
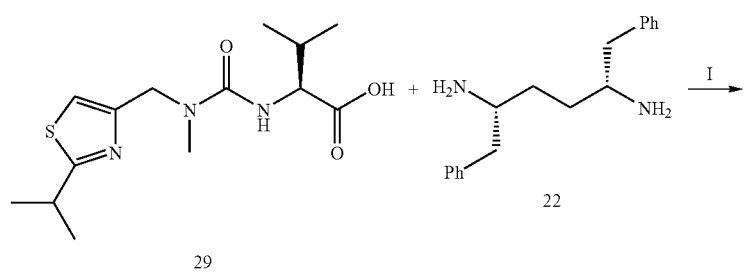
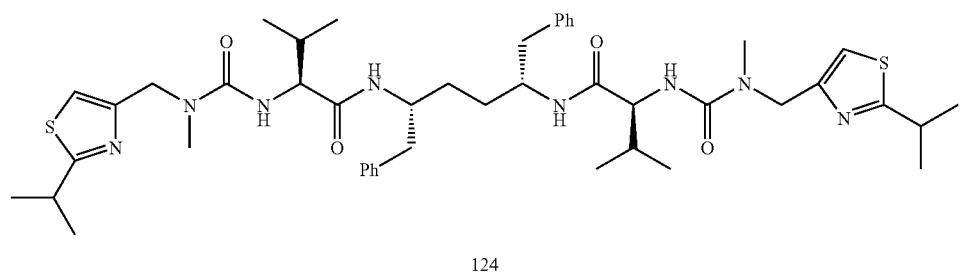
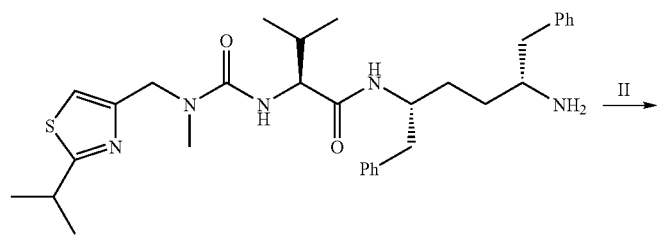
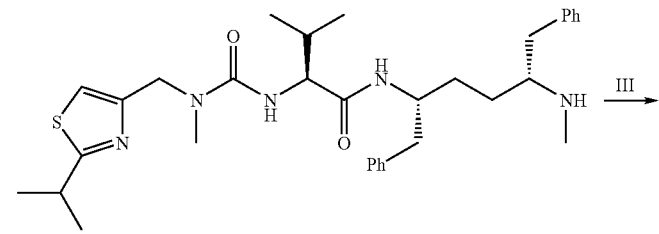

-continued

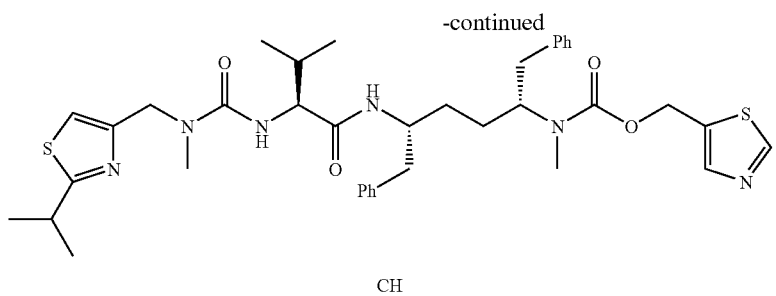

CH

I. EDCl/HOBt/iPr₂NEt/THF;
II. HCHO/NaBH(OAc)₃/HOAc/CH₃CN;
III. Cmpd. 16/iPr₂NEt/CH₃CN Compounds 124 and 125

To a solution of Compound 29 (135 mg, 0.43 mmol) and Compound 22 (116 mg, 0.43 mmol) in THF (5 mL) were added HOBt (70 mg, 0.52 mmol), EDC (94 µL, 0.52 mmol), and diisopropylethylamine (150 µL, 0.83 mmol). The mixture was stirred for 12 hours and concentrated. Purification by reverse HPLC gave Compound 124 (70 mg) and Compound 125 (120 mg). Compound 124: $^1$H-NMR (CDCl₃) δ 7.2-7.1 (10H, m), 7.0 (2H, s), 6.45 (2H, m), 6.15 (2H, m), 4.45 (4H, s), 4.1 (2H, m), 3.96 (2H, m), 3.3 (2H, m), 2.98 (6H, s), 2.7 (4H, m), 2.1 (2H, m), 1.6-1.3 (16H, m), 0.90 (12H, m). m/z 859.3 (M+H)⁺; Compound 125: m/z 564.3 (M+H)⁺

Compound 126

To a solution of Compound 125 (120 mg, 0.21 mmol) in CH₃CN (1 mL) was added 37% formaldehyde solution (17 µL, 0.23 mmol), followed by HOAc (24 µl, 0.42 mmol). The mixture was stirred for 2 hours, and NaBH(OAc)₃ (140 mg, 0.63 mmol) was added. The mixture was stirred for 2 additional hours and diluted with EtOAc. The organic phase was washed with saturated Na₂CO₃ solution, water, and brine, and dried over Na₂SO₄. Concentration gave Compound 126, which was used in the next step without further purification. m/z 578.3 (M+H)⁺

Example CH

Example CH (26 mg) was prepared following the procedure used to prepare Example L, except that Compound 126 was used instead of Compound 22. $^1$H-NMR (CDCl₃) δ 8.91 (1H, m), 7.82 (1H, m), 7.2-7.0 (11H, m), 6.4 (1H, m), 6.2 (1H, m), 5.23-5.05 (2H, m), 4.44 (2H, s), 4.44 (1H, m), 4.2 (1H, m), 3.95 (1H, m), 3.32 (1H, m), 2.98 (3H, s), 2.8-2.5 (7H, m), 2.15 (1H, m), 1.7-1.2 (10H, m), 0.88 (6H, m). m/z 719.3 (M+H)⁺

Preparation of Example CI

-continued

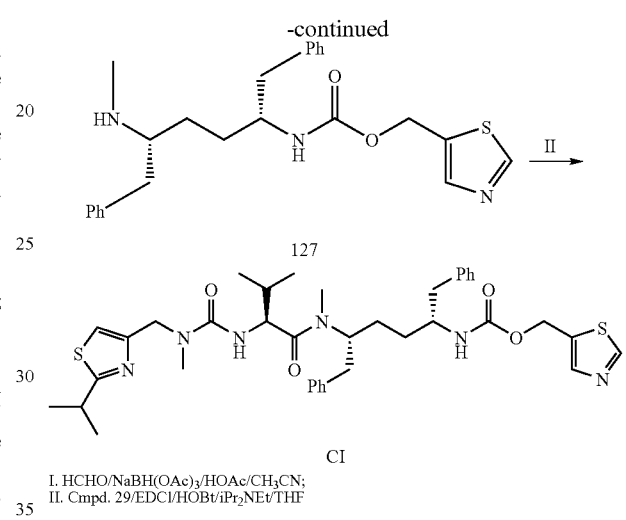

CI

I. HCHO/NaBH(OAc)₃/HOAc/CH₃CN;
II. Cmpd. 29/EDCl/HOBt/iPr₂NEt/THF

Compound 127

Compound 127 (110 mg) was prepared following the procedure used to prepare Compound 126, except that Compound 8 was used instead of Compound 125. m/z 424.4 (M+H)⁺

Example CI

Example CI (7 mg) was prepared following the procedure used to prepare Example C, except that Compounds 127 and 29 were used instead of Compounds 8 and 7. $^1$H-NMR (CDCl₃) δ 9.0 (1H, s), 8.92 (1H, s), 7.4-7.0 (11H, m), 5.25 (2H, m), 4.6-4.0 (5H, m), 3.4 (1H, m), 3.1-2.6 (10H, m), 1.9 (1H, m), 1.8 (10H, m), 0.9 (6H, m); m/z 719.2 (M+H)⁺

Preparation of Compound CJ

Scheme 72

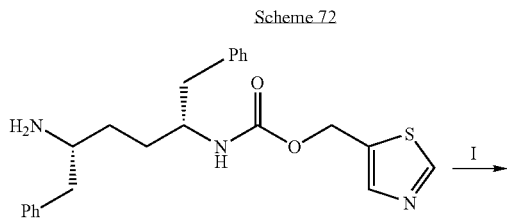

8

Scheme 73

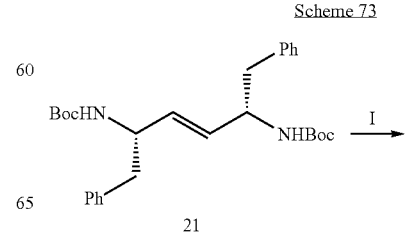

21

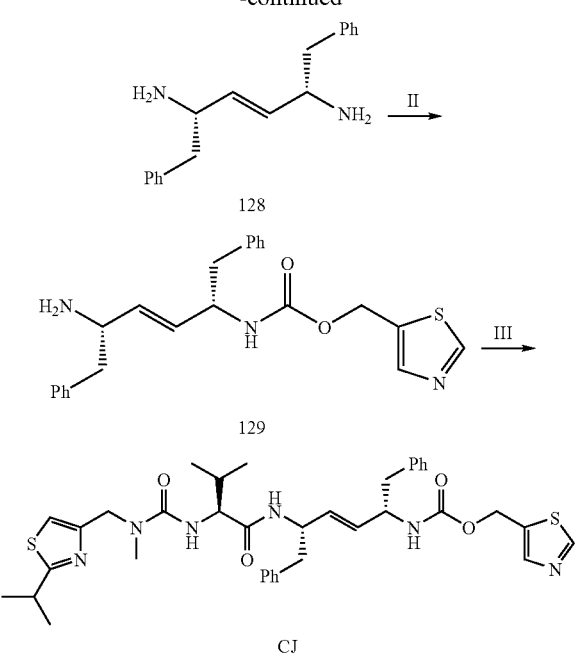

I. a. TFA/CH₂Cl₂; b. Na₂CO₃;
II. Cmpd. 16/iPr₂NEt/CH₃CN;
III. Cmpd. 29/EDCI/HOBt/iPr₂NEt/THF Compound 128

To a solution of Compound 21 (100 mg) in dichloromethane (5 mL) was added TFA (1 mL). The mixture was stirred for 3 hours, and excess reagents were evaporated. The oil was diluted with EtOAc, and then was washed with saturated Na₂CO₃ solution (2×), water (2×), and brine, and dried over Na₂SO₄. Concentration gave Compound 128 (46 mg). m/z 267.1 (M+H)⁺

Compound 129

Compound 129 (44 mg) was prepared following the procedure for Compound 8, except that Compound 128 was used instead of Compound 22. m/z 408.10 (M+H)⁺

Example CJ

Example CJ (55 mg) was prepared following the procedure for Example C, except that Compounds 129 and 29 were used instead of Compounds 8 and 7. ¹H-NMR (CDCl₃) δ 8.81 (1H, s), 7.85 (1H, s), 7.2-7.0 (11H, m), 6.4 (1H, m), 6.12 (1H, m), 5.44 (2H, m), 5.26 (2H, s), 4.85 (1H, m), 4.70 (1H, m), 4.4 (3H, m), 4.06 (1H, m), 3.25 (1H, m), 2.98 (3H, s), 2.78 (4H, m), 2.21 (1H, m), 1.38 (6H, m), 0.88 (6H, m); m/z 703.2 (M+H)⁺

Preparation of Compounds CK and CL

Scheme 74

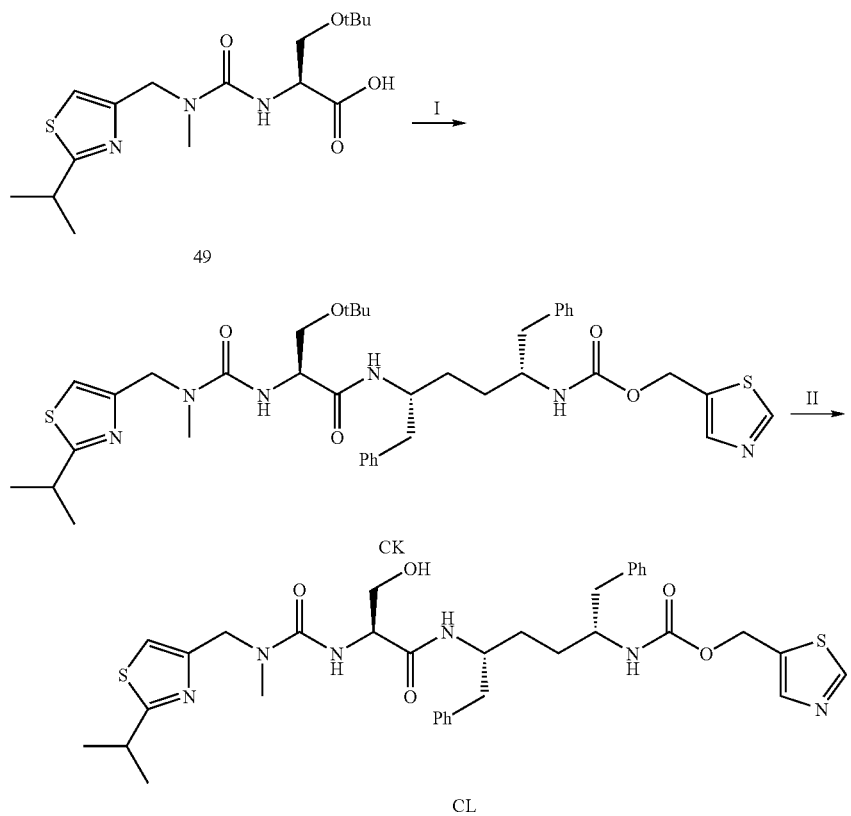

I. Cmpd 8/EDC/HOBt; II. a. TFA; b. NaOH/THF

Example CK

Example CK (88 mg) was prepared following the procedure used to prepare Example C, except that Compound 49 was used instead of Compound 7. m/z 749.2 (M+H)+

Example CL

A mixture of Example CK (85 mg) and TFA (5 mL) was stirred for 3 hours. Excess TFA was evaporated and the mixture was dried under high vacuum. The mixture was dissolved in THF (5 mL), and 1.0 N sodium hydroxide solution was added until the pH was 11. The solution was stirred for 10 minutes, and extracted with EtOAc. The organic phase was washed with water, brine, and dried over Na$_2$SO$_4$. Concentration and purification by flash column chromatography (EtOAc) gave Example CL (66 mg). $^1$H-NMR (CDCl$_3$) δ 8.81 (1H, s), 7.84 (1H, s), 7.30-6.96 (11H, m), 5.22 (2H, s), 4.90 (1H, m), 4.45 (1H, m), 4.35-4.0 (4H, m), 3.8 (1H, m), 3.6 (1H, m), 3.21 (1H, m), 2.95 (3H, s), 2.8-2.6 (4H, m), 2.0-1.4 (4H, m), 1.25 (6H, m). m/z 693.2 (M+H)+.

Preparation of Example CM

Scheme 75

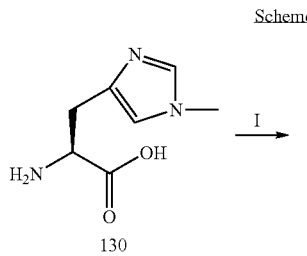
130

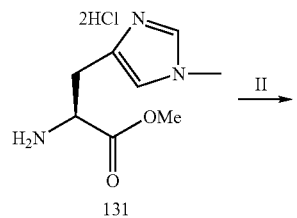
131

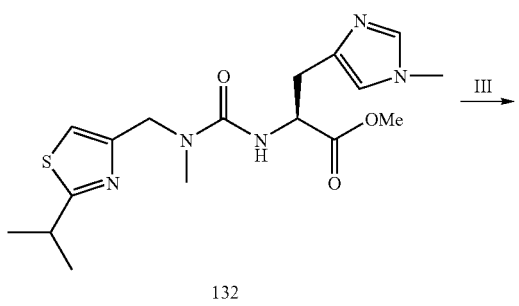
132

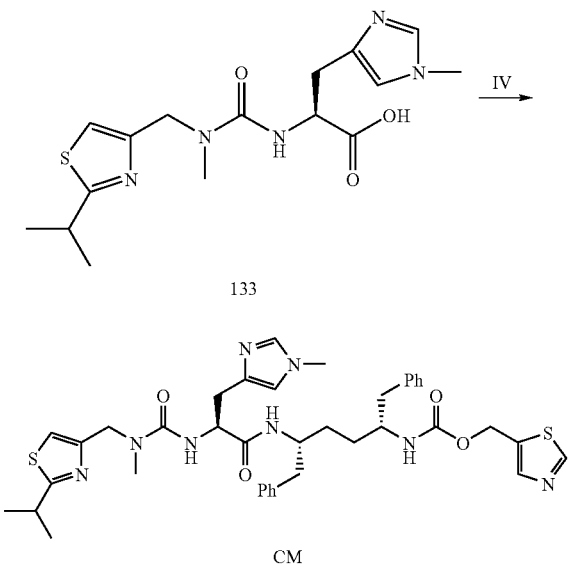
133

CM

I. SOCl$_2$/MeOH; II. a. CDI/iPr$_2$NEt; b. Cmpd. 9; III. a. NaOH/THF/H$_2$O; b. HCl; IV. Cmpd. 8/EDC/HOBt;

Compound 130

Compound 130 is commercially available from (TCI), and was used as received.

Compound 131

To the solution of Compound 130 (510 mg, 3 mmol) in methanol (12 mL) at 0° C. was added thionyl chloride (0.5 mL, 6.6 mmol), dropwise. The mixture was stirred at 0° C. for 30 minutes and brought to reflux for 3 hours. Concentration gave Compound 131 as a white solid.

Compound 132

To a stirred solution of Compound 131 (3 mmol) and diisopropylethylamine (2 mL, 12 mmol) in dichloromethane (35 mL) was added CDI (486 mg, 3 mmol). The mixture was stirred for 12 hours. Compound 9 was added, and the mixture was stirred for 12 additional hours. Concentration and purification by flash column chromatography (CH$_2$Cl$_2$/iPrOH=10/1) gave Compound 132 (414 mg). m/z 380.0 (M+H)+

Compound 133

Compound 133 was prepared following the procedure for Compound 67, except that Compound 132 was used instead of Compound 66. m/z 364.0 (M−H)−

Example CM

Example CM (600 mg) was prepared following the procedure for Example C, except Compound 133 was used instead of Compound 7. $^1$H-NMR (CDCl3) δ 9.18 (1H, s), 8.35 (1H, s), 7.95 (1H, s), 7.6 (1H, m), 7.3-7.0 (11H, m), 5.22 (2H, m), 4.70 (1H, m), 4.50 (2H, m), 4.05 (1H, m), 3.86 (3H, s), 3.80 (2H, m), 3.55 (1H, m), 3.10 (1H, m), 2.90 (3H, s), 2.70 (4H, m), 1.45 (10H, m); m/z 757.3 (M+H)+

Preparation of Examples O, P, CN, and CO

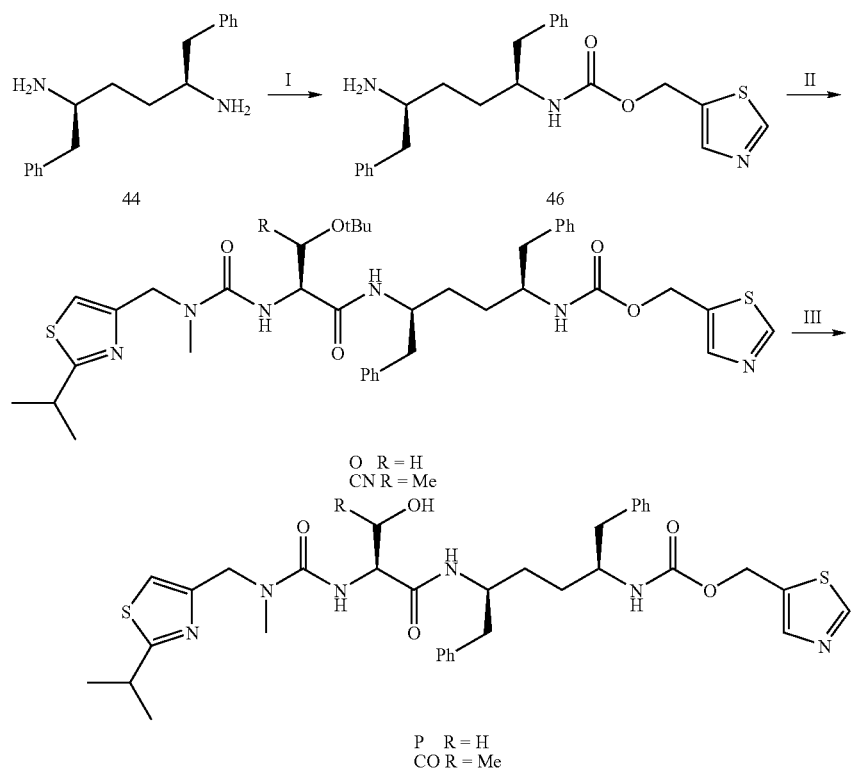

I. Cmpd. 16/iPr2NEt; II. Cmpd. 13d or Cmpd. 49/EDC/HOBt; III. a. TFA; b. NaOH/THF Example O Example O (17 mg) was prepared following the procedure for Example C, except Compounds 46 and 49 were used instead of Compounds 8 and 7. m/z 749.3 (M+H)+

Example CN

Example CN (22 mg) was prepared following the procedure used to prepare Example C, except Compounds 46 and 13e were used instead of Compounds 8 and 7. m/z 763.2 (M+H)+

Example P

Example P (12 mg) was prepared following the procedure used to prepare Example CM, except Example O was used instead of Example CL. $^1$H-NMR (CDCl$_3$) δ 8.76 (1H, s), 7.79 (1H, s), 7.25-6.9 (11H, m), 6.51 (1H, broad), 5.42 (1H, m), 5.18 (2H, m), 4.42 (2H, m), 4.22 (1H, m), 4.10 (1H, m), 3.95 (1H, m), 3.79 (1H, m), 3.58 (1H, m), 3.23 (1H, m), 2.93 (3H. s), 2.9-2.5 (4H, m), 1.6-1.2 (10H, m); m/z: 693.2 (M+H)+.

Compound CO

Example CO (13 mg) was prepared following the procedure used to prepare Example CL, except Example CN was used instead of Compound CK. $^1$H-NMR (CDCl$_3$) δ 8.85 (1H, m), 7.88 (1H, m), 7.3-7.0 (11H, m), 6.55 (1H, m), 6.24 (1H, m), 5.45 (1H, m), 5.23 (2H, m), 4.6 (2H, m), 4.2 (1H, m), 4.0 (2H, m), 3.7 (1H, m), 3.5 (1H, m), 3.02 (3H, s), 2.70 (4H, m), 1.6-1.0 (13H, m); m/z: 707.3 (M+H)+.

Preparation of Examples CP-CS

Scheme 77

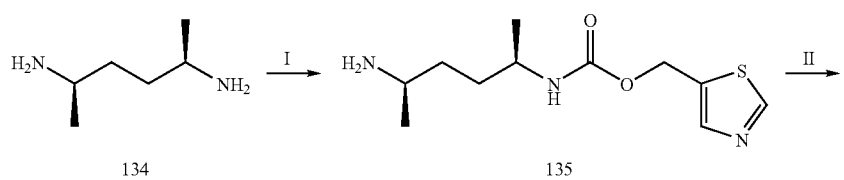

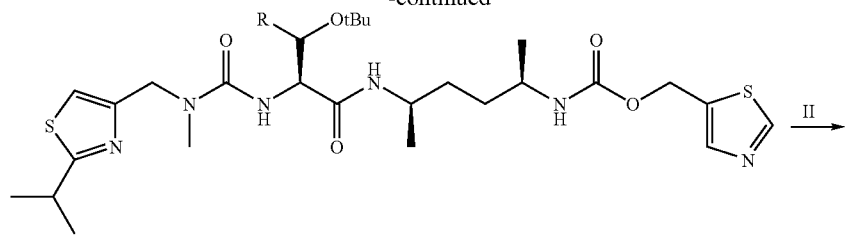

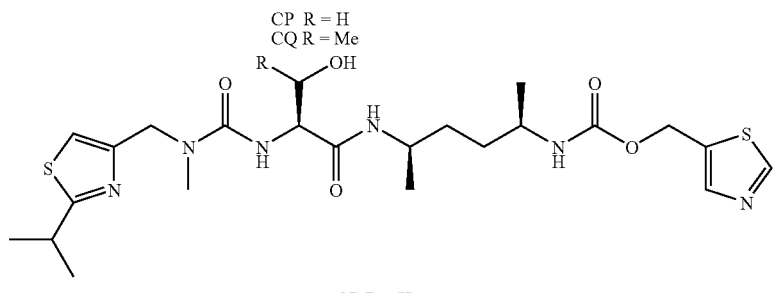

CP R = H
CQ R = Me

CR R = H
CS R = Me

I. Cmpd. 16/iPr2NEt; II. Cmpd. 13d or 49/EDC/HOBt; III. a. TFA; b. NaOH/THF

Compound 134

Compound 134 was prepared using procedure described for Compound 76, except that CBZ-D-alaminol was used instead of CBZ-L-alaminol.

Compound 135

Compound 135 was prepared following the procedure used to prepare Compound 8, except Compound 134 was used instead of Compound 22.

Example CP

Example CP (12 mg) was prepared following the procedure used to prepare Example C, except Compounds 135 and 49 were used instead of Compounds 8 and 7. m/z 597.2 (M+H)$^+$.

Example CQ

Example CQ (11 mg) was prepared following the procedure used to prepare Example C, except Compounds 135 and 13d were used instead of Compounds 8 and 7. m/z 611.2 (M+H)$^+$.

Example CR

Example CR (7 mg) was prepared following the procedure used to prepare Example P, except that Example CP was used instead of Example O. $^1$H-NMR (CDCl$_3$) δ 8.82 (1H, s), 7.88 (1H, s), 7.02 (1H, s), 6.92 (1H, m), 5.28 (2H, s), 5.10 (1H, m), 4.5 (2H, m), 4.15 (2H, m), 3.88 (1H, m), 3.8-3.5 (2H, m), 3.35 (1H, m), 3.0 (3H, s), 1.5-1.0 (16H, m); m/z: 541.1 (M+H)$^+$.

Example CS

Example CS (8 mg) was prepared following the procedure used to prepare Example CO, except that Example CQ was used instead of Example CN. $^1$H-NMR (CDCl$_3$) δ 8.83 (1H, s), 7.88 (1H, s), 6.98 (1H, s), 6.81 (1H, m), 6.58 (1H, m), 5.28 (2H, s), 5.18 (1H, m), 4.4-4.3 (2H, m), 4.03 (1H, m), 3.85 (1H, m), 3.58 (2H, m), 3.3 (1H, m), 2.99 (3H, s), 1.5-0.98 (19H, m); m/z: 555.2 (M+H)$^+$.

Preparation of Examples CT-CV

Scheme 78

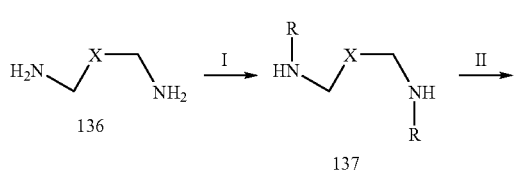

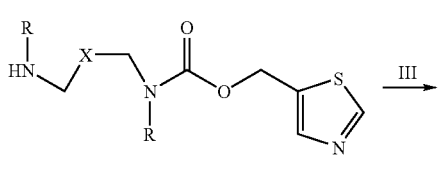

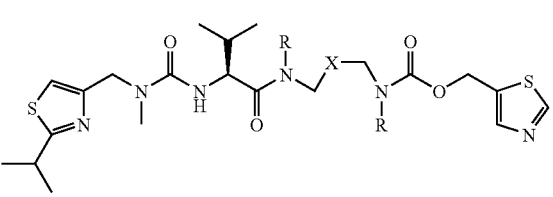

CT X = CH$_2$CH$_2$; R = H
CU X = CH$_2$CH$_2$; R = Bn
CV X = CH$_2$; R = Bn

I. PhCHO/NaBH$_4$; II. Cmpd 16/iPr2NEt; II. Cmpd 13d/EDC/HOBt;

Compound 136

Compounds 136a-c are commercially available (Sigma-Aldrich).

Compound 137

To a solution of Compound 136 (20 mmol) in methanol (25 mL) was added benzaldehyde (40 mmol) dropwise. The mixture was stirred for 2 hours and was cooled to 0° C. Sodium borohydride (44 mmol) was added in portions. The mixture was warmed to 25° C. and stirred for 2 hours. Acetic acid (10 mL) was added and the mixture was stirred for 10 minutes. Methanol was removed and the mixture was partitioned between EtOAc and 3 N NaOH solution. The organic layer was separated and water phase was extracted with EtOAc (2×). The combined organic layers was washed with water, brine, and dried over $Na_2SO_4$. Concentration gave Compound 137.

Compound 138

Compound 138 was prepared following the procedure used to prepare Compound 8, except that Compound 137 was used instead of Compound 22.

Example CT

Example CT (70 mg) was prepared following the procedure used to prepare Example C, except that Compounds 29 and 138a was used instead of Compounds 13a and 8. $^1$H-NMR (CDCl$_3$) δ 8.79 (1H, s), 7.86 (1H, s), 6.97 (1H, s), 6.49 (1H, m), 6.15 (1H, m), 5.28 (2H, s), 5.20 (1H, m), 4.44 (2H, m), 4.05 (1H, m), 3.25 (5H, m), 3.0 (3H, s), 2.24 (1H, m), 1.8-1.45 (4H, m), 1.38 (6H, m), 0.97 (6H, m); m/z: 525.2 (M+H)$^+$.

Example CU

Example CU (140 mg) was prepared following the procedure used to prepare Example C, except that Compounds 29 and 138b was used instead of Compounds 13a and 8. $^1$H-NMR (CDCl$_3$) δ 8.78 (1H, s), 7.85 (1H. m), 7.4-7.05 (10H, m), 6.93 (1H, s), 5.90 (1H, m), 5.35 (2H, s), 4.9-4.6 (2H, m), 4.6-4.4 (4H, m), 4.2 (1H, m), 3.4-3.05 (5H, m), 3.0 (3H, s), 2.0 (1H, m), 1.8-1.3 (10H, m), 0.90 (6H, m); m/z: 705.2 (M+H)$^+$.

Example CV

Example CV (145 mg) was prepared following the procedure used to prepare Example C, except that Compounds 29 and 138c was used instead of Compounds 13a and 8. $^1$H-NMR (CDCl$_3$) δ 8.76 (1H, m), 7.86 (1H, m), 7.4-7.02 (10H, m), 6.97 (1H, m), 5.75 (1H, m), 5.38 (2H, m), 4.95-4.3 (6H, m), 4.15 (1H, m), 3.4-3.0 (5H, m), 3.0 (3H, s), 2.2-1.6 (3H, m), 1.4 (6H, m), 0.88 (6H, m); m/z: 691.2 (M+H)$^+$.

Preparation of Example CW

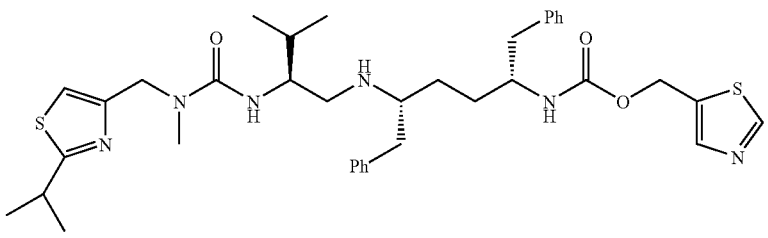

CW

Example CW could be prepared, e.g. by reacting Compound 8 with a compound having the following structure:

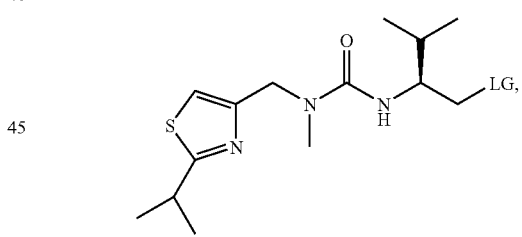

where "LG" is a leaving group such as a halogen. Such compounds could be prepared by one-carbon degradation of the corresponding carboxylic acid or ester (e.g., Compounds 28 or 29) by known methods such as the Hunsdieker reaction or the Kochi reaction or similar methods.

Preparation of Examples CX and CY

Scheme 79

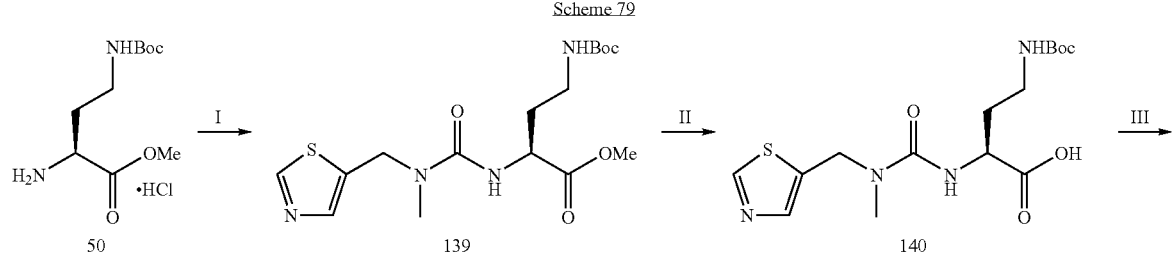

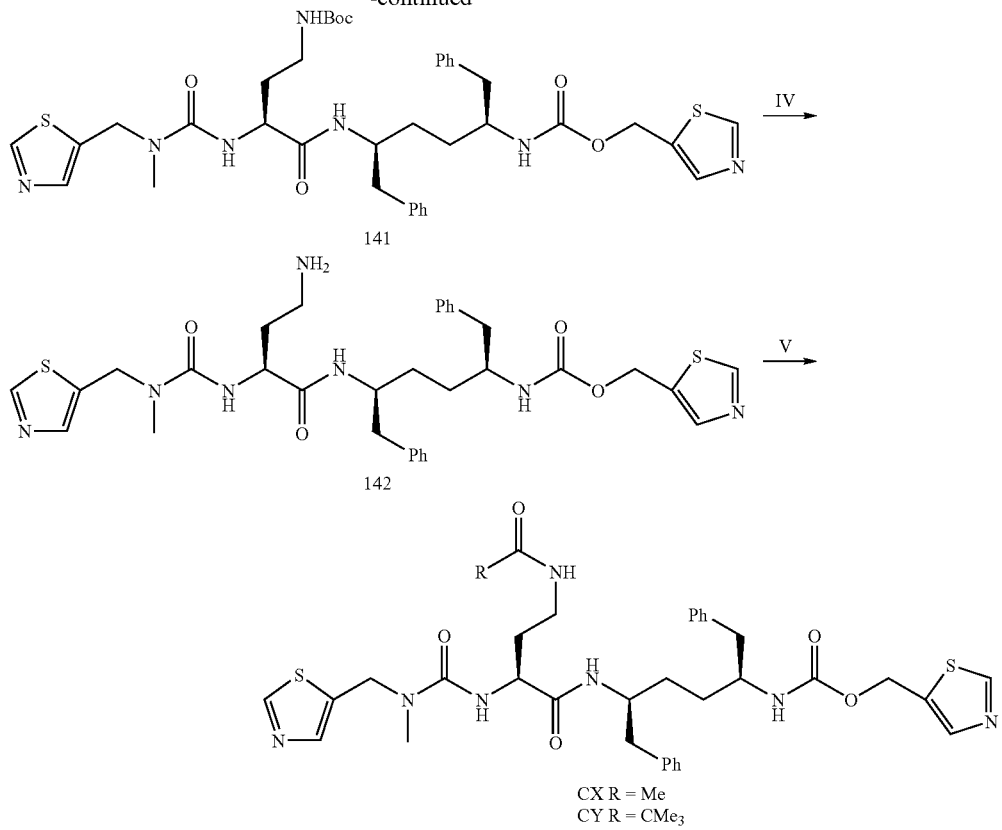

1. a. Cl₃COCOOCCl₃/DIPEA; b. Compound 68;
II. a. NaOH/THF/H₂O; b. HCl;
III. Compound 46/EDC/HOBt/DIPEA;
IV. a. TFA/DCM; b. NaOH;
V. AcOH/HOBt/EDC/DIPEA/DMF, or (Me₃CCO)₂O/DIPEA Compound 139

To a solution of triphosgene (1.1 g, 3.7 mmol) in dichloromethane (20 mL) at 0° C., Compound 50 (2.69 g, 10 mmol) and diisopropylethylamine (3.74 mL) were slowly added in a solution of dichloromethane (35 mL). The mixture was stirred for 30 minutes. A solution of Compound 68 (1.27 g, 10 mmol) and diisopropylethylamine (3.75 mL) in dichloromethane (20 mL) was added. The mixture was stirred for 12 hours and diluted with EtOAc. The organic phase was washed with saturated sodium carbonate solution (2×) and brine, and dried over Na₂SO₄. Concentration and purification by flash column chromatography (10-100% EtOAc in hexanes) gave Compound 139 (1.63 g). m/z: 386.8 (M+H)⁺.

Compound 140

Compound 140 was prepared following the procedure used to prepare Compound 7, except that Compound 139 was used instead of Compound 6.

Compound 141

Compound 141 (3 g) was prepared following the procedure used to prepare Example C, except that Compounds 140 and 46 were used instead of Compounds 7 and 8. m/z: 764.1 (M+H)⁺.

Compound 142

To a solution of Compound 141 (3 g) in dichloromethane (20 mL) was added trifluoroacetic acid (20 mL). The mixture was stirred for 2 hours and concentrated under reduced pressure. The mixture was diluted with EtOAc, and washed with 2N sodium hydroxide solution (2×), water, and brine, and dried over Na₂SO₄. Concentration gave Compound 142 (2.5 g).

Example CX

Example CX (1.56 g) was prepared following the procedure used to prepare Example C, except that Compound 142 and acetic acid were used instead of Compounds 7 and 8. m/z: 706.1 (M+H)⁺. ¹H NMR (CD₃OD) δ 8.91 (1H, s), 8.88 (1H, s), 7.80 (2H, m), 7.22-7.05 (10H, m), 5.20 (2H, s), 4.8-4.6 (2H, m), 4.2-4.05 (2H, m), 3.75 (1H, m), 3.05 (1H, m), 3.0-2.6 (8H, m), 1.94 (3H, s), 1.7-1.3 (6H, m).

Example CY

To a solution of Compound 142 (50 mg, 0.075 mmol) in dichloromethane (1 mL) was added trimethylacetic anhydride (17 μl, 0.0825 mmol), followed by diisopropylethylamine (30 μl, 0.15 mmol). The mixture was stirred for 12 hours. Concentration and purification by flash column chromatography (0-10% MeOH in dichloromethane) gave Example CY (40 mg). m/z: 748.2 (M+H)⁺. ¹H NMR (CD₃OD) δ 8.98 (1H, s), 8.88 (1H, s), 7.80 (2H, m), 7.22-7.05 (10H, m), 5.20 (2H, s), 4.8-4.6 (2H, m), 4.2-4.0 (2H, m), 3.8 (1H, m), 3.2-3.05 (1H, m), 2.9-2.6 (8H, m), 1.65-1.40 (6H, m), 1.19 (9H, s).

Preparation of Example CZ

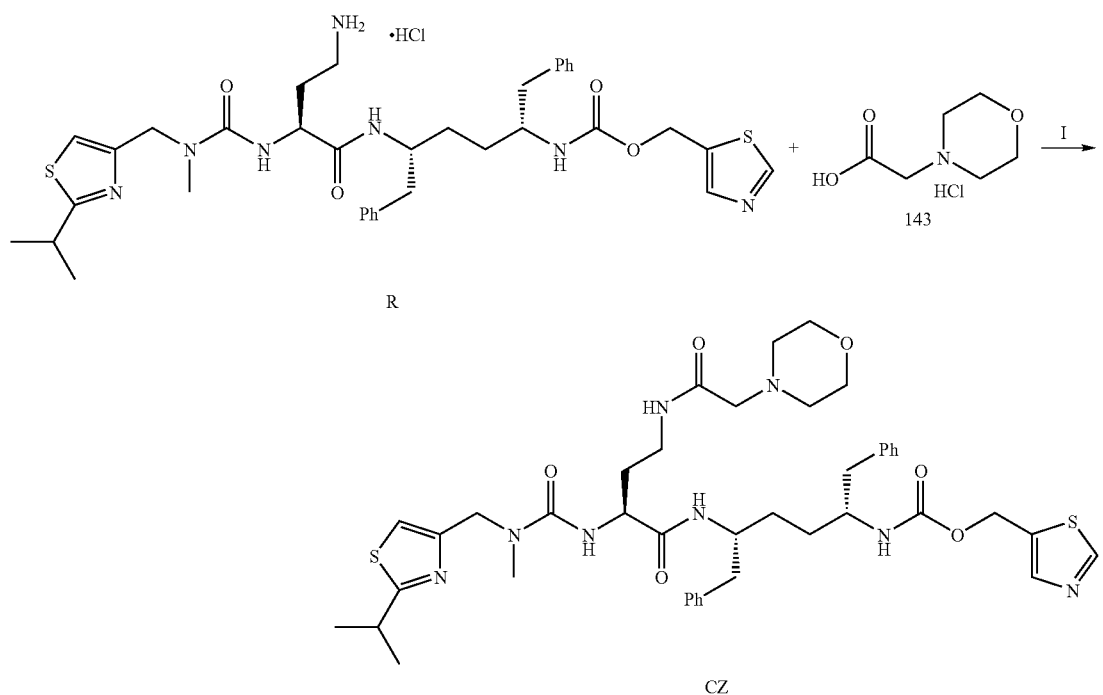

I. EDC/HOBt/DIPEA/DMF

Compound 143

Compound 143 is commercially available from Aldrich Chemical Co. and was used without further purification.

Example CZ

Example CZ (60 mg) was prepared following the procedure used to prepare Example C, except that Compound 143 and Example R were used instead of Compounds 7 and 8. m/z: 833.2 (M+H)$^+$. $^1$H NMR (CD$_3$OD) δ 8.99 (1H, s), 7.83 (1H, s), 7.25-7.02 (11H, m), 5.21 (2H, s), 4.54 (2H, m), 4.2-4.0 (2H, m), 3.8-3.6 (5H, m), 3.3 (2H, m), 3.10 (1H, m), 3.0-2.9 (5H, m), 2.65 (4H, m), 2.45 (4H, m), 1.9-1.6 (2H, m), 1.6-1.4 (4H, m), 1.37 (6H, d, J=7.0 Hz).

Preparation of Examples DA and DB

Scheme 81

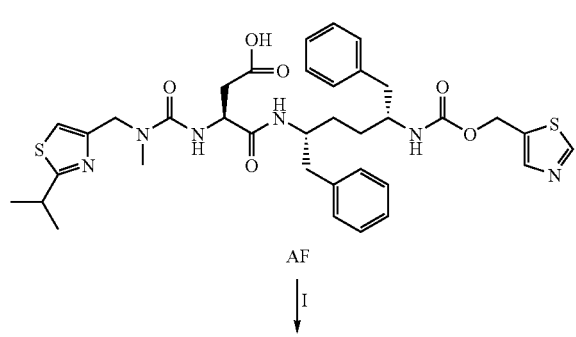

AF

↓ I

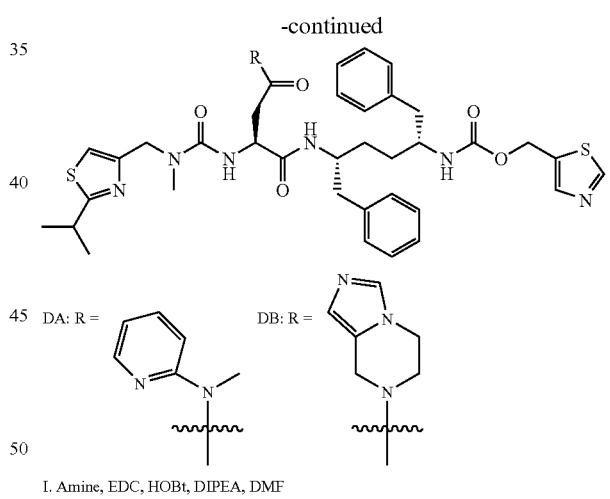

DA: R =     DB: R =

I. Amine, EDC, HOBt, DIPEA, DMF

Example DA

Example DA was prepared in a similar fashion to Example CB except that 2-(methylamino)pyridine (2.77 mmol; purchased from Aldrich) was reacted with Compound AF (0.28 mmol) instead of morpholine and DIPEA (1.11 mmol) was added. Reaction under these conditions produced 0.017 g (9%) of Example DA as white solid. m/z 811.0 (M+H)$^+$; $^1$H-NMR (CD$_3$OD, 300 MHz): 8.98 (s, 1H); 8.45 (d, J=2 Hz, 1H); 7.95 (m, 1H); 7.82 (s, 1H); 7.45 (d, J=4 Hz, 1H); 7.37 (m, 1H); 7.20-7.08 (m, 11H); 5.20 (s, 2H); 4.59 (d, J=2 Hz, 1H); 4.54 (m, 2H); 4.03 (s, 1H); 3.74 (s, 1H); 3.32-3.29 (m, 4H); 2.95 (d, J=4 Hz, 3H); 2.90 (s, 1H); 2.69 (s, 3H); 2.54 (s, 2H); 1.55-1.44 (m, 4H); 1.33-1.30 (m, 6H).

Example DB

Example DB was prepared in a similar fashion to Example CB except that 5,6,7,8-tetrahydroimidazo[1,5-a]pyrazine (0.24 mmol; purchased from GeneTech Inc.) was reacted with Compound AF (0.24 mmol) instead of morpholine and DIPEA (0.96 mmol) was added. Reaction under these conditions produced 0.025 g (15%) of Example DB as clear oil. m/z 826.2 (M+H)$^+$; $^1$H-NMR (CD$_3$OD, 300 MHz): 8.97 (s, 1H); 7.82 (s, 1H); 7.61 (s, 1H); 7.18 (s, 1H); 7.14 (s, 10H); 6.80 (d, J=8 Hz, 1H); 5.20 (s, 2H); 4.80 (s, 1H); 4.73-4.66 (m, 2H); 4.49 (d, J=4 Hz, 2H); 4.18-4.10 (m, 1H); 4.06 (s, 1H); 3.92-3.76 (m, 4H); 3.32 (s, 1H); 2.94-2.83 (m, 4H); 2.71-2.66 (m, 5H); 1.52-1.447 (m, 4H); 1.37-1.34 (m, 6H).

Compound 144

Compound 144 was prepared according to the procedure of *J. Med. Chem.* 2005, 48, 141.

Example DC

Example DC was prepared in a similar fashion to Example CB except that 3-(trifluoromethyl)-5,6,7,8-tetrahydro-1,2,4-triazolo[4,3-a]pyrazine (Compound 144) (0.08 mmol) was reacted with Compound AF (0.08 mmol) instead of morpholine and DIPEA (0.32 mmol) was added. Reaction under these conditions produced 0.010 g (13%) of Example DC as clear oil. m/z 895.1 (M+H)$^+$; $^1$H-NMR (CD$_3$OD, 300 MHz): 8.97 (s, 1H); 7.82 (s, 1H); 7.15 (s, 1H); 7.14 (s, 10H); 5.20 (s, 2H); 5.01 (s, 1H); 4.94 (s, 1H); 4.68-4.64 (m, 1H); 4.50 (s, 2H); 4.31 (s, 1H); 4.20-4.02 (m, 4H); 3.76 (s, 1H); 3.32 (s, 1H); 2.73-2.67 (m, 4H); 1.53-1.45 (m, 4H); 1.36 (d, J=4 Hz, 6H).

Preparation of Example DC

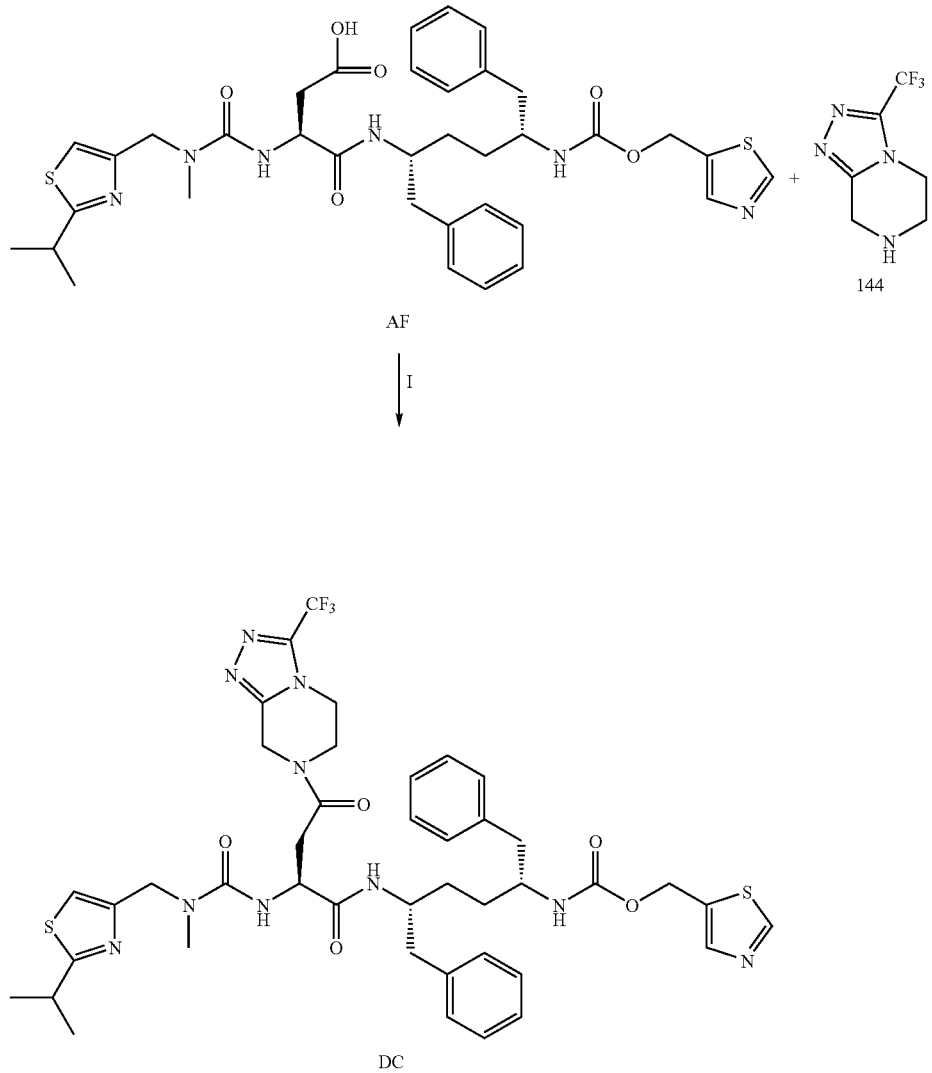

Scheme 82

I. EDC, HOBt, DIPEA, DMF

Preparation of Examples DD-DI

Scheme 83

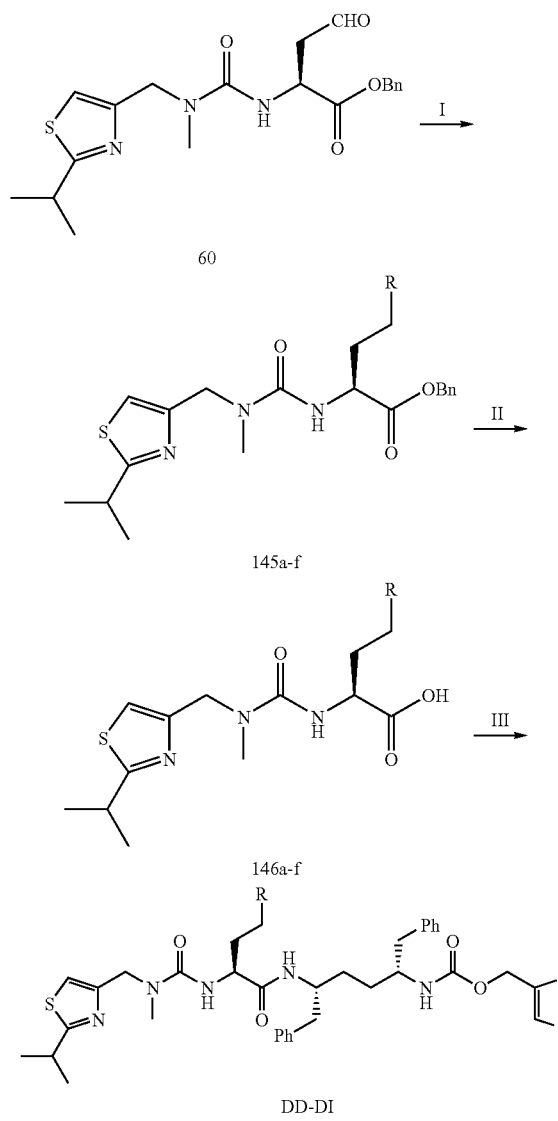

R for 145a-f, 146a-f, and DD-DI:

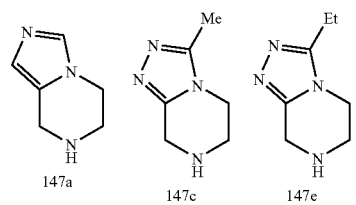

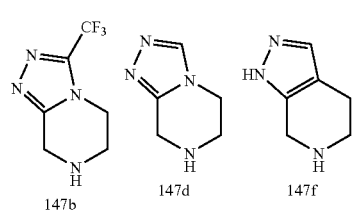

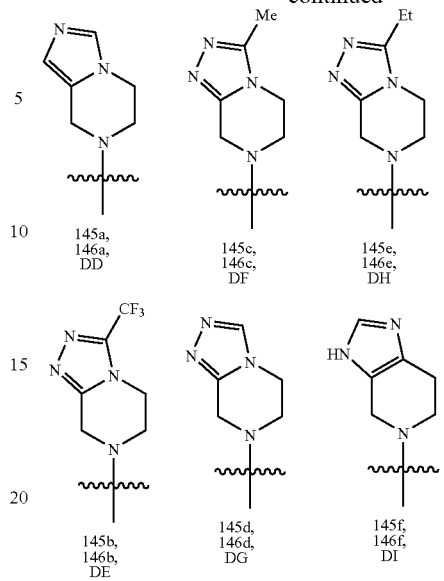

I. One of Compounds 147a-f/NaBH(OAc)₃/AcOH/CH₃CN; II. a. NaOH/EtOH/H₂O; b. HCl; III. Compound 8/EDC/HOBt/DIPEA Compound 147a Compound 147a is commercially available from GeneTech Inc. and was used without further purification.

Compound 145a To a solution of Compound 60 (82 mg, 0.20 mmol) in CH₃CN (1 mL) was added a solution of 5,6,7,8-tetrahydroimidazo[1,5-a]pyrazine (Compound 147a) (49 mg, 0.40 mmol) in CH₃CN (1 mL), followed by HOAc (23 μL, 0.40 mmol) and NaBH(OAc)₃ (129 g, 0.60 mmol). The mixture was stirred for 12 hours and diluted with EtOAc. The organic phase was washed with saturated Na₂CO₃ solution, water, and brine, and dried over Na₂SO₄. Concentration and purification by flash column chromatography (0-5% MeOH in dichloromethane) gave Compound 145a (88 mg). m/z: 511.2 (M+H)⁺.

Compound 146a

To a solution of Compound 145a (88 mg, 0.17 mmol) in ethyl alcohol (2 mL) was added 1.0 N sodium hydroxide solution (0.26 mL, 0.26 mmol). The mixture was stirred for 1 hour and the solvents were removed under reduced pressure. 4.0 N Hydrochloric acid in dioxane (70 μL, 0.26 mmol) was added, and the mixture was evaporated. Coevaporation with DMF (2×100 mL) gave Compound 146a, which was used without further purification in the next step.

Example DD

Example DD (73 mg) was prepared following the procedure used to prepare Example C, except that Compound 146a was used instead of Compound 7. m/z: 811.0 (M+H)⁺. ¹H NMR (CD₃OD, 300 MHz): δ 8.97 (s, 1H); 7.81 (s, 1H); 7.52 (s, 1H); 7.25-7.11 (m, 11H); 6.69 (s, 1H), 5.19 (d, J=2 Hz, 2H); 4.52-4.39 (m, 2H); 4.28-4.24 (m, 1H); 4.13 (s, 1H); 4.06-4.03 (m, 2H); 3.76 (s, 1H); 3.61 (AB d, J=20 Hz, 2H); 3.35 (s, 1H); 2.80-2.74 (m, 6H); 2.71-2.68 (m, 3H); 2.50 (s, 2H); 1.94-1.77 (m, 2H); 1.55-1.49 (m, 4H); 1.38 (d, J=3 Hz, 6H).

Compound 147b

Compound 147b was prepared according to the procedure of J. Med. Chem. 2005, 48, 141.

Compound 145b

Compound 145b (60 mg) was prepared following the procedure used to prepare Compound 145a, except that 3-(trifluoromethyl)-5,6,7,8-tetrahydro-1,2,4-triazolo[4,3-a]pyrazine (Compound 147b) was used instead of 5,6,7,8-tetrahydroimidazo[1,5-a]pyrazine (Compound 147a). m/z: 580.2 (M+H)$^+$.

Compound 146b

Compound 146b was prepared following the procedure used to prepare Compound 146a, except that Compound 145b was used instead of Compound 145a.

Example DE

Example DE (51 mg) was prepared following the procedure used to prepare Example DD, except that Compound 146b was used instead of Compound 146a. m/z: 881.2 (M+H)$^+$. $^1$H NMR (CD$_3$OD, 300 MHz) δ 8.97 (s, 1H); 7.81 (s, 1H); 7.26-7.14 (m, 11H); 5.20 (s, 2H); 4.49 (s, 2H); 4.32-4.27 (m, 1H); 4.21-4.17 (m, 2H); 4.09 (s, 1H); 3.85-3.75 (m, 3H); 3.35 (s, 1H); 2.94-2.88 (m, 5H); 2.75-2.69 (m, 4H); 2.59-2.56 (m, 2H); 1.94-1.73 (m, 2H); 1.55-1.47 (m, 4H); 1.38 (d, J=4 Hz, 6H).

Compound 147c

Compound 147c was prepared according to the procedure of J. Med. Chem. 2005, 48, 141.

Compound 145c

To a solution of Compound 60 in CH$_3$CN (1 mL) is added a solution of 3-methyl-5,6,7,8-tetrahydroimidazo[4,3-a]pyrazine (Compound 147c) in CH$_3$CN (1 mL), followed by HOAc and NaBH(OAC)$_3$. The mixture is stirred for 12 hours and is diluted with EtOAc. The organic phase is washed with saturated Na$_2$CO$_3$ solution, water, and brine, and dried over Na$_2$SO$_4$. Concentration and purification by flash column chromatography (0-5% MeOH in dichloromethane) gives Compound 145c.

Compound 146c

To a solution of Compound 145c in ethyl alcohol is added 1.0 N sodium hydroxide solution. The mixture is stirred for 1 hour, and the solvents are removed under reduced pressure. 4.0 N Hydrochloric acid in dioxane is added, and the mixture is evaporated. Co-evaporation with DMF gave Compound 146c, which is used without further purification in the next step.

Example DF

Example DF is prepared following the procedure used to prepare Example DD, except that Compound 146c is used instead of Compound 146a.

Compounds 147d, 147e, and 147f

Compounds 147d and 147f are commercially available from Chem-Impex International and ASDI Inc., respectively. Compound 147e is prepared according to the procedure of J. Med. Chem. 2005, 48, 141.

Example DG

Example DG is prepared following the procedure used to prepare Example DD, except that Compound 146d is used instead of Compound 146a.

Example DH

Example DH is prepared following the procedure used to prepare Example DD, except that Compound 146e is used instead of Compound 146a.

Example DI

Example DI is prepared following the procedure used to prepare Example DD, except that Compound 146f is used instead of Compound 146a.

Preparation of Examples DJ, DK, and DL

Scheme 84

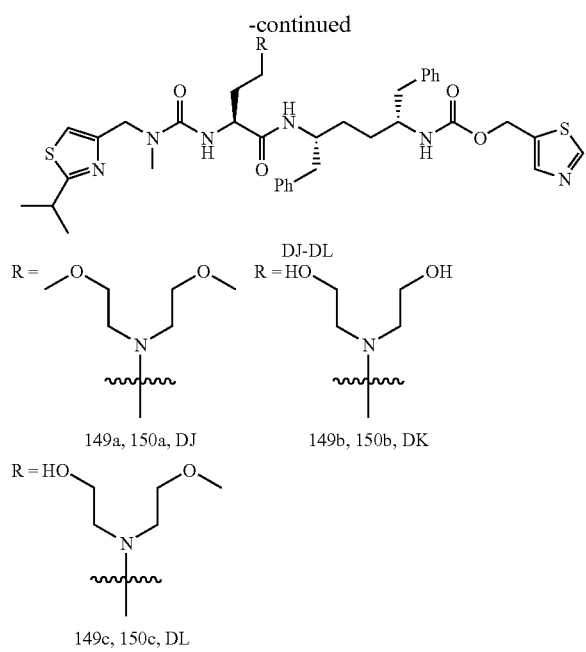

I. TMS/EtOH/DCM; II. amine/DCM; III. a. NaOH/THF/H₂O; b. HCl; IV. Compound 8/EDC/HOBt/DIPEA/DMF Compound 148

To the solution of Compound 122 (2.1 g, 7 mmol) in dichloromethane (9 mL) was added ethyl alcohol (2.6 mL, 45 mmol), followed by iodotrimethylsilane (3.5 mL, 25 mmol). The mixture. was stirred for 12 hours, and the solvents were removed under reduced pressure. The mixture was diluted with EtOAc, and washed with saturated sodium bicarbonate solution (2×), 10% NaHSO₃ solution, and brine. The organic solution was dried over Na₂SO₄. Concentration gave Compound 148. m/z: 453.8 (M+H)⁺.

Compound 149a

To the solution of bis(2-methoxyethyl)amine (665 mg, 5 mmol) in dichloromethane (2 mL) was added a solution of Compound 148 (458 mg, 1 mmol) in dichloromethane (1 mL). The mixture was stirred for 12 hours, and the solvents were removed under reduced pressure. Purification by flash column chromatography (0-20% MeOH in dichloromethane) gave Compound 149a (350 mg). m/z: 459.0 (M+H)⁺.

Compound 149b

Compound 149b (303 mg) was prepared following the procedure used to prepare Compound 149a, except that bis (2-hydroxyethyl)amine was used instead of bis(2-methoxyethyl)amine. m/z: 431.0 (M+H)⁺.

Compound 149c

Compound 149c (1.1 g) was prepared following the procedure used to prepare Compound 149a, except that N-(2-hydroxyethyl)-N-(2-methoxyethyl)amine was used instead of bis(2-methoxyethyl)amine. m/z: 445.0 (M+H)⁺.

Compound 150a

Compound 150a was prepared following the procedure used to prepare Compound 7, except that Compound 149a was used instead of Compound 6. m/z: 431.0 (M+H)⁺.

Compound 150b

Compound 150b was prepared following the procedure used to prepare Compound 7, except that Compound 149b was used instead of Compound 6. m/z: 403.0 (M+H)⁺.

Compound 150c

Compound 150c was prepared following the procedure used to prepare Compound 7, except that Compound 149c was used instead of Compound 6. m/z: 417.0 (M+H)⁺.

Example DJ

Example DJ (280 mg) was prepared following the procedure used to prepare Example C, except that Compound 150a was used instead of Compound 7. m/z: 822.3 (M+H)⁺. ¹H NMR (CD₃OD) δ 8.98 (1H, s), 7.82 (1H, s), 7.24-7.10 (11H, m), 5.20 (2H, m), 4.52 (2H, m), 4.2-4.0 (2H, m), 3.75 (1H, m), 3.4 (3H, m), 3.3-3.2 (8H, m), 2.97 (3H, s), 2.8-2.4 (10H, m), 1.8-1.4 (6H, m), 1.37 (6H, d, J=7.0 Hz).

Example DK

Example DK (8 mg) was prepared following the procedure used to prepare Example C, except that Compound 150b was used instead of Compound 7. m/z: 794.3 (M+H)⁺. ¹H NMR (CD₃OD) δ 9.01 (1H, s), 7.84 (1H, s), 7.22-7.10 (11H, m), 5.20 (2H, s), 4.65-4.45 (2H, m), 4.25 (1H, m), 4.12 (1H, m), 3.85 (4H, m), 3.80 (1H, m), 3.4-3.2 (7H, m), 2.95 (3H, s), 2.8-2.6 (4H, m), 2.2-1.8 (2H, m), 1.6-1.4 (4H, m), 1.37 (6H, d, J=6.5 Hz).

Example DL

Example DL (5 mg) was prepared following the procedure used to prepare Example C, except that compound 150c was used instead of Compound 7. m/z: 808.2 (M+H)⁺. ¹H NMR (CD₃OD) δ 9.0 (1H, s), 7.83 (1H, s), 7.22-7.05 (11H, m), 5.21 (2H, s), 4.55 (2H, m), 4.25 (1H, m), 4.15 (1H, m), 3.9-3.65 (5H, m), 3.45-3.20 (10H, m), 2.96 (3H, s), 2.8-2.6 (4H, m), 2.2-1.8 (2H, m), 1.6-1.4 (4H, m), 1.37 (6H, d, J=7.0 Hz).

Preparation of Example DM

Scheme 85

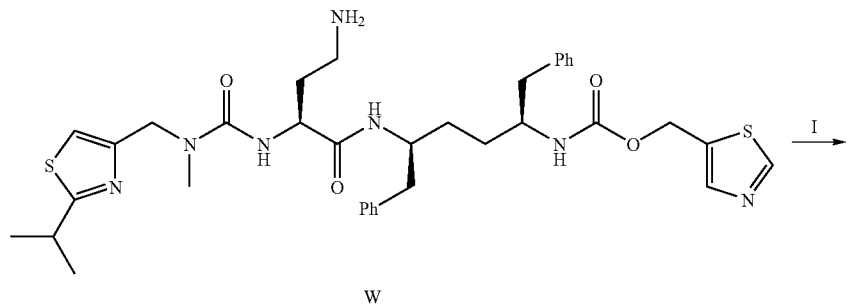

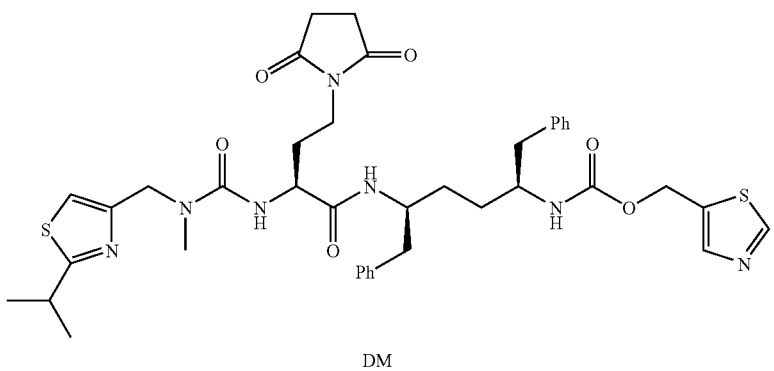

DM

I. a. succinic anhydride/ClCH₂CH₂Cl; b. Ac₂O/NaOAc

Example DM

To a solution of Example W (1.36 g, 1.9 mmol) in dichloroethane (8 mL) was added succinic anhydride (231 mg, 2.3 mmol). The mixture was heated at 45° C. for 12 hours. The solvent was removed, and the resulting white solid was dried under high vacuum. To the dried solid was added sodium acetate (57 mg, 0.69 mmol), followed by acetic anhydride (8 mL). The mixture was heated at 85° C. for 1 hour, and the solvent was removed under reduced pressure. The residue was diluted with EtOAc, and was washed with water, saturated NaHCO₃, water, and brine, and dried over Na₂SO₄. Concentration and purification by flash column chromatography (0-15% iPrOH (gradient) in dichloromethane) gave Example DM (130 mg). m/z: 788.1 (M+H)⁺. ¹H NMR (CD₃OD) δ 8.97 (1H. s), 7.82 (1H, s), 7.22-7.01 (11H, m), 5.20 (2H, s), 4.56 (2H, m), 4.15-3.95 (2H, m), 3.75 (1H, m), 3.5-3.2 (3H, m), 3.0 (3H, s), 2.8-2.5 (8H, m), 1.8-1.35 (6H, m), 1.34 (6H, m).

Preparation of Example DN

Scheme 86

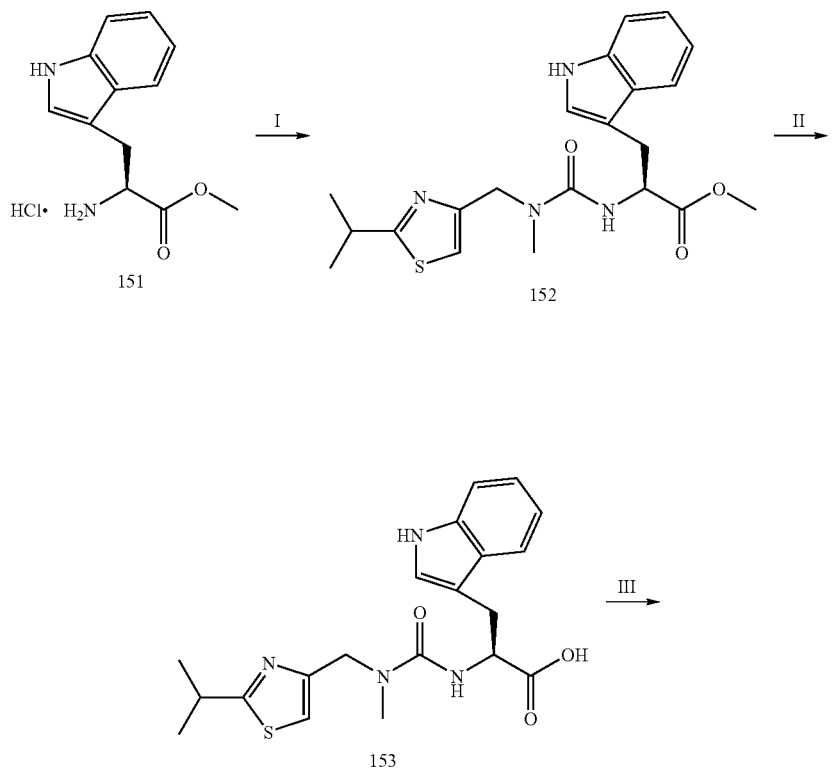

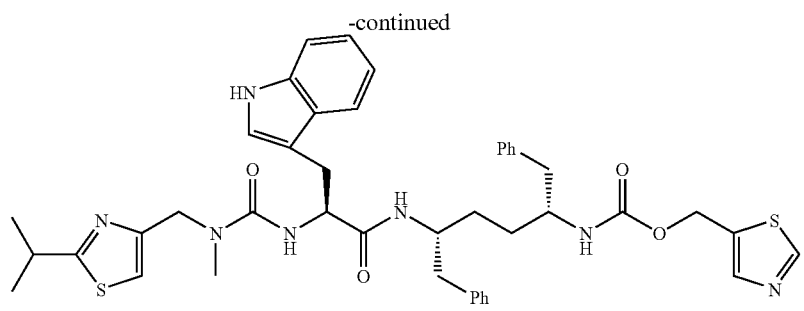

DN

I. a. CDI/DIPEA/DMF; b. Compound 9; II. LiOH/THF/water; III. EDC/HOBT/DIPEA/Compound 8/DMF Compound 151

Compound 151 is commercially available from Aldrich Chemical Co. and was used without purification.

Compound 152

Compound 152 was prepared using procedures similar to those used to prepare Compound 132, except that Compound 151 was used instead of Compound 131. m/z 415.0 (M+H)$^+$.

Compound 153

Compound 153 was prepared following the procedure used to prepare Compound 7, except that Compound 152 was used instead of Compound 6. $^1$H-NMR (300 MHz, CD$_3$OD) δ 7.59 (d, J=7.8 Hz, 1H), 7.34 (d, J=7.8 Hz, 1H), 7.13-7.05 (m, 2H), 6.97 (t, J=7.8 Hz, 1H), 6.75 (s, 1H), 4.68-4.60 (m, 1H), 4.50-4.30 (m, 2H), 3.44-3.14 (m, 3H), 2.85 (s, 3H), 1.36-1.38 (m, 6H).

Example DN

Example DN was prepared following the procedure used in Example C, except that compound 153 was used instead of Compound 7. $^1$H-NMR (300 MHz, CD$_3$OD) δ 8.93 (s, 1H), 7.80 (s, 1H), 7.63 (d, J=7.8 Hz, 1H), 7.35 (d, J=7.8 Hz, 1H), 7.25-6.95 (m, 13H), 6.68 (s, 1H), 5.18 (s, 2H), 4.60-4.30 (m, 3H), 4.10-3.95 (m, 1H), 3.75-3.60 (m, 1H), 3.30-2.95 (m, 3H), 2.90-2.80 (m, 4H), 2.75-2.50 (m, 4H), 1.50-1.05 (m, 10H); m/z 792.1 (M+H)$^+$.

Preparation of Example DO

Scheme 87

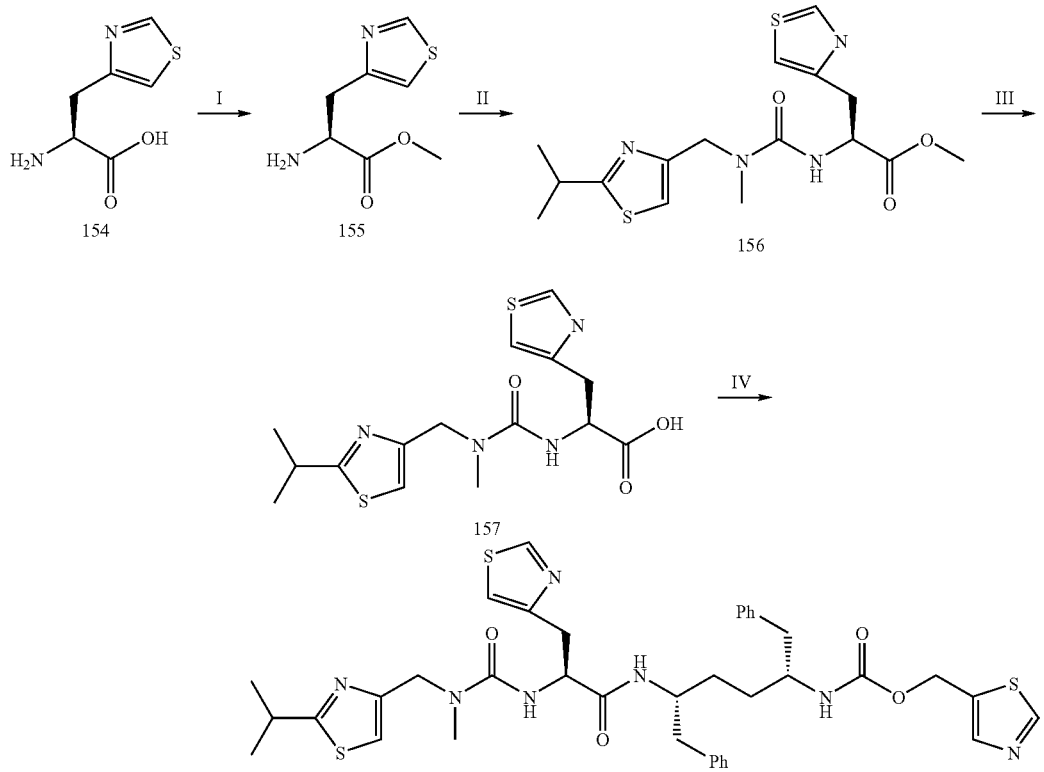

DO

I. thionylchloride/methanol; II. a. CDI/DIPEA/DMF; b. Compound 9; III. LiOH/THF/water; IV. EDC/HOBt/DIPEA/Compound 8/DMF Compound 154

Compound 154 is commercially available from Chem-Impex and was used without purification.

Compound 155

Compound 155 was prepared following the procedure used to make Compound 94, except that Compound 154 was used instead of Compound 93. $^1$H-NMR (300 MHz, D$_2$O) δ 9.0 (s, 1H), 7.42 (s, 1H), 4.40 (t, J=7.8 Hz, 1H), 3.65 (s, 3H), 3.50-3.25 (m, 2H).

Compound 156

Compound 156 was prepared following procedures similar to those used to prepare Compound 132, except that Compound 155 was used instead of Compound 131. m/z 383.1 (M+H)$^+$.

Compound 157

Compound 157 was prepared following the procedure used to prepare Compound 7, except that Compound 156 was used instead of compound 6. m/z 368.9 (M+H)$^+$; 367.0 (M−H)$^−$.

Example DO

Example DO was prepared following the procedure used in Example C, except that Compound 157 was used instead of Compound 7. $^1$H-NMR (300 MHz, CD$_3$OD) δ 8.97 (s, 1H), 8.89 (s, 1H), 7.98 (s, 1H), 7.83 (s, 1H), 7.25-7.00 (m, 11H), 5.20 (s, 2H), 4.60-4.35 (m, 3H), 4.10-3.95 (m, 1H), 3.80-3.65 (m, 1H), 3.20-3.02 (m, 2H), 3.02-2.82 (m, 7H), 2.75-2.60 (m, 4H), 1.60-1.25 (m, 10H); m/z 760.0 (M+H)$^+$.

Preparation of Example DP

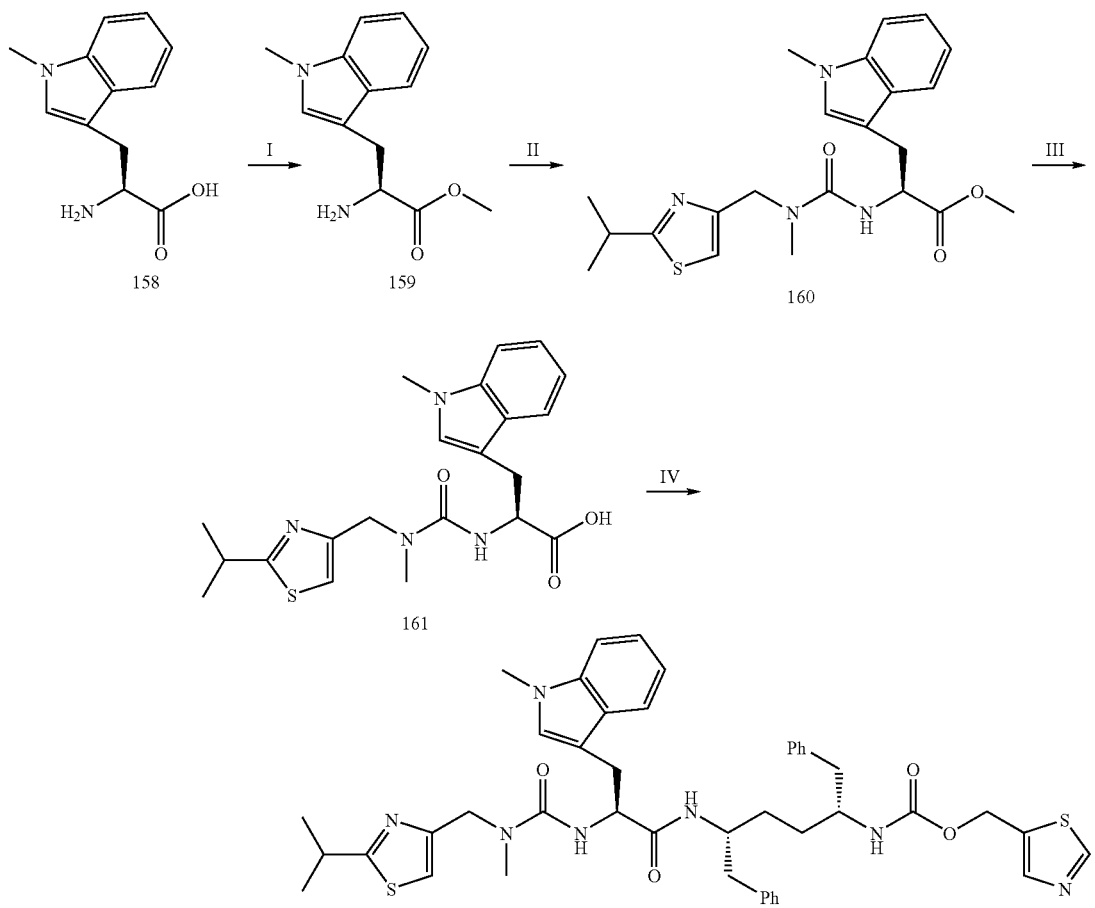

Scheme 88

I. thionylchloride/methanol; II. a. Phosgene solution/DIPEA/DCM; b. Compound 9; III. LiOH/THF/water; IV. EDC/HOBt/DIPEA/Compound 8/DMF Compound 158

Compound 158 is commercially available from Aldrich Chemical Co. and was used without further purification.

Compound 159

Compound 159 was prepared following the procedure used to make Compound 94, except that compound 158 was used instead of Compound 93. m/z 232.9 (M+H)$^+$.

Compound 160

To a stirred solution of Compound 159 (150 mg, 0.56 mmol) and DIPEA (0.39 mL, 2.24 mmol) in dichloromethane (10 mL) was added slowly a solution of phosgene in toluene (0.44 mL, 20% in toluene, 0.84 mmol) at 0° C. The mixture was stirred at 0° C. for 2 hours and then diluted with more dichloromethane (50 mL). The organic layer was washed with water and dried over Na$_2$SO$_4$. After filtration, the filtrate was concentrated under vacuum. The resulting residue was dissolved in dichloromethane (5 mL), and then DIPEA (0.39 mL, 2.24 mmol) and Compound 9 (143 mg, 0.84 mmol) was added. The mixture was stirred at room temperature for 16 hours, then diluted with dichloromethane (50 mL). The organic layer was washed with water (2×) and brine (1×), and dried over $Na_2SO_4$. Concentration and purification by column chromatography gave Compound 160 (100 mg). m/z 429.0 $(M+H)^+$.

Compound 161

Compound 161 was prepared following the procedure used to prepare Compound 7, except that Compound 160 was used instead of compound 6. m/z 415.0 $(M+H)^+$, 413.2 $(M-H)^-$.

Example DP

Example DP was prepared following the procedure used in Example C, except that Compound 161 was used instead of Compound 7. $^1$H-NMR (300 MHz, $CD_3OD$) δ 8.94 (s, 1H), 7.82 (s, 1H), 7.55 (d, J=7.8 Hz, 1H), 7.32 (d, J=7.8 Hz, 1H), 7.25-6.95 (m, 13H), 6.41 (s, 1H), 5.22 (s, 2H), 4.85-4.75 (m, 1H), 4.30-4.00 (m, 3H), 3.90-3.75 (m, 1H), 3.30-2.95 (m, 3H), 2.90-2.50 (m, 4H), 2.42 (s, 3H), 2.33 (s, 3H), 1.65-1.25 (m, 10H); m/z 806.1 $(M+H)^+$.

$IC_{50}$ Determinations for Human Liver Cytochrome P450

Materials and General Methods

Pooled (n≧15 donors) human hepatic microsomal fraction was obtained from BD-Gentest (Woburn, Mass.) who also supplied hydroxy-terfenadine, 4'-hydroxydiclofenac and NADPH regenerating system. Ritonavir was prepared from commercial Norvir® oral solution (Abbott Laboratories, Abbott Park, Ill.). Other reagents were from Sigma-Aldrich (St. Louis, Mo.) and included terfenadine, fexofenadine, BRL 15572, diclofenac and mefenamic acid.

Incubations were performed in duplicate in 50 mM potassium phosphate buffer, pH 7.4 with NADPH regenerating system used as described by the manufacturer. The final microsomal protein concentrations had previously been determined to be within the linear range for activity and resulted in less than 20% consumption of substrate over the course of the incubation. The final substrate concentrations used were equal to the apparent Km values for the activities determined under the same conditions. Inhibitors were dissolved in DMSO, and the final concentration of DMSO, from both substrate and inhibitor vehicles, was 1% (v/v). Incubations were performed at 37° C. with shaking and were initiated by addition of substrate. Aliquots were then removed at 0, 7 and 15 minutes. Samples were quenched by treatment with an acetonitrile, formic acid, water (94.8%/0.2%/5%, v/v/v) mixture containing internal standard. Precipitated protein was removed by centrifugation at 3000 rpm for 10 min and aliquots of the supernatant were then subjected to LC-MS analysis.

The LC-MS system consisted of a Waters Acquity HPLC, with a binary solvent manager and a refrigerated (8° C.) sample organizer and sample manager, interfaced to a Micromass Quattro Premier tandem mass spectrometer operating in electrospray ionization mode. The column was a Waters Acquity. HPLC BEH $C_{18}$ 2.1×50 mm, 1.7 µm pore size. Mobile phases consisted of mixtures of acetonitrile, formic acid and water, the composition for mobile phase A being 1%/0.2%/98.8% (v/v/v) and that for mobile phase B being 94.8%/0.2%/5% (v/v/v). The injection volumes were 5 µL and the flow rate was 0.8 mL/min. Concentrations of metabolites were determined by reference to standard curves generated with authentic analytes under the same conditions as the incubations.

$IC_{50}$ values (the concentration of inhibitor reducing CYP3A activity by 50%) were calculated by non-linear regression using GraphPad Prism 4.0 software and a sigmoidal model.

CYP3A Inhibition Assay

The potencies of the compounds as inhibitors of human hepatic cytochromes P450 of the CYP3A subfamily (particularly CYP3A4) were assessed using terfenadine oxidase, a well-characterized CYP3A-selective activity described in Ling, K.-H. J., et al Drug Metab. Dispos., 23, 631-636, (1995) and Jurima-Romet, et al Drug Metab. Dispos., 22, 849-857, (1994). The final concentrations of microsomal protein and terfenadine substrate were 0.25 mg/mL and 3 µM, respectively. Metabolic reactions were terminated by treatment with seven volumes of quench solution containing 0.1 µM BRL 15572 as internal standard. A further 8 volumes of water were added before centrifugation and aliquots of the supernatant were removed for analysis.

For LC-MS analysis chromatographic elution was achieved by a series of linear gradients starting at 20% B and holding for 0.1 minutes, then increasing to 80% B over 1.5 minutes, holding for 0.4 minutes and then returning to the starting conditions for 0.05 min. The system was allowed to re-equilibrate for at least 0.25 minutes prior to the next injection. The mass spectrometer was operated in positive ion mode and the following precursor ($[M+H]^+$)/product ion pairs were monitored and quantified using MassLynx 4.0 (SP4, 525) software: hydroxy-terfenadine 488.7/452.4, fexofenadine 502.7/466.4 and BRL 15572 407.5/209.1. Terfenadine oxidase activity was determined from the sum of hydroxy-terfenadine and carboxy-terfenadine (fexofenadine) metabolites.

CYP2C9 Inhibition Assay

The potencies of the compounds as inhibitors of human hepatic CYP2C9 were assessed using diclofenac 4'-hydroxylase, an activity specific for this enzyme, as described in Leeman, T., et al Life Sci. 52, 29-34, (1992). The final concentrations of microsomal protein and diclofenac substrate were 0.08 mg/mL and 4 µM, respectively. Metabolic reactions were terminated by treatment with three volumes of quench solution containing 1 µM mefenamic acid as internal standard. After centrifugation a further 4 volumes of water were added. Aliquots of the supernatant were then subjected to LC-MS analysis.

For LC-MS analysis chromatographic elution was achieved by a series of linear gradients starting at 20% B and holding for 0.3 minutes, then increasing to 99% B over 1.2 minutes, holding for 0.5 minutes and then returning to the starting conditions for 0.25 min. The system was allowed to re-equilibrate for at least 0.25 minutes prior to the next injection. The mass spectrometer was operated in negative ion mode and the following precursor ($[M-H]^-$)/product ion pairs were monitored and quantified: 4'-hydroxy-diclofenac 312.4/294.2 and mefenamic acid 242.4/224.2.

Biological Assays Used for the Characterization of HIV Protease Inhibitors

HIV-1 Protease Enzyme Assay (Ki)

The assay is based on the fluorimetric detection of synthetic hexapeptide substrate cleavage by HIV-1 protease in a defined reaction buffer as initially described by M. V. Toth and G. R. Marshall, Int. J. Peptide Protein Res. 36, 544 (1990) (herein incorporated by reference in its entirety for all purposes).

The assay employed (2-aminobenzoyl)Thr-Ile-Nle-(p-nitro)Phe-Gln-Arg as the substrate and recombinant HIV-1 protease expressed in *E. Coli* as the enzyme. Both of the reagents were supplied by Bachem California, Inc. (Torrance, Calif.;

Cat. no. H-2992). The buffer for this reaction was 100 mM ammonium acetate, pH 5.3, 1 M sodium chloride, 1 mM ethylenediaminetetraacetic acid, 1 mM dithiothreitol, and 10% dimethylsulfoxide.

To determine the inhibition constant $K_i$, a series of solutions were prepared containing identical amount of the enzyme (1 to 2.5 nM) and the inhibitor to be tested at different concentrations in the reaction buffer. The solutions were subsequently transferred into a white 96-well plate (190 µL each) and preincubated for 15 min at 37° C. The substrate was solubilized in 100% dimethylsulfoxide at a concentration of 800 µM and 10 µL of 800 µM substrate was added into each well to reach a final substrate concentration of 40 µM. The real-time reaction kinetics was measured at 37 C using a Gemini 96-well plate fluorimeter (Molecular Devices, Sunnyvale, Calif.) at $\lambda(Ex)$=330 nm and $\lambda(Em)$=420 nm. Initial velocities of the reactions with different inhibitor concentrations were determined and the K value (in picomolar concentration units) was calculated by using EnzFitter program (Biosoft, Cambridge, U.K.) according to an algorithm for tight-binding competitive inhibition described by Ermolieff J., Lin X., and Tang J., Biochemistry 36, 12364 (1997).

HIV-1 Protease Enzyme Assay ($IC_{50}$)

As for the $K_i$ assay, above, the $IC_{50}$ assay is based on the fluorimetric detection of synthetic hexapeptide substrate cleavage by HIV-1 protease in a defined reaction buffer as initially described by M. V. Toth and G. R. Marshall, Int. J. Peptide Protein Res. 36, 544 (1990).

The assay employed (2-aminobenzoyl)Thr-Ile-Nle-(p-nitro)Phe-Gln-Arg as the substrate and recombinant HIV-1 protease expressed in *E. Coli* as the enzyme. Both of the reagents were supplied by Bachem California, Inc. (Torrance, Calif.; Cat. nos. H-2992 and H-9040, respectively). The buffer for this reaction was 100 mM ammonium acetate, pH 5.5, 1 M sodium chloride, 1 mM ethylenediaminetetraacetic acid, and 1 mM dithiothreitol, and 10% dimethylsulfoxide.

To determine the $IC_{50}$ value, 170 µL of reaction buffer was transferred into the wells of a white 96-well microtiter plate. A series of 3-fold dilutions in DMSO of the inhibitor to be tested was prepared, and 10 µL of the resulting dilutions was transferred into the wells of the microtiter plate. 10 µL of a 20-50 nM enzyme stock solution in reaction buffer was added to each well of the 96-well plate to provide a final enzyme concentration of 1-2.5 nM. The plates were then preincubated for 10 minutes at 37° C. The substrate was solubilized in 100% dimethylsulfoxide at a concentration of 400 µM and 10 µL of the 400 µM substrate was added into each well to reach a final substrate concentration of 20 µM. The real-time reaction kinetics were measured using a Gemini 96-well plate fluorimeter (Molecular Devices, Sunnyvale, Calif.) at $\lambda(Ex)$=330 nm and $\lambda(Em)$=420 nm. Initial velocities of the reactions with different inhibitor concentrations were determined and the $IC_{50}$ value (in nanomolar concentration units) was calculated by using GraphPad Prism™ software to fit nonlinear regression curves.

Anti-HIV-1 Cell Culture Assay ($EC_{50}$)

The assay is based on quantification of the HIV-1-associated cytopathic effect by a calorimetric detection of the viability of virus-infected cells in the presence or absence of tested inhibitors. HIV-1-induced cell death was determined using a metabolic substrate 2,3-bis(2-methoxy-4-nitro-5-sulfophenyl)-2H-tetrazolium-5-carboxanilide (XTT) which is converted only by intact cells into a product with specific absorption characteristics as described by Weislow O S, Kiser R, Fine D L, Bader J, Shoemaker R H and Boyd M R, J. Natl. Cancer Inst. 81, 577 (1989) (herein incorporated by reference in its entirety for all purposes).

MT2 cells (NIH AIDS reagent program, Cat # 237) maintained in RPMI-1640 medium supplemented with 5% fetal bovine serum and antibiotics were infected with the wild-type HIV-1 strain 111B (Advanced Biotechnologies, Columbia, Md.) for 3 hours at 37° C. using the virus inoculum corresponding to a multiplicity of infection equal to 0.01. The infected cells in culture media were distributed into a 96-well plate (20,000 cells in 100 µL/well), and incubated in the presence of a set of solutions containing 5-fold serial dilutions of the tested inhibitor (100 µL/well) for 5 days at 37° C. Samples with untreated infected and untreated mock-infected control cells were also distributed to the 96-well plate and incubated under the same conditions.

To determine the antiviral activity of the tested inhibitors, a substrate XTT solution (6 mL per assay plate) at a concentration of 2 mg/mL in a phosphate-buffered saline pH 7.4 was heated in water-bath for 5 min at 55° C. before 50 µL of N-methylphenazinium methosulfate (5 µg/mL) was added per 6 mL of XTT solution. After removing 100 µL media from each well on the assay plate, 100 µL of the XTT substrate solution was added to each well. The cells and the XTT solution were incubated at 37° C. for 45 to 60 min in a $CO_2$ incubator. To inactivate the virus, 20 µL of 2% Triton X-100 was added to each well. Viability, as determined by the amount of XTT metabolites produced, was quantified spectrophotometrically by the absorbance at 450 nm (with subtraction of the background absorbance at 650 nm). Data from the assay was expressed as the percentage absorbance relative to untreated control and the fifty percent effective concentration ($EC_{50}$) was calculated as the concentration of compound that effected an increase in the percentage of XTT metabolite production in infected, compound treated cells to 50% of that produced by uninfected, compound-free cells.

Anti-HIV-1 Cell Culture Assay ($EC_{50}$) in Presence of 40% Human Serum or Human Serum Proteins This assay is almost identical to the Anti-HIV-1 Cell Culture Assay described above, except that the infection was made in the presence or absence of 40% human serum (Type AB Male Cambrex 14-498E) or human serum proteins (Human α-acid Glycoprotein, Sigma G-9885; Human Serum Albumin, Sigma A1653, 96-99%) at physiological concentration. The HIV-1-induced cell death was determined as described above, except that the infected cells distributed in the 96-well plate were incubated in 80% Human Serum (2× concentration) or in 2 mg/mL Human α-acid Glycoprotein+ 70 mg/mL HSA (2× concentration) rather than in culture media.

Cytotoxicity Cell Culture Assay ($CC_{50}$)

The assay is based on the evaluation of cytotoxic effect of tested compounds using a metabolic substrate 2,3-bis(2-methoxy-4-nitro-5-sulfophenyl)-2H-tetrazolium-5-carboxanilide (XTT) as described by Weislow O S, Kiser R, Fine D L, Bader J, Shoemaker R H and Boyd M R, J. Natl. Cancer Inst. 81, 577 (1989). This assay is almost identical to the previous assay described (Anti-HIV-1 Cell Culture Assay), except that the cells were not infected. The compound induced cell death (or growth reduction) was determined as previously described.

MT-2 cells maintained in RPMI-1640 medium supplemented with 5% fetal bovine serum and antibiotics were distributed into a 96-well plate (20,000 cells in 100 µL/well) and incubated in the presence or absence of 5-fold serial dilutions of the tested inhibitor (100 µL/well) for 5 days at 37° C. Controls included untreated infected cells and infected cells protected by 1 µM of P4405 (Podophyllotoxin, Sigma Cat # P4405).

To determine cytotoxicity, an XTT solution (6 mL per assay plate) at a concentration of 2 mg/mL in phosphate-buffered saline pH 7.4 was heated in the dark in a water-bath for 5 min at 55° C. before 50 μL of N-methylphenazinium methosulfate (5 μg/mL) was added per 6 mL of XTT solution. After removing 100 μL media from each well on the assay plate, 100 μL of the XTT substrate solution was added to each well. The cells and the XTT solution were incubated at 37° C. for 45 to 60 min in a $CO_2$ incubator. To inactivate the virus, 20 μL of 2% Triton X-100 was added to each well. Viability, as determined by the amount of XTT metabolites produced, is quantified spectrophotometrically by the absorbance at 450 nm (with subtraction of the background absorbance at 650 nm). Data from the assay is expressed as the percentage absorbance relative to untreated control, and the fifty percent cytotoxicity concentration ($EC_{50}$) was calculated as the concentration of compound that effected an increase in the percentage of cell growth in compound treated cells to 50% of the cell growth provided by uninfected, compound-free cells.

Experimental data based on representative Examples CX-CZ, DA, and DM-DN demonstrate that the compounds of Formula IV of the present invention can have a CYP450 3A inhibition activity in a range represented by an $IC_{50}$ from about 100 nM to about 4700 nM, and a CYP450 2C9 inhibition activity in a range represented by an $IC_{50}$ from about 500 nM to greater than about 25,000 nM.

Experimental data based on representative Examples CX-CZ, DA-DE, DJ-DK, and DM demonstrate that the compounds of Formula IV of the present invention can have a protease inhibition activity in a range represented by HIV $EC_{50}$ from about 300 nM to greater than about 30,000 nM.

Experimental data based on representative Examples CX-CZ, DA, DJ-DK, and DM have a CYP450 3A inhibition activity in a range represented by an $IC_{50}$ from about 80-350 nM, a CYP450 2C9 inhibition activity in a range represented by an $IC_{50}$ from about 1000-12,000 nM, and a protease inhibition activity in a range represented by HIV $EC_{50}$ greater than about 20,000 nM.

What is claimed is:

1. A compound of Formula IV:

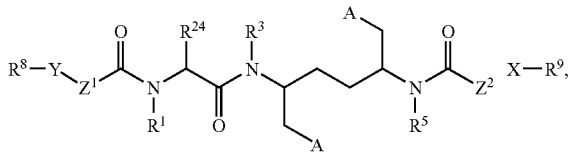

Formula IV or a pharmaceutically acceptable salt, and/or ester thereof, wherein:
each A is independently aryl or heterocyclyl;
$Z^1$ and $Z^2$ are each independently —O— or —N($R^7$)—;
X and Y are each independently aryl, arylalkyl, heterocyclyl, or heterocyclylalkyl;
$R^1$, $R^3$, and $R^5$ are each independently selected from the group consisting of H, alkyl, substituted alkyl, arylalkyl, and substituted arylalkyl;
each $R^7$ is independently selected from the group consisting of H, alkyl, substituted alkyl, heteroalkyl, substituted heteroalkyl, carbocyclyl, substituted carbocyclyl, heterocyclyl, and substituted heterocyclyl;
$R^8$ and $R^9$ are each one or more substituents independently selected from the group consisting of H, alkyl, halogen, aryl, heterocyclyl, and CN; and
$R^{24}$ is selected from the group consisting of -alkylene-$NR^5$—C(O)—$R^{25}$, -alkylene-C(O)—$NR^5$—$R^{26}$, -alkylene-N($R^{27}$)$_2$, —$CH_2$-heterocyclyl, and substituted —$CH_2$-heterocyclyl;
$R^{25}$ is alkyl, heterocyclylalkyl, or substituted heterocyclylalkyl;
$R^{26}$ is a substituted or unsubstituted heterocyclyl; or
$R^5$ and $R^{26}$ together with the nitrogen atom to which they are both shown attached, form a substituted or unsubstituted bicyclic heterocyclyl;
each $R^{27}$ is independently a substituted alkyl which may be the same or different; or
each $R^{27}$, together with the nitrogen atom to which they are both shown attached, form a substituted or unsubstituted bicyclic heterocyclyl;
with the following provisos:
  (i) when X and Y are both thiazolylmethyl, $Z^1$ is —N($R^7$)—, $Z^2$ is —O—, each A is phenyl, and $R^{24}$ is —$CH_2CH_2$—$NR^5$—C(O)-alkyl,
    then each $R^8$ and $R^9$ are H; and
  (ii) when X and Y are both thiazolylmethyl, $Z^1$ is —N($R^7$)—, $Z^2$ is —O—, each A is phenyl, and $R^{24}$ is —$CH_2$—C(O)—$NR^5$-pyridyl or —$CH_2$—C(O)—$NR^5$-pyrrolidinyl,
    then $R^5$ is alkyl, substituted alkyl, arylalkyl, or substituted arylalkyl; and
  (iii) when X and Y are both thiazolylmethyl, $Z^1$ is —N($R^7$)—, $Z^2$ is —O—, each A is phenyl, and $R^{24}$ is substituted or unsubstituted —$CH_2$-heterocyclyl,
    then said substituted or unsubstituted —$CH_2$-heterocyclyl is not pyridylmethyl, pyrazolylmethyl, imidazolidine-2,4-dione-5-yl-methyl, imidazolylmethyl, or morpholinylmethyl.

2. The compound of claim 1, wherein $R^{24}$ is —$(CH_2)_{1-4}$NHC(O)—$R^{25}$, —$(CH_2)_{1-4}$C(O)$NR^5R^{26}$, —$(CH_2)_{1-4}$N($R^{27}$)$_2$, or —$CH_2$-heteroaryl.

3. The compound of claim 1, wherein each A is aryl.

4. The compound of claim 3, wherein each A is unsubstituted phenyl.

5. The compound of claim 1, wherein $R^1$, $R^3$, and $R^5$ are H.

6. The compound of claim 1, wherein X and Y are heterocyclylalkyl.

7. The compound of claim 1, having the formula:

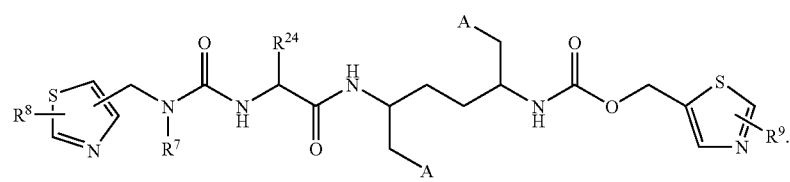

8. The compound of claim 7, having the formula:

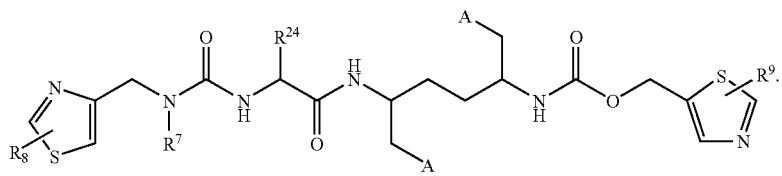

9. The compound of claim 7, having the formula:

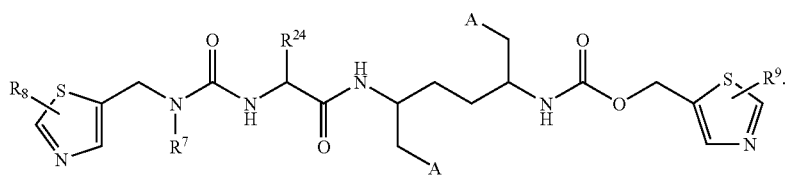

10. The compound of claim 7, wherein $R^{24}$ is —(CH$_2$)$_2$NHC(O)-alkyl.

11. The compound of claim 7, wherein $R^{24}$ is —CH$_2$C(O)NR$^5$R$^{26}$.

12. The compound of claim 7, wherein $R^{24}$ is —(CH$_2$)$_2$N(R$^{27}$)$_2$.

13. The compound of claim 7, wherein $R^{24}$ is substituted or unsubstituted —(CH$_2$)— heteroaryl.

14. A compound selected from the group consisting of:

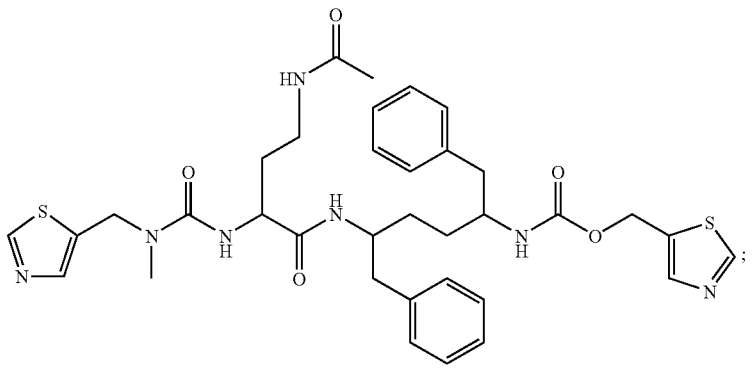

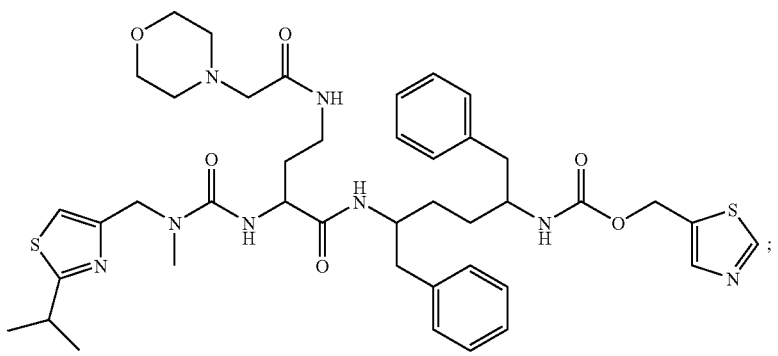

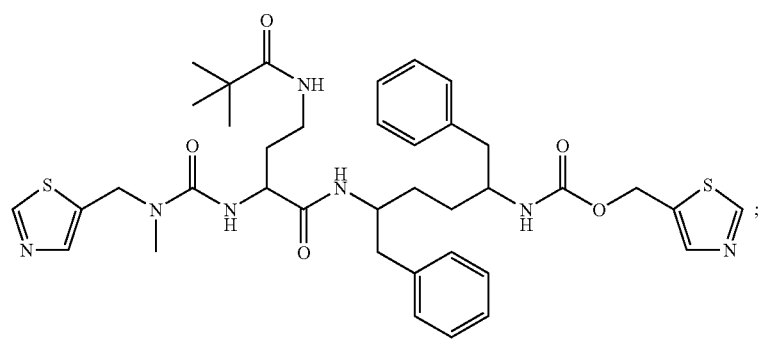
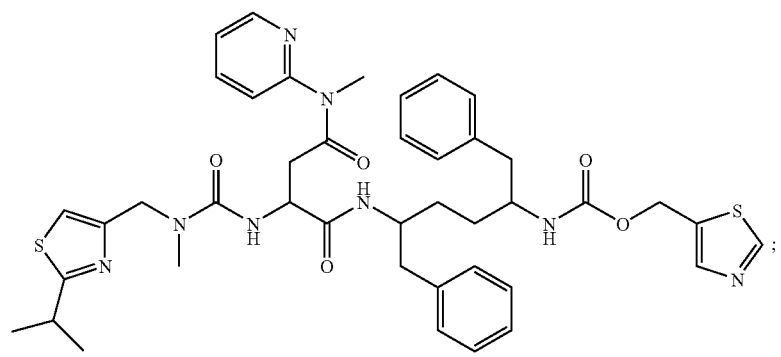
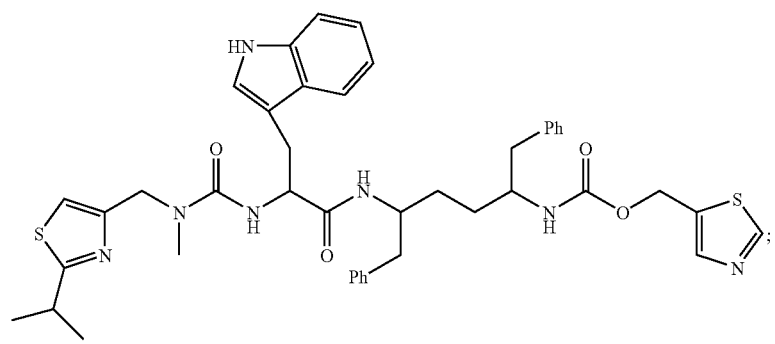
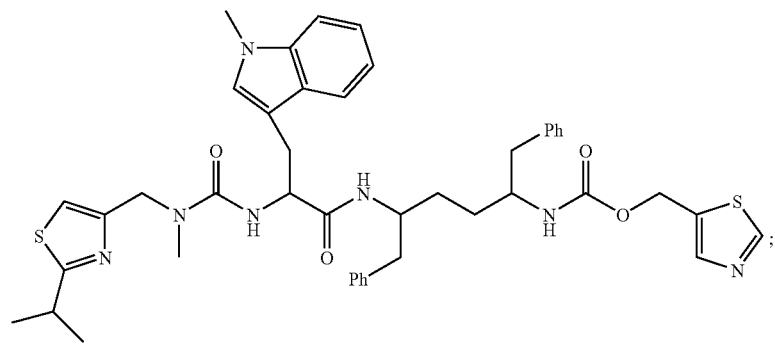
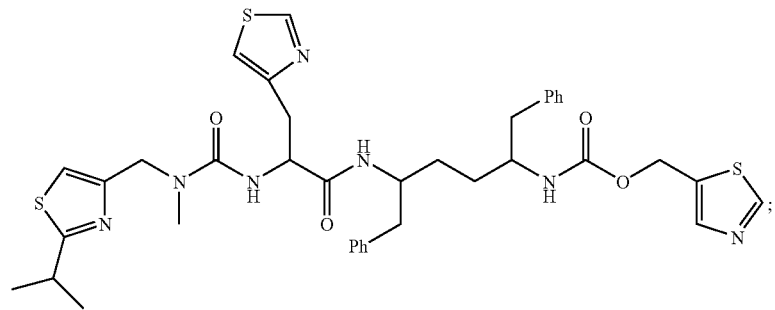

-continued
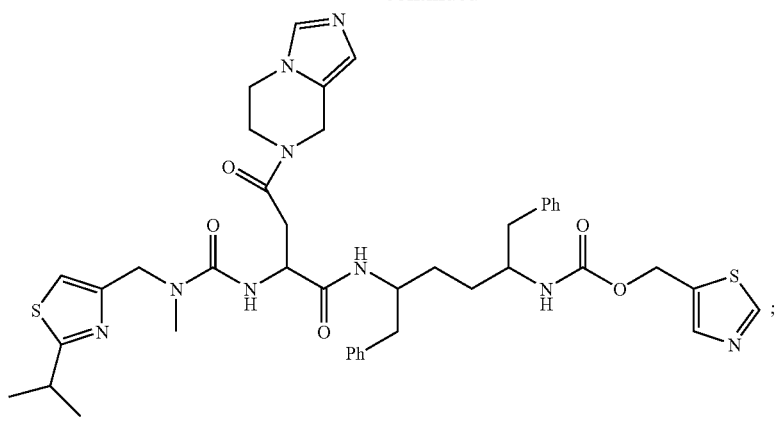
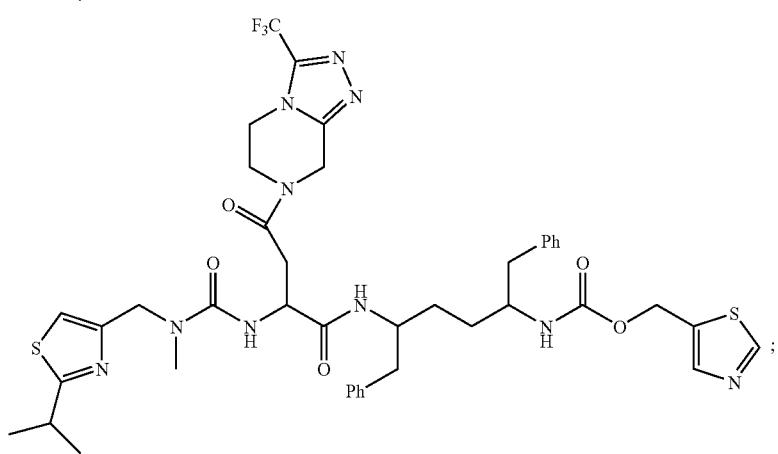
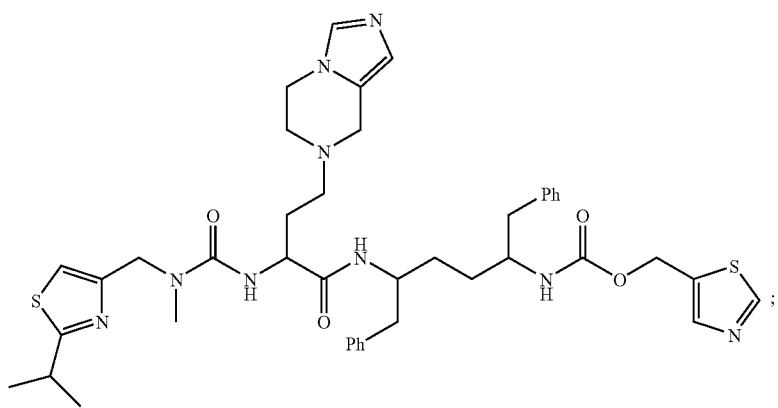
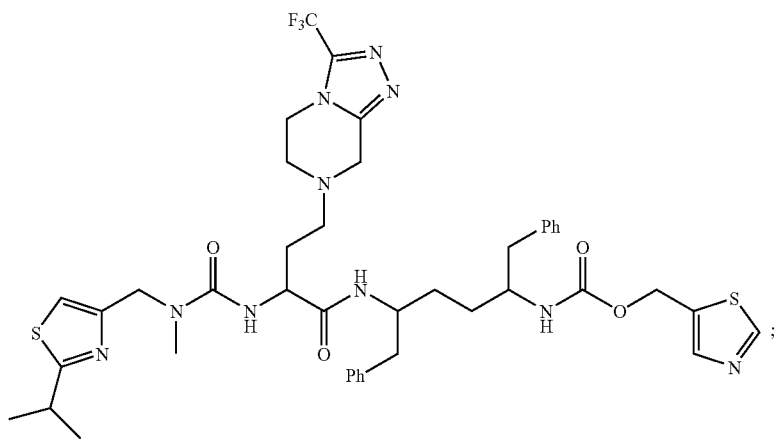

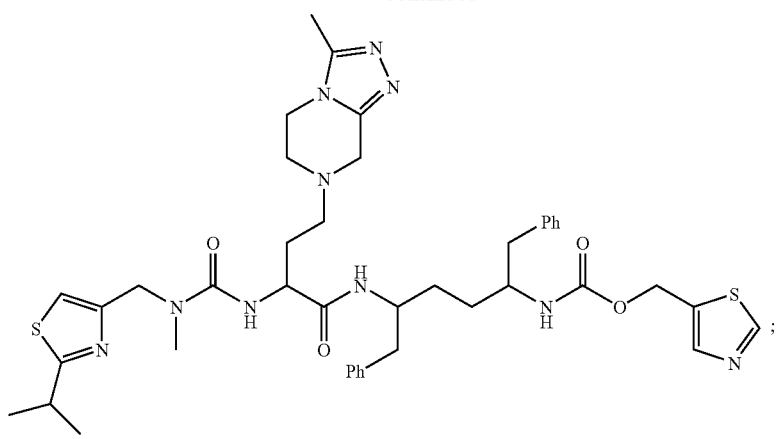
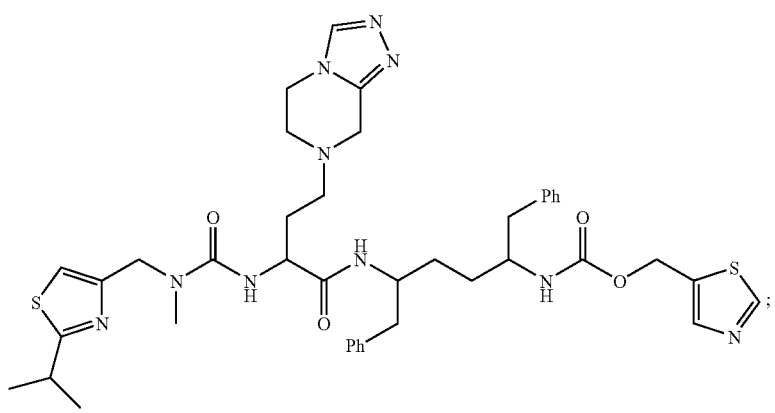
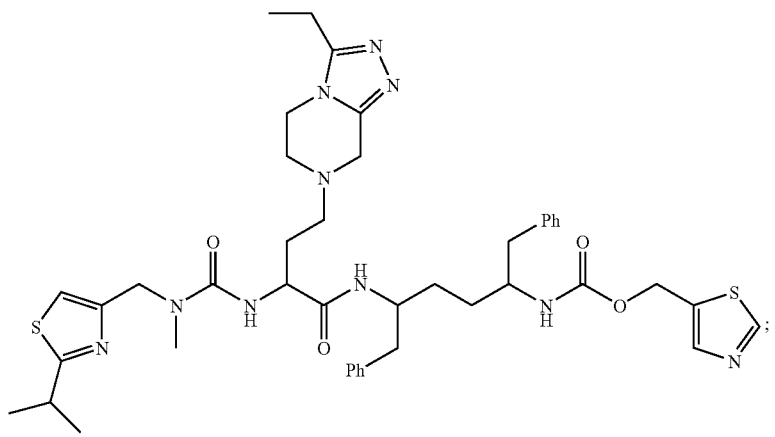
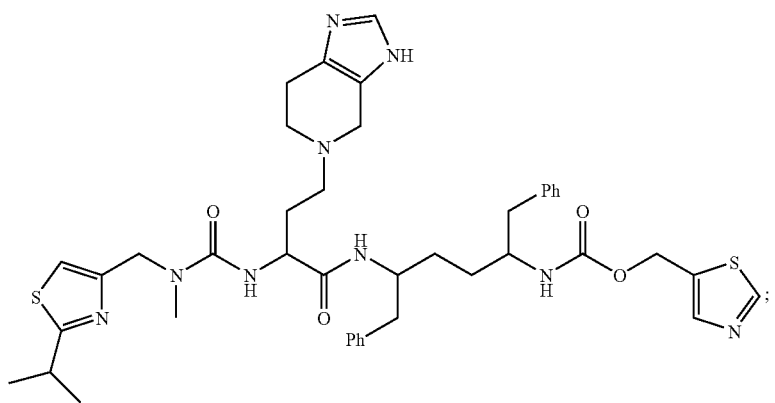

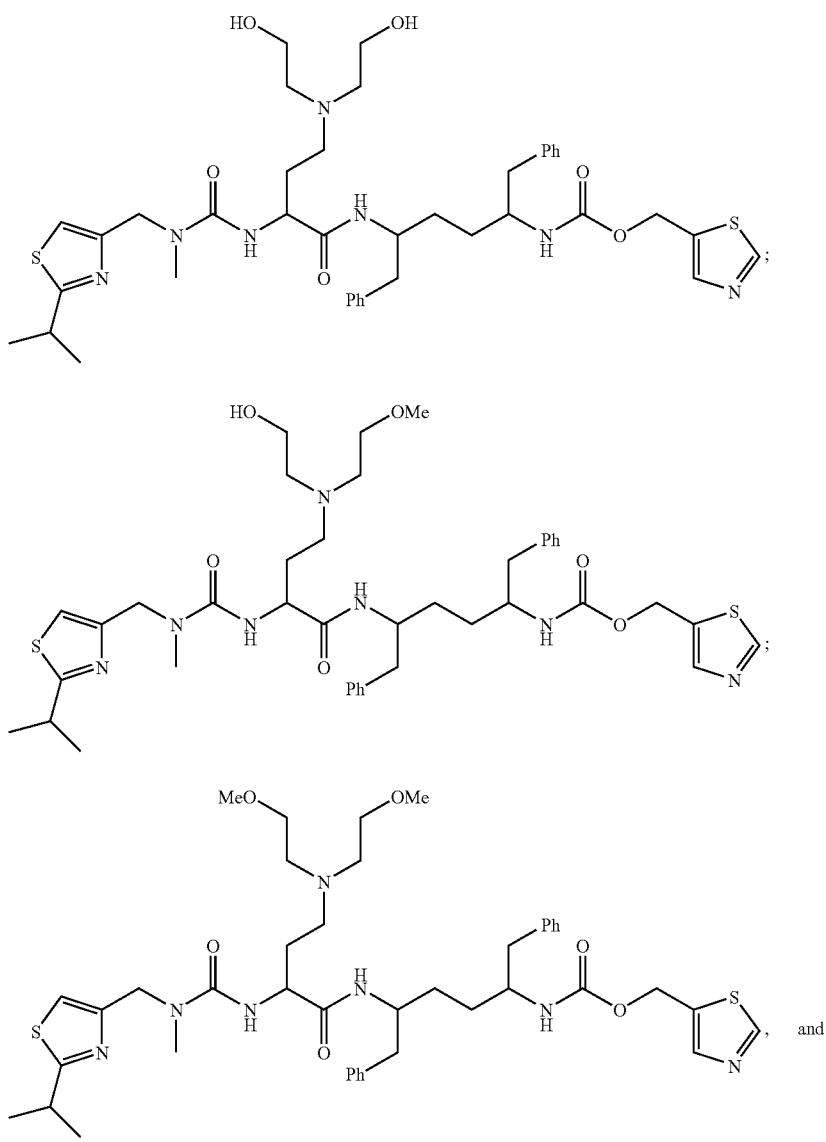
pharmaceutically acceptable salts, esters, and/or stereoisomers thereof.
15. A compound having the following structure:
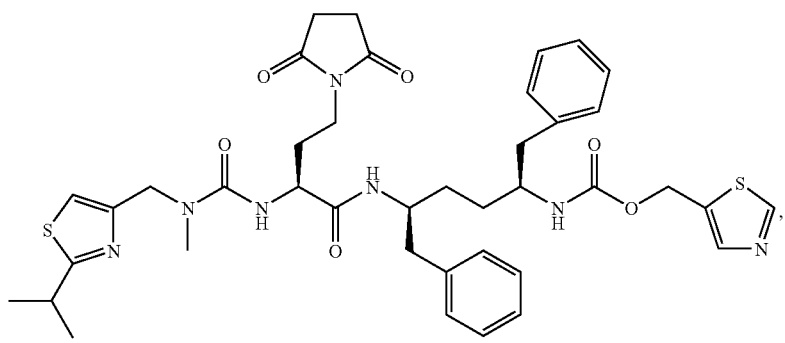

or pharmaceutically acceptable salts, and/or esters thereof.

16. A pharmaceutical composition comprising a compound of claim 1, or a pharmaceutically acceptable salt, and/or ester thereof, and a pharmaceutically acceptable carrier or exipient.

17. The pharmaceutical composition of claim 16, further comprising at least one therapeutic agent.

18. The pharmaceutical composition of claim 17, wherein said at least one therapeutic agent is metabolized by cytochrome P450 monooxygenase.

19. The pharmaceutical composition of claim 16, wherein the at least one therapeutic agent is selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, CCR8 inhibitors, RNase H inhibitors, maturation inhibitors, other drugs for treating HIV, interferons, ribavirin, taribavirin, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, other drugs for treating HCV, and mixtures thereof.

20. The pharmaceutical composition of claim 19, wherein:
(1) said HIV protease inhibitors are selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, DG17, GS-8374, MK-8122 (PPL-100), DG35, AG 1859, SPI-256, TMC 52390, PL-337, SM-322377, SM-309515, GRL-02031, CRS-074, CRS-075, KB-98, and A-790742;
(2) said HIV non-nucleoside inhibitors of reverse transcriptase are selected from the group consisting of capravirine, emivirine, delaviridine, efavirenz, nevirapine, (+) calanolide A, calanolide B, etravirine, GW5634, DPC-083, DPC-961, DPC-963, MIV-150, MIV-160, TMC-120 (dapiravine), TMC-278 (rilpivirene), BILR 355 BS, VRX 840773, UK-453061, RDEA806, RDEA806, RDEA 427, RDEA 640, IDX 899, ANX-201, R-1206, LOC-dd, IQP-0410 (SJ-3366), YM-215389, YM-228855, CMX-052, and CMX-182;
(3) said HIV nucleoside inhibitors of reverse transcriptase are selected from the group consisting of zidovudine, emtricitabine, didanosine, stavudine, zalcitabine, lamivudine, abacavir, amdoxovir, elvucitabine, alovudine, MIV-210, ±-FTC, D-d4FC, phosphazide, fozivudine tidoxil, apricitibine (AVX754), GS-7340, KP-1461, OBP-601, dioxolane thymine, TMC-254072, INK-20, PPI-801, PPI-802, MIV-410, 4'-Ed4T, B-108, and fosalvudine tidoxil (formerly HDP 99.0003);
(4) said HIV nucleotide inhibitors of reverse transcriptase are selected from the group consisting of tenofovir disoproxil fumarate, and adefovir dipivoxil;
(5) said HIV integrase inhibitors are selected from the group consisting of curcumin, chicoric acid, 3,5-dicaffeoylquinic acid, aurintricarboxylic acid, caffeic acid phenethyl ester, tyrphostin, quercetin, S-1360, AR-177, L-870812, L-870810, MK-0518 (raltegravir), elvitegravir (GS-9137), GSK-349572 (S-349572), GSK-265744 (S-265744), GSK-247303 (S-247303), S-1360 (GW810871), 1,5-DCQA, INH-001, INT-349, V-165, RIN-25, BFX-1001, BFX-1002, BFX-1003, RSC-1838, BCH-33040BMS-538158, GSK364735C, BMS-707035, MK-2048, and BA 011;
(6) said gp41 inhibitors are selected from the group consisting of enfuvirtide, sifuvirtide, MPI-451936, FB006M, Z-329029, and TRI-1144;
(7) said CXCR4 inhibitor is selected from the group consisting of AMD-070, KRH-3955 (CS-3955), AMD-9370, AMD-3451, RPI-MN, MSX-122, and POL-2438;
(8) said entry inhibitor is selected from the group consisting of SP01A, PA-161, SPC3, TNX-355, DES6, SP-10, SP-03, CT-319, and CT-326;
(9) said gp120 inhibitor is selected from the group consisting of BMS-488043, R-15-K, KPC-2, and MNLP62;
(10) said CCR5 inhibitors are selected from the group consisting of aplaviroc, nifeviroc, vicriviroc (SCH-417690), maraviroc, PRO-140, PRO-542, INCB15050, INCB9471, PF-232798, SCH-532706, GSK-706769, TAK-652, TAK-220, ESN-196, RO-1752, ZM-688523, AMD-887, YM-370749, NIBR-1282, SCH-350634, ZM-688523, and CCR5 mAb004;
(11) said CCR8 inhibitor is ZK-756326,
(12) said RNase H inhibitor is ODN-93 or ODN-112,
(13) said maturation inhibitors are selected from the group consisting of bevirimat (PA-457), PA-040, MPC-9055 (vicecon, MPI-49839), ACH-100703, and ACH-100706;
(14) said other drugs for treating HIV are selected from the group consisting of REP 9, SP-01A, TNX-355, DES6, ODN-93, ODN-112, VGV-1, PA-457 (bevirimat), rintatolimod, HRG214, anti-leukocyte adhesion MAb, VGX-410, KD-247, AMZ 0026, CYT 99007A-221 HIV, DEBIO-025, BAY 50-4798, MDX010 (ipilimumab), PBS 119, BIT-225, UBT-8147, ITI-367, AFX-400, BL-1050, GRN-139951, GRN-140665, AX-38679, RGB-340638, PPI-367, and ALG 889;
(15) said interferons are selected from the group consisting of pegylated rIFN-alpha 2b, pegylated rIFN-alpha 2a, rIFN-alpha 2b, rIFN-alpha 2a, interferon alpha, interferon alfacon-1, interferon alpha-n1, interferon alpha-n3, interferon-beta, interferon-omega, albinterferon alpha-2b, IFN alpha-2b XL, BLX-883, DA-3021, glycosylated interferon alpha-2b, pegylatedinterferon alfacon-1, pegylated interferon lambda-1, and belerofon;
(16) said HCV NS3 protease inhibitors are selected from the group consisting of boceprevir (SCH-503034, SCH-7), telaprevir (VX-950), TMC435350, BI-1335, BI-1230, MK-7009, VBY-376, VX-500, BMS-790052, BMS-605339, PHX-1766, AS-101, YH-5258, YH5530, YH5531, and ITMN-191,
(17) said alpha-glucosidase 1 inhibitors are selected from the group consisting of celgosivir (MX-3253), miglitol, and UT-231B,
(18) said hepatoprotectants are selected from the group consisting of IDN-6556, ME 3738, LB-84451, silibilin, and mitoquinone/mitoquinol,
(19) said nucleoside or nucleotide inhibitors of HCV NSSB polymerase are selected from the group consisting of R1626, R7128 (R4048), IDX184, IDX-102, BCX-4678, valopicitabine (NM-283), and MK-0608,
(20) said non-nucleoside inhibitors of HCV NS5B polymerase are selected from the group consisting of PF-868554, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190,

(21) said HCV NS5A inhibitors are selected from the group consisting of AZD-2836 (A-831) and A-689,
(22) said TLR-7 agonists are selected from the group consisting of ANA-975 and SM-360320
(23) said cyclophillin inhibitors are selected from the group consisting of DEBIO-025, SCY-635, and NIM811,
(24) said HCV IRES inhibitors are MCI-067, and
(25) other drugs for treating HCV are selected from the group consisting of thymosin alpha 1, nitazoxanide (NTZ), BIVN-401, PYN-17, KPE02003002, CPG-10101, KRN-7000, hepatitis C immune globulin human antibodies, GI-5005, XTL-6865, BIT225, PTX-111, ITX2865, TT-033i, ANA 971, NOV-205, EHC-18, VGX-410C, EMZ-702, AVI 4065, BMS-650032, BMS-791325, bavituximab, MDX-1106 (ONO-4538), oglufanide, and VX-497 (merimepodib).

21. A method for inhibiting cytochrome P450 monooxygenase in a patient comprising administering to a patient in need thereof an amount of a compound of claim 1, or a pharmaceutically acceptable salt, and/or ester thereof, effective to inhibit cytochrome P450 monooxygenase.

* * * * *